United States Patent
Emini et al.

(10) Patent No.: US 7,598,362 B2
(45) Date of Patent: Oct. 6, 2009

(54) HEPATITIS C VIRUS VACCINE

(75) Inventors: Emilio A. Emini, Wayne, PA (US); David C. Kaslow, Rancho Santa Fe, CA (US); Andrew J. Bett, Lansdale, PA (US); John W. Shiver, Chalfont, PA (US); Alfredo Nicosia, Rome (IT); Armin Lahm, Rome (IT); Alessandra Luzzago, Rome (IT); Riccardo Cortese, Rome (IT); Stefano Colloca, Rome (IT)

(73) Assignees: Merck & Co., Inc., Rahway, NJ (US); Istituto Di Ricerche Di Biologia Molecolare P. Angeletti S.p.A., Rome (IT)

( * ) Notice: Subject to any disclaimer, the term of this patent is extended or adjusted under 35 U.S.C. 154(b) by 878 days.

(21) Appl. No.: 10/492,178

(22) PCT Filed: Oct. 10, 2002

(86) PCT No.: PCT/US02/32512

§ 371 (c)(1),
(2), (4) Date: Apr. 7, 2004

(87) PCT Pub. No.: WO03/031588

PCT Pub. Date: Apr. 17, 2003

(65) Prior Publication Data

US 2004/0247615 A1    Dec. 9, 2004

Related U.S. Application Data

(60) Provisional application No. 60/363,774, filed on Mar. 13, 2002, provisional application No. 60/328,655, filed on Oct. 11, 2001.

(51) Int. Cl.
*C07H 21/04* (2006.01)
*C12N 7/00* (2006.01)

(52) U.S. Cl. .................. 536/23.1; 536/23.4; 424/218.1

(58) Field of Classification Search ............... 424/189.1
See application file for complete search history.

(56) References Cited

U.S. PATENT DOCUMENTS

| 5,122,458 | A |   | 6/1992  | Post et al. |
|-----------|---|---|---------|-------------|
| 5,731,172 | A | * | 3/1998  | Saito et al. ............... 435/91.42 |
| 5,739,002 | A |   | 4/1998  | De Francesco et al. |
| 5,792,462 | A |   | 8/1998  | Johnston et al. |
| 5,847,101 | A |   | 12/1998 | Okayama et al. |
| 5,994,083 | A |   | 11/1999 | Felici et al. |
| 6,033,908 | A |   | 3/2000  | Bout et al. |
| 6,127,116 | A | * | 10/2000 | Rice et al. ........................ 435/6 |
| 6,156,558 | A |   | 12/2000 | Johnston et al. |
| 6,511,832 | B1| * | 1/2003  | Guarino et al. ............ 435/91.1 |
| 6,544,780 | B1| * | 4/2003  | Wang ....................... 435/320.1 |
| 7,049,428 | B1| * | 5/2006  | Rice et al. ................. 536/23.72 |

FOREIGN PATENT DOCUMENTS

| EP | 0 173 552 A1 | 3/1986 |
|----|--------------|--------|
| EP | 0 173 552 B1 | 10/1991 |
| EP | 464287 A * | 1/1992 |
| WO | WO 95/32733 | 12/1995 |
| WO | WO 96/37619 | 11/1996 |
| WO | WO 97/47358 | 12/1997 |
| WO | WO 98/43702 | 10/1998 |
| WO | WO 99/38880 | 8/1999 |
| WO | WO 99/52463 | 10/1999 |
| WO | WO 99/60132 | 11/1999 |
| WO | WO 01/02607 | 1/2001 |
| WO | WO 01/30812 | 5/2001 |
| WO | WO 01/38360 | 5/2001 |
| WO | WO 01/47551 | 7/2001 |
| WO | WO 02/22080 | 3/2002 |

OTHER PUBLICATIONS

Danthne X. and Imperiale MJ. Production of first generation adenovirus vectors: a review. (2000) Gene Therapy, 7, pp. 1707-1714.*

Takamizawa et al. Structure and organization of the Hepatitis C virus genome isolated from human carriers. Journal of Virology, 1991, vol. 65, p. 1105-1113.*

Bartenschlager, R. et al. "Nonstructural Protein 3 of the Hepatitis C Virus Encodes a Serine-Type Proteinase Required for Cleavage at the NS3/4 and NS4/5 Junctions", Journal of Virology, 1993, vol. 67, pp. 3835-3844.

Behrens, S. et al. "Identification and properties of the RNA-dependent RNA polymerase of hepatitis C virus", The EMBO Journal, 1996, vol. 15, pp. 12-22.

Bett, A. et al. "Packaging Capacity and Stability of Human Adenovirus Type 5 Vectors", Journal of Virology, 1993, vol. 67, pp. 5911-5921.

Brenner, M. "Gene Transfer by Adenovectors", Blood, 1999, vol. 94, pp. 3965-3967.

Chamberlain, B. et al. "Complete nucleotide sequence of type 4 hepatitis C virus variant, the predominant genotype in the Middle East", Journal of General Virology, 1997, vol. 78, pp. 1341-1347.

(Continued)

*Primary Examiner*—Bruce Campell
*Assistant Examiner*—Agnieszka Boesen
(74) *Attorney, Agent, or Firm*—Sheldon O. Heber

(57) ABSTRACT

The present invention features Ad6 vectors and a nucleic acid encoding a Met-NS3-NS4A-NS4B-NS5A-NS5B polypeptide containing an inactive NS5B RNA-dependent RNA polymerase region. The nucleic acid is particularly useful as a component of an adenovector or DNA plasmid vaccine providing a broad range of antigens for generating an HCV specific cell mediated immune (CMI) response against HCV.

50 Claims, 92 Drawing Sheets

OTHER PUBLICATIONS

Chapman, B. et al. "Effect of intron A from cytomegalovirus (Towne) immediate-early gene on hterologous expression in mammalian cells", Nucleic Acids Research, 1991, vol. 19, pp. 3979-3986.

Chartier, C. et al. "Efficient Generation of Recombinant Adenovirus Vectors by Homologous Recombinaation in *Escherichia coli*", Journal of Virology, 1996, vol. 70, pp. 4805-4810.

Cho, J. et al. "Enhanced cellular immunity to hepatitis C virus nonstructural proteins by codelivery of granulocyte macrophage-colony stimulating factor gene in intramuscular DNA immunization", Vaccine, 1999, vol. 17, pp. 1136-1144.

Choo, Q. et al. "Isolation of a cDNA Clone Derived from a Blood-Borne Non-A, Non-B Viral Hepatitis Genome", Science, 1989, vol. 244, pp. 359-362.

Chroboczek, J. et al. "The Sequence of the Genome of Adenovirus Type 5 and Its Comparison with the Genome of Adenovirus Type 2", Virology, 1992, vol. 186, pp. 280-285.

Chung, J. et al. A 5' Element of the Chicken B-Globin Domain Serves as an Insulator in Human Erythroid Cells and Protects against Position Effect in *Drosophila*, Cell, 1993, vol. 74, pp. 505-514.

Danthinne, X. et al. "Production of first generation adenovirus vectors: a review", Gene Therapy, 2000, vol. 7, pp. 1707-1714.

De Francesco, R. et al. "Biochemical and Immunologic Properties of the Nonstructural Proteins of the Hepatitis C Virus: Implications for Development of Antiviral Agents and Vaccines", Seminars in Liver Disease, 2000, vol. 20, pp. 69-83.

Donnelly, J. et al. "DNA Vaccines", Annual Review of Immunology, 1997, vol. 15, pp. 617-648.

Donnelly, J. et al. "Minireview DNA Vaccines" Life Sciences, 1997, vol. 60, pp. 163-172.

Failla, C. et al. "Both NS3 and NS4A Are Required for Proteolytic Processing of Hepatitis C Virus Nonstructural Proteins", Journal of Virology, 1994, vol. 68, pp. 3753-3760.

Fallaux, F. et al. "New Helper Cells and Matched Early Region 1-Deleted Adenovirus Vectors Prevent Generation of Replication-Competent Adenoviruses", Human Gene Therapy, 1998, vol. 9, pp. 1909-1917.

Foecking, M. et al. "Powerful and versatile enhancer-promoter unit for mammalian expression vectors", Gene, 1986, vol. 45, pp. 101-105.

Gilbert, S et al. "Enhanced CD8 T cell immunogenicity and protective efficacy in a mouse malaria model usinga recombinant adenoviral vaccine in heterologous prime-boost immunisation regimes", Vaccine, 2002, vol. 20, pp. 1039-1045.

Graham, F. et al. "Characteristics of a Human Cell Line Transformed by DNA from Human Adenovirus Type 5", Journal General Virology, 1977, vol. 36, pp. 59-74.

Graham, F. "Covalently closed circles of human adenovirus DNA are infectious", The EMBO Journal, 1984, vol. 3, pp. 2917-2922.

Grakoui, A. et al. "A second hepatitis C virus-encoded proteinase", Proc. Natl. Acad. Sci. USA, 1993, vol. 90, pp. 10583-10587.

Grakoui, A. et al. "Expression and Identification of Hepatitis C Virus Polyprotein Cleavage Products", Journal of Virology, 1993, vol. 67, pp. 1385-1395.

Hagstrom, J. et al. "Improved muscle-derived expression of human coagulation factor IX from a skeletal actin/CMV hybrid enhancer/promoter", Blood, 2000, vol. 95, pp. 2536-2542.

Hijikata, M. et al.. "Proteolytic processing and membrane association of putative monstructural proteins of hepatitis C virus", Proc. Natl. Acad. Sci. USA, 1993, vol. 90, pp. 10773-10777.

Hitt, M. et al. "Human Adenovirus Vectors for Gene Transfer into Mammalian Cells", Advances in Pharmacology, 1997, vol. 40, pp. 137-206.

Hitt, M. et al. "Techniques of Human Adenovirus Vector Construction and Characterization", Methods in Molecular Genetics, 1995, vol. 7, pp. 13-30.

Kolykhalov, A. et al. "Hepatits C Virus-Encoded Enzymatic Activities and Conserved RNA Elements in the 3' Nontranslated Region Are Essential for Virus Replication In Vivo", Journal of Virology, 2000, vol. 74, pp. 2046-2051.

Kozak, M. "Point Mutations Define a Sequence Flanking the AUG Initiator Codon That Modulates Translation by Eukaryotic Ribosomes", Cell, 1986, vol. 44, pp. 283-292.

Kuo, G. et al. "An Assay for Circulating Antibodies to a Major Etiologic Virus of Human Non-A, Non-B Hepatitis", Science, 1989, vol. 244, pp. 362-364.

Lechner, F. et al. "Analysis of Successful Immune Responses in Persons Infected with Hepatitis C Virus", Journal of Experimental Medicine, 2000, vol. 9, pp. 1499-1512.

Li, X. et al. "Synthetic muscle promoters: activities exceeding naturally occuring regulatory sequences", Nature Biotechnology, 1999, vol. 17, pp. 241-245.

Lohmann, V. et al. "Biochemical and Kinetic Analysesof NS5B RNA-Dependent Poymerase of the Hepatitis C Virus", Virology, 1998, vol. 249, pp. 108-118.

Lohmann, V. et al. "Biochemical Properties of Hepatitis C Virus NS5B RNA-Dependent RNA Polymerase and Identification of Amino Acid Seqeunce Motifs Essential for Enzymatic Activity", Journal of Virology, 1997, vol. 71, pp. 8416-8428.

Mizushima, H. et al. "Analysis of N-Terminal Processing of Hepatitis C Virus Nonstructural Protein 2", Journal of Virology, 1994, vol. 68, pp. 2731-2734.

Montgomery, D. et al. "Heterologous and Homologous Protection Against Influenza A by DNA Vaccination: Optimization of DNA Vectors", DNA and Cell Biology, 1993, vol. 12, pp. 777-783.

Pawlotsky, J. "Hepatitic C virus (HCV) NS5A protein: role in HCV replication and resistance to intereron-a", Journal of Viral Hepatitis, 1999, vol. 6, Suppl. 1, pp. 47-48.

Rehermann, B. et al. "Cell Mediated Immune Response to the Hepatitis C Virus", Current Topic in Microbiology and Immunology, 2000, vol. 242, pp. 299-325.

Restifo, N. et al. "The promise of nucleic acids vaccines", Gene Therapy, 2000, vol. 7, pp. 89-92.

Rodriguez, F. et al. "Enhancing DNA Immunization", Virology, 2000, vol. 268, pp. 233-238.

Russell, W. "Update on adenovirus and its vectors", Journal of General Virology, 2000, vol. 81, pp. 2573-2604.

Schiedner, G. et al. "Efficient Transformation of Pimary Human Amniocytes by E1 Functions of Ad5: Generation of New Cel Lines for Adenoviral Vector Production", Human Gene Therapy, 2000, vol. 11, pp. 2105-2116.

Simmonds, P. "The origin and evolution of hepatitis viruses in humans", Journal of General Virology, 2001, vol. 82, pp. 693-712.

Stunnenberg, H. et al. "High expression of functional adenovirus DNA polymerase and precursor terminal protein using recombinant vaccine virus", Nucleic Acids Research, 1988, vol. 16, pp. 2431-2444.

Takamizawa, A. et al. "Structure and Organization of the Hepatitis C Virus Genome Isolated from Human Carriers", Journal of Virology, 1991, vol. 65, pp. 1105-1113.

Tomei, L. et al. "NS3 Is a Serine Protease Required for Processing of Hepatitis C Virus Polyprotein", Journal of Virology, 1993, vol. 67, pp. 4017-4026.

Bassett, S. et al. "Protective Immune Response to Hepatitis C Virus in Chimpanzees Rechallenged Following Clearance of Primary Infection", Hepatology, 2001, vol. 33, pp. 1479-1487.

Major, M. et al. "Previously Infected and Recovered Chimpanzees Exhibit Rapid Responses That Control Hepatitis C Virus Replication upon Rechallenge", Journal of Virology, 2002, vol. 76, pp. 6586-6595.

Mehta, S. et al. "Protection against persistence of hepatitis C", The Lancet, 2002, vol. 359, pp. 1478-1483.

Encke, J. et al. "Genetic Immunization Generates Cellular and Humoral Immune Responses Against the Nonstructural Proteins of the Hepatitis C Virus in a Murine Model", The Journal of Immunology, 1998, vol. 161, pp. 4917-4923.

Urbani, S. et al. "Identification of Immunodominant Hepatitis C Virus (HCV)-Specific Cytotoxic T-Cell Epitopes by Stimulation With Endogenously Synthesized HCV Antigens", Hepatology, 2001, vol. 33, pp. 1533-1543.

Capone et al., "A Novel Adenovirus Type 6 (Ad6)-Based Hepatitis C Virus Vector That Overcomes Preexisting Anti-Ad5 Immunity and Induces Potent and Broad Cellular Immune Responses in *Rhesus macaques*", Journal of Virology, vol. 80, No. 4, pp. 1688-1699 (Feb. 2006).

Capone et al., "Modulation of the Immune Response Induced by Gene Electrotransfer of a Hepatitis C Virus DNA Vaccine in Nonhuman Primates", The Journal of Immunology, vol. 177, pp. 7462-7471 (2006).

Fattori et al., "Efficient immunization of *Rhesus macaques* with an HCV candidate vaccine by heterologous priming-boosting with novel adenoviral vectors based on different serotypes", Gene Therapy, vol. 13, pp. 1088-1096 (2006).

Folgori et al, "A T-cell HCV vaccine eliciting effective immunity against heterologous virus challenge in chimpanzees", Nature Medicine, vol. 12, No. 2, pp. 190-197 (Feb. 2006).

Kolykhalov et al., "Hepatitis C Virus-Encoded Enzymatic Activities and Conserved RNA Elements in the 3' Nontranslated Region Are Essential for Virus Replication in Vivo", Journal of Virology, vol. 74, No. 4, pp. 2046-2051 (Feb. 2000).

Lauer et al., "Vaccine Induced T-Cell Responses Against HCV: One Step Taken, More To Follow", Gastroenterology, vol. 132, No. 4, pp. 1626-1628 (Apr. 2007).

Naroditsky et al., "Analysis of DNA From Human Adenovirus Type 6 With Restriction Endonucleases HindIII, BgIIII and BamHI", Biochimica et Biophysica Acta, vol. 606, pp. 214-227 (1980).

Oh et al, "Template Requirement and Initiation Site Selection by Hepatitis C Virus Polymerase on a Minimal Viral RNA Template", The Journal of Biological Chemistry, vol. 275, No. 23, pp. 17710-17717 (2000).

Tikchonenko et al, "Biophysical Properties of Virions of Human Adenovirus of the Type 6 and Its DNA", Archives of Virology, vol. 62, pp. 117-130 (1979).

\* cited by examiner

| | | | | |
|---|---|---|---|---|
| 1 | MAPITAYSQQ | TRGLLGCIIT | SLTGRDKNQV | EGEVQVVSTA | TQSFLATCVN |
| 51 | GVCWTVYHGA | GSKTLAGPKG | PITQMYTNVD | QDLVGWQAPP | GARSLTPCTC |
| 101 | GSSDLYLVTR | HADVIPVRRR | GDSRGSLLSP | RPVSYLKGSS | GGPLLCPSGH |
| 151 | AVGIFRAAVC | TRGVAKAVDF | VPVESMETTM | RSPVFTDNSS | PPAVPQSFQV |
| 201 | AHLHAPTGSG | KSTKVPAAYA | AQGYKVLVLN | PSVAATLGFG | AYMSKAHGID |
| 251 | PNIRTGVRTI | TTGAPVTYST | YGKFLADGGC | SGGAYDIIIC | DECHSTDSTT |
| 301 | ILGIGTVLDQ | AETAGARLVV | LATATPPGSV | TVPHPNIEEV | ALSNTGEIPF |
| 351 | YGKAIPIEAI | RGGRHLIFCH | SKKKCDELAA | KLSGLGINAV | AYYRGLDVSV |
| 401 | IPTIGDVVVV | ATDALMTGYT | GDFDSVIDCN | TCVTQTVDFS | LDPTFTIETT |
| 451 | TVPQDAVSRS | QRRGRTGRGR | RGIYRFVTPG | ERPSGMFDSS | VLCECYDAGC |
| 501 | AWYELTPAET | SVRLRAYLNT | PGLPVCQDHL | EFWESVFTGL | THIDAHFLSQ |
| 551 | TKQAGDNFPY | LVAYQATVCA | RAQAPPPSWD | QMWKCLIRLK | PTLHGPTPLL |
| 601 | YRLGAVQNEV | TLTHPITKYI | MACMSADLEV | VTSTWVLVGG | VLAALAAYCL |
| 651 | TTGSVVIVGR | IILSGRPAIV | PDREFLYQEF | DEMEECASHL | PYIEQGMQLA |
| 701 | EQFKQKALGL | LQTATKQAEA | AAPVVESKWR | ALETFWAKHM | WNFISGIQYL |
| 751 | AGLSTLPGNP | AIASLMAFTA | SITSPLTTQS | TLLFNILGGW | VAAQLAPPSA |
| 801 | ASAFVGAGIA | GAAVGSIGLG | KVLVDILAGY | GAGVAGALVA | FKVMSGEMPS |
| 851 | TEDLVNLLPA | ILSPGALVVG | VVCAAILRRH | VGPGEGAVQW | MNRLIAFASR |
| 901 | GNHVSPTHYV | PESDAAARVT | QILSSLTITQ | LLKRLHQWIN | EDCSTPCSGS |
| 951 | WLRDVWDWIC | TVLTDFKTWL | QSKLLPQLPG | VPFFSCQRGY | KGVWRGDGIM |
| 1001 | QTTCPCGAQI | TGHVKNGSMR | IVGPKTCSNT | WHGTFPINAY | TTGPCTPSPA |
| 1051 | PNYSRALWRV | AAEEYVEVTR | VGDFHYVTGM | TTDNVKCPCQ | VPAPEFFTEV |
| 1101 | DGVRLHRYAP | ACRPLLREEV | TFQVGLNQYL | VGSQLPCEPE | PDVAVLTSML |
| 1151 | TDPSHITAET | AKRRLARGSP | PSLASSSASQ | LSAPSLKATC | TTHHVSPDAD |
| 1201 | LIEANLLWRQ | EMGGNITRVE | SENKVVVLDS | FDPLRAEEDE | REVSVPAEIL |
| 1251 | RKSKKFPAAM | PIWARPDYNP | PLLESWKDPD | YVPPVVHGCP | LPPIKAPPIP |
| 1301 | PPRRKRTVVL | TESSVSSALA | ELATKTFGSS | ESSAVDSGTA | TALPDQASDD |
| 1351 | GDKGSDVESY | SSMPPLEGEP | GDPDLSDGSW | STVSEEASED | VVCCSMSYTW |
| 1401 | TGALITPCAA | EESKLPINAL | SNSLLRHHNM | VYATTSRSAG | LRQKKVTFDR |
| 1451 | LQVLDDHYRD | VLKEMKAKAS | TVKAKLLSVE | EACKLTPPHS | AKSKFGYGAK |
| 1501 | DVRNLSSKAV | NHIHSVWKDL | LEDTVTPIDT | TIMAKNEVFC | VQPEKGGRKP |
| 1551 | ARLIVFPDLG | VRVCEKMALY | DVVSTLPQVV | MGSSYGFQYS | PGQRVEFLVN |
| 1601 | TWKSKKNPMG | FSYDTRCFDS | TVTENDIRVE | ESIYQCCDLA | PEARQAIKSL |
| 1651 | TERLYIGGPL | TNSKGQNCGY | RRCRASGVLT | TSCGNTLTCY | LKASAACRAA |

FIG. 1A

```
1701    KLQDCTMLVN AAGLVVICES AGTQEDAASL RVFTEAMTRY SAPPGDPPQP
1751    EYDLELITSC SSNVSVAHDA SGKRVYYLTR DPTTPLARAA WETARHTPVN
1801    SWLGNIIMYA PTLWARMILM THFFSILLAQ EQLEKALDCQ IYGACYSIEP
1851    LDLPQIIERL HGLSAFSLHS YSPGEINRVA SCLRKLGVPP LRVWRHRARS
1901    VRARLLSQGG RAATCGKYLF NWAVKTKLKL TPIPAASQLD LSGWFVAGYS
1951    GGDIYHSLSR ARPRWFMLCL LLLSVGVGIY LLPNR
```

FIG. 1B

```
   1    GCCACCATGG CGCCCATCAC GGCCTACTCC CAACAGACGC GGGGCCTACT
  51    TGGTTGCATC ATCACTAGCC TTACAGGCCG GGACAAGAAC CAGGTCGAGG
 101    GAGAGGTTCA GGTGGTTTCC ACCGCAACAC AATCCTTCCT GGCGACCTGC
 151    GTCAACGGCG TGTGTTGGAC CGTTTACCAT GGTGCTGGCT CAAAGACCTT
 201    AGCCGGCCCA AAGGGGCCAA TCACCCAGAT GTACACTAAT GTGGACCAGG
 251    ACCTCGTCGG CTGGCAGGCG CCCCCGGGG CGCGTTCCTT GACACCATGC
 301    ACCTGTGGCA GCTCAGACCT TTACTTGGTC ACGAGACATG CTGACGTCAT
 351    TCCGGTGCGC CGGCGGGGCG ACAGTAGGGG GAGCCTGCTC TCCCCAGGC
 401    CTGTCTCCTA CTTGAAGGGC TCTTCGGGTG GTCCACTGCT CTGCCCTTCG
 451    GGGCACGCTG TGGGCATCTT CCGGGCTGCC GTATGCACCC GGGGGGTTGC
 501    GAAGGCGGTG GACTTTGTGC CCGTAGAGTC CATGGAAACT ACTATGCGGT
 551    CTCCGGTCTT CACGGACAAC TCATCCCCCC CGGCCGTACC GCAGTCATTT
 601    CAAGTGGCCC ACCTACACGC TCCCACTGGC AGCGGCAAGA GTACTAAAGT
 651    GCCGGCTGCA TATGCAGCCC AAGGGTACAA GGTGCTCGTC CTCAATCCGT
 701    CCGTTGCCGC TACCTTAGGG TTTGGGGCGT ATATGTCTAA GGCACACGGT
 751    ATTGACCCCA ACATCAGAAC TGGGGTAAGG ACCATTACCA CAGGCGCCCC
 801    CGTCACATAC TCTACCTATG GCAAGTTTCT TGCCGATGGT GGTTGCTCTG
 851    GGGGCGCTTA TGACATCATA ATATGTGATG AGTGCCATTC AACTGACTCG
 901    ACTACAATCT TGGGCATCGG CACAGTCCTG GACCAAGCGG AGACGGCTGG
 951    AGCGCGGCTT GTCGTGCTCG CCACCGCTAC GCCTCCGGGA TCGGTCACCG
1001    TGCCACACCC AAACATCGAG GAGGTGGCCC TGTCTAATAC TGGAGAGATC
1051    CCCTTCTATG GCAAAGCCAT CCCCATTGAA GCCATCAGGG GGGAAGGCA
1101    TCTCATTTTC TGTCATTCCA AGAAGAAGTG CGACGAGCTC GCCGCAAAGC
1151    TGTCAGGCCT CGGAATCAAC GCTGTGGCGT ATTACCGGGG GCTCGATGTG
1201    TCCGTCATAC CAACTATCGG AGACGTCGTT GTCGTGGCAA CAGACGCTCT
1251    GATGACGGGC TATACGGGCG ACTTTGACTC AGTGATCGAC TGTAACACAT
1301    GTGTCACCCA GACAGTCGAC TTCAGCTTGG ATCCCACCTT CACCATTGAG
1351    ACGACGACCG TGCCTCAAGA CGCAGTGTCG CGCTCGCAGC GGCGGGGTAG
1401    GACTGGCAGG GGTAGGAGAG CATCTACAG GTTTGTGACT CCGGGAGAAC
1451    GGCCCTCGGG CATGTTCGAT TCCTCGGTCC TGTGTGAGTG CTATGACGCG
1501    GGCTGTGCTT GGTACGAGCT CACCCCCGCC GAGACCTCGG TTAGGTTGCG
1551    GGCCTACCTG AACACACCAG GGTTGCCCGT TGCCAGGAC CACCTGGAGT
1601    TCTGGGAGAG TGTCTTCACA GGCCTCACCC ACATAGATGC ACACTTCTTG
1651    TCCCAGACCA AGCAGGCAGG AGACAACTTC CCCTACCTGG TAGCATACCA
```

FIG. 2A

```
1701  AGCCACGGTG TGCGCCAGGG CTCAGGCCCC ACCTCCATCA TGGGATCAAA
1751  TGTGGAAGTG TCTCATACGG CTGAAACCTA CGCTGCACGG GCCAACACCC
1801  TTGCTGTACA GGCTGGGAGC CGTCCAAAAT GAGGTCACCC TCACCCACCC
1851  CATAACCAAA TACATCATGG CATGCATGTC GGCTGACCTG GAGGTCGTCA
1901  CTAGCACCTG GGTGCTGGTG GGCGGAGTCC TTGCAGCTCT GGCCGCGTAT
1951  TGCCTGACAA CAGGCAGTGT GGTCATTGTG GGTAGGATTA TCTTGTCCGG
2001  GAGGCCGGCT ATTGTTCCCG ACAGGGAGTT CTCTACCAG GAGTTCGATG
2051  AAATGGAAGA GTGCGCCTCG CACCTCCCTT ACATCGAGCA GGGAATGCAG
2101  CTCGCCGAGC AATTCAAGCA GAAAGCGCTC GGGTTACTGC AAACAGCCAC
2151  CAAACAAGCG GAGGCTGCTG CTCCCGTGGT GGAGTCCAAG TGGCGAGCCC
2201  TTGAGACATT CTGGGCGAAG CACATGTGGA ATTTCATCAG CGGGATACAG
2251  TACTTAGCAG GCTTATCCAC TCTGCCTGGG AACCCCGCAA TAGCATCATT
2301  GATGGCATTC ACAGCCTCTA TCACCAGCCC GCTCACCACC CAAAGTACCC
2351  TCCTGTTTAA CATCTTGGGG GGGTGGGTGG CTGCCCAACT CGCCCCCCCC
2401  AGCGCCGCTT CGGCTTTCGT GGGCGCCGGC ATCGCCGGTG CGGCTGTTGG
2451  CAGCATAGGC CTTGGGAAGG TGCTTGTGGA CATTCTGGCG GGTTATGGAG
2501  CAGGAGTGGC CGGCGCGCTC GTGGCCTTCA AGGTCATGAG CGGCGAGATG
2551  CCCTCCACCG AGGACCTGGT CAATCTACTT CCTGCCATCC TCTCTCCTGG
2601  CGCCCTGGTC GTCGGGGTCG TGTGTGCAGC AATACTGCGT CGACACGTGG
2651  GTCCGGGAGA GGGGGCTGTG CAGTGGATGA ACCGGCTGAT AGCGTTCGCC
2701  TCGCGGGGTA ATCATGTTTC CCCCACGCAC TATGTGCCTG AGAGCGACGC
2751  CGCAGCGCGT GTTACTCAGA TCCTCTCCAG CCTTACCATC ACTCAGCTGC
2801  TGAAAAGGCT CCACCAGTGG ATTAATGAAG ACTGCTCCAC ACCGTGTTCC
2851  GGCTCGTGGC TAAGGGATGT TTGGGACTGG ATATGCACGG TGTTGACTGA
2901  CTTCAAGACC TGGCTCCAGT CCAAGCTCCT GCCGCAGCTA CCGGGAGTCC
2951  CTTTTTTCTC GTGCCAACGC GGGTACAAGG GAGTCTGGCG GGGAGACGGC
3001  ATCATGCAAA CCACCTGCCC ATGTGGAGCA CAGATCACCG GACATGTCAA
3051  AAACGGTTCC ATGAGGATCG TCGGGCCTAA GACCTGCAGC AACACGTGGC
3101  ATGGAACATT CCCCATCAAC GCATACACCA CGGGCCCCTG CACACCCTCT
3151  CCAGCGCCAA ACTATTCTAG GGCGCTGTGG CGGGTGGCCG CTGAGGAGTA
3201  CGTGGAGGTC ACGCGGGTGG GGGATTTCCA CTACGTGACG GGCATGACCA
3251  CTGACAACGT AAAGTGCCCA TGCCAGGTTC CGGCTCCTGA ATTCTTCACG
3301  GAGGTGGACG GAGTGCGGTT GCACAGGTAC GCTCCGGCGT GCAGGCCTCT
3351  CCTACGGGAG GAGGTTACAT TCCAGGTCGG GCTCAACCAA TACCTGGTTG
```

FIG. 2B

```
3401   GGTCACAGCT ACCATGCGAG CCCGAACCGG ATGTAGCAGT GCTCACTTCC
3451   ATGCTCACCG ACCCCTCCCA CATCACAGCA GAAACGGCTA AGCGTAGGTT
3501   GGCCAGGGGG TCTCCCCCCT CCTTGGCCAG CTCTTCAGCT AGCCAGTTGT
3551   CTGCGCCTTC CTTGAAGGCG ACATGCACTA CCCACCATGT CTCTCCGGAC
3601   GCTGACCTCA TCGAGGCCAA CCTCCTGTGG CGGCAGGAGA TGGGCGGGAA
3651   CATCACCCGC GTGGAGTCGG AGAACAAGGT GGTAGTCCTG GACTCTTTCG
3701   ACCCGCTTCG AGCGGAGGAG GATGAGAGGG AAGTATCCGT TCCGGCGGAG
3751   ATCCTGCGGA AATCCAAGAA GTTCCCCGCA GCGATGCCCA TCTGGGCGCG
3801   CCCGGATTAC AACCCTCCAC TGTTAGAGTC CTGGAAGGAC CCGGACTACG
3851   TCCCTCCGGT GGTGCACGGG TGCCCGTTGC CACCTATCAA GGCCCCTCCA
3901   ATACCACCTC CACGGAGAAA GAGGACGGTT GTCCTAACAG AGTCCTCCGT
3951   GTCTTCTGCC TTAGCGGAGC TCGCTACTAA GACCTTCGGC AGCTCCGAAT
4001   CATCGGCCGT CGACAGCGGC ACGGCGACCG CCCTTCCTGA CCAGGCCTCC
4051   GACGACGGTG ACAAAGGATC CGACGTTGAG TCGTACTCCT CCATGCCCCC
4101   CCTTGAGGGG GAACCGGGGG ACCCCGATCT CAGTGACGGG TCTTGGTCTA
4151   CCGTGAGCGA GGAAGCTAGT GAGGATGTCG TCTGCTGCTC AATGTCCTAC
4201   ACATGGACAG GCGCCTTGAT CACGCCATGC GCTGCGGAGG AAAGCAAGCT
4251   GCCCATCAAC GCGTTGAGCA ACTCTTTGCT GCGCCACCAT AACATGGTTT
4301   ATGCCACAAC ATCTCGCAGC GCAGGCCTGC GGCAGAAGAA GGTCACCTTT
4351   GACAGACTGC AAGTCCTGGA CGACCACTAC CGGGACGTGC TCAAGGAGAT
4401   GAAGGCGAAG GCGTCCACAG TTAAGGCTAA ACTCCTATCC GTAGAGGAAG
4451   CCTGCAAGCT GACGCCCCCA CATTCGGCCA AATCCAAGTT TGGCTATGGG
4501   GCAAAGGACG TCCGGAACCT ATCCAGCAAG GCCGTTAACC ACATCCACTC
4551   CGTGTGGAAG GACTTGCTGG AAGACACTGT GACACCAATT GACACCACCA
4601   TCATGGCAAA AAATGAGGTT TTCTGTGTCC AACCAGAGAA AGGAGGCCGT
4651   AAGCCAGCCC GCCTTATCGT ATTCCCAGAT CTGGGAGTCC GTGTATGCGA
4701   GAAGATGGCC CTCTATGATG TGGTCTCCAC CCTTCCTCAG GTCGTGATGG
4751   GCTCCTCATA CGGATTCCAG TACTCTCCTG GGCAGCGAGT CGAGTTCCTG
4801   GTGAATACCT GGAAATCAAA GAAAAACCCC ATGGGCTTTT CATATGACAC
4851   TCGCTGTTTC GACTCAACGG TCACCGAGAA CGACATCCGT GTTGAGGAGT
4901   CAATTTACCA ATGTTGTGAC TTGGCCCCCG AAGCCAGACA GGCCATAAAA
4951   TCGCTCACAG AGCGGCTTTA TATCGGGGGT CCTCTGACTA ATTCAAAAGG
5001   GCAGAACTGC GGTTATCGCC GGTGCCGCGC GAGCGGCGTG CTGACGACTA
5051   GCTGCGGTAA CACCCTCACA TGTTACTTGA AGGCCTCTGC AGCCTGTCGA
```

FIG. 2C

```
5101  GCTGCGAAGC TCCAGGACTG CACGATGCTC GTGAACGCCG CCGGCCTTGT
5151  CGTTATCTGT GAAAGCGCGG GAACCCAAGA GGACGCGGCG AGCCTACGAG
5201  TCTTCACGGA GGCTATGACT AGGTACTCTG CCCCCCCCGG GGACCCGCCC
5251  CAACCAGAAT ACGACTTGGA GCTGATAACA TCATGTTCCT CCAATGTGTC
5301  GGTCGCCCAC GATGCATCAG GCAAAAGGGT GTACTACCTC ACCCGTGATC
5351  CCACCACCCC CCTCGCACGG GCTGCGTGGG AAACAGCTAG ACACACTCCA
5401  GTTAACTCCT GGCTAGGCAA CATTATCATG TATGCGCCCA CTTTGTGGGC
5451  AAGGATGATT CTGATGACTC ACTTCTTCTC CATCCTTCTA GCACAGGAGC
5501  AACTTGAAAA AGCCCTGGAC TGCCAGATCT ACGGGGCCTG TTACTCCATT
5551  GAGCCACTTG ACCTACCTCA GATCATTGAA CGACTCCATG GCCTTAGCGC
5601  ATTTTCACTC CATAGTTACT CTCCAGGTGA GATCAATAGG GTGGCTTCAT
5651  GCCTCAGGAA ACTTGGGGTA CCACCCTTGC GAGTCTGGAG ACATCGGGCC
5701  AGGAGCGTCC GCGCTAGGCT ACTGTCCCAG GGGGGGAGGG CCGCCACTTG
5751  TGGCAAGTAC CTCTTCAACT GGGCAGTGAA GACCAAACTC AAACTCACTC
5801  CAATCCCGGC TGCGTCCAG CTGGACTTGT CCGGCTGGTT CGTTGCTGGT
5851  TACAGCGGGG GAGACATATA TCACAGCCTG TCTCGTGCCC GACCCCGCTG
5901  GTTCATGCTG TGCCTACTCC TACTTTCTGT AGGGGTAGGC ATCTACCTGC
5951  TCCCCAACCG ATAAA
```

FIG. 2D

| | | | | |
|---|---|---|---|---|
| 1 | GCCACCATGG | CCCCCATCAC | CGCCTACAGC | CAGCAGACCC | GCGGCCTGCT |
| 51 | GGGCTGCATC | ATCACCAGCC | TGACCGGCCG | CGACAAGAAC | CAGGTGGAGG |
| 101 | GCGAGGTGCA | GGTGGTGAGC | ACCGCCACCC | AGAGCTTCCT | GGCCACCTGC |
| 151 | GTGAACGGCG | TGTGCTGGAC | CGTGTACCAC | GGCGCCGGCA | GCAAGACCCT |
| 201 | GGCCGGCCCC | AAGGGCCCCA | TCACCCAGAT | GTACACCAAC | GTGGACCAGG |
| 251 | ACCTGGTGGG | CTGGCAGGCC | CCCCCGGCG | CCCGCAGCCT | GACCCCTGC |
| 301 | ACCTGCGGCA | GCAGCGACCT | GTACCTGGTG | ACCCGCCACG | CCGACGTGAT |
| 351 | CCCCGTGCGC | CGCCGCGGCG | ACAGCCGCGG | CAGCCTGCTG | AGCCCCGCC |
| 401 | CCGTGAGCTA | CCTGAAGGGC | AGCAGCGGCG | GCCCCCTGCT | GTGCCCCAGC |
| 451 | GGCCACGCCG | TGGGCATCTT | CCGCGCCGCC | GTGTGCACCC | GCGGCGTGGC |
| 501 | CAAGGCCGTG | GACTTCGTGC | CGTGGAGAG | CATGGAGACC | ACCATGCGCA |
| 551 | GCCCCGTGTT | CACCGACAAC | AGCAGCCCCC | CGCCGTGCC | CCAGAGCTTC |
| 601 | CAGGTGGCCC | ACCTGCACGC | CCCCACCGGC | AGCGGCAAGA | GCACCAAGGT |
| 651 | GCCCGCCGCC | TACGCCGCCC | AGGGCTACAA | GGTGCTGGTG | CTGAACCCCA |
| 701 | GCGTGGCCGC | CACCCTGGGC | TTCGGCGCCT | ACATGAGCAA | GGCCCACGGC |
| 751 | ATCGACCCCA | ACATCCGCAC | CGGCGTGCGC | ACCATCACCA | CCGGCGCCCC |
| 801 | CGTGACCTAC | AGCACCTACG | GCAAGTTCCT | GGCCGACGGC | GGCTGCAGCG |
| 851 | GCGGCGCCTA | CGACATCATC | ATCTGCGACG | AGTGCCACAG | CACCGACAGC |
| 901 | ACCACCATCC | TGGGCATCGG | CACCGTGCTG | GACCAGGCCG | AGACCGCCGG |
| 951 | CGCCCGCCTG | GTGGTGCTGG | CCACCGCCAC | CCCCCCCGGC | AGCGTGACCG |
| 1001 | TGCCCCACCC | CAACATCGAG | GAGGTGGCCC | TGAGCAACAC | CGGCGAGATC |
| 1051 | CCCTTCTACG | GCAAGGCCAT | CCCCATCGAG | GCCATCCGCG | GCGGCCGCCA |
| 1101 | CCTGATCTTC | TGCCACAGCA | AGAAGAAGTG | CGACGAGCTG | GCCGCCAAGC |
| 1151 | TGAGCGGCCT | GGGCATCAAC | GCCGTGGCCT | ACTACCGCGG | CCTGGACGTG |
| 1201 | AGCGTGATCC | CCACCATCGG | CGACGTGGTG | GTGGTGGCCA | CCGACGCCCT |
| 1251 | GATGACCGGC | TACACCGGCG | ACTTCGACAG | CGTGATCGAC | TGCAACACCT |
| 1301 | GCGTGACCCA | GACCGTGGAC | TTCAGCCTGG | ACCCCACCTT | CACCATCGAG |
| 1351 | ACCACCACCG | TGCCCCAGGA | CGCCGTGAGC | CGCAGCCAGC | GCCGCGGCCG |
| 1401 | CACCGGCCGC | GGCCGCCGCG | GCATCTACCG | CTTCGTGACC | CCGGCGAGC |
| 1451 | GCCCCAGCGG | CATGTTCGAC | AGCAGCGTGC | TGTGCGAGTG | CTACGACGCC |
| 1501 | GGCTGCGCCT | GGTACGAGCT | GACCCCCGCC | GAGACCAGCG | TGCGCCTGCG |
| 1551 | CGCCTACCTG | AACACCCCCG | GCCTGCCCGT | GTGCCAGGAC | CACCTGGAGT |
| 1601 | TCTGGGAGAG | CGTGTTCACC | GGCCTGACCC | ACATCGACGC | CCACTTCCTG |
| 1651 | AGCCAGACCA | GCAGGCCGG | CGACAACTTC | CCCTACCTGG | TGGCCTACCA |

FIG. 3A

| | | | | | |
|---|---|---|---|---|---|
| 1701 | GGCCACCGTG | TGCGCCCGCG | CCCAGGCCCC | CCCCCCCAGC | TGGGACCAGA |
| 1751 | TGTGGAAGTG | CCTGATCCGC | CTGAAGCCCA | CCCTGCACGG | CCCCACCCCC |
| 1801 | CTGCTGTACC | GCCTGGGCGC | CGTGCAGAAC | GAGGTGACCC | TGACCCACCC |
| 1851 | CATCACCAAG | TACATCATGG | CCTGCATGAG | CGCCGACCTG | GAGGTGGTGA |
| 1901 | CCAGCACCTG | GGTGCTGGTG | GGCGGCGTGC | TGGCCGCCCT | GGCCGCCTAC |
| 1951 | TGCCTGACCA | CCGGCAGCGT | GGTGATCGTG | GCCGCATCA | TCCTGAGCGG |
| 2001 | CCGCCCCGCC | ATCGTGCCCG | ACCGCGAGTT | CCTGTACCAG | GAGTTCGACG |
| 2051 | AGATGGAGGA | GTGCGCCAGC | CACCTGCCCT | ACATCGAGCA | GGGCATGCAG |
| 2101 | CTGGCCGAGC | AGTTCAAGCA | GAAGGCCCTG | GGCCTGCTGC | AGACCGCCAC |
| 2151 | CAAGCAGGCC | GAGGCCGCCG | CCCCCGTGGT | GGAGAGCAAG | TGGCGCGCCC |
| 2201 | TGGAGACCTT | CTGGGCCAAG | CACATGTGGA | ACTTCATCAG | CGGCATCCAG |
| 2251 | TACCTGGCCG | GCCTGAGCAC | CCTGCCCGGC | AACCCCGCCA | TCGCCAGCCT |
| 2301 | GATGGCCTTC | ACCGCCAGCA | TCACCAGCCC | CCTGACCACC | CAGAGCACCC |
| 2351 | TGCTGTTCAA | CATCCTGGGC | GGCTGGGTGG | CCGCCCAGCT | GGCCCCCCCC |
| 2401 | AGCGCCGCCA | GCGCCTTCGT | GGGCGCCGGC | ATCGCCGGCG | CCGCCGTGGG |
| 2451 | CAGCATCGGC | CTGGGCAAGG | TGCTGGTGGA | CATCCTGGCC | GGCTACGGCG |
| 2501 | CCGGCGTGGC | CGGCGCCCTG | GTGGCCTTCA | AGGTGATGAG | CGGCGAGATG |
| 2551 | CCCAGCACCG | AGGACCTGGT | GAACCTGCTG | CCCGCCATCC | TGAGCCCCGG |
| 2601 | CGCCCTGGTG | GTGGGCGTGG | TGTGCGCCGC | CATCCTGCGC | CGCCACGTGG |
| 2651 | GCCCCGGCGA | GGGCGCCGTG | CAGTGGATGA | ACCGCCTGAT | CGCCTTCGCC |
| 2701 | AGCCGCGGCA | ACCACGTGAG | CCCCACCCAC | TACGTGCCCG | AGAGCGACGC |
| 2751 | CGCCGCCCGC | GTGACCCAGA | TCCTGAGCAG | CCTGACCATC | ACCCAGCTGC |
| 2801 | TGAAGCGCCT | GCACCAGTGG | ATCAACGAGG | ACTGCAGCAC | CCCCTGCAGC |
| 2851 | GGCAGCTGGC | TGCGCGACGT | GTGGGACTGG | ATCTGCACCG | TGCTGACCGA |
| 2901 | CTTCAAGACC | TGGCTGCAGA | GCAAGCTGCT | GCCCCAGCTG | CCCGGCGTGC |
| 2951 | CCTTCTTCAG | CTGCCAGCGC | GGCTACAAGG | GCGTGTGGCG | CGGCGACGGC |
| 3001 | ATCATGCAGA | CCACCTGCCC | CTGCGGCGCC | CAGATCACCG | GCCACGTGAA |
| 3051 | GAACGGCAGC | ATGCGCATCG | TGGGCCCCAA | GACCTGCAGC | AACACCTGGC |
| 3101 | ACGGCACCTT | CCCCATCAAC | GCCTACACCA | CCGGCCCCTG | CACCCCCAGC |
| 3151 | CCCGCCCCCA | ACTACAGCCG | CGCCCTGTGG | CGCGTGGCCG | CCGAGGAGTA |
| 3201 | CGTGGAGGTG | ACCCGCGTGG | GCGACTTCCA | CTACGTGACC | GGCATGACCA |
| 3251 | CCGACAACGT | GAAGTGCCCC | TGCCAGGTGC | CGCCCCCGA | GTTCTTCACC |
| 3301 | GAGGTGGACG | GCGTGCGCCT | GCACCGCTAC | GCCCCCGCCT | GCCGCCCCCT |
| 3351 | GCTGCGCGAG | GAGGTGACCT | TCCAGGTGGG | CCTGAACCAG | TACCTGGTGG |

FIG. 3B

```
3401  GCAGCCAGCT GCCCTGCGAG CCCGAGCCCG ACGTGGCCGT GCTGACCAGC
3451  ATGCTGACCG ACCCCAGCCA CATCACCGCC GAGACCGCCA AGCGCCGCCT
3501  GGCCCGCGGC AGCCCCCCCA GCCTGGCCAG CAGCAGCGCC AGCCAGCTGA
3551  GCGCCCCCAG CCTGAAGGCC ACCTGCACCA CCCACCACGT GAGCCCCGAC
3601  GCCGACCTGA TCGAGGCCAA CCTGCTGTGG CGCCAGGAGA TGGGCGGCAA
3651  CATCACCCGC GTGGAGAGCG AGAACAAGGT GGTGGTGCTG GACAGCTTCG
3701  ACCCCCTGCG CGCCGAGGAG GACGAGCGCG AGGTGAGCGT GCCCGCCGAG
3751  ATCCTGCGCA AGAGCAAGAA GTTCCCCGCC GCCATGCCCA TCTGGGCCCG
3801  CCCCGACTAC AACCCCCCCC TGCTGGAGAG CTGGAAGGAC CCCGACTACG
3851  TGCCCCCCGT GGTGCACGGC TGCCCCCTGC CCCCCATCAA GGCCCCCCCC
3901  ATCCCCCCCC CCGCCGCAA GCGCACCGTG GTGCTGACCG AGAGCAGCGT
3951  GAGCAGCGCC CTGGCCGAGC TGGCCACCAA GACCTTCGGC AGCAGCGAGA
4001  GCAGCGCCGT GGACAGCGGC ACCGCCACCG CCCTGCCCGA CCAGGCCAGC
4051  GACGACGGCG ACAAGGGCAG CGACGTGGAG AGCTACAGCA GCATGCCCCC
4101  CCTGGAGGGC GAGCCCGGCG ACCCCGACCT GAGCGACGGC AGCTGGAGCA
4151  CCGTGAGCGA GGAGGCCAGC GAGGACGTGG TGTGCTGCAG CATGAGCTAC
4201  ACCTGGACCG GCGCCCTGAT CACCCCCTGC GCCGCCGAGG AGAGCAAGCT
4251  GCCCATCAAC GCCCTGAGCA ACAGCCTGCT GCGCCACCAC AACATGGTGT
4301  ACGCCACCAC CAGCCGCAGC GCCGGCCTGC GCCAGAAGAA GGTGACCTTC
4351  GACCGCCTGC AGGTGCTGGA CGACCACTAC CGCGACGTGC TGAAGGAGAT
4401  GAAGGCCAAG GCCAGCACCG TGAAGGCCAA GCTGCTGAGC GTGGAGGAGG
4451  CCTGCAAGCT GACCCCCCCC CACAGCGCCA AGAGCAAGTT CGGCTACGGC
4501  GCCAAGGACG TGCGCAACCT GAGCAGCAAG GCCGTGAACC ACATCCACAG
4551  CGTGTGGAAG GACCTGCTGG AGGACACCGT GACCCCCATC GACACCACCA
4601  TCATGGCCAA GAACGAGGTG TTCTGCGTGC AGCCCGAGAA GGGCGGCCGC
4651  AAGCCCGCCC GCCTGATCGT GTTCCCCGAC CTGGGCGTGC GCGTGTGCGA
4701  GAAGATGGCC CTGTACGACG TGGTGAGCAC CCTGCCCCAG GTGGTGATGG
4751  GCAGCAGCTA CGGCTTCCAG TACAGCCCCG GCCAGCGCGT GGAGTTCCTG
4801  GTGAACACCT GGAAGAGCAA GAAGAACCCC ATGGGCTTCA GCTACGACAC
4851  CCGCTGCTTC GACAGCACCG TGACCGAGAA CGACATCCGC GTGGAGGAGA
4901  GCATCTACCA GTGCTGCGAC CTGGCCCCCG AGGCCCGCCA GGCCATCAAG
4951  AGCCTGACCG AGCGCCTGTA CATCGGCGGC CCCCTGACCA ACAGCAAGGG
5001  CCAGAACTGC GGCTACCGCC GCTGCCGCGC CAGCGGCGTG CTGACCACCA
5051  GCTGCGGCAA CACCCTGACC TGCTACCTGA AGGCCAGCGC CGCCTGCCGC
```

FIG. 3C

```
5101    GCCGCCAAGC TGCAGGACTG CACCATGCTG GTGAACGCCG CCGGCCTGGT
5151    GGTGATCTGC GAGAGCGCCG GCACCCAGGA GGACGCCGCC AGCCTGCGCG
5201    TGTTCACCGA GGCCATGACC CGCTACAGCG CCCCCCCCGG CGACCCCCCC
5251    CAGCCCGAGT ACGACCTGGA GCTGATCACC AGCTGCAGCA GCAACGTGAG
5301    CGTGGCCCAC GACGCCAGCG GCAAGCGCGT GTACTACCTG ACCCGCGACC
5351    CCACCACCCC CCTGGCCCGC GCCGCCTGGG AGACCGCCCG CCACACCCCC
5401    GTGAACAGCT GGCTGGGCAA CATCATCATG TACGCCCCCA CCCTGTGGGC
5451    CCGCATGATC CTGATGACCC ACTTCTTCAG CATCCTGCTG GCCCAGGAGC
5501    AGCTGGAGAA GGCCCTGGAC TGCCAGATCT ACGGCGCCTG CTACAGCATC
5551    GAGCCCCTGG ACCTGCCCCA GATCATCGAG CGCCTGCACG GCCTGAGCGC
5601    CTTCAGCCTG CACAGCTACA GCCCCGGCGA GATCAACCGC GTGGCCAGCT
5651    GCCTGCGCAA GCTGGGCGTG CCCCCCCTGC GCGTGTGGCG CCACCGCGCC
5701    CGCAGCGTGC GCGCCCGCCT GCTGAGCCAG GGCGGCCGCG CCGCCACCTG
5751    CGGCAAGTAC CTGTTCAACT GGGCCGTGAA GACCAAGCTG AAGCTGACCC
5801    CCATCCCCGC CGCCAGCCAG CTGGACCTGA GCGGCTGGTT CGTGGCCGGC
5851    TACAGCGGCG GCGACATCTA CCACAGCCTG AGCCGCGCCC GCCCCCGCTG
5901    GTTCATGCTG TGCCTGCTGC TGCTGAGCGT GGGCGTGGGC ATCTACCTGC
5951    TGCCCAACCG CTAAA
```

FIG. 3D

```
   1 catcatcaat aatatacctt attttggatt gaagccaata tgataatgag ggggtggagt
  61 ttgtgacgtg gcgcggggcg tgggaacggg gcgggtgacg tagtagtgtg gcggaagtgt
 121 gatgttgcaa gtgtggcgga acacatgtaa gcgacggatg tggcaaaagt gacgtttttg
 181 gtgtgcgccg gtgtacacag gaagtgacaa ttttcgcgcg gttttaggcg gatgttgtag
 241 taaatttggg cgtaaccgag taagatttgg ccatttcgc gggaaaactg aataagagga
 301 agtgaaatct gaataatttt gtgttactca tagcgcgtaa tatttgtcta gggccgcggg
 361 gactttgacc gtttacgtgg agactcgccc aggtgttttt ctcaggtgtt ttccgcgttc
 421 cgggtcaaag ttggcgtttt attattatag gcggccgcga tccattgcat acgttgtatc
 481 catatcataa tatgtacatt tatattggct catgtccaac attaccgcca tgttgacatt
 541 gattattgac tagttattaa tagtaatcaa ttacggggtc attagttcat agcccatata
 601 tggagttccg cgttacataa cttacggtaa atggcccgcc tggctgaccg cccaacgacc
 661 cccgcccatt gacgtcaata atgacgtatg ttcccatagt aacgccaata gggactttcc
 721 attgacgtca atgggtggag tatttacggt aaactgccca cttggcagta catcaagtgt
 781 atcatatgcc aagtacgccc cctattgacg tcaatgacgg taaatggccc gcctggcatt
 841 atgcccagta catgacctta tgggactttc ctacttggca gtacatctac gtattagtca
 901 tcgctattac catggtgatg cggttttggc agtacatcaa tgggcgtgga tagcggtttg
 961 actcacgggg atttccaagt ctccacccca ttgacgtcaa tgggagtttg ttttggcacc
1021 aaaatcaacg ggactttcca aaatgtcgta acaactccgc cccattgacg caaatgggcg
1081 gtaggcgtgt acggtgggag gtctatataa gcagagctcg tttagtgaac cgtcagatcg
1141 cctggagacg ccatccacgc tgttttgacc tccatagaag acaccgggac cgatccagcc
1201 tccgcggccg gaacggtgc attggaacgc ggattccccg tgccaagagt gagatctgcc
1261 accatggcgc ccatcacggc ctactcccaa cagcgcggg gcctacttgg ttgcatcatc
1321 actagcctta caggccggga caagaaccag gtcgagggag aggttcaggt ggtttccacc
1381 gcaacacaat ccttcctggc gacctgcgtc aacggcgtgt gttggaccgt ttaccatggt
1441 gctggctcaa agaccttagc cggcccaaag gggccaatca cccagatgta cactaatgtg
1501 gaccaggacc tcgtcggctg gcaggcgccc cccggggcgc gttccttgac accatgcacc
1561 tgtggcagct cagaccttta cttggtcacg agacatgctg acgtcattcc ggtgcgccgg
1621 cggggcgaca gtaggggag cctgctctcc cccaggcctg tctcctactt gaagggctct
1681 tcgggtggtc cactgctctg cccttcgggg cacgctgtgg gcatcttccg ggctgccgta
1741 tgcacccggg gggttgcgaa ggcggtggac tttgtgcccg tagagtccat ggaaactact
1801 atgcggtctc cggtcttcac ggacaactca tcccccccgg ccgtaccgca gtcatttcaa
1861 gtggcccacc tacacgctcc cactggcagc ggcaagagta ctaaagtgcc ggctgcatat
1921 gcagcccaag ggtacaaggt gctcgtcctc aatccgtccg ttgccgctac cttagggttt
1981 ggggcgtata tgtctaaggc acacggtatt gaccccaaca tcagaactgg ggtaaggacc
2041 attaccacag gcgcccccgt cacatactct acctatggca agtttcttgc cgatggtggt
2101 tgctctgggg gcgcttatga catcataata tgtgatgagt gccattcaac tgactcgact
2161 acaatcttgg gcatcggcac agtcctggac caagcggaga cggctggagc gcggcttgtc
2221 gtgctcgcca ccgctacgcc tccgggatcg gtcaccgtgc cacacccaaa catcgaggag
2281 gtggccctgt ctaatactgg agagatcccc ttctatggca aagccatccc cattgaagcc
2341 atcaggggg gaaggcatct cattttctgt cattccaaga agaagtgcga cgagctcgcc
2401 gcaaagctgt caggcctcgg aatcaacgct gtggcgtatt accgggggct cgatgtgtcc
2461 gtcataccaa ctatcggaga cgtcgttgtc gtggcaacag acgctctgat gacgggctat
2521 acgggcgact ttgactcagt gatcgactgt aacacatgtg tcacccagac agtcgacttc
2581 agcttggatc ccaccttcac cattgagacg acgaccgtgc ctcaagacgc agtgtcgcgc
2641 tcgcagcggc ggggtaggac tggcaggggt aggagaggca tctacaggtt tgtgactccg
2701 ggagaacggc cctcgggcat gttcgattcc tcggtcctgt gtgagtgcta tgacgcgggc
2761 tgtgcttggt acgagctcac ccccgccgag acctcggtta ggttgcgggc ctacctgaac
2821 acaccagggt tgcccgtttg ccaggaccac ctggagttct gggagagtgt cttcacaggc
2881 ctcacccaca tagatgcaca cttcttgtcc cagaccaagc aggcaggaga caacttcccc
2941 tacctggtag cataccaagc cacggtgtgc gccagggctc aggccccacc tccatcatgg
3001 gatcaaatgt ggaagtgtct catacggctg aaacctacgc tgcacgggcc aacacccttg
3061 ctgtacaggc tgggagccgt ccaaaatgag gtcacccctca cccacccat aaccaaatac
3121 atcatggcat gcatgtcggc tgacctggag gtcgtcacta gcacctgggt gctggtgggc
3181 ggagtccttg cagctctggc cgcgtattgc ctgacaacag gcagtgtggt cattgtgggt
3241 aggattatct tgtccgggag gccggctatt gttcccgaca gggagttct ctaccaggag
```

FIG. 4B

```
3361  gccgagcaat  tcaagcagaa  agcgctcggg  ttactgcaaa  cagccaccaa  acaagcggag
3421  gctgctgctc  ccgtggtgga  gtccaagtgg  cgagcccttg  agacattctg  ggcgaagcac
3481  atgtggaatt  tcatcagcgg  gatacagtac  ttagcaggct  tatccactct  gcctgggaac
3541  cccgcaatag  catcattgat  ggcattcaca  gcctctatca  ccagcccgct  caccacccaa
3601  agtaccctcc  tgtttaacat  cttgggggggg  tgggtggctg  cccaactcgc  ccccccagc
3661  gccgcttcgg  ctttcgtggg  cgccggcatc  gccggtgcgg  ctgttggcag  cataggcctt
3721  gggaaggtgc  ttgtggacat  tctggcgggt  tatggagcag  gagtggccgg  cgcgctcgtg
3781  gccttcaagg  tcatgagcgg  cgagatgccc  tccaccgagg  acctggtcaa  tctacttcct
3841  gccatcctct  ctcctggcgc  cctggtcgtc  ggggtcgtgt  gtgcagcaat  actgcgtcga
3901  cacgtgggtc  cgggagaggg  ggctgtgcag  tggatgaacc  ggctgatagc  gttcgcctcg
3961  cggggtaatc  atgtttcccc  cacgcactat  gtgcctgaga  gcgacgccgc  agcgcgtgtt
4021  actcagatcc  tctccagcct  taccatcact  cagctgctga  aaaggctcca  ccagtggatt
4081  aatgaagact  gctccacacc  gtgttccggc  tcgtggctaa  gggatgtttg  ggactggata
4141  tgcacggtgt  tgactgactt  caagacctgg  ctccagtcca  agctcctgcc  gcagctaccg
4201  ggagtccctt  ttttctcgtg  ccaacgcggg  tacaagggag  tctggcgggg  agacggcatc
4261  atgcaaacca  cctgcccatg  tggagcacag  atcaccggac  atgtcaaaaa  cggttccatg
4321  aggatcgtcg  ggcctaagac  ctgcagcaac  acgtggcatg  gaacattccc  catcaacgca
4381  tacaccacgg  gccctgcac   accctctcca  gcgccaaact  attctagggc  gctgtggcgg
4441  gtggccgctg  aggagtacgt  ggaggtcacg  cgggtggggg  atttccacta  cgtgacgggc
4501  atgaccactg  acaacgtaaa  gtgcccatgc  caggttccgg  ctcctgaatt  cttcacggag
4561  gtggacggag  tgcggttgca  caggtacgct  ccggcgtgca  ggcctctcct  acggaggag
4621  gttacattcc  aggtcgggct  caaccaatac  ctggttgggt  cacagctacc  atgcgagccc
4681  gaaccggatg  tagcagtgct  cacttccatg  ctcaccgacc  cctcccacat  cacagcagaa
4741  acggctaagc  gtaggttggc  caggggggtct  ccccctcct  tggccagctc  ttcagctagc
4801  cagttgtctg  cgccttcctt  gaaggcgaca  tgcactaccc  accatgtctc  tccggacgct
4861  gacctcatcg  aggccaacct  cctgtggcgg  caggagatgg  gcgggaacat  cacccgcgtg
4921  gagtcggaga  acaaggtggt  agtcctggac  tctttcgacc  cgcttcgagc  ggaggaggat
4981  gagagggaag  tatccgttcc  ggcggagatc  ctgcggaaat  ccaagaagtt  ccccgcagcg
5041  atgcccatct  gggcgcgccc  ggattacaac  cctccactgt  tagagtcctg  gaaggacccg
5101  gactacgtcc  ctccggtggt  gcacgggtgc  ccgttccac   ctatcaaggc  cctccaata
5161  ccacctccac  ggagaaagag  gacggttgtc  ctaacagagt  cctccgtgtc  ttctgcctta
5221  gcggagctcg  ctactaagac  cttcggcagc  tccgaatcat  cggccgtcga  cagcggcacg
5281  gcgaccgccc  ttcctgacca  ggcctccgac  gacggtgaca  aaggatccga  cgttgagtcg
5341  tactcctcca  tgccccccct  tgagggggaa  ccggggggacc  ccgatctcag  tgacgggtct
5401  tggtctaccg  tgagcgagga  agctagtgag  gatgtcgtct  gctgctcaat  gtcctacaca
5461  tggacaggcg  ccttgatcac  gccatgcgct  gcggaggaaa  gcaagctgcc  catcaacgcg
5521  ttgagcaact  ctttgctgcg  ccaccataac  atggtttatg  ccacaacatc  tcgcagcgca
5581  ggcctgcggc  agaagaaggt  cacctttgac  agactgcaag  tcctggacga  ccactaccgg
5641  gacgtgctca  aggagatgaa  ggcgaaggcg  tccacagtta  aggctaaact  cctatccgta
5701  gaggaagcct  gcaagctgac  gccccacat   tcggccaaat  ccaagtttgg  ctatggggca
5761  aaggacgtcc  ggaacctatc  cagcaaggcc  gttaaccaca  tccactccgt  gtggaaggac
5821  ttgctggaag  acactgtgac  accaattgac  accaccatca  tggcaaaaaa  tgaggttttc
5881  tgtgtccaac  cagagaaagg  aggccgtaag  ccagcccgcc  ttatcgtatt  cccagatctg
5941  ggagtccgtg  tatgcgagaa  gatggccctc  tatgatgtgg  tctccaccct  tcctcaggtc
6001  gtgatggct   cctcatacgg  attccagtac  tctcctgggc  agcgagtcga  gttcctggtg
6061  aatacctgga  atcaaagaa   aaaccccatg  gcttttcat   atgacactcg  ctgtttcgac
6121  tcaacggtca  ccgagaacga  catccgtgtt  gaggagtcaa  tttaccaatg  ttgtgacttg
6181  gcccccgaag  ccagacaggc  cataaaatcg  ctcacagagc  ggctttatat  cggggggtcct
6241  ctgactaatt  caaaagggca  gaactgcggt  tatcgccggt  gccgcgcgag  cggcgtgctg
6301  acgactagct  gcggtaacac  cctcacatgt  tacttgaagg  cctctgcagc  ctgtcgagct
6361  gcgaagctcc  aggactgcac  gatgctcgtg  aacgccgccg  gccttgtcgt  tatctgtgaa
6421  agcgcgggaa  cccaagagga  cgcggcgagc  ctacgagtct  tcacggaggc  tatgactagg
6481  tactctgccc  ccccgggga   cccgcccaa   ccagaatacg  acttggagct  gataacatca
6541  tgttcctcca  atgtgtcggt  cgcccacgat  gcatcaggca  aagggtgta   ctacctcacc
6601  cgtgatccca  ccaccccccct  cgcacgggct  gcgtgggaaa  cagctagaca  cactccagtt
```

FIG. 4C

```
6661 aactcctggc taggcaacat tatcatgtat gcgcccactt tgtgggcaag gatgattctg
6721 atgactcact tcttctccat ccttctagca caggagcaac ttgaaaaagc cctggactgc
6781 cagatctacg ggcctgtta ctccattgag ccacttgacc tacctcagat cattgaacga
6841 ctccatggcc ttagcgcatt ttcactccat agttactctc caggtgagat caatagggtg
6901 gcttcatgcc tcaggaaact ggggtacca cccttgcgag tctggagaca tcgggccagg
6961 agcgtccgcg ctaggctact gtcccagggg gggagggccg ccacttgtgg caagtacctc
7021 ttcaactggg cagtgaagac caaactcaaa ctcactccaa tcccggctgc gtcccagctg
7081 gacttgtccg gctggttcgt tgctggttac agcggggag acatatatca cagcctgtct
7141 cgtgcccgac cccgctggtt catgctgtgc ctactcctac tttctgtagg ggtaggcatc
7201 tacctgctcc ccaaccggta aatctagagc tgtgccttct agttgccagc catctgttgt
7261 ttgcccctcc ccgtgccttt ccttgaccct ggaaggtgcc actcccactg tcctttccta
7321 ataaaatgag gaaattgcat cgcattgtct gagtaggtgt cattctattc tggggggtgg
7381 ggtggggcag gacagcaagg gggaggattg gaagacaat agcaggcatg ctggggatgc
7441 ggtgggctct atggccgatc ggcgcgccgt actgaaatgt gtgggcgtgg cttaagggtg
7501 ggaaagaata tataaggtgg gggtcttatg tagttttgta tctgttttgc agcagccgcc
7561 gccgccatga gcaccaactc gtttgatgga agcattgtga gctcatattt gacaacgcgc
7621 atgccccat gggccggggt gcgtcagaat gtgatgggct ccagcattga tggtcgcccc
7681 gtcctgcccg caaactctac taccttgacc tacgagaccg tgtctggaac gccgttggag
7741 actgcagcct ccgccgccgc ttcagccgct gcagccaccg cccgcgggat tgtgactgac
7801 tttgcttttcc tgagcccgct tgcaagcagt gcagcttccc gttcatccgc ccgcgatgac
7861 aagttgacgg ctctttttggc acaattggat tctttgaccc gggaacttaa tgtcgtttct
7921 cagcagctgt tggatctgcg ccagcaggtt tctgccctga aggcttcctc ccctcccaat
7981 gcggtttaaa acataaataa aaaaccagac tctgtttgga tttggatcaa gcaagtgtct
8041 tgctgtcttt atttaggggt tttgcgcgcg cggtaggccc gggaccagcg gtctcggtcg
8101 ttgagggtcc tgtgtatttt ttccaggacg tggtaaaggt gactctggat gttcagatac
8161 atgggcataa gcccgtctct ggggtggagg tagcaccact gcagagcttc atgctgcggg
8221 gtggtgttgt agatgatcca gtcgtagcag gagcgctggg cgtggtgcct aaaaatgtct
8281 ttcagtagca agctgattgc caggggcagg cccttggtgt aagtgtttac aaagcggtta
8341 agctgggatg ggtgcatacg tggggatatg agatgcatct tggactgtat ttttaggttg
8401 gctatgttcc cagccatatc cctccgggga ttcatgttgt gcagaaccac cagcacagtg
8461 tatccggtgc acttgggaaa tttgtcatgt agcttagaag gaatgcgtg gaagaacttg
8521 gagacgccct tgtgacctcc aagattttcc atgcattcgt ccataatgat ggcaatgggc
8581 ccacgggcgg cggcctgggc gaagatattt ctgggatcac taacgtcata gttgtgttcc
8641 aggatgagat cgtcataggc cattttaca aagcgcgggc ggagggtgcc agactgcggt
8701 ataatggttc catccggccc aggggcgtag ttaccctcac agatttgcat ttcccacgct
8761 ttgagttcag atggggggat catgtctacc tgcggggcga tgaagaaaac ggtttcgggg
8821 gtaggggaga tcagctggga agaaagcagg ttcctgagca gctgcgactt accgcagccg
8881 gtgggcccgt aaatcacacc tattaccggc tgcaactggt agttaagaga gctgcagctg
8941 ccgtcatccc tgagcagggg ggccacttcg ttaagcatgt ccctgactcg catgttttcc
9001 ctgaccaaat ccgccagaag gcgctcgccg cccagcgata gcagttcttg caaggaagca
9061 aagttttca acggtttgag accgtccgcc gtaggcatgc ttttgagcgt ttgaccaagc
9121 agttccaggc ggtcccacag ctcggtcacc tgctctacgg catctcgatc cagcatatct
9181 cctcgtttcg cggggttgggg cggctttcgc tgtacggcag tagtcggtgc tcgtccagac
9241 gggccagggt catgtctttc cacgggcgca gggtcctcgt cagcgtagtc tgggtcacgg
9301 tgaagggtg cgctccgggc tgcgcgctgg ccagggtgcg cttgaggctg gtcctgctgg
9361 tgctgaagcg ctgccggtct tcgccctgcg cgtcggccag gtagcatttg accatggtgt
9421 catagtccag cccctccgcg gcgtggccct tggcgcgcag cttgcccttg gaggaggcgc
9481 cgcacgaggg gcagtgcaga ctttttgaggg cgtagagctt gggcgcgaga ataccgatt
9541 ccggggagta ggcatccgcg ccgcaggccc gcagacggt ctcgcattcc acgagccagg
9601 tgagctctgg ccgttcgggg tcaaaaacca ggtttccccc atgcttttg atgcgtttct
9661 tacctctggt ttccatgagc cggtgtccac gctcggtgac gaaaaggctg tccgtgtccc
9721 cgtatacaga cttgagaggc ctgtcctcga gcggtgttcc gcggtcctcc tcgtatagaa
9781 actcggacca ctctgagacg aaggctgcg tccaggccag cacgaaggag gctaagtggg
9841 aggggtagcg gtcgttgtcc actaggggt ccactcgctc agggtgtga agacacatgt
9901 cgccctcttc ggcatcaagg aaggtgattg gtttataggt gtaggccacg tgaccgggtg
```

FIG. 4D

```
 9961 ttcctgaagg ggggctataa aaggggggtgg gggcgcgttc gtcctcactc tcttccgcat
10021 cgctgtctgc gagggccagc tgttggggtg agtactccct ctcaaaagcg ggcatgactt
10081 ctgcgctaag attgtcagtt tccaaaaacg aggaggattt gatattcacc tggcccgcgg
10141 tgatgccttt gagggtggcc gcgtccatct ggtcagaaaa gacaatcttt ttgttgtcaa
10201 gcttggtggc aaacgacccg tagagggcgt tggacagcaa cttggcgatg gagcgcaggg
10261 tttggttttt gtcgcgatcg gcgcgctcct tggccgcgat gtttagctgc acgtattcgc
10321 gcgcaacgca ccgccattcg ggaaagacgg tggtgcgctc gtcgggcact aggtgcacgc
10381 gccaaccgcg gttgtgcagg gtgacaaggt caacgctggt ggctacctct ccgcgtaggc
10441 gctcgttggt ccagcagagg cggccgccct tgcgcgagca gaatggcggt agtgggtcta
10501 gctgcgtctc gtccgggggg tctgcgtcca cggtaaagac cccgggcagc aggcgcgcgt
10561 cgaagtagtc tatcttgcat ccttgcaagt ctagcgcctg ctgccatgcg cgggcggcaa
10621 gcgcgcgctc gtatgggttg agtgggggac cccatggcat ggggtgggtg agcgcggagg
10681 cgtacatgcc gcaaatgtcg taaacgtaga ggggctctct gagtattcca agatatgtag
10741 ggtagcatct tccaccgcgg atgctggcgc gcacgtaatc gtatagttcg tgcgagggag
10801 cgaggaggtc gggaccgagg ttgctacggg cgggctgctc tgctcggaag actatctgcc
10861 tgaagatggc atgtgagttg gatgatatgg ttggacgctg gaagacgttg aagctggcgt
10921 ctgtgagacc taccgcgtca cgcacgaagg aggcgtagga gtcgcgcagc ttgttgacca
10981 gctcggcggt gacctgcacg tctagggcgc agtagtccag ggtttccttg atgatgtcat
11041 acttatcctg tccctttttt ttccacagct cgcggttgag gacaaactct tcgcggtctt
11101 tccagtactc ttggatcgga aacccgtcgg cctccgaacg gtaagagcct agcatgtaga
11161 actggttgac ggcctggtag gcgcagcatc ccttttctac gggtagcgcg tatgcctgcg
11221 cggccttccg gagcgaggtg tgggtgagcg caaaggtgtc cctaaccatg actttgaggt
11281 actggtattt gaagtcagtg tcgtcgcatc cgccctgctc ccagagcaaa aagtccgtgc
11341 gcttttttgga acgcgggttt ggcagggcga aggtgacatc gttgaagagt atctttcccg
11401 cgcgaggcat aaagttgcgt gtgatgcgga agggtcccgg cacctcggaa cggttgttaa
11461 ttacctgggc ggcgagcacg atctcgtcaa agccgttgat gttgtggccc acaatgtaaa
11521 gttccaagaa gcgcgggatg cccttgatgg aaggcaattt tttaagttcc tcgtaggtga
11581 gctcttcagg ggagctgagc ccgtgctctg aaagggccca gtctgcaaga tgagggttgg
11641 aagcgacgaa tgagctccac aggtcacggg ccattagcat ttgcaggtgg tcgcgaaagg
11701 tcctaaactg gcgacctatg gccattttttt ctggggtgat gcagtagaag gtaagcgggt
11761 cttgttccca gcggtcccat ccaaggtccg cggctaggtc tcgcgcggcg gtcactagag
11821 gctcatctcc gccgaacttc atgaccagca tgaagggcac gagctgcttc ccaaaggccc
11881 ccatccaagt ataggtctct acatcgtagg tgacaaagag acgctcggtg cgaggatgcg
11941 agccgatcgg gaagaactgg atctcccgcc accagttgga ggagtggctg ttgatgtggt
12001 gaaagtagaa gtccctgcga cgggccgaac actcgtgctg gcttttgtaa aaacgtgcgc
12061 agtactggca gcggtgcacg ggctgtacat cctgacgag gttgacctga cgaccgcgca
12121 caaggaagca gagtgggaat ttgagcccct cgcctggcgg gttttggctgg tggtcttcta
12181 cttcggctgc ttgtccttga ccgtctggct gctcgagggg agttacggtg gatcggacca
12241 ccacgccgcg cgagcccaaa gtccagatgt ccgcgcgcgg cggtcggagc ttgatgacaa
12301 catcgcgcag atgggagctg tccatggtct ggagctcccg cggcgtcagg tcaggcggga
12361 gctcctgcag gtttacctcg catagccggg tcagggcgcg ggctaggtcc aggtgatacc
12421 tgatttccag gggctggttg gtggcggcgt cgatggcttg caagaggccg catccccgcg
12481 gcgcgactac ggtaccgccg ggcggccgg gggccgcggg ggtgtccttg gatgatgcat
12541 ctaaaagcgg tgacgcgggc gggccccgg aggtaggggg ggctcgggac ccgccgggag
12601 aggggggcagg ggcacgtcgg cgccgcgcgc gggcaggagc tggtgctgcg cgcggaggtt
12661 gctggcgaac gcgacgacgc ggcggttgat ctcctgaatc tggcgcctct gcgtgaagac
12721 gacgggcccg gtgagcttga acctgaaaga gagttcgaca gaatcaattt cggtgtcgtt
12781 gacggcggcc tggcgcaaaa tctcctgcac gtctcctgag ttgtcttgat aggcgatctc
12841 ggccatgaac tgctcgatct cttcctcctg gagatctccg cgtccggctc gctccacggt
12901 ggcggcgagg tcgttggaga tgcgggccat gagctgcgag aaggcgttga ggcctccctc
12961 gttccagacg cggctgtaga ccacgccccc ttcggcatcg cgggcgcgca tgaccacctg
13021 cgcgagattg agctccacgt gccgggcgaa gacggcgtag tttcgcaggc gctgaaagag
13081 gtagttgagg gtggtggcgg tgtgttctgc cacgaagaag tacataaccc agcgccgcaa
13141 cgtggattcg ttgatatccc ccaaggcctc aaggcgctcc atggcctcgt agaagtccac
13201 ggcgaagttg aaaaactggg agttgcgcgc cgacacggtt aactcctcct ccagaagacg
```

FIG. 4E

```
13261 gatgagctcg gcgacagtgt cgcgcacctc gcgctcaaag gctacagggg cctcttcttc
13321 ttcttcaatc tcctcttcca taagggcctc cccttcttct tcttctggcg gcggtggggg
13381 aggggggaca cggcggcgac gacggcgcac cgggaggcgg tcgacaaagc gctcgatcat
13441 ctccccgcgg cgacggcgca tggtctcggt gacggcgcgg ccgttctcgc ggggcgcag
13501 ttggaagacg ccgccgtca tgtcccggtt atgggttggc gggggctgc cgtgcggcag
13561 ggatacggcg ctaacgatgc atctcaacaa ttgttgtgta ggtactccgc caccgaggga
13621 cctgagcgag tccgcatcga ccggatcgga aaacctctcg agaaaggcgt ctaaccagtc
13681 acagtcgcaa ggtaggctga gcaccgtggc gggcggcagc gggcggcggt cggggttgtt
13741 tctggcggag gtgctgctga tgatgtaatt aaagtaggcg gtcttgagac ggcggatggt
13801 cgacagaagc accatgtcct tgggtccggc ctgctgaatg cgcaggcggt cggccatgcc
13861 ccaggcttcg ttttgacatc ggcgcaggtc tttgtagtag tcttgcatga gcctttctac
13921 cggcacttct tcttctcctt cctcttgtcc tgcatctctt gcatctatcg ctgcggcggc
13981 ggcggagttt ggccgtaggt ggcgccctct tcctcccatg cgtgtgaccc cgaagcccct
14041 catcggctga agcagggcca ggtcggcgac aacgcgctcg gctaatatgg cctgctgcac
14101 ctgcgtgagg gtagactgga agtcgtccat gtccacaaag cggtggtatg cgcccgtgtt
14161 gatggtgtaa gtgcagttgg ccataacgga ccagttaacg gtctggtgac ccggctgcga
14221 gagctcggtg tacctgagac gcgagtaagc ccttgagtca aagacgtagt cgttgcaagt
14281 ccgcaccagg tactggtatc ccaccaaaaa gtgcggcggc ggctggcggt agaggggcca
14341 gcgtagggtg gccggggctc cgggggcgag gtcttccaac ataaggcgat gatatccgta
14401 gatgtacctg gacatccagg tgatgccggc ggcggtggtg gaggcgcgcg gaaagtcacg
14461 gacgcggttc cagatgttgc gcagcggcaa aaagtgctcc atggtcggga cgctctggcc
14521 ggtcaggcgc gcgcagtcgt tgacgctcta gaccgtgcaa aaggagagcc tgtaagcggg
14581 cactcttccg tggtctggtg gataaattcg caagggtatc atggcggacg accggggttc
14641 gaaccccgga tccggccgtc cgccgtgatc catgcggtta ccgcccgcgt gtcgaaccca
14701 ggtgtgcgac gtcagacaac gggggagcgc tccttttggc ttccttccag gcgcggcgga
14761 tgctgcgcta gcttttttgg ccactggccg cgcgcggcgt aagcggttag gctggaaagc
14821 gaaagcatta agtggctcgc tccctgtagc cggagggtta ttttccaagg gttgagtcgc
14881 gggaccccg gttcgagtct cgggccggcc ggactgcggc aacggggt ttgcctcccc
14941 gtcatgcaag accccgcttg caaattcctc cggaaacagg gacgagcccc ttttttgctt
15001 ttcccagatg catccggtgc tgcggcagat gcgccccct cctcagcagc ggcaagagca
15061 agagcagcgg cagacatgca gggcaccctc cccttctcct accgcgtcag gaggggcaac
15121 atccgcggct gacgcggcgg cagatggtga ttacgaaccc ccgcggcgcc ggacccggca
15181 ctacttggac ttggaggagg gcgagggcct ggcgcggcta ggagcgccct ctcctgagcg
15241 acacccaagg gtgcagctga agcgtgacac gcgcgaggcg tacgtgccgc ggcagaacct
15301 gtttcgcgac cgcgagggag aggagcccga ggagatgcgg gatcgaaagt tccatgcagg
15361 gcgcgagttg cggcatggcc tgaaccgcga gcggttgctg cgcgaggagg actttgagcc
15421 cgacgcgcgg accgggatta gtcccgcgcg cgcacgtg gcggccgcg acctggtaac
15481 cgcgtacgag cagacggtga accaggagat taactttcaa aaaagcttta caaccacgt
15541 gcgcacgctt gtggcgcgcg aggaggtggc tataggactg atgcatctgt gggactttgt
15601 aagcgcgctg gagcaaaacc caaatagcaa gccgctcatg gcgcagctgt tccttatagt
15661 gcagcacagc agggacaacg aggcattcag ggatgcgctg ctaaacatag tagagcccga
15721 gggccgctgg ctgctcgatt tgataaacat tctgcagagc atagtggtgc aggagcgcag
15781 cttgagcctg gctgacaagg tggccgccat taactattcc atgctcagtc tgggcaagtt
15841 ttacgcccgc aagatatacc ataccccctta cgttcccata gacaaggagg taaagatcga
15901 ggggttctac atgcgcatgg cgctgaaggt gcttaccttg agcgacgacc tgggcgttta
15961 tcgcaacgag cgcatccaca aggccgtgag cgtgagccgg cggcgcgagc tcagcgaccg
16021 cgagctgatg cacagcctgc aaagggccct ggctggcacg ggcagcggcg atagagaggc
16081 cgagtcctac tttgacgcgg gcgctgacct cgctgggcc caagccgac gcgccctgga
16141 ggcagctggg gccggacctg ggctggcggt ggcacccgcg cgcgctggca acgtcggcgg
16201 cgtggaggaa tatgacgagg acgatgagta cgagccagag gacggcgagt actaagcggt
16261 gatgtttctg atcagatgat gcaagacgca acggacccgg cggtgcgggc ggcgctgcag
16321 agccagccgt ccggccttaa ctccacggac gactggcgcc aggtcatgga ccgcatcatg
16381 tcgctgactg cgcgcaaccc tgacgcgttc cggcagcagc gcaggccaa ccggctctcc
16441 gcaattctgg aagcggtggt cccggcgcgc gcaaaccca cgcacgagaa ggtgctggcg
16501 atcgtaaacg cgctggccga aaacagggcc atccggcccg atgaggccgg cctggtctac
```

FIG. 4F

```
16561 gacgcgctgc ttcagcgcgt ggctcgttac aacagcagca acgtgcagac caacctggac
16621 cggctggtgg gggatgtgcg cgaggccgtg gcgcagcgtg agcgcgcgca gcagcagggc
16681 aacctgggct ccatggttgc actaaacgcc ttcctgagta cacagcccgc caacgtgccg
16741 cggggacagg aggactacac caactttgtg agcgcactgc ggctaatggt gactgagaca
16801 ccgcaaagtg aggtgtatca gtccgggcca gactattttt tccagaccag tagacaaggc
16861 ctgcagaccg taaacctgag ccaggctttc aagaacttgc aggggctgtg ggggggtgcgg
16921 gctcccacag gcgaccgcgc gaccgtgtct agcttgctga cgcccaactc gcgcctgttg
16981 ctgctgctaa tagcgcccctt cacggacagt ggcagcgtgt cccgggacac atacctaggt
17041 cacttgctga cactgtaccg cgaggccata ggtcaggcgc atgtggacga gcatactttc
17101 caggagatta caagtgttag ccgcgcgctg gggcaggagg acacgggcag cctggaggca
17161 accctgaact acctgctgac caaccggcgg caaaaaatcc cctcgttgca cagtttaaac
17221 agcgaggagg agcgcatttt gcgctatgtg cagcagagcg tgagccttaa cctgatgcgc
17281 gacggggtaa cgcccagcgt ggcgctggac atgaccgcgc gcaacatgga accgggcatg
17341 tatgcctcaa accggccgtt tatcaatcgc ctaatggact acttgcatcg cgcggccgcc
17401 gtgaaccccg agtatttcac caatgccatc ttgaacccgc actggctacc gccccctggt
17461 ttctacaccg ggggattcga ggtgcccgag ggtaacgatg gattcctctg ggacgacata
17521 gacgacagcg tgttttcccc gcaaccgcag accctgctag agttgcaaca acgcgagcag
17581 gcagaggcgg cgctgcgaaa ggaaagcttc gcaggccaa gcagcttgtc cgatctaggc
17641 gctgcggccc cgcggtcaga tgctagtagc ccatttccaa gcttgatagg gtctcttacc
17701 agcactcgca ccacccgccc gcgcctgctg ggcgaggagg agtacctaaa caactcgctg
17761 ctgcagccgc agcgcgaaaa gaacctgcct ccggcgtttc caacaacgg gatagagagc
17821 ctagtggaca agatgagtag atggaagacg tatgcgcagg agcacaggga tgtgcccggc
17881 ccgcgcccgc ccacccgtcg tcaaaggcac gaccgtcagc ggggtctggt gtgggaggac
17941 gatgactcgg cagacgacag cagcgtcttg gatttgggag ggagtggcaa cccgtttgca
18001 caccttcgcc ccaggctggg gagaatgttt taaaaaaaag catgatgcaa aataaaaaac
18061 tcaccaaggc catggcaccg agcgttggtt ttcttgtatt cccccttagta tgcggcgcgc
18121 ggcgatgtat gaggaaggtc ctcctccctc ctacgagagc gtggtgagcg cggcgccagt
18181 ggcggcggcg ctgggttcac ccttcgatgc tccctggac ccgccgttcg tgcctccgcg
18241 gtacctgcgg cctaccgggg ggagaaacag catccgttac tctgagttgg caccctatt
18301 cgacaccacc cgtgtgtacc ttgtggacaa caagtcaacg gatgtggcat ccctgaacta
18361 ccagaacgac cacagcaact ttctaaccac ggtcattcaa aacaatgact acagcccggg
18421 ggaggcaagc acacagacca tcaatcttga cgaccggtcg cactggggcg gcgacctgaa
18481 aaccatcctg cataccaaca tgccaaatgt gaacgagttc atgtttacca ataagtttaa
18541 ggcgcgggtg atggtgtcgc gctcgcttac taaggacaaa caggtggagc tgaaatacga
18601 gtgggtggag ttcacgctgc ccgagggcaa ctactccgag accatgacca tagaccttat
18661 gaacaacgcg atcgtggagc actacttgaa agtgggcagg cagaacgggg ttctggaaag
18721 cgacatcggg gtaaagtttg acacccgcaa cttcagactg gggtttgacc cagtcactgg
18781 tcttgtcatg cctgggggtat atacaaacga agccttccat ccagacatca ttttgctgcc
18841 aggatgcggg gtggacttca cccacagccg cctgagcaac ttgttgggca tccgcaagcg
18901 gcaacccttc caggagggct ttaggatcac ctacgatgac ctggagggtg gtaacattcc
18961 cgcactgttg gatgtggacg cctaccaggc aagcttgaaa gatgacaccg aacagggcgg
19021 gggtggcgca ggcggcggca acaacagtgg cagcggcgcg aagagaact ccaacgcggc
19081 agctgcggca atgcagccgg tggaggacat gaacgatcat gccattgcg gcgacacctt
19141 tgccacacgg gcggaggaga agcgcgctga ggccgaggca gcggccgaag ctgccgcccc
19201 cgctgcggag gctgcacaac ccgaggtcga aagcctcag aagaaaccgg tgattaaacc
19261 cctgacagag gacagcaaga acgcagtta aacctaata agcaatgaca gcaccttcac
19321 ccagtaccgc agctggtacc ttgcatacaa ctacggcgac cctcaggccg ggatccgctc
19381 atggaccctg ctttgcactc ctgacgtaac ctgcggctcg gagcaggtat actggtcgtt
19441 gcccgacatg atgcaagacc ccgtgacctt ccgctccacg cgccagatca gcaactttcc
19501 ggtggtgggc gccgagctgt gcccgtgca ctccaagagc ttctacaacg accaggccgt
19561 ctactcccag ctcatccgcc agtttacctc tctgacccac gtgttcaatc gctttcccga
19621 gaaccagatt ttggcgcgcc cgccagcccc caccatcacc accgtcagtg aaaacgttcc
19681 tgctctcaca gatcacggga cgctaccgct gcgcaacagc atcggaggag tccagcgagt
19741 gaccattact gacgccagac gccgcacctg ccctacgtt tacaaggccc tgggcatagt
19801 ctcgccgcgc gtcctatcga gccgcacttt ttgagcaagc atgtccatcc ttatatcgcc
```

FIG. 4G

```
19861 cagcaataac acaggctggg gcctgcgctt cccaagcaag atgtttggcg gggccaagaa
19921 gcgctccgac caacacccag tgcgcgtgcg cgggcactac cgcgcgccct ggggcgcgca
19981 caaacgcggc cgcactgggc gcaccaccgt cgatgacgcc atcgacgcgg tggtggagga
20041 ggcgcgcaac tacacgccca cgccgccgcc agtgtccacc gtggacgcgg ccattcagac
20101 cgtggtgcgc ggagcccggc gctacgctaa aatgaagaga cggcggaggc gcgtagcacg
20161 tcgccaccgc cgccgacccg gcactccgc ccaacgcgcg gcggcgccc tgcttaaccg
20221 cgcacgtcgc accggccgac gggcggccat gcgagccgct cgaaggctgg ccgcgggtat
20281 tgtcactgtg cccccaggt ccaggcgacg agcggccgcc gcagcagccg cggccattag
20341 tgctatgact cagggtcgca ggggcaacgt gtactgggtg cgcgactcgg ttagcggcct
20401 gcgcgtgccc gtgcgcaccc gcccccgcg caactagatt gcaataaaaa actacttaga
20461 ctcgtactgt tgtatgtatc cagcggcggc ggcgcgcatc gaagctatgt ccaagcgcaa
20521 aatcaaagaa gagatgctcc aggtcatcgc gccggagatc tatgcccccc cgaagaagga
20581 agagcaggat tacaagcccc gaaagctaaa gcgggtcaaa aagaaaaaga aagatgatga
20641 tgatgatgaa cttgacgacg aggtggaact gttgcacgcg accgcgccca ggcgacgggt
20701 acagtggaaa ggtcgacgcg taagacgtgt tttgcgaccc ggcaccaccg tagtctttac
20761 gcccggtgag cgctccaccc gcacctacaa gcgcgtgtat gatgaggtgt acggcgacga
20821 ggacctgctt gagcaggcca acgagcgcct cggggagttt gcctacggaa agcggcataa
20881 ggacatgctg gcgttccgc tggacgaggg caacccaaca cctagcctaa agcccgtgac
20941 actgcagcag gtgctgcccg cgcttgcacc gtccgaagaa aagcgcggcc taaagcgcga
21001 gtctggtgac ttggcaccca ccgtgcagct gatggtaccc aagcgtcagc gactggaaga
21061 tgtcttggaa aaaatgaccg tggagcctgg gctggagccc gaggtccgcg tgcggccaat
21121 caagcaggtg gcaccgggac tgggcgtgca gaccgtggac gttcagatac caccaccag
21181 tagcactagt attgccactg ccacagaggg catggagaca caaacgtccc cggttgcctc
21241 ggcggtggca gatgccgcgg tgcaggcggc cgctgcggcc gcgtccaaga cctctacgga
21301 ggtgcaaacg gacccgtgga tgtttcgtgt ttcagccccc cggcgtccgc gccgttcaag
21361 gaagtacggc gccgccagcg cgctactgcc cgaatatgcc ctacatcctt ccatcgcgcc
21421 taccccggc tatcgtggct acacctaccg cccagaagaa cgagcaacta cccgacgccg
21481 aaccaccact ggaacccgcc gccgccgtcg ccgtcgccag cccgtgctgg ccccgatttc
21541 cgtgcgcagg gtggctcgcg aaggaggcag gaccctggtg ctgccaacag cgcgctacca
21601 ccccagcatc gtttaaaagc cggtctttgt ggttcttgca gatatggccc tcacctgccg
21661 cctccgtttc ccggtgccgg gattccgagg aagaatgcac cgtaggaggg gcatggccgg
21721 ccacggcctg acgggcggca tgcgtcgtgc gcaccaccgg cggcggcgcg cgtcgcaccg
21781 tcgcatgcgc ggcggtatcc tgcccctcct tattccactg atcgccgcgg cgattggcgc
21841 cgtgcccgga attgcatccg tggccttgca ggcgcagaga cactgattaa aaacaagtta
21901 catgtggaaa aatcaaaata aaagtctgga ctctcacgct cgcttggtcc tgtaactatt
21961 ttgtagaatg aagacatca actttgcgtc actggccccg cgacacggct cgcgcccgtt
22021 catgggaaac tggcaagata tcggcaccag caatatgagc ggtggcgcct tcagctgggg
22081 ctcgctgtgg agcggcatta aaaatttcgg ttcgccgtt aagaactatg cagcaaagc
22141 ctggaacagc agcacaggcc agatgctgag ggacaagttg aaagagcaaa atttccaaca
22201 aaaggtggta gatggcctgg cctctggcat tagcggggtg gtggacctgg ccaaccaggc
22261 agtgcaaaat aagattaaca gtaagcttga tccccgccct cccgtagagg agcctccacc
22321 ggccgtggag acagtgtctc cagaggggcg tggcgaaaag cgtccgcgac ccgacaggga
22381 agaaactctg gtgacgcaaa tagacgagcc tccctcgtac gaggaggcac taaagcaagg
22441 cctgcccacc acccgtccca tcgcgcccat ggctaccgga gtgctgggcc agcacacacc
22501 cgtaacgctg gacctgcctc cccccgccga cacccagcag aaacctgtgc tgccaggcc
22561 gtccgccgtt gttgtaaccc gtcctagccg cgcgtccctg cgccgcgccg ccagcggtcc
22621 gcgatcgttg cggcccgtag ccagtggcaa ctggcaaagc acactgaaca gcatcgtggg
22681 tttggggtg caatccctga agcgccacg atgcttctga tagctaacgt gtcgtatgtg
22741 tgtcatgtat gcgtccatgt cgccgcaga ggagctgctg agccgccgcg cgccgcttt
22801 ccaagatggc taccccttcg atgatgccgc agtggtctta catgcacatc tcgggccagg
22861 acgcctcgga gtacctgagc cccgggctgg tgcagttcgc ccgcgccacc gagacgtact
22921 tcagcctgaa taacaagttt agaaacccca cggtggcgcc tacgcacgac gtgaccacag
22981 accggtctca gcgtttgacg ctgcggttca tccccgtgga ccgcgaggat actgcgtact
23041 cgtacaaggc gcggttcacc ctagctgtgg gtgataaccg tgtgctagac atggcttcca
23101 cgtactttga catccgcggc gtgctggaca ggggcctac ttttaagccc tactctggca
```

FIG. 4H

```
23161 ctgcctacaa cgcactggcc cccaagggtg cccccaactc gtgcgagtgg gaacaaaatg
23221 aaactgcaca agtggatgct caagaacttg acgaagagga gaatgaagcc aatgaagctc
23281 aggcgcgaga acaggaacaa gctaagaaaa cccatgtata tgcccaggct ccactgtccg
23341 gaataaaaat aactaaagaa ggtctacaaa taggaactgc cgacgccaca gtagcaggtg
23401 ccggcaaaga aattttcgca gacaaaactt ttcaacctga accacaagta ggagaatctc
23461 aatggaacga agcggatgcc acagcagctg gtggaagggt tcttaaaaag acaactccca
23521 tgaaaccctg ctatggctca tacgctagac ccaccaattc caacggcgga cagggcgtta
23581 tggttgaaca aaatggtaaa ttggaaagtc aagtcgaaat gcaattttt tccacatcca
23641 caaatgccac aaatgaagtt aacaatatac aaccaacagt tgtattgtac agcgaagatg
23701 taaacatgga aactccagat actcatcttt cttataaacc taaatgggg gataaaaatg
23761 ccaaagtcat gcttggacaa caagcaatgc caaacagacc aaattacatt gcttttagag
23821 acaattttat tggtctcatg tattacaaca gcacaggtaa catgggtgtc cttgctggtc
23881 aggcatcgca gttgaacgct gttgtagatt tgcaagacag aaacacagag ctgtcctacc
23941 agcttttgct tgattcaatt ggcgacagaa caagatactt ttcaatgtgg aatcaagctg
24001 ttgacagcta tgatccagat gtcagaatta ttgagaacca tggaactgag gatgagttgc
24061 caaattattg ctttcctctt ggtggaattg ggattactga cactttttca gctgttaaaa
24121 caactgctgc taacggggac caaggcaata ctacctggca aaaagattca acatttgcag
24181 aacgcaatga aataggggtg ggaaataact tgccatgga aattaacctg aatgccaacc
24241 tatggagaaa tttcctttac tccaatattg cgctgtacct gccagacaag ctaaaataca
24301 accccaccaa tgtggaaata tctgacaacc caacaccta cgactacatg aacaagcgag
24361 tggtggctcc tgggcttgta gactgctaca ttaaccttgg ggcgcgctgg tctctggact
24421 acatggacaa cgttaatccc tttaaccacc accgcaatgc gggcctgcgt taccgctcca
24481 tgttgttggg aaacggccgc tacgtgccct ttcacattca ggtgccccaa aagttttttg
24541 ccattaaaaa cctcctcctc ctgccaggct catacacata tgaatggaac ttcaggaagg
24601 atgttaacat ggttctgcag agctctctgg gaaacgacct tagagttgac ggggctagca
24661 ttaagtttga cagcatttgt ctttacgcca ccttcttccc catggcccac aacacggcct
24721 ccacgctgga agccatgctc agaaatgaca ccaacgacca gtcctttaat gactaccttt
24781 ccgccgccaa catgctatat cccataccg ccaacgccac caacgtgccc atctccatcc
24841 catcgcgcaa ctgggcagca tttcgcggtt gggccttcac acgcttgaag acaaaggaaa
24901 cccctccct gggatcaggc tacgaccctt actacaccta ctctggctcc ataccatacc
24961 ttgacggaac cttctatctt aatcacacct taagaaggt ggccattact tttgactctt
25021 ctgttagctg gccgggcaac gaccgcctgc ttactcccaa tgagtttgag attaagcgct
25081 cagttgacgg ggagggctat aacgtagctc agtgcaacat gacaaaggac tggttcctag
25141 tgcagatgtt ggccaactac aatattggct accagggctt ctacattcca gaaagctaca
25201 aagaccgcat gtactcgttc ttcagaaact tccagcccat gagccggcaa gtggtggacg
25261 atactaaata caaagattat cagcaggttg gaattatcca ccagcataac aactcaggct
25321 tcgtaggcta cctcgctccc accatgcgcg agggacaagc ttacccgct aatgttccct
25381 acccactaat aggcaaaacc gcggttgata gtattaccca gaaaaagttt ctttgcgacc
25441 gcaccctgtg gcgcatcccc ttctccagta actttatgtc catgggtgcg ctcacagacc
25501 tgggccaaaa ccttctctac gcaaactccg cccacgcgct agacatgacc tttgaggtgg
25561 atcccatgga cgagcccacc cttctttatg ttttgtttga agtctttgac gtggtccgtg
25621 tgcaccagcc gcaccgcggc gtcatcgaga ccgtgtacct gcgcacgccc ttctcggccg
25681 gcaacgccac aacataaaga agcaagcaac atcaacaaca gctgccgcca tgggctccag
25741 tgagcaggaa ctgaaagcca ttgtcaaaga tcttggttgt gggccatatt ttttgggcac
25801 ctatgacaag cgcttcccag gctttgtttc cccacacaag ctcgcctgcg ccatagttaa
25861 cacggccggt cgcgagactg ggggcgtaca ctggatggcc tttgcctgga cccgcgctc
25921 aaaaacatgc tacctctttg agccctttgg cttttctgac caacgtctca agcaggttta
25981 ccagtttgag tacgagtcac tcctgcgccg tagcgccatt gcctcttccc ccgaccgctg
26041 tataacgctg gaaaagtcca cccaaagcgt gcaggggccc aactcggccg cctgtggcct
26101 attctgctgc atgtttctcc acgcctttgc caactggccc caaactccca tggatcacaa
26161 ccccaccatg aaccttatta ccggggtacc caactccatg cttaacagtc ccaggtaca
26221 gcccaccctg cgccgcaacc aggaacagct ctacagcttc ctggagcgcc actcgcccta
26281 cttccgcagc cacagtgcgc aaattaggag cgccacttct ttttgtcact gaaaaacat
26341 gtaaaaataa tgtactagga gacactttca ataaaggcaa atgtttttat ttgtacactc
26401 tcgggtgatt atttacccc acccttgccg tctgcgccgt ttaaaaatca aaggggttct
```

FIG. 41

```
26461 gccgcgcatc gctatgcgcc actggcaggg acacgttgcg atactggtgt ttagtgctcc
26521 acttaaactc aggcacaacc atccgcggca gctcggtgaa gttttcactc cacaggctgc
26581 gcaccatcac caacgcgttt agcaggtcgg gcgccgatat cttgaagtcg cagttggggc
26641 ctccgccctg cgcgcgcgag ttgcgataca cagggttaca gcactggaac actatcagcg
26701 ccgggtggtg cacgctggcc agcacgctct tgtcggagat cagatccgcg tccaggtcct
26761 ccgcgttgct cagggcgaac ggagtcaact ttggtagctg ccttcccaaa aagggtgcat
26821 gcccaggctt tgagttgcac tcgcaccgta gtggcatcag aaggtgaccg tgcccagtct
26881 gggcgttagg atacagcgcc tgcatgaaag ccttgatctg cttaaaagcc acctgagcct
26941 ttgcgccttc agagaagaac atgccgcaag acttgccgga aaactgattg gccggacagg
27001 ccgcgtcatg cacgcagcac cttgcgtcgg tgttggagat ctgcaccaca tttcggcccc
27061 accggttctt cacgatcttg gccttgctag actgctcctt cagcgcgcgc tgcccgtttt
27121 cgctcgtcac atccatttca atcacgtgct ccttatttat cataatgctc ccgtgtagac
27181 acttaagctc gccttcgatc tcagcgcagc ggtgcagcca caacgcgcag cccgtgggct
27241 cgtggtgctt gtaggttacc tctgcaaacg actgcaggta cgcctgcagg aatcgcccca
27301 tcatcgtcac aaaggtcttg ttgctggtga aggtcagctg caacccgcgg tgctcctcgt
27361 ttagccaggt cttgcatacg gccgccagag cttccacttg gtcaggcagt agcttgaagt
27421 ttgcctttag atcgttatcc acgtggtact tgtccatcaa cgcgcgcgca gcctccatgc
27481 ccttctccca cgcagacacg atcggcaggc tcagcgggtt tatcaccgtg ctttcacttt
27541 ccgcttcact ggactcttcc ttttcctctt gcatccgcat accccgcgcc actgggtcgt
27601 cttcattcag ccgccgcacc gtgcgcttac ctcccttgcc gtgcttgatt agcaccggtg
27661 ggttgctgaa acccaccatt tgtagcgcca catcttctct ttcttcctcg ctgtccacga
27721 tcacctctgg ggatggcggg cgctcgggct tgggagaggg gcgcttcttt ttcttttgg
27781 acgcaatggc caaatccgcc gtcgaggtcg atggccgcgg gctgggtgtg cgcggcacca
27841 gcgcatcttg tgacgagtct tcttcgtcct cggactcgag acgccgcctc agccgctttt
27901 tggggggcgc gcggggaggc ggcggcgacg gcgacgggga cgagacgtcc tccatggttg
27961 gtggacgtcg cgccgcaccg cgtccgcgct cggggggtggt tcgcgctgc tcctcttccc
28021 gactggccat ttccttctcc tataggcaga aaagatcat ggagtcagtc gagaaggagg
28081 acagcctaac cgccccccttt gagttcgcca ccaccgcctc caccgatgcc gccaacgcgc
28141 ctaccacctt ccccgtcgag gcaccccgc ttgaggagga ggaagtgatt atcgagcagg
28201 acccaggttt tgtaagcgaa gacgacgaag atcgctcagt accaacagag gataaaaagc
28261 aagaccagga cgacgcagag gcaaacgagg aacaagtcgg gcgggggggac caaaggcatg
28321 gcgactacct agatgtggga gacgacgtgc tgttgaagca tctgcagcgc cagtgcgcca
28381 ttatctgcga cgcgttgcaa gagcgcagcg atgtgcccct cgccatagcg gatgtcagcc
28441 ttgcctacga acgccacctg ttctcaccgc gcgtaccccc caaacgccaa gaaaacggca
28501 catgcgagcc caacccgcgc ctcaacttct accccgtatt tgccgtgcca gaggtgcttg
28561 ccacctatca catcttttc caaaactgca agatacccct atcctgccgt gccaaccgca
28621 gccgagcgga caagcagctg gccttgcggc agggcgctgt catacctgat atcgcctcgc
28681 tcgacgaagt gccaaaaatc tttgagggtc ttggacgcga cgagaagcgc gcggcaaacg
28741 ctctgcaaca agaaaacagc gaaatgaaa gtcactgtgg agtgctggtg gaacttgagg
28801 gtgacaacgc gcgcctagcc gtgctgaaac gcagcatcga ggtcacccac tttgcctacc
28861 cggcacttaa cctacccccc aaggttatga gcacagtcat gagcgagctg atcgtgcgcc
28921 gtgcacgacc cctggagagg gatgcaaact tgcaagaaca aaccgaggag ggcctacccg
28981 cagttggcga tgagcagctg gcgcgctggc ttgagacgcg cgagcctgcc gacttggagg
29041 agcgacgcaa gctaatgatg ccgcagtgc ttgttaccgt ggagcttgag tgcatgcagc
29101 ggttctttgc tgacccggag atgcagcgca agctagagga aacgttgcac tacaccttc
29161 gccagggcta cgtgcgccag gcctgcaaaa tttccaacgt ggagctctgc aacctggtct
29221 cctaccttgg aattttgcac gaaaaccgcc ttgggcaaaa cgtgcttcat tccacgctca
29281 agggcgaggc gcgccgcgac tacgtccgcg actgcgttta cttattctg tgctacacct
29341 ggcaaacggc catgggcgtg tggcagcagt gcctggagga gcgcaacctg aaggagctgc
29401 agaagctgct aaagcaaaac ttgaaggacc tatgacggc cttcaacgag cgctccgtgg
29461 ccgcgcacct ggcggacatt atcttccccg aacgcctgct taaaccctg caacagggtc
29521 tgccagactt caccagtcaa agcatgttgc aaaactttag gaactttatc ctagagcgtt
29581 caggaattct gcccgccacc tgctgtgcgc ttcctagcga cttttgtgccc attaagtacc
29641 gtgaatgccc tccgccgctt tggggtcact gctaccttct gcagctagcc aactaccttg
29701 cctaccactc cgacatcatg gaagacgtga gcggtgacgg cctactggag tgtcactgtc
```

FIG. 4J

```
29761 gctgcaacct atgcacccag caccgctccc tggtctgcaa ttcacaactg cttagcgaaa
29821 gtcaaattat cggtacctt gagctgcagg gtccctcgcc tgacgaaaag tccgcggctc
29881 cggggttgaa actcactccg gggctgtgga cgtcggctta ccttcgcaaa tttgtacctg
29941 aggactacca cgcccacgag attaggttct acgaagacca atcccgcccg ccaaatgcgg
30001 agcttaccgc ctgcgtcatt acccagggcc acatccttgg ccaattgcaa gccattaaca
30061 aagcccgcca agagtttctg ctacgaaagg gacgggggt ttacttggac ccccagtccg
30121 gcgaggagct caacccaatc cccccgccgc cgcagcccta tcagcagccg cgggcccttg
30181 cttcccagga tggcacccaa aaagaagctg cagctgccgc cgccgccacc cacggacgag
30241 gaggaatact gggacagtca ggcagaggag gttttggacg aggaggagga gatgatggaa
30301 gactgggaca gcctagacga ggaagcttcc gaggccgaag aggtgtcaga cgaaacaccg
30361 tcaccctcgg tgcattccc ctcgccggcg ccccagaaat cggcaaccgt tccagcatt
30421 gctacaacct ccgctcctca ggcgccgccg gcactgcccg ttcgccgacc caaccgtaga
30481 tgggacacca ctggaaccag ggccggtaag tctaagcagc cgccgccgtt agcccaagag
30541 caacaacagc gccaaggcta ccgctcgtgg cgcgtgcaca agaacgccat agttgcttgc
30601 ttgcaagact gtgggggcaa catctccttc gcccgccgct tcttctcta ccatcacggc
30661 gtggccttcc cccgtaacat cctgcattac taccgtcatc tctacagccc ctactgcacc
30721 ggcggcagcg gcagcaacag cagcggccac gcagaagcaa aggcgaccgg atagcaagac
30781 tctgacaaag cccaagaaat ccacagcggc ggcagcagca ggaggaggag cactgcgtct
30841 ggcgcccaac gaacccgtat cgacccgcga gcttagaaac aggatttttc ccactctgta
30901 tgctatattt caacagagca ggggccaaga acaagagctg aaaataaaaa acaggtctct
30961 gcgctccctc acccgcagct gcctgtatca caaaagcgaa gatcagcttc ggcgcacgct
31021 ggaagacgcg gaggctctct tcagcaaata ctgcgcgctg actcttaagg actagtttcg
31081 cgccctttct caaatttaag cgcgaaaact acgtcatctc cagcggccac acccggcgcc
31141 agcacctgtc gtcagcgcca ttatgagcaa ggaaattccc acgccctaca tgtggagtta
31201 ccagccacaa atgggacttg cggctggagc tgcccaagac tactcaaccc gaataaacta
31261 catgagcgcg ggaccccaca tgatatcccg ggtcaacgga atccgcgccc accgaaaccg
31321 aattctcctc gaacaggcgg ctattaccac cacacctcgt aataacctta atccccgtag
31381 ttggcccgct gccctggtgt accaggaaag tcccgctccc accactgtgg tacttcccag
31441 agacgcccag gccgaagttc agatgactaa ctcaggggcg cagcttgcgg gcggctttcg
31501 tcacagggtg cggtcgcccg gcagggtat aactcacctg aaaatcagag ggcgaggtat
31561 tcagctcaac gacgagtcgg tgagctcctc tcttggtctc cgtccggacg ggacatttca
31621 gatcggcggc gctggccgct cttcatttac gccccgtcag gcgatcctaa ctctgcagac
31681 ctcgtcctcg gagccgcgct ccggaggcat tggaactcta caatttattg aggagttcgt
31741 gccttcggtt tacttcaacc ccttttctgg acctcccggc cactacccgg accagtttat
31801 tcccaacttt gacgcggtaa aagactcggc ggacggctac gactgaatga ccagtggaga
31861 ggcagagcaa ctgcgcctga cacacctcga ccactgccgc cgccacaagt gctttgcccg
31921 cggctccggt gagttttgtt actttgaatt gcccgaagag catatcgagg gcccggcgca
31981 cggcgtccgg ctcaccaccc aggtagagct tacacgtagc ctgattcggg agtttaccaa
32041 gcgcccctg ctagtggagc gggagcgggg tccctgtgtt ctgaccgtgg tttgcaactg
32101 tcctaaccct ggattacatc aagatcttat tccattcaac taacaataaa cacacaataa
32161 attacttact taaaatcagt cagcaaatct ttgtccagct tattcagcat cacctccttt
32221 ccctcctccc aactctggta tttcagcagc cttttagctg cgaactttct ccaaagtcta
32281 aatgggatgt caaattcctc atgttcttgt ccctccgcac ccactatctt catattgttg
32341 cagatgaaac gcgccagacc gtctgaagac accttcaacc ctgtgtaccc atatgacacg
32401 gaaaccggcc tccaactgt gcctttcctt acccctcct ttgtgtcgcc aaatgggttc
32461 caagaaagtc cccccggagt gctttctttg cgtctttcag aacctttggt tacctcacac
32521 ggcatgcttg cgctaaaaat gggcagcggc ctgtccctgg atcaggcagg caaccttaca
32581 tcaaatacaa tcactgtttc tcaaccgcta aaaaaacaa agtccaatat aactttggaa
32641 acatccgcgc cccttacagt cagctcaggc gccctaacca tggccacaac ttcgcctttg
32701 gtggtctctg acaacactct taccatgcaa tcacaagcac cgctaaccgt gcaagactca
32761 aaacttagca ttgctaccaa agagccactt acagtgttag atggaaaact ggccctgcag
32821 acatcagccc ccctctctgc cactgataac aacgccctca ctatcactgc tcacctcct
32881 cttactactg caaatggtag tctggctgtt accatggaaa acccacttta caacaacaat
32941 ggaaaacttg gctcaaaat tggcggtcct ttgcaagtgg ccaccgactc acatgcacta
33001 acactaggta ctggtcaggg ggttgcagtt cataacaatt tgctacatac aaaagttaca
```

FIG. 4K

```
33061 ggcgcaatag ggtttgatac atctggcaac atggaactta aaactggaga tggcctctat
33121 gtggatagcg ccggtcctaa ccaaaaacta catattaatc taaataccac aaaaggcctt
33181 gcttttgaca acaccgcaat aacaattaac gctggaaaag ggttggaatt tgaaacagac
33241 tcctcaaacg gaaatcccat aaaaacaaaa attggatcag gcatacaata taataccaat
33301 ggagctatgg ttgcaaaact tggaacaggc ctcagttttg acagctccgg agccataaca
33361 atgggcagca taaacaatga cagacttact ctttggacaa caccagaccc atccccaaat
33421 tgcagaattg cttcagataa agactgcaag ctaactctgg cgctaacaaa atgtggcagt
33481 caaattttgg gcactgtttc agctttggca gtatcaggta atatggcctc catcaatgga
33541 actctaagca gtgtaaactt ggttcttaga tttgatgaca acggagtgct tatgtcaaat
33601 tcatcactgg acaaacagta ttggaacttt agaaacgggg actccactaa cggtcaacca
33661 tacacttatg ctgttgggtt tatgccaaac ctaaaagctt acccaaaaac tcaaagtaaa
33721 actgcaaaaa gtaatattgt tagccaggtg tatcttaatg gtgacaagtc taaaccattg
33781 cattttacta ttacgctaaa tggaacagat gaaaccaacc aagtaagcaa atactcaata
33841 tcattcagtt ggtcctggaa cagtggacaa tacactaatg acaaatttgc caccaattcc
33901 tataccttct cctacattgc ccaggaataa agaatcgtga acctgttgca tgttatgttt
33961 caacgtgttt attttcaat tgcagaaaat ttcaagtcat tttcattca gtagtatagc
34021 cccaccacca catagcttat actaatcacc gtaccttaat caaactcaca gaaccctagt
34081 attcaacctg ccacctccct cccaacacac agagtacaca gtcctttctc cccggctggc
34141 cttaaacagc atcatatcat gggtaacaga catattctta ggtgttatat tccacacggt
34201 ctcctgtcga gccaaacgct catcagtgat gttaataaac tccccgggca gctcgcttaa
34261 gttcatgtcg ctgtccagct gctgagccac aggctgctgt ccaacttgcg gttgctcaac
34321 gggcggcgaa ggagaagtcc acgcctacat ggggtagag tcataatcgt gcatcaggat
34381 agggcggtgg tgctgcagca gcgcgcgaat aaactgctgc cgccgcgct ccgtcctgca
34441 ggaatacaac atggcagtgg tctcctcagc gatgattcgc accgcccgca gcataaggcg
34501 ccttgtcctc cgggcacagc agcgcaccct gatctcactt aagtcagcac agtaactgca
34561 gcacagtacc acaatattgt ttaaaatccc acagtgcaag gcgctgtatc caaagctcat
34621 ggcggggacc acagaaccca cgtggccatc ataccacaag cgcaggtaga ttaagtggcg
34681 acccctcata aacacgctgg acataaacat tacctctttt ggcatgttgt aattcaccac
34741 ctcccggtac catataaacc tctgattaaa catggcgcca tccaccacca tcctaaacca
34801 gctggccaaa acctgcccgc cggctatgca ctgcagggaa ccgggactgg aacaatgaca
34861 gtggagagcc caggactcgt aaccatggat catcatgctc gtcatgatat caatgttggc
34921 acaacacagg cacacgtgca tacacttcct caggattaca agctcctccc gcgtcagaac
34981 catatcccag ggaacaaccc attcctgaat cagcgtaaat cccacactgc agggaagacc
35041 tcgcacgtaa ctcacgttgt gcattgtcaa agtgttacat tcgggcagca gcggatgatc
35101 ctccagtatg gtagcgcggg tttctgtctc aaaaggaggt agacgatccc tactgtacgg
35161 agtgcgccga gacaaccgag atcgtgttgg tcgtagtgtc atgccaaatg aacgccgga
35221 cgtagtcata tttcctgaag caaaaccagg tgcgggcgtg acaaacagat ctgcgtctcc
35281 ggtctcgccg cttagatcgc tctgtgtagt agttgtagta tatccactct ctcaaagcat
35341 ccaggcgccc cctggcttcg ggttctatgt aaactccttc atgcgccgt gccctgataa
35401 catccaccac cgcagaataa gccacaccca gccaacctac acattcgttc tgcgagtcac
35461 acacggagg agcgggaaga gctgaagaa ccatgttttt tttttattc caaagagatta
35521 tccaaaacct caaaatgaag atctattaag tgaacgcgct cccctccggt ggcgtggtca
35581 aactctacag ccaaagaaca gataatggca tttgtaagat gttgcacaat ggcttccaaa
35641 aggcaaacgg ccctcacgtc caagtggacg taaaggctaa acccttcagg gtgaatctcc
35701 tctataaaca ttccagcacc ttcaaccatg cccaaataat tctcatctcg ccaccttctc
35761 aatatatctc taagcaaatc ccgaatatta agtccggcca ttgtaaaaat ctgctccaga
35821 gcgccctcca ccttcagcct caagcagcga atcatgattg caaaaattca ggttcctcac
35881 agacctgtat aagattcaaa agcggaacat taacaaaaat accgcgatcc cgtaggtccc
35941 ttcgcagggc cagctgaaca taatcgtgca ggtctgcacg gaccagcgcg gccacttccc
36001 cgccaggaac catgacaaaa gaacccacac tgattatgac acgcatactc ggagctatgc
36061 taaccagcgt agccccgatg taagcttgtt gcatgggcgg cgatataaaa tgcaaggtgc
36121 tgctcaaaaa atcaggcaaa gcctcgcgca aaaagaaag cacatcgtag tcatgctcat
36181 gcagataaag gcaggtaagc tccggaacca ccacagaaaa agacaccatt tttctctcaa
36241 acatgtctgc gggtttctgc ataaacacaa aataaaataa caaaaaaaca tttaaacatt
36301 agaagcctgt cttacaacag gaaaaacaac ccttataagc ataagacgga ctacggccat
```

FIG. 4L

```
36361 gccggcgtga ccgtaaaaaa actggtcacc gtgattaaaa agcaccaccg acagctcctc
36421 ggtcatgtcc ggagtcataa tgtaagactc ggtaaacaca tcaggttgat tcacatcggt
36481 cagtgctaaa aagcgaccga aatagcccgg gggaatacat acccgcaggc gtagagacaa
36541 cattacagcc cccataggag gtataacaaa attaatagga gagaaaaaca cataaacacc
36601 tgaaaaaccc tcctgcctag gcaaaatagc accctcccgc tccagaacaa catacagcgc
36661 ttccacagcg gcagccataa cagtcagcct taccagtaaa aagaaaaacc tattaaaaaa
36721 acaccactcg acacggcacc agctcaatca gtcacagtgt aaaaaagggc caagtgcaga
36781 gcgagtatat ataggactaa aaaatgacgt aacggttaaa gtccacaaaa aacacccaga
36841 aaaccgcacg cgaacctacg cccagaaacg aaagccaaaa aacccacaac ttcctcaaat
36901 cgtcacttcc gttttcccac gttacgtcac ttcccatttt aagaaaacta caattcccaa
36961 cacatacaag ttactccgcc ctaaaaccta cgtcacccgc cccgttccca cgccccgcgc
37021 cacgtcacaa actccacccc ctcattatca tattggcttc aatccaaaat aaggtatatt
37081 attgatgatg
```

FIG. 4M

```
              10                    30                    50
ATGGCGCCCATCACGGCCTACTCCCAACAGACGCGGGGCCTACTTGGTTGCATCATCACT
---------+---------+---------+---------+---------+---------+
MetAlaProIleThrAlaTyrSerGlnGlnThrArgGlyLeuLeuGlyCysIleIleThr
              10                    20

70                    90                    110
AGCCTTACAGGCCGGGACAAGAACCAGGTCGAGGGAGAGGTTCAGGTGGTTTCCACCGCA
---------+---------+---------+---------+---------+---------+
SerLeuThrGlyArgAspLysAsnGlnValGluGlyGluValGlnValValSerThrAla
              30                    40

130                   150                   170
ACACAATCCTTCCTGGCGACCTGCGTCAACGGCGTGTGTTGGACCGTTTACCATGGTGCT
---------+---------+---------+---------+---------+---------+
ThrGlnSerPheLeuAlaThrCysValAsnGlyValCysTrpThrValTyrHisGlyAla
              50                    60

190                   210                   230
GGCTCAAAGACCTTAGCCGGCCCAAAGGGGCCAATCACCCAGATGTACACTAATGTGGAC
---------+---------+---------+---------+---------+---------+
GlySerLysThrLeuAlaGlyProLysGlyProIleThrGlnMetTyrThrAsnValAsp
              70                    80

250                   270                   290
CAGGACCTCGTCGGCTGGCAGGCGCCCCCCGGGGCGCGTTCCTTGACACCATGCACCTGT
---------+---------+---------+---------+---------+---------+
GlnAspLeuValGlyTrpGlnAlaProProGlyAlaArgSerLeuThrProCysThrCys
              90                    100

310                   330                   350
GGCAGCTCAGACCTTTACTTGGTCACGAGACATGCTGACGTCATTCCGGTGCGCCGGCGG
---------+---------+---------+---------+---------+---------+
GlySerSerAspLeuTyrLeuValThrArgHisAlaAspValIleProValArgArgArg
              110                   120

370                   390                   410
GGCGACAGTAGGGGGAGCCTGCTCTCCCCCAGGCCTGTCTCCTACTTGAAGGGCTCTTCG
---------+---------+---------+---------+---------+---------+
GlyAspSerArgGlySerLeuLeuSerProArgProValSerTyrLeuLysGlySerSer
              130                   140
```

FIG. 5A

```
           430              450              470
        GGTGGTCCACTGCTCTGCCCTTCGGGGCACGCTGTGGGCATCTTCCGGGCTGCCGTATGC
        ---------+---------+---------+---------+---------+---------+
        GlyGlyProLeuLeuCysProSerGlyHisAlaValGlyIlePheArgAlaAlaValCys
                             150                              160

490              510              530
        ACCCGGGGGGTTGCGAAGGCGGTGGACTTTGTGCCCGTAGAGTCCATGGAAACTACTATG
        ---------+---------+---------+---------+---------+---------+
        ThrArgGlyValAlaLysAlaValAspPheValProValGluSerMetGluThrThrMet
                             170                              180

550              570              590
        CGGTCTCCGGTCTTCACGGACAACTCATCCCCCCCGGCCGTACCGCAGTCATTTCAAGTG
        ---------+---------+---------+---------+---------+---------+
        ArgSerProValPheThrAspAsnSerSerProProAlaValProGlnSerPheGlnVal
                             190                              200

610              630              650
        GCCCACCTACACGCTCCCACTGGCAGCGGCAAGAGTACTAAAGTGCCGGCTGCATATGCA
        ---------+---------+---------+---------+---------+---------+
        AlaHisLeuHisAlaProThrGlySerGlyLysSerThrLysValProAlaAlaTyrAla
                             210                              220

670              690              710
        GCCCAAGGGTACAAGGTGCTCGTCCTCAATCCGTCCGTTGCCGCTACCTTAGGGTTTGGG
        ---------+---------+---------+---------+---------+---------+
        AlaGlnGlyTyrLysValLeuValLeuAsnProSerValAlaAlaThrLeuGlyPheGly
                             230                              240

730              750              770
        GCGTATATGTCTAAGGCACACGGTATTGACCCCAACATCAGAACTGGGGTAAGGACCATT
        ---------+---------+---------+---------+---------+---------+
        AlaTyrMetSerLysAlaHisGlyIleAspProAsnIleArgThrGlyValArgThrIle
                             250                              260

790              810              830
        ACCACAGGCGCCCCCGTCACATACTCTACCTATGGCAAGTTTCTTGCCGATGGTGGTTGC
        ---------+---------+---------+---------+---------+---------+
        ThrThrGlyAlaProValThrTyrSerThrTyrGlyLysPheLeuAlaAspGlyGlyCys
                             270                              280
```

FIG. 5B

```
              850                870                890
TCTGGGGGCGCTTATGACATCATAATATGTGATGAGTGCCATTCAACTGACTCGACTACA
    ---------+---------+---------+---------+---------+---------+
SerGlyGlyAlaTyrAspIleIleIleCysAspGluCysHisSerThrAspSerThrThr
                                290                300

910                930                950
ATCTTGGGCATCGGCACAGTCCTGGACCAAGCGGAGACGGCTGGAGCGCGGCTTGTCGTG
    ---------+---------+---------+---------+---------+---------+
IleLeuGlyIleGlyThrValLeuAspGlnAlaGluThrAlaGlyAlaArgLeuValVal
                                310                320

970                990               1010
CTCGCCACCGCTACGCCTCCGGGATCGGTCACCGTGCCACACCCAAACATCGAGGAGGTG
    ---------+---------+---------+---------+---------+---------+
LeuAlaThrAlaThrProProGlySerValThrValProHisProAsnIleGluGluVal
                                330                340

1030               1050               1070
GCCCTGTCTAATACTGGAGAGATCCCCTTCTATGGCAAAGCCATCCCCATTGAAGCCATC
    ---------+---------+---------+---------+---------+---------+
AlaLeuSerAsnThrGlyGluIleProPheTyrGlyLysAlaIleProIleGluAlaIle
                                350                360

1090               1110               1130
AGGGGGGGAAGGCATCTCATTTTCTGTCATTCCAAGAAGAAGTGCGACGAGCTCGCCGCA
    ---------+---------+---------+---------+---------+---------+
ArgGlyGlyArgHisLeuIlePheCysHisSerLysLysLysCysAspGluLeuAlaAla
                                370                380

1150               1170               1190
AAGCTGTCAGGCCTCGGAATCAACGCTGTGGCGTATTACCGGGGGCTCGATGTGTCCGTC
    ---------+---------+---------+---------+---------+---------+
LysLeuSerGlyLeuGlyIleAsnAlaValAlaTyrTyrArgGlyLeuAspValSerVal
                                390                400

1210               1230               1250
ATACCAACTATCGGAGACGTCGTTGTCGTGGCAACAGACGCTCTGATGACGGGCTATACG
    ---------+---------+---------+---------+---------+---------+
IleProThrIleGlyAspValValValValAlaThrAspAlaLeuMetThrGlyTyrThr
                                410                420
```

FIG. 5C

```
                1270                1290                1310
       GGCGACTTTGACTCAGTGATCGACTGTAACACATGTGTCACCCAGACAGTCGACTTCAGC
       ----------+---------+---------+---------+---------+---------+
       GlyAspPheAspSerValIleAspCysAsnThrCysValThrGlnThrValAspPheSer
                                    430                440

1330                1350                1370
       TTGGATCCCACCTTCACCATTGAGACGACGACCGTGCCTCAAGACGCAGTGTCGCGCTCG
       ----------+---------+---------+---------+---------+---------+
       LeuAspProThrPheThrIleGluThrThrThrValProGlnAspAlaValSerArgSer
                                    450                460

1390                1410                1430
       CAGCGGCGGGGTAGGACTGGCAGGGGTAGGAGAGGCATCTACAGGTTTGTGACTCCGGGA
       ----------+---------+---------+---------+---------+---------+
       GlnArgArgGlyArgThrGlyArgGlyArgArgGlyIleTyrArgPheValThrProGly
                                    470                480

1450                1470                1490
       GAACGGCCCTCGGGCATGTTCGATTCCTCGGTCCTGTGTGAGTGCTATGACGCGGGCTGT
       ----------+---------+---------+---------+---------+---------+
       GluArgProSerGlyMetPheAspSerSerValLeuCysGluCysTyrAspAlaGlyCys
                                    490                500

1510                1530                1550
       GCTTGGTACGAGCTCACCCCCGCCGAGACCTCGGTTAGGTTGCGGGCCTACCTGAACACA
       ----------+---------+---------+---------+---------+---------+
       AlaTrpTyrGluLeuThrProAlaGluThrSerValArgLeuArgAlaTyrLeuAsnThr
                                    510                520

1570                1590                1610
       CCAGGGTTGCCCGTTTGCCAGGACCACCTGGAGTTCTGGGAGAGTGTCTTCACAGGCCTC
       ----------+---------+---------+---------+---------+---------+
       ProGlyLeuProValCysGlnAspHisLeuGluPheTrpGluSerValPheThrGlyLeu
                                    530                540

1630                1650                1670
       ACCCACATAGATGCACACTTCTTGTCCCAGACCAAGCAGGCAGGAGACAACTTCCCCTAC
       ----------+---------+---------+---------+---------+---------+
       ThrHisIleAspAlaHisPheLeuSerGlnThrLysGlnAlaGlyAspAsnPheProTyr
                                    550                560
```

FIG. 5D

```
            1690                1710                1730
    CTGGTAGCATACCAAGCCACGGTGTGCGCCAGGGCTCAGGCCCCACCTCCATCATGGGAT
    ---------+---------+---------+---------+---------+---------+
    LeuValAlaTyrGlnAlaThrValCysAlaArgAlaGlnAlaProProProSerTrpAsp
                         570                                 580

1750                1770                1790
    CAAATGTGGAAGTGTCTCATACGGCTGAAACCTACGCTGCACGGGCCAACACCCTTGCTG
    ---------+---------+---------+---------+---------+---------+
    GlnMetTrpLysCysLeuIleArgLeuLysProThrLeuHisGlyProThrProLeuLeu
                         590                                 600

1810                1830                1850
    TACAGGCTGGGAGCCGTCCAAAATGAGGTCACCCTCACCCACCCCATAACCAAATACATC
    ---------+---------+---------+---------+---------+---------+
    TyrArgLeuGlyAlaValGlnAsnGluValThrLeuThrHisProIleThrLysTyrIle
                         610                                 620

1870                1890                1910
    ATGGCATGCATGTCGGCTGACCTGGAGGTCGTCACTAGCACCTGGGTGCTGGTGGGCGGA
    ---------+---------+---------+---------+---------+---------+
    MetAlaCysMetSerAlaAspLeuGluValValThrSerThrTrpValLeuValGlyGly
                         630                                 640

1930                1950                1970
    GTCCTTGCAGCTCTGGCCGCGTATTGCCTGACAACAGGCAGTGTGGTCATTGTGGGTAGG
    ---------+---------+---------+---------+---------+---------+
    ValLeuAlaAlaLeuAlaAlaTyrCysLeuThrThrGlySerValValIleValGlyArg
                         650                                 660

1990                2010                2030
    ATTATCTTGTCCGGGAGGCCGGCTATTGTTCCCGACAGGGAGTTTCTCTACCAGGAGTTC
    ---------+---------+---------+---------+---------+---------+
    IleIleLeuSerGlyArgProAlaIleValProAspArgGluPheLeuTyrGlnGluPhe
                         670                                 680

2050                2070                2090
    GATGAAATGGAAGAGTGCGCCTCGCACCTCCCTTACATCGAGCAGGGAATGCAGCTCGCC
    ---------+---------+---------+---------+---------+---------+
    AspGluMetGluGluCysAlaSerHisLeuProTyrIleGluGlnGlyMetGlnLeuAla
                         690                                 700
```

FIG. 5E

```
              2110                2130                2150
       GAGCAATTCAAGCAGAAAGCGCTCGGGTTACTGCAAACAGCCACCAAACAAGCGGAGGCT
       ---------+---------+---------+---------+---------+---------+
       GluGlnPheLysGlnLysAlaLeuGlyLeuLeuGlnThrAlaThrLysGlnAlaGluAla
                               710                               720

2170                2190                2210
       GCTGCTCCCGTGGTGGAGTCCAAGTGGCGAGCCCTTGAGACATTCTGGGCGAAGCACATG
       ---------+---------+---------+---------+---------+---------+
       AlaAlaProValValGluSerLysTrpArgAlaLeuGluThrPheTrpAlaLysHisMet
                               730                               740

2230                2250                2270
       TGGAATTTCATCAGCGGGATACAGTACTTAGCAGGCTTATCCACTCTGCCTGGGAACCCC
       ---------+---------+---------+---------+---------+---------+
       TrpAsnPheIleSerGlyIleGlnTyrLeuAlaGlyLeuSerThrLeuProGlyAsnPro
                               750                               760

2290                2310                2330
       GCAATAGCATCATTGATGGCATTCACAGCCTCTATCACCAGCCCGCTCACCACCCAAAGT
       ---------+---------+---------+---------+---------+---------+
       AlaIleAlaSerLeuMetAlaPheThrAlaSerIleThrSerProLeuThrThrGlnSer
                               770                               780

2350                2370                2390
       ACCCTCCTGTTTAACATCTTGGGGGGGTGGGTGGCTGCCCAACTCGCCCCCCCCAGCGCC
       ---------+---------+---------+---------+---------+---------+
       ThrLeuLeuPheAsnIleLeuGlyGlyTrpValAlaAlaGlnLeuAlaProProSerAla
                               790                               800

2410                2430                2450
       GCTTCGGCTTTCGTGGGCGCCGGCATCGCCGGTGCGGCTGTTGGCAGCATAGGCCTTGGG
       ---------+---------+---------+---------+---------+---------+
       AlaSerAlaPheValGlyAlaGlyIleAlaGlyAlaAlaValGlySerIleGlyLeuGly
                               810                               820

2470                2490                2510
       AAGGTGCTTGTGGACATTCTGGCGGGTTATGGAGCAGGAGTGGCCGGCGCGCTCGTGGCC
       ---------+---------+---------+---------+---------+---------+
       LysValLeuValAspIleLeuAlaGlyTyrGlyAlaGlyValAlaGlyAlaLeuValAla
                               830                               840
```

FIG. 5F

```
              2530                2550                2570
      TTCAAGGTCATGAGCGGCGAGATGCCCTCCACCGAGGACCTGGTCAATCTACTTCCTGCC
      ---------+---------+---------+---------+---------+---------+
      PheLysValMetSerGlyGluMetProSerThrGluAspLeuValAsnLeuLeuProAla
                                    850                         860

2590                2610                2630
      ATCCTCTCTCCTGGCGCCCTGGTCGTCGGGGTCGTGTGTGCAGCAATACTGCGTCGACAC
      ---------+---------+---------+---------+---------+---------+
      IleLeuSerProGlyAlaLeuValValGlyValValCysAlaAlaIleLeuArgArgHis
                                    870                         880

2650                2670                2690
      GTGGGTCCGGGAGAGGGGGCTGTGCAGTGGATGAACCGGCTGATAGCGTTCGCCTCGCGG
      ---------+---------+---------+---------+---------+---------+
      ValGlyProGlyGluGlyAlaValGlnTrpMetAsnArgLeuIleAlaPheAlaSerArg
                                    890                         900

2710                2730                2750
      GGTAATCATGTTTCCCCCACGCACTATGTGCCTGAGAGCGACGCCGCAGCGCGTGTTACT
      ---------+---------+---------+---------+---------+---------+
      GlyAsnHisValSerProThrHisTyrValProGluSerAspAlaAlaAlaArgValThr
                                    910                         920

2770                2790                2810
      CAGATCCTCTCCAGCCTTACCATCACTCAGCTGCTGAAAAGGCTCCACCAGTGGATTAAT
      ---------+---------+---------+---------+---------+---------+
      GlnIleLeuSerSerLeuThrIleThrGlnLeuLeuLysArgLeuHisGlnTrpIleAsn
                                    930                         940

2830                2850                2870
      GAAGACTGCTCCACACCGTGTTCCGGCTCGTGGCTAAGGGATGTTTGGGACTGGATATGC
      ---------+---------+---------+---------+---------+---------+
      GluAspCysSerThrProCysSerGlySerTrpLeuArgAspValTrpAspTrpIleCys
                                    950                         960

2890                2910                2930
      ACGGTGTTGACTGACTTCAAGACCTGGCTCCAGTCCAAGCTCCTGCCGCAGCTACCGGGA
      ---------+---------+---------+---------+---------+---------+
      ThrValLeuThrAspPheLysThrTrpLeuGlnSerLysLeuLeuProGlnLeuProGly
                                    970                         980
```

FIG. 5G

```
              2950                  2970                  2990
      GTCCCTTTTTTCTCGTGCCAACGCGGGTACAAGGGAGTCTGGCGGGGAGACGGCATCATG
      ---------+---------+---------+---------+---------+---------+
      ValProPhePheSerCysGlnArgGlyTyrLysGlyValTrpArgGlyAspGlyIleMet
                                   990                  1000

3010                  3030                  3050
      CAAACCACCTGCCCATGTGGAGCACAGATCACCGGACATGTCAAAAACGGTTCCATGAGG
      ---------+---------+---------+---------+---------+---------+
      GlnThrThrCysProCysGlyAlaGlnIleThrGlyHisValLysAsnGlySerMetArg
                                  1010                  1020

3070                  3090                  3110
      ATCGTCGGGCCTAAGACCTGCAGCAACACGTGGCATGGAACATTCCCCATCAACGCATAC
      ---------+---------+---------+---------+---------+---------+
      IleValGlyProLysThrCysSerAsnThrTrpHisGlyThrPheProIleAsnAlaTyr
                                  1030                  1040

3130                  3150                  3170
      ACCACGGGCCCCTGCACACCCTCTCCAGCGCCAAACTATTCTAGGGCGCTGTGGCGGGTG
      ---------+---------+---------+---------+---------+---------+
      ThrThrGlyProCysThrProSerProAlaProAsnTyrSerArgAlaLeuTrpArgVal
                                  1050                  1060

3190                  3210                  3230
      GCCGCTGAGGAGTACGTGGAGGTCACGCGGGTGGGGGATTTCCACTACGTGACGGGCATG
      ---------+---------+---------+---------+---------+---------+
      AlaAlaGluGluTyrValGluValThrArgValGlyAspPheHisTyrValThrGlyMet
                                  1070                  1080

3250                  3270                  3290
      ACCACTGACAACGTAAAGTGCCCATGCCAGGTTCCGGCTCCTGAATTCTTCACGGAGGTG
      ---------+---------+---------+---------+---------+---------+
      ThrThrAspAsnValLysCysProCysGlnValProAlaProGluPhePheThrGluVal
                                  1090                  1100

3310                  3330                  3350
      GACGGAGTGCGGTTGCACAGGTACGCTCCGGCGTGCAGGCCTCTCCTACGGGAGGAGGTT
      ---------+---------+---------+---------+---------+---------+
      AspGlyValArgLeuHisArgTyrAlaProAlaCysArgProLeuLeuArgGluGluVal
                                  1110                  1120
```

FIG. 5H

```
                3370              3390              3410
        ACATTCCAGGTCGGGCTCAACCAATACCTGGTTGGGTCACAGCTACCATGCGAGCCCGAA
        ---------+---------+---------+---------+---------+---------+
        ThrPheGlnValGlyLeuAsnGlnTyrLeuValGlySerGlnLeuProCysGluProGlu
                                  1130              1140

3430              3450              3470
        CCGGATGTAGCAGTGCTCACTTCCATGCTCACCGACCCCTCCCACATCACAGCAGAAACG
        ---------+---------+---------+---------+---------+---------+
        ProAspValAlaValLeuThrSerMetLeuThrAspProSerHisIleThrAlaGluThr
                                  1150              1160

3490              3510              3530
        GCTAAGCGTAGGTTGGCCAGGGGGTCTCCCCCCTCCTTGGCCAGCTCTTCAGCTAGCCAG
        ---------+---------+---------+---------+---------+---------+
        AlaLysArgArgLeuAlaArgGlySerProProSerLeuAlaSerSerSerAlaSerGln
                                  1170              1180

3550              3570              3590
        TTGTCTGCGCCTTCCTTGAAGGCGACATGCACTACCCACCATGTCTCTCCGGACGCTGAC
        ---------+---------+---------+---------+---------+---------+
        LeuSerAlaProSerLeuLysAlaThrCysThrThrHisHisValSerProAspAlaAsp
                                  1190              1200

3610              3630              3650
        CTCATCGAGGCCAACCTCCTGTGGCGGCAGGAGATGGGCGGGAACATCACCCGCGTGGAG
        ---------+---------+---------+---------+---------+---------+
        LeuIleGluAlaAsnLeuLeuTrpArgGlnGluMetGlyGlyAsnIleThrArgValGlu
                                  1210              1220

3670              3690              3710
        TCGGAGAACAAGGTGGTAGTCCTGGACTCTTTCGACCCGCTTCGAGCGGAGGAGGATGAG
        ---------+---------+---------+---------+---------+---------+
        SerGluAsnLysValValValLeuAspSerPheAspProLeuArgAlaGluGluAspGlu
                                  1230              1240

3730              3750              3770
        AGGGAAGTATCCGTTCCGGCGGAGATCCTGCGGAAATCCAAGAAGTTCCCCGCAGCGATG
        ---------+---------+---------+---------+---------+---------+
        ArgGluValSerValProAlaGluIleLeuArgLysSerLysLysPheProAlaAlaMet
                                  1250              1260
```

FIG. 5I

```
            3790                3810                3830
CCCATCTGGGCGCGCCCGGATTACAACCCTCCACTGTTAGAGTCCTGGAAGGACCCGGAC
---------+---------+---------+---------+---------+---------+
ProIleTrpAlaArgProAspTyrAsnProProLeuLeuGluSerTrpLysAspProAsp
                    1270                1280

3850                3870                3890
TACGTCCCTCCGGTGGTGCACGGGTGCCCGTTGCCACCTATCAAGGCCCCTCCAATACCA
---------+---------+---------+---------+---------+---------+
TyrValProProValValHisGlyCysProLeuProProIleLysAlaProProIlePro
                    1290                1300

3910                3930                3950
CCTCCACGGAGAAAGAGGACGGTTGTCCTAACAGAGTCCTCCGTGTCTTCTGCCTTAGCG
---------+---------+---------+---------+---------+---------+
ProProArgArgLysArgThrValValLeuThrGluSerSerValSerSerAlaLeuAla
                    1310                1320

3970                3990                4010
GAGCTCGCTACTAAGACCTTCGGCAGCTCCGAATCATCGGCCGTCGACAGCGGCACGGCG
---------+---------+---------+---------+---------+---------+
GluLeuAlaThrLysThrPheGlySerSerGluSerSerAlaValAspSerGlyThrAla
                    1330                1340

4030                4050                4070
ACCGCCCTTCCTGACCAGGCCTCCGACGACGGTGACAAAGGATCCGACGTTGAGTCGTAC
---------+---------+---------+---------+---------+---------+
ThrAlaLeuProAspGlnAlaSerAspAspGlyAspLysGlySerAspValGluSerTyr
                    1350                1360

4090                4110                4130
TCCTCCATGCCCCCCCCTTGAGGGGGAACCGGGGGACCCCGATCTCAGTGACGGGTCTTGG
---------+---------+---------+---------+---------+---------+
SerSerMetProProLeuGluGlyGluProGlyAspProAspLeuSerAspGlySerTrp
                     1370                1380

4150                4170                4190
TCTACCGTGAGCGAGGAAGCTAGTGAGGATGTCGTCTGCTGCTCAATGTCCTACACATGG
---------+---------+---------+---------+---------+---------+
SerThrValSerGluGluAlaSerGluAspValValCysCysSerMetSerTyrThrTrp
                    1390                1400
```

FIG. 5J

```
              4210                4230                4250
     ACAGGCGCCTTGATCACGCCATGCGCTGCGGAGGAAAGCAAGCTGCCCATCAACGCGTTG
     ---------+---------+---------+---------+---------+---------+
     ThrGlyAlaLeuIleThrProCysAlaAlaGluGluSerLysLeuProIleAsnAlaLeu
                         1410                1420

4270                4290                4310
     AGCAACTCTTTGCTGCGCCACCATAACATGGTTTATGCCACAACATCTCGCAGCGCAGGC
     ---------+---------+---------+---------+---------+---------+
     SerAsnSerLeuLeuArgHisHisAsnMetValTyrAlaThrThrSerArgSerAlaGly
                         1430                1440

4330                4350                4370
     CTGCGGCAGAAGAAGGTCACCTTTGACAGACTGCAAGTCCTGGACGACCACTACCGGGAC
     ---------+---------+---------+---------+---------+---------+
     LeuArgGlnLysLysValThrPheAspArgLeuGlnValLeuAspAspHisTyrArgAsp
                         1450                1460

4390                4410                4430
     GTGCTCAAGGAGATGAAGGCGAAGGCGTCCACAGTTAAGGCTAAACTCCTATCCGTAGAG
     ---------+---------+---------+---------+---------+---------+
     ValLeuLysGluMetLysAlaLysAlaSerThrValLysAlaLysLeuLeuSerValGlu
                         1470                1480

4450                4470                4490
     GAAGCCTGCAAGCTGACGCCCCCACATTCGGCCAAATCCAAGTTTGGCTATGGGGCAAAG
     ---------+---------+---------+---------+---------+---------+
     GluAlaCysLysLeuThrProProHisSerAlaLysSerLysPheGlyTyrGlyAlaLys
                         1490                1500

4510                4530                4550
     GACGTCCGGAACCTATCCAGCAAGGCCGTTAACCACATCCACTCCGTGTGGAAGGACTTG
     ---------+---------+---------+---------+---------+---------+
     AspValArgAsnLeuSerSerLysAlaValAsnHisIleHisSerValTrpLysAspLeu
                         1510                1520

4570                4590                4610
     CTGGAAGACACTGTGACACCAATTGACACCACCATCATGGCAAAAAATGAGGTTTTCTGT
     ---------+---------+---------+---------+---------+---------+
     LeuGluAspThrValThrProIleAspThrThrIleMetAlaLysAsnGluValPheCys
                         1530                1540
```

FIG. 5K

```
              4630                4650                4670
     GTCCAACCAGAGAAAGGAGGCCGTAAGCCAGCCCGCCTTATCGTATTCCCAGATCTGGGA
     ---------+---------+---------+---------+---------+---------+
     ValGlnProGluLysGlyGlyArgLysProAlaArgLeuIleValPheProAspLeuGly
                        1550                               1560

4690                4710                4730
     GTCCGTGTATGCGAGAAGATGGCCCTCTATGATGTGGTCTCCACCCTTCCTCAGGTCGTG
     ---------+---------+---------+---------+---------+---------+
     ValArgValCysGluLysMetAlaLeuTyrAspValValSerThrLeuProGlnValVal
                        1570                               1580

4750                4770                4790
     ATGGGCTCCTCATACGGATTCCAGTACTCTCCTGGGCAGCGAGTCGAGTTCCTGGTGAAT
     ---------+---------+---------+---------+---------+---------+
     MetGlySerSerTyrGlyPheGlnTyrSerProGlyGlnArgValGluPheLeuValAsn
                        1590                               1600

4810                4830                4850
     ACCTGGAAATCAAAGAAAAACCCCATGGGCTTTTCATATGACACTCGCTGTTTCGACTCA
     ---------+---------+---------+---------+---------+---------+
     ThrTrpLysSerLysLysAsnProMetGlyPheSerTyrAspThrArgCysPheAspSer
                        1610                               1620

4870                4890                4910
     ACGGTCACCGAGAACGACATCCGTGTTGAGGAGTCAATTTACCAATGTTGTGACTTGGCC
     ---------+---------+---------+---------+---------+---------+
     ThrValThrGluAsnAspIleArgValGluGluSerIleTyrGlnCysCysAspLeuAla
                        1630                               1640

4930                4950                4970
     CCCGAAGCCAGACAGGCCATAAAATCGCTCACAGAGCGGCTTTATATCGGGGGTCCTCTG
     ---------+---------+---------+---------+---------+---------+
     ProGluAlaArgGlnAlaIleLysSerLeuThrGluArgLeuTyrIleGlyGlyProLeu
                        1650                               1660

4990                5010                5030
     ACTAATTCAAAAGGGCAGAACTGCGGTTATCGCCGGTGCCGCGCGAGCGGCGTGCTGACG
     ---------+---------+---------+---------+---------+---------+
     ThrAsnSerLysGlyGlnAsnCysGlyTyrArgArgCysArgAlaSerGlyValLeuThr
                        1670                               1680
```

FIG. 5L

```
              5050                5070                5090
         ACTAGCTGCGGTAACACCCTCACATGTTACTTGAAGGCCTCTGCAGCCTGTCGAGCTGCG
         ---------+---------+---------+---------+---------+---------+
         ThrSerCysGlyAsnThrLeuThrCysTyrLeuLysAlaSerAlaAlaCysArgAlaAla
                            1690                1700

5110                5130                5150
         AAGCTCCAGGACTGCACGATGCTCGTGAACGGAGACGACCTTGTCGTTATCTGTGAAAGC
         ---------+---------+---------+---------+---------+---------+
         LysLeuGlnAspCysThrMetLeuValAsnGlyAspAspLeuValValIleCysGluSer
                            1710                1720

5170                5190                5210
         GCGGGAACCCAAGAGGACGCGGCGAGCCTACGAGTCTTCACGGAGGCTATGACTAGGTAC
         ---------+---------+---------+---------+---------+---------+
         AlaGlyThrGlnGluAspAlaAlaSerLeuArgValPheThrGluAlaMetThrArgTyr
                            1730                1740

5230                5250                5270
         TCTGCCCCCCCCGGGGACCCGCCCCAACCAGAATACGACTTGGAGCTGATAACATCATGT
         ---------+---------+---------+---------+---------+---------+
         SerAlaProProGlyAspProProGlnProGluTyrAspLeuGluLeuIleThrSerCys
                            1750                1760

5290                5310                5330
         TCCTCCAATGTGTCGGTCGCCCACGATGCATCAGGCAAAAGGGTGTACTACCTCACCCGT
         ---------+---------+---------+---------+---------+---------+
         SerSerAsnValSerValAlaHisAspAlaSerGlyLysArgValTyrTyrLeuThrArg
                            1770                1780

5350                5370                5390
         GATCCCACCACCCCCCTCGCACGGGCTGCGTGGGAAACAGCTAGACACACTCCAGTTAAC
         ---------+---------+---------+---------+---------+---------+
         AspProThrThrProLeuAlaArgAlaAlaTrpGluThrAlaArgHisThrProValAsn
                            1790                1800

5410                5430                5450
         TCCTGGCTAGGCAACATTATCATGTATGCGCCCACTTTGTGGGCAAGGATGATTCTGATG
         ---------+---------+---------+---------+---------+---------+
         SerTrpLeuGlyAsnIleIleMetTyrAlaProThrLeuTrpAlaArgMetIleLeuMet
                            1810                1820
```

FIG. 5M

```
              5470                5490                5510
         ACTCACTTCTTCTCCATCCTTCTAGCACAGGAGCAACTTGAAAAAGCCCTGGACTGCCAG
         ---------+---------+---------+---------+---------+---------+
         ThrHisPhePheSerIleLeuLeuAlaGlnGluGlnLeuGluLysAlaLeuAspCysGln
                                     1830                1840

5530                5550                5570
         ATCTACGGGGCCTGTTACTCCATTGAGCCACTTGACCTACCTCAGATCATTGAACGACTC
         ---------+---------+---------+---------+---------+---------+
         IleTyrGlyAlaCysTyrSerIleGluProLeuAspLeuProGlnIleIleGluArgLeu
                                     1850                1860

5590                5610                5630
         CATGGCCTTAGCGCATTTTCACTCCATAGTTACTCTCCAGGTGAGATCAATAGGGTGGCT
         ---------+---------+---------+---------+---------+---------+
         HisGlyLeuSerAlaPheSerLeuHisSerTyrSerProGlyGluIleAsnArgValAla
                                     1870                1880

5650                5670                5690
         TCATGCCTCAGGAAACTTGGGGTACCACCCTTGCGAGTCTGGAGACATCGGGCCAGGAGC
         ---------+---------+---------+---------+---------+---------+
         SerCysLeuArgLysLeuGlyValProProLeuArgValTrpArgHisArgAlaArgSer
                                     1890                1900

5710                5730                5750
         GTCCGCGCTAGGCTACTGTCCCAGGGGGGGGAGGGCCGCCACTTGTGGCAAGTACCTCTTC
         ---------+---------+---------+---------+---------+---------+
         ValArgAlaArgLeuLeuSerGlnGlyGlyArgAlaAlaThrCysGlyLysTyrLeuPhe
                                     1910                1920

5770                5790                5810
         AACTGGGCAGTGAAGACCAAACTCAAACTCACTCCAATCCCGGCTGCGTCCCAGCTGGAC
         ---------+---------+---------+---------+---------+---------+
         AsnTrpAlaValLysThrLysLeuLysLeuThrProIleProAlaAlaSerGlnLeuAsp
                                     1930                1940

5830                5850                5870
         TTGTCCGGCTGGTTCGTTGCTGGTTACAGCGGGGGAGACATATATCACAGCCTGTCTCGT
         ---------+---------+---------+---------+---------+---------+
         LeuSerGlyTrpPheValAlaGlyTyrSerGlyGlyAspIleTyrHisSerLeuSerArg
                                     1950                1960
```

FIG. 5N

```
              5890                5910                5930
       GCCCGACCCCGCTGGTTCATGCTGTGCCTACTCCTACTTTCTGTAGGGGTAGGCATCTAC
       ---------+---------+---------+---------+---------+---------+
       AlaArgProArgTrpPheMetLeuCysLeuLeuLeuLeuSerValGlyValGlyIleTyr
                              1970                          1980

5950 5955
       CTGCTCCCCAACCGA         (SEQ. ID. NO. 5)
       ---------+-----
       LeuLeuProAsnArg         (SEQ. ID. NO. 6)
                1985
```

FIG. 5O

```
   1  TCGCGCGTTT CGGTGATGAC GGTGAAAACC TCTGACACAT GCAGCTCCCG
  51  GAGACGGTCA CAGCTTGTCT GTAAGCGGAT GCCGGGAGCA GACAAGCCCG
 101  TCAGGGCGCG TCAGCGGGTG TTGGCGGGTG TCGGGCTGG  CTTAACTATG
 151  CGGCATCAGA GCAGATTGTA CTGAGAGTGC ACCATATGCG GTGTGAAATA
 201  CCGCACAGAT GCGTAAGGAG AAAATACCGC ATCAGATTGG CTATTGGCCA
 251  TTGCATACGT TGTATCCATA TCATAATATG TACATTTATA TTGGCTCATG
 301  TCCAACATTA CCGCCATGTT GACATTGATT ATTGACTAGT TATTAATAGT
 351  AATCAATTAC GGGGTCATTA GTTCATAGCC CATATATGGA GTTCCGCGTT
 401  ACATAACTTA CGGTAAATGG CCCGCCTGGC TGACCGCCCA ACGACCCCCG
 451  CCCATTGACG TCAATAATGA CGTATGTTCC CATAGTAACG CCAATAGGGA
 501  CTTTCCATTG ACGTCAATGG GTGGAGTATT TACGGTAAAC TGCCCACTTG
 551  GCAGTACATC AAGTGTATCA TATGCCAAGT ACGCCCCCTA TTGACGTCAA
 601  TGACGGTAAA TGGCCCGCCT GGCATTATGC CCAGTACATG ACCTTATGGG
 651  ACTTTCCTAC TTGGCAGTAC ATCTACGTAT TAGTCATCGC TATTACCATG
 701  GTGATGCGGT TTTGGCAGTA CATCAATGGG CGTGGATAGC GGTTTGACTC
 751  ACGGGGATTT CCAAGTCTCC ACCCCATTGA CGTCAATGGG AGTTTGTTTT
 801  GGCACCAAAA TCAACGGGAC TTTCCAAAAT GTCGTAACAA CTCCGCCCCA
 851  TTGACGCAAA TGGGCGGTAG GCGTGTACGG TGGGAGGTCT ATATAAGCAG
 901  AGCTCGTTTA GTGAACCGTC AGATCGCCTG GAGACGCCAT CCACGCTGTT
 951  TTGACCTCCA TAGAAGACAC CGGGACCGAT CCAGCCTCCG CGGCCGGGAA
1001  CGGTGCATTG GAACGCGGAT TCCCCGTGCC AAGAGTGACG TAAGTACCGC
1051  CTATAGACTC TATAGGCACA CCCCTTTGGC TCTTATGCAT GCTATACTGT
1101  TTTTGGCTTG GGGCCTATAC ACCCCGCTT  CCTTATGCTA TAGGTGATGG
1151  TATAGCTTAG CCTATAGGTG TGGGTTATTG ACCATTATTG ACCACTCCCC
1201  TATTGGTGAC GATACTTTCC ATTACTAATC CATAACATGG CTCTTTGCCA
1251  CAACTATCTC TATTGGCTAT ATGCCAATAC TCTGTCCTTC AGAGACTGAC
1301  ACGGACTCTG TATTTTTACA GGATGGGGTC CCATTTATTA TTTACAAATT
1351  CACATATACA ACAACGCCGT CCCCCGTGCC CGCAGTTTTT ATTAAACATA
1401  GCGTGGGATC TCCACGCGAA TCTCGGGTAC GTGTTCCGGA CATGGGCTCT
1451  TCTCCGGTAG CGGCGGAGCT TCCACATCCG AGCCCTGGTC CCATGCCTCC
1501  AGCGGCTCAT GGTCGCTCGG CAGCTCCTTG CTCCTAACAG TGGAGGCCAG
1551  ACTTAGGCAC AGCACAATGC CCACCACCAC CAGTGTGCCG CACAAGGCCG
1601  TGGCGGTAGG GTATGTGTCT GAAAATGAGC GTGGAGATTG GGCTCGCACG
1651  GCTGACGCAG ATGGAAGACT TAAGGCAGCG GCAGAAGAAG ATGCAGGCAG
1701  CTGAGTTGTT GTATTCTGAT AAGAGTCAGA GGTAACTCCC GTTGCGGTGC
1751  TGTTAACGGT GGAGGGCAGT GTAGTCTGAG CAGTACTCGT TGCTGCCGCG
1801  CGCGCCACCA GACATAATAG CTGACAGACT AACAGACTGT TCCTTTCCAT
1851  GGGTCTTTTC TGCAGTCACC GTCCTTAGAT CTAGGTACCA GATATCAGAA
1901  TTCAGTCGAC AGCGGCCGCG ATCTGCTGTG CCTTCTAGTT GCCAGCCATC
1951  TGTTGTTTGC CCCTCCCCCG TGCCTTCCTT GACCCTGGAA GGTGCCACTC
2001  CCACTGTCCT TTCCTAATAA AATGAGGAAA TTGCATCGCA TTGTCTGAGT
2051  AGGTGTCATT CTATTCTGGG GGGTGGGGTG GGGCAGGACA GCAAGGGGGA
```

FIG. 6A

```
2101  GGATTGGGAA GACAATAGCA GGCATGCTGG GGATGCGGTG GGCTCTATGG
2151  CCGCTGCGGC CAGGTGCTGA AGAATTGACC CGGTTCCTCC TGGGCCAGAA
2201  AGAAGCAGGC ACATCCCCTT CTCTGTGACA CACCCTGTCC ACGCCCCTGG
2251  TTCTTAGTTC CAGCCCCACT CATAGGACAC TCATAGCTCA GGAGGGCTCC
2301  GCCTTCAATC CCACCCGCTA AGTACTTGG AGCGGTCTCT CCCTCCCTCA
2351  TCAGCCCACC AAACCAAACC TAGCCTCCAA GAGTGGGAAG AAATTAAAGC
2401  AAGATAGGCT ATTAAGTGCA GAGGGAGAGA AAATGCCTCC AACATGTGAG
2451  GAAGTAATGA GAGAAATCAT AGAATTTCTT CCGCTTCCTC GCTCACTGAC
2501  TCGCTGCGCT CGGTCGTTCG GCTGCGGCGA GCGGTATCAG CTCACTCAAA
2551  GGCGGTAATA CGGTTATCCA CAGAATCAGG GGATAACGCA GGAAAGAACA
2601  TGTGAGCAAA AGGCCAGCAA AAGGCCAGGA ACCGTAAAAA GGCCGCGTTG
2651  CTGGCGTTTT TCCATAGGCT CCGCCCCCT GACGAGCATC ACAAAAATCG
2701  ACGCTCAAGT CAGAGGTGGC GAAACCCGAC AGGACTATAA AGATACCAGG
2751  CGTTTCCCCC TGGAAGCTCC CTCGTGCGCT CTCCTGTTCC GACCCTGCCG
2801  CTTACCGGAT ACCTGTCCGC CTTTCTCCCT TCGGGAAGCG TGGCGCTTTC
2851  TCATAGCTCA CGCTGTAGGT ATCTCAGTTC GGTGTAGGTC GTTCGCTCCA
2901  AGCTGGGCTG TGTGCACGAA CCCCCCGTTC AGCCCGACCG CTGCGCCTTA
2951  TCCGGTAACT ATCGTCTTGA GTCCAACCCG GTAAGACACG ACTTATCGCC
3001  ACTGGCAGCA GCCACTGGTA ACAGGATTAG CAGAGCGAGG TATGTAGGCG
3051  GTGCTACAGA GTTCTTGAAG TGGTGGCCTA ACTACGGCTA CACTAGAAGA
3101  ACAGTATTTG GTATCTGCGC TCTGCTGAAG CCAGTTACCT TCGGAAAAAG
3151  AGTTGGTAGC TCTTGATCCG GCAAACAAAC CACCGCTGGT AGCGGTGGTT
3201  TTTTTGTTTG CAAGCAGCAG ATTACGCGCA GAAAAAAAGG ATCTCAAGAA
3251  GATCCTTTGA TCTTTTCTAC GGGGTCTGAC GCTCAGTGGA ACGAAAACTC
3301  ACGTTAAGGG ATTTTGGTCA TGAGATTATC AAAAAGGATC TTCACCTAGA
3351  TCCTTTTAAA TTAAAAATGA AGTTTTAAAT CAATCTAAAG TATATATGAG
3401  TAAACTTGGT CTGACAGTTA CCAATGCTTA ATCAGTGAGG CACCTATCTC
3451  AGCGATCTGT CTATTTCGTT CATCCATAGT TGCCTGACTC GGGGGGGGG
3501  GGCGCTGAGG TCTGCCTCGT GAAGAAGGTG TTGCTGACTC ATACCAGGCC
3551  TGAATCGCCC CATCATCCAG CCAGAAAGTG AGGGAGCCAC GGTTGATGAG
3601  AGCTTTGTTG TAGGTGGACC AGTTGGTGAT TTTGAACTTT GCTTTGCCA
3651  CGGAACGGTC TGCGTTGTCG GAAGATGCG TGATCTGATC CTTCAACTCA
3701  GCAAAAGTTC GATTTATTCA ACAAAGCCGC CGTCCCGTCA AGTCAGCGTA
3751  ATGCTCTGCC AGTGTTACAA CCAATTAACC AATTCTGATT AGAAAAACTC
3801  ATCGAGCATC AAATGAAACT GCAATTTATT CATATCAGGA TTATCAATAC
3851  CATATTTTTG AAAAAGCCGT TTCTGTAATG AAGGAGAAAA CTCACCGAGG
3901  CAGTTCCATA GGATGGCAAG ATCCTGGTAT CGGTCTGCGA TTCCGACTCG
3951  TCCAACATCA ATACAACCTA TTAATTTCCC CTCGTCAAAA ATAAGGTTAT
4001  CAAGTGAGAA ATCACCATGA GTGACGACTG AATCCGGTGA GAATGGCAAA
4051  AGCTTATGCA TTTCTTTCCA GACTTGTTCA ACAGGCCAGC CATTACGCTC
4101  GTCATCAAAA TCACTCGCAT CAACCAAACC GTTATTCATT CGTGATTGCG
4151  CCTGAGCGAG ACGAAATACG CGATCGCTGT TAAAAGGACA ATTACAAACA
```

FIG. 6B

```
4201  GGAATCGAAT GCAACCGGCG CAGGAACACT GCCAGCGCAT CAACAATATT
4251  TTCACCTGAA TCAGGATATT CTTCTAATAC CTGGAATGCT GTTTTCCCGG
4301  GGATCGCAGT GGTGAGTAAC CATGCATCAT CAGGAGTACG GATAAAATGC
4351  TTGATGGTCG GAAGAGGCAT AAATTCCGTC AGCCAGTTTA GTCTGACCAT
4401  CTCATCTGTA ACATCATTGG CAACGCTACC TTTGCCATGT TTCAGAAACA
4451  ACTCTGGCGC ATCGGGCTTC CCATACAATC GATAGATTGT CGCACCTGAT
4501  TGCCCGACAT TATCGCGAGC CCATTTATAC CCATATAAAT CAGCATCCAT
4551  GTTGGAATTT AATCGCGGCC TCGAGCAAGA CGTTTCCCGT TGAATATGGC
4601  TCATAACACC CCTTGTATTA CTGTTTATGT AAGCAGACAG TTTTATTGTT
4651  CATGATGATA TATTTTTATC TTGTGCAATG TAACATCAGA GATTTTGAGA
4701  CACAACGTGG CTTTCCCCCC CCCCCATTA TTGAAGCATT TATCAGGGTT
4751  ATTGTCTCAT GAGCGGATAC ATATTTGAAT GTATTTAGAA AAATAAACAA
4801  ATAGGGGTTC CGCGCACATT TCCCCGAAAA GTGCCACCTG ACGTCTAAGA
4851  AACCATTATT ATCATGACAT TAACCTATAA AAATAGGCGT ATCACGAGGC
4901  CCTTTCGTC
```

FIG. 6C

```
   1  CATCATCAAT AATATACCTT ATTTTGGATT GAAGCCAATA TGATAATGAG GGGGTGGAGT
  61  TTGTGACGTG GCGCGGGGCG TGGGAACGGG GCGGGTGACG TAGTAGTGTG GCGGAAGTGT
 121  GATGTTGTAA GTGTGGCGGA ACACATGTAA GCGCCGGATG TGGTAAAAGT GACGTTTTTG
 181  GTGTGCGCCG GTGTACACGG GAAGTGACAA TTTTCGCGCG GTTTTAGGCG GATGTTGTAG
 241  TAAATTTGGG CGTAACCAAG TAATATTTGG CCATTTTCGC GGGAAAACTG AATAAGAGGA
 301  AGTGAAATCT GAATAATTCT GTGTTACTCA TAGCGCGTAA TATTTGTCTA GGGCCGCGGG
 361  GACTTTGACC GTTTACGTGG AGACTCGCCC AGGTGTTTTT CTCAGGTGTT TTCCGCGTTC
 421  CGGGTCAAAG TTGGCGTTTT ATTATTATAG TCAGCTGACG CGCAGTGTAT TTATACCCGG
 481  TGAGTTCCTC AAGAGGCCAC TCTTGAGTGC CAGCGAGTAG AGTTTTCTCC TCCGAGCCGC
 541  TCCGACACCG GGACTGAAAA TGAGACATAT TATCTGCCAC GGAGGTGTTA TTACCGAAGA
 601  AATGGCCGCC AGTCTTTTGG ACCAGCTGAT CGAAGAGGTA CTGGCTGATA ATCTTCCACC
 661  TCCTAGCCAT TTTGAACCAC CTACCCTTCA CGAACTGTAT GATTTAGACG TGACGGCCCC
 721  CGAAGATCCC AACGAGGAGG CGGTTTCGCA GATTTTTCCC GAGTCTGTAA TGTTGGCGGT
 781  GCAGGAAGGG ATTGACTTAT TCACTTTTCC GCCGGCGCCC GGTTCTCCGG AGCCGCCTCA
 841  CCTTTCCCGG CAGCCCGAGC AGCCGGAGCA GAGAGCCTTG GGTCCGGTTT CTATGCCAAA
 901  CCTTGTGCCG GAGGTGATCG ATCTTACCTG CCACGAGGCT GGCTTTCCAC CCAGTGACGA
 961  CGAGGATGAA GAGGGTGAGG AGTTTGTGTT AGATTATGTG GAGCACCCCG GCACGGTTG
1021  CAGGTCTTGT CATTATCACC GGAGGAATAC GGGGGACCCA GATATTATGT GTTCGCTTTG
1081  CTATATGAGG ACCTGTGGCA TGTTTGTCTA CAGTAAGTGA AAAATTATGG CAGTGGGTG
1141  ATAGAGTGGT GGGTTTGGTG TGGTAATTTT TTTTTAATT TTTACAGTTT TGTGGTTTAA
1201  AGAATTTTGT ATTGTGATTT TTTAAAAGGT CCTGTGTCTG AACCTGAGCC TGAGCCCGAG
1261  CCAGAACCGG AGCCTGCAAG ACCTACCCGG CGTCCTAAAT TGGTGCCTGC TATCCTGAGA
1321  CGCCCGACAT CACCTGTGTC TAGAGAATGC AATAGTAGTA CGGATAGCTG TGACTCCGGT
1381  CCTTCTAACA CACCTCCTGA GATACACCCG GTGGTCCCGC TGTGCCCCAT TAAACCAGTT
1441  GCCGTGAGAG TTGGTGGGCG TCGCCAGGCT GTGGAATGTA TCGAGGACTT GCTTAACGAG
1501  TCTGGGCAAC CTTTGGACTT GAGCTGTAAA CGCCCCAGGC CATAAGGTGT AAACCTGTGA
1561  TTGCGTGTGT GGTTAACGCC TTTGTTTGCT GAATGAGTTG ATGTAAGTTT AATAAAGGGT
1621  GAGATAATGT TTAACTTGCA TGGCGTGTTA AATGGGGCGG GGCTTAAAGG GTATATAATG
1681  CGCCGTGGGC TAATCTTGGT TACATCTGAC CTCATGGAGG CTTGGGAGTG TTTGGAAGAT
1741  TTTTCTGCTG TGCGTAACTT GCTGGAACAG AGCTCTAACA GTACCTCTTG GTTTTGGAGG
1801  TTTCTGTGGG GCTCCTCCCA GGCAAAGTTA GTCTGCAGAA TTAAGGAGGA TTACAAGTGG
1861  GAATTTGAAG AGCTTTTGAA ATCCTGTGGT GAGCTGTTTG ATTCTTTGAA TCTGGGTCAC
1921  CAGGCGCTTT TCCAAGAGAA GGTCATCAAG ACTTTGGATT TTTCCACACC GGGGCGCGCT
1981  GCGGCTGCTG TTGCTTTTTT GAGTTTTATA AAGGATAAAT GGAGCGAAGA AACCCATCTG
2041  AGCGGGGGGT ACCTGCTGGA TTTTCTGGCC ATGCATCTGT GGAGAGCGGT GGTGAGACAC
2101  AAGAATCGCC TGCTACTGTT GTCTTCCGTC CGCCCGGCAA TAATACCGAC GGAGGAGCAA
2161  CAGCAGGAGG AAGCCAGGCG GCGGCGGCGG CAGGAGCAGA GCCCATGGAA CCCGAGAGCC
2221  GGCCTGGACC CTCGGGAATG AATGTTGTAC AGGTGGCTGA ACTGTTTCCA GAACTGAGAC
2281  GCATTTTAAC CATTAACGAG GATGGGCAGG GGCTAAAGGG GGTAAAGAAG GAGCGGGGGG
2341  CTTCTGAGGC TACAGAGGAG GCTAGGAATC TAACTTTTAG CTTAATGACC AGACACCGTC
2401  CTGAGTGTGT TACTTTTCAG CAGATTAAGG ATAATTGCGC TAATGAGCTT GATCTGCTGG
2461  CGCAGAAGTA TTCCATAGAG CAGCTGACCA CTTACTGGCT GCAGCCAGGG GATGATTTTG
```

FIG. 7A

```
2521 AGGAGGCTAT TAGGGTATAT GCAAAGGTGG CACTTAGGCC AGATTGCAAG TACAAGATTA
2581 GCAAACTTGT AAATATCAGG AATTGTTGCT ACATTTCTGG AACGGGGCC  GAGGTGGAGA
2641 TAGATACGGA GGATAGGGTG GCCTTTAGAT GTAGCATGAT AAATATGTGG CCGGGGGTGC
2701 TTGGCATGGA CGGGGTGGTT ATTATGAATG TGAGGTTTAC TGGTCCCAAT TTTAGCGGTA
2761 CGGTTTTCCT GGCCAATACC AATCTTATCC TACACGGTGT AAGCTTCTAT GGGTTTAACA
2821 ATACCTGTGT GGAAGCCTGG ACCGATGTAA GGGTTCGGGG CTGTGCCTTT TACTGCTGCT
2881 GGAAGGGGGT GGTGTGTCGC CCCAAAAGCA GGGCTTCAAT TAAGAAATGC CTGTTTGAAA
2941 GGTGTACCTT GGGTATCCTG TCTGAGGGTA ACTCCAGGGT GCGCCACAAT GTGGCCTCCG
3001 ACTGTGGTTG CTTTATGCTA GTGAAAGCG  TGGCTGTGAT TAAGCATAAC ATGGTGTGTG
3061 GCAACTGCGA GGACAGGGCC TCTCAGATGC TGACCTGCTC GGACGGCAAC TGTCACTTGC
3121 TGAAGACCAT TCACGTAGCC AGCCACTCTC GCAAGGCCTG GCCAGTGTTT GAGCACAACA
3181 TACTGACCCG CTGTTCCTTG CATTTGGGTA ACAGGAGGGG GGTGTTCCTA CCTTACCAAT
3241 GCAATTTGAG TCACACTAAG ATATTGCTTG AGCCCGAGAG CATGTCCAAG GTGAACCTGA
3301 ACGGGGTGTT TGACATGACC ATGAAGATCT GGAAGGTGCT GAGGTACGAT GAGACCCGCA
3361 CCAGGTGCAG ACCCTGCGAG TGTGGCGGTA AACATATTAG GAACCAGCCT GTGATGCTGG
3421 ATGTGACCGA GGAGCTGAGG CCCGATCACT TGGTGCTGGC CTGCACCCGC GCTGAGTTTG
3481 GCTCTAGCGA TGAAGATACA GATTGAGGTA CTGAAATGTG TGGGCGTGGC TTAAGGGTGG
3541 GAAAGAATAT ATAAGGTGGG GGTCTCATGT AGTTTTGTAT CTGTTTTGCA GCAGCCGCCG
3601 CCATGAGCGC CAACTCGTTT GATGGAAGCA TTGTGAGCTC ATATTTGACA ACGCGCATGC
3661 CCCCATGGGC CGGGGTGCGT CAGAATGTGA TGGGCTCCAG CATTGATGGT CGCCCCGTCC
3721 TGCCCGCAAA CTCTACTACC TTGACCTACG AGACCGTGTC TGGAACGCCG TTGGAGACTG
3781 CAGCCTCCGC CGCCGCTTCA GCCGCTGCAG CCACCGCCCG CGGGATTGTG ACTGACTTTG
3841 CTTTCCTGAG CCCGCTTGCA AGCAGTGCAG CTTCCCGTTC ATCCGCCCGC GATGACAAGT
3901 TGACGGCTCT TTTGGCACAA TTGGATTCTT TGACCCGGGA ACTTAATGTC GTTTCTCAGC
3961 AGCTGTTGGA TCTGCGCCAG CAGGTTTCTG CCCTGAAGGC TTCCTCCCCT CCCAATGCGG
4021 TTTAAAACAT AAATAAAAAC CAGACTCTGT TTGGATTTGG ATCAAGCAAG TGTCTTGCTG
4081 TCTTTATTTA GGGGTTTTGC GCGCGCGGTA GGCCCGGGAC CAGCGGTCTC GGTCGTTGAG
4141 GGTCCTGTGT ATTTTTTCCA GGACGTGGTA AAGGTGACTC TGGATGTTCA GATACATGGG
4201 CATAAGCCCG TCTCTGGGGT GGAGGTAGCA CCACTGCAGA GCTTCATGCT GCGGGGTGGT
4261 GTTGTAGATG ATCCAGTCGT AGCAGGAGCG CTGGGCGTGG TGCCTAAAAA TGTCTTTCAG
4321 TAGCAAGCTG ATTGCCAGGG GCAGGCCCTT GGTGTAAGTG TTTACAAAGC GGTTAAGCTG
4381 GGATGGGTGC ATACGTGGGG ATATGAGATG CATCTTGGAC TGTATTTTTA GGTTGGCTAT
4441 GTTCCCAGCC ATATCCCTCC GGGGATTCAT GTTGTGCAGA ACCACCAGCA CAGTGTATCC
4501 GGTGCACTTG GGAAATTTGT CATGTAGCTT AGAAGGAAAT GCGTGGAAGA ACTTGGAGAC
4561 GCCCTTGTGA CCTCCAAGAT TTTCCATGCA TTCGTCCATA ATGATGGCAA TGGGCCCACG
4621 GGCGGCGGCC TGGGCGAAGA TATTTCTGGG ATCACTAACG TCATAGTTGT GTTCCAGGAT
4681 GAGATCGTCA TAGGCCATTT TTACAAAGCG CGGGCGGAGG GTGCCAGACT GCGGTATAAT
4741 GGTTCCATCC GGCCCAGGGG CGTAGTTACC CTCACAGATT TGCATTTCCC ACGCTTTGAG
4801 TTCAGATGGG GGGATCATGT CTACCTGCGG GGCGATGAAG AAAACCGTTT CCGGGGTAGG
4861 GGAGATCAGC TGGAAGAAA  GCAGGTTCCT AAGCAGCTGC GACTTACCGC AGCCGGTGGG
4921 CCCGTAAATC ACACCTATTA CCGGCTGCAA CTGGTAGTTA AGAGAGCTGC AGCTGCCGTC
4981 ATCCCTGAGC AGGGGGGCCA CTTCGTTAAG CATGTCCCTG ACTTGCATGT TTTCCCTGAC
```

FIG. 7B

```
5041 CAAATCCGCC AGAAGGCGCT CGCCGCCCAG CGATAGCAGT TCTTGCAAGG AAGCAAAGTT
5101 TTTCAACGGT TTGAGGCCGT CCGCCGTAGG CATGCTTTTG AGCGTTTGAC CAAGCAGTTC
5161 CAGGCGGTCC CACAGCTCGG TCACGTGCTC TACGGCATCT CGATCCAGCA TATCTCCTCG
5221 TTTCGCGGGT TGGGCGGCT TTCGCTGTAC GGCAGTAGTC GGTGCTCGTC CAGACGGGCC
5281 AGGGTCATGT CTTTCCACGG GCGCAGGGTC CTCGTCAGCG TAGTCTGGGT CACGGTGAAG
5341 GGGTGCGCTC CGGGTTGCGC GCTGGCCAGG GTGCGCTTGA GGCTGGTCCT GCTGGTGCTG
5401 AAGCGCTGCC GGTCTTCGCC CTGCGCGTCG GCCAGGTAGC ATTTGACCAT GGTGTCATAG
5461 TCCAGCCCCT CCGCGGCGTG GCCCTTGGCG CGCAGCTTGC CCTTGGAGGA GGCGCCGCAC
5521 GAGGGGCAGT GCAGACTTTT AAGGGCGTAG AGCTTGGGCG CGAGAAATAC CGATTCCGGG
5581 GAGTAGGCAT CCGCGCCGCA GGCCCCGCAG ACGGTCTCGC ATTCCACGAG CCAGGTGAGC
5641 TCTGGCCGTT CGGGGTCAAA AACCAGGTTT CCCCCATGCT TTTTGATGCG TTTCTTACCT
5701 CTGGTTTCCA TGAGCCGGTG TCCACGCTCG GTGACGAAAA GGCTGTCCGT GTCCCCGTAT
5761 ACAGACTTGA GAGGCCTGTC CTCGAGCGGT GTTCCGCGGT CCTCCTCGTA TAGAAACTCG
5821 GACCACTCTG AGACGAAGGC TCGCGTCCAG GCCAGCACGA AGGAGGCTAA GTGGGAGGGG
5881 TAGCGGTCGT TGTCCACTAG GGGGTCCACT CGCTCCAGGG TGTGAAGACA CATGTCGCCC
5941 TCTTCGGCAT CAAGGAAGGT GATTGGTTTA TAGGTGTAGG CCACGTGACC GGGTGTTCCT
6001 GAAGGGGGGC TATAAAAGGG GGTGGGGGCG CGTTCGTCCT CACTCTCTTC CGCATCGCTG
6061 TCTGCGAGGG CCAGCTGTTG GGGTGAGTAC TCCCTCTCAA AAGCGGGCAT GACTTCTGCG
6121 CTAAGATTGT CAGTTTCCAA AAACGAGGAG GATTTGATAT TCACCTGGCC CGCGGTGATG
6181 CCTTTGAGGG TGGCCGCGTC CATCTGGTCA GAAAAGACAA TCTTTTTGTT GTCAAGCTTG
6241 GTGGCAAACG ACCCGTAGAG GGCGTTGGAC AGCAACTTGG CGATGGAGCG CAGGGTTTGG
6301 TTTTTGTCGC GATCGGCGCG CTCCTTGGCC GCGATGTTTA GCTGCACGTA TTCGCGCGCA
6361 ACGCACCGCC ATTCGGGAAA GACGGTGGTG CGCTCGTCGG GCACTAGGTG CACGCGCCAA
6421 CCGCGGTTGT GCAGGGTGAC AAGGTCAACG CTGGTGGCTA CCTCTCCGCG TAGGCGCTCG
6481 TTGGTCCAGC AGAGGCGGCC GCCCTTGCGC GAGCAGAATG GCGGTAGTGG GTCTAGCTGC
6541 GTCTCGTCCG GGGGTCTGC GTCCACGGTA AAGACCCCGG GCAGCAGGCG CGCGTCGAAG
6601 TAGTCTATCT TGCATCCTTG CAAGTCTAGC GCCTGCTGCC ATGCGCGGGC GGCAAGCGCG
6661 CGCTCGTATG GGTTGAGTGG GGGACCCCAT GGCATGGGGT GGGTGAGCGC GGAGGCGTAC
6721 ATGCCGCAAA TGTCGTAAAC GTAGAGGGGC TCTCTGAGTA TTCCAAGATA TGTAGGGTAG
6781 CATCTTCCAC CGCGGATGCT GGCGCGCACG TAATCGTATA GTTCGTGCGA GGGAGCGAGG
6841 AGGTCGGGAC CGAGGTTGCT ACGGGCGGGC TGCTCTGCTC GGAAGACTAT CTGCCTGAAG
6901 ATGGCATGTG AGTTGGATGA TATGGTTGGA CGCTGGAAGA CGTTGAAGCT GGCGTCTGTG
6961 AGACCTACCG CGTCACGCAC GAAGGAGGCG TAGGAGTCGC GCAGCTTGTT GACCAGCTCG
7021 GCGGTGACCT GCACGTCTAG GGCGCAGTAG TCCAGGGTTT CCTTGATGAT GTCATACTTA
7081 TCCTGTCCCT TTTTTTTCCA CAGCTCGCGG TTGAGGACAA ACTCTTCGCG GTCTTTCCAG
7141 TACTCTTGGA TCGGAAACCC GTCGGCCTCC GAACGGTAAG AGCCTAGCAT GTAGAACTGG
7201 TTGACGGCCT GGTAGGCGCA GCATCCCTTT TCTACGGGTA GCGCGTATGC CTGCGCGGCC
7261 TTCCGGAGCG AGGTGTGGGT GAGCGCAAAG GTGTCCCTAA CCATGACTTT GAGGTACTGG
7321 TATTTGAAGT CAGTGTCGTC GCATCCGCCC TGCTCCCAGA GCAAAAGTC CGTGCGCTTT
7381 TTGGAACGCG GGTTTGGCAG GGCGAAGGTG ACATCGTTGA AGAGTATCTT TCCCGCGCGA
7441 GGCATAAAGT TGCGTGTGAT GCGGAAGGGT CCCGGCACCT CGGAACGGTT GTTAATTACC
7501 TGGGCGGCGA GCACGATCTC GTCAAAGCCG TTGATGTTGT GGCCCACAAT GTAAAGTTCC
```

FIG. 7C

```
7561  AAGAAGCGCG GGATGCCCTT GATGGAAGGC AATTTTTTAA GTTCCTCGTA GGTGAGCTCT
7621  TCAGGGGAGC TGAGCCCGTG CTCTGAAAGG GCCCAGTCTG CAAGATGAGG GTTGGAAGCG
7681  ACGAATGAGC TCCACAGGTC ACGGGCCATT AGCATTTGCA GGTGGTCGCG AAAGGTCCTA
7741  AACTGGCGAC CTATGGCCAT TTTTTCTGGG GTGATGCAGT AGAAGGTAAG CGGGTCTTGT
7801  TCCCAGCGGT CCCATCCAAG GTCCGCGGCT AGGTCTCGCG CGGCGGTCAC TAGAGGCTCA
7861  TCTCCGCCGA ACTTCATGAC CAGCATGAAG GCACGAGCT GCTTCCCAAA GGCCCCATC
7921  CAAGTATAGG TCTCTACATC GTAGGTGACA AAGAGACGCT CGGTGCGAGG ATGCGAGCCG
7981  ATCGGGAAGA ACTGGATCTC CCGCCACCAG TTGGAGGAGT GGCTGTTGAT GTGGTGAAAG
8041  TAGAAGTCCC TGCGACGGGC CGAACACTCG TGCTGGCTTT TGTAAAAACG TGCGCAGTAC
8101  TGGCAGCGGT GCACGGGCTG TACATCCTGC ACGAGGTTGA CCTGACGACC GCGCACAAGG
8161  AAGCAGAGTG GGAATTTGAG CCCCTCGCCT GGCGGGTTTG GCTGGTGGTC TTCTACTTCG
8221  GCTGCTTGTC CTTGACCGTC TGGCTGCTCG AGGGGAGTTA CGGTGGATCG GACCACCACG
8281  CCGCGCGAGC CCAAAGTCCA GATGTCCGCG CGCGGCGGTC GGAGCTTGAT GACAACATCG
8341  CGCAGATGGG AGCTGTCCAT GGTCTGGAGC TCCCGCGGCG TCAGGTCAGG CGGGAGCTCC
8401  TGCAGGTTTA CCTCGCATAG CCGGGTCAGG GCGCGGGCTA GGTCCAGGTG ATACCTGATT
8461  TCCAGGGGCT GGTTGGTGGC GGCGTCGATG GCTTGCAAGA GGCCGCATCC CCGCGGCGCG
8521  ACTACGGTAC CGCGCGGCGG GCGGTGGGCC GCGGGGGTGT CCTTGGATGA TGCATCTAAA
8581  AGCGGTGACG CGGGCGGGCC CCCGGAGGTA GGGGGGGCTC GGGACCCGCC GGGAGAGGGG
8641  GCAGGGGCAC GTCGGCGCCG CGCGCGGGCA GGAGCTGGTG CTGCGCGCGG AGGTTGCTGG
8701  CGAACGCGAC GACGCGGCGG TTGATCTCCT GAATCTGGCG CCTCTGCGTG AAGACGACGG
8761  GCCCGGTGAG CTTGAACCTG AAAGAGAGTT CGACAGAATC AATTTCGGTG TCGTTGACGG
8821  CGGCCTGGCG CAAAATCTCC TGCACGTCTC CTGAGTTGTC TTGATAGGCG ATCTCGGCCA
8881  TGAACTGCTC GATCTCTTCC TCCTGGAGAT CTCCGCGTCC GGCTCGCTCC ACGGTGGCGG
8941  CGAGGTCGTT GGAGATGCGG GCCATGAGCT GCGAGAAGGC GTTGAGGCCT CCCTCGTTCC
9001  AGACGCGGCT GTAGACCACG CCCCCTTCGG CATCGCGGGC GCGCATGACC ACCTGCGCGA
9061  GATTGAGCTC CACGTGCCGG GCGAAGACGG CGTAGTTTCG CAGGCGCTGA AAGAGGTAGT
9121  TGAGGGTGGT GGCGGTGTGT CTGCCACGA AGAAGTACAT AACCCAGCGC CGCAACGTGG
9181  ATTCGTTGAT ATCCCCAAG GCCTCAAGGC GCTCCATGGC CTCGTAGAAG TCCACGGCGA
9241  AGTTGAAAAA CTGGGAGTTG CGCGCCGACA CGGTTAACTC CTCCTCCAGA AGACGGATGA
9301  GCTCGGCGAC AGTGTCGCGC ACCTCGCGCT CAAAGGCTAC AGGGGCCTCT TCTTCTTCTT
9361  CAATCTCCTC TTCCATAAGG GCCTCCCCTT CTTCTTCTTC TGGCGGCGGT GGGGGAGGGG
9421  GGACACGGCG GCGACGACGG CGCACCGGGA GGCGGTCGAC AAAGCGCTCG ATCATCTCCC
9481  CGCGGCGACG GCGCATGGTC TCGGTGACGG CGCGGCCGTT CTCGCGGGGG CGCAGTTGGA
9541  AGACGCCGCC CGTCATGTCC CGGTTATGGG TTGGCGGGGG GCTGCCGTGC GGCAGGGATA
9601  CGGCGCTAAC GATGCATCTC AACAATTGTT GTGTAGGTAC TCCGCCACCG AGGGACCTGA
9661  GCGAGTCCGC ATCGACCGGA TCGGAAAACC TCTCGAGAAA GGCGTCTAAC CAGTCACAGT
9721  CGCAAGGTAG GCTGAGCACC GTGGCGGGCG GCAGCGGGCG GCGGTCGGGG TTGTTTCTGG
9781  CGGAGGTGCT GCTGATGATG TAATTAAAGT AGGCGGTCTT GAGACGGCGG ATGGTCGACA
9841  GAAGCACCAT GTCCTTGGGT CCGGCCTGCT GAATGCGCAG GCGGTCGGCC ATGCCCCAGG
9901  CTTCGTTTTG ACATCGGCGC AGGTCTTTGT AGTAGTCTTG CATGAGCCTT TCTACCGGCA
9961  CTTCTTCTTC TCCTTCCTCT TGTCCTGCAT CTCTTGCATC TATCGCTGCG GCGGCGGCGG
10021 AGTTTGGCCG TAGGTGGCGC CCTCTTCCTC CCATGCGTGT GACCCCGAAG CCCCTCATCG
```

FIG. 7D

```
10081 GCTGAAGCAG GGCCAGGTCG GCGACAACGC GCTCGGCTAA TATGGCCTGC TGCACCTGCG
10141 TGAGGGTAGA CTGGAAGTCG TCCATGTCCA CAAAGCGGTG GTATGCGCCC GTGTTGATGG
10201 TGTAAGTGCA GTTGGCCATA ACGGACCAGT TAACGGTCTG GTGACCCGGC TGCGAGAGCT
10261 CGGTGTACCT GAGACGCGAG TAAGCCCTTG AGTCAAAGAC GTAGTCGTTG CAAGTCCGCA
10321 CCAGGTACTG GTATCCCACC AAAAAGTGCG GCGGCGGCTG GCGGTAGAGG GGCCAGCGTA
10381 GGGTGGCCGG GGCTCCGGGG GCGAGGTCTT CCAACATAAG GCGATGATAT CCGTAGATGT
10441 ACCTGGACAT CCAGGTGATG CCGGCGGCGG TGGTGGAGGC GCGCGGAAAG TCACGGACGC
10501 GGTTCCAGAT GTTGCGCAGC GGCAAAAAGT GCTCCATGGT CGGGACGCTC TGGCCGGTCA
10561 GGCGCGCGCA GTCGTTGACG CTCTAGACCG TGCAAAAGGA GAGCCTGTAA GCGGGCACTC
10621 TTCCGTGGTC TGGTGGATAA ATTCGCAAGG GTATCATGGC GGACGACCGG GGTTCGAACC
10681 CCGGATCCGG CCGTCCGCCG TGATCCATGC GGTTACCGCC CGCGTGTCGA ACCCAGGTGT
10741 GCGACGTCAG ACAACGGGGG AGCGCTCCTT TTGGCTTCCT TCCAGGCGCG GCGGATGCTG
10801 CGCTAGCTTT TTTGGCCACT GGCCGCGCGC GGCGTAAGCG GTTAGGCTGG AAAGCGAAAG
10861 CATTAAGTGG CTCGCTCCCT GTAGCCGGAG GGTTATTTTC CAAGGGTTGA GTCGCGGGAC
10921 CCCCGGTTCG AGTCTCGGGC CGGCCGGACT GCGGCGAACG GGGGTTTGCC TCCCCGTCAT
10981 GCAAGACCCC GCTTGCAAAT TCCTCCGGAA ACAGGGACGA GCCCCTTTTT TGCTTTTCCC
11041 AGATGCATCC GGTGCTGCGG CAGATGCGCC CCCCTCCTCA GCAGCGGCAA GAGCAAGAGC
11101 AGCGGCAGAC ATGCAGGGCA CCCTCCCCTT CTCCTACCGC GTCAGGAGGG GCAACATCCG
11161 CGGCTGACGC GGCGGCAGAT GGTGATTACG AACCCCGCGC GCGCCGGACC CGGCACTACT
11221 TGGACTTGGA GGAGGGCGAG GGCCTGGCGC GGCTAGGAGC GCCCTCTCCT GAGCGACACC
11281 CAAGGGTGCA GCTGAAGCGT GACACGCGCG AGGCGTACGT GCCGCGGCAG AACCTGTTTC
11341 GCGACCGCGA GGGAGAGGAG CCCGAGGAGA TGCGGGATCG AAAGTTCCAT GCAGGGCGCG
11401 AGTTGCGGCA TGGCCTGAAC CGCGAGCGGT TGCTGCGCGA GGAGGACTTT GAGCCCGACG
11461 CGCGGACCGG GATTAGTCCC GCGCGCGCAC ACGTGGCGGC CGCCGACCTG GTAACCGCGT
11521 ACGAGCAGAC GGTGAACCAG GAGATTAACT TTCAAAAAAG CTTTAACAAC CACGTGCGCA
11581 CGCTTGTGGC GCGCGAGGAG GTGGCTATAG GACTGATGCA TCTGTGGGAC TTTGTAAGCG
11641 CGCTGGAGCA AAACCCAAAT AGCAAGCCGC TCATGGCGCA GCTGTTCCTT ATAGTGCAGC
11701 ACAGCAGGGA CAACGAGGCA TTCAGGGATG CGCTGCTAAA CATAGTAGAG CCCGAGGGCC
11761 GCTGGCTGCT CGATTTGATA AACATTCTGC AGAGCATAGT GGTGCAGGAG CGCAGCTTGA
11821 GCCTGGCTGA CAAGGTGGCC GCCATTAACT ATTCCATGCT CAGTCTGGGC AAGTTTTACG
11881 CCCGCAAGAT ATACCATACC CCTTACGTTC CCATAGACAA GGAGGTAAAG ATCGAGGGGT
11941 TCTACATGCG CATGGCGCTG AAGGTGCTTA CCTTGAGCGA CGACCTGGGC GTTTATCGCA
12001 ACGAGCGCAT CCACAAGGCC GTGAGCGTGA GCCGGCGGCG CGAGCTCAGC GACCGCGAGC
12061 TGATGCACAG CCTGCAAAGG GCCCTGGCTG GCACGGGCAG CGGCGATAGA GAGGCCGAGT
12121 CCTACTTTGA CGCGGGCGCT GACCTGCGCT GGGCCCCAAG CCGACGCGCC CTGGAGGCAG
12181 CTGGGGCCGG ACCTGGGCTG CGGTGGCAC CCGCGCGCGC TGGCAACGTC GGCGGCGTGG
12241 AGGAATATGA CGAGGACGAT GAGTACGAGC CAGAGGACGG CGAGTACTAA GCGGTGATGT
12301 TTCTGATCAG ATGATGCAAG ACGCAACGGA CCCGGCGGTG CGGGCGGCGC TGCAGAGCCA
12361 GCCGTCCGGC CTTAACTCCA CGGACGACTG GCGCCAGGTC ATGGACCGCA TCATGTCGCT
12421 GACTGCGCGC AACCCTGACG CGTTCCGGCA GCAGCCGCAG GCCAACCGGC TCTCCGCAAT
12481 TCTGGAAGCG GTGGTCCCGG CGCGCGCAAA CCCCACGCAC GAGAAGGTGC TGGCGATCGT
12541 AAACGCGCTG GCCGAAAACA GGGCCATCCG GCCCGATGAG GCCGGCCTGG TCTACGACGC
```

FIG. 7E

```
12601 GCTGCTTCAG CGCGTGGCTC GTTACAACAG CAGCAACGTG CAGACCAACC TGGACCGGCT
12661 GGTGGGGGAT GTGCGCGAGG CCGTGGCGCA GCGTGAGCGC GCGCAGCAGC AGGGCAACCT
12721 GGGCTCCATG GTTGCACTAA ACGCCTTCCT GAGTACACAG CCCGCCAACG TGCCGCGGGG
12781 ACAGGAGGAC TACACCAACT TTGTGAGCGC ACTGCGGCTA ATGGTGACTG AGACACCGCA
12841 AAGTGAGGTG TATCAGTCCG GGCCAGACTA TTTTTTCCAG ACCAGTAGAC AAGGCCTGCA
12901 GACCGTAAAC CTGAGCCAGG CTTTCAAGAA CTTGCAGGGG CTGTGGGGGG TGCGGGCTCC
12961 CACAGGCGAC CGCGCGACCG TGTCTAGCTT GCTGACGCCC AACTCGCGCC TGTTGCTGCT
13021 GCTAATAGCG CCCTTCACGG ACAGTGGCAG CGTGTCCCGG GACACATACC TAGGTCACTT
13081 GCTGACACTG TACCGCGAGG CCATAGGTCA GGCGCATGTG GACGAGCATA CTTTCCAGGA
13141 GATTACAAGT GTTAGCCGCG CGCTGGGGCA GGAGGACACG GGCAGCCTGG AGGCAACCCT
13201 GAACTACCTG CTGACCAACC GGCGGCAAAA AATCCCCTCG TTGCACAGTT TAAACAGCGA
13261 GGAGGAGCGC ATTTTGCGCT ATGTGCAGCA GAGCGTGAGC CTTAACCTGA TGCGCGACGG
13321 GGTAACGCCC AGCGTGGCGC TGGACATGAC CGCGCGCAAC ATGGAACCGG GCATGTATGC
13381 CTCAAACCGG CCGTTTATCA ATCGCCTAAT GGACTACTTG CATCGCGCGG CCGCCGTGAA
13441 CCCCGAGTAT TTCACCAATG CCATCTTGAA CCCGCACTGG CTACCGCCCC CTGGTTTCTA
13501 CACCGGGGGA TTCGAGGTGC CGAGGGTAA CGATGGATTC CTCTGGGACG ACATAGACGA
13561 CAGCGTGTTT TCCCCGCAAC CGCAGACCCT GCTAGAGTTG CAACAACGCG AGCAGGCAGA
13621 GGCGGCGCTG CGAAAGGAAA GCTTCGCAG GCCAAGCAGC TTGTCCGATC TAGGCGCTGC
13681 GGCCCCGCGG TCAGATGCTA GTAGCCCATT TCCAAGCTTG ATAGGGTCTC TTACCAGCAC
13741 TCGCACCACC CGCCCGCGCC TGCTGGGCGA GGAGGAGTAC CTAAACAACT CGCTGCTGCA
13801 GCCGCAGCGC GAAAAGAACC TGCCTCCGGC GTTTCCCAAC AACGGGATAG AGAGCCTAGT
13861 GGACAAGATG AGTAGATGGA AGACGTATGC GCAGGAGCAC AGGGATGTGC CCGGCCCGCG
13921 CCCGCCCACC CGTCGTCAAA GGCACGACCG TCAGCGGGGT CTGGTGTGGG AGGACGATGA
13981 CTCGGCAGAC GACAGCAGCG TCTTGGATTT GGGAGGGAGT GGCAACCCGT TTGCACACCT
14041 TCGCCCCAGG CTGGGGAGAA TGTTTTAAAA AAAGCATGAT GCAAAATAAA AAACTCACCA
14101 AGGCCATGGC ACCGAGCGTT GGTTTTCTTG TATTCCCCTT AGTATGCGGC GCGCGGCGAT
14161 GTATGAGGAA GGTCCTCCTC CCTCCTACGA GAGCGTGGTG AGCGCGGCGC CAGTGGCGGC
14221 GGCGCTGGGT TCACCCTTCG ATGCTCCCCT GGACCCGCCG TTCGTGCCTC CGCGGTACCT
14281 GCGGCCTACC GGGGGGAGAA ACAGCATCCG TTACTCTGAG TTGGCACCCC TATTCGACAC
14341 CACCCGTGTG TACCTTGTGG ACAACAAGTC AACGGATGTG CATCCCTGA ACTACCAGAA
14401 CGACCACAGC AACTTTCTAA CCACGGTCAT TCAAAACAAT GACTACAGCC CGGGGGAGGC
14461 AAGCACACAG ACCATCAATC TTGACGACCG GTCGCACTGG GGCGGCGACC TGAAAACCAT
14521 CCTGCATACC AACATGCCAA ATGTGAACGA GTTCATGTTT ACCAATAAGT TTAAGGCGCG
14581 GGTGATGGTG TCGCGCTCGC TTACTAAGGA CAAACAGGTG GAGCTGAAAT ACGAGTGGGT
14641 GGAGTTCACG CTGCCCGAGG GCAACTACTC CGAGACCATG ACCATAGACC TTATGAACAA
14701 CGCGATCGTG GAGCACTACT TGAAAGTGGG CAGGCAGAAC GGGGTTCTGG AAAGCGACAT
14761 CGGGGTAAAG TTTGACACCC GCAACTTCAG ACTGGGGTTT GACCCAGTCA CTGGTCTTGT
14821 CATGCCTGGG GTATATACAA ACGAAGCCTT CCATCCAGAC ATCATTTTGC TGCCAGGATG
14881 CGGGGTGGAC TTCACCCACA GCCGCCTGAG CAACTTGTTG GGCATCCGCA GCGGCAACC
14941 CTTCCAGGAG GGCTTTAGGA TCACCTACGA TGACCTGGAG GGTGGTAACA TTCCCGCACT
15001 GTTGGATGTG GACGCCTACC AGGCAAGCTT GAAAGATGAC ACCGAACAGG GCGGGGGTGG
15061 CGCAGGCGGC GGCAACAACA GTGGCAGCGG CGCGGAAGAG AACTCCAACG CGGCAGCTGC
```

FIG. 7F

```
15121  GGCAATGCAG CCGGTGGAGG ACATGAACGA TCATGCCATT CGCGGCGACA CCTTTGCCAC
15181  ACGGGCGGAG GAGAAGCGCG CTGAGGCCGA GGCAGCGGCC GAAGCTGCCG CCCCCGCTGC
15241  GGAGGCTGCA CAACCCGAGG TCGAGAAGCC TCAGAAGAAA CCGGTGATTA AACCCCTGAC
15301  AGAGGACAGC AAGAAACGCA GTTACAACCT AATAAGCAAT GACAGCACCT TCACCCAGTA
15361  CCGCAGCTGG TACCTTGCAT ACAACTACGG CGACCCTCAG GCCGGGATCC GCTCATGGAC
15421  CCTGCTTTGC ACTCCTGACG TAACCTGCGG CTCGGAGCAG GTATACTGGT CGTTGCCCGA
15481  CATGATGCAA GACCCCGTGA CCTTCCGCTC CACGCGCCAG ATCAGCAACT TTCCGGTGGT
15541  GGGCGCCGAG CTGTTGCCCG TGCACTCCAA GAGCTTCTAC AACGACCAGG CCGTCTACTC
15601  CCAGCTCATC CGCCAGTTTA CCTCTCTGAC CCACGTGTTC AATCGCTTTC CGAGAACCA
15661  GATTTTGGCG CGCCCGCCAG CCCCCACCAT CACCACCGTC AGTGAAAACG TTCCTGCTCT
15721  CACAGATCAC GGGACGCTAC CGCTGCGCAA CAGCATCGGA GGAGTCCAGC GAGTGACCAT
15781  TACTGACGCC AGACGCCGCA CCTGCCCCTA CGTTTACAAG GCCCTGGGCA TAGTCTCGCC
15841  GCGCGTCCTA TCGAGCCGCA CTTTTTGAGC AAGCATGTCC ATCCTTATAT CGCCCAGCAA
15901  TAACACAGGC TGGGGCCTGC GCTTCCCAAG CAAGATGTTT GGCGGGGCCA AGAAGCGCTC
15961  CGACCAACAC CCAGTGCGCG TGCGCGGGCA CTACCGCGCG CCCTGGGGCG CGCACAAACG
16021  CGGCCGCACT GGGCGCACCA CCGTCGATGA CGCCATCGAC GCGGTGGTGG AGGAGGCGCG
16081  CAACTACACG CCCACGCCGC CGCCAGTGTC CACCGTGGAC GCGGCCATTC AGACCGTGGT
16141  GCGCGGAGCC CGGCGCTACG CTAAAATGAA GAGACGGCGG AGGCGCGTAG CACGTCGCCA
16201  CCGCCGCCGA CCCGGCACTG CCGCCCAACG CGGCGGCGGC GCCCTGCTTA ACCGCGCACG
16261  TCGCACCGGC CGACGGGCGG CCATGCGAGC CGCTCGAAGG CTGGCCGCGG GTATTGTCAC
16321  TGTGCCCCCC AGGTCCAGGC GACGAGCGGC CGCCGCAGCA GCCGCGGCCA TTAGTGCTAT
16381  GACTCAGGGT CGCAGGGGCA ACGTGTACTG GGTGCGCGAC TCGGTTAGCG GCCTGCGCGT
16441  GCCCGTGCGC ACCCGCCCCC CGCGCAACTA GATTGCAATA AAAAACTACT TAGACTCGTA
16501  CTGTTGTATG TATCCAGCGG CGGCGGCGCG CATCGAAGCT ATGTCCAAGC GCAAAATCAA
16561  AGAAGAGATG CTCCAGGTCA TCGCGCCGGA GATCTATGGC CCCCCGAAGA AGGAAGAGCA
16621  GGATTACAAG CCCCGAAAGC TAAAGCGGGT CAAAAAGAAA AGAAAGATG ATGATGATGA
16681  TGAACTTGAC GACGAGGTGG AACTGTTGCA CGCGACCGCG CCCAGGCGAC GGGTACAGTG
16741  GAAAGGTCGA CGCGTAAGAC GTGTTTTGCG ACCCGGCACC ACCGTAGTCT TTACGCCCGG
16801  TGAGCGCTCC ACCCGCACCT ACAAGCGCGT GTATGATGAG GTGTACGGCG ACGAGGACCT
16861  GCTTGAGCAG GCCAACGAGC GCCTCGGGGA GTTTGCCTAC GGAAAGCGGC ATAAGGACAT
16921  GCTGGCGTTG CCGCTGGACG AGGGCAACCC AACACCTAGC CTAAAGCCCG TGACACTGCA
16981  GCAGGTGCTG CCCGCGCTTG CACCGTCCGA AGAAAAGCGC GGCCTAAAGC GCGAGTCTGG
17041  TGACTTGGCA CCCACCGTGC AGCTGATGGT ACCCAAGCGT CAGCGACTGG AAGATGTCTT
17101  GGAAAAAATG ACCGTGGAGC CTGGGCTGGA GCCCGAGGTC CGCGTGCGGC AATCAAGCA
17161  GGTGGCACCG GGACTGGGCG TGCAGACCGT GGACGTTCAG ATACCCACCA CCAGTAGCAC
17221  TAGTATTGCC ACTGCCACAG AGGGCATGGA GACACAAACG TCCCCGGTTG CCTCGGCGGT
17281  GGCAGATGCC GCGGTGCAGG CGGCCGCTGC GGCCGCGTCC AAGACCTCTA CGGAGGTGCA
17341  AACGGACCCG TGGATGTTTC GTGTTTCAGC CCCCCGGCGT CCGCGCCGTT CAAGGAAGTA
17401  CGGCGCCGCC AGCGCGCTAC TGCCCGAATA TGCCCTACAT CCTTCCATCG CGCCTACCCC
17461  CGGCTATCGT GGCTACACCT ACCGCCCCAG AAGACGAGCA ACTACCCGAC GCCGAACCAC
17521  CACTGGAACC CGCCGCCGCC GTCGCCGTCG CCAGCCCGTG CTGGCCCCGA TTTCCGTGCG
17581  CAGGGTGGCT CGCGAAGGAG CAGGACCCT GGTGCTGCCA CAGCGCGCT ACCACCCCAG
```

FIG. 7G

17641 CATCGTTTAA AAGCCGGTCT TTGTGGTTCT TGCAGATATG GCCCTCACCT GCCGCCTCCG
17701 TTTCCCGGTG CCGGGATTCC GAGGAAGAAT GCACCGTAGG AGGGGCATGG CCGGCCACGG
17761 CCTGACGGGC GGCATGCGTC GTGCGCACCA CCGGCGGCGG CGCGCGTCGC ACCGTCGCAT
17821 GCGCGGCGGT ATCCTGCCCC TCCTTATTCC ACTGATCGCC GCGGCGATTG GCGCCGTGCC
17881 CGGAATTGCA TCCGTGGCCT TGCAGGCGCA GAGACACTGA TTAAAAACAA GTTACATGTG
17941 GAAAAATCAA AATAAAAGTC TGGACTCTCA CGCTCGCTTG GTCCTGTAAC TATTTTGTAG
18001 AATGGAAGAC ATCAACTTTG CGTCACTGGC CCCGCGACAC GGCTCGCGCC CGTTCATGGG
18061 AAACTGGCAA GATATCGGCA CCAGCAATAT GAGCGGTGGC GCCTTCAGCT GGGGCTCGCT
18121 GTGGAGCGGC ATTAAAAATT TCGGTTCCGC CGTTAAGAAC TATGGCAGCA AAGCCTGGAA
18181 CAGCAGCACA GGCCAGATGC TGAGGGACAA GTTGAAAGAG CAAAATTTCC AACAAAAGGT
18241 GGTAGATGGC CTGGCCTCTG GCATTAGCGG GGTGGTGGAC CTGGCCAACC AGGCAGTGCA
18301 AAATAAGATT AACAGTAAGC TTGATCCCCG CCCTCCCGTA GAGGAGCCTC CACCGGCCGT
18361 GGAGACAGTG TCTCCAGAGG GGCGTGGCGA AAAGCGTCCG CGACCCGACA GGGAAGAAAC
18421 TCTGGTGACG CAAATAGACG AGCCTCCCTC GTACGAGGAG GCACTAAAGC AAGGCCTGCC
18481 CACCACCCGT CCCATCGCGC CCATGGCTAC CGGAGTGCTG GGCCAGCACA CACCCGTAAC
18541 GCTGGACCTG CCTCCCCCCG CCGACACCCA GCAGAAACCT GTGCTGCCAG GCCCGTCCGC
18601 CGTTGTTGTA ACCCGTCCTA GCCGCGCGTC CCTGCGCCGC GCCGCCAGCG GTCCGCGATC
18661 GTTGCGGCCC GTAGCCAGTG GCAACTGGCA AAGCACACTG AACAGCATCG TGGGTTTGGG
18721 GGTGCAATCC CTGAAGCGCC GACGATGCTT CTGATAGCTA ACGTGTCGTA TGTGTGTCAT
18781 GTATGCGTCC ATGTCGCCGC CAGAGGAGCT GCTGAGCCGC CGCGCGCCCG CTTTCCAAGA
18841 TGGCTACCCC TTCGATGATG CCGCAGTGGT CTTACATGCA CATCTCGGGC AGGACGCCT
18901 CGGAGTACCT GAGCCCCGGG CTGGTGCAGT TCGCCCGCGC CACCGAGACG TACTTCAGCC
18961 TGAATAACAA GTTTAGAAAC CCCACGGTGG CGCCTACGCA CGACGTGACC ACAGACCGGT
19021 CTCAGCGTTT GACGCTGCGG TTCATCCCCG TGGACCGCGA GGATACTGCG TACTCGTACA
19081 AGGCGCGGTT CACCCTAGCT GTGGGTGATA ACCGTGTGCT AGACATGGCT TCCACGTACT
19141 TTGACATCCG CGGCGTGCTG GACAGGGGCC CTACTTTTAA GCCCTACTCT GGCACTGCCT
19201 ACAACGCACT GGCCCCCAAG GGTGCCCCCA ACTCGTGCGA GTGGGAACAA AATGAAACTG
19261 CACAAGTGGA TGCTCAAGAA CTTGACGAAG AGGAGAATGA AGCCAATGAA GCTCAGGCGC
19321 GAGAACAGGA ACAAGCTAAG AAAACCCATG TATATGCCCA GGCTCCACTG TCCGGAATAA
19381 AAATAACTAA AGAAGGTCTA CAAATAGGAA CTGCCGACGC CACAGTAGCA GGTGCCGGCA
19441 AAGAAATTTT CGCAGACAAA ACTTTTCAAC CTGAACCACA AGTAGGAGAA TCTCAATGGA
19501 ACGAAGCGGA TGCCACAGCA GCTGGTGGAA GGGTTCTTAA AAAGACAACT CCCATGAAAC
19561 CCTGCTATGG CTCATACGCT AGACCACCA ATTCCAACGG CGGACAGGGC GTTATGGTTG
19621 AACAAAATGG TAAATTGGAA AGTCAAGTCG AAATGCAATT TTTTTCCACA TCCACAAATG
19681 CCACAAATGA AGTTAACAAT ATACAACCAA CAGTTGTATT GTACAGCGAA GATGTAAACA
19741 TGGAAACTCC AGATACTCAT CTTTCTTATA AACCTAAAAT GGGGGATAAA AATGCCAAAG
19801 TCATGCTTGG ACAACAAGCA ATGCCAAACA GACCAAATTA CATTGCTTTT AGAGACAATT
19861 TTATTGGTCT CATGTATTAC AACAGCACAG GTAACATGGG TGTCCTTGCT GGTCAGGCAT
19921 CGCAGTTGAA CGCTGTTGTA GATTTGCAAG ACAGAAACAC AGAGCTGTCC TACCAGCTTT
19981 TGCTTGATTC AATTGGCGAC AGAACAAGAT ACTTTTCAAT GTGGAATCAA GCTGTTGACA
20041 GCTATGATCC AGATGTCAGA ATTATTGAGA ACCATGGAAC TGAGGATGAG TTGCCAAATT
20101 ATTGCTTTCC TCTTGGTGGA ATTGGGATTA CTGACACTTT TCAAGCTGTT AAAACAACTG

FIG. 7H

```
20161 CTGCTAACGG GGACCAAGGC AATACTACCT GGCAAAAAGA TTCAACATTT GCAGAACGCA
20221 ATGAAATAGG GGTGGGAAAT AACTTTGCCA TGGAAATTAA CCTGAATGCC AACCTATGGA
20281 GAAATTTCCT TTACTCCAAT ATTGCGCTGT ACCTGCCAGA CAAGCTAAAA TACAACCCCA
20341 CCAATGTGGA AATATCTGAC AACCCCAACA CCTACGACTA CATGAACAAG CGAGTGGTGG
20401 CTCCTGGGCT TGTAGACTGC TACATTAACC TTGGGGCGCG CTGGTCTCTG GACTACATGG
20461 ACAACGTTAA TCCCTTTAAC CACCACCGCA ATGCGGGCCT GCGTTACCGC TCCATGTTGT
20521 TGGGAAACGG CCGCTACGTG CCCTTTCACA TTCAGGTGCC CCAAAAGTTT TTTGCCATTA
20581 AAAACCTCCT CCTCCTGCCA GGCTCATACA CATATGAATG GAACTTCAGG AAGGATGTTA
20641 ACATGGTTCT GCAGAGCTCT CTGGGAAACG ACCTTAGAGT TGACGGGGCT AGCATTAAGT
20701 TTGACAGCAT TTGTCTTTAC GCCACCTTCT TCCCCATGGC CCACAACACG GCCTCCACGC
20761 TGGAAGCCAT GCTCAGAAAT GACACCAACG ACCAGTCCTT TAATGACTAC CTTTCCGCCG
20821 CCAACATGCT ATATCCCATA CCCGCCAACG CCACCAACGT GCCCATCTCC ATCCATCGC
20881 GCAACTGGGC AGCATTTCGC GGTTGGGCCT TCACACGCTT GAAGACAAAG GAAACCCCTT
20941 CCCTGGGATC AGGCTACGAC CCTTACTACA CCTACTCTGG CTCCATACCA TACCTTGACG
21001 GAACCTTCTA TCTTAATCAC ACCTTTAAGA AGGTGGCCAT TACTTTTGAC TCTTCTGTTA
21061 GCTGGCCGGG CAACGACCGC CTGCTTACTC CCAATGAGTT TGAGATTAAG CGCTCAGTTG
21121 ACGGGGAGGG CTATAACGTA GCTCAGTGCA ACATGACAAA GGACTGGTTC CTAGTGCAGA
21181 TGTTGGCCAA CTACAATATT GGCTACCAGG GCTTCTACAT TCCAGAAAGC TACAAAGACC
21241 GCATGTACTC GTTCTTCAGA AACTTCCAGC CCATGAGCCG GCAAGTGGTG GACGATACTA
21301 AATACAAAGA TTATCAGCAG GTTGGAATTA TCCACCAGCA TAACAACTCA GGCTTCGTAG
21361 GCTACCTCGC TCCCACCATG CGCGAGGGAC AAGCTTACCC CGCTAATGTT CCCTACCCAC
21421 TAATAGGCAA AACCGCGGTT GATAGTATTA CCCAGAAAAA GTTTCTTTGC GACCGCACCC
21481 TGTGGCGCAT CCCCTTCTCC AGTAACTTTA TGTCCATGGG TGCGCTCACA GACCTGGGCC
21541 AAAACCTTCT CTACGCAAAC TCCGCCCACG CGCTAGACAT GACCTTTGAG GTGGATCCCA
21601 TGGACGAGCC CACCCTTCTT TATGTTTTGT TTGAAGTCTT TGACGTGGTC CGTGTGCACC
21661 AGCCGCACCG CGGCGTCATC GAGACCGTGT ACCTGCGCAC GCCCTTCTCG GCCGGCAACG
21721 CCACAACATA AAGAAGCAAG CAACATCAAC AACAGCTGCC GCCATGGGCT CCAGTGAGCA
21781 GGAACTGAAA GCCATTGTCA AAGATCTTGG TTGTGGGCCA TATTTTTTGG GCACCTATGA
21841 CAAGCGCTTC CCAGGCTTTG TTTCCCCACA CAAGCTCGCC TGCGCCATAG TTAACACGGC
21901 CGGTCGCGAG ACTGGGGGCG TACACTGGAT GGCCTTTGCC TGGAACCCGC GCTCAAAAAC
21961 ATGCTACCTC TTTGAGCCCT TTGGCTTTTC TGACCAACGT CTCAAGCAGG TTTACCAGTT
22021 TGAGTACGAG TCACTCCTGC GCCGTAGCGC CATTGCCTCT TCCCCCGACC GCTGTATAAC
22081 GCTGGAAAAG TCCACCCAAA GCGTGCAGGG GCCCAACTCG GCCGCCTGTG GCCTATTCTG
22141 CTGCATGTTT CTCCACGCCT TTGCCAACTG GCCCCAAACT CCCATGGATC ACAACCCCAC
22201 CATGAACCTT ATTACCGGGG TACCCAACTC CATGCTTAAC AGTCCCCAGG TACAGCCCAC
22261 CCTGCGCCGC AACCAGGAAC AGCTCTACAG CTTCCTGGAG CGCCACTCGC CTACTTCCG
22321 CAGCCACAGT GCGCAAATTA GGAGCGCCAC TTCTTTTGT CACTTGAAAA ACATGTAAAA
22381 ATAATGTACT AGGAGACACT TTCAATAAAG GCAAATGTTT TTATTTGTAC ACTCTCGGGT
22441 GATTATTTAC CCCCACCCTT GCCGTCTGCG CCGTTTAAAA ATCAAAGGGG TTCTGCCGCG
22501 CATCGCTATG CGCCACTGGC AGGGACACGT TGCGATACTG GTGTTTAGTG CTCCACTTAA
22561 ACTCAGGCAC AACCATCCGC GGCAGCTCGG TGAAGTTTTC ACTCCACAGG CTGCGCACCA
22621 TCACCAACGC GTTTAGCAGG TCGGGCGCCG ATATCTTGAA GTCGCAGTTG GGGCCTCCGC
```

FIG. 71

22681 CCTGCGCGCG CGAGTTGCGA TACACAGGGT TACAGCACTG GAACACTATC AGCGCCGGGT
22741 GGTGCACGCT GGCCAGCACG CTCTTGTCGG AGATCAGATC CGCGTCCAGG TCCTCCGCGT
22801 TGCTCAGGGC GAACGGAGTC AACTTTGGTA GCTGCCTTCC CAAAAAGGGT GCATGCCCAG
22861 GCTTTGAGTT GCACTCGCAC CGTAGTGGCA TCAGAAGGTG ACCGTGCCCA GTCTGGGCGT
22921 TAGGATACAG CGCCTGCATG AAAGCCTTGA TCTGCTTAAA AGCCACCTGA GCCTTTGCGC
22981 CTTCAGAGAA GAACATGCCG CAAGACTTGC CGGAAAACTG ATTGGCCGGA CAGGCCGCGT
23041 CATGCACGCA GCACCTTGCG TCGGTGTTGG AGATCTGCAC CACATTTCGG CCCCACCGGT
23101 TCTTCACGAT CTTGGCCTTG CTAGACTGCT CCTTCAGCGC GCGCTGCCCG TTTTCGCTCG
23161 TCACATCCAT TTCAATCACG TGCTCCTTAT TTATCATAAT GCTCCCGTGT AGACACTTAA
23221 GCTCGCCTTC GATCTCAGCG CAGCGGTGCA GCCACAACGC GCAGCCCGTG GGCTCGTGGT
23281 GCTTGTAGGT TACCTCTGCA AACGACTGCA GGTACGCCTG CAGGAATCGC CCATCATCG
23341 TCACAAAGGT CTTGTTGCTG GTGAAGGTCA GCTGCAACCC GCGGTGCTCC TCGTTTAGCC
23401 AGGTCTTGCA TACGGCCGCC AGAGCTTCCA CTTGGTCAGG CAGTAGCTTG AAGTTTGCCT
23461 TTAGATCGTT ATCCACGTGG TACTTGTCCA TCAACGCGCG CGCAGCCTCC ATGCCCTTCT
23521 CCCACGCAGA CACGATCGGC AGGCTCAGCG GGTTTATCAC CGTGCTTTCA CTTTCCGCTT
23581 CACTGGACTC TTCCTTTTCC TCTTGCATCC GCATACCCCG CGCCACTGGG TCGTCTTCAT
23641 TCAGCCGCCG CACCGTGCGC TTACCTCCCT TGCCGTGCTT GATTAGCACC GGTGGGTTGC
23701 TGAAACCCAC CATTTGTAGC GCCACATCTT CTCTTTCTTC CTCGCTGTCC ACGATCACCT
23761 CTGGGGATGG CGGGCGCTCG GGCTTGGGAG AGGGGCGCTT CTTTTTCTTT TTGGACGCAA
23821 TGGCCAAATC CGCCGTCGAG GTCGATGGCC GCGGGCTGGG TGTGCGCGGC ACCAGCGCAT
23881 CTTGTGACGA GTCTTCTTCG TCCTCGGACT CGAGACGCCG CCTCAGCCGC TTTTTTGGGG
23941 GCGCGCGGGG AGGCGGCGGC GACGGCGACG GGGACGAGAC GTCCTCCATG GTTGGTGGAC
24001 GTCGCGCCGC ACCGCGTCCG CGCTCGGGGG TGGTTTCGCG CTGCTCCTCT TCCCGACTGG
24061 CCATTTCCTT CTCCTATAGG CAGAAAAAGA TCATGGAGTC AGTCGAGAAG GAGGACAGCC
24121 TAACCGCCCC CTTTGAGTTC GCCACCACCG CCTCCACCGA TGCCGCCAAC GCGCCTACCA
24181 CCTTCCCCGT CGAGGCACCC CCGCTTGAGG AGGAGGAAGT GATTATCGAG CAGGACCCAG
24241 GTTTTGTAAG CGAAGACGAC GAAGATCGCT CAGTACCAAC AGAGGATAAA AAGCAAGACC
24301 AGGACGACGC AGAGGCAAAC GAGGAACAAG TCGGGCGGGG GGACCAAAGG CATGGCGACT
24361 ACCTAGATGT GGGAGACGAC GTGCTGTTGA AGCATCTGCA GCGCCAGTGC GCCATTATCT
24421 GCGACGCGTT GCAAGAGCGC AGCGATGTGC CCCTCGCCAT AGCGGATGTC AGCCTTGCCT
24481 ACGAACGCCA CCTGTTCTCA CCGCGCGTAC CCCCCAAACG CCAAGAAAAC GGCACATGCG
24541 AGCCCAACCC GCGCCTCAAC TTCTACCCCG TATTTGCCGT GCCAGAGGTG CTTGCCACCT
24601 ATCACATCTT TTTCCAAAAC TGCAAGATAC CCCTATCCTG CCGTGCCAAC CGCAGCCGAG
24661 CGGACAAGCA GCTGGCCTTG CGGCAGGGCG CTGTCATACC TGATATCGCC TCGCTCGACG
24721 AAGTGCCAAA AATCTTTGAG GGTCTTGGAC GCGACGAGAA GCGCGCGGCA AACGCTCTGC
24781 AACAAGAAAA CAGCGAAAAT GAAAGTCACT GTGGAGTGCT GGTGGAACTT GAGGGTGACA
24841 ACGCGCGCCT AGCCGTGCTG AAACGCAGCA TCGAGGTCAC CCACTTTGCC TACCCGGCAC
24901 TTAACCTACC CCCCAAGGTT ATGAGCACAG TCATGAGCGA GCTGATCGTG CGCCGTGCAC
24961 GACCCCTGGA GAGGGATGCA AACTTGCAAG AACAAACCGA GGAGGGCCTA CCCGCAGTTG
25021 GCGATGAGCA GCTGGCGCGC TGGCTTGAGA CGCGCGAGCC TGCCGACTTG GAGGAGCGAC
25081 GCAAGCTAAT GATGGCCGCA GTGCTTGTTA CCGTGGAGCT TGAGTGCATG CAGCGGTTCT
25141 TTGCTGACCC GGAGATGCAG CGCAAGCTAG AGGAAACGTT GCACTACACC TTTCGCCAGG

FIG. 7J

```
25201 GCTACGTGCG CCAGGCCTGC AAAATTTCCA ACGTGGAGCT CTGCAACCTG GTCTCCTACC
25261 TTGGAATTTT GCACGAAAAC CGCCTTGGGC AAAACGTGCT TCATTCCACG CTCAAGGGCG
25321 AGGCGCGCCG CGACTACGTC CGCGACTGCG TTTACTTATT TCTGTGCTAC ACCTGGCAAA
25381 CGGCCATGGG CGTGTGGCAG CAGTGCCTGG AGGAGCGCAA CCTGAAGGAG CTGCAGAAGC
25441 TGCTAAAGCA AAACTTGAAG GACCTATGGA CGGCCTTCAA CGAGCGCTCC GTGGCCGCGC
25501 ACCTGGCGGA CATTATCTTC CCCGAACGCC TGCTTAAAAC CCTGCAACAG GGTCTGCCAG
25561 ACTTCACCAG TCAAAGCATG TTGCAAAACT TTAGGAACTT TATCCTAGAG CGTTCAGGAA
25621 TTCTGCCCGC CACCTGCTGT GCGCTTCCTA GCGACTTTGT GCCCATTAAG TACCGTGAAT
25681 GCCCTCCGCC GCTTTGGGGT CACTGCTACC TTCTGCAGCT AGCCAACTAC CTTGCCTACC
25741 ACTCCGACAT CATGGAAGAC GTGAGCGGTG ACGGCCTACT GGAGTGTCAC TGTCGCTGCA
25801 ACCTATGCAC CCCGCACCGC TCCCTGGTCT GCAATTCACA ACTGCTTAGC GAAAGTCAAA
25861 TTATCGGTAC CTTTGAGCTG CAGGGTCCCT CGCCTGACGA AAAGTCCGCG GCTCCGGGGT
25921 TGAAACTCAC TCCGGGGCTG TGGACGTCGG CTTACCTTCG CAAATTTGTA CCTGAGGACT
25981 ACCACGCCCA CGAGATTAGG TTCTACGAAG ACCAATCCCG CCCGCCAAAT GCGGAGCTTA
26041 CCGCCTGCGT CATTACCCAG GGCCACATCC TTGGCCAATT GCAAGCCATT AACAAAGCCC
26101 GCCAAGAGTT TCTGCTACGA AAGGGACGGG GGGTTTACTT GGACCCCCAG TCCGGCGAGG
26161 AGCTCAACCC AATCCCCCCG CCGCCGCAGC CCTATCAGCA GCCGCGGGCC CTTGCTTCCC
26221 AGGATGGCAC CCAAAAAGAA GCTGCAGCTG CCGCCGCCGC CACCCACGGA CGAGGAGGAA
26281 TACTGGGACA GTCAGGCAGA GGAGGTTTTG GACGAGGAGG AGGAGATGAT GGAAGACTGG
26341 GACAGCCTAG ACGAGGAAGC TTCCGAGGCC GAAGAGGTGT CAGACGAAAC ACCGTCACCC
26401 TCGGTCGCAT TCCCCTCGCC GGCGCCCCAG AAATCGGCAA CCGTTCCCAG CATTGCTACA
26461 ACCTCCGCTC CTCAGGCGCC GCCGGCACTG CCCGTTCGCC GACCCAACCG TAGATGGGAC
26521 ACCACTGGAA CCAGGGCCGG TAAGTCTAAG CAGCCGCCGC CGTTAGCCCA AGAGCAACAA
26581 CAGCGCCAAG GCTACCGCTC GTGGCGCGTG CACAAGAACG CCATAGTTGC TTGCTTGCAA
26641 GACTGTGGGG GCAACATCTC CTTCGCCCGC CGCTTTCTTC TCTACCATCA CGGCGTGGCC
26701 TTCCCCCGTA ACATCCTGCA TTACTACCGT CATCTCTACA GCCCCTACTG CACCGGCGGG
26761 AGCGGCAGCA ACAGCAGCGG CCACGCAGAA GCAAAGGCGA CCGGATAGCA AGACTCTGAC
26821 AAAGCCCAAG AAATCCACAG CGGCGGCAGC AGCAGGAGGA GGAGCACTGC GTCTGGCGCC
26881 CAACGAACCC GTATCGACCC GCGAGCTTAG AAACAGGATT TTTCCCACTC TGTATGCTAT
26941 ATTTCAACAG AGCAGGGGCC AAGAACAAGA GCTGAAAATA AAAACAGGT CTCTGCGCTC
27001 CCTCACCCGC AGCTGCCTGT ATCACAAAAG CGAAGATCAG CTTCGGCGCA CGCTGGAAGA
27061 CGCGGAGGCT CTCTTCAGCA AATACTGCGC GCTGACTCTT AAGGACTAGT TTCGCGCCCT
27121 TTCTCAAATT TAAGCGCGAA AACTACGTCA TCTCCAGCGG CCACACCCGG CGCCAGCACC
27181 TGTCGTCAGC GCCATTATGA GCAAGGAAAT TCCCACGCCC TACATGTGGA GTTACCAGCC
27241 ACAAATGGGA CTTGCGGCTG GAGCTGCCCA AGACTACTCA ACCCGAATAA ACTACATGAG
27301 CGCGGGACCC CACATGATAT CCCGGGTCAA CGGAATCCGC GCCCACCGAA ACCGAATTCT
27361 CCTCGAACAG GCGGCTATTA CCACCACACC TCGTAATAAC CTTAATCCCC GTAGTTGGCC
27421 CGCTGCCCTG GTGTACCAGG AAAGTCCCGC TCCCACCACT GTGGTACTTC CCAGAGACGC
27481 CCAGGCCGAA GTTCAGATGA CTAACTCAGG GGCGCAGCTT GCGGCGGCT TCGTCACAG
27541 GGTGCGGTCG CCCGGGCAGG GTATAACTCA CCTGAAAATC AGAGGGCGAG GTATTCAGCT
27601 CAACGACGAG TCGGTGAGCT CCTCTCTTGG TCTCCGTCCG GACGGGACAT TTCAGATCGG
27661 CGGCGCTGGC CGCTCTTCAT TTACGCCCCG TCAGGCGATC CTAACTCTGC AGACCTCGTC
```

FIG. 7K

```
27721 CTCGGAGCCG CGCTCCGGAG GCATTGGAAC TCTACAATTT ATTGAGGAGT TCGTGCCTTC
27781 GGTTTACTTC AACCCCTTTT CTGGACCTCC CGGCCACTAC CCGGACCAGT TTATTCCCAA
27841 CTTTGACGCG GTAAAAGACT CGGCGGACGG CTACGACTGA ATGACCAGTG GAGAGGCAGA
27901 GCAACTGCGC CTGACACACC TCGACCACTG CCGCCGCCAC AAGTGCTTTG CCCGCGGCTC
27961 CGGTGAGTTT TGTTACTTTG AATTGCCCGA AGAGCATATC GAGGGCCCGG CGCACGGCGT
28021 CCGGCTCACC ACCCAGGTAG AGCTTACACG TAGCCTGATT CGGGAGTTTA CCAAGCGCCC
28081 CCTGCTAGTG GAGCGGGAGC GGGGTCCCTG TGTTCTGACC GTGGTTTGCA ACTGTCCTAA
28141 CCCTGGATTA CATCAAGATC TTTGTTGTCA TCTCTGTGCT GAGTATAATA AATACAGAAA
28201 TTAGAATCTA CTGGGGCTCC TGTCGCCATC CTGTGAACGC CACCGTTTTT ACCCACCCAA
28261 AGCAGACCAA AGCAAACCTC ACCTCCGGTT TGCACAAGCG GGCCAATAAG TACCTTACCT
28321 GGTACTTTAA CGGCTCTTCA TTTGTAATTT ACAACAGTTT CCAGCGAGAC GAAGTAAGTT
28381 TGCCACACAA CCTTCTCGGC TTCAACTACA CCGTCAAGAA AAACACCACC ACCACCCTCC
28441 TCACCTGCCG GGAACGTACG AGTGCGTCAC CGGTTGCTGC GCCCACACCT ACAGCCTGAG
28501 CGTAACCAGA CATTACTCCC ATTTTCCCAA AACAGGAGGT GAGCTCAACT CCCGGAACTC
28561 AGGTCAAAAA AGCATTTTGC GGGGTGCTGG GATTTTTAA TTAAGTATAT GAGCAATTCA
28621 AGTAACTCTA CAAGCTTGTC TAATTTTTCT GGAATTGGGG TCGGGGTTAT CCTTACTCTT
28681 GTAATTCTGT TTATTCTTAT ACTAGCACTT CTGTGCCTTA GGGTTGCCGC CTGCTGCACG
28741 CACGTTTGTA CCTATTGTCA GCTTTTAAA CGCTGGGGGC GACATCCAAG ATGAGGTACA
28801 TGATTTTAGG CTTGCTCGCC CTTGCGGCAG TCTGCAGCGC TGCCAAAAAG GTTGAGTTTA
28861 AGGAACCAGC TTGCAATGTT ACATTTAAAT CAGAAGCTAA TGAATGCACT ACTCTTATAA
28921 AATGCACCAC AGAACATGAA AAGCTTATTA TTCGCCACAA AGACAAAATT GGCAAGTATG
28981 CTGTATATGC TATTTGGCAG CCAGGTGACA CTAACGACTA TAATGTCACA GTCTTCCAAG
29041 GTGAAAATCG TAAAACTTTT ATGTATAAAT TTCCATTTTA TGAAATGTGC GATATTACCA
29101 TGTACATGAG CAAACAGTAC AAGTTGTGGC CCCCACAAAA GTGTTTAGAG AACACTGGCA
29161 CCTTTTGTTC CACCGCTCTG CTTATTACAG CGCTTGCTTT GGTATGTACC TTACTTTATC
29221 TCAAATACAA AAGCAGACGC AGTTTTATTG ATGAAAAGAA AATGCCTTGA TTTTCCGCTT
29281 GCTTGTATTC CCCTGGACAA TTTACTCTAT GTGGGATATG CGCCAGGCGG GAAAGATTAT
29341 ACCCACAACC TTCAAATCAA ACTTTCCTGG ACGTTAGCGC CTGACTTCTG CCAGCGCCTG
29401 CACTGCAAAT TTGATCAAAC CCAGCTTCAG CTTGCCTGCT CCAGAGATGA CCGGCTCAAC
29461 CATCGCGCCC ACAACGGACT ATCGCAACAC CACTGCTACC GGACTAAAAT CTGCCCTAAA
29521 TTTACCCCAA GTTCATGCCT TTGTCAATGA CTGGGCGAGC TTGGGCATGT GGTGGTTTTC
29581 CATAGCGCTT ATGTTTGTTT GCCTTATTAT TATGTGGCTT ATTTGTTGCC TAAAGCGCAG
29641 ACGCGCCAGA CCCCCCATCT ATAGGCCTAT CATTGTGCTC AACCCACACA ATGAAAAAAT
29701 TCATAGATTG GACGGTCTCA AACCATGTTC TCTTCTTTTA CAGTATGATT AAATGAGACA
29761 TGATTCCTCG AGTCCTTATA TTATTGACCC TTGTTGCGCT TTTCTGTGCG TGCTCTACAT
29821 TGGCTGCGGT CGCTCACATC GAAGTAGATT GCATCCCACC TTTCACAGTT TACCTGCTTT
29881 ACGGATTTGT CACCCTTATC CTCATCTGCA GCCTCGTCAC TGTAGTCATC GCCTTCATTC
29941 AGTTCATTGA CTGGATTTGT GTGCGCATTG CGTACCTTAG GCACCATCCG CAATACAGAG
30001 ACAGGACTAT AGCTGATCTT CTCAGAATTC TTTAATTATG AAACGGATTG TCACTTTTGT
30061 TTTGCTGATT TTCTGCGCCC TACCTGTGCT TTGCTCCCAA ACCTCAGCGC CTCCCAAAAG
30121 ACATATTTCC TGCAGATTCA CTCAAATATG GAACATTCCC AGCTGCTACA CAAACAGAG
30181 CGATTTGTCA GAAGCCTGGT TATACGCCAT CATCTCTGTC ATGGTTTTTT GCAGTACCAT
```

FIG. 7L

```
30241  TTTTGCCCTA  GCCATATACC  CATACCTTGA  CATTGGTTGG  AATGCCATAG  ATGCCATGAA
30301  CCACCCTACT  TTCCCAGCGC  CCAATGTCAT  ACCACTGCAA  CAGGTTATTG  CCCCAATCAA
30361  TCAGCCTCGC  CCCCCTTCTC  CCACCCCCAC  TGAGATTAGC  TACTTTAATT  TGACAGGTGG
30421  AGATGACTGA  ATCTCTAGAT  CTAGAATTGG  ATGGAATTAA  CACCGAACAG  CGCCTACTAG
30481  AAAGGCGCAA  GGCGGCGTCC  GAGCGAGAAC  GCCTAAAACA  AGAAGTTGAA  GACATGGTTA
30541  ACCTGCACCA  GTGTAAAAGA  GGTATCTTTT  GTGTGGTCAA  GCAGGCCAAA  CTTACCTACG
30601  AAAAAACCAC  TACCGGCAAC  CGCCTTAGCT  ACAAGCTACC  CACCCAGCGC  CAAAAACTGG
30661  TGCTTATGGT  GGGAGAAAAA  CCTATCACCG  TCACCCAGCA  CTCGGCAGAA  ACAGAAGGCT
30721  GCCTGCACTT  CCCCTATCAG  GGTCCAGAGG  ACCTCTGCAC  TCTTATTAAA  ACCATGTGTG
30781  GCATTAGAGA  TCTTATTCCA  TTCAACTAAC  AATAAACACA  CAATAAATTA  CTTACTTAAA
30841  ATCAGTCAGC  AAATCTTTGT  CCAGCTTATT  CAGCATCACC  TCCTTTCCCT  CCTCCCAACT
30901  CTGGTATTTC  AGCAGCCTTT  TAGCTGCGAA  CTTTCTCCAA  AGTCTAAATG  GGATGTCAAA
30961  TTCCTCATGT  TCTTGTCCCT  CCGCACCCAC  TATCTTCATA  TTGTTGCAGA  TGAAACGCGC
31021  CAGACCGTCT  GAAGACACCT  TCAACCCTGT  GTACCCATAT  GACACGGAAA  CCGGCCCTCC
31081  AACTGTGCCT  TTCCTTACCC  CTCCCTTTGT  GTCGCCAAAT  GGGTTCCAAG  AAAGTCCCCC
31141  CGGAGTGCTT  TCTTTGCGTC  TTTCAGAACC  TTTGGTTACC  TCACACGGCA  TGCTTGCGCT
31201  AAAAATGGGC  AGCGGCCTGT  CCCTGGATCA  GGCAGGCAAC  CTTACATCAA  ATACAATCAC
31261  TGTTTCTCAA  CCGCTAAAAA  AAACAAAGTC  AATATAACT   TTGGAAACAT  CCGCGCCCCT
31321  TACAGTCAGC  TCAGGCGCCC  TAACCATGGC  ACAACTTCG   CCTTTGGTGG  TCTCTGACAA
31381  CACTCTTACC  ATGCAATCAC  AAGCACCGCT  AACCGTGCAA  GACTCAAAAC  TTAGCATTGC
31441  TACCAAAGAG  CCACTTACAG  TGTTAGATGG  AAAACTGGCC  CTGCAGACAT  CAGCCCCCCT
31501  CTCTGCCACT  GATAACAACG  CCCTCACTAT  CACTGCCTCA  CCTCCTCTTA  CTACTGCAAA
31561  TGGTAGTCTG  GCTGTTACCA  TGGAAAACCC  ACTTTACAAC  AACAATGGAA  AACTTGGGCT
31621  CAAAATTGGC  GGTCCTTTGC  AAGTGGCCAC  CGACTCACAT  GCACTAACAC  TAGGTACTGG
31681  TCAGGGGGTT  GCAGTTCATA  ACAATTTGCT  ACATACAAAA  GTTACAGGCG  CAATAGGGTT
31741  TGATACATCT  GGCAACATGG  AACTTAAAAC  TGGAGATGGC  CTCTATGTGG  ATAGCGCCGG
31801  TCCTAACCAA  AAACTACATA  TTAATCTAAA  TACCACAAAA  GGCCTTGCTT  TTGACAACAC
31861  CGCAATAACA  ATTAACGCTG  GAAAAGGGTT  GGAATTTGAA  ACAGACTCCT  CAAACGGAAA
31921  TCCCATAAAA  ACAAAAATTG  GATCAGGCAT  ACAATATAAT  ACCAATGGAG  CTATGGTTGC
31981  AAAACTTGGA  ACAGGCCTCA  GTTTTGACAG  CTCCGGAGCC  ATAACAATGG  GCAGCATAAA
32041  CAATGACAGA  CTTACTCTTT  GGACAACACC  AGACCCATCC  CCAAATTGCA  GAATTGCTTC
32101  AGATAAAGAC  TGCAAGCTAA  CTCTGGCGCT  AACAAAATGT  GGCAGTCAAA  TTTTGGGCAC
32161  TGTTTCAGCT  TTGGCAGTAT  CAGGTAATAT  GGCCTCCATC  AATGGAACTC  TAAGCAGTGT
32221  AAACTTGGTT  CTTAGATTTG  ATGACAACGG  AGTGCTTATG  TCAAATTCAT  CACTGGACAA
32281  ACAGTATTGG  AACTTTAGAA  ACGGGGACTC  CACTAACGGT  CAACCATACA  CTTATGCTGT
32341  TGGGTTTATG  CCAAACCTAA  AAGCTTACCC  AAAAACTCAA  AGTAAAACTG  CAAAAAGTAA
32401  TATTGTTAGC  CAGGTGTATC  TTAATGGTGA  CAAGTCTAAA  CCATTGCATT  TTACTATTAC
32461  GCTAAATGGA  ACAGATGAAA  CCAACCAAGT  AAGCAAATAC  TCAATATCAT  TCAGTTGGTC
32521  CTGGAACAGT  GGACAATACA  CTAATGACAA  ATTTGCCACC  AATTCCTATA  CCTTCTCCTA
32581  CATTGCCCAG  GAATAAAGAA  TCGTGAACCT  GTTGCATGTT  ATGTTTCAAC  GTGTTTATTT
32641  TTCAATTGCA  GAAAATTTCA  AGTCATTTTT  CATTCAGTAG  TATAGCCCCA  CCACCACATA
32701  GCTTATACTA  ATCACCGTAC  CTTAATCAAA  CTCACAGAAC  CCTAGTATTC  AACCTGCCAC
```

FIG. 7M

```
32761 CTCCCTCCCA ACACACAGAG TACACAGTCC TTTCTCCCCG GCTGGCCTTA AACAGCATCA
32821 TATCATGGGT AACAGACATA TTCTTAGGTG TTATATTCCA CACGGTCTCC TGTCGAGCCA
32881 AACGCTCATC AGTGATGTTA ATAAACTCCC CGGGCAGCTC GCTTAAGTTC ATGTCGCTGT
32941 CCAGCTGCTG AGCCACAGGC TGCTGTCCAA CTTGCGGTTG CTCAACGGGC GGCGAAGGAG
33001 AAGTCCACGC CTACATGGGG GTAGAGTCAT AATCGTGCAT CAGGATAGGG CGGTGGTGCT
33061 GCAGCAGCGC GCGAATAAAC TGCTGCCGCC GCCGCTCCGT CCTGCAGGAA TACAACATGG
33121 CAGTGGTCTC CTCAGCGATG ATTCGCACCG CCCGCAGCAT AAGGCGCCTT GTCCTCCGGG
33181 CACAGCAGCG CACCCTGATC TCACTTAAGT CAGCACAGTA ACTGCAGCAC AGTACCACAA
33241 TATTGTTTAA AATCCCACAG TGCAAGGCGC TGTATCCAAA GCTCATGGCG GGGACCACAG
33301 AACCCACGTG GCCATCATAC CACAAGCGCA GGTAGATTAA GTGGCGACCC CTCATAAACA
33361 CGCTGGACAT AAACATTACC TCTTTTGGCA TGTTGTAATT CACCACCTCC CGGTACCATA
33421 TAAACCTCTG ATTAAACATG GCGCCATCCA CCACCATCCT AAACCAGCTG GCCAAAACCT
33481 GCCCGCCGGC TATGCACTGC AGGGAACCGG GACTGGAACA ATGACAGTGG AGAGCCCAGG
33541 ACTCGTAACC ATGGATCATC ATGCTCGTCA TGATATCAAT GTTGGCACAA CACAGGCACA
33601 CGTGCATACA CTTCCTCAGG ATTACAAGCT CCTCCCGCGT CAGAACCATA TCCCAGGGAA
33661 CAACCCATTC CTGAATCAGC GTAAATCCCA CACTGCAGGG AAGACCTCGC ACGTAACTCA
33721 CGTTGTGCAT TGTCAAAGTG TTACATTCGG GCAGCAGCGG ATGATCCTCC AGTATGGTAG
33781 CGCGTGTCTC TGTCTCAAAA GGAGGTAGGC GATCCCTACT GTACGGAGTG CGCCGAGACA
33841 ACCGAGATCG TGTTGGTCGT AGTGTCATGC CAAATGGAAC GCCGGACGTA GTCATATTTC
33901 CTGAAGCAAA ACCAGGTGCG GGCGTGACAA ACAGATCTGC GTCTCCGGTC TCGTCGCTTA
33961 GCTCGCTCTG TGTAGTAGTT GTAGTATATC CACTCTCTCA AAGCATCCAG GCGCCCCCTG
34021 GCTTCGGGTT CTATGTAAAC TCCTTCATGC GCCGCTGCCC TGATAACATC CACCACCGCA
34081 GAATAAGCCA CACCCAGCCA ACCTACACAT TCGTTCTGCG AGTCACACAC GGGAGGAGCG
34141 GGAAGAGCTG GAAGAACCAT GTTTTTTTTT TTATTCCAA AAGATTATCC AAAACCTCAA
34201 AATGAAGATC TATTAAGTGA ACGCGCTCCC CTCCGGTGGC GTGGTCAAAC TCTACAGCCA
34261 AAGAACAGAT AATGGCATTT GTAAGATGTT GCACAATGGC TTCCAAAAGG CAAACTGCCC
34321 TCACGTCCAA GTGGACGTAA AGGCTAAACC CTTCAGGGTG AATCTCCTCT ATAAACATTC
34381 CAGCACCTTC AACCATGCCC AAATAATTTT CATCTCGCCA CCTTATCAAT ATGTCTCTAA
34441 GCAAATCCCG AATATTAAGT CCGGCCATTG TAAAAATCTG CTCCAGAGCG CCCTCCACCT
34501 TCAGCCTCAA GCAGCGAATC ATGATTGCAA AAATTCAGGT TCCTCACAGA CCTGTATAAG
34561 ATTCAAAAGC GGAACATTAA CAAAAATACC GCGATCCCGT AGGTCCCTTC GCAGGGCCAG
34621 CTGAACATAA TCGTGCAGGT CTGCACGGAC CAGCGCGGCC ACTTCCCCGC CAGGAACCAT
34681 GACAAAAGAA CCCACACTGA TTATGACACG CATACTCGGA GCTATGCTAA CCAGCGTAGC
34741 CCCGATGTAA GCTTGTTGCA TGGGCGGCGA TATAAAATGC AAGGTACTGC TCAAAAAATC
34801 AGGCAAAGCC TCGCGCAAAA AAGCAAGCAC ATCGTAGTCA TGCTCATGCA GATAAAGGCA
34861 GGTAAGTTCC GGAACCACCA CAGAAAAAGA CACCATTTTT CTCTCAAACA TGTCTGCGGG
34921 TTCCTGCATA AACACAAAAT AAAATAACAA AAAAAAAAAA ACATTTAAAC ATTAGAAGCC
34981 TGTNTTACAA CAGGAAAAAC AACCCTTATA AGCATAAGAC GGACTACGGC CATGCCGGCG
35041 TGACCGTAAA AAAACTGGTC ACCGTGATTA AAAGCACCA CCGACAGTTC CTCGGTCATG
35101 TCCGGAGTCA TAATGTAAGA CTCGGTAAAC ACATCAGGTT GGTTAACATC GGTCAGTGCT
35161 AAAAAGCGAC CGAAATAGCC CGGGGGAATA CATACCCGCA GGCGTAGAGA CAACATTACA
35221 GCCCCCATAG GAGGTATAAC AAAATTAATA GGAGAGAAAA ACACATAAAC ACCTGAAAAA
```

FIG. 7N

```
35281 CCCTCCTGCC TAGGCAAAAT AGCACCCTCC CGCTCCAGAA CAACATACAG CGCTTCCACA
35341 GCGGCAGCCA TAACAGTCAG CCTTACCAGT AAAAAAACCT ATTAAAAAAC ACCACTCGAC
35401 ACGGCACCAG CTCAATCAGT CACAGTGTAA AAAGGGCCAA GTACAGAGCG AGTATATATA
35461 GGACTAAAAA ATGACGTAAC GGTTAAAGTC CACAAAAACC ACCCAGAAAA CCGCACGCGA
35521 ACCTACGCCC AGAAACGAAA GCCAAAAAAC CCACAACTTC CTCAAATCTT CACTTCCGTT
35581 TTCCCACGAT ACGTCACTTC CCATTTTAAA AAAAACTAC AATTCCCAAT ACATGCAAGT
35641 TACTCCGCCC TAAAACCTAC GTCACCCGCC CCGTTCCCAC GCCCCGCGCC ACGTCACAAA
35701 CTCCACCCCC TCATTATCAT ATTGGCTTCA ATCCAAAATA AGGTATATTA TTGATGATG
```

FIG. 70

```
   1 CATCATCAAT AATATACCTT ATTTTGGATT GAAGCCAATA TGATAATGAG GGGGTGGAGT
  61 TTGTGACGTG GCGCGGGGCG TGGGAACGGG GCGGGTGACG TAGTAGTGTG GCGGAAGTGT
 121 GATGTTGCAA GTGTGGCGGA ACACATGTAA GCGACGGATG TGGCAAAAGT GACGTTTTTG
 181 GTGTGCGCCG GTGTACACAG GAAGTGACAA TTTTCGCGCG GTTTTAGGCG GATGTTGTAG
 241 TAAATTTGGG CGTAACCGAG TAAGATTTGG CCATTTTCGC GGGAAAACTG AATAAGAGGA
 301 AGTGAAATCT GAATAATTTT GTGTTACTCA TAGCGCGTAA TATTTGTCTA GGGCCGCGGG
 361 GACTTTGACC GTTTACGTGG AGACTCGCCC AGGTGTTTTT CTCAGGTGTT TTCCGCGTTC
 421 CGGGTCAAAG TTGGCGTTTT ATTATTATAG TCAGCTGACG TGTAGTGTAT TTATACCCGG
 481 TGAGTTCCTC AAGAGGCCAC TCTTGAGTGC CAGCGAGTAG AGTTTTCTCC TCCGAGCCGC
 541 TCCGACACCG GGACTGAAAA TGACACATAT TATCTGCCAC GGAGGTGTTA TTACCGAAGA
 601 AATGGCCGCC AGTCTTTTGG ACCAGCTGAT CGAAGAGGTA CTGGCTGATA ATCTTCCACC
 661 TCCTAGCCAT TTTGAACCAC CTACCCTTCA CGAACTGTAT GATTTAGACG TGACGGCCCC
 721 CGAAGATCCC AACGAGGAGG CGGTTTCGCA GATTTTTCCC GACTCTGTAA TGTTGGCGGT
 781 GCAGGAAGGG ATTGACTTAC TCACTTTTCC GCCGGCGCCC GGTTCTCCGG AGCCGCCTCA
 841 CCTTTCCCGG CAGCCCGAGC AGCCGGAGCA GAGAGCCTTG GGTCCGGTTT CTATGCCAAA
 901 CCTTGTACCG GAGGTGATCG ATCTTACCTG CCACGAGGCT GGCTTTCCAC CCAGTGACGA
 961 CGAGGATGAA GAGGGTGAGG AGTTTGTGTT AGATTATGTG GAGCACCCCG GGCACGGTTG
1021 CAGGTCTTGT CATTATCACC GGAGGAATAC GGGGGACCCA GATATTATGT GTTCGCTTTG
1081 CTATATGAGG ACCTGTGGCA TGTTTGTCTA CAGTAAGTGA AAATTATGGG CAGTGGGTGA
1141 TAGAGTGGTG GGTTTGGTGT GGTAATTTTT TTTTTAATTT TTACAGTTTT GTGGTTTAAA
1201 GAATTTTGTA TTGTGATTTT TTTAAAAGGT CCTGTGTCTG AACCTGAGCC TGAGCCCGAG
1261 CCAGAACCGG AGCCTGCAAG ACCTACCCGC CGTCCTAAAA TGGCGCCTGC TATCCTGAGA
1321 CGCCCGACAT CACCTGTGTC TAGAGAATGC AATAGTAGTA CGGATAGCTG TGACTCCGGT
1381 CCTTCTAACA CACCTCCTGA GATACACCCG GTGGTCCCGC TGTGCCCCAT TAAACCAGTT
1441 GCCGTGAGAG TTGGTGGGCG TCGCCAGGCT GTGGAATGTA TCGAGGACTT GCTTAACGAG
1501 CCTGGGCAAC CTTTGGACTT GAGCTGTAAA CGCCCCAGGC CATAAGGTGT AAACCTGTGA
1561 TTGCGTGTGT GGTTAACGCC TTTGTTTGCT GAATGAGTTG ATGTAAGTTT AATAAAGGGT
1621 GAGATAATGT TTAACTTGCA TGGCGTGTTA AATGGGGCGG GGCTTAAAGG GTATATAATG
1681 CGCCGTGGGC TAATCTTGGT TACATCTGAC CTCATGGAGG CTTGGGAGTG TTTGGAAGAT
1741 TTTTCTGCTG TGCGTAACTT GCTGGAACAG AGCTCTAACA GTACCTCTTG GTTTGGAGG
1801 TTTCTGTGGG GCTCATCCCA GGCAAAGTTA GTCTGCAGAA TTAAGGAGGA TTACAAGTGG
1861 GAATTTGAAG AGCTTTTGAA ATCCTGTGGT GAGCTGTTTG ATTCTTTGAA TCTGGGTCAC
1921 CAGGCGCTTT TCCAAGAGAA GGTCATCAAG ACTTTGGATT TTTCCACACC GGGGCGCGCT
1981 GCGGCTGCTG TTGCTTTTTT GAGTTTTATA AAGGATAAAT GGAGCGAAGA AACCCATCTG
2041 AGCGGGGGGT ACCTGCTGGA TTTTCTGGCC ATGCATCTGT GGAGAGCGGT TGTGAGACAC
2101 AAGAATCGCC TGCTACTGTT GTCTTCCGTC CGCCCGGCGA TAATACCGAC GGAGGAGCAG
2161 CAGCAGCAGC AGGAGGAAGC CAGGCGGCGG CGGCAGGAGC AGAGCCCATG GAACCCGAGA
2221 GCCGGCCTGG ACCCTCGGGA ATGAATGTTG TACAGGTGGC TGAACTGTAT CCAGAACTGA
2281 GACGCATTTT GACAATTACA GAGGATGGGC AGGGGCTAAA GGGGGTAAAG AGGGAGCGGG
2341 GGGCTTGTGA GGCTACAGAG GAGGCTAGGA ATCTAGCTTT TAGCTTAATG ACCAGACACC
2401 GTCCTGAGTG TATTACTTTT CAACAGATCA AGGATAATTG CGCTAATGAG CTTGATCTGC
2461 TGGCGCAGAA GTATTCCATA GAGCAGCTGA CCACTTACTG GCTGCAGCCA GGGGATGATT
2521 TTGAGGAGGC TATTAGGGTA TATGCAAAGG TGGCACTTAG GCCAGATTGC AAGTACAAGA
2581 TCAGCAAACT TGTAAATATC AGGAATTGTT GCTACATTTC TGGGAACGGG GCCGAGGTGG
2641 AGATAGATAC GGAGGATAGG GTGGCCTTTA GATGTAGCAT GATAAATATG TGGCCGGGGG
2701 TGCTTGGCAT GGACGGGGTG GTTATTATGA ATGTAAGGTT TACTGGCCCC AATTTTAGCG
2761 GTACGGTTTT CCTGGCCAAT ACCAACCTTA TCCTACACGG TGTAAGCTTC TATGGGTTTA
2821 ACAATACCTG TGTGGAAGCC TGGACCGATG TAAGGGTTCG GGCTGTGCC TTTTACTGCT
2881 GCTGGAAGGG GGTGGTGTGT CGCCCCAAAA GCAGGGCTTC AATTAAGAAA TGCCTCTTTG
2941 AAAGGTGTAC CTTGGGTATC CTGTCTGAGG GTAACTCCAG GGTGCGCCAC AATGTGGCCT
3001 CCGACTGTGG TTGCTTCATG CTAGTGAAAA GCGTGGCTGT GATTAAGCAT AACATGGTAT
3061 GTGGCAACTG CGAGGACAGG GCCTCTCAGA TGCTGACCTG CTCGGACGGC AACTGTCACC
3121 TGCTGAAGAC CATTCACGTA GCCAGCCACT CTCGCAAGGC CTGGCCAGTG TTTGAGCATA
3181 ACATACTGAC CCGCTGTTCC TTGCATTTGG GTAACAGGAG GGGGGTGTTC CTACCTTACC
3241 AATGCAATTT GAGTCACACT AAGATATTGC TTGAGCCCGA GAGCATGTCC AAGGTGAACC
```

FIG. 8A

```
3301 TGAACGGGGT GTTTGACATG ACCATGAAGA TCTGGAAGGT GCTGAGGTAC GATGAGACCC
3361 GCACCAGGTG CAGACCCTGC GAGTGTGGCG GTAAACATAT TAGGAACCAG CCTGTGATGC
3421 TGGATGTGAC CGAGGAGCTG AGGCCCGATC ACTTGGTGCT GGCCTGCACC CGCGCTGAGT
3481 TTGGCTCTAG CGATGAAGAT ACAGATTGAG GTACTGAAAT GTGTGGGCGT GGCTTAAGGG
3541 TGGGAAAGAA TATATAAGGT GGGGGTCTTA TGTAGTTTTG TATCTGTTTT GCAGCAGCCG
3601 CCGCCGCCAT GAGCACCAAC TCGTTTGATG GAAGCATTGT GAGCTCATAT TTGACAACGC
3661 GCATGCCCCC ATGGGCCGGG GTGCGTCAGA ATGTGATGGG CTCCAGCATT GATGGTCGCC
3721 CCGTCCTGCC CGCAAACTCT ACTACCTTGA CCTACGAGAC CGTGTCTGGA ACGCCGTTGG
3781 AGACTGCAGC CTCCGCCGCC GCTTCAGCCG CTGCAGCCAC CGCCCGCGGG ATTGTGACTG
3841 ACTTTGCTTT CCTGAGCCCG CTTGCAAGCA GTGCAGCTTC CCGTTCATCC GCCCGCGATG
3901 ACAAGTTGAC GGCTCTTTTG GCACAATTGG ATTCTTTGAC CCGGGAACTT AATGTCGTTT
3961 CTCAGCAGCT GTTGGATCTG CGCCAGCAGG TTTCTGCCCT GAAGGCTTCC TCCCCTCCCA
4021 ATGCGGTTTA AAACATAAAT AAAAAACCAG ACTCTGTTTG GATTTGGATC AAGCAAGTGT
4081 CTTGCTGTCT TTATTTAGGG GTTTTGCGCG CGCGGTAGGC CCGGGACCAG CGGTCTCGGT
4141 CGTTGAGGGT CCTGTGTATT TTTTCCAGGA CGTGGTAAAG GTGACTCTGG ATGTTCAGAT
4201 ACATGGGCAT AAGCCCGTCT CTGGGGTGGA GGTAGCACCA CTGCAGAGCT TCATGCTGCG
4261 GGGTGGTGTT GTAGATGATC CAGTCGTAGC AGGAGCGCTG GGCGTGGTGC CTAAAAATGT
4321 CTTTCAGTAG CAAGCTGATT GCCAGGGGCA GGCCCTTGGT GTAAGTGTTT ACAAAGCGGT
4381 TAAGCTGGGA TGGGTGCATA CGTGGGGATA TGAGATGCAT CTTGGACTGT ATTTTTAGGT
4441 TGGCTATGTT CCCAGCCATA TCCCTCCGGG GATTCATGTT GTGCAGAACC ACCAGCACAG
4501 TGTATCCGGT GCACTTGGGA AATTTGTCAT GTAGCTTAGA AGGAAATGCG TGGAAGAACT
4561 TGGAGACGCC CTTGTGACCT CCAAGATTTT CCATGCATTC GTCCATAATG ATGGCAATGG
4621 GCCCACGGGC GGCGGCCTGG GCGAAGATAT TTCTGGGATC ACTAACGTCA TAGTTGTGTT
4681 CCAGGATGAG ATCGTCATAG GCCATTTTTA CAAAGCGCGG GCGGAGGGTG CCAGACTGCG
4741 GTATAATGGT TCCATCCGGC CCAGGGGCGT AGTTACCCTC ACAGATTTGC ATTTCCCACG
4801 CTTTGAGTTC AGATGGGGGG ATCATGTCTA CCTGCGGGGC GATGAAGAAA ACGGTTTCCG
4861 GGGTAGGGGA GATCAGCTGG GAAGAAAGCA GGTTCCTGAG CAGCTGCGAC TTACCGCAGC
4921 CGGTGGGCCC GTAAATCACA CCTATTACCG GGTGCAACTG GTAGTTAAGA GAGCTGCAGC
4981 TGCCGTCATC CCTGAGCAGG GGGCCACTT CGTTAAGCAT GTCCCTGACT CGCATGTTTT
5041 CCCTGACCAA ATCCGCCAGA AGGCGCTCGC CGCCCAGCGA TAGCAGTTCT TGCAAGGAAG
5101 CAAAGTTTTT CAACGGTTTG AGACCGTCCG CCGTAGGCAT GCTTTGAGC GTTTGACCAA
5161 GCAGTTCCAG GCGGTCCAC AGCTCGGTCA CCTGCTCTAC GGCATCTCGA TCCAGCATAT
5221 CTCCTCGTTT CGCGGGTTGG GGCGGCTTTC GCTGTACGGC AGTAGTCGGT GCTCGTCCAG
5281 ACGGGCCAGG GTCATGTCTT TCCACGGGCG CAGGGTCCTC GTCAGCGTAG TCTGGGTCAC
5341 GGTGAAGGGG TGCGCTCCGG GCTGCGCGCT GGCCAGGGTG CGCTTGAGGC TGGTCCTGCT
5401 GGTGCTGAAG CGCTGCCGGT CTTCGCCCTG CGCGTCGGCC AGGTAGCATT TGACCATGGT
5461 GTCATAGTCC AGCCCCTCCG CGGCGTGGCC CTTGGCGCGC AGCTTGCCCT TGGAGGAGGC
5521 GCCGCACGAG GGGCAGTGCA GACTTTTGAG GGCGTAGAGC TTGGGCGCGA GAAATACCGA
5581 TTCCGGGGAG TAGGCATCCG CGCCGCAGGC CCCGCAGACG GTCTCGCATT CCACGAGCCA
5641 GGTGAGCTCT GGCCGTTCGG GGTCAAAAAC CAGGTTTCCC CCATGCTTTT TGATGCGTTT
5701 CTTACCTCTG GTTTCCATGA GCCGGTGTCC ACGCTCGGTG ACGAAAAGGC TGTCCGTGTC
5761 CCCGTATACA GACTTGAGAG GCCTGTCCTC GAGCGGTGTT CCGCGGTCCT CCTCGTATAG
5821 AAACTCGGAC CACTCTGAGA CAAAGGCTCG CGTCCAGGCC AGCACGAAGG AGGCTAAGTG
5881 GGAGGGGTAG CGGTCGTTGT CCACTAGGGG GTCCACTCGC TCCAGGGTGT GAAGACACAT
5941 GTCGCCCTCT TCGGCATCAA GGAAGGTGAT TGGTTTGTAG GTGTAGGCCA CGTGACCGGG
6001 TGTTCCTGAA GGGGGGCTAT AAAAGGGGGT GGGGGCGCGT TCGTCCTCAC TCTCTTCCGC
6061 ATCGCTGTCT GCGAGGGCCA GCTGTTGGGG TGAGTACTCC CTCTGAAAAG CGGGCATGAC
6121 TTCTGCGCTA AGATTGTCAG TTTCCAAAAA CGAGGAGGAT TTGATATTCA CCTGGCCCGC
6181 GGTGATGCCT TTGAGGGTGG CCGCATCCAT CTGGTCAGAA AAGACAATCT TTTTGTTGTC
6241 AAGCTTGGTG GCAAACGACC CGTAGAGGGC GTTGGACAGC AACTTGGCGA TGGAGCGCAG
6301 GGTTTGGTTT TTGTCGCGAT CGGCGCGCTC CTTGGCCGCG ATGTTTAGCT GCACGTATTC
6361 GCGCGCAACG CACCGCCATT CGGGAAAGAC GGTGGTGCGC TCGTCGGGCA CCAGGTGCAC
6421 GCGCCAACCG CGGTTGTGCA GGGTGACAAG GTCAACGCTG GTGGCTACCT CTCCGCGTAG
6481 GCGCTCGTTG GTCCAGCAGA GGCGGCCGCC CTTGCGCGAG CAGAATGGCG GTAGGGGGTC
6541 TAGCTGCGTC TCGTCCGGGG GGTCTGCGTC CACGGTAAAG ACCCCGGGCA GCAGGCGCGC
```

FIG. 8B

```
6601 GTCGAAGTAG TCTATCTTGC ATCCTTGCAA GTCTAGCGCC TGCTGCCATG CGCGGGCGGC
6661 AAGCGCGCGC TCGTATGGGT TGAGTGGGGG ACCCCATGGC ATGGGGTGGG TGAGCGCGGA
6721 GGCGTACATG CCGCAAATGT CGTAAACGTA GAGGGGCTCT CTGAGTATTC CAAGATATGT
6781 AGGGTAGCAT CTTCCACCGC GGATGCTGGC GCGCACGTAA TCGTATAGTT CGTGCGAGGG
6841 AGCGAGGAGG TCGGGACCGA GGTTGCTACG GGCGGGCTGC TCTGCTCGGA AGACTATCTG
6901 CCTGAAGATG GCATGTGAGT TGGATGATAT GGTTGGACGC TGGAAGACGT TGAAGCTGGC
6961 GTCTGTGAGA CCTACCGCGT CACGCACGAA GGAGGCGTAG GAGTCGCGCA GCTTGTTGAC
7021 CAGCTCGGCG GTGACCTGCA CGTCTAGGGC GCAGTAGTCC AGGGTTTCCT TGATGATGTC
7081 ATACTTATCC TGTCCCTTTT TTTTCCACAG CTCGCGGTTG AGGACAAACT CTTCGCGGTC
7141 TTTCCAGTAC TCTTGGATCG GAAACCCGTC GGCCTCCGAA CGGTAAGAGC CTAGCATGTA
7201 GAACTGGTTG ACGGCCTGGT AGGCGCAGCA TCCCTTTTCT ACGGGTAGCG CGTATGCCTG
7261 CGCGGCCTTC CGGAGCGAGG TGTGGGTGAG CGCAAAGGTG TCCCTGACCA TGACTTTGAG
7321 GTACTGGTAT TTGAAGTCAG TGTCGTCGCA TCCGCCCTGC TCCCAGAGCA AAAAGTCCGT
7381 GCGCTTTTTG GAACGCGGAT TTGGCAGGGC GAAGGTGACA TCGTTGAAGA GTATCTTTCC
7441 CGCGCGAGGC ATAAAGTTGC GTGTGATGCG GAAGGGTCCC GGCACCTCGG AACGGTTGTT
7501 AATTACCTGG GCGGCGAGCA CGATCTCGTC AAAGCCGTTG ATGTTGTGGC CCACAATGTA
7561 AAGTTCCAAG AAGCGCGGGA TGCCCTTGAT GGAAGGCAAT TTTTTAAGTT CCTCGTAGGT
7621 GAGCTCTTCA GGGGAGCTGA GCCCGTGCTC TGAAAGGGCC CAGTCTGCAA GATGAGGGTT
7681 GGAAGCGACG AATGAGCTCC ACAGGTCACG GGCCATTAGC ATTTGCAGGT GGTCGCGAAA
7741 GGTCCTAAAC TGGCGACCTA TGGCCATTTT TTCTGGGGTG ATGCAGTAGA AGGTAAGCGG
7801 GTCTTGTTCC CAGCGGTCCC ATCCAAGGTT CGCGGCTAGG TCTCGCGCGG CAGTCACTAG
7861 AGGCTCATCT CCGCCGAACT TCATGACCAG CATGAAGGGC ACGAGCTGCT TCCCAAAGGC
7921 CCCCATCCAA GTATAGGTCT CTACATCGTA GGTGACAAAG AGACGCTCGG TGCGAGGATG
7981 CGAGCCGATC GGGAAGAACT GGATCTCCCG CCACCAATTG AGGGAGTGGC TATTGATGTG
8041 GTGAAAGTAG AAGTCCCTGC GACGGGCCGA ACACTCGTGC TGGCTTTTGT AAAAACGTGC
8101 GCAGTACTGG CAGCGGTGCA CGGGCTGTAC ATCCTGCACG AGGTTGACCT GACGACCGCG
8161 CACAAGGAAG CAGAGTGGGA ATTTGAGCCC CTCGCCTGGC GGGTTTGGCT GGTGGTCTTC
8221 TACTTCGGCT GCTTGTCCTT GACCGTCTGG CTGCTCGAGG GGAGTTACGG TGGATCGGAC
8281 CACCACGCCG CGCGAGCCCA AAGTCCAGAT GTCCGCGCGC GGCGGTCGGA GCTTGATGAC
8341 AACATCGCGC AGATGGGAGC TGTCCATGGT CTGGAGCTCC CGCGGCGTCA GGTCAGGCGG
8401 GAGCTCCTGC AGGTTTACCT CGCATAGACG GGTCAGGGCG CGGGCTAGAT CCAGGTGATA
8461 CCTAATTTCC AGGGGCTGGT TGGTGGCGGC GTCGATGGCT TGCAAGAGGC CGCATCCCCG
8521 CGGCGCGACT ACGGTACCGC GCGGCGGGCG GTGGGCCGCG GGGTGTCCT TGGATGATGC
8581 ATCTAAAAGC GGTGACGCGG GCGAGCCCCC GGAGGTAGGG GGGCTCCGG ACCCGCCGGG
8641 AGAGGGGGCA GGGGCACGTC GGCGCCGCGC GCGGGCAGGA GCTGGTGCTG CGCGCGTAGG
8701 TTGCTGGCGA ACGCGACGAC GCGGCGGTTG ATCCTGAA TCTGGCGCCT CTGCGTGAAG
8761 ACGACGGGCC CGGTGAGCTT GAGCCTGAAA GAGAGTTCGA CAGAATCAAT TCGGTGTCG
8821 TTGACGGCGG CCTGGCGCAA AATCTCCTGC ACGTCTCCTG AGTTGTCTTG ATAGGCGATC
8881 TCGGCCATGA ACTGCTCGAT CTCTTCCTCC TGGAGATCTC CGCGTCCGGC TCGCTCCACG
8941 GTGGCGGCGA GGTCGTTGGA AATGCGGGCC ATGAGCTGCG AGAAGGCGTT GAGGCCTCCC
9001 TCGTTCCAGA CGCGGCTGTA GACCACGCCC CCTTCGGCAT CGCGGGCGCG CATGACCACC
9061 TGCGCGAGAT TGAGCTCCAC GTGCCGGGCG AAGACGGCGT AGTTTCGCAG CGCTGAAAG
9121 AGGTAGTTGA GGGTGGTGGC GGTGTGTTCT GCCACGAAGA AGTACATAAC CCAGCGTCGC
9181 AACGTGGATT CGTTGATATC CCCCAAGGCC TCAAGGCGCT CCATGGCCTC GTAGAAGTCC
9241 ACGGCGAAGT TGAAAAACTG GGAGTTGCGC GCCGACACGG TTAACTCCTC CTCCAGAAGA
9301 CGGATGAGCT CGGCGACAGT GTCGCGCACC TCGCGCTCAA AGGCTACAGG GGCCTCTTCT
9361 TCTTCTTCAA TCTCCTCTTC CATAAGGGCC TCCCCTTCTT CTTCTTCTGG CGGCGGTGGG
9421 GGAGGGGGGA CACGGCGGCG ACGACGGCGC ACCGGGAGGC GGTCGACAAA GCGCTCGATC
9481 ATCTCCCCGC GGCGACGGCG CATGGTCTCG GTGACGGCGC GGCCGTTCTC GCGGGGCGCG
9541 AGTTGGAAGA CGCCGCCCGT CATGTCCCGG TTATGGGTTG GCGGGGGGCT GCCATGCGGC
9601 AGGGATACGG CGCTAACGAT GCATCTCAAC AATTGTTGTG TAGGTACTCC GCCGCCGAGG
9661 GACCTGAGCG AGTCCGCATC GACCGGATCG GAAACCTCT CGAGAAAGGC GTCTAACCAG
9721 TCACAGTCGC AAGGTAGGCT GAGCACCGTG GCGGGCGGCA GCGGGCGGCG GTCGGGGTTG
9781 TTTCTGGCGG AGGTGCTGCT GATGATGTAA TTAAAGTAGG CGGTCTTGAG ACGGCGGATG
9841 GTCGACAGAA GCACCATGTC CTTGGGTCCG GCCTGCTGAA TGCGCAGGCG GTCGGCCATG
```

FIG. 8C

```
9901  CCCCAGGCTT CGTTTTGACA TCGGCGCAGG TCTTTGTAGT AGTCTTGCAT GAGCCTTTCT
9961  ACCGGCACTT CTTCTTCTCC TTCCTCTTGT CCTGCATCTC TTGCATCTAT CGCTGCGGCG
10021 GCGGCGGAGT TTGGCCGTAG GTGGCGCCCT CTTCCTCCCA TGCGTGTGAC CCCGAAGCCC
10081 CTCATCGGCT GAAGCAGGGC TAGGTCGGCG ACAACGCGCT CGGCTAATAT GGCCTGCTGC
10141 ACCTGCGTGA GGGTAGACTG GAAGTCATCC ATGTCCACAA AGCGGTGGTA TGCGCCCGTG
10201 TTGATGGTGT AAGTGCAGTT GGCCATAACG GACCAGTTAA CGGTCTGGTG ACCCGGCTGC
10261 GAGAGCTCGG TGTACCTGAG ACGCGAGTAA GCCCTCGAGT CAAATACGTA GTCGTTGCAA
10321 GTCCGCACCA GGTACTGGTA TCCCACCAAA AAGTGCGGCG GCGGCTGGCG GTAGAGGGGC
10381 CAGCGTAGGG TGGCCGGGGC TCCGGGGGCG AGATCTTCCA ACATAAGGCG ATGATATCCG
10441 TAGATGTACC TGGACATCCA GGTGATGCCG GCGGCGGTGG TGGAGGCGCG CGGAAAGTCG
10501 CGGACGCGGT TCCAGATGTT GCGCAGCGGC AAAAAGTGCT CCATGGTCGG GACGCTCTGG
10561 CCGGTCAGGC GCGCGCAATC GTTGACGCTC TAGACCGTGC AAAAGGAGAG CCTGTAAGCG
10621 GGCACTCTTC CGTGGTCTGG TGGATAAATT CGCAAGGGTA TCATGGCGGA CGACCGGGGT
10681 TCGAGCCCCG TATCCGGCCG TCCGCCGTGA TCCATGCGGT TACCGCCCGC GTGTCGAACC
10741 CAGGTGTGCG ACGTCAGACA ACGGGGGAGT GCTCCTTTTG GCTTCCTTCC AGGCGCGGCG
10801 GCTGCTGCGC TAGCTTTTTT GGCCACTGGC CGCGCGCAGC GTAAGCGGTT AGGCTGGAAA
10861 GCGAAAGCAT TAAGTGGCTC GCTCCTGTA GCCGGAGGGT TATTTTCCAA GGGTTGAGTC
10921 GCGGGACCCC CGGTTCGAGT CTCGGACCGG CCGGACTGCG GCGAACGGGG GTTTGCCTCC
10981 CCGTCATGCA AGACCCCGCT TGCAAATTCC TCCGGAAACA GGGACGAGCC CCTTTTTTGC
11041 TTTTCCCAGA TGCATCCGGT GCTGCGGCAG ATGCGCCCCC CTCCTCAGCA GCGGCAAGAG
11101 CAAGAGCAGC GGCAGACATG CAGGGCACCC TCCCCTCCTC CTACCGCGTC AGGAGGGGCG
11161 ACATCCGCGG TTGACGCGGC AGCAGATGGT GATTACGAAC CCCCGCGGCG CCGGGCCCGG
11221 CACTACCTGG ACTTGGAGGA GGGCGAGGGC CTGGCGCGGC TAGGAGCGCC CTCTCCTGAG
11281 CGGTACCCAA GGGTGCAGCT GAAGCGTGAT ACGCGTGAGG CGTACGTGCC GCGGCAGAAC
11341 CTGTTTCGCG ACCGCGAGGG AGAGGAGCCC GAGGAGATGC GGGATCGAAA GTTCCACGCA
11401 GGGCGCGAGC TGCGGCATGG CCTGAATCGC GAGCGGTTGC TGCGCGAGGA GGACTTTGAG
11461 CCCGACGCGC GAACCGGGAT TAGTCCCGCG CGCGCACACG TGGCGGCCGC CGACCTGGTA
11521 ACCGCATACG AGCAGACGGT GAACCAGGAG ATTAACTTTC AAAAAAGCTT TAACAACCAC
11581 GTGCGTACGC TTGTGGCGCG CGAGGAGGTG GCTATAGGAC TGATGCATCT GTGGGACTTT
11641 GTAAGCGCGC TGGAGCAAAA CCCAAATAGC AAGCCGCTCA TGGCGCAGCT GTTCCTTATA
11701 GTGCAGCACA GCAGGGACAA CGAGGCATTC AGGGATGCGC TGCTAAACAT AGTAGAGCCC
11761 GAGGGCCGCT GGCTGCTCGA TTTGATAAAC ATCCTGCAGA GCATAGTGGT GCAGGAGCGC
11821 AGCTTGAGCC TGGCTGACAA GGTGGCCGCC ATCAACTATT CCATGCTTAG CCTGGGCAAG
11881 TTTTACGCCC GCAAGATATA CCATACCCCT TACGTTCCCA TAGACAAGGA GGTAAAGATC
11941 GAGGGGTTCT ACATGCGCAT GGCGCTGAAG GTGCTTACCT TGAGCGACGA CCTGGGCGTT
12001 TATCGCAACG AGCGCATCCA CAAGGCCGTG AGCGTGAGCC GGCGGCGCGA GCTCAGCGAC
12061 CGCGAGCTGA TGCACAGCCT GCAAAGGGCC CTGGCTGGCA CGGGCAGCGG CGATAGAGAG
12121 GCCGAGTCCT ACTTTGACGC GGGCGCTGAC CTGCGCTGGG CCCCAAGCCG ACGCGCCCTG
12181 GAGGCAGCTG GGGCCGGACC TGGGCTGGCG GTGGCACCCG CGCGCGCTGG CAACGTCGGC
12241 GGCGTGGAGG AATATGACGA GGACGATGAG TACGAGCCAG AGGACGGCGA GTACTAAGCG
12301 GTGATGTTTC TGATCAGATG ATGCAAGACG CAACGGACCC GGCGGTGCGG GCGGCGCTGC
12361 AGAGCCAGCC GTCCGGCCTT AACTCCACGG ACGACTGGCG CCAGGTCATG GACCGCATCA
12421 TGTCGCTGAC TGCGCGCAAT CCTGACGCGT TCCGGCAGCA GCCGCAGGCC AACCGGCTCT
12481 CCGCAATTCT GGAAGCGGTG GTCCCGGCGC GCGCAAACCC CACGCACGAG AAGGTGCTGG
12541 CGATCGTAAA CGCGCTGGCC GAAAACAGGG CCATCCGGCC CGACGAGGCC GGCCTGGTCT
12601 ACGACGCGCT GCTTCAGCGC GTGGCTCGTT ACAACAGCGG CAACGTGCAG ACCAACCTGG
12661 ACCGGCTGGT GGGGGATGTG CGCGAGGCCG TGGCGCAGCG TGAGCGCGCG CAGCAGCAGG
12721 GCAACCTGGG CTCCATGGTT GCACTAAACG CCTTCCTGAG TACACAGCCC GCCAACGTGC
12781 CGCGGGGACA GGAGGACTAC ACCAACTTTG TGAGCGCACT GCGGCTAATG GTGACTGAGA
12841 CACCGCAAAG TGAGGTGTAC CAGTCTGGGC AGACTATTT TTTCCAGACC AGTAGACAAG
12901 GCCTGCAGAC CGTAAACCTG AGCCAGGCTT TCAAAAACTT GCAGGGGCTG TGGGGGGTGC
12961 GGGCTCCCAC AGGCGACCGC GCGACCGTGT CTAGCTTGCT GACGCCCAAC TCGCGCCTGT
13021 TGCTGCTGCT AATAGCGCCC TTCACGGACA GTGGCAGCGT GTCCCGGGAC ACATACCTAG
13081 GTCACTTGCT GACACTGTAC CGCGAGGCCA TAGGTCAGGC GCATGTGGAC GAGCATACTT
13141 TCCAGGAGAT TACAAGTGTC AGCCGCGCGC TGGGGCAGGA GGACACGGGC AGCCTGGAGG
```

FIG. 8D

```
13201 CAACCCTAAA CTACCTGCTG ACCAACCGGC GGCAGAAGAT CCCCTCGTTG CACAGTTTAA
13261 ACAGCGAGGA GGAGCGCATT TTGCGCTACG TGCAGCAGAG CGTGAGCCTT AACCTGATGC
13321 GCGACGGGGT AACGCCCAGC GTGGCGCTGG ACATGACCGC GCGCAACATG GAACCGGGCA
13381 TGTATGCCTC AAACCGGCCG TTTATCAACC GCCTAATGGA CTACTTGCAT CGCGCGGCCG
13441 CCGTGAACCC CGAGTATTTC ACCAATGCCA TCTTGAACCC GCACTGGCTA CCGCCCCCTG
13501 GTTTCTACAC CGGGGGATTC GAGGTGCCCG AGGGTAACGA TGGATTCCTC TGGGACGACA
13561 TAGACGACAG CGTGTTTTCC CCGCAACCGC AGACCCTGCT AGAGTTGCAA CAGCGCGAGC
13621 AGGCAGAGGC GGCGCTGCGA AAGGAAAGCT TCCGCAGGCC AAGCAGCTTG TCCGATCTAG
13681 GCGCTGCGGC CCCGCGGTCA GATGCTAGTA GCCCATTTCC AAGCTTGATA GGGTCTCTTA
13741 CCAGCACTCG CACCACCCGC CCGCGCCTGC TGGGCGAGGA GGAGTACCTA AACAACTCGC
13801 TGCTGCAGCC GCAGCGCGAA AAAAACCTGC CTCCGGCATT TCCCAACAAC GGGATAGAGA
13861 GCCTAGTGGA CAAGATGAGT AGATGGAAGA CGTACGCGCA GGAGCACAGG GACGTGCCAG
13921 GCCCGCGCCC GCCCACCCGT CGTCAAAGGC ACGACCGTCA GCGGGGTCTG GTGTGGGAGG
13981 ACGATGACTC GGCAGACGAC AGCAGCGTCC TGGATTTGGG AGGGAGTGGC AACCCGTTTG
14041 CGCACCTTCG CCCCAGGCTG GGGAGAATGT TTTAAAAAAA AAAAAGCATG ATGCAAAATA
14101 AAAAACTCAC CAAGGCCATG GCACCGAGCG TTGGTTTTCT TGTATTCCCC TTAGTATGCG
14161 GCGCGCGGCG ATGTATGAGG AAGGTCCTCC TCCCTCCTAC GAGAGTGTGG TGAGCGCGGC
14221 GCCAGTGGCG GCGGCGCTGG GTTCTCCCTT CGATGCTCCC CTGGACCCGC CGTTTGTGCC
14281 TCCGCGGTAC CTGCGGCCTA CCGGGGGGAG AAACAGCATC CGTTACTCTG AGTTGGCACC
14341 CCTATTCGAC ACCACCCGTG TGTACCTGGT GGACAACAAG TCAACGGATG TGGCATCCCT
14401 GAACTACCAG AACGACCACA GCAACTTTCT GACCACGGTC ATTCAAAACA ATGACTACAG
14461 CCCGGGGGAG GCAAGCACAC AGACCATCAA TCTTGACGAC CGGTCGCACT GGGGCGGCGA
14521 CCTGAAAACC ATCCTGCATA CCAACATGCC AAATGTGAAC GAGTTCATGT TTACCAATAA
14581 GTTTAAGGCG CGGGTGATGG TGTCGCGCTT GCCTACTAAG GACAATCAGG TGGAGCTGAA
14641 ATACGAGTGG GTGGAGTTCA CGCTGCCCGA GGGCAACTAC TCCGAGACCA TGACCATAGA
14701 CCTTATGAAC AACGCGATCG TGGAGCACTA CTTGAAAGTG GGCAGACAGA ACGGGGTTCT
14761 GGAAAGCGAC ATCGGGGTAA AGTTTGACAC CCGCAACTTC AGACTGGGGT TTGACCCCGT
14821 CACTGGTCTT GTCATGCCTG GGGTATATAC AAACGAAGCC TTCCATCCAG ACATCATTTT
14881 GCTGCCAGGA TGCGGGGTGG ACTTCACCCA CAGCCGCCTG AGCAACTTGT GGGCATCCG
14941 CAAGCGGCAA CCCTTCCAGG AGGGCTTTAG GATCACCTAC GATGATCTGG AGGGTGGTAA
15001 CATTCCCGCA CTGTTGGATG TGGACGCCTA CCAGGCGAGC TTGAAAGATG ACACCGAACA
15061 GGGCGGGGGT GGCGCAGGCG GCAGCAACAG CAGTGGCAGC GGCGCGGAAG AGAACTCCAA
15121 CGCGGCAGCC GCGGCAATGC AGCCGGTGGA GGACATGAAC GATCATGCCA TTCGCGGCGA
15181 CACCTTTGCC ACACGGGCTG AGGAGAAGCG CGCTGAGGCC GAAGCAGCGG CCGAAGCTGC
15241 CGCCCCCGCT GCGCAACCCG AGGTCGAGAA GCCTCAGAAG AAACCGGTGA TCAAACCCCT
15301 GACAGAGGAC AGCAAGAAAC GCAGTTACAA CCTAATAAGC AATGACAGCA CCTTCACCCA
15361 GTACCGCAGC TGGTACCTTG CATACAACTA CGGCGACCCT CAGACCGGAA TCCGCTCATG
15421 GACCCTGCTT TGCACTCCTG ACGTAACCTG CGGCTCGGAG CAGGTCTACT GGTCGTTGCC
15481 AGACATGATG CAAGACCCCG TGACCTTCCG CTCCACGCGC CAGATCAGCA ACTTTCCGGT
15541 GGTGGGCGCC GAGCTGTTGC CCGTGCACTC CAAGAGCTTC TACAACGACC AGGCCGTCTA
15601 CTCCCAACTC ATCCGCCAGT TTACCTCTCT GACCCACGTG TTCAATCGCT TTCCCGAGAA
15661 CCAGATTTTG GCGCGCCCGC CAGCCCCCAC CATCACCACC GTCAGTGAAA ACGTTCCTGC
15721 TCTCACAGAT CACGGGACGC TACCGCTGCG CAACAGCATC GGAGGAGTCC AGCGAGTGAC
15781 CATTACTGAC GCCAGACGCC GCACCTGCCC CTACGTTTAC AAGGCCCTGG GCATAGTCTC
15841 GCCGCGCGTC CTATCGAGCC GCACTTTTTG AGCAAGCATG TCCATCCTTA TATCGCCCAG
15901 CAATAACACA GGCTGGGCCT GCGCTTCCC AAGCAAGATG TTTGGCGGGG CCAAGAAGCG
15961 CTCCGACCAA CACCCAGTGC GCGTGCGCGG GCACTACCGC GCGCCCTGGG GCGCGCACAA
16021 ACGCGGCCGC ACTGGGCGCA CCACCGTCGA TGACGCCATC GACGCGGTGG TGGAGGAGGC
16081 GCGCAACTAC ACGCCCACGC CGCCACCAGT GTCCACAGTG GACGCGGCCA TTCAGACCGT
16141 GGTGCGCGGA GCCCGGCGCT ATGCTAAAAT GAAGAGACGG CGGAGGCGCG TAGCACGTCG
16201 CCACCGCCGC CGACCCGGCA CTGCCGCCCA ACGCGCGGCG GCGGCCCTGC TTAACCGCGC
16261 ACGTCGCACC GGCCGACGGG CGGCCATGCG GGCCGCTCGA AGGCTGGCCG CGGGTATTGT
16321 CACTGTGCCC CCCAGGTCCA GGCGACGAGC GGCCGCCGCA GCAGCCGCGG CCATTAGTGC
16381 TATGACTCAG GGTCGCAGGG GCAACGTGTA TTGGGTGCGC GACTCGGTTA GCGGCCTGCG
16441 CGTGCCCGTG CGCACCCGCC CCCCGCGCAA CTAGATTGCA AGAAAAAACT ACTTAGACTC
```

```
16501 GTACTGTTGT ATGTATCCAG CGGCGGCGGC GCGCAACGAA GCTATGTCCA AGCGCAAAAT
16561 CAAAGAAGAG ATGCTCCAGG TCATCGCGCC GGAGATCTAT GGCCCCCCGA AGAAGGAAGA
16621 GCAGGATTAC AAGCCCCGAA AGCTAAAGCG GGTCAAAAAG AAAAAGAAAG ATGATGATGA
16681 TGAACTTGAC GACGAGGTGG AACTGCTGCA CGCTACCGCG CCCAGGCGAC GGGTACAGTG
16741 GAAAGGTCGA CGCGTAAAAC GTGTTTTGCG ACCCGGCACC ACCGTAGTCT TTACGCCCGG
16801 TGAGCGCTCC ACCCGCACCT ACAAGCGCGT GTATGATGAG GTGTACGGCG ACGAGGACCT
16861 GCTTGAGCAG GCCAACGAGC GCCTCGGGGA GTTTGCCTAC GGAAAGCGGC ATAAGGACAT
16921 GCTGGCGTTG CCGCTGGACG AGGGCAACCC AACACCTAGC CTAAAGCCCG TAACACTGCA
16981 GCAGGTGCTG CCCGCGCTTG CACCGTCCGA AGAAAAGCGC GGCCTAAAGC GCGAGTCTGG
17041 TGACTTGGCA CCCACCGTGC AGCTGATGGT ACCCAAGCGC CAGCGACTGG AAGATGTCTT
17101 GGAAAAAATG ACCGTGGAAC CTGGGCTGGA GCCCGAGGTC CGCGTGCGGC CAATCAAGCA
17161 GGTGGCGCCG GGACTGGGCG TGCAGACCGT GGACGTTCAG ATACCCACTA CCAGTAGCAC
17221 CAGTATTGCC ACCGCCACAG AGGGCATGGA GACACAAACG TCCCCGGTTG CCTCAGCGGT
17281 GGCGGATGCC GCGGTGCAGG CGGTCGCTGC GGCCGCGTCC AAGACCTCTA CGGAGGTGCA
17341 AACGGACCCG TGGATGTTTC GCGTTTCAGC CCCCCGGCGC CCGCGCGGTT CGAGGAAGTA
17401 CGGCGCCGCC AGCGCGCTAC TGCCCGAATA TGCCCTACAT CCTTCCATTG CGCCTACCCC
17461 CGGCTATCGT GGCTACACCT ACCGCCCCAG AAGACGAGCA ACTACCCGAC GCCGAACCAC
17521 CACTGGAACC CGCCGCCGCC GTCGCCGTCG CCAGCCCGTG CTGGCCCCGA TTTCCGTGCG
17581 CAGGGTGGCT CGCGAAGGAG GCAGGACCCT GGTGCTGCCA ACAGCGCGCT ACCACCCCAG
17641 CATCGTTTAA AAGCCGGTCT TTGTGGTTCT TGCAGATATG CCCTCACCT GCCGCCTCCG
17701 TTTCCGGTG CCGGGATTCC GAGGAAGAAT GCACCGTAGG AGGGGCATGG CCGGCCACGG
17761 CCTGACGGGC GGCATGCGTC GTGCGCACCA CCGGCGGCGG CGCGCGTCGC ACCGTCGCAT
17821 GCGCGGCGGT ATCCTGCCCC TCCTTATTCC ACTGATCGCC GCGGCGATTG GCGCCGTGCC
17881 CGGAATTGCA TCCGTGGCCT TGCAGGCGCA GAGACACTGA TTAAAAACAA GTTGCATGTG
17941 GAAAAATCAA AATAAAAAGT CTGGACTCTC ACGCTCGCTT GGTCCTGTAA CTATTTTGTA
18001 GAATGGAAGA CATCAACTTT GCGTCTCTGG CCCCGCGACA CGGCTCGCGC CCGTTCATGG
18061 GAAACTGGCA AGATATCGGC ACCAGCAATA TGAGCGGTGG CGCCTTCAGC TGGGGCTCGC
18121 TGTGGAGCGG CATTAAAAAT TTCGGTTCCA CCGTTAAGAA CTATGGCAGC AAGGCCTGGA
18181 ACAGCAGCAC AGGCCAGATG CTGAGGGATA AGTTGAAAGA GCAAAATTTC CAACAAAAGG
18241 TGGTAGATGG CCTGGCCTCT GGCATTAGCG GGTGGTGGA CCTGGCCAAC CAGGCAGTGC
18301 AAAATAAGAT TAACAGTAAG CTTGATCCCC GCCCTCCCGT AGAGGAGCCT CCACCGGCCG
18361 TGGAGACAGT GTCTCCAGAG GGGCGTGGCG AAAAGCGTCC GCGCCCCGAC AGGGAAGAAA
18421 CTCTGGTGAC GCAAATAGAC GAGCCTCCCT CGTACGAGGA GGCACTAAAG CAAGGCCTGC
18481 CCACCACCCG TCCCATCGCG CCCATGGCTA CCGGAGTGCT GGGCCAGCAC ACACCCGTAA
18541 CGCTGGACCT GCCTCCCCCC GCCGACACCC AGCAGAAACC TGTGCTGCCA GGCCCGACCG
18601 CCGTTGTTGT AACCCGTCCT AGCCGCGCGT CCCTGCGCCG CGCCGCCAGC GGTCCGCGAT
18661 CGTTGCGGCC CGTAGCCAGT GGCAACTGGC AAAGCACACT GAACAGCATC GTGGGTCTGG
18721 GGGTGCAATC CCTGAAGCGC CGACGATGCT TCTGAATAGC TAACGTGTCG TATGTGTGTC
18781 ATGTATGCGT CCATGTCGCC GCCAGAGGAG CTGCTGAGCC GCCGCGCGCC CGCTTTCCAA
18841 GATGGCTACC CCTTCGATGA TGCCGCAGTG GTCTTACATG CACATCTCGG GCCAGGACGC
18901 CTCGGAGTAC CTGAGCCCCG GGCTGGTGCA GTTTGCCCGC GCCACCGAGA CGTACTTCAG
18961 CCTGAATAAC AAGTTTAGAA ACCCCACGGT GGCGCCTACG CACGACGTGA CCACAGACCG
19021 GTCCCAGCGT TTGACGCTGC GGTTCATCCC TGTGGACCGT GAGGATACTG CGTACTCGTA
19081 CAAGGCGCGG TTCACCCTAG CTGTGGGTGA TAACCGTGTG CTGGACATGG CTTCCACGTA
19141 CTTTGACATC CGCGGCGTGC TGGACAGGGG CCCTACTTTT AAGCCCTACT CTGGCACTGC
19201 CTACAACGCC CTGGCTCCCA AGGGTGCCCC AAATCCTTGC GAATGGGATG AAGCTGCTAC
19261 TGCTCTTGAA ATAAACCTAG AAGAAGAGGA CGATGACAAC GAAGACGAAG TAGACGAGCA
19321 AGCTGAGCAG CAAAAAACTC ACGTATTTGG GCAGGCGCCT TATTCTGGTA TAAATATTAC
19381 AAAGGAGGGT ATTCAAATAG GTGTCGAAGG TCAAACACCT AAATATGCCG ATAAACATT
19441 TCAACCTGAA CCTCAAATAG GAGAATCTCA GTGGTACGAA ACTGAAATTA ATCATGCAGC
19501 TGGGAGAGTC CTTAAAAAGA CTACCCCAAT GAAACCATGT TACGGTTCAT ATGCAAAACC
19561 CACAAATGAA AATGGAGGGC AAGGCATTCT TGTAAAGCAA CAAAATGGAA AGCTAGAAAG
19621 TCAAGTGGAA ATGCAATTTT TCTCAACTAC TGAGGCGACC GCAGGCAATG GTGATAACTT
19681 GACTCCTAAA GTGGTATTGT ACAGTGAAGA TGTAGATATA GAAACCCCAG ACACTCATAT
19741 TTCTTACATG CCCACTATTA AGGAAGGTAA CTCACGAGAA CTAATGGGCC AACAATCTAT
```

FIG. 8F

```
19801 GCCCAACAGG CCTAATTACA TTGCTTTTAG GGACAATTTT ATTGGTCTAA TGTATTACAA
19861 CAGCACGGGT AATATGGGTG TTCTGGCGGG CCAAGCATCG CAGTTGAATG CTGTTGTAGA
19921 TTTGCAAGAC AGAAACACAG AGCTTTCATA CCAGCTTTTG CTTGATTCCA TTGGTGATAG
19981 AACCAGGTAC TTTTCTATGT GGAATCAGGC TGTTGACAGC TATGATCCAG ATGTTAGAAT
20041 TATTGAAAAT CATGGAACTG AAGATGAACT TCCAAATTAC TGCTTTCCAC TGGGAGGTGT
20101 GATTAATACA GAGACTCTTA CCAAGGTAAA ACCTAAAACA GGTCAGGAAA ATGGATGGGA
20161 AAAAGATGCT ACAGAATTTT CAGATAAAAA TGAAATAAGA GTTGGAAATA ATTTTGCCAT
20221 GGAAATCAAT CTAAATGCCA ACCTGTGGAG AAATTTCCTG TACTCCAACA TAGCGCTGTA
20281 TTTGCCCGAC AAGCTAAAGT ACAGTCCTTC CAACGTAAAA ATTTCTGATA ACCCAAACAC
20341 CTACGACTAC ATGAACAAGC GAGTGGTGGC TCCCGGGTTA GTGGACTGCT ACATTAACCT
20401 TGGAGCACGC TGGTCCCTTG ACTATATGGA CAACGTCAAC CCATTTAACC ACCACCGCAA
20461 TGCTGGCCTG CGCTACCGCT CAATGTTGCT GGGGCAATGG CGCTATGTGC CCTTCCACAT
20521 CCAGGTGCCT CAGAAGTTCT TTGCCATTAA AAACCTCCTT CTCCTGCCGG GCTCATACAC
20581 CTACGAGTGG AACTTCAGGA AGGATGTTAA CATGGTTCTG CAGAGCTCCC TAGGAAATGA
20641 CCTAAGGGTT GACGGAGCCA GCATTAAGTT TGATAGCATT TGCCTTTACG CCACCTTCTT
20701 CCCCATGGCC CACAACACCG CCTCCACGCT TGAGGCCATG CTTAGAAACG ACACCAACGA
20761 CCAGTCCTTT AACGACTATC TCTCCGCCGC CAACATGCTC TACCCTATAC CCGCCAACGC
20821 TACCAACGTG CCCATATCCA TCCCCTCCCG CAACTGGGCG CTTTCCGCG GCTGGGCCTT
20881 CACGCGCCTT AAGACTAAGG AAACCCCATC ACTGGGCTCG GGCTACGACC CTTATTACAC
20941 CTACTCTGGC TCTATACCCT ACCTAGATGG AACCTTTTAC CTCAACCACA CCTTTAAGAA
21001 GGTGGCCATT ACCTTTGACT CTTCTGTCAG CTGGCCTGGC AATGACCGCC TGCTTACCCC
21061 CAACGAGTTT GAAATTAAGC GCTCAGTTGA CGGGGAGGGT TACAACGTTG CCCAGTGTAA
21121 CATGACCAAA GACTGGTTCC TGGTACAAAT GCTAGCTAAC TACAACATTG GCTACCAGGG
21181 CTTCTATATC CCAGAGAGCT ACAAGGACCG CATGTACTCC TTCTTTAGAA ACTTCCAGCC
21241 CATGAGCCGT CAGGTGGTGG ATGATACTAA ATACAAGGAC TACCAACAGG TGGGCATCCT
21301 ACACCAACAC AACAACTCTG GATTTGTTGG CTACCTTGCC CCCACCATGC GCGAAGGACA
21361 GGCCTACCCT GCTAACTTCC CCTATCCGCT TATAGGCAAG ACCGCAGTTG ACAGCATTAC
21421 CCAGAAAAAG TTTCTTTGCG ATCGCACCCT TTGGCGCATC CCATTCTCCA GTAACTTTAT
21481 GTCCATGGGC GCACTCACAG ACCTGGGCCA AAACCTTCTC TACGCCAACT CCGCCCACGC
21541 GCTAGACATG ACTTTTGAGG TGGATCCCAT GGACGAGCCC ACCCTTCTTT ATGTTTTGTT
21601 TGAAGTCTTT GACGTGGTCC GTGTGCACCG GCCGCACCGC GGCGTCATCG AAACCGTGTA
21661 CCTGCGCACG CCCTTCTCGG CCGGCAACGC CACAACATAA AGAAGCAAGC AACATCAACA
21721 ACAGCTGCCG CCATGGGCTC CAGTGAGCAG GAACTGAAAG CCATTGTCAA AGATCTTGGT
21781 TGTGGGCCAT ATTTTTGGG CACCTATGAC AAGCGCTTTC CAGGCTTTGT TTCTCCACAC
21841 AAGCTCGCCT GCGCCATAGT CAATACGGCC GGTCGCGAGA CTGGGGGCGT ACACTGGATG
21901 GCCTTTGCCT GGAACCCGCA CTCAAAAACA TGCTACCTCT TTGAGCCCTT TGGCTTTTCT
21961 GACCAGCGAC TCAAGCAGGT TTACCAGTTT GAGTACGAGT CACTCCTGCG CCGTAGCGCC
22021 ATTGCTTCTT CCCCCGACCG CTGTATAACG CTGGAAAAGT CCACCCAAAG CGTACAGGGG
22081 CCCAACTCGG CCGCCTGTGG ACTATTCTGC TGCATGTTTC TCCACGCCTT TGCCAACTGG
22141 CCCCAAACTC CCATGGATCA CAACCCCACC ATGAACCTTA TTACCGGGGT ACCCAACTCC
22201 ATGCTCAACA GTCCCCAGGT ACAGCCCACC CTGCGTCGCA ACCAGGAACA GCTCTACAGC
22261 TTCCTGGAGC GCCACTCGCC CTACTTCCGC AGCCACAGTG CGCAGATTAG GAGCGCCACT
22321 TCTTTTTGTC ACTTGAAAAA CATGTAAAAA TAATGTACTA GAGACACTTT CAATAAAGGC
22381 AAATGCTTTT ATTTGTACAC TCTCGGGTGA TTATTTACCC CCACCCTTGC CGTCTGCGCC
22441 GTTTAAAAAT CAAAGGGGTT CTGCCGCGCA TCGCTATGCG CCACTGGCAG GGACACGTTG
22501 CGATACTGGT GTTTAGTGCT CCACTTAAAC TCAGGCACAA CCATCCGCGG CAGCTCGGTG
22561 AAGTTTTCAC TCCACAGGCT GCGCACCATC ACCAACGCGT TTAGCAGGTC GGGCGCCGAT
22621 ATCTTGAAGT CGCAGTTGGG GCCTCCGCCC TGCGCGCGCG AGTTGCGATA CACAGGGTTG
22681 CAGCACTGGA ACACTATCAG CGCCGGGTGG TGCACGCTGG CCAGCACGCT CTTGTCGGAG
22741 ATCAGATCCG CGTCCAGGTC CTCCGCGTTG CTCAGGGCGA ACGGAGTCAA CTTTGGTAGC
22801 TGCCTTCCCA AAAAGGGCGC GTGCCCAGGC TTTGAGTTGC ACTCGCACCG TAGTGGCATC
22861 AAAAGGTGAC CGTGCCCGGT CTGGGCGTTA GGATACAGCG CCTGCATAAA AGCCTTGATC
22921 TGCTTAAAAG CCACCTGAGC CTTTGCGCCT TCAGAGAAGA ACATGCCGCA AGACTTGCCG
22981 GAAAACTGAT TGGCCGGACA GGCCGCGTCG TGCACGCAGC ACCTTGCGTC GGTGTTGGAG
23041 ATCTGCACCA CATTTCGGCC CCACCGGTTC TTCACGATCT TGGCCTTGCT AGACTGCTCC
```

FIG. 8G

```
23101 TTCAGCGCGC GCTGCCCGTT TTCGCTCGTC ACATCCATTT CAATCACGTG CTCCTTATTT
23161 ATCATAATGC TTCCGTGTAG ACACTTAAGC TCGCCTTCGA TCTCAGCGCA GCGGTGCAGC
23221 CACAACGCGC AGCCCGTGGG CTCGTGATGC TTGTAGGTCA CCTCTGCAAA CGACTGCAGG
23281 TACGCCTGCA GGAATCGCCC CATCATCGTC ACAAAGGTCT TGTTGCTGGT GAAGGTCAGC
23341 TGCAACCCGC GGTGCTCCTC GTTCAGCCAG GTCTTGCATA CGGCCGCCAG AGCTTCCACT
23401 TGGTCAGGCA GTAGTTTGAA GTTCGCCTTT AGATCGTTAT CCACGTGGTA CTTGTCCATC
23461 AGCGCGCGCG CAGCCTCCAT GCCCTTCTCC CACGCAGACA CGATCGGCAC ACTCAGCGGG
23521 TTCATCACCG TAATTTCACT TTCCGCTTCG CTGGGCTCTT CCTCTTCCTC TTGCGTCCGC
23581 ATACCACGCG CCACTGGGTC GTCTTCATTC AGCCGCCGCA CTGTGCGCTT ACCTCCTTTG
23641 CCATGCTTGA TTAGCACCGG TGGGTTGCTG AAACCCACCA TTTGTAGCGC ACACATCTTCT
23701 CTTTCTTCCT CGCTGTCCAC GATTACCTCT GGTGATGGCG GGCGCTCGGG CTTGGGAGAA
23761 GGGCGCTTCT TTTTCTTCTT GGGCGCAATG GCCAAATCCG CCGCCGAGGT CGATGGCCGC
23821 GGGCTGGGTG TGCGCGGCAC CAGCGCGTCT TGTGATGAGT CTTCCTCGTC CTCGGACTCG
23881 ATACGCCGCC TCATCCGCTT TTTTGGGGGC GCCCGGGGAG GCGGCGGCGA CGGGGACGGG
23941 GACGACACGT CCTCCATGGT TGGGGGACGT CGCGCCGCAC CGCGTCCGCG CTCGGGGGTG
24001 GTTTCGCGCT GCTCCTCTTC CCGACTGGCC ATTTCCTTCT CCTATAGGCA GAAAAAGATC
24061 ATGGAGTCAG TCGAGAAGAA GGACAGCCTA ACCGCCCCT CTGAGTTCGC CACCACCGCC
24121 TCCACCGATG CCGCCAACGC GCCTACCACC TTCCCCGTCG AGGCACCCCC GCTTGAGGAG
24181 GAGGAAGTGA TTATCGAGCA GGACCCAGGT TTTGTAAGCG AAGACGACGA GGACCGCTCA
24241 GTACCAACAG AGGATAAAAA GCAAGACCAG GACAACGCAG AGGCAAACGA GGAACAAGTC
24301 GGGCGGGGGG ACGAAAGGCA TGGCGACTAC CTAGATGTGG GAGACGACGT GCTGTTGAAG
24361 CATCTGCAGC GCCAGTGCGC CATTATCTGC GACGCGTTGC AAGAGCGCAG CGATGTGCCC
24421 CTCGCCATAG CGGATGTCAG CCTTGCCTAC GAACGCCACC TATTCTACC GCGCGTACCC
24481 CCCAAACGCC AAGAAAACGG CACATGCGAG CCCAACCCGC GCCTCAACTT CTACCCCGTA
24541 TTTGCCGTGC CAGAGGTGCT TGCCACCTAT CACATCTTTT TCCAAAACTG CAAGATACCC
24601 CTATCCTGCC GTGCCAACCG CAGCCGAGCG GACAAGCAGC TGGCCTTGCG GCAGGGCGCT
24661 GTCATACCTG ATATCGCCTC GCTCAACGAA GTGCCAAAAA TCTTTGAGGG TCTTGGACGC
24721 GACGAGAAGC GCGCGGCAAA CGCTCTGCAA CAGGAAAACA GCGAAAATGA AAGTCACTCT
24781 GGAGTGTTGG TGGAACTCGA GGGTGACAAC GCGCGCCTAG CCGTACTAAA ACGCAGCATC
24841 GAGGTCACCC ACTTTGCCTA CCCGGCACTT AACCTACCCC CCAAGGTCAT GAGCACAGTC
24901 ATGAGTGAGC TGATCGTGCG CCGTGCGCAG CCCTGGAGA GGGATGCAAA TTTGCAAGAA
24961 CAAACAGAGG AGGGCCTACC CGCAGTTGGC GACGAGCAGC TAGCGCGCTG GCTTCAAACG
25021 CGCGAGCCTG CCGACTTGGA GGAGCGACGC AAACTAATGA TGGCCGCAGT GCTCGTTACC
25081 GTGGAGCTTG AGTGCATGCA GCGGTTCTTT GCTGACCCGG AGATGCAGCG CAAGCTAGAG
25141 GAAACATTGC ACTACACCTT TCGACAGGGC TACGTACGCC AGGCCTGCAA GATCTCCAAC
25201 GTGGAGCTCT GCAACCTGGT CTCCTACCTT GGAATTTTGC ACGAAAACCG CCTTGGGCAA
25261 AACGTGCTTC ATTCCACGCT CAAGGGCGAG GCGCGCCGCG ACTACGTCCG CGACTGCGTT
25321 TACTTATTTC TATGCTACAC CTGGCAGACG GCCATGGGCG TTTGGCAGCA GTGCTTGGAG
25381 GAGTGCAACC TCAAGGAGCT GCAGAAACTG CTAAAGCAAA ACTTGAAGGA CCTATGGACG
25441 GCCTTCAACG AGCGCTCCGT GGCCGCGCAC CTGGCGGACA TCATTTTCCC CGAACGCCTG
25501 CTTAAAACCC TGCAACAGGG TCTGCCAGAC TTCACCAGTC AAAGCATGTT GCAGAACTTT
25561 AGGAACTTTA TCCTAGAGCG CTCAGGAATC TTGCCCGCCA CCTGCTGTGC ACTTCCTAGC
25621 GACTTTGTGC CCATTAAGTA CCGCGAATGC CCTCCGCCGC TTTGGGGCCA CTGCTACCTT
25681 CTGCAGCTAG CCAACTACCT TGCCTACCAC TCTGACATAA TGGAAGACGT GAGCGGTGAC
25741 GGTCTACTGG AGTGTCACTG TCGCTGCAAC CTATGCACCC CGCACCGCTC CCTGGTTTGC
25801 AATTCGCAGC TGCTTAACGA AAGTCAAATT ATCGGTACCT TGAGCTGCA GGGTCCCTCG
25861 CCTGACGAAA AGTCCGCGG TCCGGGGTTG AAACTCACTC CGGGGCTGTG GACGTCGGCT
25921 TACCTTCGCA AATTTGTACC TGAGGACTAC CACGCCACG AGATTAGGTT CTACGAAGAC
25981 CAATCCCGCC CGCCAAATGC GGAGCTTACC GCCTGCGTCA TTACCCAGGG CCACATTCTT
26041 GGCCAATTGC AAGCCATCAA CAAAGCCCGC AAGAGTTTC TGCTACGAAA GGGACGGGGG
26101 GTTTACTTGG ACCCCCAGTC CGGCGAGGAG CTCAACCCAA TCCCCCCGCC GCCGCAGCCC
26161 TATCAGCAGC AGCCGCGGGC CCTTGCTTCC AGGATGGCA CCCAAAAAGA AGCTGCAGCT
26221 GCCGCCGCCA CCCACGGACG AGGAGGAATA CTGGGACAGT CAGGCAGAGG AGGTTTTGGA
26281 CGAGGAGGAG GAGGACATGA TGAAGACTG GGAGAGCCTA GACGAGGAAG CTTCCGAGGT
26341 CGAAGAGGTG TCAGACGAAA CACCGTCACC CTCGGTCGCA TTCCCCTCGC CGGCGCCCCA
```

FIG. 8H

```
26401 GAAATCGGCA ACCGGTTCCA GCATGGCTAC AACCTCCGCT CCTCAGGCGC CGCCGGCACT
26461 GCCCGTTCGC CGACCCAACC GTAGATGGGA CACCACTGGA ACCAGGGCCG GTAAGTCCAA
26521 GCAGCCGCCG CCGTTAGCCC AAGAGCAACA ACAGCGCCAA GGCTACCGCT CATGGCGCGG
26581 GCACAAGAAC GCCATAGTTG CTTGCTTGCA AGACTGTGGG GGCAACATCT CCTTCGCCCG
26641 CCGCTTTCTT CTCTACCATC ACGGCGTGGC CTTCCCCCGT AACATCCTGC ATTACTACCG
26701 TCATCTCTAC AGCCCATACT GCACCGGCGG CAGCGGCAGC GGCAGCAACA GCAGCGGCCA
26761 CACAGAAGCA AAGGCGACCG GATAGCAAGA CTCTGACAAA GCCCAAGAAA TCCACAGCGG
26821 CGGCAGCAGC AGGAGGAGGA GCGCTGCGTC TGGCGCCCAA CGAACCCGTA TCGACCCGCG
26881 AGCTTAGAAA CAGGATTTTT CCCACTCTGT ATGCTATATT TCAACAGAGC AGGGGCCAAG
26941 AACAAGAGCT GAAAATAAAA AACAGGTCTC TGCGATCCCT CACCCGCAGC TGCCTGTATC
27001 ACAAAAGCGA AGATCAGCTT CGGCGCACGC TGGAAGACGC GGAGGCTCTC TTCAGTAAAT
27061 ACTGCGCGCT GACTCTTAAG GACTAGTTTC GCGCCCTTTC TCAAATTTAA GCGCGAAAAC
27121 TACGTCATCT CCAGCGGCCA CACCCGGCGC CAGCACCTGT CGTCAGCGCC ATTATGAGCA
27181 AGGAAATTCC CACGCCCTAC ATGTGGAGTT ACCAGCCACA AATGGGACTT GCGGCTGGAG
27241 CTGCCCAAGA CTACTCAACC CGAATAAACT ACATGAGCGC GGGACCCCAC ATGATATCCC
27301 GGGTCAACGG AATCCGCGCC CACCGAAACC GAATTCTCTT GGAACAGGCG GCTATTACCA
27361 CCACACCTCG TAATAACCTT AATCCCCGTA GTTGGCCCGC TGCCCTGGTG TACCAGGAAA
27421 GTCCCGCTCC CACCACTGTG GTACTTCCCA GAGACGCCCA GGCCGAAGTT CAGATGACTA
27481 ACTCAGGGGC GCAGCTTGCG GGCGGCTTTC GTCACAGGGT GCGGTCGCCC GGGCAGGGTA
27541 TAACTCACCT GACAATCAGA GGGCGAGGTA TTCAGCTCAA CGACGAGTCG GTGAGCTCCT
27601 CGCTTGGTCT CCGTCCGGAC GGGACATTTC AGATCGGCGG CGCCGGCCGT CCTTCATTCA
27661 CGCCTCGTCA GGCAATCCTA ACTCTGCAGA CCTCGTCCTC TGAGCCGCGC TCTGGAGGCA
27721 TTGGAACTCT GCAATTTATT GAGGAGTTTG TGCCATCGGT CTACTTTAAC CCCTTCTCGG
27781 GACCTCCCGG CCACTATCCG GATCAATTTA TTCCTAACTT TGACGCGGTA AAGGACTCGG
27841 CGGACGGCTA CGACTGAATG TTAAGTGGAG AGGCAGAGCA ACTGCGCCTG AAACACCTGG
27901 TCCACTGTCG CCGCCACAAG TGCTTTGCCC GCGACTCCGG TGAGTTTTGC TACTTTGAAT
27961 TGCCCGAGGA TCATATCGAG GGCCCGGCGC ACGGCGTCCG GCTTACCGCC CAGGGAGAGC
28021 TTGCCCGTAG CCTGATTCGG GAGTTTACCC AGCGCCCCCT GCTAGTTGAG CGGGACAGGG
28081 GACCCTGTGT TCTCACTGTG ATTTGCAACT GTCCTAACCT TGGATTACAT CAAGATCTTT
28141 GTTGCCATCT CTGTGCTGAG TATAATAAAT ACAGAAATTA AAATATACTG GGGCTCCTAT
28201 CGCCATCCTG TAAACGCCAC CGTCTTCACC CGCCCAAGCA AACCAAGGCG AACCTTACCT
28261 GGTACTTTTA ACATCTCTCC CTCTGTGATT TACAACAGTT TCAACCCAGA CGGAGTGAGT
28321 CTACGAGAGA ACCTCTCCGA GCTCAGCTAC TCCATCAGAA AAAACACCAC CCTCCTTACC
28381 TGCCGGGAAC GTACGAGTGC GTCACCGGCC GCTGCACCAC ACCTACCGCC TGACCGTAAA
28441 CCAGACTTTT TCCGGACAGA CCTCAATAAC TCTGTTTACC AGAACAGGAG GTGAGCTTAG
28501 AAAACCCTTA GGGTATTAGG CCAAAGGCGC AGCTACTGTG GGGTTTATGA ACAATTCAAG
28561 CAACTCTACG GGCTATTCTA ATTCAGGTTT CTCTAGAATC GGGGTTGGGG TTATTCTCTG
28621 TCTTGTGATT CTCTTTATTC TTATACTAAC GCTTCTCTGC CTAAGGCTCG CCGCCTGCTG
28681 TGTGCACATT TGCATTTATT GTCAGCTTTT TAAACGCTGG GGTCGCCACC AAGATGATT
28741 AGGTACATAA TCCTAGGTTT ACTCACCCTT GCGTCAGCCC ACGGTACCAC CCAAAAGGTG
28801 GATTTTAAGG AGCCAGCCTG TAATGTTACA TTCGCAGCTG AAGCTAATGA GTGCACCACT
28861 CTTATAAAAT GCACCACAGA ACATGAAAAG CTGCTTATTC GCCACAAAAA CAAAATTGGC
28921 AAGTATGCTG TTTATGCTAT TTGGCAGCCA GGTGACACTA CAGAGTATAA TGTTACAGTT
28981 TTCCAGGGTA AAAGTCATAA AACTTTTATG TATACTTTTC CATTTTATGA AATGTGCGAC
29041 ATTACCATGT ACATGAGCAA ACAGTATAAG TTGTGGCCCC ACAAAATTG TGTGGAAAAC
29101 ACTGGCACTT TCTGCTGCAC TGCTATGCTA ATTACAGTGC TCGCTTTGGT CTGTACCCTA
29161 CTCTATATTA AATACAAAAG CAGACGCAGC TTTATTGAGG AAAAGAAAAT GCCTTAATTT
29221 ACTAAGTTAC AAAGCTAATG TCACCACTAA CTGCTTTACT CGCTGCTTGC AAAACAAATT
29281 CAAAAAGTTA GCATTATAAT TAGAATAGGA TTTAAACCCC CCGGTCATTT CCTGCTCAAT
29341 ACCATTCCCC TGAACAATTG ACTCTATGTG GGATATGCTC CAGCGCTACA ACCTTGAAGT
29401 CAGGCTTCCT GGATGTCAGC ATCTGACTTT GGCCAGCACC TGTCCCGCGG ATTTGTTCCA
29461 GTCCAACTAC AGCGACCCAC CCTAACAGAG ATGACCAACA CAACCAACGC GGCCGCCGCT
29521 ACCGGACTTA CATCTACCAC AAATACACCC CAAGTTTCTG CCTTTGTCAA TAACTGGGAT
29581 AACTTGGGCA TGTGGTGGTT CTCCATAGCG CTTATGTTTG TATGCCTTAT TATTATGTGG
29641 CTCATCTGCT GCCTAAAGCG CAAACGCGCC CGACCACCCA TCTATAGTCC CATCATTGTG
```

FIG. 81

```
29701 CTACACCCAA ACAATGATGG AATCCATAGA TTGGACGGAC TGAAACACAT GTTCTTTTCT
29761 CTTACAGTAT GATTAAATGA GACATGATTC CTCGAGTTTT TATATTACTG ACCCTTGTTG
29821 CGCTTTTTTG TGCGTGCTCC ACATTGGCTG CGGTTTCTCA CATCGAAGTA GACTGCATTC
29881 CAGCCTTCAC AGTCTATTTG CTTTACGGAT TTGTCACCCT CACGCTCATC TGCAGCCTCA
29941 TCACTGTGGT CATCGCCTTT ATCCAGTGCA TTGACTGGGT CTGTGTGCGC TTTGCATATC
30001 TCAGACACCA TCCCCAGTAC AGGGACAGGA CTATAGCTGA GCTTCTTAGA ATTCTTTAAT
30061 TATGAAATTT ACTGTGACTT TTCTGCTGAT TATTTGCACC CTATCTGCGT TTTGTTCCCC
30121 GACCTCCAAG CCTCAAAGAC ATATATCATG CAGATTCACT CGTATATGGA ATATTCCAAG
30181 TTGCTACAAT GAAAAAAGCG ATCTTTCCGA AGCCTGGTTA TATGCAATCA TCTCTGTTAT
30241 GGTGTTCTGC AGTACCATCT TAGCCCTAGC TATATATCCC TACCTTGACA TTGGCTGGAA
30301 ACGAATAGAT GCCATGAACC ACCCAACTTT CCCCGCGCCC GCTATGCTTC CACTGCAACA
30361 AGTTGTTGCC GGCGGCTTTG TCCCAGCCAA TCAGCCTCGC CCCACTTCTC CCACCCCCAC
30421 TGAAATCAGC TACTTTAATC TAACAGGAGG AGATGACTGA CACCCTAGAT CTAGAAATGG
30481 ACGGAATTAT TACAGAGCAG CGCCTGCTAG AAAGACGCAG GGCAGCGGCC GAGCAACAGC
30541 GCATGAATCA AGAGCTCCAA GACATGGTTA ACTTGCACCA GTGCAAAAGG GGTATCTTTT
30601 GTCTGGTAAA GCAGGCCAAA GTCACCTACG ACAGTAATAC CACCGGACAC CGCCTTAGCT
30661 ACAAGTTGCC AACCAAGCGT CAGAAATTGG TGGTCATGGT GGGAGAAAAG CCCATTACCA
30721 TAACTCAGCA CTCGGTAGAA ACCGAAGGCT GCATTCACTC ACCTTGTCAA GGACCTGAGG
30781 ATCTCTGCAC CCTTATTAAG ACCCTGTGCG GTCTCAAAGA TCTTATTCCC TTTAACTAAT
30841 AAAAAAAAAT AATAAAGCAT CACTTACTTA AAATCAGTTA GCAAATTTCT GTCCAGTTTA
30901 TTCAGCAGCA CCTCCTTGCC CTCCTCCCAG CTCTGGTATT GCAGCTTCCT CCTGGCTGCA
30961 AACTTTCTCC ACAATCTAAA TGGAATGTCA GTTTCCTCCT GTTCCTGTCC ATCCGCACCC
31021 ACTATCTTCA TGTTGTTGCA GATGAAGCGC GCAAGACCGT CTGAAGATAC CTTCAACCCC
31081 GTGTATCCAT ATGACACGGA AACCGGTCCT CCAACTGTGC CTTTTCTTAC TCCTCCCTTT
31141 GTATCCCCCA ATGGGTTTCA AGAGAGTCCC CCTGGGGTAC TCTCTTTGCG CCTATCCGAA
31201 CCTCTAGTTA CCTCCAATGG CATGCTTGCG CTCAAAATGG CAACGGCCT CTCTCTGGAC
31261 GAGGCCGGCA ACCTTACCTC CCAAAATGTA CCACTGTGA GCCCACCTCT CAAAAAACC
31321 AAGTCAAACA TAAACCTGGA AATATCTGCA CCCCTCACAG TTACCTCAGA AGCCCTAACT
31381 GTGGCTGCCG CCGCACCTCT AATGGTCGCG GGCAACACAC TCACCATGCA ATCACAGGCC
31441 CCGCTAACCG TGCACGACTC CAAACTTAGC ATTGCCACCC AAGGACCCCT CACAGTGTCA
31501 GAAGGAAAGC TAGCCCTGCA ACATCAGGC CCCCTCACCA CCACCGATAG CAGTACCCTT
31561 ACTATCACTG CCTCACCCCC TCTAACTACT GCCACTGGTA GCTTGGGCAT TGACTTGAAA
31621 GAGCCCATTT ATACACAAAA TGGAAAACTA GGACTAAAGT ACGGGGCTCC TTTGCATGTA
31681 ACAGACGACC TAAACACTTT GACCGTAGCA ACTGGTCCAG GTGTGACTAT TAATAATACT
31741 TCCTTGCAAA CTAAAGTTAC TGGAGCCTTG GGTTTTGATT CACAAGGCAA TATGCAACTT
31801 AATGTAGCAG GAGGACTAAG GATTGATTCT CAAAACAGAC GCCTTATACT TGATGTTAGT
31861 TATCCGTTTG ATGCTCAAAA CCAACTAAAT CTAAGACTAG GACAGGGCCC TCTTTTTATA
31921 AACTCAGCCC ACAACTTGGA TATTAACTAC AACAAAGGCC TTTACTTGTT TACAGCTTCA
31981 AACAATTCCA AAAAGCTTGA GGTTAACCTA AGCACTGCCA AGGGGTTGAT GTTTGACGCT
32041 ACAGCCATAG CCATTAATGC AGGAGATGGG CTTGAATTTG GTTCACCTAA TGCACCAAAC
32101 ACAAATCCCC TCAAAACAAA AATTGGCCAT GGCCTAGAAT TTGATTCAAA CAAGGCTATG
32161 GTTCCTAAAC TAGGAACTGG CCTTAGTTTT GACAGCACAG GTGCCATTAC AGTAGGAAAC
32221 AAAAATAATG ATAAGCTAAC TTTGTGGACC ACACCAGCTC CATCTCCTAA CTGTAGACTA
32281 AATGCAGAGA AAGATGCTAA ACTCACTTTG GTCTTAACAA AATGTGGCAG TCAAATACTT
32341 GCTACAGTTT CAGTTTTGGC TGTTAAAGGC AGTTGGCTC AATATCTGG AACAGTTCAA
32401 AGTGCTCATC TTATTATAAG ATTTGACGAA AATGGAGTGC TACTAAACAA TTCCTTCCTG
32461 GACCCAGAAT ATTGGAACTT TAGAAATGGA GATCTTACTG AAGGCACAGC CTATACAAAC
32521 GCTGTTGGAT TTATGCCTAA CCTATCAGCT TATCCAAAAT CTCACGGTAA AACTGCCAAA
32581 AGTAACATTG TCAGTCAAGT TTACTTAAAC GGAGACAAAA CTAAACCTGT AACACTAACC
32641 ATTACACTAA ACGGTACACA GGAAACAGGA GACACAACTC AAGTGCATA CTCTATGTCA
32701 TTTTCATGGG ACTGGTCTGG CCACAACTAC ATTAATGAAA TATTTGCCAC ATCCTCTTAC
32761 ACTTTTTCAT ACATTGCCCA AGAATAAAGA ATCGTTTGTG TTATGTTTCA ACGTGTTTAT
32821 TTTTCAATTG CAGAAAATTT CAAGTCATTT TCATTCAGT AGTATAGCCC CACCACCACA
32881 TAGCTTATAC AGATCACCGT ACCTTAATCA AACTCACAGA ACCCTAGTAT TCAACCTGCC
32941 ACCTCCCTCC CAACACACAG AGTACACAGT CCTTTCTCCC CGGCTGGCCT TAAAAAGCAT
```

FIG. 8J

```
33001 CATATCATGG GTAACAGACA TATTCTTAGG TGTTATATTC CACACGGTTT CCTGTCGAGC
33061 CAAACGCTCA TCAGTGATAT TAATAAACTC CCCGGGCAGC TCACTTAAGT TCATGTCGCT
33121 GTCCAGCTGC TGAGCCACAG GCTGCTGTCC AACTTGCGGT TGCTTAACGG GCGGCGAAGG
33181 AGAAGTCCAC GCCTACATGG GGGTAGAGTC ATAATCGTGC ATCAGGATAG GGCGGTGGTG
33241 CTGCAGCAGC GCGCGAATAA ACTGCTGCCG CCGCCGCTCC GTCCTGCAGG AATACAACAT
33301 GGCAGTGGTC TCCTCAGCGA TGATTCGCAC CGCCCGCAGC ATAAGGCGCC TTGTCCTCCG
33361 GGCACAGCAG CGCACCCTGA TCTCACTTAA ATCAGCACAG TAACTGCAGC ACAGCACCAC
33421 AATATTGTTC AAAATCCCAC AGTGCAAGGC GCTGTATCCA AAGCTCATGG CGGGGACCAC
33481 AGAACCCACG TGGCCATCAT ACCACAAGCG CAGGTAGATT AAGTGGCGAC CCCTCATAAA
33541 CACGCTGGAC ATAAACATTA CCTCTTTTGG CATGTTGTAA TTCACCACCT CCCGGTACCA
33601 TATAAACCTC TGATTAAACA TGGCGCCATC CACCACCATC CTAAACCAGC TGGCCAAAAC
33661 CTGCCCGCCG GCTATACACT GCAGGGAACC GGGACTGGAA CAATGACAGT GGAGAGCCCA
33721 GGACTCGTAA CCATGGATCA TCATGCTCGT CATGATATCA ATGTTGGCAC AACACAGGCA
33781 CACGTGCATA CACTTCCTCA GGATTACAAG CTCCTCCCGC GTTAGAACCA TATCCCAGGG
33841 AACAACCCAT TCCTGAATCA GCGTAAATCC CACACTGCAG GAAGACCTC GCACGTAACT
33901 CACGTTGTGC ATTGTCAAAG TGTTACATTC GGGCAGCAGC GGATGATCCT CCAGTATGGT
33961 AGCGCGGGTT TCTGTCTCAA AAGGAGGTAG ACGATCCCTA CTGTACGGAG TGCGCCGAGA
34021 CAACCGAGAT CGTGTTGGTC GTAGTGTCAT GCCAAATGGA ACGCCGGACG TAGTCATATT
34081 TCCTGAAGCA AAACCAGGTG CGGGCGTGAC AAACAGATCT GCGTCTCCGG TCTCGCCGCT
34141 TAGATCGCTC TGTGTAGTAG TTGTAGTATA TCCACTCTCT CAAAGCATCC AGGCGCCCCC
34201 TGGCTTCGGG TTCTATGTAA ACTCCTTCAT GCGCCGCTGC CCTGATAACA TCCACCACCG
34261 CAGAATAAGC CACACCCAGC CAACCTACAC ATTCGTTCTG CGAGTCACAC ACGGGAGGAG
34321 CGGGAAGAGC TGGAAGAACC ATGTTTTTTT TTTTATTCCA AAAGATTATC CAAAACCTCA
34381 AAATGAAGAT CTATTAAGTG AACGCGCTCC CCTCCGGTGG CGTGGTCAAA CTCTACAGCC
34441 AAAGAACAGA TAATGGCATT TGTAAGATGT TGCACAATGG CTTCCAAAAG GCAAACGGCC
34501 CTCACGTCCA AGTGGACGTA AAGGCTAAAC CCTTCAGGGT GAATCTCCTC TATAAACATT
34561 CCAGCACCTT CAACCATGCC CAAATAATTC TCATCTCGCC ACCTTCTCAA TATATCTCTA
34621 AGCAAATCCC GAATATTAAG TCCGGCCATT GTAAAAATCT GCTCCAGAGC GCCCTCCACC
34681 TTCAGCCTCA AGCAGCGAAT CATGATTGCA AAAATTCAGG TTCCTCACAG ACCTGTATAA
34741 GATTCAAAAG CGGAACATTA ACAAAAATAC CGCGATCCCG TAGGTCCCTT CGCAGGGCCA
34801 GCTGAACATA ATCGTGCAGG TCTGCACGGA CCAGCGCGGC CACTTCCCCG CCAGGAACCT
34861 TGACAAAAGA ACCCACACTG ATTATGACAC GCATACTCGG AGCTATGCTA ACCAGCGTAG
34921 CCCCGATGTA AGCTTTGTTG CATGGGCGGC GATATAAAAT GCAAGGTGCT GCTCAAAAAA
34981 TCAGGCAAAG CCTCGCGCAA AAAAGAAAGC ACATCGTAGT CATGCTCATG CAGATAAAGG
35041 CAGGTAAGCT CCGGAACCAC CACAGAAAAA GACACCATTT TTCTCTCAAA CATGTCTGCG
35101 GGTTTCTGCA TAAACACAAA ATAAATAAC AAAAAAACAT TTAAACATTA GAAGCCTGTC
35161 TTACAACAGG AAAAACAACC CTTATAAGCA TAAGACGGAC TACGGCCATG CCGGCGTGAC
35221 CGTAAAAAAA CTGGTCACCG TGATTAAAAA GCACCACCGA CAGCTCCTCG GTCATGTCCG
35281 GAGTCATAAT GTAAGACTCG GTAAACACAT CAGGTTGATT CATCGGTCAG TGCTAAAAAG
35341 CGACCGAAAT AGCCCGGGGG AATACATACC CGCAGGCGTA GAGACAACAT TACAGCCCCC
35401 ATAGGAGGTA TAACAAAATT AATAGGAGAG AAAAACACAT AAACACCTGA AAAACCCTCC
35461 TGCCTAGGCA AAATAGCACC CTCCCGCTCC AGAACAACAT ACAGCGCTTC ACAGCGGCAG
35521 CCTAACAGTC AGCCTTACCA GTAAAAAAGA AAACCTATTA AAAAACACC ACTCGACACG
35581 GCACCAGCTC AATCAGTCAC AGTGTAAAAA AGGGCCAAGT GCAGAGCGAG TATATATAGG
35641 ACTAAAAAAT GACGTAACGG TTAAAGTCCA CAAAAAACAC CCAGAAAACC GCACGCGAAC
35701 CTACGCCCAG AAACGAAAGC CAAAAAACCC ACAACTTCCT CAAATCGTCA CTTCCGTTTT
35761 CCCACGTTAC GTAACTTCCC ATTTTAAGAA AACTACAATT CCCAACACAT ACAAGTTACT
35821 CCGCCCTAAA ACCTACGTCA CCCGCCCCGT TCCCACGCCC CGCGCCACGT CACAAACTCC
35881 ACCCCCTCAT TATCATATTG GCTTCAATCC AAAATAAGGT ATATTATTGA TGATG
```

FIG. 8K

Western blot on whole-cell extracts from 293 cells transfected with plasmid DNA expressing the different HCV NS cassettes. Mature NS3 and NS5A products were detected with specific antibodies.

|  | | Pep pool | | | | | | |
|---|---|---|---|---|---|---|---|---|
| | mouse | F(NS3p) | G(NS3h) | H(NS4) | I(NS5a) | L(NS35b) | M(NS5b) | 1480(CD8 ep) | DMSO |
| | #31 | 41 | 135 | 19 | 44 | 25 | 17 | 137 | 8 |
| | #32 | 121 | 783 | 77 | 144 | 13 | 22 | 604 | 4 |
| | #33 | 8 | 32 | 3 | 11 | 6 | 6 | 43 | 3 |
| | #34 | 16 | 139 | 13 | 47 | 31 | 25 | 151 | 2 |
| pV1jns-NS | #35 | 21 | 101 | 40 | 32 | 21 | 20 | 75 | 1 |
| | #36 | 18 | 26 | 24 | 25 | 5 | 7 | 29 | 6 |
| | #37 | 19 | 73 | 15 | 39 | 8 | 20 | 49 | 2 |
| | #38 | 133 | 575 | 74 | 345 | 75 | 63 | 515 | 5 |
| | #39 | 40 | 183 | 10 | 85 | 14 | 9 | 148 | 2 |
| | #40 | 66 | 465 | 29 | 111 | 15 | 16 | 189 | 0 |
| | Geomean | 33 | 146 | 21 | 57 | 15 | 16 | 123 | na |

|  | | Pep pool | | | | | | |
|---|---|---|---|---|---|---|---|---|
| | mouse | F(NS3p) | G(NS3h) | H(NS4) | I(NS5a) | L(NS35b) | M(NS5b) | 1480(CD8 ep) | DMSO |
| | #41 | 39 | 293 | 58 | 187 | 5 | 4 | 248 | 1 |
| | #42 | 21 | 220 | 46 | 107 | 26 | 10 | 189 | 4 |
| | #43 | 76 | 134 | 12 | 78 | 8 | 6 | 144 | 2 |
| | #44 | 30 | 45 | 20 | 52 | 4 | 8 | 40 | 4 |
| pV1jns-NSmut | #45 | 36 | 100 | 17 | 56 | 4 | 6 | 116 | 3 |
| | #46 | 67 | 172 | 16 | 138 | 8 | 9 | 145 | 3 |
| | #47 | 34 | 131 | 28 | 38 | 9 | 5 | 118 | 1 |
| | #48 | 55 | 316 | 43 | 107 | 9 | 7 | 277 | 5 |
| | #49 | 6 | 131 | 5 | 25 | 4 | 1 | 91 | 0 |
| | #50 | 13 | 93 | 11 | 11 | 5 | 1 | 76 | 1 |
| | Geomean | 30 | 142 | 20 | 61 | 7 | 5 | 126 | na |

|  | | Pep pool | | | | | | |
|---|---|---|---|---|---|---|---|---|
| | mouse | F(NS3p) | G(NS3h) | H(NS4) | I(NS5a) | L(NS35b) | M(NS5b) | 1480(CD8 ep) | DMSO |
| | #51 | 53 | 409 | 34 | 84 | 11 | 25 | 271 | 4 |
| | #52 | 140 | 660 | 65 | 276 | 23 | 36 | 377 | 2 |
| | #53 | 58 | 553 | 48 | 105 | 23 | 18 | 564 | 1 |
| | #54 | 50 | 105 | 35 | 134 | 10 | 16 | 80 | 2 |
| V1jns-NSOPTmut | #55 | 14 | 80 | 11 | 35 | 4 | 7 | 91 | 6 |
| | #56 | 14 | 342 | 30 | 101 | 23 | 14 | 207 | 1 |
| | #57 | 63 | 325 | 66 | 239 | 17 | 24 | 123 | 1 |
| | #58 | 75 | 542 | 66 | 168 | 127 | 93 | 191 | 0 |
| | #59 | 65 | 468 | 40 | 124 | 18 | 23 | 344 | 4 |
| | #60 | 27 | 142 | 48 | 16 | 7 | 8 | 77 | 0 |
| | Geomean | 45 | 295 | 40 | 99 | 16 | 20 | 188 | na |

IFNγ ELIspot on splenocytes from C57black6 mice immunized with two injections of 25μg DNA/dose with GET of plasmid vectors expressing the different HCV NS cassettes. Data are expressed as SFC/$10^6$ PBMC.

FIG. 13A

|  | | Pep pool | | | | | | |
|---|---|---|---|---|---|---|---|---|
| | mouse | F(NS3p) | G(NS3h) | H(NS4) | I(NS5a) | L(NS35b) | M(NS5b) | DMSO |
| pV1jns-NS | #51 | 219 | 699 | 634 | 486 | 487 | 264 | 34 |
| | #52 | 67 | 302 | 347 | 167 | 111 | 87 | 9 |
| | #53 | 59 | 460 | 400 | 246 | 244 | 136 | 26 |
| | #54 | 139 | 817 | 685 | 236 | 547 | 223 | 24 |
| | #55 | 96 | 904 | 542 | 277 | 256 | 337 | 17 |
| | #56 | 225 | 603 | 686 | 156 | 350 | 240 | 56 |
| | #57 | 44 | 288 | 211 | 148 | 100 | 141 | 4 |
| | #58 | 37 | 262 | 221 | 53 | 58 | 62 | 3 |
| | #59 | 131 | 975 | 928 | 159 | 305 | 284 | 14 |
| | #60 | 93 | 475 | 464 | 77 | 206 | 113 | 12 |
| | geo mean | 111 | 579 | 512 | 201 | 266 | 189 | 20 |

|  | | Pep pool | | | | | | |
|---|---|---|---|---|---|---|---|---|
| | mouse | F(NS3p) | G(NS3h) | H(NS4) | I(NS5a) | L(NS35b) | M(NS5b) | DMSO |
| pV1jns-NSmut | #61 | 72 | 840 | 515 | 219 | 278 | 249 | 19 |
| | #62 | 294 | 1881 | 1266 | 365 | 434 | 411 | 63 |
| | #63 | 73 | 415 | 422 | 103 | 141 | 99 | 41 |
| | #64 | 66 | 824 | 486 | 175 | 162 | 144 | 18 |
| | #66 | 24 | 313 | 168 | 53 | 47 | 42 | 5 |
| | #67 | 15 | 230 | 253 | 94 | 25 | 39 | 2 |
| | #68 | 53 | 354 | 252 | 89 | 101 | 86 | 15 |
| | #69 | 271 | 895 | 909 | 518 | 322 | 285 | 74 |
| | #70 | 417 | 1303 | 1186 | 468 | 557 | 267 | 34 |
| | geo mean | 143 | 784 | 606 | 232 | 230 | 180 | 30 |

|  | | Pep pool | | | | | | |
|---|---|---|---|---|---|---|---|---|
| | mouse | F(NS3p) | G(NS3h) | H(NS4) | I(NS5a) | L(NS35b) | M(NS5b) | DMSO |
| V1jns-NSOPTmut | #71 | 206 | 944 | 890 | 342 | 207 | 397 | 47 |
| | #72 | 393 | 1655 | 1151 | 575 | 626 | 401 | 72 |
| | #73 | 123 | 522 | 515 | 319 | 223 | 198 | 21 |
| | #74 | 500 | 1414 | 1419 | 878 | 1035 | 1122 | 137 |
| | #75 | 286 | 812 | 873 | 382 | 543 | 267 | 31 |
| | #76 | 224 | 1143 | 942 | 218 | 420 | 281 | 22 |
| | #77 | 95 | 643 | 630 | 169 | 385 | 218 | 15 |
| | #78 | 401 | 1302 | 1068 | 538 | 608 | 623 | 12 |
| | #79 | 108 | 1190 | 914 | 199 | 265 | 215 | 4 |
| | #80 | 122 | 511 | 546 | 189 | 286 | 190 | 13 |
| | geo mean | 209 | 941 | 854 | 331 | 406 | 329 | 24 |

IFNγ ELIspot on splenocytes from BalbC mice immunized with two injections of 50μg DNA/dose with GET of plasmid vectors expressing the different HCV NS cassettes. Data are expressed as SFC/$10^6$ PBMC.

FIG. 13B

Western blot on whole-cell extracts from HeLa cells infected at different multiplicity of infection (m.o.i.; indicated at the top) with Adenovectors expressing the different HCV NS cassettes. Mature NS5B and NS5A products were detected with specific antibodies.

|  | mouse | Pep pool | | | | | | |
|---|---|---|---|---|---|---|---|---|
|  |  | F(NS3p) | G(NS3h) | H(NS4) | I(NS5a) | L+M(NS35b) | 1480(CD8 ep) | DMSO |
| Ad5-NS | #1 | 14 | 492 | 9 | 27 | 10 | 554 | 7 |
|  | #2 | 8 | 440 | 2 | 26 | 5 | 438 | 0 |
|  | #3 | 12 | 92 | 5 | 12 | 7 | 73 | 4 |
|  | #4 | 16 | 388 | 6 | 40 | 6 | 228 | 2 |
|  | #6 | 8 | 210 | 4 | 31 | 3 | 238 | 3 |
|  | #7 | 7 | 133 | 13 | 16 | 0 | 128 | 9 |
|  | #8 | 11 | 342 | 25 | 55 | 22 | 267 | 12 |
|  | #9 | 5 | 345 | 0 | 45 | 5 | 285 | 3 |
|  | #10 | 22 | 888 | 3 | 65 | 25 | 799 | 1 |
|  | Geomean | 10 | 305 | na | 31 | na | 269 | na |

|  | mouse | Pep pool | | | | | | |
|---|---|---|---|---|---|---|---|---|
|  |  | F(NS3p) | G(NS3h) | H(NS4) | I(NS5a) | L+M(NS35b) | 1480(CD8 ep) | DMSO |
| MRKAd5-NSmut | #11 | 14 | 1009 | 13 | 75 | 7 | 751 | 6 |
|  | #12 | 15 | 695 | 3 | 39 | 9 | 552 | 1 |
|  | #13 | 12 | 389 | 4 | 20 | 7 | 352 | 3 |
|  | #14 | 7 | 459 | 6 | 50 | 1 | 274 | 1 |
|  | #15 | 5 | 549 | 3 | 22 | 6 | 485 | 0 |
|  | #16 | 10 | 631 | 1 | 6 | 4 | 600 | 3 |
|  | #17 | 5 | 257 | 3 | 9 | 1 | 245 | 3 |
|  | #18 | 13 | 659 | 6 | 43 | 7 | 555 | 1 |
|  | #19 | 12 | 758 | 1 | 37 | 5 | 669 | 0 |
|  | #20 | 22 | 1380 | 5 | 163 | 8 | 1003 | 4 |
|  | Geomean | 10 | 615 | 3 | 31 | 4 | 504 | na |

|  | mouse | Pep pool | | | | | | |
|---|---|---|---|---|---|---|---|---|
|  |  | F(NS3p) | G(NS3h) | H(NS4) | I(NS5a) | L+M(NS35b) | 1480(CD8 ep) | DMSO |
| MRKAd6-NSmut | #21 | 6 | 584 | 5 | 27 | 4 | 491 | 2 |
|  | #22 | 6 | 231 | 3 | 12 | 3 | 235 | 0 |
|  | #23 | 8 | 482 | 1 | 18 | 1 | 511 | 0 |
|  | #24 | 14 | 1120 | 6 | 38 | 10 | 1004 | 5 |
|  | #25 | 1 | 311 | 3 | 9 | 0 | 382 | 1 |
|  | #26 | 29 | 903 | 3 | 60 | 5 | 751 | 5 |
|  | #27 | 35 | 1573 | 4 | 40 | 4 | 1277 | 4 |
|  | #28 | 7 | 406 | 5 | 15 | 1 | 443 | 3 |
|  | #29 | 4 | 461 | 3 | 12 | 3 | 515 | 3 |
|  | Geomean | 8 | 567 | 3 | 21 | na | 554 | na |

IFNγ ELISPOT on splenocytes from C57black6 mice immunized with two injections of $10^9$ vp/dose of Adenovectors expressing the different HCV NS cassettes. Data are expressed as SFC/$10^6$ PBMC.

FIG. 15

| | Ad5-NS $10^{10}$ vp/dose | | |
|---|---|---|---|
| Pep pools | 96074 | 134T | 063Q |
| F (NS3p) | 374 | 11 | 74 |
| G (NS3h) | 359 | 1070 | 1455 |
| H (NS4) | 376 | 30 | 64 |
| I (NS5a) | 240 | 40 | 63 |
| L (NS5b) | 226 | 29 | 121 |
| M (NS5b) | 511 | 23 | 35 |
| DMSO | 128 | 3 | 31 |

| | MRK Ad6-NSmut $10^{10}$ vp/dose | | |
|---|---|---|---|
| Pep pools | S207 | 035Q | 057Q |
| F (NS3p) | 363 | 382 | 150 |
| G (NS3h) | 180 | 316 | 119 |
| H (NS4) | 126 | 113 | 62 |
| I (NS5a) | 1780 | 688 | 114 |
| L (NS5b) | 447 | 111 | 81 |
| M (NS5b) | 153 | 38 | 16 |
| DMSO | 9 | 6 | 9 |

IFNγ ELISPOT on PBMC from Rhesus monkeys immunized with one injection of $10^{10}$ vp/dose of Adenovectors expressing the different HCV NS cassettes. Data are expressed as SFC/$10^6$ PBMC.

FIG. 16A

| Pep pools | MRK Ad5-NSmut $10^{10}$ vp/dose | | |
|---|---|---|---|
| | S201 | 075Q | 137Q |
| F (NS3p) | 928 | 69 | 254 |
| G (NS3h) | 317 | 436 | 98 |
| H (NS4) | 56 | 101 | 45 |
| I (NS5a) | 1530 | 1100 | 413 |
| L (NS5b) | 149 | 23 | 92 |
| M (NS5b) | 398 | 32 | 80 |
| DMSO | 29 | 6 | 29 |

| Pep pools | MRK Ad6-NSOPTmut $10^{10}$ vp/dose | | |
|---|---|---|---|
| | 98D209 | 106Q | 113Q |
| F (NS3p) | 3110 | 263 | 404 |
| G (NS3h) | 2115 | 642 | 1008 |
| H (NS4) | 373 | 72 | 19 |
| I (NS5a) | 103 | 37 | 347 |
| L (NS5b) | 149 | 22 | 10 |
| M (NS5b) | 314 | 428 | 19 |
| DMSO | 0 | 1 | 3 |

IFNγ ELISPOT on PBMC from Rhesus monkeys immunized with one injection of $10^{10}$ vp/dose of Adenovectors expressing the different HCV NS cassettes. Data are expressed as SFC/$10^6$ PBMC.

FIG. 16B

| Pep pools | Ad5-NS $10^{11}$ vp/dose | | | |
|---|---|---|---|---|
| | 99C008 | 97N104 | 97X008 | 99C026 |
| F (NS3p) | 28 | 1026 | 579 | 889 |
| G (NS3h) | 1279 | 188 | 103 | 2453 |
| H (NS4) | 18 | 39 | 138 | 109 |
| I (NS5a) | 131 | 1068 | 172 | 141 |
| L (NS5b) | 78 | 144 | 103 | 32 |
| M (NS5b) | 24 | 68 | 47 | 84 |
| DMSO | 3 | 16 | 1 | 19 |

| Pep pools | MRKAd6-NSmut $10^{11}$ vp/dose | | | |
|---|---|---|---|---|
| | 98C047 | 97C055 | 93G | 97X014 |
| F (NS3p) | 477 | 25 | 93 | 1022 |
| G (NS3h) | 959 | 398 | 81 | 1513 |
| H (NS4) | 36 | 14 | 99 | 53 |
| I (NS5a) | 171 | 45 | 1237 | 98 |
| L (NS5b) | 18 | 32 | 23 | 51 |
| M (NS5b) | 88 | 4 | 13 | 40 |
| DMSO | 8 | 3 | 1 | 5 |

IFNγ ELISPOT on PBMC from Rhesus monkeys immunized with two injections of $10^{11}$ vp/dose of Adenovectors expressing the different HCV NS cassettes. Data are expressed as SFC/$10^6$ PBMC.

FIG. 16C

| Pep pools | MRKAd5-NSmut $10^{11}$ vp/dose | | | |
| --- | --- | --- | --- | --- |
| | 99C059 | 99C060 | 97X009 | 96069 |
| F (NS3p) | 28 | 81 | 1308 | 1618 |
| G (NS3h) | 2600 | 161 | 1008 | 123 |
| H (NS4) | 31 | 74 | 101 | 40 |
| I (NS5a) | 181 | 99 | 69 | 96 |
| L (NS5b) | 24 | 31 | 40 | 20 |
| M (NS5b) | 11 | 58 | 38 | 164 |
| DMSO | 6 | 15 | 1 | 16 |

IFNγ ELISPOT on PBMC from Rhesus monkeys immunized with two injections of $10^{11}$ vp/dose of Adenovectors expressing the different HCV NS cassettes. Data are expressed as SFC/$10^6$ PBMC.

FIG. 16D

| Pep pools | MRK Ad5-NSmut $10^{10}$ vp/dose | | |
|---|---|---|---|
| | *S201* | *075Q* | *137Q* |
| *pool F (NS3p)* | 881 | 1755 | 73 |
| *pool G (NS3h)* | 573 | | |
| *pool H (NS4)* | | 3541 | |
| *pool I (NS5a)* | 2094 | | 39 |
| *pool L (NS5b)* | | | |
| *pool M (NS5b)* | 756 | | |
| *DMSO* | 319 | 117 | 44 |

| Pep pools | MRK Ad6-NSOPTmut $10^{10}$ vp/dose | | |
|---|---|---|---|
| | *98D209* | *106Q* | *113Q* |
| *pool F (NS3p)* | 5073 | 84 | 952 |
| *pool G (NS3h)* | 2376 | 160 | 3325 |
| *pool H (NS4)* | 700 | | |
| *pool I (NS5a)* | | | 1106 |
| *pool L (NS5b)* | | | |
| *pool M (NS5b)* | 530 | 706 | |
| *DMSO* | 43 | 47 | 28 |

| Pep pools | MRK Ad6-NSmut $10^{10}$ vp/dose | | |
|---|---|---|---|
| | *S207* | *035Q* | *057Q* |
| *pool F (NS3p)* | 118 | 480 | |
| *pool G (NS3h)* | | 196 | |
| *pool H (NS4)* | | | |
| *pool I (NS5a)* | 3340 | 933 | |
| *pool L (NS5b)* | 118 | | |
| *pool M (NS5b)* | | | |
| *DMSO* | 145 | 34 | |

IFNγ ICS on PBMC from Rhesus monkeys immunized with two injections at four weeks interval with $10^{10}$ vp/dose of Adenovectors expressing the different HCV NS cassettes. Data are expressed as number of positive IFNγ/CD3/CD8 per $10^6$ lymphocytes.

FIG. 17A

| Pep pools | Ad5-NS 10$^{11}$ vp/dose | | | |
|---|---|---|---|---|
| | 99C008 | 97N104 | 97X008 | 99C026 |
| F (NS3p) | | 1703 | 1136 | 615 |
| G (NS3h) | 3153 | | | 2787 |
| H (NS4) | | | | |
| I (NS5a) | | 2233 | | |
| L (NS5b) | | | | |
| M (NS5b) | | | | |
| DMSO | 125 | 98 | 130 | 0 |

| Pep pools | MRKAd6-NSmut 10$^{11}$ vp/dose | | | |
|---|---|---|---|---|
| | 98C047 | 97C055 | 93G | 97X014 |
| F (NS3p) | 1024 | | | 948 |
| G (NS3h) | 3246 | 353 | | 1074 |
| H (NS4) | | | 316 | |
| I (NS5a) | | | 6224 | |
| L (NS5b) | | | | |
| M (NS5b) | | | | |
| DMSO | 49 | 23 | 37 | 93 |

| Pep pools | MRKAd5-NSmut 10$^{11}$ vp/dose | | | |
|---|---|---|---|---|
| | 99C059 | 99C060 | 97X009 | 96069 |
| F (NS3p) | | | 2266 | 5053 |
| G (NS3h) | 2434 | 316 | 1018 | |
| H (NS4) | | | | |
| I (NS5a) | | | | |
| L (NS5b) | | | | |
| M (NS5b) | | | | 205 |
| DMSO | 13 | 110 | 119 | 15 |

IFNγ ICS on PBMC from Rhesus monkeys immunized with two injections at four weeks interval with 10$^{11}$ vp/dose of Adenovectors expressing the different HCV NS cassettes. Data are expressed as number of positive IFNγ/CD3/CD8 per 10$^6$ lymphocytes.

FIG. 17B

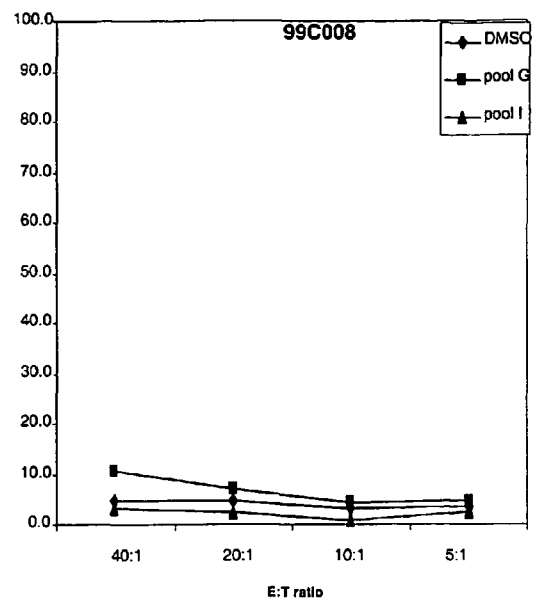
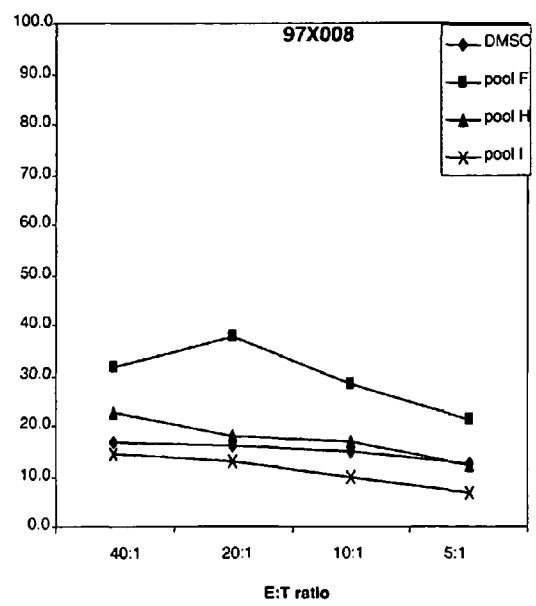
Bulk CTL assays on PBMC from Rhesus monkeys immunized with two injections of $10^{11}$ vp/dose of Ad5-NS.
FIG. 18A

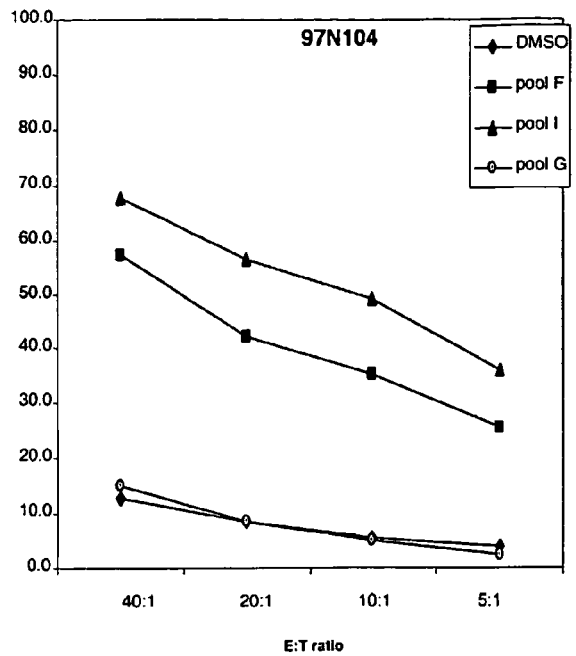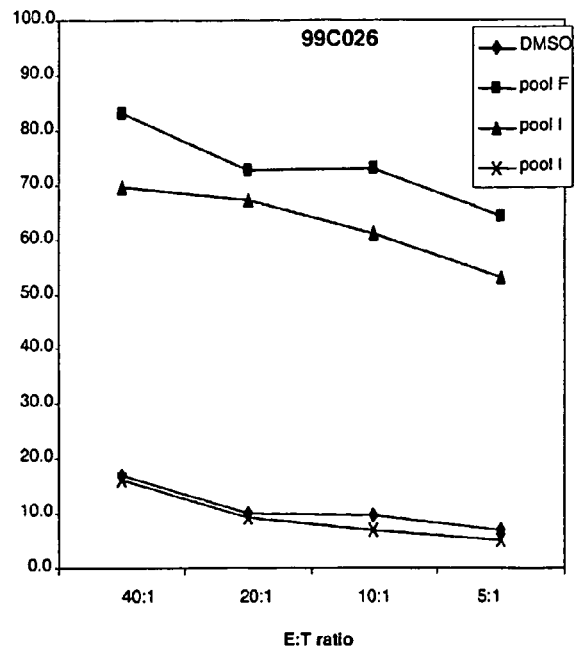
Bulk CTL assays on PBMC from Rhesus monkeys immunized with two injections of $10^{11}$vp/dose of Ad5-NS.
FIG. 18B

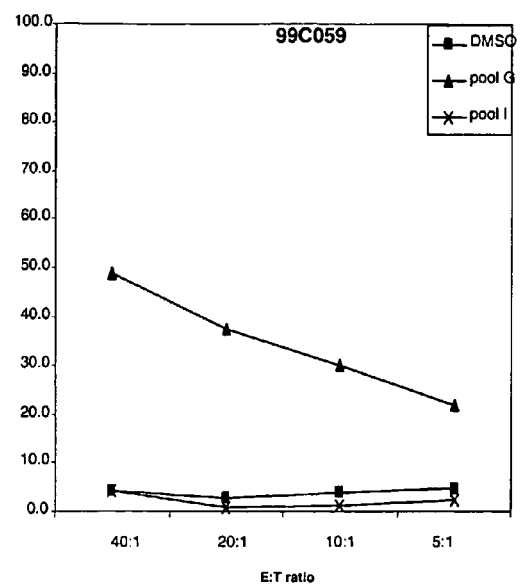
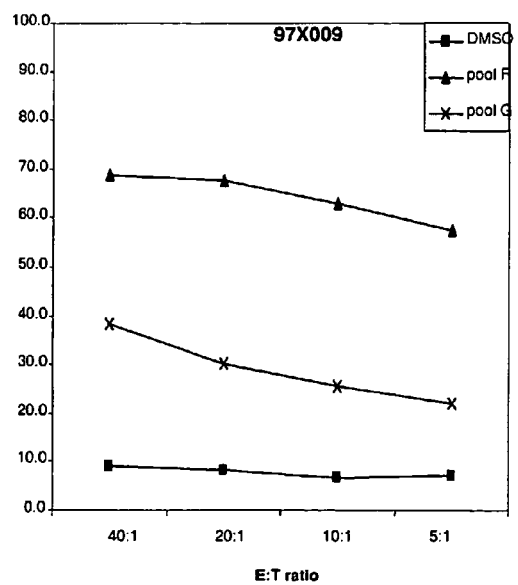
Bulk CTL assays on PBMC from Rhesus monkeys immunized with two injections of $10^{11}$ vp/dose of MRKAd5-NSmut.
FIG. 18C

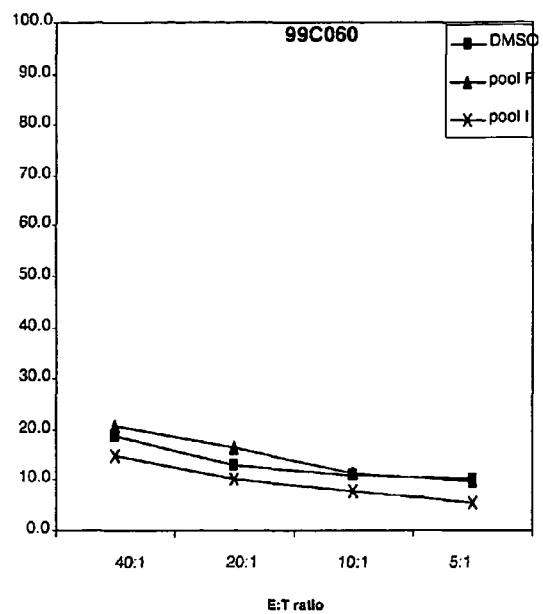
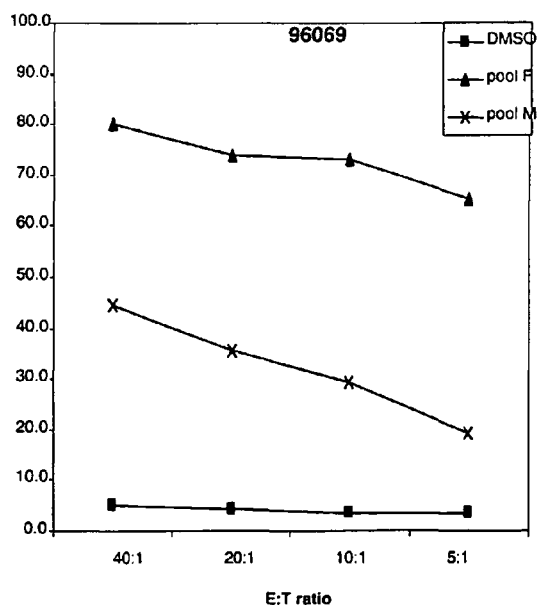
Bulk CTL assays on PBMC from Rhesus monkeys immunized with two injections of $10^{11}$ vp/dose of MRKAd5-NSmut
FIG. 18D

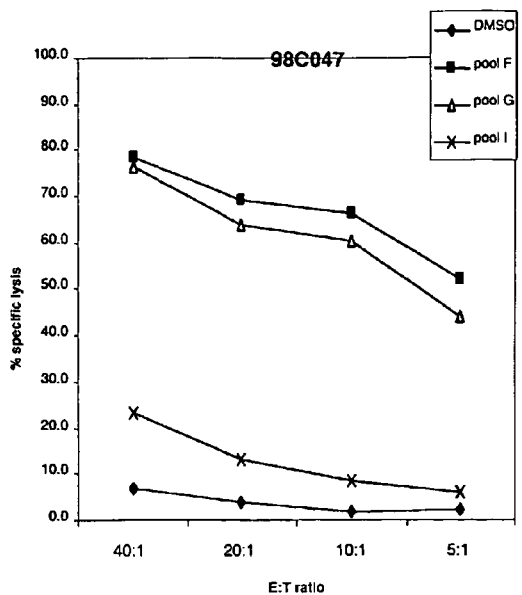
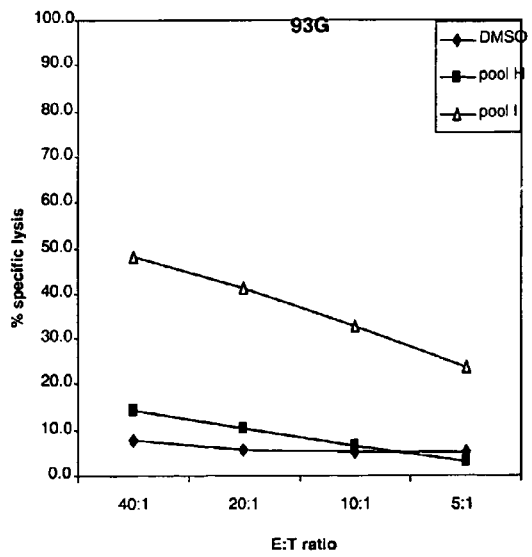
Bulk CTL assays on PBMC from Rhesus monkeys immunized with two injections of $10^{11}$ vp/dose of MRKAd6-NSmut.
FIG. 18E

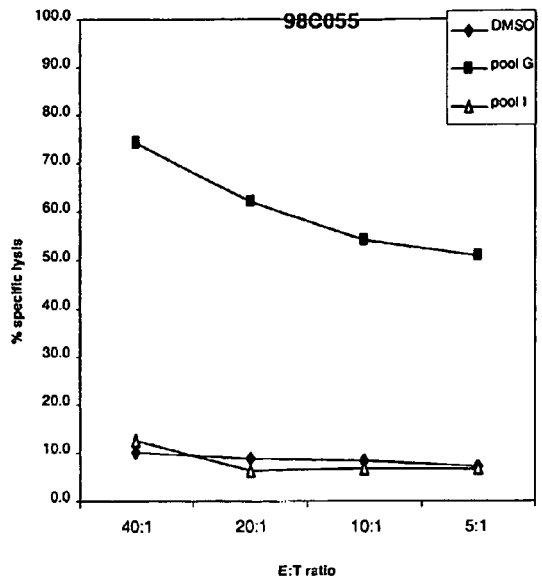
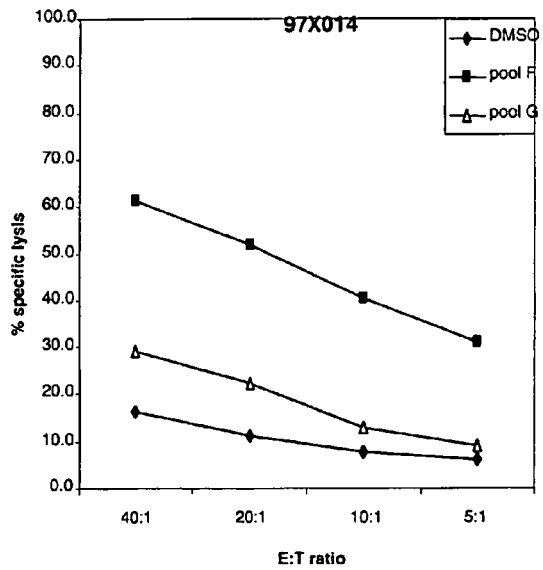
Bulk CTL assays on PBMC from Rhesus monkeys immunized with two injections of $10^{11}$ vp/dose of MRKAd6-NSmut.
FIG. 18F

```
   1  GCCACCATGG CCCCCATCAC CGCCTACAGC CAGCAGACCA GGGGCCTGCT
  51  GGGCTGCATC ATCACCAGCC TGACCGGACG CGACAAGAAC CAGGTGGAGG
 101  GAGAGGTGCA GGTGGTGAGC ACCGCTACCC AGAGCTTCCT GGCCACCTGC
 151  GTGAACGGCG TGTGCTGGAC CGTGTACCAC GGAGCCGGAA GCAAGACCCT
 201  GGCCGGACCC AAGGGCCCTA TCACCCAGAT GTACACCAAT GTGGATCAGG
 251  ATCTGGTGGG CTGGCAGGCC CCTCCCGGAG CCAGGAGCCT GACACCCTGT
 301  ACCTGTGGAA GCAGCGACCT GTACCTGGTG ACACGCCACG CCGATGTGAT
 351  CCCCGTGAGG CGCAGGGGCG ATTCTCGCGG AAGCCTGCTG AGCCCTAGGC
 401  CCGTGAGCTA CCTGAAGGGC AGCAGCGGAG GACCCCTGCT GTGTCCTTCT
 451  GGCCATGCCG TGGGCATTTT TCGCGCTGCC GTGTGTACCA GGGGCGTGGC
 501  CAAAGCCGTG GATTTTGTGC CCGTGGAAAG CATGGAGACC ACCATGCGCA
 551  GCCCTGTGTT CACCGACAAC AGCTCTCCCC CTGCCGTGCC CCAATCATTC
 601  CAGGTGGCTC ACCTGCACGC CCCTACCGGA TCTGGCAAGA GCACCAAGGT
 651  GCCCGCTGCC TACGCCGCTC AGGGCTACAA GGTGCTGGTG CTGAACCCCA
 701  GCGTGGCCGC TACCCTGGGC TTCGGCGCTT ACATGAGCAA GGCCCATGGC
 751  ATCGACCCCA ACATCCGCAC AGGCGTGCGC ACCATCACCA CCGGGAGCTCC
 801  CGTGACCTAC AGCACCTACG GCAAGTTCCT GGCCGATGGA GGCTGCAGCG
 851  GAGGAGCCTA CGACATCATC ATCTGCGACG AGTGCCACAG CACCGACAGC
 901  ACCACCATCC TGGGCATTGG CACCGTGCTG GATCAGGCCG AAACAGCTGG
 951  AGCCAGGCTG GTGGTGCTGG CCACAGCTAC CCCTCCTGGC AGCGTGACCG
1001  TGCCCCATCC CAATATCGAG GAGGTGGCCC TGAGCAACAC AGGCGAGATC
1051  CCCTTCTACG GCAAGGCCAT CCCCATCGAG GCCATCCGCG GAGGCAGGCA
1101  CCTGATCTTC TGCCACAGCA AGAAGAAGTG CGACGAGCTG GCTGCCAAGC
1151  TGAGCGGACT GGGCATCAAC GCCGTGGCCT ACTACAGGGG CCTGGACGTG
1201  TCAGTGATCC CCACCATCGG CGATGTGGTG GTGGTGGCCA CCGACGCCCT
1251  GATGACAGGC TACACCGGAG ACTTCGACAG CGTGATCGAC TGCAACACCT
1301  GCGTGACCCA GACCGTGGAC TTCAGCCTGG ACCCCACCTT CACCATCGAA
1351  ACCACCACCG TGCCTCAGGA TGCTGTGAGC AGGAGCCAGA GGCGCGGACG
1401  CACCGGAAGG GGCAGGCGCG GAATTTATCG CTTTGTGACC CCTGGCGAAA
1451  GGCCCTCTGG CATGTTCGAC AGCAGCGTGC TGTGCGAGTG CTACGACGCT
1501  GGCTGCGCTT GGTACGAGCT GACACCCGCT GAAACCAGCG TGCGCCTGCG
1551  CGCTTATCTG AATACCCCTG GCCTGCCCGT GTGTCAGGAC CACCTGGAGT
```

FIG. 20A

1601 TCTGGGAGAG CGTGTTCACA GGACTGACCC ACATCGACGC CCATTTCCTG
1651 AGCCAGACCA AGCAGGCTGG CGACAACTTC CCCTATCTGG TGGCCTATCA
1701 GGCCACCGTG TGTGCTAGGG CCCAAGCTCC ACCTCCTTCA TGGGACCAGA
1751 TGTGGAAGTG CCTGATCCGC CTGAAGCCCA CCCTGCACGG CCCTACCCCT
1801 CTGCTGTACC GCCTGGGAGC CGTGCAGAAC GAGGTGACCC TGACCCACCC
1851 CATCACCAAG TACATCATGG CCTGCATGAG CGCTGATCTG GAAGTGGTGA
1901 CCAGCACCTG GGTGCTGGTG GGAGGCGTGC TGGCCGCTCT GGCTGCCTAC
1951 TGCCTGACCA CCGGAAGCGT GGTGATCGTG GACGCATCA TCCTGAGCGG
2001 AAGGCCCGCT ATCGTGCCCG ATCGCGAGTT CCTGTACCAG GAGTTCGACG
2051 AGATGGAGGA GTGTGCCAGC CACCTGCCCT ACATCGAGCA GGGCATGCAG
2101 CTGGCCGAAC AGTTCAAGCA GAAGGCCCTG GCCTGCTGC AGACAGCCAC
2151 CAAACAGGCC GAAGCTGCCG CTCCCGTGGT GGAAAGCAAG TGGAGGGCCC
2201 TGGAGACCTT CTGGGCTAAG CACATGTGGA ACTTCATCTC TGGCATCCAG
2251 TACCTGGCCG GACTGAGCAC CCTGCCTGGC AACCCCGCTA TCGCCAGCCT
2301 GATGGCCTTC ACCGCTAGCA TCACCTCTCC CCTGACCACC CAGAGCACCC
2351 TGCTGTTCAA CATTCTGGGC GGATGGGTGG CCGCTCAGCT GGCCCCTCCT
2401 TCAGCTGCTT CTGCCTTTGT GGGCGCTGGC ATTGCCGGAG CCGCTGTGGG
2451 CAGCATTGGC CTGGGCAAAG TGCTGGTGGA TATTCTGGCT GGCTATGGCG
2501 CTGGCGTGGC CGGAGCCCTG GTGGCCTTCA AGGTGATGAG CGGAGAGATG
2551 CCCAGCACCG AGGACCTGGT GAACCTGCTG CCTGCCATTC TGAGCCCTGG
2601 AGCCCTGGTG GTGGGCGTGG TGTGTGCTGC CATTCTGAGG CGCCATGTGG
2651 GACCCGGAGA GGGCGCTGTG CAGTGGATGA ACCGCCTGAT CGCCTTCGCC
2701 TCTCGCGGAA ACCACGTGAG CCCTACCCAC TACGTGCCTG AGAGCGACGC
2751 CGCTGCCAGG GTGACCCAGA TCCTGAGCAG CCTGACCATC ACCCAGCTGC
2801 TGAAGCGCCT GCACCAGTGG ATCAACGAGG ACTGCAGCAC ACCCTGCAGC
2851 GGAAGCTGGC TGAGGGACGT GTGGGACTGG ATCTGCACCG TGCTGACCGA
2901 CTTCAAGACC TGGCTGCAGA GCAAGCTGCT GCCCCAACTG CCTGGCGTGC
2951 CCTTCTTCTC ATGCCAGCGC GGATACAAGG GCGTGTGGAG GGGCGATGGC
3001 ATCATGCAGA CCACCTGTCC CTGCGGAGCC CAGATCACAG GCCACGTGAA
3051 GAACGGCAGC ATGCGCATCG TGGGCCCTAA GACCTGCAGC AACACCTGGC
3101 ACGGCACCTT CCCCATCAAC GCCTACACCA CCGGACCCTG CACACCCAGC
3151 CCTGCTCCCA ACTACAGCAG GGCCCTGTGG AGGGTGGCTG CCGAGGAGTA

FIG. 20B

3201 CGTGGAGGTG ACCAGGGTGG GAGACTTCCA CTACGTGACC GGAATGACCA
3251 CCGACAACGT GAAGTGTCCC TGTCAGGTGC CCGCTCCCGA ATTTTTTACC
3301 GAAGTGGATG GCGTGCGCCT GCATCGCTAT GCCCCTGCCT GTAGGCCCCT
3351 GCTGCGCGAA GAAGTGACCT TCCAGGTGGG CCTGAACCAG TACCTGGTGG
3401 GCAGCCAGCT GCCCTGCGAG CCTGAGCCCG ATGTGGCCGT GCTGACCAGC
3451 ATGCTGACCG ACCCCAGCCA CATCACAGCC GAAACCGCTA AAAGGCGCCT
3501 GGCCAGGGGC TCTCCTCCAA GCCTGGCCTC AAGCAGCGCT AGCCAGCTGT
3551 CTGCTCCCAG CCTGAAGGCC ACCTGCACCA CCCACCACGT GAGCCCCGAC
3601 GCCGACCTGA TCGAGGCCAA CCTGCTGTGG CGCCAGGAGA TGGGCGGCAA
3651 CATCACCCGC GTGGAGAGCG AGAACAAGGT GGTGGTGCTG ACAGCTTCG
3701 ACCCCCTGCG CGCCGAGGAG GACGAGCGCG AGGTGAGCGT GCCCGCCGAG
3751 ATCCTGCGCA AGAGCAAGAA GTTCCCCGCT GCCATGCCCA TCTGGGCTAG
3801 ACCTGATTAC AACCCTCCCC TGCTGGAGAG CTGGAAGGAC CCTGATTACG
3851 TGCCTCCAGT GGTGCATGGC TGTCCTCTGC CTCCCATTAA AGCCCCTCCT
3901 ATTCCACCTC CTAGGCGCAA AAGGACCGTG GTGCTGACAG AAAGCAGCGT
3951 GAGCTCTGCT CTGGCCGAAC TGGCCACCAA GACCTTTGGC AGCAGCGAGA
4001 GCTCTGCCGT GGACAGCGGA ACAGCCACCG CTCTGCCTGA CCAGGCCAGC
4051 GACGACGGCG ATAAGGGCAG CGATGTGGAG AGCTATAGCA GCATGCCTCC
4101 CCTGGAAGGC GAACCTGGCG ATCCCGATCT GAGCGATGGC AGCTGGAGCA
4151 CCGTGAGCGA AGAGGCCAGC GAGGACGTGG TGTGTTGCAG CATGAGCTAC
4201 ACCTGGACAG GCGCTCTGAT CACACCCTGC GCTGCCGAGG AGAGCAAGCT
4251 GCCCATCAAC GCCCTGAGCA ACAGCCTGCT GAGGCACCAC AACATGGTGT
4301 ACGCCACCAC CAGCAGGTCT GCCGGACTGA GGCAGAAGAA GGTGACCTTC
4351 GACCGCCTGC AGGTGCTGGA CGACCACTAC CGCGATGTGC TGAAGGAGAT
4401 GAAGGCCAAG GCCAGCACCG TGAAGGCCAA GCTGCTGAGC GTGGAGGAGG
4451 CCTGCAAGCT GACCCCCCCC CACAGCGCCA AGAGCAAGTT CGGCTACGGC
4501 GCCAAGGACG TGCGCAACCT GAGCAGCAAG GCCGTGAACC ACATCCACAG
4551 CGTGTGGAAG GACCTGCTGG AGGACACCGT GACCCCCATC GACACCACCA
4601 TCATGGCCAA GAACGAGGTG TTCTGCGTGC AGCCCGAGAA GGGCGGCCGC
4651 AAGCCCGCTC GCCTGATCGT GTTCCCCGAT CTGGGCGTGC GCGTGTGCGA
4701 GAAGATGGCC CTGTACGACG TGGTGAGCAC CCTGCCTCAG GTGGTGATGG
4751 GCTCAAGCTA CGGCTTCCAG TACAGCCCTG CCAGCGCGT GGAGTTCCTG

FIG. 20C

```
4801  GTGAACACCT GGAAGAGCAA GAAGAACCCC ATGGGCTTCA GCTACGACAC
4851  ACGCTGCTTC GACAGCACCG TGACCGAGAA CGACATCCGC GTGGAGGAGA
4901  GCATCTACCA GTGCTGCGAC CTGGCCCCTG AGGCCAGGCA GGCCATCAAG
4951  AGCCTGACCG AGCGCCTGTA CATCGGAGGC CCTCTGACCA ACAGCAAGGG
5001  ACAGAACTGC GGATACAGGC GCTGTAGGGC CTCTGGCGTG CTGACCACCA
5051  GCTGTGGCAA CACCCTGACC TGCTACCTGA AGGCCAGCGC TGCCTGTCGC
5101  GCTGCCAAGC TGCAGGACTG CACCATGCTG GTGAACGCCG CTGGCCTGGT
5151  GGTGATTTGT GAAAGCGCTG GCACCCAGGA AGATGCTGCC AGCCTGCGCG
5201  TGTTCACCGA GGCCATGACC AGGTACTCTG CCCCTCCCGG AGACCCCCCT
5251  CAGCCCGAAT ACGACCTGGA GCTGATCACC AGCTGCTCAA GCAACGTGAG
5301  CGTGGCTCAC GACGCCAGCG AAAGCGCGT GTACTACCTG ACACGCGATC
5351  CCACCACCCC TCTGGCTCGC GCTGCCTGGG AAACCGCTCG CCATACACCC
5401  GTGAACAGCT GGCTGGGCAA CATCATCATG TACGCCCCTA CCCTGTGGGC
5451  TCGCATGATC CTGATGACCC ACTTCTTCAG CATCCTGCTG GCTCAGGAGC
5501  AGCTGGAGAA GGCCCTGGAC TGCCAGATTT ACGGCGCTTG CTACAGCATC
5551  GAGCCCCTGG ACCTGCCCCA AATCATCGAG CGCCTGCACG GCCTGTCTGC
5601  CTTCAGCCTG CACAGCTACA GCCCTGGCGA AATTAATCGC GTGGCCAGCT
5651  GTCTGCGCAA ACTGGGCGTG CCTCCTCTGC GCGTGTGGAG GCATAGGGCT
5701  AGGAGCGTGA GGGCTAGGCT GCTGAGCCAG GGAGGCAGGG CCGCTACCTG
5751  TGGAAAGTAC CTGTTCAACT GGGCCGTGAA GACCAAGCTG AAGCTGACCC
5801  CTATCCCTGC CGCTAGCCAG CTGGACCTGA GCGGATGGTT CGTGGCTGGC
5851  TACAGCGGAG CGACATCTA CCACAGCCTG TCTCGCGCTC GCCCTCGCTG
5901  GTTCATGCTG TGCCTGCTGC TGCTGAGCGT GGGCGTGGGC ATCTACCTGC
5951  TGCCCAACCG CTAAA
```

FIG. 20D

HEPATITIS C VIRUS VACCINE

RELATED APPLICATIONS

The present application claims priority to provisional applications U.S. Ser. No. 60/363,774, filed Mar. 13, 2002, and U.S. Ser. No. 60/328,655, filed Oct. 11, 2001, each of which are hereby incorporated by reference herein.

BACKGROUND OF THE INVENTION

The references cited in the present application are not admitted to be prior art to the claimed invention.

About 3% of the world's population are infected with the Hepatitis C virus (HCV). (Wasley et al., *Semin. Liver Dis.* 20, 1-16, 2000.) Exposure to HCV results in an overt acute disease in a small percentage of cases, while in most instances the virus establishes a chronic infection causing liver inflammation and slowly progresses into liver failure and cirrhosis. (Iwarson, *FEMS Microbiol. Rev.* 14, 201-204, 1994.) In addition, epidemiological surveys indicate an important role of HCV in the pathogenesis of hepatocellular carcinoma. (Kew, *FEMS Microbiol. Rev.* 14, 211-220, 1994, Alter, *Blood* 85, 1681-1695, 1995.)

Prior to the implementation of routine blood screening for HCV in 1992, most infections were contracted by inadvertent exposure to contaminated blood, blood products or transplanted organs. In those areas where blood screening of HCV is carried out, HCV is primarily contracted through direct percutaneous exposure to infected blood, i.e., intravenous drug use. Less frequent methods of transmission include perinatal exposure, hemodialysis, and sexual contact with an HCV infected person. (Alter et al., *N. Engl. J. Med.* 341(8), 556-562, 1999, Alter, *J. Hepatol.* 31 *Suppl.* 88-91, 1999. *Semin. Liver. Dis.* 201, 1-16, 2000.)

The HCV genome consists of a single strand RNA about 9.5 kb encoding a precursor polyprotein of about 3000 amino acids. (Choo et al., *Science* 244, 362-364, 1989, Choo et al., *Science* 244, 359-362, 1989, Takamizawa et al., *J. Virol.* 65, 1105-1113, 1991.) The HCV polyprotein contains the viral proteins in the order: C-E1-E2-p7-NS2-NS3-NS4A-NS4B-NS5A-NS5B.

Individual viral proteins are produced by proteolysis of the HCV polyprotein. Host cell proteases release the putative structural proteins C, E1, E2, and p7, and create the N-terminus of NS2 at amino acid 810. (Mizushima et al., *J. Virol.* 68, 2731-2734, 1994, Hijikata et al., *P.N.A.S. USA* 90, 10773-10777, 1993.)

The non-structural proteins NS3, NS4A, NS4B, NS5A and NS5B presumably form the virus replication machinery and are released from the polyprotein. A zinc-dependent protease associated with NS2 and the N-terminus of NS3 is responsible for cleavage between NS2 and NS3. (Grakoui et al., *J. Virol.* 67, 1385-1395, 1993, Hijikata et al., *P.N.A.S. USA* 90, 10773-10777, 1993.) A distinct serine protease located in the N-terminal domain of NS3 is responsible for proteolytic cleavages at the NS3/NS4A, NS4A/NS4B, NS4B/NS5A and NS5A/NS5B junctions. (Bartenschlager et al., *J. Virol.* 67, 3835-3844, 1993, Grakoui et al., *Proc. Natl. Acad. Sci. USA* 90, 10583-10587, 1993, Tomei et al., *J. Virol.* 67, 4017-4026, 1993.) NS4A provides a cofactor for NS3 activity. (Failla et al., *J. Virol.* 68, 3753-3760, 1994, De Francesco et al., U.S. Pat. No. 5,739,002.)

NS5A is a highly phosphorylated protein conferring interferon resistance. (De Francesco et al., *Semin. Liver Dis.*, 20(1), 69-83, 2000, Pawlotsky, *Viral Hepat. Suppl.* 1, 47-48, 1999.)

NS5B provides an RNA-dependent RNA polymerase. (De Francesco et al., International Publication Number WO 96/37619, Behrens et al., *EMBO* 15, 12-22, 1996, Lohmann et al., *Virology* 249, 108-118, 1998.)

SUMMARY OF THE INVENTION

The present invention features Ad6 vectors and a nucleic acid encoding a Met-NS3-NS4A-NS4B-NS5A-NS5B polypeptide containing an inactive NS5B RNA-dependent RNA polymerase region. The nucleic acid is particularly useful as a component of an adenovector or DNA plasmid vaccine providing a broad range of antigens for generating an HCV specific cell mediated immune (CMI) response against HCV.

A HCV specific CMI response refers to the production of cytotoxic T lymphocytes and T helper cells that recognize an HCV antigen. The CMI response may also include non-HCV specific immune effects.

Preferred nucleic acids encode a Met-NS3-NS4A-NS4B-NS5A-NS5B polypeptide that is substantially similar to SEQ. ID. NO. 1 and has sufficient protease activity to process itself to produce at least a polypeptide substantially similar to the NS5B region present in SEQ. ID. NO. 1. The produced polypeptide corresponding to NS5B is enzymatically inactive. More preferably, the HCV polypeptide has sufficient protease activity to produce polypeptides substantially similar to the NS3, NS4A, NS4B, NS5A, and NS5B regions present in SEQ. ID. NO. 1.

Reference to a "substantially similar sequence" indicates an identity of at least about 65% to a reference sequence. Thus, for example, polypeptides having an amino acid sequence substantially similar to SEQ. ID. NO. 1 have an overall amino acid identity of at least about 65% to SEQ. ID. NO. 1.

Polypeptides corresponding to NS3, NS4A, NS4B, NS5A, and NS5B have an amino acid sequence identity of at least about 65% to the corresponding region in SEQ. ID. NO. 1. Such corresponding polypeptides are also referred to herein as NS3, NS4A, NS4B, NS5A, and NS5B polypeptides.

Thus, a first aspect of the present invention describes a nucleic acid comprising a nucleotide sequence encoding a Met-NS3-NS4A-NS4B-NS5A-NS5B polypeptide substantially similar to SEQ. ID. NO. 1. The encoded polypeptide has sufficient protease activity to process itself to produce an NS5B polypeptide that is enzymatically inactive.

In a preferred embodiment, the nucleic acid is an expression vector capable of expressing the Met-NS3-NS4A-NS4B-NS5A-NS5B polypeptide in a desired human cell. Expression inside a human cell has therapeutic applications for actively treating an HCV infection and for prophylactically treating against an HCV infection.

An expression vector contains a nucleotide sequence encoding a polypeptide along with regulatory elements for proper transcription and processing. The regulatory elements that may be present include those naturally associated with the nucleotide sequence encoding the polypeptide and exogenous regulatory elements not naturally associated with the nucleotide sequence. Exogenous regulatory elements such as an exogenous promoter can be useful for expression in a particular host, such as in a human cell. Examples of regulatory elements useful for functional expression include a promoter, a terminator, a ribosome binding site, and a polyadenylation signal.

Another aspect of the present invention describes a nucleic acid comprising a gene expression cassette able to express in a human cell a Met-NS3-NS4A-NS4B-NS5A-NS5B polypeptide substantially similar to SEQ. ID. NO. 1. The polypeptide can process itself to produce an enzymatically inactive NS5B protein. The gene expression cassette contains at least the following:

a) a promoter transcriptionally coupled to a nucleotide sequence encoding a polypeptide;

b) a 5' ribosome binding site functionally coupled to the nucleotide sequence, c) a terminator joined to the 3' end of the nucleotide sequence, and d) a 3' polyadenylation signal functionally coupled to the nucleotide sequence.

Reference to "transcriptionally coupled" indicates that the promoter is positioned such that transcription of the nucleotide sequence can be brought about by RNA polymerase binding at the promoter. Transcriptionally coupled does not require that the sequence being transcribed is adjacent to the promoter.

Reference to "functionally coupled" indicates the ability to mediate an effect on the nucleotide sequence. Functionally coupled does not require that the coupled sequences be adjacent to each other. A 3' polyadenylation signal functionally coupled to the nucleotide sequence facilitates cleavage and polyadenylation of the transcribed RNA. A 5' ribosome binding site functionally coupled to the nucleotide sequence facilitates ribosome binding.

In preferred embodiments the nucleic acid is a DNA plasmid vector or an adenovector suitable for either therapeutic application in treating HCV or as an intermediate in the production of a therapeutic vector. Treating HCV includes actively treating an HCV infection and prophylactically treating against an HCV infection.

Another aspect of the present invention describes an adenovector comprising a Met-NS3-NS4A-NS4B-NS5A-NS5B expression cassette able to express a polypeptide substantially similar to SEQ. ID. NO. 1 that is produced by a process involving (a) homologous recombination and (b) adenovector rescue. The homologous recombinant step produces an adenovirus genome plasmid. The adenovector rescue step produces the adenovector from the adenogenome plasmid.

Adenovirus genome plasmids described herein contain a recombinant adenovirus genome having a deletion in the E1 region and optionally in the E3 region and a gene expression cassette inserted into one of the deleted regions. The recombinant adenovirus genome is made of regions substantially similar to one or more adenovirus serotypes.

Another aspect of the present invention describes an adenovector consisting of the nucleic acid sequence of SEQ. ID. NO. 4 or a derivative thereof, wherein said derivative thereof has the HCV polyprotein encoding sequence present in SEQ. ID. NO. 4 replaced with the HCV polyprotein encoding sequence of either SEQ. ID. NO. 3, SEQ. ID. NO. 10 or SEQ. ID. NO. 11.

Another aspect of the present invention describes a cultured recombinant cell comprising a nucleic acid containing a sequence encoding a Met-NS3-NS4A-NS4B-NS5A-NS5B polypeptide substantially similar to SEQ. ID. NO. 1. The recombinant cell has a variety of uses such as being used to replicate nucleic acid encoding the polypeptide in vector construction methods.

Another aspect of the present invention describes a method of making an adenovector comprising a Met-NS3-NS4A-NS4B-NS5A-NS5B expression cassette able to express a polypeptide substantially similar to SEQ. ID. NO. 1. The method involves the steps of (a) producing an adenovirus genome plasmid containing a recombinant adenovirus genome with deletions in the E1 and E3 regions and a gene expression cassette inserted into one of the deleted regions and (b) rescuing the adenovector from the adenovirus genome plasmid.

Another aspect of the present invention describes a pharmaceutical composition comprising a vector for expressing a Met-NS3-NS4A-NS4B-NS5A-NS5B polypeptide substantially similar to SEQ. ID. NO. 1 and a pharmaceutically acceptable carrier. The vector is suitable for administration and polypeptide expression in a patient.

A "patient" refers to a mammal capable of being infected with HCV. A patient may or may not be infected with HCV. Examples of patients are humans and chimpanzees.

Another aspect of the present invention describes a method of treating a patient comprising the step of administering to the patient an effective amount of a vector expressing a Met-NS3-NS4A-NS4B-NS5A-NS5B polypeptide substantially similar to SEQ. ID. NO. 1. The vector is suitable for administration and polypeptide expression in the patient.

The patient undergoing treatment may or may not be infected with HCV. For a patient infected with HCV, an effective amount is sufficient to achieve one or more of the following effects: reduce the ability of HCV to replicate, reduce HCV load, increase viral clearance, and increase one or more HCV specific CMI responses. For a patient not infected with HCV, an effective amount is sufficient to achieve one or more of the following: an increased ability to produce one or more components of a HCV specific CMI response to a HCV infection, a reduced susceptibility to HCV infection, and a reduced ability of the infecting virus to establish persistent infection for chronic disease.

Another aspect of the present invention features a recombinant nucleic acid comprising an Ad6 region and a region not present in Ad6. Reference to "recombinant" nucleic acid indicates the presence of two or more nucleic acid regions not naturally associated with each other. Preferably, the Ad6 recombinant nucleic acid contains Ad6 regions and a gene expression cassette coding for a polypeptide heterologous to Ad6.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIGS. 1A and 1B illustrate SEQ. ID. NO. 1.

FIGS. 2A, 2B, 2C, and 2D illustrate SEQ. ID. NO. 2. SEQ. ID. NO. 2 provides a nucleotide sequence coding for SEQ. ID. NO. 1 along with an optimized internal ribosome entry site and TAAA termination. Nucleotides 1-6 provides an optimized internal ribosome entry site. Nucleotides 7-5961 code for a HCV Met-NS3-NS4A-NS4B-NS5A-NS5B polypeptide with nucleotides in positions 5137 to 5145 providing a AlaAlaGly sequence in amino acid positions 1711 to 1713 that renders NS5B inactive. Nucleotides 5962-5965 provide a TAAA termination.

FIGS. 3A, 3B, 3C, and 3D illustrate SEQ. ID. NO. 3. SEQ. ID. NO. 3 is a codon optimized version of SEQ. ID. NO. 2. Nucleotides 7-5961 encode a HCV Met-NS3-NS4A-NS4B-NS5A-NS5B polypeptide.

FIGS. 4A-4M illustrate MRKAd6-NSmut (SEQ. ID. NO. 4). SEQ. ID. NO. 4 is an adenovector containing an expression cassette where the polypeptide of SEQ. ID. NO. 1 is encoded by SEQ. ID. NO. 2. Base pairs 1-450 correspond to the Ad5 bp 1 to 450; base pairs 462 to 1252 correspond to the human CMV promoter; base pairs 1258 to 1267 correspond to the Kozak sequence; base pairs 1264 to 7222 correspond to the NS genes; base pairs 7231 to 7451 correspond to the BGH polyadenylation signal; base pairs 7469 to 9506 correspond to Ad5 base pairs 3511 to 5548; base pairs 9507 to 32121 correspond to Ad6 base pairs 5542 to 28156; base pairs 32122 to 35117 correspond to Ad6 base pairs 30789 to 33784; and base pairs 35118 to 37089 correspond to Ad5 base pairs 33967 to 35935.

FIGS. 5A-5O illustrate SEQ. ID. NOs. 5 and 6. SEQ. ID. NO. 5 encodes a HCV Met-NS3-NS4A-NS4B-NS5A-NS5B polypeptide with an active RNA dependent RNA polymerase. SEQ. ID. NO. 6 provides the amino acid sequence for the polypeptide.

FIGS. 6A-6C provide the nucleic acid sequence for pV1JnsA (SEQ. ID. NO. 7).

FIGS. 7A-7N provide the nucleic acid sequence for the Ad6 genome (SEQ. ID. NO. 8).

FIGS. 8A-8K provide the nucleic acid sequence for the Ad5 genome (SEQ. ID. NO. 9).

FIGS. 13A and 13B illustrate T cell responses by IFNγ ELIspot induced in C57black6 mice (A) and BalbC mice (B) by two injections of 25 μg and 50 μg, respectively, of plasmid DNA encoding the different HCV NS cassettes with Gene Electro-Transfer (GET).

FIG. 15 illustrates T cell responses by IFNγ ELIspot induced in C57black6 mice by two injections of $10^9$ vp of adenovectors containing different HCV non-structural gene cassettes.

FIGS. 16A-16D illustrate T cell responses by IFNγ ELIspot induced in Rhesus monkeys by one or two injections of $10^{10}$ vp (A) or $10^{11}$ vp (B) of adenovectors containing different HCV non-structural gene cassettes.

FIGS. 17A and 17B illustrates CD8+ T cell responses by IFNγ ICS induced in Rhesus monkeys by two injections of $10^{10}$ vp (A) or $10^{11}$ vp (B) of adenovectors encoding the different HCV non-structural gene cassettes.

FIGS. 18A-18F illustrate T cell responses by bulk CTL assay induced in Rhesus monkeys by two injections of $10^{11}$ vp of Ad5-NS (A), MRKAd5-NSmut (B), or MRKAd6-NS-mut (C).

FIGS. 20A-D illustrates the partial codon optimized sequence NSsuboptmut (SEQ. ID. NO. 10). Coding sequence for the Met-NS3-NS4A-NS4B-NS5A-NS5B polypeptide is from base 7 to 5961.

DETAILED DESCRIPTION OF THE INVENTION

Figure 4A:
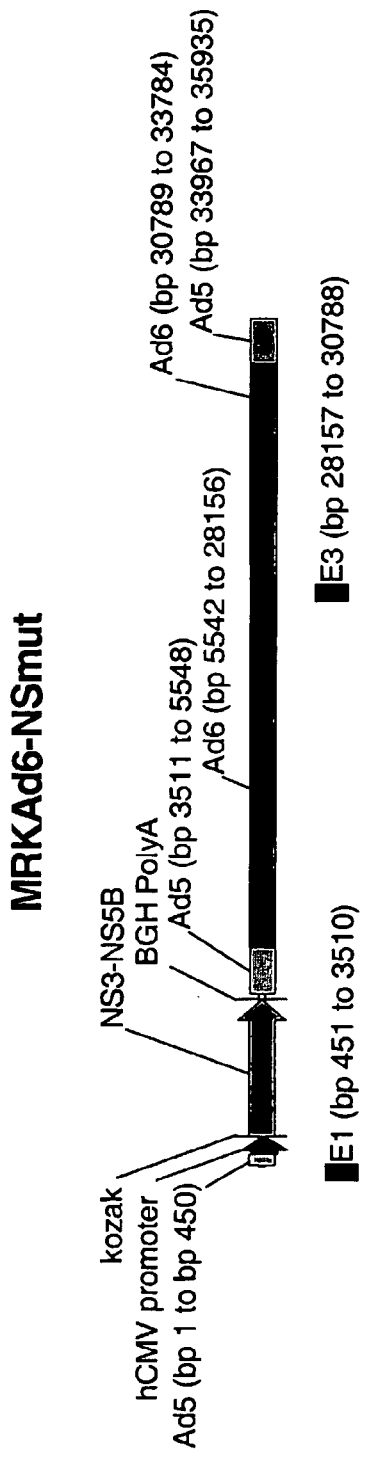

The present invention features Ad6 vectors and nucleic acid encoding a Met-NS3-NS4A-NS4B-NS5A-NS5B polypeptide that contains an inactive NS5B region. Providing an inactive NS5B region supplies NS5B antigens while reducing the possibility of adverse side effects due to an active viral RNA polymerase. Uses of the featured nucleic acid include use as a vaccine component to introduce into a cell an HCV polypeptide that provides a broad range of antigens for generating a CMI response against HCV, and as an intermediate for producing such a vaccine component.

The adaptive cellular immune response can function to recognize viral antigens in HCV infected cells throughout the body due to the ubiquitous distribution of major histocompatibility complex (MHC) class I and II expression, to induce immunological memory, and to maintain immunological memory. These functions are attributed to antigen-specific CD4+ T helper (Th) and CD8+ cytotoxic T cells (CTL).

Upon activation via their specific T cell receptors, HCV specific Th cells fulfill a variety of immunoregulatory functions, most of them mediated by Th1 and Th2 cytokines. HCV specific Th cells assist in the activation and differentiation of B cells and induction and stimulation of virus-specific cytotoxic T cells. Together with CTL, Th cells may also secrete IFN-γ and TNF-α that inhibit replication and gene expression of several viruses. Additionally, Th cells and CTL, the main effector cells, can induce apoptosis and lysis of virus infected cells.

HCV specific CTL are generated from antigens processed by professional antigen presenting cells (pAPCs). Antigens can be either synthesized within or introduced into pAPCs. Antigen synthesis in a pAPC can be brought about by introducing into the cell an expression cassette encoding the antigen.

A preferred route of nucleic acid vaccine administration is an intramuscular route. Intramuscular administration appears to result in the introduction and expression of nucleic acid into somatic cells and pAPCs. HCV antigens produced in the somatic cells can be transferred to pAPCs for presentation in the context of MHC class I molecules. (Donnelly et al., *Annu. Rev. Immunol.* 15:617-648, 1997.)

pAPCs process longer length antigens into smaller peptide antigens in the proteasome complex. The antigen is translocated into the endoplasmic reticulum/Golgi complex secretory pathway for association with MHC class I proteins. CD8+ T lymphocytes recognize antigen associated with class I MHC via the T cell receptor (TCR) and the CD8 cell surface protein.

Using a nucleic acid encoding a Met-NS3-NS4A-NS4B-NS5A-NS5B polypeptide as a vaccine component allows for production of a broad range of antigens capable of generating CMI responses from a single vector. The polypeptide should be able to process itself sufficiently to produce at least a region corresponding to NS5B. Preferred nucleic acids encode an amino acid sequence substantially similar to SEQ. ID. NO. 1 that has sufficient protease activity to process itself to produce individual HCV polypeptides substantially similar to the NS3, NS4A, NS4B, NS5A, and NS5B regions present in SEQ. ID. NO. 1.

A polypeptide substantially similar to SEQ. ID. NO. 1 with sufficient protease activity to process itself in a cell provides the cell with T cell epitopes that are present in several different HCV strains. Protease activity is provided by NS3 and NS3/NS4A proteins digesting the Met-NS3-NS4A-NS4B-NS5A-NS5B polypeptide at the appropriate cleavage sites to release polypeptides corresponding to NS3, NS4A, NS4B, NS5A, and NS5B. Self-processing of the Met-NS3-NS4A-NS4B-NS5A-NS5B generates polypeptides that approximate naturally occurring HCV polypeptides.

Based on the guidance provided herein a sufficiently strong immune response can be generated to achieve beneficial effects in a patient. The provided guidance includes information concerning HCV sequence selection, vector selection, vector production, combination treatment, and administration.

I. HCV SEQUENCES

A variety of different nucleic acid sequences can be used as a vaccine component to supply a HCV Met-NS3-NS4A-NS4B-NS5A-NS5B polypeptide to a cell or as an intermediate to produce vaccine components. The starting point for obtaining suitable nucleic acid sequences are preferably naturally occurring NS3-NS4A-NS4B-NS5A-NS5B polypeptide sequences modified to produce an inactive NS5B.

The use of a HCV nucleic acid sequence providing HCV non-structural antigens to generate a CMI response is mentioned by Cho et al., Vaccine 17:1136-1144, 1999, Paliard et al., International Publication Number WO 01/30812 (not admitted to be prior art to the claimed invention), and Coit et al., International Publication Number WO 01/38360 (not admitted to be prior art to the claimed invention). Such references fail to describe, for example, a polypeptide that processes itself to produce an inactive NS5B, and the particular combinations of HCV sequences and delivery vehicles employed herein.

Modifications to a HCV Met-NS3-NS4A-NS4B-NS5A-NS5B polypeptide sequence can be produced by altering the encoding nucleic acid. Alterations can be performed to create deletions, insertions and substitutions.

Small modifications can be made in NS5B to produce an inactive polymerase by targeting motifs essentially for replication. Examples of motifs critical for NS5B activity and modifications that can be made to produce an inactive NS5B are described by Lohmann et al., *Journal of Virology* 71:8416-8426, 1997, and Kolykhalov et al., *Journal of Virology* 74:2046-2051, 2000.

Additional factors to take into account when producing modifications to a HCV Met-NS3-NS4A-NS4B-NS5A-NS5B polypeptide include maintaining the ability to self-process and maintaining T cell antigens. The ability of the HCV polypeptide to process itself is determined to a large extent by a functional NS3 protease. Modifications that maintain NS3 activity protease activity can be obtained by taking into account the NS3 protein, NS4A which serves as a cofactor for NS3, and NS3 protease recognition sites present within the NS3-NS4A-NS4B-NS5A-NS5B polypeptide.

Different modifications can be made to naturally occurring NS3-NS4A-NS4B-NS5A-NS5B polypeptide sequences to produce polypeptides able to elicit a broad range of T cell responses. Factors influencing the ability of a polypeptide to elicit a broad T cell response include the preservation or introduction of HCV specific T cell antigen regions and prevalence of different T cell antigen regions in different HCV isolates.

Numerous examples of naturally occurring HCV isolates are well known in the art. HCV isolates can be classified into the following six major genotypes comprising one or more subtypes: HCV-1/(1a,1b,1c), HCV-2/(2a,2b,2c), HCV-3/(3a, 3b, 10a), HCV-4/(4a), HCV-5/(5a) and HCV-6/(6a,6b,7b,8b, 9a,11a). (Simmonds, *J. Gen. Virol.*, 693-712, 2001.) Examples of particular HCV sequences such as HCV-BK, HCV-J, HCV-N, HCV-H, have been deposited in GenBank and described in various publications. (See, for example, Chamberlain et al., *J. Gen. Virol.*, 1341-1347, 1997.)

HCV T cell antigens can be identified by, for example, empirical experimentation. One way of identifying T cell antigens involves generating a series of overlapping short peptides from a longer length polypeptide and then screening the T-cell populations from infected patients for positive clones. Positive clones are activated/primed by a particular peptide. Techniques such as EFNγ-ELISPOT, IFNγ-Intracellular staining and bulk CTL assays can be used to measure peptide activity. Peptides thus identified can be considered to represent T-cell epitopes of the respective pathogen.

HCV T cell antigen regions from different HCV isolates can be introduced into a single sequence by, for example, producing a hybrid NS3-NS4A-NS4B-NS5A-NS5B polypeptide containing regions from two or more naturally occurring sequences. Such a hybrid can contain additional modifications, which preferably do not reduce the ability of the polypeptide to produce an HCV CMI response.

The ability of a modified Met-NS3-NS4A-NS4B-NS5A-NS5B polypeptide to process itself and produce a CMI response can be determined using techniques described herein or well known in the art. Such techniques include the use of IFNγ-ELISPOT, IFNγ-Intracellular staining and bulk CTL assays to measure a HCV specific CMI response.

A. Met-NS3-NS4A-NS4B-NS5A-NS5B Sequences

SEQ. ID. NO. 1 provides a preferred Met-NS3-NS4A-NS4B-NS5A-NS5B sequence. SEQ. ID. NO. 1 contains a large number of HCV specific T cell antigens that are present in several different HCV isolates. SEQ. ID. NO. 1 is similar to the NS3-NS4A-NS4B-NS5A-NS5B portion of the HCV BK strain nucleotide sequence (GenBank accession number M58335).

In SEQ. ID. NO. 1 anchor positions important for recognition by MHC class I molecules are conserved or represent conservative substitutions for 18 out of 20 known T-cell epitopes in the NS3-NS4A-NS4B-NS5A-NS5B portion of HCV polyproteins. With respect to the remaining two known T-cell epitopes, one has a non-conservative anchor substitution in SEQ. ID. NO. 1 that may still be recognized by a different HLA supertype and one epitope has one anchor residue not conserved. HCV T-cell epitopes are described in Chisari et al., *Curr. Top. Microbiol Immunol.,* 242:299-325, 2000, and Lechner et al. *J. Exp. Med.* 9:1499-1512, 2000.

Differences between the HCV-BK NS3-NS4A-NS4B-NS5A-NS5B nucleotide sequence and SEQ. ID. NO. 1 include the introduction of a methionine at the 5' end and the presence of modified NS5B active site residues in SEQ. ID. NO. 1. The modification replaces GlyAspAsp with AlaAlaGly (residues 1711-1713) to inactivate NS5B.

The encoded HCV Met-NS3-NS4A-NS4B-NS5A-NS5B polypeptide preferably has an amino acid sequence substantially similar to SEQ. ID. NO. 1. In different embodiments, the encoded HCV Met-NS3-NS4A-NS4B-NS5A-NS5B polypeptide has an amino acid identify to SEQ. ID. NO. 1 of at least 65%, at least 75%, at least 85%, at least 95%, at least 99% or 100%; or differs from SEQ. ID. NO. 1 by 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, or 1-20 amino acids.

Amino acid differences between a Met-NS3-NS4A-NS4B-NS5A-NS5B polypeptide and SEQ. ID. NO. 1 are calculated by determining the minimum number of amino acid modifications in which the two sequences differ. Amino acid modifications can be deletions, additions, substitutions or any combination thereof.

Amino acid sequence identity is determined by methods well known in the art that compare the amino acid sequence of one polypeptide to the amino acid sequence of a second polypeptide and generate a sequence alignment. Amino acid identity is calculated from the alignment by counting the number of aligned residue pairs that have identical amino acids.

Methods for determining sequence identity include those described by Schuler, G. D. in *Bioinformatics: A Practical Guide to the Analysis of Genes and Proteins*, Baxevanis, A. D. and Ouelette, B. F. F., eds., John Wiley & Sons, Inc, 2001; Yona, et al., in *Bioinformatics: Sequence, structure and databanks*, Higgins, D. and Taylor, W. eds, Oxford University Press, 2000; and *Bioinformatics: Sequence and Genome Analysis*, Mount, D. W., ed., Cold Spring Harbor Laboratory Press, 2001). Methods to determine amino acid sequence identity are codified in publicly available computer programs such as GAP (Wisconsin Package Version 10.2, Genetics Computer Group (GCG), Madison, Wis.), BLAST (Altschul et al., *J. Mol. Biol.* 215(3):403-10, 1990), and FASTA (Pearson, *Methods in Enzymology* 183:63-98, 1990, R. F. Doolittle, ed.).

In an embodiment of the present invention sequence identity between two polypeptides is determined using the GAP program (Wisconsin Package Version 10.2, Genetics Computer Group (GCG), Madison, Wis.). GAP uses the alignment method of Needleman and Wunsch. (Needleman, et al., *J. Mol. Biol.* 48:443-453, 1970.) GAP considers all possible alignments and gap positions between two sequences and creates a global alignment that maximizes the number of matched residues and minimizes the number and size of gaps. A scoring matrix is used to assign values for symbol matches. In addition, a gap creation penalty and a gap extension penalty are required to limit the insertion of gaps into the alignment. Default program parameters for polypeptide comparisons using GAP are the BLOSUM62 (Henikoff et al., *Proc. Natl. Acad. Sci. USA,* 89:10915-10919, 1992) amino acid scoring matrix (MATrix=blosum62.cmp), a gap creation parameter (GAPweight=8) and a gap extension parameter (LENgthweight=2).

More preferred HCV Met-NS3-NS4A-NS4B-NS5A-NS5B polypeptides in addition to being substantially similar to SEQ. ID. NO. 1 across their entire length produce individual NS3, NS4A, NS4B, NS5A and NS5B regions that are substantially similar to the corresponding regions present in SEQ. ID. NO. 1. The corresponding regions in SEQ. ID. NO. 1 are provided as follows: Met-NS3 amino acids 1-632; NS4A amino acids 633-686; NS4B amino acids 687-947; NS5A amino acids 948-1394; and NS5B amino acids 1395-1985.

In different embodiments a NS3, NS4A, NS4B, NS5A and/or NS5B region has an amino acid identity to the corresponding region in SEQ. ID. NO. 1 of at least 65%, at least 75%, at least 85%, at least 95%, at least 99%, or 100%; or an amino acid difference of 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, or 1-20 amino acids.

Amino acid modifications to SEQ. ID. NO. 1 preferably maintain all or most of the T-cell antigen regions. Differences in naturally occurring amino acids are due to different amino acid side chains (R groups). An R group affects different properties of the amino acid such as physical size, charge, and hydrophobicity. Amino acids can be divided into different groups as follows: neutral and hydrophobic (alanine, valine, leucine, isoleucine, proline, tyrptophan, phenylalanine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide tertiary structure.

Starting with a particular amino acid sequence and the known degeneracy of the genetic code, a large number of different encoding nucleic acid sequences can be obtained. The degeneracy of the genetic code arises because almost all amino acids are encoded by different combinations of nucleotide triplets or "codons". The translation of a particular codon into a particular amino acid is well known in the art (see, e.g., Lewin GENES IV, p. 119, Oxford University Press, 1990). Amino acids are encoded by codons as follows:

A=Ala=Alanine: codons GCA, GCC, GCG, GCU

C=Cys=Cysteine: codons UGC, UGU

D=Asp=Aspartic acid: codons GAC, GAU

E=Glu=Glutamic acid: codons GAA, GAG

F=Phe=Phenylalanine: codons UUC, UUU

G=Gly=Glycine: codons GGA, GGC, GGG, GGU

H=His=Histidine: codons CAC, CAU

I=Ile=Isoleucine: codons AUA, AUC, AUU

K=Lys=Lysine: codons AAA, AAG

L=Leu=Leucine: codons UUA, UUG, CUA, CUC, CUG, CUU

M=Met=Methionine: codon AUG

N=Asn=Asparagine: codons AAC, AAU

P=Pro=Proline: codons CCA, CCC, CCG, CCU Q=Gln=Glutamine: codons CAA, CAG R=Arg=Arginine: codons AGA, AGG, CGA, CGC, CGG, CGU S=Ser=Serine: codons AGC, AGU, UCA, UCC, UCG, UCU T=Thr=Threonine: codons ACA, ACC, ACG, ACU V=Val=Valine: codons GUA, GUC, GUG, GUU W=Trp=Tryptophan: codon UGG Y=Tyr=Tyrosine: codons UAC, UAU.

Nucleic acid sequences can be optimized in an effort to enhance expression in a host. Factors to be considered include C:G content, preferred codons, and the avoidance of inhibitory secondary structure. These factors can be combined in different ways in an attempt to obtain nucleic acid sequences having enhanced expression in a particular host. (See, for example, Donnelly et al., International Publication Number WO 97/47358.)

The ability of a particular sequence to have enhanced expression in a particular host involves some empirical experimentation. Such experimentation involves measuring expression of a prospective nucleic acid sequence and, if needed, altering the sequence.

B. Encoding Nucleotide Sequences

SEQ. ID. NOs. 2 and 3 provide two examples of nucleotide sequences encoding a Met-NS3-NS4A-NS4B-NS5A-NS5B sequence. The coding sequence of SEQ. ID. NO. 2 is similar (99.4% nucleotide sequence identity) to the NS3-NS4A-NS4B-NS5A-NS5B region of the naturally occurring HCV-BK sequence (GenBank accession number M58335). SEQ. ID. NO. 3 is a codon-optimized version of SEQ. ID. NO. 2. SEQ. ID. NOs. 2 and 3 have a nucleotide sequence identity of 78.3%.

Differences between the HCV-BK NS3-NS4A-NS4B-NS5A-NS5B nucleotide (GenBank accession number M58335) and SEQ. ID. NO. 2, include SEQ. ID. NO. 2 having a ribosome binding site, an ATG methionine codon, a region coding for a modified NS5B catalytic domain, a TAAA stop signal and an additional 30 nucleotide differences. The modified catalytic domain codes for a AlaAlaGly (residues 1711-1713) instead of GlyAspAsp to inactivate NS5B.

A nucleotide sequence encoding a HCV Met-NS3-NS4A-NS4B-NS5A-NS5B polypeptide is preferably substantially similar to the SEQ. ID. NO. 2 coding region. In different embodiments, the nucleotide sequence encoding a HCV Met-NS3-NS4A-NS4B-NS5A-NS5B polypeptide has a nucleotide sequence identify to the SEQ. ID. NO. 2 coding region of at least 65%, at least 75%, at least 85%, at least 95%, at least 99%, or 100%; or differs from SEQ. ID. NO. 2 by 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-25, 1-30, 1-35, 1-40, 1-45, or 1-50 nucleotides.

Nucleotide differences between a sequence coding Met-NS3-NS4A-NS4B-NS5A-NS5B and the SEQ. ID. NO. 2 coding region are calculated by determining the minimum number of nucleotide modifications in which the two sequences differ. Nucleotide modifications can be deletions, additions, substitutions or any combination thereof.

Nucleotide sequence identity is determined by methods well known in the art that compare the nucleotide sequence of one sequence to the nucleotide sequence of a second sequence and generate a sequence alignment. Sequence identity is determined from the alignment by counting the number of aligned positions having identical nucleotides.

Methods for determining nucleotide sequence identity between two polynucleotides include those described by Schuler, in Bioinformatics: A Practical Guide to the Analysis of Genes and Proteins, Baxevanis, A. D. and Ouelette, B. F. F., eds., John Wiley & Sons, Inc, 2001; Yona et al., in Bioinformatics: Sequence, structure and databanks, Higgins, D. and Taylor, W. eds, Oxford University Press, 2000; and Bioinformatics: Sequence and Genome Analysis, Mount, D. W., ed., Cold Spring Harbor Laboratory Press, 2001). Methods to determine nucleotide sequence identity are codified in publicly available computer programs such as GAP (Wisconsin Package Version 10.2, Genetics Computer Group (GCG), Madison, Wis.), BLAST (Altschul et al., J. Mol. Biol. 215(3): 403-10, 1990), and FASTA (Pearson, W. R., Methods in Enzymology 183:63-98, 1990, R. F. Doolittle, ed.).

In an embodiment of the present invention, sequence identity between two polynucleotides is determined by application of GAP (Wisconsin Package Version 10.2, Genetics Computer Group (GCG), Madison, Wis.). GAP uses the alignment method of Needleman and Wunsch. (Needleman et al., J. Mol. Biol. 48:443-453, 1970.) GAP considers all possible alignments and gap positions between two sequences and creates a global alignment that maximizes the number of matched residues and minimizes the number and size of gaps. A scoring matrix is used to assign values for symbol matches. In addition, a gap creation penalty and a gap extension penalty are required to limit the insertion of gaps into the alignment. Default program parameters for polynucleotide comparisons using GAP are the nwsgapdna.cmp scoring matrix (MATrix=nwsgapdna.cmp), a gap creation parameter (GAPweight=50) and a gap extension parameter (LENgthweight=3).

More preferred HCV Met-NS3-NS4A-NS4B-NS5A-NS5B nucleotide sequences in addition to being substantially similar across its entire length, produce individual NS3, NS4A, NS4B, NS5A and NS5B regions that are substantially similar to the corresponding regions present in SEQ. ID. NO. 2. The corresponding coding regions in SEQ. ID. NO. 2 are provided as follows: Met-NS3, nucleotides 7-1902; NS4A nucleotides 1903-2064; NS4B nucleotides 2065-2847; NS5A nucleotides 2848-4188: NS5B nucleotides 4189-5661.

In different embodiments a NS3, NS4A, NS4B, NS5A and/or NS5B encoding region has a nucleotide sequence identity to the corresponding region in SEQ. ID. NO. 2 of at least 65%, at least 75%, at least 85%, at least 95%, at least 99% or 100%; or a nucleotide difference to SEQ. ID. NO. 2 of 1-2, 1-3, 14, 1-5, 1-6, 1-7, 1-8, 1-9, 1-10, 1-11, 1-12, 1-13, 1-14, 1-15, 1-16, 1-17, 1-18, 1-19, 1-20, 1-25, 1-30, 1-35, 1-40, 1-45, or 1-50 nucleotides.

C. Gene Expression Cassettes

A gene expression cassette contains elements needed for polypeptide expression. Reference to "polypeptide" does not provide a size limitation and includes protein. Regulatory elements present in a gene expression cassette generally include: (a) a promoter transcriptionally coupled to a nucleotide sequence encoding the polypeptide, (b) a 5' ribosome binding site functionally coupled to the nucleotide sequence, (c) a terminator joined to the 3' end of the nucleotide sequence, and (d) a 3' polyadenylation signal functionally coupled to the nucleotide sequence. Additional regulatory elements useful for enhancing or regulating gene expression or polypeptide processing may also be present.

Promoters are genetic elements that are recognized by an RNA polymerase and mediate transcription of downstream regions. Preferred promoters are strong promoters that provide for increased levels of transcription. Examples of strong promoters are the immediate early human cytomegalovirus promoter (CMV), and CMV with intron A. (Chapman et al, *Nucl. Acids Res.* 19:3979-3986, 1991.) Additional examples of promoters include naturally occurring promoters such as the EFI alpha promoter, the murine CMV promoter, Rous sarcoma virus promoter, and SV40 early/late promoters and the β-actin promoter; and artificial promoters such as a synthetic muscle specific promoter and a chimeric muscle-specific/CMV promoter (Li et al., *Nat. Biotechnol.* 17:241-245, 1999, Hagstrom et al., *Blood* 95:2536-2542, 2000).

The ribosome binding site is located at or near the initiation codon. Examples of preferred ribosome binding sites include CCACCAUGG, CCGCCAUGG, and ACCAUGG, where AUG is the initiation codon. (Kozak, *Cell* 44:283-292, 1986). Another example of a ribosome binding site is GCCACCAUGG (SEQ. ID. NO. 12).

The polyadenylation signal is responsible for cleaving the transcribed RNA and the addition of a poly (A) tail to the RNA. The polyadenylation signal in higher eukaryotes contains an AAUAAA sequence about 11-30 nucleotides from the polyadenylation addition site. The AAUAAA sequence is involved in signaling RNA cleavage. (Lewin, Genes I V, Oxford University Press, NY, 1990.) The poly (A) tail is important for the mRNA processing.

Polyadenylation signals that can be used as part of a gene expression cassette include the minimal rabbit β-globin polyadenylation signal and the bovine growth hormone polyadenylation (BGH). (Xu et al., *Gene* 272:149-156, 2001, Post et al., U.S. Pat. No. 5,122,458.) Additional examples include the Synthetic Polyadenylation Signal (SPA) and SV40 polyadenylation signal. The SPA sequence is as follows: AAUAAAAGAUCUUUAUUUUCAUUAGAUCUGUGUGUUGGUUUUUUGUGUG (SEQ. ID. NO. 13).

Examples of additional regulatory elements useful for enhancing or regulating gene expression or polypeptide processing that may be present include an enhancer, a leader sequence and an operator. An enhancer region increases transcription. Examples of enhancer regions include the CMV enhancer and the SV40 enhancer. (Hitt et al., *Methods in Molecular Genetics* 7:13-30, 1995, Xu, et al., *Gene* 272:149-156, 2001.) An enhancer region can be associated with a promoter.

A leader sequence is an amino acid region on a polypeptide that directs the polypeptide into the proteasome. Nucleic acid encoding the leader sequence is 5' of a structural gene and is transcribed along the structural gene. An example of a leader sequences is tPA.

An operator sequence can be used to regulate gene expression. For example, the Tet operator sequence can be used to repress gene expression.

II. THERAPEUTIC VECTORS

Nucleic acid encoding a Met-NS3-NS4A-NS4B-NS5A-NS5B polypeptide can be introduced into a patient using vectors suitable for therapeutic administration. Suitable vectors can deliver nucleic acid into a target cell without causing an unacceptable side effect.

Cellular expression is achieved using a gene expression cassette encoding a Met-NS3-NS4A-NS4B-NS5A-NS5B polypeptide. The gene expression cassette contains regulatory elements for producing and processing a sufficient amount of nucleic acid inside a target cell to achieve a beneficial effect.

Examples of vectors that can be used for therapeutic applications include first and second generation adenovectors, helper dependent adenovectors, adeno-associated viral vectors, retroviral vectors, alpha virus vectors, Venezuelan Equine Encephalitis virus vector, and plasmid vectors. (Hitt, et al., *Advances in Pharmacology* 40:137-206, 1997, Johnston et al., U.S. Pat. No. 6,156,588, and Johnston et al., International Publication Number WO 95/32733.) Preferred vectors for introducing a Met-NS3-NS4A-NS4B-NS5A-NS5B polypeptide into a subject are first generation adenoviral vectors and plasmid DNA vectors.

A. First Generation Adenovectors

First generation adenovector for expressing a gene expression cassette contain the expression cassette in an E1 and optionally E3 deleted recombinant adenovirus genome. The deletion in the E1 region is sufficiently large to remove elements needed for adenoviral replication.

First generation adenovectors for expressing a Met-NS3-NS4A-NS4B-NS5A-NS5B polypeptide contain a E1 and E3 deleted recombinant adenovirus genome. The deletion in the E1 region is sufficiently large to remove elements needed for adenoviral replication. The combinations of deletions of the E1 and E3 regions are sufficiently large to accommodate a gene expression cassette encoding a Met-NS3-NS4A-NS4B-NS5A-NS5B polypeptide.

The adenovirus has a double-stranded linear genome with inverted terminal repeats at both ends. During viral replication, the genome is packaged inside a viral capsid to form a virion. The virus enters its target cell through viral attachment followed by internalization. (Hitt et al., *Advances in Pharmacology* 40:137-206, 1997.)

Adenovectors can be based on different adenovirus serotypes such as those found in humans or animals. Examples of animal adenoviruses include bovine, porcine, chimp, murine, canine, and avian (CELO). Preferred adenovectors are based on human serotypes, more preferably Group B, C, or D serotypes. Examples of human adenovirus Group B, C, D, or E serotypes include types 2 ("Ad2"), 4 ("Ad4"), ("Ad5"), 6 ("Ad6"), 24 ("Ad24"), 26 ("Ad26"), 34 ("Ad34") and 35 ("Ad35"). Adenovectors can contain regions from a single adenovirus or from two or more adenovirus.

In different embodiments adenovectors are based on Ad5, Ad6, or a combination thereof. Ad5 is described by Chroboczek, et al., *J. Virology* 186:280-285, 1992. Ad6 is described in FIGS. 7A-7N. An Ad6 based vector containing Ad5 regions is described in the Example section provided below.

Adenovectors do not need to have their E1 and E3 regions completely removed. Rather, a sufficient amount the E1 region is removed to render the vector replication incompetent in the absence of the E1 proteins being supplied in trans; and the E1 deletion or the combination of the E1 and E3 deletions are sufficiently large enough to accommodate a gene expression cassette.

E1 deletions can be obtained starting at about base pair 342 going up to about base pair 3523 of Ad5, or a corresponding region from other adenoviruses. Preferably, the deleted region involves removing a region from about base pair 450 to about base pair 3511 of Ad5, or a corresponding region from other adenoviruses. Larger E1 region deletions starting at about base pair 341 removes elements that facilitate virus packaging.

E3 deletions can be obtained starting at about base pair 27865 to about base pair 30995 of Ad5, or the corresponding region of other adenovectors. Preferably the deletion region involves removing a region from about base pair 28134 up to about base pair 30817 of Ad5, or the corresponding region of other adenovectors.

The combination of deletions to the E1 region and optionally the E3 region should be sufficiently large so that the overall size of the recombinant genome containing the gene expression cassette does not exceed about 105% of the wild type adenovirus genome. For example, as recombinant adenovirus Ad5 genomes increase size above about 105% the genome becomes unstable. (Bett et al., *Journal of Virology* 67:5911-5921, 1993.)

Preferably, the size of the recombinant adenovirus genome containing the gene expression cassette is about 85% to about 105% the size of the wild type adenovirus genome. In different embodiments, the size of the recombinant adenovirus genome containing the expression cassette is about 100% to about 105.2%, or about 100%, the size of the wild type genome.

Approximately 7,500 kb can be inserted into an adenovirus genome with a E1 and E3 deletion. Without any deletion, the Ad5 genome is 35,935 base pairs and the Ad6 genome is 35,759 base pairs.

Replication of first generation adenovectors can be performed by supplying the E1 gene products in trans. The E1 gene product can be supplied in trans, for example, by using cell lines that have been transformed with the adenovirus E1 region. Examples of cells and cells lines transformed with the adenovirus E1 region are HEK 293 cells, 911 cells, PERC.6™ cells, and transfected primary human aminocytes cells. (Graham et al., *Journal of Virology* 36:59-72, 1977, Schiedner et al., *Human Gene Therapy* 11:2105-2116, 2000, Fallaux et al., *Human Gene Therapy* 9:1909-1917, 1998, Bout et al., U.S. Pat. No. 6,033,908.)

A Met-NS3-NS4A-NS4B-NS5A-NS5B expression cassette should be inserted into a recombinant adenovirus genome in the region corresponding to the deleted E1 region or the deleted E3 region. The expression cassette can have a parallel or anti-parallel orientation. In a parallel orientation the transcription direction of the inserted gene is the same direction as the deleted E1 or E3 gene. In an anti-parallel orientation transcription the opposite strand serves as a template and the transcription direction is in the opposite direction.

In an embodiment of the present invention the adenovector has a gene expression cassette inserted in the E1 deleted region. The vector contains:

a) a first adenovirus region from about base pair 1 to about base pair 450 corresponding to either Ad5 or Ad6;

b) a gene expression cassette in a E1 parallel or E1 anti-parallel orientation joined to the first region;

c) a second adenovirus region from about base pair 3511 to about base pair 5548 corresponding to Ad5 or from about base pair 3508 to about base pair 5541 corresponding to Ad6, joined to the expression cassette;

d) a third adenovirus region from about base pair 5549 to about base pair 28133 corresponding to Ad5 or from about base pair 5542 to about base pair 28156 corresponding to Ad6, joined to the second region;

e) a fourth adenovirus region from about base pair 30818 to about base pair 33966 corresponding to Ad5 or from about base pair 30789 to about base pair 33784 corresponding to Ad6, joined to the third region; and f) a fifth adenovirus region from about base pair 33967 to about base pair 35935 corresponding to Ad5 or from about base pair 33785 to about base pair 35759 corresponding to Ad6 joined to the fourth region.

In another embodiment of the present invention the adenovector has an expression cassette inserted in the E3 deleted region. The vector contains:

a) a first adenovirus region from about base pair 1 to about base pair 450 corresponding to either Ad5 or Ad6;

b) a second adenovirus region from about base pair 3511 to about base pair 5548 corresponding to Ad5 or from about base pair 3508 to about base pair 5541 corresponding to Ad6, joined to the first region;

c) a third adenovirus region from about base pair 5549 to about base pair 28133 corresponding to Ad5 or from about base pair 5542 to about base pair 28156 corresponding to Ad6, joined to the second region;

d) a gene expression cassette in a E3 parallel or E3 anti-parallel orientation joined to the third region;

e) a fourth adenovirus region from about base pair 30818 to about base pair 33966 corresponding to Ad5 or from about base pair 30789 to about base pair 33784 corresponding to Ad6, joined to the gene expression cassette; and f) a fifth adenovirus region from about base pair 33967 to about base pair 35935 corresponding to Ad5 or from about base pair 33785 to about base pair 35759 corresponding to Ad6, joined to the fourth region.

In preferred different embodiments concerning adenovirus regions that are present: (1) the first, second, third, fourth, and fifth region corresponds to Ad5; (2) the first, second, third, fourth, and fifth region corresponds to Ad6; and (3) the first region corresponds to Ad5, the second region corresponds to Ad5, the third region corresponds to Ad6, the fourth region corresponds to Ad6, and the fifth region corresponds to Ad5.

B. DNA Plasmid Vectors

DNA vaccine plasmid vectors contain a gene expression cassette along with elements facilitating replication and preferably vector selection. Preferred elements provide for replication in non-mammalian cells and a selectable marker. The vectors should not contain elements providing for replication in human cells or for integration into human nucleic acid.

The selectable marker facilitates selection of nucleic acids containing the marker. Preferred selectable markers are those that confer antibiotic resistance. Examples of antibiotic selection genes include nucleic acid encoding resistance to ampicillin, neomycin, and kanamycin.

Suitable DNA vaccine vectors can be produced starting with a plasmid containing a bacterial origin of replication and a selectable marker. Examples of bacterial origins of replication providing for higher yields include the ColE1 plasmid-derived bacterial origin of replication. (Donnelly et al., *Annu. Rev. Immunol.* 15:617-648, 1997.)

The presence of the bacterial origin of replication and selectable marker allows for the production of the DNA vector in a bacterial strain such as *E. coli*. The selectable marker is used to eliminate bacteria not containing the DNA vector.

III. Ad6 RECOMBINANT NUCLEIC ACID

Ad6 recombinant nucleic acid comprises an Ad6 region substantially similar to an Ad6 region found in SEQ. ID. NO. 8, and a region not present in Ad6 nucleic acid. Recombinant nucleic acid comprising Ad6 regions have different uses such as in producing different Ad6 regions, as intermediates in the production of Ad6 based vectors, and as a vector for delivering a recombinant gene.

Figure 9:
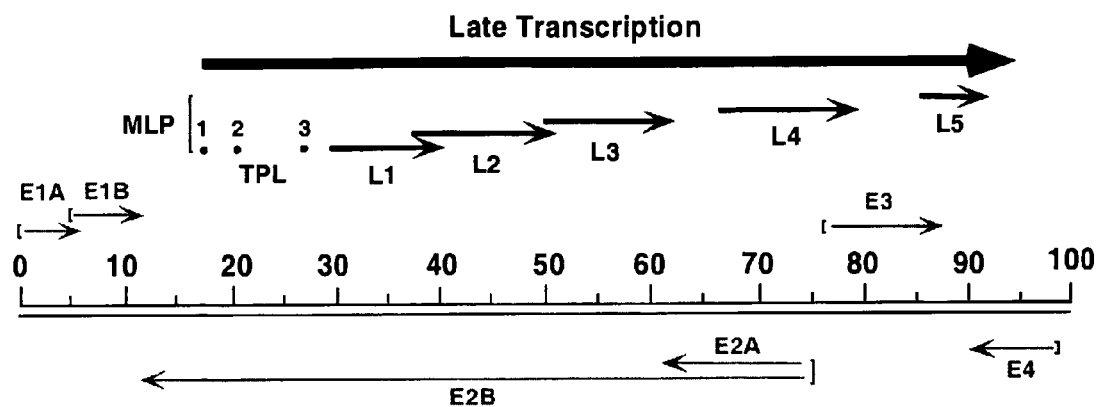
FIG. 9 illustrates different regions of the Ad6 genome. The linear (35759 bp) ds DNA genome is indicated by two parallel lines and is divided into 100 map units. Transcription units are shown relative to their position and orientation in the genome. Early genes (E1A, E1B, E2A/B, E3 and E4 are indicated by gray arrows. Late genes (L1 to L5), indicated by black arrows, are produced by alternative splicing of a transcript produced from the major late promoter (MLP) and all contain the tripartite leader (1, 2, 3) at their 5' ends. The E1 region is located from approximately 1.0 to 11.5 map units, the E2 region from 75.0 to 11.5 map units, E3 from 76.1 to 86.7 map units, and E4 from 99.5 to 91.2 map units. The major late transcription unit is located between 16.0 and 91.2 map units.

As depicted in FIG. 9, the genomic organization of Ad6 is very similar to the genomic organization of Ad5. The homology between Ad5 and Ad6 is approximately 98%.

In different embodiments, the Ad6 recombinant nucleic acid comprises a nucleotide region substantially similar to E1A, E1B, E2B, E2A, E3, E4, L1, L2, L3, or L4, or any combination thereof. A substantially similar nucleic acid region to an Ad6 region has a nucleotide sequence identity of at least 65%, at least 75%, at least 85%, at least 95%, at least 99% or 100%; or a nucleotide difference of 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-25, 1-30, 1-35, 1-40, 1-45, or 1-50 nucleotides. Techniques and embodiments for determining substantially similar nucleic acid sequences are described in Section I.B. supra.

Preferably, the recombinant Ad6 nucleic acid contains an expression cassette coding for a polypeptide not found in Ad6. Examples of expression cassettes include those coding for HCV regions and those coding for other types of polypeptides.

Different types of adenoviral vectors can be produced incorporating different amounts of Ad6, such as first and second generation adenovectors. As noted in Section II.A. supra. first generation adenovectors are defective in E1 and can replicate when E1 is supplied in trans.

Second generation adenovectors contain less adenoviral genome than first generation vectors and can be used in conjugation with complementing cell lines and/or helper vectors supplying adenoviral proteins. Second generation adenovectors are described in different references such as Russell, *Journal of General Virology* 81:2573-2604, 2000; Hitt et al., 1997, Human Ad vectors for Gene Transfer, Advances in Pharmacology, Vol 40 Academic Press.

In an embodiment of the present invention, the Ad6 recombinant nucleic acid is an adenovirus vector defective in E1 that is able to replicate when E1 is supplied in trans. Expression cassettes can be inserted into a deleted E1 region and/or a deleted E3 region.

An example of an Ad6 based adenoviral vector with an expression cassette provided in a deleted E1 region comprises or consists of:

a) a first adenovirus region from about base pair 1 to about base pair 450 corresponding to either Ad5 or Ad6;

b) a gene expression cassette in a E1 parallel or E1 anti-parallel orientation joined to the first region;

c) a second adenovirus region from about base pair 3511 to about base pair 5548 corresponding to Ad5 or from about base pair 3508 to about base pair 5541 corresponding to Ad6, joined to the expression cassette;

d) a third adenovirus region from about base pair 5549 to about base pair 28133 corresponding to Ad5 or from about base pair 5542 to about base pair 28156 corresponding to Ad6, joined to the second region;

e) an optionally present fourth region from about base pair 28134 to about base pair 30817 corresponding to Ad5, or from about base pair 28157 to about base pair 30788 corresponding to Ad6, joined to the third region;

f) a fifth adenovirus region from about base pair 30818 to about base pair 33966 corresponding to Ad5 or from about base pair 30789 to about base pair 33784 corresponding to Ad6, wherein the fifth region is joined to the fourth region if the fourth region is present, or the fifth is joined to the third region if the fourth region is not present; and g) a sixth adenovirus region from about base pair 33967 to about base pair 35935 corresponding to Ad5 or from about base pair 33785 to about base pair 35759 corresponding to Ad6, joined to the fifth region;

wherein at least one Ad6 region is present.

In different embodiments of the invention, all of the regions are from Ad6; all of the regions expect for the first and second are from Ad6; and 1, 2, 3, or 4 regions selected from the second, third, fourth, and fifth regions are from Ad6.

An example of an Ad6 based adenoviral vector with an expression cassette provided in a deleted E3 region comprises or consists of:

a) a first adenovirus region from about base pair 1 to about base pair 450 corresponding to either Ad5 or Ad6;

b) a second adenovirus region from about base pair 3511 to about base pair 5548 corresponding to Ad5 or from about base pair 3508 to about base pair 5541 corresponding to Ad6, joined to the first region;

c) a third adenovirus region from about base pair 5549 to about base pair 28133 corresponding to Ad5 or from about base pair 5542 to about base pair 28156 corresponding to Ad6, joined to the second region;

d) a gene expression cassette in a E3 parallel or E3 anti-parallel orientation joined to the third region;

e) a fourth adenovirus region from about base pair 30818 to about base pair 33966 corresponding to Ad5 or from about base pair 30789 to about base pair 33784 corresponding to Ad6, joined to the gene expression cassette; and f) a fifth adenovirus region from about base pair 33967 to about base pair 35935 corresponding to Ad5 or from about base pair 33785 to about base pair 35759 corresponding to Ad6, joined to the fourth region;

wherein at least one Ad6 region is present.

In different embodiment of the invention, all of the regions are from Ad6; all of the regions expect for the first and second are from Ad6; and 1, 2, 3, or 4 regions selected from the second, third, fourth and fifth regions are from Ad6.

IV. VECTOR PRODUCTION

Vectors can be produced using recombinant nucleic acid techniques such as those involving the use of restriction enzymes, nucleic acid ligation, and homologous recombination. Recombinant nucleic acid techniques are well known in the art. (Ausubel, *Current Protocols in Molecular Biology*, John Wiley, 1987-1998, and Sambrook et al., *Molecular Cloning, A Laboratory Manual*, $2^{nd}$ Edition, Cold Spring Harbor Laboratory Press, 1989.)

Intermediate vectors are used to derive a therapeutic vector or to transfer an expression cassette or portion thereof from one vector to another vector. Examples of intermediate vectors include adenovirus genome plasmids and shuttle vectors.

Useful elements in an intermediate vector include an origin of replication, a selectable marker, homologous recombination regions, and convenient restriction sites. Convenient restriction sites can be used to facilitate cloning or release of a nucleic acid sequence.

Homologous recombination regions provide nucleic acid sequence regions that are homologous to a target region in another nucleic acid molecule. The homologous regions flank the nucleic acid sequence that is being inserted into the target region. In different embodiments homologous regions are preferably about 150 to 600 nucleotides in length, or about 100 to 500 nucleotides in length.

An embodiment of the present invention describes a shuttle vector containing a Met-NS3-NS4A-NS4B-NS5A-NS5B expression cassette, a selectable marker, a bacterial origin of replication, a first adenovirus homology region and a second adenovirus homologous region that target the expression cassette to insert in or replace an E1 region. The first and second homology regions flank the expression cassette. The first homology region contains at least about 100 base pairs substantially homologous to at least the right end (3' end) of a wild-type adenovirus region from about base pairs 4-450. The second homology contains at least about 100 base pairs substantially homologous to at least the left end (5' end) of Ad5 from about base pairs 3511-5792, or the corresponding region from another adenovirus.

Reference to "substantially homologous" indicates a sufficient degree of homology to specifically recombine with a target region. In different embodiments substantially homologous refers to at least 85%, at least 95%, or 100% sequence identity. Sequence identity can be calculated as described in Section I.B. supra.

One method of producing adenovectors is through the creation of an adenovirus genome plasmid containing an expression cassette. The pre-Adenovirus plasmid contains all the adenovirus sequences needed for replication in the desired complimenting cell line. The pre-Adenovirus plasmid is then digested with a restriction enzyme to release the viral ITR's and transfected into the complementing cell line for virus rescue. The ITR's must be released from plasmid sequences to allow replication to occur. Adenovector rescue results in the production on an adenovector containing the expression cassette.

A. Adenovirus Genome Plasmids

Adenovirus genome plasmids contain an adenovector sequence inside a longer-length plasmid (which may be a cosmid). The longer-length plasmid may contain additional elements such as those facilitating growth and selection in eukaryotic or bacterial cells depending upon the procedures employed to produce and maintain the plasmid. Techniques for producing adenovirus genome plasmids include those involving the use of shuttle vectors and homologous recombination, and those involving the insertion of a gene expression cassette into an adenovirus cosmid. (Hitt et al., *Methods in Molecular Genetics* 7:13-30, 1995, Danthinne et al., *Gene Therapy* 7:1707-1714, 2000.)

Adenovirus genome plasmids preferably have a gene expression cassette inserted into a E1 or E3 deleted region. In an embodiment of the present invention, the adenovirus genome plasmid contains a gene expression cassette inserted in the E1 deleted region, an origin of replication, a selectable marker, and the recombinant adenovirus region is made up of:

a) a first adenovirus region from about base pair 1 to about base 450 corresponding to either Ad5 or Ad6;

b) a gene expression cassette in a E1 parallel or E1 anti-parallel orientation joined to the first region;

c) a second adenovirus region from about base pair 3511 to about base pair 5548 corresponding to Ad5 or from about base pair 3508 to about base pair 5541 corresponding to Ad6, joined to the expression cassette;

d) a third adenovirus region from about base pair 5549 to about base pair 28133 corresponding to Ad5 or from about base pair 5542 to about base pair 28156 corresponding to Ad6, joined to the second region;

e) a fourth adenovirus region from about base pair 30818 to about base pair 33966 corresponding to Ad5 or from about base pair 30789 to about base pair 33784 corresponding to Ad6, joined to the third region;

f) a fifth adenovirus region from about base pair 33967 to about base pair 35935 corresponding to Ad5 or from about base pair 33785 to about base pair 35759 corresponding to Ad6, joined to the fourth region, and g) an optionally present E3 region corresponding to all or part of the E3 region present in Ad5 or Ad6, which may be present for smaller inserts taking into account the overall size of the desired adenovector.

In another embodiment of the present invention the recombinant adenovirus genome plasmid has the gene expression cassette inserted in the E3 deleted region. The vector contains an origin of replication, a selectable marker, and the following:

a) a first adenovirus region from about base pair 1 to about base pair 450 corresponding to either Ad5 or Ad6;

b) a second adenovirus region from about base pair 3511 to about base pair 5548 corresponding to Ad5 or from about base pair 3508 to about base pair 5541 corresponding to Ad6, joined to the expression cassette;

c) a third adenovirus region from about base pair 5549 to about base pair 28133 corresponding to Ad5 or from about base pair 5542 to about base pair 28156 corresponding to Ad6, joined to the second region;

d) the gene expression cassette in a E3 parallel or E3 anti-parallel orientation joined to the third region;

e) a fourth adenovirus region from about base pair 30818 to about base pair 33966 corresponding to Ad5 or from about base pair 30789 to about base pair 33784 corresponding to Ad6, joined to the gene expression cassette; and f) a fifth adenovirus region from about base pair 33967 to about base pair 35935 corresponding to Ad5 or from about base pair 33785 to about base pair 35759 corresponding to Ad6, joined to the fourth region.

In different embodiments concerning adenovirus regions that are present: (1) the first, second, third, fourth, and fifth region corresponds to Ad5; (2) the first, second, third, fourth, and fifth region corresponds to Ad6; and (3) the first region corresponds to Ad5, the second region corresponds to Ad5, the third region corresponds to Ad6, the fourth region corresponds to Ad6, and the fifth region corresponds to Ad5.

An embodiment of the present invention describes a method of making an adenovector involving a homologous recombination step to produce a adenovirus genome plasmid and an adenovirus rescue step. The homologous recombination step involves the use of a shuttle vector containing a Met-NS3-NS4A-NS4B-NS5A-NS5B expression cassette flanked by adenovirus homology regions. The adenovirus homology regions target the expression cassette into either the E1 or E3 deleted region.

In an embodiment of the present invention concerning the production of an adenovirus genome plasmid, the gene expression cassette is inserted into a vector comprising: a first adenovirus region from about base pair 1 to about base pair 450 corresponding to either Ad5 or Ad6; a second adenovirus region from about base pair 3511 to about base pair 5548 corresponding to Ad5 or from about base pair 3508 to about base pair 5541 corresponding to Ad6, joined to the second region; a third adenovirus region from about base pair 5549 to about base pair 28133 corresponding to Ad5 or from about base pair 5542 to about base pair 28156 corresponding to Ad6, joined to the second region; a fourth adenovirus region from about base pair 30818 to about base pair 33966 corresponding to Ad5 or from about base pair 30789 to about base pair 33784 corresponding to Ad6, joined to the third region; and a fifth adenovirus region from about 33967 to about 35935 corresponding to Ad5 or from about base pair 33785 to about base pair 35759 corresponding to Ad6, joined to the fourth region. The adenovirus genome plasmid should contain an origin of replication and a selectable marker, and may contain all or part of the Ad5 or Ad6 E3 region.

In different embodiments concerning adenovirus regions that are present: (1) the first, second, third, fourth, and fifth region corresponds to Ad5; (2) the first, second, third, fourth, and fifth region corresponds to Ad6; and (3) the first region corresponds to Ad5, the second region corresponds to Ad5, the third region corresponds to Ad6, the fourth region corresponds to Ad6, and the fifth region corresponds to Ad5.

B. Adenovector Rescue

An adenovector can be rescued from a recombinant adenovirus genome plasmid using techniques known in the art or described herein. Examples of techniques for adenovirus rescue well known in the art are provided by Hitt et al., *Methods in Molecular Genetics* 7:13-30, 1995, and Danthinne et al., *Gene Therapy* 7:1707-1714, 2000.

A preferred method of rescuing an adenovector described herein involves boosting adenoviral replication. Boosting adenoviral replication can be performed, for example, by supplying adenoviral functions such as E2 proteins (polymerase, pre-terminal protein and DNA binding protein) as well as E4 orf6 on a separate plasmid. Example 10 infra. illustrates the boosting of adenoviral replication to rescue an adenovector containing a codon optimized Met-NS3-NS4A-NS4B-NS5A-NS5B expression cassette.

V. PARTIAL-OPTIMIZED HCV ENCODING SEQUENCES

Partial optimization of HCV polyprotein encoding nucleic acid provides for a lesser amount of codons optimized for expression in a human than complete optimization. The overall objective is to provide the benefits of increased expression due to codon optimization, while facilitating the production of an adenovector containing HCV polyprotein encoding nucleic acid having optimized codons.

Complete optimization of an HCV polyprotein encoding sequence provides the most frequently observed human codon for each amino acid. Complete optimization can be performed using codon frequency tables well known in the art and using programs such as the BACKTRANSLATE program (Wisconsin Package version 10, Genetics Computer Group, GCG, Madison, Wis.).

Partial optimization can be preformed on an entire HCV polyprotein encoding sequence that is present (e.g., NS3-NS5B), or one or more local regions that are present. In different embodiments the GC content for the entire HCV encoded polyprotein that is present is no greater than at least about 65%; and the GC content for one or more local regions is no greater than about 70%.

Local regions are regions present in HCV encoding nucleic acid, and can vary in size. For example, local regions can be about 60, about 70, about 80, about 90 or about 100 nucleotides in length.

Partial optimization can be achieved by initially constructing an HCV encoding polyprotein sequence to be partially optimized based on a naturally occurring sequence. Alternatively, an optimized HCV encoding sequence can be used as basis of comparison to produce a partial optimized sequence.

VI. HCV COMBINATION TREATMENT

The HCV Met-NS3-NS4A-NS4B-NS5A-NS5B vaccine can be used by itself to treat a patient, can be used in conjunction with other HCV therapeutics, and can be used with agents targeting other types of diseases. Additional therapeutics include additional therapeutic agents to treat HCV and diseases having a high prevalence in HCV infected persons. Agents targeting other types of disease include vaccines directed against HIV and HBV.

Additional therapeutics for treating HCV include vaccines and non-vaccine agents. (Zein, *Expert Opin. Investig. Drugs* 10:1457-1469, 2001.) Examples of additional HCV vaccines include vaccines designed to elicit an immune response against an HCV core antigen and the HCV E1, E2 or p7 region. Vaccine components can be naturally occurring HCV polypeptides, HCV mimotope polypeptides or nucleic acid encoding such polypeptides.

HCV mimotope polypeptides contain HCV epitopes, but have a different sequence than a naturally occurring HCV antigen. A HCV mimotope can be fused to a naturally occurring HCV antigen. References describing techniques for producing mimotopes in general and describing different HCV mimotopes are provided in Felici et al. U.S. Pat. No. 5,994,083 and Nicosia et al., International Application Number WO 99/60132.

VII. PHARMACEUTICAL ADMINISTRATION

HCV vaccines can be formulated and administered to a patient using the guidance provided herein along with techniques well known in the art. Guidelines for pharmaceutical administration in general are provided in, for example, *Modern Vaccinology*, Ed. Kurstak, Plenum Med. Co. 1994*; Remington's Pharmaceutical Sciences* $18^{th}$ Edition, Ed. Gennaro, Mack Publishing, 1990; and *Modern Pharmaceutics* $2^{nd}$ Edition, Eds. Banker and Rhodes, Marcel Dekker, Inc., 1990, each of which are hereby incorporated by reference herein.

HCV vaccines can be administered by different routes such intravenous, intraperitoneal, subcutaneous, intramuscular, intradermal, impression through the skin, or nasal. A preferred route is intramuscular.

Intramuscular administration can be preformed using different techniques such as by injection with or without one or more electric pulses. Electric mediated transfer can assist genetic immunization by stimulating both humoral and cellular immune responses.

Vaccine injection can be performed using different techniques, such as by employing a needle or a needless injection system. An example of a needless injection system is a jet injection device. (Donnelly et al., International Publication Number WO 99/52463.)

A. Electrically Mediated Transfer

Electrically mediated transfer or Gene Electro-Transfer (GET) can be performed by delivering suitable electric pulses after nucleic acid injection. (See Mathiesen, International Publication Number WO 98/43702). Plasmid injection and electroporation can be performed using stainless needles. Needles can be used in couples, triplets or more complex patterns. In one configuration the needles are soldered on a printed circuit board that is a mechanical support and connects the needles to the electrical field generator by means of suitable cables.

The electrical stimulus is given in the form of electrical pulses. Pulses can be of different forms (square, sinusoidal, triangular, exponential decay) and different polarity (monopolar of positive or negative polarity, bipolar). Pulses can be delivered either at constant voltage or constant current modality.

Different patterns of electric treatment can be used to introduce nucleic acid vaccines including HCV and other nucleic acid vaccines into a patient. Possible patterns of electric treatment include the following:

Treatment 1: 10 trains of 1000 square bipolar pulses delivered every other second, pulse length 0.2 msec/phase, frequency 1000 Hz, constant voltage mode, 45 Volts/phase, floating current.

Treatment 2: 2 trains of 100 square bipolar pulses delivered every other second, pulse length 2 msec/phase, frequency 100 Hz, constant current mode, 100 mA/phase, floating voltage.

Treatment 3: 2 trains of bipolar pulses at a pulse length of about 2 msec/phase, for a total length of about 3 seconds, where the actual current going through the tissue is fixed at about 50 mA.

Electric pulses are delivered through an electric field generator. A suitable generator can be composed of three independent hardware elements assembled in a common chassis and driven by a portable PC which runs the driving program. The software manages both basic and accessory functions. The elements of the device are: (1) signal generator driven by a microprocessor, (2) power amplifier and (3) digital oscilloscope.

The signal generator delivers signals having arbitrary frequency and shape in a given range under software control. The same software has an interactive editor for the waveform to be delivered. The generator features a digitally controlled current limiting device (a safety feature to control the maximal current output). The power amplifier can amplify the signal generated up to +/−150 V. The oscilloscope is digital and is able to sample both the voltage and the current being delivered by the amplifier.

B. Pharmaceutical Carriers

Pharmaceutically acceptable carriers facilitate storage and administration of a vaccine to a subject. Examples of pharmaceutically acceptable carriers are described herein. Additional pharmaceutical acceptable carriers are well known in the art.

Pharmaceutically acceptable carriers may contain different components such a buffer, normal saline or phosphate buffered saline, sucrose, salts and polysorbate. An example of a pharmaceutically acceptable carrier is follows: 2.5-10 mM TRIS buffer, preferably about 5 mM TRIS buffer; 25-100 mM NaCl, preferably about 75 mM NaCl; 2.5-10% sucrose, preferably about 5% sucrose; 0.01-2 mM $MgCl_2$; and 0.001%-0.01% polysorbate 80 (plant derived). The pH is preferably from about 7.0-9.0, more preferably about 8.0. A specific example of a carrier contains 5 mM TRIS, 75 mM NaCl, 5% sucrose, 1 mM $MgCl_2$, 0.005% polysorbate 80 at pH 8.0.

C. Dosing Regimes

Suitable dosing regimens can be determined taking into account the efficacy of a particular vaccine and factors such as age, weight, sex and medical condition of a patient; the route of administration; the desired effect; and the number of doses. The efficacy of a particular vaccine depends on different factors such as the ability of a particular vaccine to produce polypeptide that is expressed and processed in a cell and presented in the context of MHC class I and II complexes.

HCV encoding nucleic acid administered to a patient can be part of different types of vectors including viral vectors such as adenovector, and DNA plasmid vaccines. In different embodiments concerning administration of a DNA plasmid, about 0.1 to 10 mg of plasmid is administered to a patient, and about 1 to 5 mg of plasmid is administered to a patient. In different embodiments concerning administration of a viral vector, preferably an adenoviral vector, about $10^5$ to $10^{11}$ viral particles are administered to a patient, and about $10^7$ to $10^{10}$ viral particles are administered to a patient.

Viral vector vaccines and DNA plasmid vaccines may be administered alone, or may be part of a prime and boost administration regimen. A mixed modality priming and booster inoculation involves either priming with a DNA vaccine and boosting with viral vector vaccine, or priming with a viral vector vaccine and boosting with a DNA vaccine.

Multiple priming, for example, about to 2-4 or more may be used. The length of time between priming and boost may typically vary from about four months to a year, but other time frames may be used. The use of a priming regimen with a DNA vaccine may be preferred in situations where a person has a pre-existing anti-adenovirus immune response.

In an embodiment of the present invention, $1 \times 10^7$ to $1 \times 10^{12}$ particles and preferably about $1 \times 10^{10}$ to $1 \times 10^{11}$ particles of adenovector is administered directly into muscle tissue. Following initial vaccination a boost is performed with an adenovector or DNA vaccine.

In another embodiment of the present invention initial vaccination is performed with a DNA vaccine directly into muscle tissue. Following initial vaccination a boost is performed with an adenovector or DNA vaccine.

Agents such as interleukin-12, GM-CSF, B7-1, B7-2, IP10, Mig-1 can be coadministered to boost the immune response. The agents can be coadministered as proteins or through use of nucleic acid vectors.

D. Heterologous Prime-Boost

Heterologous prime-boost is a mixed modality involving the use of one type of viral vector for priming and another type of viral vector for boosting. The heterologous prime-boost can involve related vectors such as vectors based on different adenovirus serotypes and more distantly related viruses such as adenovirus and poxvirus. The use of poxvirus and adenovirus vectors to protect mice against malaria is illustrated by Gilbert et al., *Vaccine* 20:1039-1045, 2002.

Different embodiments concerning priming and boosting involve the following types of vectors expressing desired antigens such as Met-NS3-NS4A-NS4B-NS5A-NS5B: Ad5 vector followed by Ad6 vector; Ad6 vector followed by Ad5 vector; Ad5 vector followed by poxvirus vector; poxvirus vector followed by Ad5 vector; Ad6 vector followed by poxvirus vector; and poxvirus vector followed by Ad6 vector.

The length of time between priming and boosting typically varies from about four months to a year, but other time frames may be used. The minimum time frame should be sufficient to allow for an immunological rest. In an embodiment, this rest is for a period of at least 6 months. Priming may involve multiple priming with one type of vector, such as 2-4 primings.

Expression cassettes present in a poxvirus vector should contain a promoter either native to, or derived from, the poxvirus of interest or another poxvirus member. Different strategies for constructing and employing different types of poxvirus based vectors including those based on vaccinia virus, modified vaccinia virus, avipoxvirus, raccoon poxvirus, modified vaccinia virus Ankara, canarypoxviruses (such as ALVAC), fowlpoxviruses, cowpoxviruses, and NYVAC are well known in the art. (Moss, *Current Topics in Microbiology and Immunology* 158:25-38, 1982; Earl et al., In *Current Protocols in Molecular Biology*, Ausubel et al. eds., New York: Greene Publishing Associates & Wiley Interscience; 1991:16.16.1-16.16.7, Child et al., *Virology* 174(2):625-9, 1990; Tartaglia et al., *Virology* 188:217-232, 1992; U.S. Pat. Nos. 4,603,112, 4,722,848, 4,769,330, 5,110,587, 5,174,993, 5,185,146, 5,266,313, 5,505,941, 5,863,542, and 5,942,235.

E. Adjuvants

HCV vaccines can be formulated with an adjuvant. Adjuvants are particularly useful for DNA plasmid vaccines. Examples of adjuvants are alum, $AlPO_4$, alhydrogel, Lipid-A and derivatives or variants thereof, Freund's incomplete adjuvant, neutral liposomes, liposomes containing the vaccine and cytokines, non-ionic block copolymers, and chemokines.

Non-ionic block polymers containing polyoxyethylene (POE) and polyxylpropylene (POP), such as POE-POP-POE block copolymers may be used as an adjuvant. (Newman et al., *Critical Reviews in Therapeutic Drug Carrier Systems*

15:89-142, 1998.) The immune response of a nucleic acid can be enhanced using a non-ionic block copolymer combined with an anionic surfactant.

A specific example of an adjuvant formulation is one containing CRL-1005 (CytRx Research Laboratories), DNA, and benzylalkonium chloride (BAK). The formulation can be prepared by adding pure polymer to a cold (<5° C.) solution of plasmid DNA in PBS using a positive displacement pipette. The solution is then vortexed to solubilize the polymer. After complete solubilization of the polymer a clear solution is obtained at temperatures below the cloud point of the polymer (~6-7° C.). Approximately 4 mM BAK is then added to the DNA/CRL-1005 solution in PBS, by slow addition of a dilute solution of BAK dissolved in PBS. The initial DNA concentration is approximately 6 mg/mL before the addition of polymer and BAK, and the final DNA concentration is about 5 mg/mL. After BAK addition the formulation is vortexed extensively, while the temperature is allowed to increase from ~2° C. to above the cloud point. The formulation is then placed on ice to decrease the temperature below the cloud point. Then, the formulation is vortexed while the temperature is allowed to increase from ~2° C. to above the cloud point. Cooling and mixing while the temperature is allowed to increase from ~2° C. to above the cloud point is repeated several times, until the particle size of the formulation is about 200-500 nm, as measured by dynamic light scattering. The formulation is then stored on ice until the solution is clear, then placed in storage at −70° C. Before use, the formulation is allowed to thaw at room temperature.

F. Vaccine Storage

Adenovector and DNA vaccines can be stored using different types of buffers. For example, buffer A105 described in Example 9 infra. can be used to for vector storage.

Storage of DNA can be enhanced by removal or chelation of trace metal ions. Reagents such as succinic or malic acid, and chelators can be used to enhance DNA vaccine stability. Examples of chelators include multiple phosphate ligands and EDTA. The inclusion of non-reducing free radical scavengers, such as ethanol or glycerol, can also be useful to prevent damage of DNA plasmid from free radical production. Furthermore, the buffer type, pH, salt concentration, light exposure, as well as the type of sterilization process used to prepare the vials, may be controlled in the formulation to optimize the stability of the DNA vaccine.

VII. EXAMPLES

Examples are provided below to further illustrate different features of the present invention. The examples also illustrate useful methodology for practicing the invention. These examples do not limit the claimed invention.

Example 1

Met-NS3-NS4A-NS4B-NS5A-NS5B Expression Cassettes

Different gene expression cassettes encoding HCV NS3-NS4A-NS4B-NS5A-NS5B were constructed based on a 1b subtype HCV BK strain. The encoded sequences had either (1) an active NS5B sequence ("NS"), (2) an inactive NS5B sequence ("NSmut"), (3) a codon optimized sequence with an inactive NS5B sequence ("NSOPTmut"). The expression cassettes also contained a CMV promoter/enhancer and the BGH polyadenylation signal.

The NS nucleotide sequence (SEQ. ID. NO. 5) differs from HCV BK strain GenBank accession number M58335 by 30 out of 5952 nucleotides. The NS amino acid sequence (SEQ. ID. NO. 6) differs from the corresponding 1b genotype HCV BK strain by 7 out of 1984 amino acids. To allow for initiation of translation an ATG codon is present at the 5' end of the NS sequence. A TGA termination sequence is present at the 3' end of the NS sequence.

The NSmut nucleotide sequence (SEQ. ID. NO. 2, FIG. 2), is similar to the NS sequence. The differences between NSmut and NS include NSmut having an altered NS5B catalytic site; an optimal ribosome binding site at the 5' end; and a TAAA termination sequence at the 3' end. The alterations in NS5B comprise bases 5138 to 5146, which encode amino acids 1711 to 1713. The alterations result in a change of amino acids GlyAspAsp into AlaAlaGly and creates an inactive form of the NS5B RNA-dependent RNA-polymerase NS5B.

The NSOPTmut sequence (SEQ. ID. NO. 3, FIG. 3) was designed based on the amino acid sequence encoded by NSmut. The NSmut amino acid sequence was back translated into a nucleotide sequence with the GCG (Wisconsin Package version 10, Genetics Computer Group, GCG, Madison, Wis.) BACKTRANSLATE program. To generate a NSOPTmut nucleotide sequence where each amino acid is coded for by the corresponding most frequently observed human codon, the program was run choosing as parameter the generation of the most probable nucleotide sequence and specifying the codon frequency table of highly expressed human genes (human_high.cod) available within the GCG Package as translation scheme.

Example 2

Generation pV1Jns Plasmid with NS, NSmut or NSOPTmut Sequences pV1Jns plasmids containing either the NS sequence, NSmut sequence or NSOPTmut sequences were generated and characterised as follows:

pV1Jns Plasmid with the NS Sequence

The coding region Met-NS3-NS4A-NS4B-NS5A and the coding region Met-NS3-NS4A-NS4B-NS5A-NS5B from a HCV BK type strain (Tomei et al., *J. Virol.* 67:4017-4026, 1993) were cloned into pcDNA3 plasmid (Invitrogen), generating pcD3-5a and pcD3-5b vectors, respectively. PcD3-5A was digested with Hind III, blunt-ended with Klenow fill-in and subsequently digested with Xba I, to generate a fragment corresponding to the coding region of Met-NS3-NS4A-NS4B-NS5A. The fragment was cloned into pV1Jns-poly, digested with Bgl II blunt-ended with Klenow fill-in and subsequently digested with Xba I, generating pV1JnsNS3-5A.

pV1Jns-poly is a derivative of pV1JnsA plasmid (Montgomery et al., *DNA and Cell Biol.* 12:777-783, 1993), modified by insertion of a polylinker containing recognition sites for XbaI, PmeI, PacI into the unique BglII and NotI restriction sites. The pV1Jns plasmid with the NS sequence (pV1JnsNS3-5B) was obtained by homologous recombination into the bacterial strain BJ5183, co-transforming pV1JNS3-5A linearized with XbaI and NotI digestion and a PCR fragment containing approximately 200 bp of NS5A, NS5B coding sequence and approximately 60 bp of the BGH polyadenylation signal. The resulting plasmid represents pV1Jns-NS.

pV1Jns-NS can be summarized as follows:

Bases 1 to 1881 of pV1JnsA an additional AGCTT then the Met-NS3-NS5B sequence (SEQ. ID. NO. 5)

then the wt TGA stop an additional TCTAGAGCGTTTAAACCCTTAATTAAGG (SEQ. ID. NO. 14)

Bases 1912 to 4909 of pV1JnsA pV1Jns Plasmid with the NSmut Sequence

The V1JnsNS3-5A plasmid was modified at the 5' of the NS3 coding sequence by addition of a full Kozak sequence. The plasmid (V1JNS3-5Akozak) was obtained by homologous recombination into the bacterial strain BJ5183, co-transforming V1JNS3-5A linearized by AflIII digestion and a PCR fragment containing the proximal part of Intron A, the restriction site BglII, a full Kozak translation initiation sequence and part of the NS3 coding sequence.

The resulting plasmid (V1JNS3-5Akozak) was linearized with Xba I digestion and co-transformed into the bacterial strain BJ5183 with a PCR fragment, containing approximately 200 bp of NS5A, the NS5B mutated sequence, the strong translation termination TAAA and approximately 60 bp of the BGH polyadenylation signal. The PCR fragment was obtained by assembling two 22 bp-overlapping fragments where mutations were introduced by the oligonucleotides used for their amplification. The resulting plasmid represents pV1Jns-NSmut.

pV1Jns-NSmut can be summarized as follows:

Bases 1 to 1882 of pV1JnsA then the kozak Met-NS3-NS5B(mut) TAAA sequence (SEQ. ID. NO. 2)

an additional TCTAGA

Bases 1925 to 4909 of pV1JnsA pV1Jns Plasmid with the NSOPTmut Sequence

The human codon-optimized synthetic gene (NSOPTmut) with mutated NS5B to abrogate enzymatic activity, full Kozak translation initiation sequence and a strong translation termination was digested with BamHI and SalI restriction sites present at the 5' and 3' end of the gene. The gene was then cloned into the BglII and SalI restriction sites present in the polylinker of pV1JnsA plasmid, generating pV1Jns-NSOPTmut.

pV1Jns-NSOPTmut can be summarized as follows:

Bases 1 to 1881 of pV1JnsA an additional C then kozak Met-NS3-NS5B(optmut) TAAA sequence (SEQ. ID. NO. 3)

an additional TTTAAATGTTTAAAC (SEQ. ID. NO. 15)

Bases 1905 to 4909 of pV1JnsA

Plasmids Characterization

Expression of HCV NS proteins was tested by transfection of HEK 293 cells, grown in 10% FCS/DMEM supplemented by L-glutamine (final 4 mM). Twenty-four hours before transfection, cells were plated in 6-well 35 mm diameter, to reach 90-95% confluence on the day of transfection. Forty nanograms of plasmid DNA (previously assessed as a non-saturating DNA amount) were co-transfected with 100 ng of pRSV-Luc plasmid containing the luciferase reporter gene under the control of Rous sarcoma virus promoter, using the LIPOFECTAMINE 2000 reagent. Cells were kept in a $CO_2$ incubator for 48 hours at 37° C.

Figure 12:
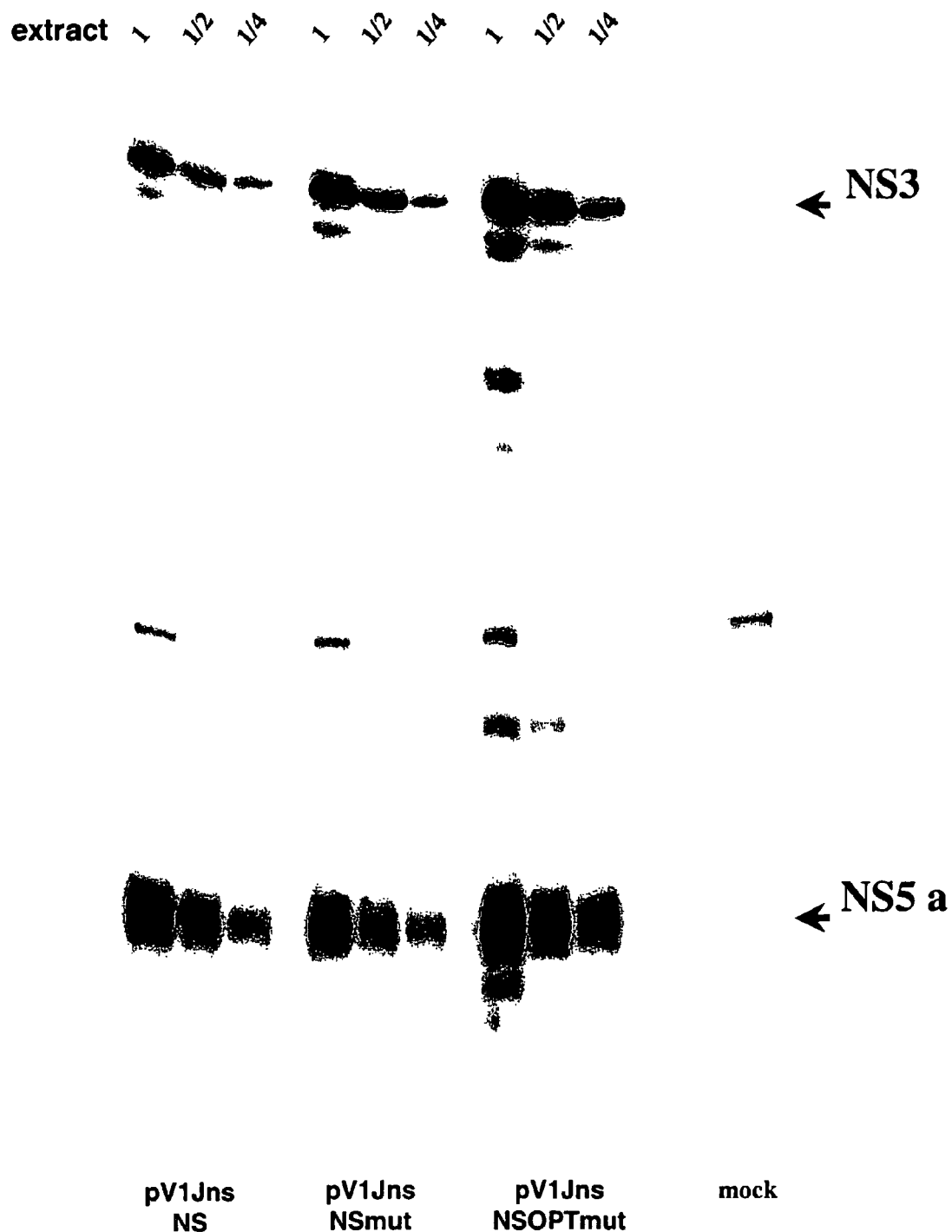
FIG. 12 illustrates a western blot on whole-cell extracts from 293 cells transfected with plasmid DNA expressing different HCV NS cassettes. Mature NS3 and NS5A products were detected with specific antibodies. "pV1Jns-NS" refers to a pV1JnsA plasmid where a Met-NS3-NS4A-NS4B-NS5A-NS5B polypeptide is encoded by SEQ. ID. NO. 5, and SEQ. ID. NO. 5 is inserted between bases 1881 and 1912 of SEQ. ID. NO. 7. "pV1Jns-NSmut" refers to a pV1JnsA plasmid where SEQ. ID. NO. 2 is inserted between bases 1882 and 1925 of SEQ. ID. NO. 7. "pV1Jns-NSOPTmut" refers to a pV1JnsA plasmid where SEQ. ID. NO. 3 is inserted between bases 1881 and 1905 of SEQ. ID. NO. 7.

Cell extracts were prepared in 1% Triton/TEN buffer. The extracts were normalized for Luciferase activity, and run in serial dilution on 10% SDS-acrylamide gel. Proteins were transferred on nitrocellulose and assayed with antibodies directed against NS3, NS5A and NS5B to assess strength of expression and correct proteolytic cleavage. Mock-transfected cells were used as a negative control. Results from representative experiments testing pV1JnsNS, pV1JnsNSmut and pV1JnsNSOPTmut are shown in FIG. 12.

Example 3

Mice Immunization with Plasmid DNA Vectors

The DNA plasmids pV1Jns-NS, pV1Jns-NSmut and pV1Jns-NSOPTmut were injected in different mice strains to evaluate their potential to elicit anti-HCV immune responses. Two different strains (Balb/C and C57Black6, N=9-10) were injected intramuscularly with 25 or 50 µg of DNA followed by electrical pluses. Each animal received two doses at three weeks interval.

Humoral immune response elicited in C57Black6 mice against the NS3 protein was measured in post dose two sera by ELISA on bacterially expressed NS3 protease domain. Antibodies specific for the tested antigen were detected in animals immunized with all three vectors with geometric mean titers (GMT) ranging from 94000 to 133000 (Tables 1-3).

TABLE 1

| | pV1jns-NS | | | | | | | | | |
|---|---|---|---|---|---|---|---|---|---|---|
| Mice n. | 1 | 2 | 3 | 4 | 5 | 6 | 7 | 8 | 9 | GMT |
| Titer | 105466 | 891980 | 78799 | 39496 | 543542 | 182139 | 32351 | 95028 | 67800 | 94553 |

TABLE 2

| | | | | | pV1jns-NSmut | | | | | | |
|---|---|---|---|---|---|---|---|---|---|---|---|
| Mice n. | 11 | 12 | 13 | 14 | 15 | 16 | 17 | 18 | 19 | 20 | GMT |
| Titer | 202981 | 55670 | 130786 | 49748 | 17672 | 174958 | 44304 | 37337 | 78182 | 193695 | 75083 |

TABLE 3

| | | | | | pV1jns-NSOPTmut | | | | | | |
|---|---|---|---|---|---|---|---|---|---|---|---|
| Mice n. | 21 | 22 | 23 | 24 | 25 | 26 | 27 | 28 | 29 | 30 | GMT |
| Titer | 310349 | 43645 | 63496 | 82174 | 630778 | 297259 | 66861 | 146735 | 173506 | 77732 | 133165 |

A T cell response was measured in C57Black6 mice immunized with two intramuscular injections at three weeks interval with 25 μg of plasmid DNA. Quantitative ELIspot assay was performed to determine the number of IFNγ secreting T cells in response to five pools of 20mer peptides overlapping by ten residues encompassing the NS3-NS5B sequence. Specific CD8+ response was analyzed by the same assay using a 20mer peptide encompassing a CD8+ epitope for C57Black6 mice (pep1480).

Cells secreting IFNγ in an antigen specific-manner were detected using a standard ELIspot assay. T cell response in C57Black6 mice immunized with two intramuscular injections at three weeks interval with 50 μg of plasmid DNA, was analyzed by the same ELIspot assay measuring the number of IFNγ secreting T cells in response to five pools of 20mer peptides overlapping by ten residues encompassing the NS3-NS5B sequence.

Spleen cells were prepared from immunized mice and re-suspended in R10 medium (RPMI 1640 supplemented with 10% FCS, 2 mM L-Glutamine, 50 U/ml-50 μg/ml Penicillin/Streptomycin, 10 mM Hepes, 50 μM 2-mercapto-ethanol). Multiscreen 96-well Filtration Plates (Millipore, Cat. No. MAIPS4510, Millipore Corporation, 80 Ashby Road Bedford, Mass.) were coated with purified rat anti-mouse INFγ antibody (PharMingen, Cat. No. 18181D, PharmiMingen, 10975 Torreyana Road, San Diego, Calif. 92121-1111 USA). After overnight incubation, plates were washed with PBS 1×/0.005% Tween and blocked with 250 μl/well of R10 medium.

Splenocytes from immunized mice were prepared and incubated for twenty-four hours in the presence or absence of 10 μM peptide at a density of $2.5 \times 10^5$/well or $5 \times 10^5$/well. After extensive washing (PBS 1×/0.005% Tween), biotinylated rat anti-mouse IFNγ antibody (PharMingen, Cat. No. 18112D, PharMingen, 10975 Torreyana Road, San Diego, Calif. 92121-1111 USA) was added and incubated overnight at 4° C. For development, streptavidin-AKP (PharMingen, Cat. No. 13043E, PharMingen, 10975 Torreyana Road, San Diego, Calif. 92121-1111 USA) and 1-Step™ NBT-BCIP development solution (Pierce, Cat. No. 34042, Pierce, P.O. Box 117, Rockford, Ill. 61105 USA) were added.

Pools of 20mer overlapping peptides encompassing the entire sequence of the HCV BK strain NS3 to NS5B were used to reveal HCV-specific IFNγ-secreting T cells. Similarly a single 20mer peptide encompassing a CD8+ epitope for C57Black6 mice was used to detect CD8 response. Representative data from groups of C57Black6 and Balb/C mice (N=9-10) immunized with two injections of 25 or 50 μg of plasmid vectors pV1Jns-NS, pV1Jns-NSmut and pV1Jns-NSOPTmut are shown in FIGS. 13A and 13B.

Example 4

Immunization of Rhesus Macaques

Rhesus macaques (N=3) were immunized by intramuscular injection with 5 mg of plasmid pV1Jns-NSOPTmut in 7.5 mg/ml CRL1005, Benzalkonium chloride 0.6 mM. Each animal received two doses in the deltoid muscle at 0, and 4 weeks.

CMI was measured at different time points by IFN-γ ELISPOT. This assay measures HCV antigen-specific CD8+ and CD4+ T lymphocyte responses, and can be used for a variety of mammals, such as humans, rhesus monkeys, mice, and rats.

The use of a specific peptide or a pool of peptides can simplify antigen presentation in CTL cytotoxicity assays, interferon-gamma ELISPOT assays and interferon-gamma intracellular staining assays. Peptides based on the amino acid sequence of various HCV proteins (core, E2, NS3, NS4A, NS4B, NS5A, NS5B) were prepared for use in these assays to measure immune responses in HCV DNA and adenovirus vector vaccinated rhesus monkeys, as well as in HCV-infected humans. The individual peptides are overlapping 20-mers, offset by 10 amino acids. Large pools of peptides can be used to detect an overall response to HCV proteins while smaller pools and individual peptides may be used to define the epitope specificity of a response.

IFNγELISPOT

The IFNγ-ELISPOT assay provides a quantitative determination of HCV-specific T lymphocyte responses. PBMC are serially diluted and placed in microplate wells coated with anti-rhesus IFN-γ antibody (MD-1 U-Cytech). They are cultured with a HCV peptide pool for 20 hours, resulting in the restimulation of the precursor cells and secretion of IFN-γ. The cells are washed away, leaving the secreted IFN bound to the antibody-coated wells in concentrated areas where the cells were sitting. The captured IFN is detected with biotinylated anti-rhesus IFN antibody (detector Ab U-Cytech) followed by alkaline phosphatase-conjugated streptavidin (Pharmingen 13043E). The addition of insoluble alkaline phosphatase substrate results in dark spots in the wells at the sites where the cells were located, leaving one spot for each T cell that secreted IFN-γ.

The number of spots per well is directly related to the precursor frequency of antigen-specific T cells. Gamma interferon was selected as the cytokine visualized in this assay (using species specific anti-gamma interferon monoclonal antibodies) because it is the most common, and one of the most abundant cytokines synthesized and secreted by activated T lymphocytes. For this assay, the number of spot forming cells (SFC) per million PBMCs is determined for samples in the presence and absence (media control) of peptide antigens. Data from Rhesus macaques on PBMC from post dose two material are shown in Table 4.

TABLE 4

| | PV1J-NSOPTmut | | |
|---|---|---|---|
| Pep pools | 21G | 99C161 | 99C166 |
| F (NS3p) | 8 | 10 | 170 |
| G (NS3h) | 7 | 592 | 229 |
| H (NS4) | 3 | 14 | 16 |
| I (NS5a) | 5 | 71 | 36 |
| L (NS5b) | 14 | 23 | 11 |
| M (NS5b) | 3 | 35 | 8 |
| DMSO | 2 | 4 | 5 |

INFγELISPOT on PBMC from Rhesus monkeys immunized with two injections of 5 mg DNA/dose in OPTIVAX/BAK of plasmid pV1Jns-NSOPTmut. Data are expressed as SFC7 $10^6$ PBMC.

Example 5

Construction of Ad6 Pre-Adenovirus Plasmids

Ad6 pre-adenovirus plasmids were obtained as follows:

Construction of pAd6 E1-E3+Pre-Adenovirus Plasmid

An Ad6 based pre-adenovirus plasmid which can be used to generate first generation Ad6 vectors was constructed either taking advantage of the extensive sequence identity (approx. 98%) between Ad5 and Ad6 or containing only Ad6 regions. Homologous recombination was used to clone wtAd6 sequences into a bacterial plasmid.

Figure 10:
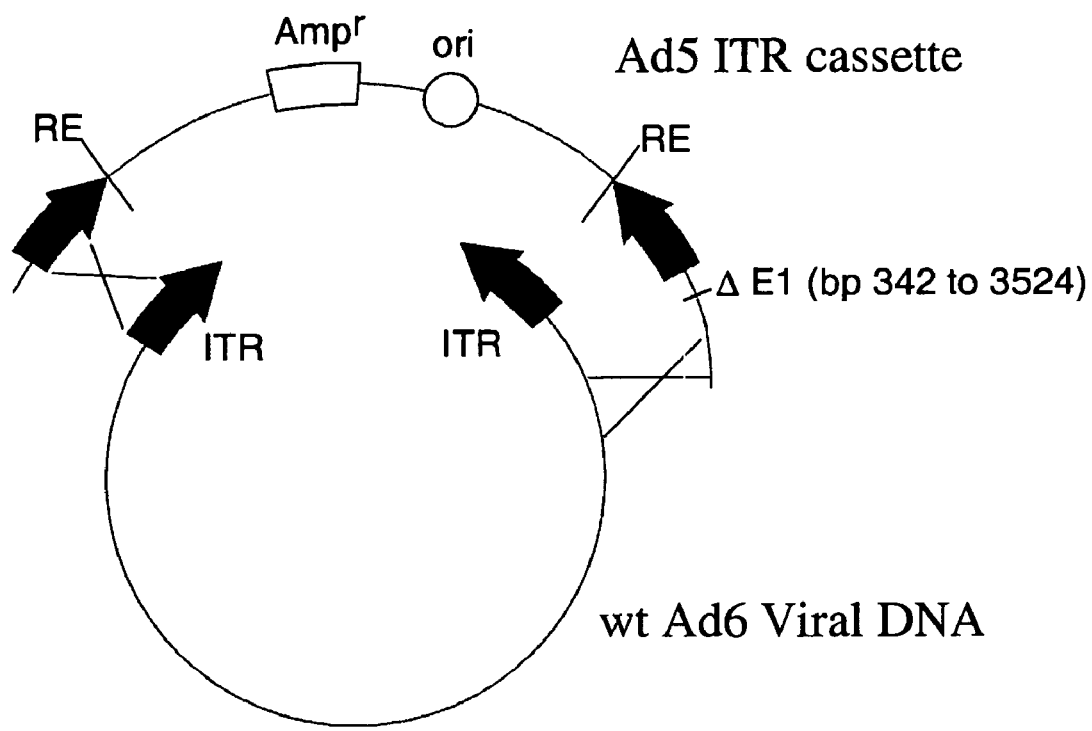
FIG. 10 illustrates homologous recombination to recover pAdE1-E3+ containing Ad6 and Ad5 regions.

A general strategy used to recover pAd6E1-E3+ as a bacterial plasmid containing Ad5 and Ad6 regions is illustrated in FIG. 10. Cotransformation of BJ 5183 bacteria with purified wt Ad6 viral DNA and a second DNA fragment termed the Ad5 ITR cassette resulted in the circularization of the viral genome by homologous recombination. The ITR cassette contains sequences from the right (bp 33798 to 35935) and left (bp 1 to 341 and bp 3525 to 5767) end of the Ad5 genome separated by plasmid sequences containing a bacterial origin of replication and an ampicillin resistance gene. The ITR cassette contains a deletion of E1 sequences from Ad5 342 to 3524. The Ad5 sequences in the ITR cassette provide regions of homology with the purified Ad6 viral DNA in which recombination can occur.

Potential clones were screened by restriction analysis and one clone was selected as pAd6E1-E3+. This clone was then sequenced in it entirety. pAd6E1-E3+ contains Ad5 sequences from bp 1 to 341 and from bp 3525 to 5548, Ad6 bp 5542 to 33784, and Ad5 bp 33967 to 35935 (bp numbers refer to the wt sequence for both Ad5 and Ad6). pAd6E1-E3+ contains the coding sequences for all Ad6 virion structural proteins which constitute its serotype specificity.

Figure 11:
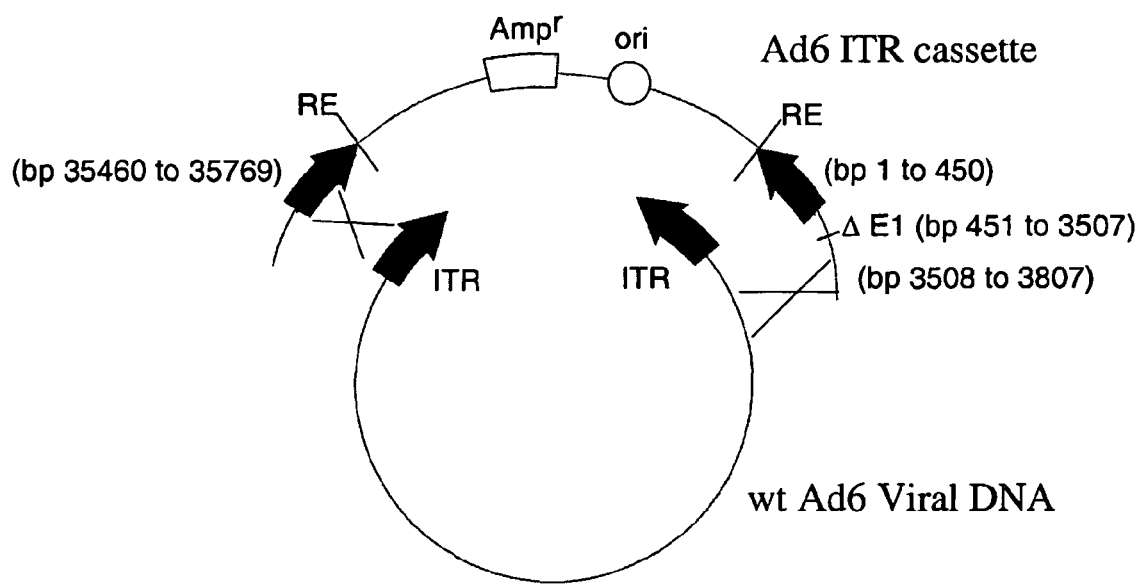
FIG. 11 illustrates homologous recombinant to recover a pAdE1-E3+ containing Ad6 regions.

A general strategy used to recover pAd6E1-E3+ as a bacterial plasmid containing Ad6 regions is illustrated in FIG. 11. Cotransformation of BJ 5183 bacteria with purified wt Ad6 viral DNA and a second DNA fragment termed the Ad6 ITR cassette resulted in the circularization of the viral genome by homologous recombination. The ITR cassette contains sequences from the right (bp 35460 to 35759) and left (bp 1 to 450 and bp 3508 to 3807) end of the Ad6 genome separated by plasmid sequences containing a bacterial origin of replication and an ampicillin resistance gene. These three segments were generated by PCR and cloned sequentially into pNEB193, generating pNEBAd6-3 (the ITR cassette). The ITR cassette contains a deletion of E1 sequences from Ad5 451 to 3507. The Ad6 sequences in the ITR cassette provide regions of homology with the purified Ad6 viral DNA in which recombination can occur.

Construction of pAd6 E1-E3-Pre-Adenovirus Plasmids

Ad6 based vectors containing A5 regions and deleted in the E3 region were constructed starting with pAd6E1-E3+ containing Ad5 regions. A 5322 bp subfragment of pAd6E1-E3+ containing the E3 region (Ad6 bp 25871 to 31192) was subcloned into pABS.3 generating pABSAd6E3. Three E3 deletions were then made in this plasmid generating three new plasmids pABSAd6E3 (1.8 Kb) (deleted for Ad6 bp 28602 to 30440), pABSAd6E3 (2.3 Kb) (deleted for Ad6 bp 28157 to 30437) and pABSAd6E3 (2.6 Kb) (deleted for Ad6 bp 28157 to 30788). Bacterial recombination was then used to substitute the three E3 deletions back into pAd6E1-E3+ generating the Ad6 genome plasmids pAd6E1-E3-1.8 Kb, pAd6E1-E3-2.3 Kb and pAd6E1-E3-2.6 Kb.

Example 6

Generation of Ad5 Genome Plasmid with the NS Sequence

A pcDNA3 plasmid (Invitrogen) containing the coding region NS3-NS4A-NS4B-NS5A was digested with XmnI and NruI restriction sites and the DNA fragment containing the CMV promoter, the NS3-NS4A-NS4B-NS5A coding sequence and the Bovine Growth Hormone (BGH) polyadenylation signal was cloned into the unique EcorV restriction site of the shuttle vector pDelE1Spa, generating the Sva3-5A vector.

A pcDNA3 plasmid containing the coding region NS3-NS4A-NS4B-NS5A-NS5B was digested with XmnI and EcorI (partial digestion), and the DNA fragment containing part of NS5A, NS5B gene and the BGH polyadenylation signal was cloned into the Sva3-5A vector, digested EcorI and BglII blunted with Klenow, generating the Sva3-5B vector.

The Sva3-5B vector was finally digested SspI and Bst1107I restriction sites and the DNA fragment containing the expression cassette (CMV promoter, NS3-NS4A-NS4B-NS5A-NS5B coding sequence and the BGH polyadenylation signal) flanked by adenovirus sequences was co-transformed with pAd5HVO (E1-,E3-) ClaI linearized genome plasmid into the bacterial strain BJ5183, to generate pAd5HVONS. pAd5HVO contains Ad5 bp 1 to 341, bp 3525 to 28133 and bp 30818 to 35935.

Example 7

Generation of Adenovirus Genome Plasmids with the NSmut Sequence

Adenovirus genome plasmids containing an NS-mut sequence were generated in an Ad5 or Ad6 background. The Ad6 background contained Ad5 regions at bases 1 to 450, 3511 to 5548 and 33967 to 35935.

pV1JNS3-5Akozak was digested with BglII and XbaI restriction enzymes and the DNA fragment containing the Kozak sequence and the sequence coding NS3-NS4A-NS4B-NS5A was cloned into a BglII and XbaI digested polypM-RKpdelE1 shuttle vector. The resulting vector was designated shNS3-5Akozak.

PolypMRKpdelE1 is a derivative of RKpdelE1 (Pac/pIX/pack450)+CMVmin+BGHpA(str.) modified by the insertion of a polylinker containing recognition sites for BglII, PmeI, SwaI, XbaI, SalI, into the unique BglII restriction site present downstream the CMV promoter. MRKpdelE1 (Pac/pIX/pack450)+CMVmin+BGHpA(str.) contains Ad5 sequences from bp 1 to 5792 with a deletion of E1 sequences from bp 451 to 3510. The human CMV promoter and BGH polyadenylation signal were inserted into the E1 deletion in an E1 parallel orientation with a unique BglII site separating them.

The NS5B fragment, mutated to abrogate enzymatic activity and with a strong translation termination at the 3' end, was obtained by assembly PCR and inserted into the shNS3-5Akozak vector via homologous recombination, generating polypMRKpdelE1NSmut. In polypMRKpdelE1NSmut the NS-mut coding sequence is under the control of CMV promoter and the BGH polyadenylation signal is present downstream.

The gene expression cassette and the flanking regions which contain adenovirus sequences allowing homologous recombination were excised by digestion with PacI and Bst1107I restriction enzymes and co-transformed with either pAd5HVO (E1-,E3-) or pAd6E1-E3-2.6 Kb ClaI linearized genome plasmids into the bacterial strain BJ5183, to generate pAd5HVONSmut and pAd6E1-,E3-NSmut, respectively.

pAd6E1-E3-2.6 Kb contains Ad5 bp 1 to 341 and from bp 3525 to 5548, Ad6 bp 5542 to 28157 and from bp 30788 to 33784, and Ad5 bp 33967 to 35935 (bp numbers refer to the wt sequence for both Ad5 and Ad6). In both plasmids the viral ITR's are joined by plasmid sequences that contain the bacterial origin of replication and an ampicillin resistance gene.

Example 8

Generation of Adenovirus Genome Plasmids with the NSOPTmut

The human codon-optimized synthetic gene (NSOPTmut) provided by SEQ. ID. NO. 3 cloned into a pCRBlunt vector (Invitrogen) was digested with BamHI and SalI restriction enzymes and cloned into the BglII and SalI restriction sites present in the shuttle vector polypMRKpdelE1. The resulting clone (polypMRKpdelE1NSOPTmut) was digested with PacI and Bst1107I restriction enzymes and co-transformed with either pAd5HVO (E1-,E3-) or pAd6E1-E3-2.6 Kb ClaI linearized genome plasmids, into the bacterial strain BJ5183, to generate pAd5HVONSOPTmut and pAd6E1-,E3-NSOPTmut, respectively.

Example 9

Rescue and Amplification of Adenovirus Vectors

Adenovectors were rescued in Per.6 cells. Per.C6 were grown in 10% FCS/DMEM supplemented by L-glutamine (final 4 mM), penicillin/streptomycin (final 100 IU/ml) and 10 mM $MgCl_2$. After infection, cells were kept in the same medium supplemented by 5% horse serum (HS). For viral rescue, $2.5 \times 10^6$ Per.C6 were plated in 6 cm ø Petri dishes.

Twenty-four hours after plating, cells were transfected by calcium phosphate method with 10 µg of the Pac I linearized adenoviral DNA. The DNA precipitate was left on the cells for 4 hours. The medium was removed and 5% HS/DMEM was added.

Cells were kept in a $CO_2$ incubator until a cytopathic effect was visible (1 week). Cells and supernatant were recovered and subjected to 3× freeze/thawing cycles (liquid nitrogen/water bath at 37° C.). The lysate was centrifuged at 3000 rpm at -4° C. for 20 minutes and the recovered supernatant (corresponding to a cell lysate containing virus passed on cells only once; P1) was used, in the amount of 1 ml/dish, to infect 80-90% confluent Per.C6 in 10 cm ø Petri dishes. The infected cells were incubated until a cytopathic effect was visible, cells and supernatant recovered and the lysate prepared as described above (P2).

P2 lysate (4 ml) were used to infect $2 \times 15$ cm ø Petri dishes. The lysate recovered from this infection (P3) was kept in aliquots at -80° C. as a stock of virus to be used as starting point for big viral preparations. In this case, 1 ml of the stock was enough to infect $2 \times 15$ cm ø Petri dishes and resulting lysate (P4) was used for the infection of the Petri dishes devoted to the large scale infection.

Further amplification was obtained from the P4 lysate which was diluted in medium without FCS and used to infect $30 \times 15$ cm ø Petri dishes (with Per.C6 80%-90% confluent) in the amount of 10 ml/dish. Cells were incubated 1 hour in the $CO_2$ incubator, mixing gently every 20 minutes. 12 ml/dish of 5% HS/DMEM was added and cells were incubated until a cytopathic effect was visible (about 48 hours).

Cells and supernatant were collected and centrifuged at 2K rpm for 20 minutes at 4° C. The pellet was resuspended in 15 ml of 0.1 M Tris pH=8.0. Cells were lysed by 3× freeze/thawing cycles (liquid nitrogen/water bath at 37° C.). 150 µl of 2 M $MgCl_2$ and 75 µl of DNAse (10 mg of bovine pancreatic deoxyribonuclease I in 10 ml of 20 mM Tris-HCl pH=7.4, 50 mM NaCl, 1 mM dithiothreitol, 0.1 mg/ml bovine serum albumin, 50% glycerol) were added. After a 1 hour incubation at 37° C. in a water bath (vortex every 15 minutes) the lysate was centrifuged at 4K rpm for 15 minutes at 4° C. The recovered supernatant was ready to be applied on CsCl gradient.

The CsCl gradients were prepared in SW40 ultra-clear tubes as follows:

0.5 ml of 1.5 d CsCl 3 ml of 1.35 d CsCl 3 ml of 1.25 d CsCl 5-ml/tube of viral supernatant was applied.

If necessary, the tubes were topped up with 0.1 M tris-Cl pH=8.0. Tubes were centrifuged at 35K rpm for 1 hour at -10° C. with rotor SW40. The viral bands (located at the 1.25/1.35 interface) were collected using a syringe.

The virus was transferred into a new SW40 ultraclear tube and 1.35 d CsCl was added to top the tube up. After centrifugation at 35K rpm for 24 hours at 10° C. in the rotor SW40, the virus was collected in the smallest possible volume and dialyzed extensively against buffer A105 (5 mM Tris, 5% sucrose, 75 mM NaCl, 1 mM $MgCl_2$, 0.005% polysorbate 80 pH=8.0). After dialysis, glycerol was added to final 10% and the virus was stored in aliquots at -80° C.

Example 10

Enhanced Adenovector Rescue

First generation Ad5 and Ad6 vectors carrying HCV NSOPTmut transgene were found to be difficult to rescue. A possible block in the rescue process might be attributed to an inefficient replication of plasmid DNA that is a sub-optimal template for the replication machinery of adenovirus. The absence of the terminal protein linked to the 5' ends of the DNA (normally present in the viral DNA), associated with the very high G-C content of the transgene inserted in the E1 region of the vector, may be causing a substantial reduction in replication rate of the plasmid-derived adenovirus.

Figure 19:
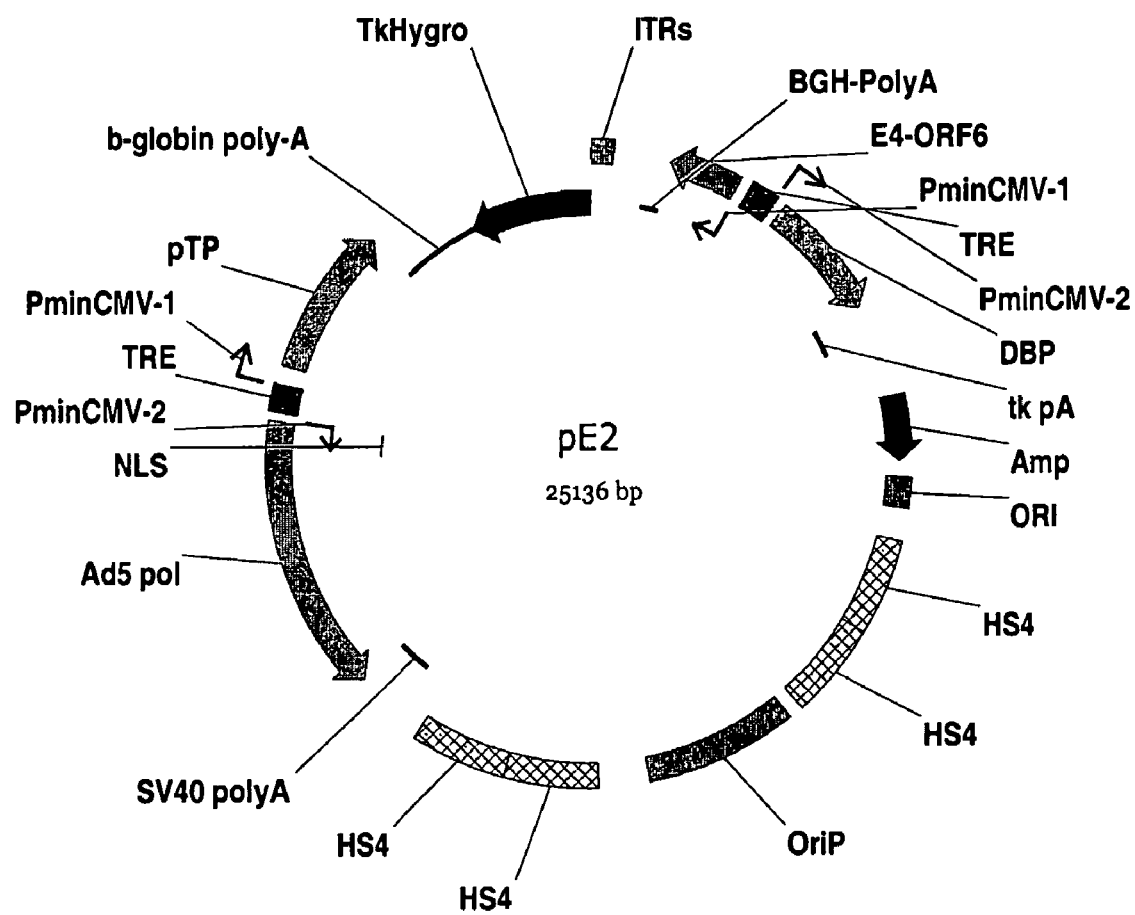
FIG. 19 illustrates the plasmid pE2.

To set up a more efficient and reproducible procedure for rescuing Ad vectors, an expression vector (pE2; FIG. 19) containing all E2 proteins (polymerase, pre-terminal protein and DNA binding protein) as well as E4 orf6 under the control of tet-inducible promoter was employed. The transfection of pE2 in combination with a normal preadeno plasmid in PerC6 and in 293 leads to a strong increase of Ad DNA replication and to a more efficient production of complete infectious adenovirus particles.

Plasmid Construction pE2 is based on the cloning vector pBI (CLONTECH) with the addition of two elements to allow episomal replication and selection in cell culture: (1) the EBV-OriP (EBV [nt] 7421-8042) region permitting plasmid replication in synchrony with the cell cycle when EBNA-1 is expressed and (2) the hygromycin-B phosphotransferase (HPH)-resistance gene allowing a positive selection of transformed cells. The two transcriptional units for the adenoviral genes E2 a and b and E4-Orf6 were constructed and assembled in pE2 as described below.

The Ad5-Polymerase ClaI/SphI fragment and the Ad5-pTP Acc65/EcoRV fragment were obtained from pVac-Pol and pVac-pTP (Stunnenberg et al. *NAR* 16:2431-2444, 1988). Both fragments were filled with Klenow and cloned into the SalI (filled) and EcoRV sites of pBI, respectively obtaining pBI-Pol/pTP.

EBV-OriP element from pCEP4 (Invitrogen) was first inserted within two chicken β-globin insulator dimers by cloning it into BamHI site of pJC13-1 (Chung et al., *Cell* 74(3):505-14, 1993). HS4-OriP fragment from pJC13-OriP was then cloned inside pSA1mv (a plasmid containing tk-Hygro-B resistance gene expression cassette as well as Ad5 replication origin), the ITR's arranged as head-to-tail junction, obtained by PCR from pFG140 (Graham, *EMBO J.* 3:2917-2922, 1984) using the following primers: 5'-TC-GAATCGATACGCGAACCTACGC-3' (SEQ. ID. NO. 16) and 5'-TCGACGTGTCGACTTCGAAGCGCACAC-CAAAAACGTC-3' (SEQ. ID. NO. 17), thus generating pMVHS4Orip. A DNA fragment from pMVHS4Orip, containing the insulated OriP, Ad5 ITR junction and tk-HygroB cassette, was then inserted into pBI-Pol/pTP vector restricted AseI/AatII generating pBI-Pol/pTPHS4.

To construct the second transcriptional unit expressing Ad5-Orf6 as well as Ad5-DBP, E4orf6 (Ad 5 [nt] 33193-34077) obtained by PCR was first inserted into pBI vector, generating pBI-Orf6. Subsequently, DBP coding DNA sequence (Ad 5 [nt] 22443-24032) was inserted into pBI-Orf6 obtaining the second bi-directional Tet-regulated expression vector (pBI-DBP/E4orf6). The original polyA signals present in pBI were substituted with BGH and SV40 polyA.

pBI-DBP/E4orf6 was then modified by inserting a DNA fragment containing the Adeno5-ITRs arranged in head-to-tail junction plus the hygromicin B resistance gene obtained from plasmid pSA-1mv. The new plasmid pBI-DBP/E4orf6shuttle was then used as donor plasmid to insert the second tet-regulated transcriptional unit into pBI-Pol/pT-PHS4 by homologous recombination using *E. coli* strain BJ5183 obtaining pE2.

Cell Lines, Transfections and Virus Amplification

PerC6 cells were cultured in Dulbecco's modified Eagle's Medium (DMEM) plus 10% fetal bovine serum (FBS), 10 mM $MgCl_2$, penicillin (100 U/ml), streptomycin (100 μg/ml) and 2 mM glutamine.

All transient transfections were performed using Lipofectamine2000 (Invitrogen) as described by the manufacturer. 90% confluent PERC.6™ planted in 6-cm plates were transfected with 3.5 μg of Ad5/6NSOPTmut pre-adeno plasmids, digested with PacI, alone or in combination with 5 μg pE2 plus 1 μg pUHD52.1. pUHD52.1 is the expression vector for the reverse tet transactivator 2 (rtTA2) (Urlinger et al., *Proc. Natl. Acad. Sci. U.S.A.* 97(14):7963-7968, 2000). Upon transfection, cells were cultivated in the presence of 1 μg/ml of doxycycline to activate pE2 expression. 7 days post-transfection cells were harvested and cell lysate was obtained by three cycles of freeze-thaw. Two ml of cell lysate were used to infect a second 6-cm dish of PerC6. Infected cells were cultivated until a full CPE was observed then harvested. The virus was serially passaged five times as described above, then purified on CsCl gradient. The DNA structure of the purified virus was controlled by endonuclease digestion and agarose gel electrophoresis analysis and compared to the original pre-adeno plasmid restriction pattern.

Example 11

Partial Optimizeation of HCV Polyprotein Encoding Nucleic Acid

Partial optimization of HCV polyprotein encoding nucleic acid was performed to facilitate the production of adenovectors containing codons optimized for expression in a human host. The overall objective was to provide for increased expression due to codon optimization, while facilitating the production of an adenovector encoding HCV polyprotein.

Several difficulties were encountered in producing an adenovector encoding HCV polyprotein with codons optimized for expression in a human host. An adenovector containing an optimized sequence (SEQ. ID. NO. 3) was found to be more difficult to synthesize and rescue than an adenovector containing a non-optimized sequence (SEQ. ID. NO. 2).

The difficulties in producing an adenovector containing SEQ. ID. NO. 3 were attributed to a high GC content. A particularly problemetic region was the region at about position 3900 of NSOPTmut (SEQ. ID. NO. 3).

Alternative versions of optimized HCV encoding nucleic acid sequence were designed to facilitate its use in an adenovector. The alternative versions, compared to NSOPTmut, were designed to have a lower overall GC content, to reduce/avoid the presence of potentially problematic motifs of consecutive G's or C's, while maintaining a high level of codon optimization to allow improved expression of the encoded polyprotein and the individual cleavage products.

A starting point for the generation of a suboptimally codon-optimized sequence is the coding region of the NSOPTmut nucleotide sequence (bases 7 to 5961 of SEQ. ID. NO. 3). Values for codon usage frequencies (normalized to a total of 1.0 for each amino acid) were taken from the file human_high.cod available in the Wisconsin Package Version 10.3 (Accelrys Inc., a wholly owned subsidiary of Pharmacopeia, Inc).

To reduce the local and overall GC content a table defining preferred codon substitutions for each amino acid was manually generated. For each amino acid the codon having 1) a lower GC content as compared to the most frequent codon and 2) a relatively high observed codon usage frequency (as defined in human_high.cod) was chosen as the replacement codon. For example for Arg the codon with the highest frequency is CGC. Out of the other five alternative codons encoding Arg (CGG, AGG, AGA, CGT, CGA) three (AGG, CGT, CGA) reduce the GC content by 1 base, one (AGA) by two bases and one (CGG) by 0 bases. Since the AGA codon is listed in human_high.cod as having a relatively low usage frequency (0.1), the codon substituting CGC was therefore chosen to be AGG with a relative frequency of 0.18. Similar criteria were applied in order to establish codon replacements for the other amino acids resulting in the list shown in Table 5. Parameters applied in the following optimization procedure were determined empirically such that the resulting sequence maintained a considerably improved codon usage (for each amino acid) and the GC content (overall and in form of local stretches of consecutive G's and/or C's) was decreased.

Two examples of partial optimized HCV encoding sequences are provided by SEQ. ID. NO. 10 and SEQ. ID. NO. 11. SEQ. ID. NO. 10 provides a HCV encoding sequence that is partially optimized throughout. SEQ. ID. NO. 11 provides an HCV encoding sequence fully optimized for codon usage with the exception of a region that was partially optimized.

Codon optimization was performed using the following procedure:

Step 1) The coding region of the input fully optimized NSOPTmut sequence was analyzed using a sliding window of 3 codons (9 bases) shifting the window by one codon after each cycle. Whenever a stretch containing 5 or more consecutive C's and/or G's was detected in the window the following replacement rule was applied: Let N indicate the number of codon replacements previously performed. If N is odd replace the middle codon in the window with the codon specified in Table 5, if N is even replace the third terminal codon in the window with the codon specified in a codon optimization table such as human_high.cod. If Leu or Val is present at the second or third codon do not apply any replacement in order not to introduce Leu or Val codons with very low relative codon usage frequency (see, for example, human_high.cod). In the following cycle analysis of the shifted window was then applied to a sequence containing the replacements of the previous cycle.

The alternating replacement of the middle and terminal codon in the 3 codon window was found empirically to give a more satisfying overall maintenance of optimized codon usage while also reducing GC content (as judged from the final sequence after the procedure). In general, however, the precise replacement strategy depends on the amino acid sequence encoded by the nucleotide sequence under analysis and will have to be determined empirically.

Step 2) The sequence containing all the codon replacements performed during step 1) was then subjected to an additional analysis using a sliding window of 21 codons (63 bases) in length: according to an adjustable parameter the overall GC content in the window was determined. If the GC content in the window was higher than 70% the following codon replacement strategy was applied: In the window replace the codons for the amino acids Asn, Asp, Cys, Glu, His, Ile, Lys, Phe, Tyr by the codons given in Table 5. Restriction of the replacement to this set of amino acids was motivated by the fact that a) the replacement codon still has an accetably high frequency of usage in human_high.cod and b) the average overall human codon usage in CUTG for the replacement codon is nearly as high as the most frequent codon. In the following cycle analysis of the shifted window is then applied to a sequence containing the replacements of the previous cycle.

The threshold 70% was determined empirically by compromising between an overall reduction in GC content and maintenance of a high codon optimization for the individual amino acids. As in step 1) the precise replacement strategy (choice of amino acids and GC content threshold value) will again depend on the amino acid sequence encoded by the nucleotide sequence under analysis and will have to be determined empirically.

Step 3) The sequence generated by steps 1) and 2) was then manually edited and additional codons were changed according to the following criteria: Regions still having a GC content higher than 70% over a window of 21 codons were examined manually and a few codons were replaced again following the scheme given in Table 5.

Subsequent steps were performed to provide for useful restriction sites, remove possible open reading frames on the complementary strand, to add homologous recombinant regions, to add a Kozac signal, and to add a terminator. These steps are numbered 4-7

Step 4) The sequence generated in step 3 was examined for the absence of certain restriction sites (BglII, PmeI and XbaI) and presence of only 1 StuI site to allow a subsequent cloning strategy using a subset of restriction enzymes. Two sites (one for BglII and one for StuI) were removed from the sequence by replacing codons that were part of the respective recognition sites.

Step 5) The sequence generated by steps 1) through 4) was then modified according to allow subsequent generation of a modified NSOPTmut sequence (by homologous recombination). In the sequence obtained from steps 1) through 4) the segment comprising base 3556 to 3755 and the segment comprising base 4456 to 4656 were replaced by the corresponding segments from NSOPTmut. The segment comprising bases 3556 to 4656 of SEQ. ID. NO. 10 can be used to replace the problematic region in NSOPTmut (around position 3900) by homologous recombination thus creating the variant of NSOPTmut having the sequence of SEQ. ID. NO. 11.

Step 6) Analysis of the sequence generated through steps 1) to 5) revealed a potential open reading frame spanning nearly the complete fragment on the complementary strand. Removal of all codons CTA and TTA (Leu) and TCA (Ser) from the sense strand effectively removed all stop codons in one of the reading frames on the complementary strand. Although the likelyhood for transcription of this complementary strand open reading frame and subsequent translation into protein is very small, in order to exclude a potential interference with the transcription and subsequent translation of the sequence encoded on the sense strand, TCA codons for Ser were introduced on the sense approximately every 500 bases. No changes were introduced in the segments introduced during step 5) to allow homologous recombination. The TCA codon for Ser was preferred over the CTA and TTA codons for Leu because of the higher relative frequency for TCA (0.05) as compared to CTA (0.02) and TTA (0.03) in human_high.cod. In addition, the average human codon usage from CUTG favored TCA (0.14 against 0.07 for CTA and TTA).

Step 7) In a final step GCCACC was added at the 5' end of the sequence to generate an optimized internal ribosome entry site (Kozak signal) and a TAAA stop signal was added at the 3'. To maintain the initiation of translation properties of NSsuboptmut the first 8 codons of the coding region were kept identical to the NSOPTmut sequence. The resulting sequence was again checked for the absence of BglII, PmeI and XbaI recognition sites and the presence of only 1 StuI site.

The NSsuboptmut sequence (SEQ. D. NO. 10) has an overall reduced GC content (63.5%) as compared to NSOPTmut (70.3%) and maintains a well optimized level of codon usage optimization. Nucleotide sequence identity of NSsuboptmut is 77.2% with respect to NSmut.

TABLE 5

Definition of codon replacements performed during steps 1) and 2).

| Amino Acid | Most frequent codon | Relative frequency | Reduction in GC content (bases) | Replacement codon | Relative frequency |
|---|---|---|---|---|---|
| Amino Acids where the replacement codon reduces the codon GC-content by 1 base ||||||
| Ala | GCC | 0.51 | 1 | GCT | 0.17 |
| Arg | CGC | 0.37 | 1 | AGG | 0.18 |
| Asn | AAC | 0.78 | 1 | AAT | 0.22 |
| Asp | GAC | 0.75 | 1 | GAT | 0.25 |
| Cys | TGC | 0.68 | 1 | TGT | 0.32 |
| Glu | GAG | 0.75 | 1 | GAA | 0.25 |
| Gln | CAG | 0.88 | 1 | CAA | 0.12 |
| Gly | GGC | 0.50 | 1 | GGA | 0.14 |
| His | CAC | 0.79 | 1 | CAT | 0.21 |
| Ile | ATC | 0.77 | 1 | ATT | 0.18 |
| Lys | AAG | 0.82 | 1 | AAA | 0.18 |
| Phe | TTC | 0.80 | 1 | TTT | 0.20 |
| Pro | CCC | 0.48 | 1 | CCT | 0.19 |
| Ser | AGC | 0.34 | 1 | TCT | 0.13 |
| Thr | ACC | 0.51 | 1 | ACA | 0.14 |
| Tyr | TAC | 0.74 | 1 | TAT | 0.26 |
| Amino Acids with no alternative codon ||||||
| Met | ATG | 1.00 | 0 | ATG | 1.00 |
| Trp | TGG | 1.00 | 0 | TGG | 1.00 |
| Amino Acids where the replacement codon has a very low relative frequency. These amino acids were excluded from the replacement procedure ||||||
| Leu | CTG | 0.58 | 1 | TTG | 0.06 |
| Val | GTG | 0.64 | 1 | GTT | 0.07 |

Example 12

Virus Characterization

Adenovectors were characterized by: (a) measuring the physical particles/ml; (b) running a TaqMan PCR assay; and (c) checking protein expression after infection of HeLa cells.

a) Physical Particles Determination

CsCl purified virus was diluted 1/10 and 1/100 in 0.1% SDS PBS. As a control, buffer A105 was used. These dilutions were incubated 10 minutes at 55° C. After spinning the tubes briefly, O.D. at 260 nm was measured. The amount of viral particles was calculated as follows: 1 OD 260 nm=1.1× $10^{12}$ physical particles/ml. The results were typically between $5 \times 10^{11}$ and $1 \times 10^{12}$ physical particles/ml.

b) TaqMan PCR Assay

TaqMan PCR assay was used for adenovectors genome quantification (Q-PCR particles/ml). TaqMan PCR assay was performed using the ABI Prism 7700-sequence detector. The reaction was performed in a final 50 μl volume in the presence of oligonucleotides (at final 200 nM) and probe (at final 200 μM) specific for the adenoviral backbone. The virus was diluted 1/10 in 0.1% SDS PBS and incubated 10 minutes at 55° C. After spinning the tube briefly, serial 1/10 dilutions (in water) were prepared. 10 μl the $10^{-3}$, $10^{-5}$ and $10^{-7}$ dilutions were used as templates in the PCR assay.

The amount of particles present in each sample was calculated on the basis of a standard curve run in the same experiment. Typically results were between $1 \times 10^{12}$ and $3 \times 10^{12}$ Q-PCR particles/ml.

c) Expression of HCV Non-Structural Proteins

Expression of HCV NS proteins was tested by infection of HeLa cells. Cells were plated the day before the infection at $1.5 \times 10^6$ cells/dish (10 cm ø Petri dishes). Different amounts of CsCl purified virus corresponding to m.o.i. of 50, 250 and 1250 pp/cell were diluted in medium (FCS free) up to a final volume of 5 ml. The diluted virus was added on the cells and incubated for 1 hour at 37° C. in a $CO_2$ incubator (gently mixing every 20 minutes). 5 ml of 5% HS-DMEM was added and the cells were incubated at 37° C. for 48 hours.

Figure 14:
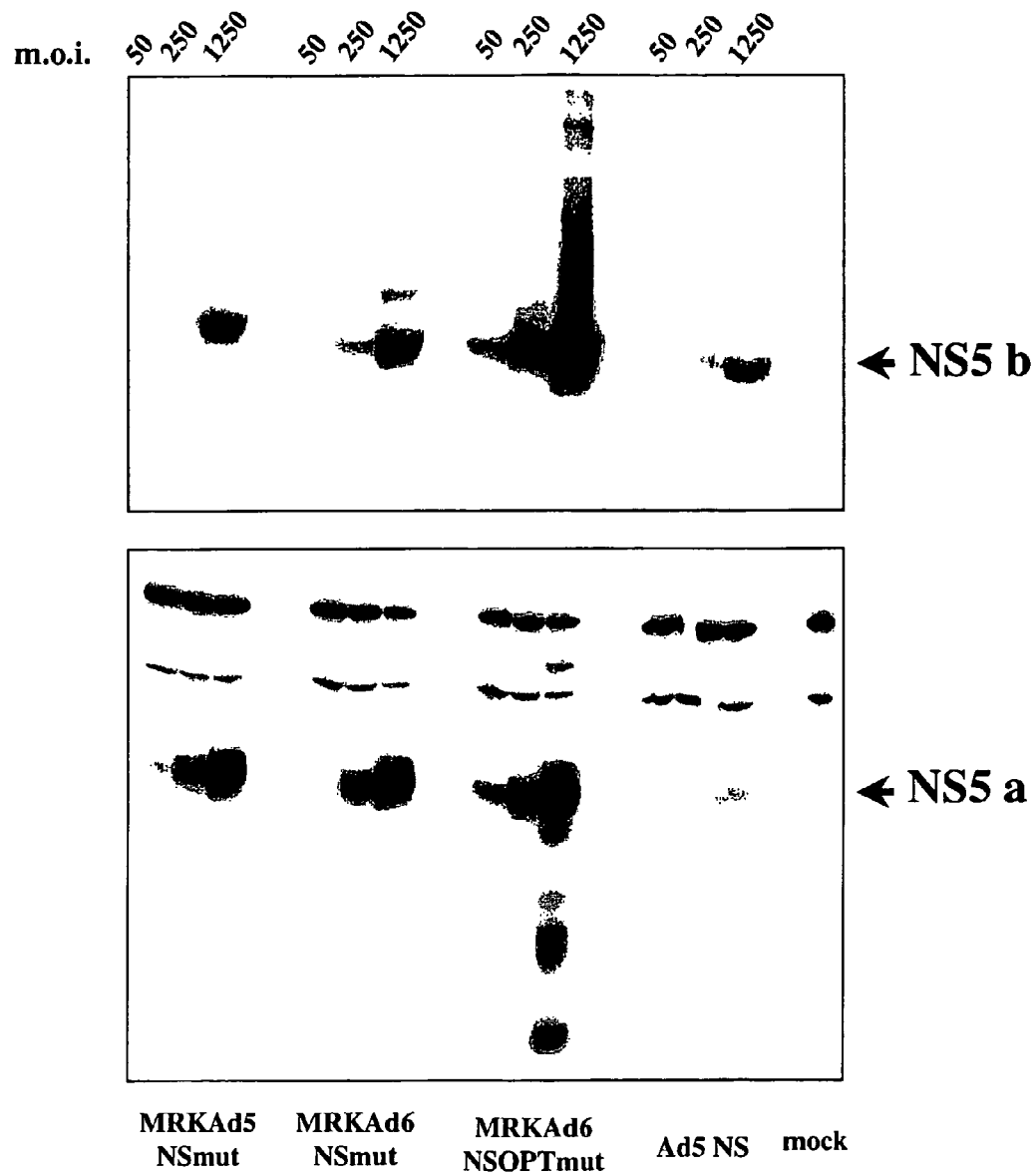
FIG. 14 illustrates protein expression from different adenovectors upon infection of HeLa cells. MRKAd5-NSmut is an adenovector based on an Ad5 sequence (SEQ. ID. NO. 9), where the Ad5 genome has an E1 deletion of base pairs 451 to 3510, an E3 deletion of base pairs 28134 to 30817, and has the NS3-NS4A-NS4B-NS5A-NS5B expression cassette as provided in base pairs 451 to 7468 of SEQ. ID. NO. 4 inserted between positions 450 and 3511. Ad5-NS is an adenovector based on an Ad5 backbone with an E1 deletion of base pairs 342 to 3523, and E3 deletion of base pairs 28134 to 30817 and containing an expression cassette encoding a NS3-NS4A-NS4B-NS5A-NS5B from SEQ. ID. NO. 5. "MRKAd6-NSOPTmut" refers to an adenovector having a modified SEQ. ID. NO. 4 sequence, wherein base pairs 1258 to 7222 of SEQ. ID. NO. 4 is replaced with SEQ. ID. NO. 3.

Cell extracts were prepared in 1% Triton/TEN buffer. The extracts were run on 10% SDS-acrylamide gel, blotted on nitrocellulose and assayed with antibodies directed against NS3, NS5a and NS5b in order to check the correct polyprotein cleavage. Mock-infected cells were used as a negative control. Results from representative experiments testing the Ad5-NS, MRKAd5-NSmut, MRKAd6-NSmut and MRKAd6-NSOPTmut are shown in FIG. 14.

Example 13

Mice Immunization with Adenovectors Encoding Different NS Cassettes

The adenovectors Ad5-NS, MRKAd5-NSmut, MRKAd6-NSmut and MRKAd6-NSOPTmut were injected in C57Black6 mice strains to evaluate their potential to elicit anti-HCV immune responses. Groups of animals (N=9-10) were injected intramuscularly with $10^9$ pp of CsCl purified virus. Each animal received two doses at three weeks interval.

Humoral immune response against the NS3 protein was measured in post dose two sera from C57Black6 immunized mice by ELISA on bacterially expressed NS3 protease domain. Antibodies specific for the tested antigen were detected with geometric mean titers (GMT) ranging from 100 to 46000 (Tables 6, 7, 8 and 9).

TABLE 6

| | Ad5-NS |||||||||||
|---|---|---|---|---|---|---|---|---|---|---|---|
| Mice n. | 1 | 2 | 3 | 4 | 5 | 6 | 7 | 8 | 9 | 10 | GMT |
| Titer | 50 | 253 | 50 | 50 | 50 | 2257 | 504 | 50 | 50 | 50 | 108 |

TABLE 7

| | Ad5-NSmut |||||||||||
|---|---|---|---|---|---|---|---|---|---|---|---|
| Mice n. | 11 | 12 | 13 | 14 | 15 | 16 | 17 | 18 | 19 | 20 | GMT |
| Titer | 3162 | 78850 | 87241 | 6796 | 12134 | 3340 | 18473 | 13093 | 76167 | 49593 | 23645 |

TABLE 8

| | MRKAd6-NSmut | | | | | | | | | |
|---|---|---|---|---|---|---|---|---|---|---|
| Mice n. | 21 | 22 | 23 | 24 | 25 | 26 | 27 | 28 | 29 | 30 | GMT |
| Titer | 125626 | 39751 | 40187 | 65834 | 60619 | 69933 | 21555 | 49348 | 29290 | 26859 | 46461 |

TABLE 9

| | MRKAd6-NSOPTmut | | | | | | | |
|---|---|---|---|---|---|---|---|---|
| Mice n. | 31 | 32 | 33 | 34 | 35 | 36 | 37 | GMT |
| Titer | 25430 | 3657 | 893 | 175 | 10442 | 49540 | 173 | 2785 |

T cell response in C57Black6 mice was analyzed by the quantitative ELISPOT assay measuring the number of IFNγ secreting T cells in response to five pools (named from F to L+M) of 20mer peptides overlapping by ten residues encompassing the NS3-NS5B sequence. Specific CD8+ response induced in C57Black6 mice was analyzed by the same assay using a 20mer peptide encompassing a CD8+ epitope for C57Black6 mice (pep1480). Cells secreting IFNγ in an antigen specific-manner were detected using a standard ELIspot assay.

Spleen cells, splenocytes and peptides were produced and treated as described in Example 3, supra. Representative data from groups of C57Black6 mice (N=9-10) immunized with two injections of $10^9$ viral particles of vectors Ad5-NS, MRKAd5-NSmut and MKAd6-NSmut are shown in FIG. 15.

Example 14

Immunization of Rhesus Macagues with Adenovectors

Rhesus macaques (N=3-4) were immunized by intramuscular injection of CsCl purified Ad5-NS, MRKAd5-NSmut, MRKAd6-NSmut or MRKAd6-NSOPTmut virus. Each animal received two doses of $10^{11}$ or $10^{10}$ vp in the deltoid muscle at 0, and 4 weeks.

CMI was measured at different time points by a) IFN-γ ELISPOT (see Example 3, supra), b) IFN-γ ICS and c) bulk CTL assays. These assays measure HCV antigen-specific CD8+ and CD4+ T lymphocyte responses, and can be used for a variety of mammals, such as humans, rhesus monkeys, mice, and rats.

The use of a specific peptide or a pool of peptides can simplify antigen presentation in CTL cytotoxicity assays, interferon-gamma ELISPOT assays and interferon-gamma intracellular staining assays. Peptides based on the amino acid sequence of various HCV proteins (core, E2, NS3, NS4A, NS4B, NS5a, NS5b) were prepared for use in these assays to measure immune responses in HCV DNA and adenovirus vector vaccinated rhesus monkeys, as well as in HCV-infected humans. The individual peptides are overlapping 20-mers, offset by 10 amino acids. Large pools of peptides can be used to detect an overall response to HCV proteins while smaller pools and individual peptides may be used to define the epitope specificity of a response.

IFN-γICS

For IFN-γ ICS, $2 \times 10^6$ PBMC in 1 ml R10 (RPMI medium, supplemented with 10% FCS) were stimulated with peptide pool antigens. Final concentration of each peptide was 2 μg/ml. Cells were incubated for 1 hour in a $CO_2$ incubator at 37° C. and then Brefeldin A was added to a final concentration of 10 μg/ml to inhibit the secretion of soluble cytokines. Cells were incubated for additional 14-16 hours at 37° C.

Stimulation was done in the presence of co-stimulatory antibodies: CD28 and CD49d (anti-humanCD28 BD340975 and anti-humanCD49d BD340976). After incubation, cells were stained with fluorochrome-conjugated antibodies for surface antigens: anti-CD3, anti-CD4, anti-CD8 (CD3-APC Biosource APS0301, CD4-PE BD345769, CD8-PerCP BD345774).

To detect intracellular cytokines, cells were treated with FACS permeabilization buffer 2 (BD340973), 2× final concentration. Once fixed and permeabilized, cells were incubated with an antibody against human IFN-γ, IFN-γFITC (Biosource AHC4338).

Cells were resuspended in 1% formaldehyde in PBS and analyzed at FACS within 24 hours. Four color FACS analysis was performed on a FACSCalibur instrument (Becton Dickinson) equipped with two lasers. Acquisition was done gating on the lymphocyte population in the Forward versus Side Scatter plot coupled with the CD3, CD8 positive populations. At least 30,000 events of the gate were taken. The positive cells are expressed as number of IFN-γ expressing cells over $10^6$ lymphocytes.

IFN-γ ELISPOT and IFN-γ ICS data from immunized monkeys after one or two injections of $10^{10}$ or $10^{11}$ vp of the different adenovectors are reported in FIGS. 16A-16D, 17A, and 17B.

Bulk CTL Assays

A distinguishing effector function of T lymphocytes is the ability of subsets of this cell population to directly lyse cells exhibiting appropriate MHC-associated antigenic peptides. This cytotoxic activity is most often associated with CD8+ T lymphocytes.

PBMC samples were infected with recombinant vaccine viruses expressing HCV antigens in vitro for approximately 14 days to provide antigen restimulation and expansion of memory T cells. Cytotoxicity against autologous B cell lines treated with peptide antigen pools was tested.

The lytic function of the culture is measured as a percentage of specific lysis resulted from chromium released from target cells during 4 hours incubation with CTL effector cells. Specific cytotoxicity is measured and compared to irrelevant antigen or excipient-treated B cell lines. This assay is semi-quantitative and is the preferred means for determining whether CTL responses were elicited by the vaccine. Data after two injections from monkeys immunized with $10^{11}$ vp/dose with adenovectors Ad5-NS, MRKAd5-NSmut and MRKAd6-NSmut are reported in FIGS. 18A-18F.

Other embodiments are within the following claims. While several embodiments have been shown and described, various modifications may be made without departing from the spirit and scope of the present invention.

What is claimed is:

1. A nucleic acid comprising a nucleotide sequence encoding a Met-NS3-NS4A-NS4B-NS5A-NS5B polypeptide substantially similar to SEQ ID NO: 1, provided that said polypeptide has sufficient protease activity to process itself to produce an NS5B protein and said NS5B protein is enzymatically inactive, wherein said polypeptide consists of SEQ ID NO: 1 or a sequence substantially similar to SEQ ID NO: 1, wherein said sequence substantially similar to SEQ ID NO: 1 differs from SEQ ID NO: 1 by 1-20 amino acids and maintains all T-cell antigen regions present in SEQ ID NO: 1.

2. The nucleic acid of claim 1, wherein said nucleic acid is an expression vector capable of expressing said polypeptide from said nucleotide sequence in a human cell.

3. A nucleic acid comprising a gene expression cassette able to express a Met-NS3-NS4A-NS4B-NS5A-NS5B polypeptide substantially similar to SEQ ID NO: 1 in a human cell, provided that said polypeptide can process itself to produce an NS5B protein and said NS5B protein is enzymatically inactive, said expression cassette comprising:
   a) a promoter transcriptionally coupled to a nucleotide sequence encoding said polypeptide;
   b) a 5' ribosome binding site functionally coupled to said nucleotide sequence,
   c) a terminator joined to the 3' end of said nucleotide sequence, and
   d) a 3' polyadenylation signal functionally coupled to said nucleotide sequence,
   wherein said polypeptide consists of SEQ ID NO: 1 or a sequence substantially similar to SEQ ID NO: 1, wherein said sequence substantially similar to SEQ ID NO: 1 differs from SEQ ID NO: 1 by 1-20 amino acids and maintains all T-cell eptitope regions present in SEQ ID NO: 1.

4. The nucleic acid of claim 3, wherein said nucleic acid is a shuttle vector further comprising a selectable marker, an origin of replication, a first adenovirus homology region and a second adenovirus homology region flanking said expression cassette, wherein said first homology region has at least about 100 base pairs substantially homologous to at least right end of a wild-type adenovirus region from about base pairs 1-425, and said second homology region has at least about 100 base pairs substantially homologous to at least the left end of a wild-type adenovirus region from about base pairs 3511-5792 of Ad5 or corresponding region of another adenovirus.

5. The nucleic acid of claim 3, wherein said nucleic acid is a plasmid suitable for administration into a human and further comprises a prokaryotic origin of replication and a gene coding for a selectable marker.

6. The nucleic acid of claim 5, wherein said nucleotide sequence encodes for a polypeptide of SEQ ID NO: 1.

7. The nucleic acid of claim 6, wherein said nucleotide sequence is the coding sequence of either SEQ ID NO: 2, SEQ ID NO: 3, SEQ ID NO: 10, or SEQ ID NO: 11.

8. The nucleic acid of claim 6, wherein said nucleotide sequence is the coding sequence of SEQ ID NO: 2 or SEQ ID NO: 3.

9. The nucleic acid of claim 6, wherein said promoter is the human intermediate early cytomegalovirus promoter (intron A), said 5' ribosome binding site consists of SEQ ID NO: 12, and said 3' polyadenylation is the bovine growth hormone (BGH) polyadenylation signal.

10. The nucleic acid of claim 3, wherein said nucleic acid is a adenovirus genome plasmid comprising a selectable marker, an origin of replication, and a recombinant adenovector genome containing an E1 deletion, an E3 deletion, and said expression cassette.

11. The nucleic acid of claim 3, wherein said nucleic acid is a adenovirus genome plasmid comprising a selectable marker, an origin of replication, and
   a) a first adenovirus region from about base pair 1 to about base pair 450 corresponding to either Ad5 or Ad6;

b) said gene expression cassette in a E1 parallel or E1 anti-parallel orientation joined to said first region;

c) a second adenovirus region from about base pair 3511 to about base pair 5548 corresponding to Ad5 or from about base pair 3508 to about base pair 5541 corresponding to Ad6, joined to said expression cassette;

d) a third adenovirus region from about base pair 5549 to about base pair 28133 corresponding to Ad5 or from about base pair 5542 to about base pair 28156 corresponding to Ad6, joined to said second region;

e) a fourth adenovirus region from about base pair 30818 to about base pair 33966 corresponding to Ad5 or from about base pair 30789 to about base pair 33784 corresponding to Ad6, joined to said third region; and f) a fifth adenovirus region from about base pair 33967 to about base pair 35935 corresponding to Ad5 or from about base pair 33785 to about base pair 35759 corresponding to Ad6, joined to said fourth region.

12. The nucleic acid of claim 3, wherein said nucleic acid is a adenovirus genome plasmid comprising an origin of replication, a selectable marker, and:

a) a first adenovirus region from about base pair 1 to about base pair 450 corresponding to either Ad5 or Ad6;

b) a second adenovirus region from about base pair 3511 to about base pair 5548 corresponding to Ad5 or from about base pair 3508 to about base pair 5541 corresponding to Ad6, joined to said first region;

c) a third adenovirus region from about base pair 5549 to about base pair 28133 corresponding to Ad5 or from about base pair 5542 to about base pair 28156 corresponding to Ad6, joined to said second region;

d) said gene expression cassette in a E3 parallel or E3 anti-parallel orientation joined to said third region;

e) a fourth adenovirus region from about base pair 30818 to about base pair 33966 corresponding to Ad5 or from about base pair 30789 to about base pair 33784 corresponding to Ad6, joined to said gene expression cassette; and f) a fifth adenovirus region from about base pair 33967 to about base pair 35935 corresponding to Ad5 or from about base pair 33785 to about base pair 35759 corresponding to Ad6, joined to said fourth region.

13. An adenovector consisting of:

a) a first adenovirus region from about base pair 1 to about base pair 450 corresponding to either Ad5 or Ad6;

b) a gene expression cassette in a E1 parallel or E1 anti-parallel orientation joined to said first region;

c) a second adenovirus region from about base pair 3511 to about base pair 5548 corresponding to Ad5 or from about base pair 3508 to about base pair 5541 corresponding to Ad6, joined to said expression cassette;

d) a third adenovirus region from about base pair 5549 to about base pair 28133 corresponding to Ad5 or from about base pair 5542 to about base pair 28156 corresponding to Ad6, joined to said second region;

e) a fourth adenovirus region from about base pair 30818 to about base pair 33966 corresponding to Ad5 or from about base pair 30789 to about base pair 33784 corresponding to Ad6, joined to said third region; and f) a fifth adenovirus region from about base pair 33967 to about base pair 35935 corresponding to Ad5 or from about base pair 33785 to about base pair 35759 corresponding to Ad6, joined to said fourth region, wherein said gene expression cassette is able to express a Met-NS3-NS4A-NS4B-NS5A-NS5B polypeptide substantially similar to SEQ ID NO: 1 in a human cell, provided that said polypeptide can process itself to produce an NS5B protein and said NS5B protein is enzymatically inactive, said expression cassette comprising:

a) a promoter transcriptionally coupled to a nucleotide sequence encoding said polypeptide;

b) a 5' ribosome binding site functionally coupled to said nucleotide sequence, c) a terminator joined to the 3' end of said nucleotide sequence, and d) a 3' polyadenylation signal functionally coupled to said nucleotide sequence, wherein said polypeptide consists of SEQ ID NO: 1 or a sequence substantially similar to SEQ ID NO: 1, wherein said substantially similar to SEQ ID NO: 1 differs from SEQ ID NO:1 by 1-20 amino acids and maintains all T-cell epitope regions present in SEQ ID NO: 1.

14. The nucleic acid of claim 13, wherein said first region corresponds to Ad5, said second region corresponds to Ad5, said third region corresponds to Ad5, said fourth region corresponds to Ad5, and said fifth region corresponds to Ad5.

15. The nucleic acid of claim 14, wherein said promoter is the human intermediate early cytomegalovirus promoter, said 5' ribosome binding site consists of SEQ ID NO: 12, and said 3' polyadenylation is the BGH polyadenylation signal.

16. The nucleic acid of claim 15, wherein said expression cassette is in an E1 anti parallel orientation and said nucleotide sequence is either SEQ ID NO: 2, SEQ ID NO: 3, SEQ ID NO: 10, or SEQ ID NO: 11.

17. The nucleic acid of claim 13, wherein said first region corresponds to Ad5 or Ad6, said second region corresponds to Ad5 or Ad6, said third region corresponds to Ad6, said fourth region corresponds to Ad6, and said fifth region corresponds to Ad5 or Ad6.

18. The nucleic acid of claim 17, where said promoter is the human intermediate early cytomegalovirus promoter, said 5' ribosome binding site consists of SEQ ID NO: 12, and said 3' polyadenylation is the BGH polyadenylation signal.

19. The nucleic acid of claim 18, wherein said expression cassette is in an E1 anti parallel orientation and said nucleotide sequence is SEQ ID NO: 2, SEQ ID NO: 3, SEQ ID NO: 10, or SEQ ID NO: 11.

20. The nucleic acid of claim 18, wherein said expression cassette is in an E1 anti parallel orientation and said nucleotide sequence is SEQ ID NO: 2 or SEQ ID NO: 3.

21. The nucleic acid of claim 3, wherein said nucleic acid is an adenovector consisting of:

a) a first adenovirus region from about base pair 1 to about base pair 450 corresponding to either Ad5 or Ad6;

b) a second adenovirus region from about base pair 3511 to about base pair 5548 corresponding to Ad5 or from about base pair 3508 to about base pair 5541 corresponding to Ad6, joined to said first region;

c) a third adenovirus region from about base pair 5549 to about base pair 28133 corresponding to Ad5 or from about base pair 5542 to about base pair 28156 corresponding to Ad6, joined to said second region;

d) said gene expression cassette in a E3 parallel or E3 anti-parallel orientation joined to said third region;

e) a fourth adenovirus region from about base pair 30818 to about base pair 33966 corresponding to Ad5 or from about base pair 30789 to about base pair 33784 corresponding to Ad6, joined to said gene expression cassette; and f) a fifth adenovirus region from about base pair 33967 to about base pair 35935 corresponding to Ad5 or from about base pair 33785 to about base pair 35759 corresponding to Ad6, joined to said fourth region.

22. The nucleic acid of claim 21, wherein said first region corresponds to Ad5, said second region corresponds to Ad5, said third region corresponds to Ad5, said fourth region corresponds to Ad5, and said fifth region corresponds to Ad5.

23. The nucleic acid of claim 21, wherein said first region corresponds to Ad5 or Ad6, said second region corresponds to Ad5 or Ad6, said third region corresponds to Ad6, said fourth region corresponds to Ad6, and said fifth region corresponds to Ad5 or Ad6.

24. An adenovector produced by a process comprising the steps of:
a) producing an adenovirus genome plasmid by homologous recombination between the shuttle vector of claim 4 and a nucleic acid comprising;
a first adenovirus region from about base pair 1 to about base pair 450 corresponding to either Ad5 or Ad6;
a second adenovirus region from about base pair 3511 to about base pair 5548 corresponding to Ad5 or from about base pair 3508 to about base pair 5541 corresponding to Ad6, joined to said first region;
a third adenovirus region from about base pair 5549 to about base pair 28133 corresponding to Ad5 or from about base pair 5542 to about base pair 28156 corresponding to Ad6, joined to said second region;
a fourth adenovirus region from about base pair 30818 to about base pair 33966 corresponding to Ad5 or from about base pair 30789 to about base pair 33784 corresponding to Ad6, joined to said third region; and
a fifth adenovirus region from about base pair 33967 to about base pair 35935 corresponding to Ad5 or from about base pair 33785 to about base pair 35759 corresponding to Ad6, joined to said fourth region; and
b) rescuing said adenovector from said adenovirus plasmid.

25. A cultured recombinant cell comprising the nucleic acid of claim 2.

26. A cultured recombinant cell comprising the nucleic acid of claim 4.

27. A method of making an adenovector comprising the steps of:
a) producing an adenovirus genome plasmid comprising a gene expression cassette by homologous recombination between the nucleic acid of claim 4 and a nucleic acid comprising;
a first adenovirus region from about base pair 1 to about base pair 450 corresponding to either Ad5 or Ad6;
a second adenovirus region from about base pair 3511 to about base pair 5548 corresponding to Ad5 or from about base pair 3508 to about base pair 5541 corresponding to Ad6, joined to said first region;
a third adenovirus region from about base pair 5549 to about base pair 28133 corresponding to Ad5 or from about base pair 5542 to about base pair 28156 corresponding to Ad6, joined to said second region;
a fourth adenovirus region from about base pair 30818 to about base pair 33966 corresponding to Ad5 or from about base pair 30789 to about base pair 33784 corresponding to Ad6, joined to said third region; and
a fifth adenovirus region from about base pair 33967 to about base pair 35935 corresponding to Ad5 or from about base pair 33785 to about base pair 35759 corresponding to Ad6, joined to the fourth region; and
b) rescuing said recombinant adenovirus from said recombinant adenovirus plasmid.

28. The nucleic acid of claim 1, wherein said polypeptide consists of SEQ ID NO: 1.

29. The nucleic acid of claim 1, wherein said polypeptide differs from SEQ ID NO: 1 by 1-20 amino acids and maintains all T-cell antigen regions present in SEQ ID NO: 1.

30. The nucleic acid of claim 1, wherein said polypeptide differs from SEQ ID NO: 1 by 1-10 amino acids and maintains all T-cell antigen regions present in SEQ ID NO: 1.

31. The nucleic acid of claim 1, wherein said nucleotide sequence is the coding sequence of either SEQ ID NO: 2, SEQ ID NO: 3, SEQ ID NO: 10 or SEQ ID NO: 11.

32. The nucleic acid of claim 1, wherein said nucleotide sequence is the coding sequence of either SEQ ID NO: 2 or SEQ ID NO: 3.

33. The nucleic acid of claim 1, wherein said nucleotide sequence is the coding sequence for SEQ ID NO: 2 or differs from SEQ ID NO: 2 by 1 to 50 nucleotides.

34. The nucleic acid of claim 3, wherein said polypeptide differs from SEQ ID NO: 1 by 1-10 amino acids and maintains all T-cell antigen regions present in SEQ ID NO: 1.

35. The nucleic acid of claim 3, wherein said polypeptide consists of SEQ ID NO: 1.

36. A pharmaceutical composition comprising:
an effective amount of a nucleic acid comprising a gene expression cassette able to express a Met-NS3-NS4A-NS4B-NS5A-NS5B polypeptide in a human cell, wherein said polypeptide consists of SEQ ID NO: 1 or a sequence substantially similar to SEQ ID NO: 1, provided that said polypeptide can process itself to produce an NS5B protein and said NS5B protein is enzymatically inactive, said expression cassette comprising:
a) a promoter transcriptionally coupled to a nucleotide sequence encoding said polypeptide;
b) a 5' ribosome binding site functionally coupled to said nucleotide sequence,
c) a terminator joined to the 3' end of said nucleotide sequence, and
d) a 3' polyadenylation signal functionally coupled to said nucleotide sequence;
wherein said sequence substantially similar to SEQ ID NO: 1 differs from SEQ ID NO: 1 by 1-20 amino acids and maintains all T-cell antigen regions present in SEQ ID NO: 1; and
a pharmaceutically acceptable carrier.

37. The pharmaceutical composition of claim 36, wherein said nucleic acid is a plasmid suitable for administration into a human and further comprises a prokaryotic origin of replication and a gene coding for a selectable marker.

38. The pharmaceutical composition of claim 37, wherein said nucleotide sequence is the coding sequence of either SEQ ID NO: 2, SEQ ID NO: 3, SEQ ID NO: 10, or SEQ ID NO: 11.

39. The pharmaceutical composition of claim 38, wherein said nucleotide sequence is the coding sequence of SEQ ID NO: 2 or SEQ ID NO: 3.

40. The pharmaceutical composition of claim 39, wherein said nucleotide sequence is the coding sequence of SEQ ID NO: 2.

41. The pharmaceutical composition of claim 37, wherein said promoter is the human intermediate early cytomegalovirus promoter (intron A), said 5' ribosome binding site consists of SEQ ID NO: 12, and said 3' polyadenylation is the bovine growth hormone (BGH) polyadenylation signal.

42. A pharmaceutical composition comprising:
an effective amount of a nucleic acid comprising a gene expression cassette able to express a Met-NS3-NS4A-NS4B-NS5A-NS5B polypeptide in a human cell, wherein said polypeptide consists of SEQ ID NO: 1 or a sequence substantially similar to SEQ ID NO: 1, provided that said polypeptide can process itself to produce an NS5B protein and said NS5B protein is enzymatically inactive, said expression cassette comprising:
a) a promoter transcriptionally coupled to a nucleotide sequence encoding said polypeptide;
b) a 5' ribosome binding site functionally coupled to said nucleotide sequence,
c) a terminator joined to the 3' end of said nucleotide sequence, and
d) a 3' polyadenylation signal functionally coupled to said nucleotide sequence;
wherein said substantially similar to SEQ ID NO: 1 differs from SEQ ID NO: 1 by 1 to amino acids and maintains all T-cell epitope regions present in SEQ ID NO: 1; and
a pharmaceutically acceptable carrier;
wherein said nucleic acid is an adenovector consisting of:
a) a first adenovirus region from about base pair 1 to about base pair 450 corresponding to either Ad5 or Ad6;
b) said gene expression cassette in a E1 parallel or E1 anti-parallel orientation joined to said first region;
c) a second adenovirus region from about base pair 3511 to about base pair 5548 corresponding to Ad5 or from about base pair 3508 to about base pair 5541 corresponding to Ad6, joined to said expression cassette;
d) a third adenovirus region from about base pair 5549 to about base pair 28133 corresponding to Ad5 or from about base pair 5542 to about base pair 28156 corresponding to Ad6, joined to said second region;
e) a fourth adenovirus region from about base pair 30818 to about base pair 33966 corresponding to Ad5 or from about base pair 30789 to about base pair 33784 corresponding to Ad6, joined to said third region; and
f) a fifth adenovirus region from about base pair 33967 to about base pair 35935 corresponding to Ad5 or from about base pair 33785 to about base pair 35759 corresponding to Ad6, joined to said fourth region.

43. The pharmaceutical composition of claim 42, wherein said first region corresponds to Ad5, said second region corresponds to Ad5, said third region corresponds to Ad5, said fourth region corresponds to Ad5, and said fifth region corresponds to Ad5.

44. The pharmaceutical composition of claim 43, wherein said promoter is the human intermediate early cytomegalovirus promoter, said 5' ribosome binding site consists of SEQ ID NO: 12, and said 3' polyadenylation is the BGH polyadenylation signal.

45. The pharmaceutical composition of claim 44, wherein said expression cassette is in an E1 anti parallel orientation and said nucleotide sequence is either SEQ ID NO: 2, SEQ ID NO: 3, SEQ ID NO: 10, or SEQ ID NO: 11.

46. The pharmaceutical composition of claim 42, wherein said first region corresponds to Ad5 or Ad6, said second region corresponds to Ad5 or Ad6, said third region corresponds to Ad6, said fourth region corresponds to Ad6, and said fifth region corresponds to Ad5 or Ad6.

47. The pharmaceutical composition of claim 46, wherein said promoter is the human intermediate early cytomegalovirus promoter, said 5' ribosome binding site consists of SEQ ID NO: 12, and said 3' polyadenylation is the BGH polyadenylation signal.

48. The pharmaceutical composition of claim 47, wherein said expression cassette is in an E1 anti parallel orientation and said nucleotide sequence is SEQ ID NO: 2, SEQ ID NO: 3, SEQ ID NO: 10, or SEQ ID NO: 11.

49. The pharmaceutical composition of claim 47, wherein said expression cassette is in an E1 anti parallel orientation and said nucleotide sequence is SEQ ID NO: 2 or SEQ ID NO: 3.

50. A pharmaceutical composition comprising:
an effective amount of a nucleic acid comprising a gene expression cassette able to express a Met-NS3-NS4A-NS4B-NS5A-NS5B polypeptide in a human cell, wherein said polypeptide consists of SEQ ID NO: 1 or a sequence substantially similar to SEQ ID NO: 1, provided that said polypeptide can process itself to produce an NS5B protein and said NS5B protein is enzymatically inactive, said expression cassette comprising:
a) a promoter transcriptionally coupled to a nucleotide sequence encoding said polypeptide;
b) a 5' ribosome binding site functionally coupled to said nucleotide sequence,
c) a terminator joined to the 3' end of said nucleotide sequence, and
d) a 3' polyadenylation signal functionally coupled to said nucleotide sequence;
wherein said sequence substantially similar to SEQ ID NO: 1 differs from SEQ ID NO: 1 by 1 to 20 amino acids and maintains all T-cell epitope regions present in SEQ ID NO: 1; and
a pharmaceutically acceptable carrier;
wherein said nucleic acid is an adenovector consisting of:
a) a first adenovirus region from about base pair 1 to about base pair 450 corresponding to either Ad5 or Ad6;
b) a second adenovirus region from about base pair 3511 to about base pair 5548 corresponding to Ad5 or from about base pair 3508 to about base pair 5541 corresponding to Ad6, joined to said first region;
c) a third adenovirus region from about base pair 5549 to about base pair 28133 corresponding to Ad5 or from about base pair 5542 to about base pair 28156 corresponding to Ad6, joined to said second region;
d) said gene expression cassette in a E3 parallel or E3 anti-parallel orientation joined to said third region;
e) a fourth adenovirus region from about base pair 30818 to about base pair 33966 corresponding to Ad5 or from about base pair 30789 to about base pair 33784 corresponding to Ad6, joined to said gene expression cassette; and
f) a fifth adenovirus region from about base pair 33967 to about base pair 35935 corresponding to Ad5 or from about base pair 33785 to about base pair 35759 corresponding to Ad6, joined to said fourth region.

* * * * *

UNITED STATES PATENT AND TRADEMARK OFFICE
CERTIFICATE OF CORRECTION

PATENT NO. : 7,598,362 B2
APPLICATION NO. : 10/492178
DATED : October 6, 2009
INVENTOR(S) : Emini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 866 days.

Signed and Sealed this

Twenty-eighth Day of September, 2010

David J. Kappos
*Director of the United States Patent and Trademark Office*

SEQUENCE LISTING

<160> NUMBER OF SEQ ID NOS: 17

<210> SEQ ID NO 1
<211> LENGTH: 1985
<212> TYPE: PRT
<213> ORGANISM: Artificial Sequence
<220> FEATURE:
<223> OTHER INFORMATION: Met-NS3-NS4A-NS4B-NS5A-NS5B polypeptide

<400> SEQUENCE: 1

```
Met Ala Pro Ile Thr Ala Tyr Ser Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
 50                  55                  60

Leu Ala Gly Pro Lys Gly Pro Ile Thr Gln Met Tyr Thr Asn Val Asp
 65                  70                  75                  80

Gln Asp Leu Val Gly Trp Gln Ala Pro Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Val Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ser Thr Thr Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Asn Thr Gly Glu Ile Pro Phe Tyr Gly
            340                 345                 350
```

```
Lys Ala Ile Pro Ile Glu Ala Ile Arg Gly Gly Arg His Leu Ile Phe
        355                 360                 365

Cys His Ser Lys Lys Cys Asp Glu Leu Ala Ala Lys Leu Ser Gly
    370                 375                 380

Leu Gly Ile Asn Ala Val Ala Tyr Tyr Arg Gly Leu Asp Val Ser Val
385                 390                 395                 400

Ile Pro Thr Ile Gly Asp Val Val Val Ala Thr Asp Ala Leu Met
            405                 410                 415

Thr Gly Tyr Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Thr Thr Val Pro Gln Asp Ala Val Ser Arg Ser Gln Arg Gly
    450                 455                 460

Arg Thr Gly Arg Gly Arg Arg Gly Ile Tyr Arg Phe Val Thr Pro Gly
465                 470                 475                 480

Glu Arg Pro Ser Gly Met Phe Asp Ser Ser Val Leu Cys Glu Cys Tyr
            485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
        515                 520                 525

His Leu Glu Phe Trp Glu Ser Val Phe Thr Gly Leu Thr His Ile Asp
        530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
            565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Ile Thr Lys Tyr Ile Met Ala Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
            645                 650                 655

Ile Val Gly Arg Ile Ile Leu Ser Gly Arg Pro Ala Ile Val Pro Asp
            660                 665                 670

Arg Glu Phe Leu Tyr Gln Glu Phe Asp Glu Met Glu Glu Cys Ala Ser
        675                 680                 685

His Leu Pro Tyr Ile Glu Gln Gly Met Gln Leu Ala Glu Gln Phe Lys
        690                 695                 700

Gln Lys Ala Leu Gly Leu Leu Gln Thr Ala Thr Lys Gln Ala Glu Ala
705                 710                 715                 720

Ala Ala Pro Val Val Glu Ser Lys Trp Arg Ala Leu Glu Thr Phe Trp
            725                 730                 735

Ala Lys His Met Trp Asn Phe Ile Ser Gly Ile Gln Tyr Leu Ala Gly
            740                 745                 750

Leu Ser Thr Leu Pro Gly Asn Pro Ala Ile Ala Ser Leu Met Ala Phe
        755                 760                 765
```

-continued

```
Thr Ala Ser Ile Thr Ser Pro Leu Thr Thr Gln Ser Thr Leu Leu Phe
    770                 775                 780
Asn Ile Leu Gly Gly Trp Val Ala Ala Gln Leu Ala Pro Pro Ser Ala
785                 790                 795                 800
Ala Ser Ala Phe Val Gly Ala Gly Ile Ala Gly Ala Ala Val Gly Ser
                805                 810                 815
Ile Gly Leu Gly Lys Val Leu Val Asp Ile Leu Ala Gly Tyr Gly Ala
                820                 825                 830
Gly Val Ala Gly Ala Leu Val Ala Phe Lys Val Met Ser Gly Glu Met
                835                 840                 845
Pro Ser Thr Glu Asp Leu Val Asn Leu Leu Pro Ala Ile Leu Ser Pro
    850                 855                 860
Gly Ala Leu Val Val Gly Val Val Cys Ala Ala Ile Leu Arg Arg His
865                 870                 875                 880
Val Gly Pro Gly Glu Gly Ala Val Gln Trp Met Asn Arg Leu Ile Ala
                885                 890                 895
Phe Ala Ser Arg Gly Asn His Val Ser Pro Thr His Tyr Val Pro Glu
                900                 905                 910
Ser Asp Ala Ala Ala Arg Val Thr Gln Ile Leu Ser Ser Leu Thr Ile
                915                 920                 925
Thr Gln Leu Leu Lys Arg Leu His Gln Trp Ile Asn Glu Asp Cys Ser
    930                 935                 940
Thr Pro Cys Ser Gly Ser Trp Leu Arg Asp Val Trp Asp Trp Ile Cys
945                 950                 955                 960
Thr Val Leu Thr Asp Phe Lys Thr Trp Leu Gln Ser Lys Leu Leu Pro
                965                 970                 975
Gln Leu Pro Gly Val Pro Phe Phe Ser Cys Gln Arg Gly Tyr Lys Gly
                980                 985                 990
Val Trp Arg Gly Asp Gly Ile Met Gln Thr Thr Cys Pro Cys Gly Ala
                995                 1000                1005
Gln Ile Thr Gly His Val Lys Asn Gly Ser Met Arg Ile Val Gly Pro
    1010                1015                1020
Lys Thr Cys Ser Asn Thr Trp His Gly Thr Phe Pro Ile Asn Ala Tyr
1025                1030                1035                1040
Thr Thr Gly Pro Cys Thr Pro Ser Pro Ala Pro Asn Tyr Ser Arg Ala
                1045                1050                1055
Leu Trp Arg Val Ala Ala Glu Glu Tyr Val Glu Val Thr Arg Val Gly
                1060                1065                1070
Asp Phe His Tyr Val Thr Gly Met Thr Thr Asp Asn Val Lys Cys Pro
    1075                1080                1085
Cys Gln Val Pro Ala Pro Glu Phe Phe Thr Glu Val Asp Gly Val Arg
    1090                1095                1100
Leu His Arg Tyr Ala Pro Ala Cys Arg Pro Leu Leu Arg Glu Glu Val
1105                1110                1115                1120
Thr Phe Gln Val Gly Leu Asn Gln Tyr Leu Val Gly Ser Gln Leu Pro
                1125                1130                1135
Cys Glu Pro Glu Pro Asp Val Ala Val Leu Thr Ser Met Leu Thr Asp
                1140                1145                1150
Pro Ser His Ile Thr Ala Glu Thr Ala Lys Arg Arg Leu Ala Arg Gly
                1155                1160                1165
Ser Pro Pro Ser Leu Ala Ser Ser Ser Ala Ser Gln Leu Ser Ala Pro
    1170                1175                1180
Ser Leu Lys Ala Thr Cys Thr Thr His His Val Ser Pro Asp Ala Asp
```

-continued

```
            1185                1190                1195                1200

Leu Ile Glu Ala Asn Leu Leu Trp Arg Gln Glu Met Gly Gly Asn Ile
                1205                1210                1215

Thr Arg Val Glu Ser Glu Asn Lys Val Val Leu Asp Ser Phe Asp
            1220                1225                1230

Pro Leu Arg Ala Glu Glu Asp Glu Arg Glu Val Ser Val Pro Ala Glu
            1235                1240                1245

Ile Leu Arg Lys Ser Lys Lys Phe Pro Ala Ala Met Pro Ile Trp Ala
            1250                1255                1260

Arg Pro Asp Tyr Asn Pro Pro Leu Leu Glu Ser Trp Lys Asp Pro Asp
1265                1270                1275                1280

Tyr Val Pro Pro Val Val His Gly Cys Pro Leu Pro Pro Ile Lys Ala
                1285                1290                1295

Pro Pro Ile Pro Pro Pro Arg Arg Lys Arg Thr Val Val Leu Thr Glu
            1300                1305                1310

Ser Ser Val Ser Ser Ala Leu Ala Glu Leu Ala Thr Lys Thr Phe Gly
            1315                1320                1325

Ser Ser Glu Ser Ser Ala Val Asp Ser Gly Thr Ala Thr Ala Leu Pro
            1330                1335                1340

Asp Gln Ala Ser Asp Asp Gly Asp Lys Gly Ser Asp Val Glu Ser Tyr
1345                1350                1355                1360

Ser Ser Met Pro Pro Leu Glu Gly Glu Pro Gly Asp Pro Asp Leu Ser
                1365                1370                1375

Asp Gly Ser Trp Ser Thr Val Ser Glu Glu Ala Ser Glu Asp Val Val
            1380                1385                1390

Cys Cys Ser Met Ser Tyr Thr Trp Thr Gly Ala Leu Ile Thr Pro Cys
            1395                1400                1405

Ala Ala Glu Glu Ser Lys Leu Pro Ile Asn Ala Leu Ser Asn Ser Leu
            1410                1415                1420

Leu Arg His His Asn Met Val Tyr Ala Thr Thr Ser Arg Ser Ala Gly
1425                1430                1435                1440

Leu Arg Gln Lys Lys Val Thr Phe Asp Arg Leu Gln Val Leu Asp Asp
                1445                1450                1455

His Tyr Arg Asp Val Leu Lys Glu Met Lys Ala Lys Ala Ser Thr Val
            1460                1465                1470

Lys Ala Lys Leu Leu Ser Val Glu Glu Ala Cys Lys Leu Thr Pro Pro
            1475                1480                1485

His Ser Ala Lys Ser Lys Phe Gly Tyr Gly Ala Lys Asp Val Arg Asn
            1490                1495                1500

Leu Ser Ser Lys Ala Val Asn His Ile His Ser Val Trp Lys Asp Leu
1505                1510                1515                1520

Leu Glu Asp Thr Val Thr Pro Ile Asp Thr Thr Ile Met Ala Lys Asn
                1525                1530                1535

Glu Val Phe Cys Val Gln Pro Glu Lys Gly Gly Arg Lys Pro Ala Arg
            1540                1545                1550

Leu Ile Val Phe Pro Asp Leu Gly Val Arg Val Cys Glu Lys Met Ala
            1555                1560                1565

Leu Tyr Asp Val Val Ser Thr Leu Pro Gln Val Met Gly Ser Ser
            1570                1575                1580

Tyr Gly Phe Gln Tyr Ser Pro Gly Gln Arg Val Glu Phe Leu Val Asn
1585                1590                1595                1600

Thr Trp Lys Ser Lys Lys Asn Pro Met Gly Phe Ser Tyr Asp Thr Arg
                1605                1610                1615
```

```
Cys Phe Asp Ser Thr Val Thr Glu Asn Asp Ile Arg Val Glu Glu Ser
            1620                1625                1630

Ile Tyr Gln Cys Cys Asp Leu Ala Pro Glu Ala Arg Gln Ala Ile Lys
        1635                1640                1645

Ser Leu Thr Glu Arg Leu Tyr Ile Gly Gly Pro Leu Thr Asn Ser Lys
    1650                1655                1660

Gly Gln Asn Cys Gly Tyr Arg Arg Cys Arg Ala Ser Gly Val Leu Thr
1665                1670                1675                1680

Thr Ser Cys Gly Asn Thr Leu Thr Cys Tyr Leu Lys Ala Ser Ala Ala
            1685                1690                1695

Cys Arg Ala Ala Lys Leu Gln Asp Cys Thr Met Leu Val Asn Ala Ala
        1700                1705                1710

Gly Leu Val Val Ile Cys Glu Ser Ala Gly Thr Gln Glu Asp Ala Ala
    1715                1720                1725

Ser Leu Arg Val Phe Thr Glu Ala Met Thr Arg Tyr Ser Ala Pro Pro
    1730                1735                1740

Gly Asp Pro Pro Gln Pro Glu Tyr Asp Leu Glu Leu Ile Thr Ser Cys
1745                1750                1755                1760

Ser Ser Asn Val Ser Val Ala His Asp Ala Ser Gly Lys Arg Val Tyr
            1765                1770                1775

Tyr Leu Thr Arg Asp Pro Thr Thr Pro Leu Ala Arg Ala Ala Trp Glu
        1780                1785                1790

Thr Ala Arg His Thr Pro Val Asn Ser Trp Leu Gly Asn Ile Ile Met
    1795                1800                1805

Tyr Ala Pro Thr Leu Trp Ala Arg Met Ile Leu Met Thr His Phe Phe
    1810                1815                1820

Ser Ile Leu Leu Ala Gln Glu Gln Leu Glu Lys Ala Leu Asp Cys Gln
1825                1830                1835                1840

Ile Tyr Gly Ala Cys Tyr Ser Ile Glu Pro Leu Asp Leu Pro Gln Ile
            1845                1850                1855

Ile Glu Arg Leu His Gly Leu Ser Ala Phe Ser Leu His Ser Tyr Ser
        1860                1865                1870

Pro Gly Glu Ile Asn Arg Val Ala Ser Cys Leu Arg Lys Leu Gly Val
    1875                1880                1885

Pro Pro Leu Arg Val Trp Arg His Arg Ala Arg Ser Val Arg Ala Arg
    1890                1895                1900

Leu Leu Ser Gln Gly Gly Arg Ala Ala Thr Cys Gly Lys Tyr Leu Phe
1905                1910                1915                1920

Asn Trp Ala Val Lys Thr Lys Leu Lys Leu Thr Pro Ile Pro Ala Ala
            1925                1930                1935

Ser Gln Leu Asp Leu Ser Gly Trp Phe Val Ala Gly Tyr Ser Gly Gly
        1940                1945                1950

Asp Ile Tyr His Ser Leu Ser Arg Ala Arg Pro Arg Trp Phe Met Leu
    1955                1960                1965

Cys Leu Leu Leu Leu Ser Val Gly Val Gly Ile Tyr Leu Leu Pro Asn
    1970                1975                1980

Arg
1985

<210> SEQ ID NO 2
<211> LENGTH: 5965
<212> TYPE: DNA
<213> ORGANISM: Artificial Sequence
<220> FEATURE:
```

<223> OTHER INFORMATION: Non-optimized cDNA sequence encoding SEQ. ID.
NO. 1

<400> SEQUENCE: 2

| | | | | | |
|---|---|---|---|---|---|
| gccaccatgg | cgcccatcac | ggcctactcc | caacagacgc | ggggcctact | tggttgcatc | 60 |
| atcactagcc | ttacaggccg | ggacaagaac | caggtcgagg | gagaggttca | ggtggtttcc | 120 |
| accgcaacac | aatccttcct | ggcgacctgc | gtcaacggcg | tgtgttggac | cgtttaccat | 180 |
| ggtgctggct | caaagacctt | agccggccca | aagggccaa | tcacccagat | gtacactaat | 240 |
| gtggaccagg | acctcgtcgg | ctggcaggcg | ccccccgggg | cgcgttcctt | gacaccatgc | 300 |
| acctgtggca | gctcagacct | ttacttggtc | acgagacatg | ctgacgtcat | tccggtgcgc | 360 |
| cggcggggcg | acagtagggg | gagcctgctc | tcccccaggc | ctgtctccta | cttgaagggc | 420 |
| tcttcgggtg | gtccactgct | ctgcccttcg | gggcacgctg | tgggcatctt | ccgggctgcc | 480 |
| gtatgcaccc | gggggttgc | gaaggcgtg | gactttgtgc | cgtagagtc | catggaaact | 540 |
| actatgcggt | ctccggtctt | cacggacaac | tcatccccc | cggccgtacc | gcagtcattt | 600 |
| caagtggccc | acctacacgc | tcccactggc | agcggcaaga | gtactaaagt | gccggctgca | 660 |
| tatgcagccc | aagggtacaa | ggtgctcgtc | ctcaatccgt | ccgttgccgc | taccttaggg | 720 |
| tttgggcgt | atatgtctaa | ggcacacggt | attgacccca | acatcagaac | tggggtaagg | 780 |
| accattacca | caggcgcccc | cgtcacatac | tctacctatg | gcaagtttct | tgccgatggt | 840 |
| ggttgctctg | ggggcgctta | tgacatcata | atatgtgatg | agtgccattc | aactgactcg | 900 |
| actacaatct | tgggcatcgg | cacagtcctg | gaccaagcgg | agacggctgg | agcgcggctt | 960 |
| gtcgtgctcg | ccaccgctac | gcctccggga | tcggtcaccg | tgccacaccc | aaacatcgag | 1020 |
| gaggtggccc | tgtctaatac | tggagagatc | cccttctatg | gcaaagccat | ccccattgaa | 1080 |
| gccatcaggg | ggggaaggca | tctcatttc | tgtcattcca | agaagaagtg | cgacgagctc | 1140 |
| gccgcaaagc | tgtcaggcct | cggaatcaac | gctgtggcgt | attaccgggg | gctcgatgtg | 1200 |
| tccgtcatac | caactatcgg | agacgtcgtt | gtcgtggcaa | cagacgctct | gatgacgggc | 1260 |
| tatacgggcg | actttgactc | agtgatcgac | tgtaacacat | gtgtcaccca | gacagtcgac | 1320 |
| ttcagcttgg | atcccaccct | taccattgag | acgacgaccg | tgcctcaaga | cgcagtgtcg | 1380 |
| cgctcgcagc | ggcggggtag | gactggcagg | ggtaggagag | gcatctacag | gtttgtgact | 1440 |
| ccgggagaac | ggccctcggg | catgttcgat | tcctcggtcc | tgtgtgagtg | ctatgacgcg | 1500 |
| ggctgtgctt | ggtacgagct | caccccccgcc | gagacctcgg | ttaggttgcg | ggcctacctg | 1560 |
| aacacaccag | ggttgcccgt | ttgccaggac | cacctggagt | tctgggagag | tgtcttcaca | 1620 |
| ggcctcaccc | acatagatgc | acacttcttg | tcccagacca | agcaggcagg | agacaacttc | 1680 |
| ccctacctgg | tagcatacca | agccacggtg | tgcgccaggg | ctcaggcccc | acctccatca | 1740 |
| tgggatcaaa | tgtggaagtg | tctcatacgg | ctgaaaccta | cgctgcacgg | gccaacaccc | 1800 |
| ttgctgtaca | ggctgggagc | cgtccaaaat | gaggtcaccc | tcacccaccc | cataaccaaa | 1860 |
| tacatcatgg | catgcatgtc | ggctgacctg | gaggtcgtca | ctagcacctg | ggtgctggtg | 1920 |
| ggcggagtcc | ttgcagctct | ggccgcgtat | tgcctgacaa | caggcagtgt | ggtcattgtg | 1980 |
| ggtaggatta | tcttgtccgg | gaggccggct | attgttcccg | acagggagtt | tctctaccag | 2040 |
| gagttcgatg | aaatgtgaaga | gtgcgcctcg | cacctcccctt | acatcgagca | gggaatgcag | 2100 |
| ctcgccgagc | aattcaagca | gaaagcgctc | gggttactgc | aaacagccac | caaacaagcg | 2160 |
| gaggctgctg | ctcccgtggt | ggagtccaag | tggcgagccc | ttgagacatt | ctgggcgaag | 2220 |

```
cacatgtgga atttcatcag cgggatacag tacttagcag gcttatccac tctgcctggg    2280
aaccccgcaa tagcatcatt gatggcattc acagcctcta tcaccagccc gctcaccacc    2340
caaagtaccc tcctgtttaa catcttgggg gggtgggtgg ctgcccaact cgccccccc     2400 agcgccgctt cggctttcgt gggcgccggc atcgccggtg cggctgttgg cagcataggc    2460
cttgggaagg tgcttgtgga cattctggcg ggttatggag caggagtggc cggcgcgctc    2520
gtggccttca aggtcatgag cggcgagatg ccctccaccg aggacctggt caatctactt    2580
cctgccatcc tctctcctgg cgccctggtc gtcggggtcg tgtgtgcagc aatactgcgt    2640
cgacacgtgg gtccgggaga gggggctgtg cagtggatga accggctgat agcgttcgcc    2700
tcgcggggta atcatgtttc ccccacgcac tatgtgcctg agagcgacgc cgcagcgcgt    2760
gttactcaga tcctctccag ccttaccatc actcagctgc tgaaaaggct ccaccagtgg    2820
attaatgaag actgctccac accgtgttcc ggctcgtggc taagggatgt ttgggactgg    2880
atatgcacgg tgttgactga cttcaagacc tggctccagt ccaagctcct gccgcagcta    2940
ccgggagtcc ctttttttctc gtgccaacgc gggtacaagg gagtctggcg gggagacggc    3000
atcatgcaaa ccacctgccc atgtggagca cagatcaccg gacatgtcaa aaacggttcc    3060
atgaggatcg tcgggcctaa gacctgcagc aacacgtggc atggaacatt ccccatcaac    3120
gcatacacca cgggcccctg cacaccctct ccagcgccaa actattctag gcgcgtgtgg    3180
cgggtggccg ctgaggagta cgtggaggtc acgcgggtgg gggatttcca ctacgtgacg    3240
ggcatgacca ctgacaacgt aaagtgccca tgccaggttc cggctcctga attcttcacg    3300
gaggtggacg gagtgcggtt gcacaggtac gctccggcgt gcaggcctct cctacgggag    3360
gaggttacat tccaggtcgg gctcaaccaa tacctggttg ggtcacagct accatgcgag    3420
cccgaaccgg atgtagcagt gctcacttcc atgctcaccg cccctccca catcacagca    3480 gaaacggcta agcgtaggtt ggccaggggg tctccccccct ccttggccag ctcttcagct    3540
agccagttgt ctgcgccttc cttgaaggcg acatgcacta cccaccatgt ctctccggac    3600
gctgacctca tcgaggccaa cctcctgtgg cggcaggaga tgggcgggaa catcacccgc    3660
gtggagtcgg agaacaaggt ggtagtcctg gactcttttcg acccgcttcg agcggaggag    3720
gatgagaggg aagtatccgt tccggcggag atcctgcgga aatccaagaa gttccccgca    3780
gcgatgccca tctgggcgcg cccggattac aaccctccac tgttagagtc ctggaaggac    3840
ccggactacg tccctccggt ggtgcacggg tgcccgttgc cacctatcaa ggcccctcca    3900
ataccacctc cacggagaaa gaggacggtt gtcctaacag agtcctccgt gtcttctgcc    3960
ttagcggagc tcgctactaa gaccttcggc agctccgaat catcggccgt cgacagcggc    4020
acggcgaccc cccttcctga ccaggcctcc gacgacggta caaaggatc cgacgttgag    4080 tcgtactcct ccatgccccc ccttgagggg gaaccggggg accccgatct cagtgacggg    4140
tcttggtcta ccgtgagcga ggaagctagt gaggatgtcg tctgctgctc aatgtcctac    4200
acatggacag gcgccttgat cacgccatgc gctgcggagg aaagcaagct gcccatcaac    4260
gcgttgagca actctttgct gcgccaccat aacatggttt atgccacaac atctcgcagc    4320
gcaggcctgc ggcagaagaa ggtcaccttt gacagactgc aagtcctgga cgaccactac    4380
cgggacgtgc tcaaggagat gaaggcgaag gcgtccacag ttaaggctaa actcctatcc    4440
gtagaggaag cctgcaagct gacgccccca cattcggcca aatccaagtt tggctatggg    4500
gcaaaggacg tccggaacct atccagcaag gccgttaacc acatccactc cgtgtggaag    4560
gacttgctgg aagacactgt gacaccaatt gacaccacca tcatggcaaa aaatgaggtt    4620
```

```
ttctgtgtcc aaccagagaa aggaggccgt aagccagccc gccttatcgt attcccagat    4680
ctgggagtcc gtgtatgcga agatggcc ctctatgatg tggtctccac ccttcctcag     4740
gtcgtgatgg gctcctcata cggattccag tactctcctg ggcagcgagt cgagttcctg   4800
gtgaatacct ggaaatcaaa gaaaaacccc atgggctttt catatgacac tcgctgtttc   4860
gactcaacgg tcaccgagaa cgacatccgt gttgaggagt caatttacca atgttgtgac   4920
ttggcccccg aagccagaca ggccataaaa tcgctcacag agcggcttta tatcgggggt   4980
cctctgacta attcaaaagg gcagaactgc ggttatcgcc ggtgccgcgc gagcggcgtg   5040
ctgacgacta gctgcggtaa caccctcaca tgttacttga aggcctctgc agcctgtcga   5100
gctgcgaagc tccaggactg cacgatgctc gtgaacgccg ccggccttgt cgttatctgt   5160
gaaagcgcgg aacccaaga ggacgcggcg agcctacgag tcttcacgga ggctatgact    5220
aggtactctg cccccccgg ggacccgccc caaccagaat acgacttgga gctgataaca    5280
tcatgttcct ccaatgtgtc ggtcgcccac gatgcatcag gcaaagggt gtactacctc    5340
acccgtgatc ccaccacccc cctcgcacgg gctgcgtggg aaacagctag acacactcca   5400
gttaactcct ggctaggcaa cattatcatg tatgcgccca ctttgtgggc aaggatgatt   5460
ctgatgactc acttcttctc catccttcta gcacaggagc aacttgaaaa agccctggac   5520
tgccagatct acggggcctg ttactccatt gagccacttg acctaccca gatcattgaa    5580
cgactccatg gccttagcgc attttcactc catagttact ctccaggtga gatcaatagg   5640
gtggcttcat gcctcaggaa acttgggta ccacccttgc gagtctggag acatcgggcc    5700
aggagcgtcc gcgctaggct actgtcccag gggggaggg ccgccacttg tggcaagtac    5760
ctcttcaact gggcagtgaa gaccaaactc aaactcactc caatcccggc tgcgtcccag   5820
ctggacttgt ccggctggtt cgttgctggt tacagcgggg gagacatata tcacagcctg   5880
tctcgtgccc gaccccgctg gttcatgctg tgcctactcc tactttctgt aggggtaggc   5940
atctacctgc tccccaaccg ataaa                                         5965
```

<210> SEQ ID NO 3
<211> LENGTH: 5965
<212> TYPE: DNA
<213> ORGANISM: Artificial Sequence
<220> FEATURE:
<223> OTHER INFORMATION: Optimized cDNA encoding SEQ ID NO: 1

<400> SEQUENCE: 3

```
gccaccatgg cccccatcac cgcctacagc cagcagaccc gcggcctgct gggctgcatc    60
atcaccagcc tgaccggccg cgacaagaac caggtggagg cgcaggtgca ggtggtgagc   120
accgccaccc agagcttcct ggccacctgc gtgaacggcg tgtgctggac cgtgtaccac   180
ggcgccggca gcaagaccct ggccggcccc aagggcccca tcacccagat gtacaccaac   240
gtggaccagg acctggtggg ctggcaggcc cccccggcg cccgcagcct gacccctgc    300
acctgcggca gcagcgacct gtacctggtg acccgccacg ccgacgtgat ccccgtgcgc   360
cgccgcggcg acagccgcgg cagcctgctg agccccgcc cgtgagcta cctgaagggc    420
agcagcggcg gccccctgct gtgccccagc ggccacgccg tgggcatctt ccgcgccgcc   480
gtgtgcaccc gcggcgtggc caaggccgtg gacttcgtgc ccgtggagag catggagacc   540
accatgcgca gccccgtgtt caccgacaac agcagccccc ccgccgtgcc ccagagcttc   600
caggtggccc acctgcacgc ccccaccggc agcggcaaga gcaccaaggt gcccgccgcc   660
```

-continued

```
tacgccgccc agggctacaa ggtgctggtg ctgaacccca gcgtggccgc caccctgggc      720
ttcggcgcct acatgagcaa ggcccacggc atcgacccca catccgcac cggcgtgcgc       780 accatcacca ccggcgcccc cgtgacctac agcacctacg gcaagttcct ggccgacggc      840
ggctgcagcg gcggcgccta cgacatcatc atctgcgacg agtgccacag caccgacagc     900
accaccatcc tgggcatcgg caccgtgctg gaccaggccg agaccgccgg cgcccgcctg      960
gtggtgctgg ccaccgccac ccccccggc agcgtgaccg tgccccaccc caacatcgag      1020
gaggtggccc tgagcaacac cggcgagatc cccttctacg gcaaggccat ccccatcgag     1080
gccatccgcg gcggccgcca cctgatcttc tgccacagca agaagaagtg cgacgagctg     1140
gccgccaagc tgagcggcct gggcatcaac gccgtggcct actaccgcgg cctggacgtg     1200
agcgtgatcc ccaccatcgg cgacgtggtg gtggtggcca ccgacgccct gatgaccggc     1260
tacaccggcg acttcgacag cgtgatcgac tgcaacacct gcgtgaccca gaccgtggac     1320
ttcagcctgg accccacctt caccatcgag accaccaccg tgccccagga cgccgtgagc     1380
cgcagccagc gccgcggccg caccggccgc ggccgccgcg catctaccg cttcgtgacc      1440 cccggcgagc gccccagcgg catgttcgac agcagcgtgc tgtgcgagtg ctacgacgcc     1500
ggctgcgcct ggtacgagct gacccccgcc gagaccagcg tgccgcctgcg cgcctacctg    1560 aacacccccg gcctgccgct gtgccaggac cacctggagt tctgggagag cgtgttcacc     1620
ggcctgaccc acatcgacgc ccacttcctg agccagacca gcaggccgg cgacaacttc      1680 ccctacctgg tggcctacca ggccaccgtg tgcgcccgcg cccaggcccc ccccccagc     1740 tgggaccaga tgtggaagtg cctgatccgc ctgaagccca cctgcacgg ccccacccc     1800 ctgctgtacc gcctgggcgc cgtgcagaac gaggtgaccc tgacccaccc catcaccaag    1860
tacatcatgg cctgcatgag cgccgacctg gaggtggtga ccagcacctg ggtgctggtg    1920
ggcggcgtgc tggccgccct ggccgcctac tgcctgacca ccggcagcgt ggtgatcgtg    1980
ggccgcatca tcctgagcgg ccgccccgcc atcgtgcccg accgcgagtt cctgtaccag    2040
gagttcgacg agatggagga gtgcgccagc cacctgccct acatcgagca gggcatgcag    2100
ctggccgagc agttcaagca gaaggccctg ggcctgctgc agaccgccac caagcaggcc    2160
gaggccgccg cccccgtggt ggagagcaag tggcgcgccc tggagacctt ctgggccaag    2220
cacatgtgga acttcatcag cggcatccag tacctggccg gcctgagcac cctgccggc     2280 aaccccgcca tcgccagcct gatggccttc accgccagca tcaccagccc cctgaccacc    2340
cagagcaccc tgctgttcaa catcctgggc ggctgggtgg ccgcccagct ggccccccc     2400 agcgccgcca gcgccttcgt gggcgccggc atcgccggcg ccgccgtggg cagcatcggc    2460
ctgggcaagg tgctggtgga catcctggcc ggctacggcg ccggcgtggc cggcgccctg    2520
gtggccttca aggtgatgag cggcgagatg cccagcaccg aggacctggt gaacctgctg    2580
cccgccatcc tgagccccgg cgccctggtg gtgggcgtgg tgtgcgccgc catcctgcgc    2640
cgccacgtgg gccccggcga gggcgccgtg cagtggatga accgcctgat cgccttcgcc    2700
agccgcggca accacgtgag ccccacccac tacgtgcccg agagcgacgc cgccgcccgc    2760
gtgacccaga tcctgagcag cctgaccatc acccagctgc tgaagcgcct gcaccagtgg    2820
atcaacgagg actgcagcac ccctgcagc ggcagctggc tgcgcgacgt gtgggactgg    2880
atctgcaccg tgctgaccga cttcaagacc tggctgcaga gcaagctgct gccccagctg    2940
cccggcgtgc ccttcttcag ctgccagcgc ggctacaagg gcgtgtggcg cggcgacggc    3000
atcatgcaga ccacctgccc ctgcggcgcc cagatcaccg gccacgtgaa gaacggcagc    3060
```

```
atgcgcatcg tgggcccaa gacctgcagc aacacctggc acggcacctt ccccatcaac    3120
gcctacacca ccggcccctg caccccagc cccgcccca actacagccg cgccctgtgg    3180
cgcgtggccg ccgaggagta cgtggaggtg acccgcgtgg gcgacttcca ctacgtgacc    3240
ggcatgacca ccgacaacgt gaagtgcccc tgccaggtgc cgcccccga gttcttcacc    3300
gaggtggacg gcgtgcgcct gcaccgctac gcccccgcct gccgcccct gctgcgcgag    3360
gaggtgacct tccaggtggg cctgaaccag tacctggtgg gcagccagct gccctgcgag    3420
cccgagcccg acgtggccgt gctgaccagc atgctgaccg accccagcca catcaccgcc    3480
gagaccgcca agcgccgcct ggcccgcggc agcccccca gcctggccag cagcagcgcc    3540
agccagctga gcgccccag cctgaaggcc acctgcacca cccaccacgt gagccccgac    3600
gccgacctga tcgaggccaa cctgctgtgg cgccaggaga tgggcggcaa catcacccgc    3660
gtggagagcg agaacaaggt ggtggtgctg acagcttcg accccctgcg cgccgaggag    3720
gacgagcgcg aggtgagcgt gccgccgag atcctgcgca agagcaagaa gttccccgcc    3780
gccatgccca tctgggcccg cccgactac aacccccc tgctggagag ctggaaggac    3840
cccgactacg tgcccccgt ggtgcacggc tgccccctgc ccccatcaa ggcccccccc    3900
atccccccc ccgccgcaa cgcaccgtg gtgctgaccg agagcagcgt gagcagcgcc    3960
ctggccgagc tggccaccaa gaccttcggc agcagcgaga gcagcgccgt ggacagcggc    4020
accgccaccg ccctgcccga ccaggccagc gacgacggcg acaagggcag cgacgtggag    4080
agctacagca gcatgccccc cctggagggc gagcccggcg accccgacct gagcgacggc    4140
agctggagca ccgtgagcga ggaggccagc gaggacgtgg tgtgctgcag catgagctac    4200
acctggaccg gcgccctgat caccccctgc gccgccgagg agagcaagct gcccatcaac    4260
gccctgagca acagcctgct gcgccaccac aacatggtgt acgccaccac cagccgcagc    4320
gccggcctgc gccagaagaa ggtgaccttc gaccgcctgc aggtgctgga cgaccactac    4380
cgcgacgtgc tgaaggagat gaaggccaag gccagcaccg tgaaggccaa gctgctgagc    4440
gtggaggagg cctgcaagct gacccccccc cacagcgcca agagcaagtt cggctacggc    4500
gccaaggacg tgcgcaacct gagcagcaag gccgtgaacc acatccacag cgtgtggaag    4560
gacctgctgg aggacaccgt gaccccatc gacaccacca tcatggccaa gaacgaggtg    4620
ttctgcgtgc agcccgagaa gggcggccgc aagcccgccc gcctgatcgt gttccccgac    4680
ctgggcgtgc gcgtgcgcga agatggcc ctgtacgacg tggtgagcac cctgccccag    4740
gtggtgatgg gcagcagcta cggcttccag tacagccccg ccagcgcgt ggagttcctg    4800
gtgaacacct ggaagagcaa gaagaacccc atgggcttca gctacgacac ccgctgcttc    4860
gacagcaccg tgaccgagaa cgacatccgc gtggaggaga gcatctacca gtgctgcgac    4920
ctggcccccg aggcccgcca ggccatcaag agcctgaccg agcgcctgta catcggcggc    4980
cccctgacca acagcaaggg ccagaactgc ggctaccgcc gctgccgcgc cagcggcgtg    5040
ctgaccacca gctgcggcaa cacccctgacc tgctacctga aggccagcgc cgcctgccgc    5100
gccgccaagc tgcaggactg caccatgctg gtgaacgccg ccggcctggt ggtgatctgc    5160
gagagcgccg gcacccagga ggacgccgcc agcctgcgcg tgttcaccga ggccatgacc    5220
cgctacagcg ccccccccgg cgaccccccc cagcccgagt acgacctgga gctgatcacc    5280
agctgcagca gcaacgtgag cgtggcccac gacgccagcg gcaagcgcgt gtactacctg    5340
acccgcgacc ccaccacccc cctggcccgc gccgcctggg agaccgcccg ccacaccccc    5400
```

| | |
|---|---|
| gtgaacagct ggctgggcaa catcatcatg tacgccccca ccctgtgggc ccgcatgatc | 5460 |
| ctgatgaccc acttcttcag catcctgctg gcccaggagc agctggagaa ggccctggac | 5520 |
| tgccagatct acggcgcctg ctacagcatc gagcccctgg acctgcccca gatcatcgag | 5580 |
| cgcctgcacg gcctgagcgc cttcagcctg cacagctaca gccccggcga gatcaaccgc | 5640 |
| gtggccagct gcctgcgcaa gctgggcgtg ccccccctgc gcgtgtggcg ccaccgcgcc | 5700 |
| cgcagcgtgc gcgcccgcct gctgagccag ggcggccgcg ccgccacctg cggcaagtac | 5760 |
| ctgttcaact gggccgtgaa gaccaagctg aagctgaccc ccatccccgc cgccagccag | 5820 |
| ctggacctga gcggctggtt cgtggccggc tacagcggcg cgacatcta ccacagcctg | 5880 |
| agccgcgccc gccccgctg gttcatgctg tgcctgctgc tgctgagcgt gggcgtgggc | 5940 |
| atctacctgc tgcccaaccg ctaaa | 5965 |

<210> SEQ ID NO 4
<211> LENGTH: 37090
<212> TYPE: DNA
<213> ORGANISM: Artificial Sequence
<220> FEATURE:
<223> OTHER INFORMATION: MRKAd6-NSmut nucleic acid

<400> SEQUENCE: 4

| | |
|---|---|
| catcatcaat aatataccett attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggccgcggg | 360 |
| gactttgacc gtttacgtgg agactcgccc aggtgttttt ctcaggtgtt ttccgcgttc | 420 |
| cgggtcaaag ttggcgtttt attattatag gcggccgcga tccattgcat acgttgtatc | 480 |
| catatcataa tatgtacatt tatattggct catgtccaac attaccgcca tgttgacatt | 540 |
| gattattgac tagttattaa tagtaatcaa ttacggggtc attagttcat agcccatata | 600 |
| tggagttccg cgttacataa cttacggtaa atggcccgcc tggctgaccg cccaacgacc | 660 |
| cccgcccatt gacgtcaata atgacgtatg ttcccatagt aacgccaata gggactttcc | 720 |
| attgacgtca atgggtggag tatttacggt aaactgccca cttggcagta catcaagtgt | 780 |
| atcatatgcc aagtacgccc cctattgacg tcaatgacgg taaatggccc gcctggcatt | 840 |
| atgcccagta catgacctta tgggactttc ctacttggca gtacatctac gtattagtca | 900 |
| tcgctattac catggtgatg cggttttggc agtacatcaa tgggcgtgga tagcggtttg | 960 |
| actcacgggg atttccaagt ctccacccca ttgacgtcaa tgggagtttg ttttggcacc | 1020 |
| aaaatcaacg ggactttcca aaatgtcgta caactccgc cccattgacg caaatgggcg | 1080 |
| gtaggcgtgt acggtgggag gtctatataa gcagagctcg tttagtgaac cgtcagatcg | 1140 |
| cctggagacg ccatccacgc tgttttgacc tccatagaag acaccgggac cgatccagcc | 1200 |
| tccgcggccg gaacggtgc attggaacgc ggattccccg tgccaagagt gagatctgcc | 1260 |
| accatgcgc ccatcacggc ctactcccaa cagacgcggg gcctacttgg ttgcatcatc | 1320 |
| actagcctta caggccggga caagaaccag gtcgagggag aggttcaggt ggtttccacc | 1380 |
| gcaacacaat cttcctggc gacctgcgtc aacggcgtgt gttggaccgt ttaccatggt | 1440 |
| gctggctcaa agaccttagc cggcccaaag gggccaatca cccagatgta cactaatgtg | 1500 |

```
gaccaggacc tcgtcggctg gcaggcgccc cccggggcgc gttccttgac accatgcacc    1560
tgtggcagct cagacccttta cttggtcacg agacatgctg acgtcattcc ggtgcgccgg    1620
cggggcgaca gtaggggag cctgctctcc ccaggcctc tctcctactt gaagggctct      1680
tcgggtggtc cactgctctg cccttcgggg cacgctgtgg gcatcttccg ggctgccgta    1740
tgcacccggg gggttgcgaa ggcggtggac tttgtgcccg tagagtccat ggaaactact    1800
atgcggtctc cggtcttcac ggacaactca tccccccgg ccgtaccgca gtcatttcaa     1860
gtggcccacc tacacgctcc cactggcagc ggcaagagta ctaaagtgcc ggctgcatat    1920
gcagcccaag ggtacaaggt gctcgtcctc aatccgtccg ttgccgctac cttagggttt    1980
ggggcgtata tgtctaaggc acacggtatt gaccccaaca tcagaactgg ggtaaggacc    2040
attaccacag gcgccccgt cacatactct acctatggca gtttcttgc cgatggtggt      2100
tgctctgggg gcgcttatga catcataata tgtgatgagt gccattcaac tgactcgact    2160
acaatcttgg gcatcggcac agtcctggac caagcggaga cggctggagc gcggcttgtc    2220
gtgctcgcca ccgctacgcc tccgggatcg gtcaccgtgc cacacccaaa catcgaggag    2280
gtggccctgt ctaatactgg agagatcccc ttctatggca aagccatccc cattgaagcc    2340
atcagggggg gaaggcatct cattttctgt cattccaaga gaagtgcga cgagctcgcc     2400
gcaaagctgt caggcctcgg aatcaacgct gtggcgtatt ccgggggct cgatgtgtcc     2460
gtcataccaa ctatcggaga cgtcgttgtc gtggcaacag cgctctgat gacgggctat     2520
acgggcgact ttgactcagt gatcgactgt aacacatgtg tcacccagac agtcgacttc    2580
agcttggatc ccaccttcac cattgagacg acgaccgtgc ctcaagacgc agtgtcgcgc    2640
tcgcagcggc ggggtaggac tggcaggggt aggagaggca tctacaggtt tgtgactccg    2700
ggagaacggc cctcgggcat gttcgattcc tcggtcctgt gtgagtgcta tgacgcgggc    2760
tgtgcttggt acgagctcac ccccgccgag acctcggtta ggttgcgggc ctacctgaac    2820
acaccagggt tgcccgtttg ccaggaccac ctggagttct gggagagtgt cttcacaggc    2880
ctcacccaca tagatgcaca cttccttgtcc cagaccaagc aggcaggaga caacttcccc   2940
tacctggtag cataccaagc cacggtgtgc gccagggctc aggccccacc tccatcatgg    3000
gatcaaatgt ggaagtgtct catacggctg aaacctacgc tgcacgggcc aacacccttg    3060
ctgtacaggc tgggagccgt ccaaaatgag gtcaccctca cccaccccat aaccaaatac    3120
atcatggcat gcatgtcggc tgacctggag gtcgtcacta gcacctgggt gctggtgggc    3180
ggagtccttg cagctctggc cgcgtattgc ctgacaacag gcagtgtggt cattgtgggt    3240
aggattatct tgtccgggag gccggctatt gttcccgaca gggagttcct ctaccaggag    3300
ttcgatgaaa tggaagagtg cgcctcgcac ctcccttaca tcgagcaggg aatgcagctc    3360
gccgagcaat tcaagcagaa agcgctcggg ttactgcaaa cagccaccaa acaagcggag    3420
gctgctgctc ccgtggtgga gtccaagtgg cgagcccttg agacattctg ggcgaagcac    3480
atgtggaatt tcatcagcgg gatacagtac ttagcaggct atccactctg cctgggaac    3540
cccgcaatag catcattgat ggcattcaca gcctctatca ccagcccgct caccacccaa    3600
agtaccctcc tgtttaacat cttggggggg tgggtggctg cccaactcgc ccccccagc    3660
gccgcttcgg cttttcgtggg cgccggcatc gccggtgcgg ctgttggcag cataggcctt    3720
gggaaggtgc ttgtggacat tctgcgggt tatggagcag gagtggccgg cgcgctcgtg    3780
gccttcaagg tcatgagcgg cgagatgccc tccaccgagg acctggtcaa tctacttcct    3840
```

```
gccatcctct ctcctggcgc cctggtcgtc ggggtcgtgt gtgcagcaat actgcgtcga   3900
cacgtgggtc cgggagaggg ggctgtgcag tggatgaacc ggctgatagc gttcgcctcg   3960
cggggtaatc atgttt cccc cacgcactat gtgcctgaga gcgacgccgc agcgcgtgtt   4020
actcagatcc tctccagcct taccatcact cagctgctga aaaggctcca ccagtggatt   4080
aatgaagact gctccacacc gtgttccggc tcgtggctaa gggatgtttg ggactggata   4140
tgcacggtgt tgactgactt caagacctgg ctccagtcca agctcctgcc gcagctaccg   4200
ggagtccctt ttttctcgtg ccaacgcggg tacaagggag tctggcgggg agacggcatc   4260
atgcaaacca cctgcccatg tggagcacag atcaccggac atgtcaaaaa cggttccatg   4320
aggatcgtcg ggcctaagac ctgcagcaac acgtggcatg aacattccc catcaacgca    4380 tacaccacgg gcccctgcac accctctcca gcgccaaact attctagggc gctgtggcgg   4440
gtggccgctg aggagtacgt ggaggtcacg cgggtggggg atttccacta cgtgacgggc   4500
atgaccactg acaacgtaaa gtgcccatgc caggttccgg ctcctgaatt cttcacggag   4560
gtggacggag tgcggttgca caggtacgct ccggcgtgca ggcctctcct acgggaggag   4620
gttacattcc aggtcgggct caaccaatac ctggttgggt cacagctacc atgcgagccc   4680
gaaccggatg tagcagtgct cacttccatg ctcaccgacc cctcccacat cacagcagaa   4740
acggctaagc gtaggttggc cagggggtct ccccc ctcct tggccagctc ttcagctagc   4800
cagttgtctg cgccttcctt gaaggcgaca tgcactaccc accatgtctc tccggacgct   4860
gacctcatcg aggccaacct cctgtggcgg caggagatgg gcgggaacat cacccgcgtg   4920
gagtcggaga caaggtggt agtcctggac tctttcgacc cgcttcgagc ggaggaggat   4980
gagagggaag tatccgttcc ggcggagatc ctgcggaaat ccaagaagtt ccccgcagcg   5040
atgcccatct gggcgcgccc ggattacaac cctccactgt tagagtcctg gaaggacccg   5100
gactacgtcc ctcggtggt gcacgggtgc ccgttgccac ctatcaaggc ccctccaata   5160
ccacctccac ggagaaagag gacggttgtc ctaacagagt cctccgtgtc ttctgcctta   5220
gcggagctcg ctactaagac cttcggcagc tccgaatcat cggccgtcga cagcggcacg   5280
gcgaccgccc ttcctgacca ggcctccgac gacggtgaca aggatccga cgttgagtcg   5340 tactcctcca tgcccccc ct tgaggggaa ccggggg acc ccgatctcag tgacgggtct   5400
tggtctaccg tgagcgagga agctagtgag gatgtcgtct gctgctcaat gtcctacaca   5460
tggacaggcg ccttgatcac gccatgcgct gcggaggaaa gcaagctgcc catcaacgcg   5520
ttgagcaact ctttgctgcg ccaccataac atggtttatg ccacaacatc tcgcagcgca   5580
ggcctgcggc agaagaaggt cacctttgac agactgcaag tcctggacga ccactaccgg   5640
gacgtgctca aggagatgaa ggcgaaggcg tccacagtta aggctaaact cctatccgta   5700
gaggaagcct gcaagctgac gccccacat tcggccaaat ccaagtttgg ctatggggca   5760
aaggacgtcc ggaacctatc cagcaaggcc gttaaccaca tccactccgt gtggaaggac   5820
ttgctggaag acactgtgac accaattgac accaccatca tggcaaaaaa tgaggttttc   5880
tgtgtccaac cagagaaagg aggccgtaag ccagcccgcc ttatcgtatt cccagatctg   5940
ggagtccgtg tatgcgagaa gatggccctc tatgatgtgg tctccaccct tcctcaggtc   6000
gtgatgggct cctcatacgg attccagtac tctcctgggc agcgagtcga gttcctggtg   6060
aatacctgga aatcaaagaa aaaccccatg ggcttttcat atgacactcg ctgtttcgac   6120
tcaacggtca ccgagaacga catccgtgtt gaggagtcaa tttaccaatg ttgtgacttg   6180 gccccgaag ccagacaggc cataaaatcg ctcacagagc ggctttatat cggggggtcct   6240
```

```
ctgactaatt caaaagggca gaactgcggt tatcgccggt gccgcgcgag cggcgtgctg    6300
acgactagct gcggtaacac cctcacatgt tacttgaagg cctctgcagc ctgtcgagct    6360
gcgaagctcc aggactgcac gatgctcgtg aacgccgccg gccttgtcgt tatctgtgaa    6420
agcgcgggaa cccaagagga cgcggcgagc ctacgagtct tcacggaggc tatgactagg    6480
tactctgccc cccccgggga cccgcccaa ccagaatacg acttggagct gataacatca    6540
tgttcctcca atgtgtcggt cgcccacgat gcatcaggca aaagggtgta ctacctcacc    6600
cgtgatccca ccacccccct cgcacgggct gcgtgggaaa cagctagaca cactccagtt    6660
aactcctggc taggcaacat tatcatgtat gcgcccactt tgtgggcaag gatgattctg    6720
atgactcact tcttctccat ccttctagca caggagcaac ttgaaaaagc cctggactgc    6780
cagatctacg ggcctgttta ctccattgag ccacttgacc tacctcagat cattgaacga    6840
ctccatggcc ttagcgcatt ttcactccat agttactctc caggtgagat caataggggtg    6900 gcttcatgcc tcaggaaact tggggtacca cccttgcgag tctggagaca tcgggccagg    6960
agcgtccgcg ctaggctact gtcccagggg gggagggccg ccacttgtgg caagtacctc    7020
ttcaactggg cagtgaagac caaactcaaa ctcactccaa tcccggctgc gtcccagctg    7080
gacttgtccg gctggttcgt tgctggttac agcgggggag acatatatca cagcctgtct    7140
cgtgcccgac cccgctggtt catgctgtgc ctactcctac tttctgtagg ggtaggcatc    7200
tacctgctcc ccaaccggta aatctagagc tgtgccttct agttgccagc catctgttgt    7260
ttgcccctcc cccgtgcctt ccttgaccct ggaaggtgcc actcccactg tccttcccta    7320
ataaaatgag gaaattgcat cgcattgtct gagtaggtgt cattctattc tggggggtgg    7380
ggtggggcag gacagcaagg gggaggattg gaagacaat agcaggcatg ctggggatgc    7440
ggtgggctct atggccgatc ggcgcgccgt actgaaatgt gtgggcgtgg cttaagggtg    7500
ggaaagaata tataaggtgg gggtcttatg tagttttgta tctgttttgc agcagccgcc    7560
gccgccatga gcaccaactc gtttgatgga agcattgtga gctcatattt gacaacgcgc    7620
atgcccccat gggccggggt gcgtcagaat gtgatgggct ccagcattga tggtcgcccc    7680
gtcctgcccg caaactctac taccttgacc tacgagaccg tgtctggaac gccgttggag    7740
actgcagcct ccgccgccgc ttcagccgct gcagccaccg cccgcgggat tgtgactgac    7800
tttgctttcc tgagcccgct tgcaagcagt gcagcttccc gttcatccgc ccgcgatgac    7860
aagttgacgg ctcttttggc acaattggat tctttgaccc gggaacttaa tgtcgtttct    7920
cagcagctgt tggatctgcg ccagcaggtt tctgccctga aggcttcctc ccctcccaat    7980
gcggtttaaa acataaataa aaaaccagac tctgtttgga tttggatcaa gcaagtgtct    8040
tgctgtcttt atttagggggt tttgcgcgcg cggtaggccc gggaccagcg gtctcggtcg    8100
ttgagggtcc tgtgtatttt ttccaggacg tggtaaaggt gactctggat gttcagatac    8160
atgggcataa gcccgtctct ggggtggagg tagcaccact gcagagcttc atgctgcggg    8220
gtggtgttgt agatgatcca gtcgtagcag gagcgctggg cgtggtgcct aaaaatgtct    8280
ttcagtagca agctgattgc cagggcagg cccttggtgt aagtgtttac aaagcggtta    8340
agctgggatg ggtgcatacg tggggatatg agatgcatct tggactgtat ttttaggttg    8400
gctatgttcc cagccatatc cctccgggga ttcatgttgt gcagaaccac cagcacagtg    8460
tatccggtgc acttgggaaa tttgtcatgt agcttagaag gaaatgcgtg gaagaacttg    8520
gagacgccct tgtgacctcc aagattttcc atgcattcgt ccataatgat ggcaatgggc    8580
```

```
ccacgggcgg cggcctgggc gaagatattt ctgggatcac taacgtcata gttgtgttcc   8640
aggatgagat cgtcataggc cattttaca aagcgcgggc ggagggtgcc agactgcggt     8700
ataatggttc catccggccc aggggcgtag ttaccctcac agatttgcat ttcccacgct    8760
ttgagttcag atgggggat catgtctacc tgcggggcga tgaagaaaac ggtttccggg     8820
gtaggggaga tcagctggga agaaagcagg ttcctgagca gctgcgactt accgcagccg   8880
gtgggcccgt aaatcacacc tattaccggc tgcaactggt agttaagaga gctgcagctg   8940
ccgtcatccc tgagcagggg ggccacttcg ttaagcatgt ccctgactcg catgttttcc    9000
ctgaccaaat ccgccagaag cgctcgccg cccagcgata gcagttcttg caaggaagca     9060
aagttttca acggtttgag accgtccgcc gtaggcatgc ttttgagcgt ttgaccaagc    9120
agttccaggc ggtcccacag ctcggtcacc tgctctacgg catctcgatc cagcatatct    9180
cctcgtttcg cgggttgggg cggctttcgc tgtacggcag tagtcggtgc tcgtccagac   9240
gggccagggt catgtctttc cacggcgca gggtcctcgt cagcgtagtc tgggcacgg      9300
tgaaggggtg cgctccgggc tgcgcgctgg ccagggtgcg cttgaggctg gtcctgctgg   9360
tgctgaagcg ctgccggtct tcgccctgcg cgtcggccag gtagcatttg accatggtgt   9420
catagtccag cccctccgcg gcgtggccct tggcgcgcag cttgcccttg gaggaggcgc    9480
cgcacgaggg gcagtgcaga cttttgaggg cgtagagctt gggcgcgaga aataccgatt   9540
ccggggagta ggcatccgcg ccgcaggccc cgcagacggt ctcgcattcc acgagccagg   9600
tgagctctgg ccgttcgggg tcaaaaacca ggtttccccc atgctttttg atgcgtttct    9660
tacctctggt ttccatgagc cggtgtccac gctcggtgac gaaaaggctg tccgtgtccc   9720
cgtatacaga cttgagaggc ctgtcctcga gcggtgttcc gcggtcctcc tcgtatagaa   9780
actcggacca ctctgagacg aaggctcgcg tccaggccag cacgaaggag gctaagtggg   9840
aggggtagcg gtcgttgtcc actagggggt ccactcgctc cagggtgtga agacacatgt    9900
cgccctcttc ggcatcaagg aaggtgattg gtttataggt gtaggccacg tgaccgggtg   9960
ttcctgaagg ggggctataa aagggggtgg gggcgcgttc gtcctcactc tcttccgcat   10020
cgctgtctgc gagggccagc tgttggggtg agtactccct ctcaaaagcg ggcatgactt   10080
ctgcgctaag attgtcagtt tccaaaaacg aggaggattt gatattcacc tggcccgcgg   10140
tgatgccttt gagggtggcc gcgtccatct ggtcagaaaa gacaatcttt tgttgtcaa    10200
gcttggtggc aaacgacccg tagagggcgt tggacagcaa cttggcgatg gagcgcaggg   10260
tttggtttt gtcgcgatcg gcgcgctcct tggccgcgat gtttagctgc acgtattcgc    10320
gcgcaacgca ccgccattcg ggaaagacgg tggtgcgctc gtcgggcact aggtgcacgc   10380
gccaaccgcg gttgtgcagg gtgacaaggt caacgctggt ggctacctct ccgcgtaggc    10440
gctcgttggt ccagcagagg cggccgccct tgcgcgagca gaatggcggt agtgggtcta   10500
gctgcgtctc gtccgggggg tctgcgtcca cggtaaagac cccgggcagc aggcgcgcgt   10560
cgaagtagtc tatcttgcat ccttgcaagt ctagcgcctg ctgccatgcg cgggcggcaa   10620
gcgcgcgctc gtatgggttg agtgggggac cccatggcat ggggtgggtg agcgcggagg   10680
cgtacatgcc gcaaatgtcg taaacgtaga ggggctctct gagtattcca agatatgtag   10740
ggtagcatct tccaccgcgg atgctggcgc gcacgtaatc gtatagttcg tgcgagggag   10800
cgaggaggtc gggaccgagg ttgctacggg cgggctgctc tgctcggaag actatctgcc   10860
tgaagatggc atgtgagttg gatgatatgg ttggacgctg gaagacgttg aagctggcgt    10920
ctgtgagacc taccgcgtca cgcacgaagg aggcgtagga gtcgcgcagc ttgttgacca   10980
```

```
gctcggcggt gacctgcacg tctagggcgc agtagtccag ggtttccttg atgatgtcat    11040
acttatcctg tcccttttt  ttccacagct cgcggttgag gacaaactct tcgcggtctt    11100
tccagtactc ttggatcgga aacccgtcgg cctccgaacg gtaagagcct agcatgtaga    11160
actggttgac ggcctggtag gcgcagcatc ccttttctac gggtagcgcg tatgcctgcg    11220
cggccttccg gagcgaggtg tgggtgagcg caaaggtgtc cctaaccatg actttgaggt    11280
actggtattt gaagtcagtg tcgtcgcatc cgccctgctc ccagagcaaa aagtccgtgc    11340
gcttttgga  acgcgggttt ggcagggcga aggtgacatc gttgaagagt atctttcccg    11400
cgcgaggcat aaagttgcgt gtgatgcgga agggtcccgg cacctcggaa cggttgttaa    11460
ttacctgggc ggcgagcacg atctcgtcaa agccgttgat gttgtggccc acaatgtaaa    11520
gttccaagaa gcgcgggatg cccttgatgg aaggcaattt tttaagttcc tcgtaggtga    11580
gctcttcagg ggagctgagc ccgtgctctg aaagggccca gtctgcaaga tgagggttgg    11640
aagcgacgaa tgagctccac aggtcacggg ccattagcat ttgcaggtgg tcgcgaaagg    11700
tcctaaactg gcgacctatg gccattttt  ctggggtgat gcagtagaag gtaagcgggt    11760
cttgttccca gcggtcccat ccaaggtccg cggctaggtc tcgcgcggcg gtcactagag    11820
gctcatctcc gccgaacttc atgaccagca tgaagggcac gagctgcttc ccaaaggccc    11880
ccatccaagt ataggtctct acatcgtagg tgacaaagag acgctcggtg cgaggatgcg    11940
agccgatcgg gaagaactgg atctcccgcc accagttgga ggagtggctg ttgatgtggt    12000
gaaagtagaa gtccctgcga cgggccgaac actcgtgctg gcttttgtaa aaacgtgcgc    12060
agtactggca gcggtgcacg ggctgtacat cctgcacgag gttgacctga cgaccgcgca    12120
caaggaagca gagtgggaat ttgagcccct cgcctggcgg gtttggctgg tggtcttcta    12180
cttcggctgc ttgtccttga ccgtctggct gctcgagggg agttacggtg gatcggacca    12240
ccacgccgcg cgagcccaaa gtccagatgt ccgcgcgcgg cggtcggagc ttgatgacaa    12300
catcgcgcag atgggagctg tccatggtct ggagctcccg cggcgtcagg tcaggcggga    12360
gctcctgcag gtttacctcg catagccggg tcagggcgcg ggctaggtcc aggtgatacc    12420
tgatttccag gggctggttg gtggcggcgt cgatggcttg caagaggccg catccccgcg    12480
gcgcgactac ggtaccgcgc ggcgggcggt gggccgcggg ggtgtccttg atgatgcat    12540
ctaaaagcgg tgacgcgggc gggccccgg  aggtaggggg ggctcgggac ccgccgggag    12600
aggggggcagg ggcacgtcgg cgccgcgcgc gggcaggagc tggtgctgcg cgcggaggtt    12660
gctggcgaac gcgacgacgc ggcggttgat ctcctgaatc tggcgcctct gcgtgaagac    12720
gacgggcccg gtgagcttga acctgaaaga gagttcgaca gaatcaattt cggtgtcgtt    12780
gacggcggcc tggcgcaaaa tctcctgcac gtctcctgag ttgtcttgat aggcgatctc    12840
ggccatgaac tgctcgatct cttcctcctg gagatctccg cgtccggctc gctccacggt    12900
ggcggcgagg tcgttggaga tgcgggcat  gagctgcgag aaggcgttga ggcctccctc    12960
gttccagacg cggctgtaga ccacgccccc ttcggcatcg cgggcgcgca tgaccacctg    13020
cgcgagattg agctccacgt gccgggcgaa gacggcgtag tttcgcaggc gctgaaagag    13080
gtagttgagg gtggtggcgg tgtgttctgc cacgaagaag tacataaccc agcgccgcaa    13140
cgtggattcg ttgatatccc ccaaggcctc aaggcgctcc atggcctcgt agaagtccac    13200
ggcgaagttg aaaaactggg agttgcgcgc cgacacggtt aactcctcct ccagaagacg    13260
gatgagctcg gcgacagtgt cgcgcacctc gcgctcaaag gctacagggg cctcttcttc    13320
```

```
ttcttcaatc tcctcttcca taagggcctc cccttcttct tcttctggcg gcggtggggg    13380
aggggggaca cggcggcgac gacggcgcac cgggaggcgg tcgacaaagc gctcgatcat    13440
ctccccgcgg cgacggcgca tggtctcggt gacggcgcgg ccgttctcgc ggggcgcag     13500
ttggaagacg ccgcccgtca tgtcccggtt atgggttggc ggggggctgc cgtgcggcag    13560
ggatacggcg ctaacgatgc atctcaacaa ttgttgtgta ggtactccgc caccgaggga    13620
cctgagcgag tccgcatcga ccggatcgga aaacctctcg agaaaggcgt ctaaccagtc    13680
acagtcgcaa ggtaggctga gcaccgtggc gggcggcagc gggcggcggt cggggttgtt    13740
tctggcggag gtgctgctga tgatgtaatt aaagtaggcg gtcttgagac ggcggatggt    13800
cgacagaagc accatgtcct tgggtccggc ctgctgaatg cgcaggcggt cggccatgcc    13860
ccaggcttcg ttttgacatc ggcgcaggtc tttgtagtag tcttgcatga gcctttctac    13920
cggcacttct tcttctcctt cctcttgtcc tgcatctctt gcatctatcg ctgcggcggc    13980
ggcggagttt ggccgtaggt ggcgccctct tcctcccatg cgtgtgaccc cgaagccccct  14040
catcggctga agcagggcca ggtcggcgac aacgcgctcg gctaatatgg cctgctgcac    14100
ctgcgtgagg gtagactgga agtcgtccat gtccacaaag cggtggtatg cgcccgtgtt    14160
gatggtgtaa gtgcagttgg ccataacgga ccagttaacg gtctggtgac ccggctgcga    14220
gagctcggtg tacctgagac gcgagtaagc ccttgagtca aagacgtagt cgttgcaagt    14280
ccgcaccagg tactggtatc ccaccaaaaa gtgcggcggc ggctggcggt agaggggcca    14340
gcgtaggggtg gccggggctc cggggcgag gtcttccaac ataaggcgat gatatccgta    14400
gatgtacctg gacatccagg tgatgccggc ggcggtggtg gaggcgcgcg gaaagtcacg    14460
gacgcggttc cagatgttgc gcagcggcaa aaagtgctcc atggtcggga cgctctggcc    14520
ggtcaggcgc gcgcagtcgt tgacgctcta gaccgtgcaa aaggagagcc tgtaagcggg    14580
cactcttccg tggtctggtg gataaattcg caagggtatc atggcggacg accgggttc    14640
gaaccccgga tccggccgtc cgccgtgatc catgcggtta ccgcccgcgt gtcgaaccca    14700
ggtgtgcgac gtcagacaac gggggagcgc tccttttggc ttccttccag gcgcggcgga    14760
tgctgcgcta gcttttttgg ccactggccg cgcgcggcgt aagcggttag gctggaaagc    14820
gaaagcatta agtggctcgc tccctgtagc cggagggtta ttttccaagg gttgagtcgc    14880
gggaccccg gttcgagtct cgggccggcc ggactgcggc gaacgggggt ttgcctcccc    14940
gtcatgcaag accccgcttg caaattcctc cggaaacagg gacgagcccc tttttttgctt   15000
ttcccagatg catccggtgc tgcggcagat gcgccccct cctcagcagc ggcaagagca     15060
agagcagcgg cagacatgca gggcacccctc cccttctcct accgcgtcag gaggggcaac    15120
atccgcggct gacgcggcgg cagatggtga ttacgaaccc ccgcggcgcc ggacccggca    15180
ctacttggac ttggaggagg gcgagggcct ggcgcggcta ggagcgccct ctcctgagcg    15240
acacccaagg gtgcagctga agcgtgacac gcgcgaggcg tacgtgccgc ggcagaacct    15300
gtttcgcgac cgcgagggag aggagcccga ggagatgcgg gatcgaaagt tccatgcagg    15360
gcgcgagttg cggcatggcc tgaaccgcga gcggttgctg cgcgaggagg actttgagcc    15420
cgacgcgcgg accggggatta gtccgcgcg cgcacacgtg gcggccgccg acctggtaac    15480
cgcgtacgag cagacggtga accaggagat taactttcaa aaaagcttta acaaccacgt    15540
gcgcacgctt gtggcgcgcg aggaggtggc tataggactg atgcatctgt gggactttgt    15600
aagcgcgctg gagcaaaacc caaatagcaa gccgctcatg cgcagctgt tccttatagt     15660
gcagcacagc agggacaacg aggcattcag ggatgcgctg ctaaacatag tagagcccga    15720
```

```
gggccgctgg ctgctcgatt tgataaacat tctgcagagc atagtggtgc aggagcgcag    15780
cttgagcctg gctgacaagg tggccgccat taactattcc atgctcagtc tgggcaagtt    15840
ttacgcccgc aagatatacc ataccccta cgttcccata gacaaggagg taaagatcga     15900
ggggttctac atgcgcatgg cgctgaaggt gcttaccttg agcgacgacc tgggcgttta    15960
tcgcaacgag cgcatccaca aggccgtgag cgtgagccgg cggcgcgagc tcagcgaccg    16020
cgagctgatg cacagcctgc aaagggccct ggctggcacg ggcagcggcg atagagaggc    16080
cgagtcctac tttgacgcgg gcgctgacct gcgctgggcc ccaagccgac gcgccctgga    16140
ggcagctggg gccggacctg ggctggcggt ggcacccgcg cgcgctggca acgtcggcgg    16200
cgtggaggaa tatgacgagg acgatgagta cgagccagag gacggcgagt actaagcggt    16260
gatgtttctg atcagatgat gcaagacgca acggacccgg cggtgcgggc ggcgctgcag    16320
agccagccgt ccggccttaa ctccacggac gactggcgcc aggtcatgga ccgcatcatg    16380
tcgctgactg cgcgcaaccc tgacgcgttc cggcagcagc cgcaggccaa ccggctctcc    16440
gcaattctgg aagcggtggt cccggcgcgc gcaaacccca cgcacgagaa ggtgctggcg    16500
atcgtaaacg cgctggccga aaacagggcc atccggcccg atgaggccgg cctggtctac    16560
gacgcgctgc ttcagcgcgt ggctcgttac aacagcagca acgtgcagac caacctggac    16620
cggctggtgg gggatgtgcg cgaggccgtg gcgcagcgtg agcgcgcgca gcagcagggc    16680
aacctgggct ccatggttgc actaaacgcc ttcctgagta cacagcccgc caacgtgccg    16740
cggggacagg aggactacac caactttgtg agcgcactgc ggctaatggt gactgagaca    16800
ccgcaaagtg aggtgtatca gtccgggcca gactatttt tccagaccag tagacaaggc     16860
ctgcagaccg taaacctgag ccaggctttc aagaacttgc aggggctgtg gggggtgcgg    16920
gctcccacag gcgaccgcgc gaccgtgtct agcttgctga cgcccaactc gcgcctgttg    16980
ctgctgctaa tagcgccctt cacgacagt ggcagcgtgt cccgggacac ataccctaggt    17040 cacttgctga cactgtaccg cgaggccata ggtcaggcgc atgtggacga gcatactttc    17100
caggagatta caagtgttag ccgcgcgctg ggcaggagg acacgggcag cctggaggca    17160
accctgaact acctgctgac caaccggcgg caaaaaatcc cctcgttgca cagtttaaac    17220
agcgaggagg agcgcatttt gcgctatgtg cagcagagcg tgagccttaa cctgatgcgc    17280
gacggggtaa cgcccagcgt ggcgctggac atgaccgcgc gcaacatgga accgggcatg    17340
tatgcctcaa accggccgtt tatcaatcgc ctaatggact acttgcatcg cgcggccgcc    17400
gtgaaccccg agtatttcac caatgccatc ttgaacccgc actggctacc gccccctggt    17460
ttctacaccg ggggattcga ggtgcccgag ggtaacgatg gattcctctg ggacgacata    17520
gacgacagcg tgtttttccc gcaaccgcag accctgctag agttgcaaca acgcgagcag    17580
gcagaggcgg cgctgcgaaa ggaaagcttc cgcaggccaa gcagcttgtc cgatctaggc    17640
gctgcggccc cgcggtcaga tgctagtagc ccatttccaa gcttgatagg gtctcttacc    17700
agcactcgca ccaccgccc gcgcctgctg ggcgaggagg agtacctaaa caactcgctg    17760
ctgcagccgc agcgcgaaaa gaacctgcct ccggcgtttc caacaacgg gatagagagc    17820 ctagtggaca agatgagtag atggaagacg tatgcgcagg agcacaggga tgtgcccggc    17880
ccgcgcccgc ccaccgtcg tcaaaggcac gaccgtcagc ggggtctggt gtgggaggac    17940
gatgactcgg cagacgacag cagcgtcttg gatttgggag ggagtggcaa cccgtttgca    18000
caccttcgcc ccaggctggg gagaatgttt taaaaaaaag catgatgcaa aataaaaaac    18060
```

```
tcaccaaggc catggcaccg agcgttggtt ttcttgtatt ccccttagta tgcggcgcgc  18120
ggcgatgtat gaggaaggtc ctcctccctc ctacgagagc gtggtgagcg cggcgccagt  18180
ggcggcggcg ctgggttcac ccttcgatgc tcccctggac ccgccgttcg tgcctccgcg  18240
gtacctgcgg cctaccgggg ggagaaacag catccgttac tctgagttgg caccccctatt 18300
cgacaccacc cgtgtgtacc ttgtggacaa caagtcaacg gatgtggcat ccctgaacta  18360
ccagaacgac cacagcaact ttctaaccac ggtcattcaa aacaatgact acagcccggg  18420
ggaggcaagc acacagacca tcaatcttga cgaccggtcg cactggggcg gcgacctgaa  18480
aaccatcctg cataccaaca tgccaaatgt gaacgagttc atgtttacca ataagtttaa  18540
ggcgcgggtg atggtgtcgc gctcgcttac taaggacaaa caggtggagc tgaaatacga  18600
gtgggtggag ttcacgctgc ccgagggcaa ctactccgag accatgacca tagaccttat  18660
gaacaacgcg atcgtggagc actacttgaa agtgggcagg cagaacgggg ttctggaaag  18720
cgacatcggg gtaaagtttg acacccgcaa cttcagactg gggtttgacc cagtcactgg  18780
tcttgtcatg cctggggtat atacaaacga agccttccat ccagacatca ttttgctgcc  18840
aggatgcggg gtggacttca cccacagccg cctgagcaac ttgttgggca tccgcaagcg  18900
gcaacccttc caggagggct ttaggatcac ctacgatgac ctggagggtg gtaacattcc  18960
cgcactgttg gatgtggacg cctaccaggc aagcttgaaa gatgacaccg aacagggcgg  19020
gggtggcgca ggcggcggca acaacagtgg cagcggcgcg aagagaact ccaacgcggc  19080
agctgcggca atgcagccgg tggaggacat gaacgatcat gccattcgcg gcgacacctt  19140
tgccacacgg gcggaggaga agcgcgctga ggccgaggca gcggccgaag ctgccgcccc  19200
cgctgcggag gctgcacaac ccgaggtcga gaagcctcag aagaaaccgg tgattaaacc  19260
cctgacagag gacagcaaga aacgcagtta caacctaata agcaatgaca gcaccttcac  19320
ccagtaccgc agctggtacc ttgcatacaa ctacggcgac cctcaggccg ggatccgctc  19380
atggaccctg ctttgcactc ctgacgtaac ctgcggctcg gagcaggtat actggtcgtt  19440
gcccgacatg atgcaagacc ccgtgacctt ccgctccacg cgccagatca gcaactttcc  19500
ggtggtgggc gccgagctgt tgcccgtgca ctccaagagc ttctacaacg accaggccgt  19560
ctactcccag ctcatccgcc agtttacctc tctgacccac gtgttcaatc gctttcccga  19620
gaaccagatt ttggcgcgcc cgccagcccc caccatcacc accgtcagtg aaaacgttcc  19680
tgctctcaca gatcacggga cgctaccgct gcgcaacagc atcggaggag tccagcgagt  19740
gaccattact gacgccagac gccgcacctg ccccctacgtt tacaaggccc tgggcatagt  19800
ctcgccgcgc gtcctatcga gccgcacttt ttgagcaagc atgtccatcc ttatatcgcc  19860
cagcaataac acaggctggg gcctgcgctt cccaagcaag atgtttggcg gggccaagaa  19920
gcgctccgac caaacccagt gcgcgtgcg cgggcactac cgcgcgccct ggggcgcgca  19980
caaacgcggc cgcactgggc gcaccaccgt cgatgacgcc atcgacgcgg tggtggagga  20040
ggcgcgcaac tacacgccca cgccgccgcc agtgtccacc gtggacgcgg ccattcagac  20100
cgtggtgcgc ggagcccggc gctacgctaa aatgaagaga cggcggaggc gcgtagcacg  20160
tcgccaccgc cgccgacccg cgactgccgc ccaacgcgcg cggcggccc tgcttaaccg  20220
cgcacgtcgc accggccgac gggcggccat gcgagccgct cgaaggctgg ccgcgggtat  20280
tgtcactgtg ccccccaggt ccaggcgacg agcggccgcc gcagcagccg cggccattag  20340
tgctatgact cagggtcgca ggggcaacgt gtactgggtg cgcgactcgg ttagcggcct  20400
gcgcgtgccc gtgcgcaccc gccccccgcg caactagatt gcaataaaaa actacttaga  20460
```

```
ctcgtactgt tgtatgtatc cagcggcggc ggcgcgcatc gaagctatgt ccaagcgcaa    20520
aatcaaagaa gagatgctcc aggtcatcgc gccggagatc tatggccccc gaagaagga    20580 agagcaggat tacaagcccc gaaagctaaa gcgggtcaaa aagaaaaaga aagatgatga    20640
tgatgatgaa cttgacgacg aggtggaact gttgcacgcg accgcgccca ggcgacgggt    20700
acagtggaaa ggtcgacgcg taagacgtgt tttgcgaccc ggcaccaccg tagtctttac    20760
gcccggtgag cgctccaccc gcacctacaa gcgcgtgtat gatgaggtgt acggcgacga    20820
ggacctgctt gagcaggcca acgagcgcct cggggagttt gcctacggaa agcggcataa    20880
ggacatgctg gcgttgccgc tggacgaggg caacccaaca cctagcctaa agcccgtgac    20940
actgcagcag gtgctgcccg cgcttgcacc gtccgaagaa aagcgcggcc taaagcgcga    21000
gtctggtgac ttggcaccca ccgtgcagct gatggtaccc aagcgtcagc gactggaaga    21060
tgtcttggaa aaaatgaccg tggagcctgg gctggagccc gaggtccgcg tgcggccaat    21120
caagcaggtg gcaccgggac tgggcgtgca gaccgtggac gttcagatac ccaccaccag    21180
tagcactagt attgccactg ccacagaggg catggagaca caaacgtccc cggttgcctc    21240
ggcggtggca gatgccgcgg tgcaggcggc cgctgcggcc gcgtccaaga cctctacgga    21300
ggtgcaaacg gacccgtgga tgtttcgtgt ttcagccccc cggcgtccgc gccgttcaag    21360
gaagtacggc gccgccagcg cgctactgcc cgaatatgcc ctacatcctt ccatcgcgcc    21420
tacccccggc tatcgtggct acacctaccg ccccagaaga cgagcaacta cccgacgccg    21480
aaccaccact ggaacccgcc gccgccgtcg ccgtcgccag cccgtgctgg ccccgatttc    21540
cgtgcgcagg gtggctcgcg aaggaggcag gaccctggtg ctgccaacag cgcgctacca    21600
ccccagcatc gtttaaaagc cggtctttgt ggttcttgca gatatggccc tcacctgccg    21660
cctccgtttc ccggtgccgg gattccgagg aagaatgcac cgtaggaggg gcatggccgg    21720
ccacggcctg acgggcggca tgcgtcgtgc gcaccaccgg cggcggcgcg cgtcgcaccg    21780
tcgcatgcgc ggcggtatcc tgcccctcct tattccactg atcgccgcgg cgattggcgc    21840
cgtgcccgga attgcatccg tggccttgca ggcgcagaga cactgattaa aaacaagtta    21900
catgtggaaa aatcaaaata aaagtctgga ctctcacgct cgcttggtcc tgtaactatt    21960
ttgtagaatg gaagacatca actttgcgtc actggccccg cgacacggct cgcgccgtt    22020 catgggaaac tggcaagata tcggcaccag caatatgagc ggtggcgcct tcagctgggg    22080
ctcgctgtgg agcggcatta aaaatttcgg ttccgccgtt aagaactatg gcagcaaagc    22140
ctggaacagc agcacaggcc agatgctgag ggacaagttg aaagagcaaa atttccaaca    22200
aaaggtggta gatggcctgg cctctggcat tagcggggtg gtggacctgg ccaaccaggc    22260
agtgcaaaat aagattaaca gtaagcttga tccccgccct cccgtagagg agcctccacc    22320
ggccgtggag acagtgtctc cagaggggcg tggcgaaaag cgtccgcgac ccgacaggga    22380
agaaactctg gtgacgcaaa tagacgagcc tccctcgtac gaggaggcac taaagcaagg    22440
cctgcccacc acccgtccca tcgcgcccat ggctaccgga gtgctgggcc agcacacacc    22500
cgtaacgctg gacctgcctc cccccgccga cacccagcag aaacctgtgc tgccaggccc    22560
gtccgccgtt gttgtaaccc gtcctagccg cgcgtccctg cgccgcgccg ccagcggtcc    22620
gcgatcgttg cggcccgtag ccagtggcaa ctggcaaagc acactgaaca gcatcgtggg    22680
tttgggggtg caatccctga agcgccgacg atgcttctga tagctaacgt gtcgtatgtg    22740
tgtcatgtat gcgtccatgt cgccgccaga ggagctgctg agccgccgcg cgcccgcttt    22800
```

```
ccaagatggc tacccttcg atgatgccgc agtggtctta catgcacatc tcgggccagg  22860
acgcctcgga gtacctgagc cccgggctgg tgcagttcgc ccgcgccacc gagacgtact  22920
tcagcctgaa taacaagttt agaaacccca cggtggcgcc tacgcacgac gtgaccacag  22980
accggtctca gcgtttgacg ctgcggttca tccccgtgga ccgcgaggat actgcgtact  23040
cgtacaaggc gcggttcacc ctagctgtgg gtgataaccg tgtgctagac atggcttcca  23100
cgtactttga catccgcggc gtgctggaca ggggccctac ttttaagccc tactctggca  23160
ctgcctacaa cgcactggcc cccaaggggtg cccccaactc gtgcgagtgg aacaaaatg  23220
aaactgcaca agtggatgct caagaacttg acgaagagga gaatgaagcc aatgaagctc  23280
aggcgcgaga acaggaacaa gctaagaaaa cccatgtata tgcccaggct ccactgtccg  23340
gaataaaaat aactaaagaa ggtctacaaa taggaactgc cgacgccaca gtagcaggtg  23400
ccggcaaaga aattttcgca gacaaaactt tcaacctga accacaagta ggagaatctc  23460
aatgaacga agcggatgcc acagcagctg gtggaagggt tcttaaaaag acaactccca  23520
tgaaaccctg ctatggctca tacgctagac ccaccaattc caacggcgga cagggcgtta  23580
tggttgaaca aaatggtaaa ttggaaagtc aagtcgaaat gcaattttt tccacatcca  23640
caaatgccac aaatgaagtt aacaatatac aaccaacagt tgtattgtac agcgaagatg  23700
taaacatgga aactccagat actcatcttt cttataaacc taaatgggg gataaaaatg  23760
ccaaagtcat gcttggacaa caagcaatgc caaacagacc aaattacatt gcttttagag  23820
acaattttat tggtctcatg tattacaaca gcacaggtaa catgggtgtc cttgctggtc  23880
aggcatcgca gttgaacgct gttgtagatt tgcaagacag aaacacagag ctgtcctacc  23940
agcttttgct tgattcaatt ggcgacagaa caagatactt ttcaatgtgg aatcaagctg  24000
ttgacagcta tgatccagat gtcagaatta ttgagaacca tggaactgag gatgagttgc  24060
caaattattg ctttcctctt ggtggaattg ggattactga cacttttcaa gctgttaaaa  24120
caactgctgc taacggggac caaggcaata ctacctggca aaaagattca acatttgcag  24180
aacgcaatga aatagggggtg ggaaataact ttgccatgga aattaacctg aatgccaacc  24240
tatggagaaa tttccttac tccaatattg cgctgtacct gccagacaag ctaaaataca  24300
accccaccaa tgtggaaata tctgacaacc ccaacaccta cgactacatg aacaagcgag  24360
tggtggctcc tgggcttgta gactgctaca ttaaccttgg ggcgcgctgg tctctggact  24420
acatggacaa cgttaatccc tttaaccacc accgcaatgc gggcctgcgt taccgctcca  24480
tgttgttggg aaacggccgc tacgtgccct ttcacattca ggtgcccaa aagttttttg  24540
ccattaaaaa cctcctcctc ctgccaggct catacacata tgaatggaac ttcaggaagg  24600
atgttaacat ggttctgcag agctctctgg gaaacgacct tagagttgac ggggctagca  24660
ttaagtttga cagcatttgt ctttacgcca ccttcttccc catggccccac aacacggcct  24720
ccacgctgga agccatgctc agaaatgaca ccaacgacca gtcctttaat gactacccttt  24780
ccgccgccaa catgctatat cccatacccg ccaacgccac caacgtgccc atctccatcc  24840
catcgcgcaa ctgggcagca tttcgcggtt gggccttcac acgcttgaag acaaaggaaa  24900
ccccttccct gggatcaggc tacgacccctt actacaccta ctctggctcc ataccatacc  24960
ttgacggaac cttctatctt aatcacacct ttaagaaggt ggccattact tttgactctt  25020
ctgttagctg gccgggcaac gaccgcctgc ttactcccaa tgagtttgag attaagcgct  25080
cagttgacgg ggagggctat aacgtagctc agtgcaacat gacaaaggac tggttcctag  25140
tgcagatgtt ggccaactac aatattggct accagggctt ctacattcca gaaagctaca  25200
```

```
aagaccgcat gtactcgttc ttcagaaact tccagcccat gagccggcaa gtggtggacg   25260
atactaaata caaagattat cagcaggttg gaattatcca ccagcataac aactcaggct   25320
tcgtaggcta cctcgctccc accatgcgcg agggacaagc ttaccccgct aatgttccct   25380
acccactaat aggcaaaacc gcggttgata gtattaccca gaaaaagttt ctttgcgacc   25440
gcaccctgtg gcgcatcccc ttctccagta actttatgtc catgggtgcg ctcacagacc   25500
tgggccaaaa ccttctctac gcaaactccg cccacgcgct agacatgacc tttgaggtgg   25560
atcccatgga cgagcccacc cttctttatg ttttgtttga agtctttgac gtggtccgtg   25620
tgcaccagcc gcaccgcggc gtcatcgaga ccgtgtacct gcgcacgccc ttctcggccg   25680
gcaacgccac aacataaaga agcaagcaac atcaacaaca gctgccgcca tgggctccag   25740
tgagcaggaa ctgaaagcca ttgtcaaaga tcttggttgt gggccatatt ttttgggcac   25800
ctatgacaag cgcttcccag gctttgtttc cccacacaag ctcgcctgcg ccatagttaa   25860
cacggccggt cgcgagactg ggggcgtaca ctggatggcc tttgcctgga acccgcgctc   25920
aaaaacatgc tacctctttg agcccttttgg cttttctgac caacgtctca agcaggttta   25980
ccagtttgag tacgagtcac tcctgcgccg tagcgccatt gcctcttccc ccgaccgctg   26040
tataacgctg gaaagtccac cccaaagcgt gcaggggccc aactcggccg cctgtggcct   26100
attctgctgc atgtttctcc acgcctttgc caactggccc caaactccca tggatcacaa   26160
ccccaccatg aaccttatta ccggggtacc caactccatg cttaacagtc cccaggtaca   26220
gcccaccctg cgccgcaacc aggaacagct ctacagcttc ctggagcgcc actcgcccta   26280
cttccgcagc cacagtgcgc aaattaggag cgccacttct ttttgtcact tgaaaaacat   26340
gtaaaaataa tgtactagga gacactttca ataaaggcaa atgttttat ttgtacactc   26400 tcgggtgatt atttacccc cccttgccg tctgcgccgt ttaaaaatca aggggttct   26460 gccgcgcatc gctatgcgcc actggcaggg acacgttgcg atactggtgt ttagtgctcc   26520
acttaaactc aggcacaacc atccgcggca gctcggtgaa gttttcactc cacaggctgc   26580
gcaccatcac caacgcgttt agcaggtcgg gcgccgatat cttgaagtcg cagttggggc   26640
ctccgccctg cgcgcgcgag ttgcgataca cagggttaca gcactggaac actatcagcg   26700
ccgggtggtg cacgctggcc agcacgctct tgtcggagat cagatccgcg tccaggtcct   26760
ccgcgttgct cagggcgaac ggagtcaact ttggtagctg ccttcccaaa aagggtgcat   26820
gcccaggctt tgagttgcac tcgcaccgta gtggcatcag aaggtgaccg tgcccagtct   26880
gggcgttagg atacagcgcc tgcatgaaag ccttgatctg cttaaaagcc acctgagcct   26940
ttgcgccttc agagaagaac atgccgcaag acttgccgga aaactgattg gccggacagg   27000
ccgcgtcatg cacgcagcac cttgcgtcgg tgttggagat ctgcaccaca tttcggcccc   27060
accggttctt cacgatcttg gccttgctag actgctcctt cagcgcgcgc tgcccgtttt   27120
cgctcgtcac atccatttca atcacgtgct ccttatttat cataatgctc ccgtgtagac   27180
acttaagctc gccttcgatc tcagcgcagc ggtgcagcca caacgcgcag cccgtgggct   27240
cgtggtgctt gtaggttacc tctgcaaacg actgcaggta cgcctgcagg aatcgcccca   27300
tcatcgtcac aaaggtcttg ttgctggtga aggtcagctg caaccgcggt gctcctcgt   27360 ttagccaggt cttgcatacg gccgccagag cttccacttg gtcaggcagt agcttgaagt   27420
ttgcctttag atcgttatcc acgtggtact tgtccatcaa cgcgcgcgca gcctccatgc   27480
ccttctccca cgcagacacg atcggcaggc tcagcgggtt tatcaccgtg ctttcacttt   27540
```

```
ccgcttcact ggactcttcc ttttcctctt gcatccgcat accccgcgcc actgggtcgt   27600
cttcattcag ccgccgcacc gtgcgcttac ctcccttgcc gtgcttgatt agcaccggtg   27660
ggttgctgaa acccaccatt tgtagcgcca catcttctct ttcttcctcg ctgtccacga   27720
tcacctctgg ggatggcggg cgctcgggct tgggagaggg gcgcttcttt ttcttttttgg  27780 acgcaatggc caaatccgcc gtcgaggtcg atggccgcgg gctgggtgtg cgcggcacca   27840
gcgcatcttg tgacgagtct tcttcgtcct cggactcgag acgccgcctc agccgctttt   27900 ttggggggcgc gcggggaggc ggcggcgacg gcgacgggga cgagacgtcc tccatggttg   27960
gtggacgtcg cgccgcaccg cgtccgcgct cggggggtggt ttcgcgctgc tcctcttccc   28020
gactggccat ttccttctcc tataggcaga aaagatcat ggagtcagtc gagaaggagg    28080
acagcctaac cgccccctt gagttcgcca ccaccgcctc caccgatgcc gccaacgcgc    28140
ctaccacctt ccccgtcgag gcaccccgc ttgaggagga ggaagtgatt atcgagcagg    28200
acccaggttt tgtaagcgaa gacgacgaag atcgctcagt accaacgag gataaaaagc    28260 aagaccagga cgacgcagag gcaaacgagg aacaagtcgg gcgggggac caaaggcatg    28320 gcgactacct agatgtggga gacgacgtgc tgttgaagca tctgcagcgc cagtgcgcca   28380
ttatctgcga cgcgttgcaa gagcgcagcg atgtgccct cgccatagcg gatgtcagcc    28440
ttgcctacga acgccacctg ttctcaccgc gcgtaccccc caaacgccaa gaaaacggca   28500
catgcgagcc caacccgcgc ctcaacttct accccgtatt tgccgtgcca gaggtgcttg   28560
ccacctatca catcttttc caaaactgca agataccct atcctgccgt gccaaccgca     28620
gccgagcgga caagcagctg gccttgcggc agggcgctgt catacctgat atcgcctcgc   28680
tcgacgaagt gccaaaaatc tttgagggtc ttggacgcga cgagaagcgc gcggcaaacg   28740
ctctgcaaca agaaaacagc gaaaatgaaa gtcactgtgg agtgctggtg gaacttgagg   28800
gtgacaacgc gcgcctagcc gtgctgaaac gcagcatcga ggtcacccac tttgcctacc   28860
cggcacttaa cctacccccc aaggttatga gcacagtcat gagcgagctg atcgtgcgcc   28920
gtgcacgacc cctggagagg gatgcaaaact tgcaagaaca aaccgaggag ggcctacccg   28980
cagttggcga tgagcagctg gcgcgctggc ttgagacgcg cgagcctgcc gacttggagg   29040
agcgacgcaa gctaatgatg gccgcagtgc ttgttaccgt ggagcttgag tgcatgcagc   29100
ggttctttgc tgacccggag atgcagcgca agctagagga aacgttgcac tacacctttc   29160
gccagggcta cgtgcgccag gcctgcaaaa tttccaacgt ggagctctgc aacctggtct   29220
cctaccttgg aattttgcac gaaaaccgcc ttgggcaaaa cgtgcttcat tccacgctca   29280
agggcgaggc gcgccgcgac tacgtccgcg actgcgttta cttatttctg tgctacacct   29340
ggcaaacggc catgggcgtg tggcagcagt gcctggagga gcgcaacctg aaggagctgc   29400
agaagctgct aaagcaaaac ttgaaggacc tatggacggc cttcaacgag cgctccgtgg   29460
ccgcgcacct ggcggacatt atcttccccg aacgcctgct taaaccctg caacagggtc    29520 tgccagactt caccagtcaa agcatgttgc aaaactttag gaactttatc ctagagcgtt   29580
caggaattct gccccgccacc tgctgtgcgc ttcctagcga ctttgtgccc attaagtacc   29640
gtgaatgccc tccgccgctt tggggtcact gctaccttct gcagctagcc aactaccttg   29700
cctaccactc cgacatcatg gaagacgtga gcggtgacgg cctactggag tgtcactgtc   29760
gctgcaacct atgcaccccg caccgctccc tggtctgcaa ttcacaactg cttagcgaaa   29820
gtcaaattat cggtacccttt gagctgcagg gtccctcgcc tgacgaaaag tccgcggctc   29880
cggggttgaa actcactccg gggctgtgga cgtcggctta ccttcgcaaa tttgtacctg   29940
```

```
aggactacca cgcccacgag attaggttct acgaagacca atcccgcccg ccaaatgcgg   30000
agcttaccgc ctgcgtcatt acccagggcc acatccttgg ccaattgcaa gccattaaca   30060
aagcccgcca agagtttctg ctacgaaagg gacgggggt ttacttggac ccccagtccg    30120
gcgaggagct caacccaatc cccccgccgc cgcagcccta tcagcagccg cgggcccttg   30180
cttcccagga tggcacccaa aaagaagctg cagctgccgc cgccgccacc cacgacgag    30240
gaggaatact gggacagtca ggcagaggag gttttggacg aggaggagga gatgatggaa   30300
gactgggaca gcctagacga ggaagcttcc gaggccgaag aggtgtcaga cgaaacaccg   30360
tcaccctcgg tcgcattccc ctcgccggcg ccccagaaat cggcaaccgt tcccagcatt   30420
gctacaacct ccgctcctca ggcgccgccg gcactgcccg ttcgccgacc caaccgtaga   30480
tgggacacca ctggaaccag ggccggtaag tctaagcagc cgccgccgtt agcccaagag   30540
caacaacagc gccaaggcta ccgctcgtgg cgcgtgcaca agaacgccat agttgcttgc   30600
ttgcaagact gtggggcaa catctccttc gcccgccgct ttcttctcta ccatcacggc    30660
gtggccttcc cccgtaacat cctgcattac taccgtcatc tctacagccc ctactgcacc   30720
ggcggcagcg gcagcaacag cagcggccac gcagaagcaa aggcgaccgg atagcaagac   30780
tctgacaaag cccaagaaat ccacagcggc ggcagcagca ggaggaggag cactgcgtct   30840
ggcgcccaac gaacccgtat cgaccgcgca gcttagaaac aggattttc ccactctgta    30900
tgctatattt caacagagca ggggccaaga acaagagctg aaaataaaaa acaggtctct   30960
gcgctccctc acccgcagct gcctgtatca caaaagcgaa gatcagcttc ggcgcacgct   31020
ggaagacgcg gaggctctct tcagcaaata ctgcgcgctg actcttaagg actagtttcg   31080
cgcccttcct caaatttaag cgcgaaaact acgtcatctc cagcggccac acccggcgcc   31140
agcacctgtc gtcagcgcca ttatgagcaa ggaaattccc acgccctaca tgtggagtta   31200
ccagccacaa atgggacttg cggctggagc tgcccaagac tactcaaccc gaataaaacta  31260
catgagcgcg ggaccccaca tgatatcccg ggtcaacgga atccgcgccc accgaaaccg   31320
aattctcctc gaacaggcgg ctattaccac cacacctcgt aataaccttc atccccgtag   31380
ttggcccgct gccctggtgt accaggaaag tcccgctccc accactgtgg tacttcccag   31440
agacgcccag gccgaagttc agatgactaa ctcaggggcg cagcttgcgg gcggcttctcg  31500
tcacagggtg cggtcgcccg gcagggtat aactcacctg aaaatcagag gcgaggtat     31560
tcagctcaac gacgagtcgg tgagctcctc tcttggtctc cgtccggacg ggacatttca   31620
gatcggcggc gctggccgct cttcatttac gccccgtcag gcgatcctaa ctctgcagac   31680
ctcgtcctcg gagccgcgct ccggaggcat tggaactcta caatttattg aggagttcgt   31740
gccttcggtt tacttcaacc ccttttctgg acctcccggc cactacccgg accagtttat   31800
tcccaacttt gacgcggtaa aagactcggc ggacggctac gactgaatga ccagtggaga   31860
ggcagagcaa ctgcgcctga cacacctcga ccactgccgc cgccacaagt gctttgcccg   31920
cggctccggt gagttttgtt actttgaatt gcccgaagag catatcgagg gcccggcgca   31980
cggcgtccgg ctcaccaccc aggtagagct tacacgtagc ctgattcggg agtttaccaa   32040
gcgccccctg ctagtggagc gggagcgggg tccctgtgtt ctgaccgtgg tttgcaactg   32100
tcctaaccct ggattacatc aagatcttat tccattcaac taacaataaa cacacaataa   32160
attacttact taaaatcagt cagcaaatct ttgtccagct tattcagcat caccctcttt   32220
ccctcctccc aactctggta tttcagcagc cttttagctg cgaactttct ccaaagtcta   32280
```

```
aatgggatgt caaattcctc atgttcttgt ccctccgcac ccactatctt catattgttg    32340
cagatgaaac gcgccagacc gtctgaagac accttcaacc ctgtgtaccc atatgacacg    32400
gaaaccggcc ctccaactgt gccttttcct acccctccct ttgtgtcgcc aaatgggttc    32460
caagaaagtc cccccggagt gctttctttg cgtctttcag aacctttggt tacctcacac    32520
ggcatgcttg cgctaaaaat gggcagcggc ctgtccctgg atcaggcagg caaccttaca    32580
tcaaatacaa tcactgtttc tcaaccgcta aaaaaaacaa agtccaatat aactttggaa    32640
acatccgcgc cccttacagt cagctcaggc gccctaacca tggccacaac ttcgcctttg    32700
gtggtctctg acaacactct taccatgcaa tcacaagcac cgctaaccgt gcaagactca    32760
aaacttagca ttgctaccaa agagccactt acagtgttag atggaaaact ggccctgcag    32820
acatcagccc ccctctctgc cactgataac aacgccctca ctatcactgc ctcacctcct    32880
cttactactg caaatggtag tctggctgtt accatggaaa acccacttta caacaacaat    32940
ggaaaacttg ggctcaaaat tggcggtcct ttgcaagtgg ccaccgactc acatgcacta    33000
acactaggta ctggtcaggg ggttgcagtt cataacaatt tgctacatac aaaagttaca    33060
ggcgcaatag ggtttgatac atctggcaac atggaactta aaactggaga tggcctctat    33120
gtggatagcg ccggtcctaa ccaaaaacta catattaatc taaataccac aaaaggcctt    33180
gcttttgaca acaccgcaat aacaattaac gctggaaaag ggttggaatt tgaaacagac    33240
tcctcaaacg gaaatcccat aaaaacaaaa attggatcag gcatacaata taataccaat    33300
ggagctatgg ttgcaaaact tggaacaggc ctcagttttg acagctccgg agccataaca    33360
atgggcagca taaacaatga cagacttact cttttggacaa caccagaccc atccccaaat    33420
tgcagaattg cttcagataa agactgcaag ctaactctgg cgctaacaaa atgtggcagt    33480
caaattttgg gcactgtttc agctttggca gtatcaggta atatggcctc catcaatgga    33540
actctaagca gtgtaaactt ggttcttaga tttgatgaca acggagtgct tatgtcaaat    33600
tcatcactgg acaaacagta ttggaacttt agaaacgggg actccactaa cggtcaacca    33660
tacacttatg ctgttgggtt tatgccaaac ctaaaagctt acccaaaaac tcaaagtaaa    33720
actgcaaaaa gtaatattgt tagccaggtg tatcttaatg gtgacaagtc taaaccattg    33780
cattttacta ttacgctaaa tggaacagat gaaaccaacc aagtaagcaa atactcaata    33840
tcattcagtt ggtcctggaa cagtggacaa tacactaatg acaaatttgc caccaattcc    33900
tataccttct cctacattgc ccaggaataa agaatcgtga acctgttgca tgttatgttt    33960
caacgtgttt attttcaat tgcagaaaat ttcaagtcat ttttcattca gtagtatagc    34020
cccaccacca catagcttat actaatcacc gtaccttaat caaactcaca gaaccctagt    34080
attcaacctg ccacctccct cccaacacac agagtacaca gtccttttctc cccggctggc    34140
cttaaacagc atcatatcat gggtaacaga catattctta ggtgttatat tccacacggt    34200
ctcctgtcga gccaaacgct catcagtgat gttaataaac tccccgggca gctcgcttaa    34260
gttcatgtcg ctgtccagct gctgagccac aggctgctgt ccaacttgcg gttgctcaac    34320
gggcggcgaa ggagaagtcc acgcctacat ggggtagag tcataatcgt gcatcaggat    34380
agggcggtgg tgctgcagca gcgcgcgaat aaactgctgc cgccgccgct ccgtcctgca    34440
ggaatacaac atggcagtgg tctcctcagc gatgattcgc accgcccgca gcataaggcg    34500
ccttgtcctc cgggcacagc agcgcaccct gatctcactt aagtcagcac agtaactgca    34560
gcacagtacc acaatattgt ttaaaatccc acagtgcaag gcgctgtatc caaagctcat    34620
ggcggggacc acagaaccca cgtggccatc ataccacaag cgcaggtaga ttaagtggcg    34680
```

```
accccctcata aacacgctgg acataaacat tacctctttt ggcatgttgt aattcaccac   34740
ctcccggtac catataaacc tctgattaaa catggcgcca tccaccacca tcctaaacca   34800
gctggccaaa acctgcccgc cggctatgca ctgcagggaa ccgggactgg aacaatgaca   34860
gtggagagcc caggactcgt aaccatggat catcatgctc gtcatgatat caatgttggc   34920
acaacacagg cacacgtgca tacacttcct caggattaca agctcctccc gcgtcagaac   34980
catatcccag ggaacaaccc attcctgaat cagcgtaaat cccacactgc agggaagacc   35040
tcgcacgtaa ctcacgttgt gcattgtcaa agtgttacat tcgggcagca gcggatgatc   35100
ctccagtatg gtagcgcggg tttctgtctc aaaaggaggt agacgatccc tactgtacgg   35160
agtgcgccga gacaaccgag atcgtgttgg tcgtagtgtc atgccaaatg gaacgccgga   35220
cgtagtcata tttcctgaag caaaaccagg tgcgggcgtg acaaacagat ctgcgtctcc   35280
ggtctcgccg cttagatcgc tctgtgtagt agttgtagta tatccactct ctcaaagcat   35340
ccaggcgccc cctggcttcg ggttctatgt aaactccttc atgcgccgct gccctgataa   35400
catccaccac cgcagaataa gccacaccca gccaacctac acattcgttc tgcgagtcac   35460
acacgggagg agcgggaaga gctggaagaa ccatgttttt ttttttattc caaaagatta   35520
tccaaaacct caaaatgaag atctattaag tgaacgcgct cccctccggt ggcgtggtca   35580
aactctacag ccaaagaaca gataatggca tttgtaagat gttgcacaat ggcttccaaa   35640
aggcaaacgg ccctcacgtc caagtggacg taaaggctaa acccttcagg gtgaatctcc   35700
tctataaaca ttccagcacc ttcaaccatg cccaaataat tctcatctcg ccaccttctc   35760
aatatatctc taagcaaatc ccgaatatta agtccggcca ttgtaaaaat ctgctccaga   35820
gcgccctcca ccttcagcct caagcagcga atcatgattg caaaaattca ggttcctcac   35880
agacctgtat aagattcaaa agcggaacat taacaaaaat accgcgatcc cgtaggtccc   35940
ttcgcagggc cagctgaaca taatcgtgca ggtctgcacg gaccagcgcg gccacttccc   36000
cgccaggaac catgacaaaa gaacccacac tgattatgac acgcatactc ggagctatgc   36060
taaccagcgt agccccgatg taagcttgtt gcatgggcgg cgatataaaa tgcaaggtgc   36120
tgctcaaaaa atcaggcaaa gcctcgcgca aaaagaaag cacatcgtag tcatgctcat   36180
gcagataaag gcaggtaagc tccggaacca ccacagaaaa agacaccatt tttctctcaa   36240
acatgtctgc gggtttctgc ataaacacaa aataaaataa caaaaaaaca tttaaacatt   36300
agaagcctgt cttacaacag gaaaaacaac ccttataagc ataagacgga ctacggccat   36360
gccggcgtga ccgtaaaaaa actggtcacc gtgattaaaa agcaccaccg acagctcctc   36420
ggtcatgtcc ggagtcataa tgtaagactc ggtaaacaca tcaggttgat tcacatcggt   36480
cagtgctaaa aagcgaccga aatagcccgg gggaatacat acccgcaggc gtagagacaa   36540
cattacagcc cccataggag gtataacaaa attaatagga gagaaaaaca cataaacacc   36600
tgaaaaaccc tcctgcctag gcaaaatagc accctcccgc tccagaacaa catacagcgc   36660
ttccacagcg gcagccataa cagtcagcct taccagtaaa aagaaaaacc tattaaaaaa   36720
acaccactcg acacggcacc agctcaatca gtcacagtgt aaaaagggc caagtgcaga   36780
gcgagtatat ataggactaa aaaatgacgt aacggttaaa gtccacaaaa acacccaga   36840
aaaccgcacg cgaacctacg cccagaaacg aaagccaaaa aacccacaac ttcctcaaat   36900
cgtcacttcc gttttcccac gttacgtcac ttcccatttt aagaaaacta caattcccaa   36960
cacatacaag ttactccgcc ctaaaaccta cgtcacccgc cccgttccca cgccccgcgc   37020
```

-continued

```
cacgtcacaa actccacccc ctcattatca tattggcttc aatccaaaat aaggtatatt    37080
attgatgatg                                                           37090
```

<210> SEQ ID NO 5
<211> LENGTH: 5955
<212> TYPE: DNA
<213> ORGANISM: Artificial Sequence
<220> FEATURE:
<223> OTHER INFORMATION: NS cDNA sequence
<220> FEATURE:
<221> NAME/KEY: CDS
<222> LOCATION: (1)...(5955)

<400> SEQUENCE: 5

```
atg gcg ccc atc acg gcc tac tcc caa cag acg cgg ggc cta ctt ggt         48
Met Ala Pro Ile Thr Ala Tyr Ser Gln Gln Thr Arg Gly Leu Leu Gly
1               5                   10                  15 tgc atc atc act agc ctt aca ggc cgg gac aag aac cag gtc gag gga         96
Cys Ile Ile Thr Ser Leu Thr Gly Arg Asp Lys Asn Gln Val Glu Gly
            20                  25                  30 gag gtt cag gtg gtt tcc acc gca aca caa tcc ttc ctg gcg acc tgc        144
Glu Val Gln Val Val Ser Thr Ala Thr Gln Ser Phe Leu Ala Thr Cys
        35                  40                  45 gtc aac ggc gtg tgt tgg acc gtt tac cat ggt gct ggc tca aag acc        192
Val Asn Gly Val Cys Trp Thr Val Tyr His Gly Ala Gly Ser Lys Thr
    50                  55                  60 tta gcc ggc cca aag ggg cca atc acc cag atg tac act aat gtg gac        240
Leu Ala Gly Pro Lys Gly Pro Ile Thr Gln Met Tyr Thr Asn Val Asp
65                  70                  75                  80 cag gac ctc gtc ggc tgg cag gcg ccc ccg ggg gcg cgt tcc ttg aca        288
Gln Asp Leu Val Gly Trp Gln Ala Pro Pro Gly Ala Arg Ser Leu Thr
                85                  90                  95 cca tgc acc tgt ggc agc tca gac ctt tac ttg gtc acg aga cat gct        336
Pro Cys Thr Cys Gly Ser Ser Asp Leu Tyr Leu Val Thr Arg His Ala
            100                 105                 110 gac gtc att ccg gtg cgc cgg cgg ggc gac agt agg ggg agc ctg ctc        384
Asp Val Ile Pro Val Arg Arg Arg Gly Asp Ser Arg Gly Ser Leu Leu
        115                 120                 125 tcc ccc agg cct gtc tcc tac ttg aag ggc tct tcg ggt ggt cca ctg        432
Ser Pro Arg Pro Val Ser Tyr Leu Lys Gly Ser Ser Gly Gly Pro Leu
    130                 135                 140 ctc tgc cct tcg ggg cac gct gtg ggc atc ttc cgg gct gcc gta tgc        480
Leu Cys Pro Ser Gly His Ala Val Gly Ile Phe Arg Ala Ala Val Cys
145                 150                 155                 160 acc cgg ggg gtt gcg aag gcg gtg gac ttt gtg ccc gta gag tcc atg        528
Thr Arg Gly Val Ala Lys Ala Val Asp Phe Val Pro Val Glu Ser Met
                165                 170                 175 gaa act act atg cgg tct ccg gtc ttc acg gac aac tca tcc ccc ccg        576
Glu Thr Thr Met Arg Ser Pro Val Phe Thr Asp Asn Ser Ser Pro Pro
            180                 185                 190 gcc gta ccg cag tca ttt caa gtg gcc cac cta cac gct ccc act ggc        624
Ala Val Pro Gln Ser Phe Gln Val Ala His Leu His Ala Pro Thr Gly
        195                 200                 205 agc ggc aag agt act aaa gtg ccg gct gca tat gca gcc caa ggg tac        672
Ser Gly Lys Ser Thr Lys Val Pro Ala Ala Tyr Ala Ala Gln Gly Tyr
    210                 215                 220 aag gtg ctc gtc ctc aat ccg tcc gtt gcc gct acc tta ggg ttt ggg        720
Lys Val Leu Val Leu Asn Pro Ser Val Ala Ala Thr Leu Gly Phe Gly
225                 230                 235                 240 gcg tat atg tct aag gca cac ggt att gac ccc aac atc aga act ggg        768
Ala Tyr Met Ser Lys Ala His Gly Ile Asp Pro Asn Ile Arg Thr Gly
```

-continued

```
              245                 250                 255
gta agg acc att acc aca ggc gcc ccc gtc aca tac tct acc tat ggc      816
Val Arg Thr Ile Thr Thr Gly Ala Pro Val Thr Tyr Ser Thr Tyr Gly
            260                 265                 270 aag ttt ctt gcc gat ggt ggt tgc tct ggg ggc gct tat gac atc ata      864
Lys Phe Leu Ala Asp Gly Gly Cys Ser Gly Gly Ala Tyr Asp Ile Ile
            275                 280                 285 ata tgt gat gag tgc cat tca act gac tcg act aca atc ttg ggc atc      912
Ile Cys Asp Glu Cys His Ser Thr Asp Ser Thr Thr Ile Leu Gly Ile
        290                 295                 300 ggc aca gtc ctg gac caa gcg gag acg gct gga gcg cgg ctt gtc gtg      960
Gly Thr Val Leu Asp Gln Ala Glu Thr Ala Gly Ala Arg Leu Val Val
305                 310                 315                 320 ctc gcc acc gct acg cct ccg gga tcg gtc acc gtg cca cac cca aac     1008
Leu Ala Thr Ala Thr Pro Pro Gly Ser Val Thr Val Pro His Pro Asn
                325                 330                 335 atc gag gag gtg gcc ctg tct aat act gga gag atc ccc ttc tat ggc     1056
Ile Glu Glu Val Ala Leu Ser Asn Thr Gly Glu Ile Pro Phe Tyr Gly
                340                 345                 350 aaa gcc atc ccc att gaa gcc atc agg ggg gga agg cat ctc att ttc     1104
Lys Ala Ile Pro Ile Glu Ala Ile Arg Gly Gly Arg His Leu Ile Phe
            355                 360                 365 tgt cat tcc aag aag aag tgc gac gag ctc gcc gca aag ctg tca ggc     1152
Cys His Ser Lys Lys Lys Cys Asp Glu Leu Ala Ala Lys Leu Ser Gly
        370                 375                 380 ctc gga atc aac gct gtg gcg tat tac cgg ggg ctc gat gtg tcc gtc     1200
Leu Gly Ile Asn Ala Val Ala Tyr Tyr Arg Gly Leu Asp Val Ser Val
385                 390                 395                 400 ata cca act atc gga gac gtc gtt gtc gtg gca aca gac gct ctg atg     1248
Ile Pro Thr Ile Gly Asp Val Val Val Val Ala Thr Asp Ala Leu Met
                405                 410                 415 acg ggc tat acg ggc gac ttt gac tca gtg atc gac tgt aac aca tgt     1296
Thr Gly Tyr Thr Gly Asp Phe Asp Ser Val Ile Asp Cys Asn Thr Cys
                420                 425                 430 gtc acc cag aca gtc gac ttc agc ttg gat ccc acc ttc acc att gag     1344
Val Thr Gln Thr Val Asp Phe Ser Leu Asp Pro Thr Phe Thr Ile Glu
            435                 440                 445 acg acg acc gtg cct caa gac gca gtg tcg cgc tcg cag cgg cgg ggt     1392
Thr Thr Thr Val Pro Gln Asp Ala Val Ser Arg Ser Gln Arg Arg Gly
        450                 455                 460 agg act ggc agg ggt agg aga ggc atc tac agg ttt gtg act ccg gga     1440
Arg Thr Gly Arg Gly Arg Arg Gly Ile Tyr Arg Phe Val Thr Pro Gly
465                 470                 475                 480 gaa cgg ccc tcg ggc atg ttc gat tcc tcg gtc ctg tgt gag tgc tat     1488
Glu Arg Pro Ser Gly Met Phe Asp Ser Ser Val Leu Cys Glu Cys Tyr
                485                 490                 495 gac gcg ggc tgt gct tgg tac gag ctc acc ccc gcc gag acc tcg gtt     1536
Asp Ala Gly Cys Ala Trp Tyr Glu Leu Thr Pro Ala Glu Thr Ser Val
                500                 505                 510 agg ttg cgg gcc tac ctg aac aca cca ggg ttg ccc gtt tgc cag gac     1584
Arg Leu Arg Ala Tyr Leu Asn Thr Pro Gly Leu Pro Val Cys Gln Asp
            515                 520                 525 cac ctg gag ttc tgg gag agt gtc ttc aca ggc ctc acc cac ata gat     1632
His Leu Glu Phe Trp Glu Ser Val Phe Thr Gly Leu Thr His Ile Asp
        530                 535                 540 gca cac ttc ttg tcc cag acc aag cag gca gga gac aac ttc ccc tac     1680
Ala His Phe Leu Ser Gln Thr Lys Gln Ala Gly Asp Asn Phe Pro Tyr
545                 550                 555                 560 ctg gta gca tac caa gcc acg gtg tgc gcc agg gct cag gcc cca cct     1728
```

```
                Leu Val Ala Tyr Gln Ala Thr Val Cys Ala Arg Ala Gln Ala Pro Pro
                                565                 570                 575 cca tca tgg gat caa atg tgg aag tgt ctc ata cgg ctg aaa cct acg          1776
Pro Ser Trp Asp Gln Met Trp Lys Cys Leu Ile Arg Leu Lys Pro Thr
            580                 585                 590 ctg cac ggg cca aca ccc ttg ctg tac agg ctg gga gcc gtc caa aat          1824
Leu His Gly Pro Thr Pro Leu Leu Tyr Arg Leu Gly Ala Val Gln Asn
            595                 600                 605 gag gtc acc ctc acc cac ccc ata acc aaa tac atc atg gca tgc atg          1872
Glu Val Thr Leu Thr His Pro Ile Thr Lys Tyr Ile Met Ala Cys Met
610             615                 620 tcg gct gac ctg gag gtc gtc act agc acc tgg gtg ctg gtg ggc gga          1920
Ser Ala Asp Leu Glu Val Val Thr Ser Thr Trp Val Leu Val Gly Gly
625             630                 635                 640 gtc ctt gca gct ctg gcc gcg tat tgc ctg aca aca ggc agt gtg gtc          1968
Val Leu Ala Ala Leu Ala Ala Tyr Cys Leu Thr Thr Gly Ser Val Val
                645                 650                 655 att gtg ggt agg att atc ttg tcc ggg agg ccg gct att gtt ccc gac          2016
Ile Val Gly Arg Ile Ile Leu Ser Gly Arg Pro Ala Ile Val Pro Asp
                660                 665                 670 agg gag ttt ctc tac cag gag ttc gat gaa atg gaa gag tgc gcc tcg          2064
Arg Glu Phe Leu Tyr Gln Glu Phe Asp Glu Met Glu Glu Cys Ala Ser
                675                 680                 685 cac ctc cct tac atc gag cag gga atg cag ctc gcc gag caa ttc aag          2112
His Leu Pro Tyr Ile Glu Gln Gly Met Gln Leu Ala Glu Gln Phe Lys
            690                 695                 700 cag aaa gcg ctc ggg tta ctg caa aca gcc acc aaa caa gcg gag gct          2160
Gln Lys Ala Leu Gly Leu Leu Gln Thr Ala Thr Lys Gln Ala Glu Ala
705             710                 715                 720 gct gct ccc gtg gtg gag tcc aag tgg cga gcc ctt gag aca ttc tgg          2208
Ala Ala Pro Val Val Glu Ser Lys Trp Arg Ala Leu Glu Thr Phe Trp
                725                 730                 735 gcg aag cac atg tgg aat ttc atc agc ggg ata cag tac tta gca ggc          2256
Ala Lys His Met Trp Asn Phe Ile Ser Gly Ile Gln Tyr Leu Ala Gly
                740                 745                 750 tta tcc act ctg cct ggg aac ccc gca ata gca tca ttg atg gca ttc          2304
Leu Ser Thr Leu Pro Gly Asn Pro Ala Ile Ala Ser Leu Met Ala Phe
            755                 760                 765 aca gcc tct atc acc agc ccg ctc acc acc caa agt acc ctc ctg ttt          2352
Thr Ala Ser Ile Thr Ser Pro Leu Thr Thr Gln Ser Thr Leu Leu Phe
            770                 775                 780 aac atc ttg ggg ggg tgg gtg gct gcc caa ctc gcc ccc ccc agc gcc          2400
Asn Ile Leu Gly Gly Trp Val Ala Ala Gln Leu Ala Pro Pro Ser Ala
785             790                 795                 800 gct tcg gct ttc gtg ggc gcc ggc atc gcc ggt gcg gct gtt ggc agc          2448
Ala Ser Ala Phe Val Gly Ala Gly Ile Ala Gly Ala Ala Val Gly Ser
                805                 810                 815 ata ggc ctt ggg aag gtg ctt gtg gac att ctg gcg ggt tat gga gca          2496
Ile Gly Leu Gly Lys Val Leu Val Asp Ile Leu Ala Gly Tyr Gly Ala
            820                 825                 830 gga gtg gcc ggc gcg ctc gtg gcc ttc aag gtc atg agc ggc gag atg          2544
Gly Val Ala Gly Ala Leu Val Ala Phe Lys Val Met Ser Gly Glu Met
            835                 840                 845 ccc tcc acc gag gac ctg gtc aat cta ctt cct gcc atc ctc tct cct          2592
Pro Ser Thr Glu Asp Leu Val Asn Leu Leu Pro Ala Ile Leu Ser Pro
850             855                 860 ggc gcc ctg gtc gtc ggg gtc gtg tgt gca gca ata ctg cgt cga cac          2640
Gly Ala Leu Val Val Gly Val Val Cys Ala Ala Ile Leu Arg Arg His
865             870                 875                 880
```

| | |
|---|---|
| gtg ggt ccg gga gag ggg gct gtg cag tgg atg aac cgg ctg ata gcg<br>Val Gly Pro Gly Glu Gly Ala Val Gln Trp Met Asn Arg Leu Ile Ala<br>885 890 895 | 2688 |
| ttc gcc tcg cgg ggt aat cat gtt tcc ccc acg cac tat gtg cct gag<br>Phe Ala Ser Arg Gly Asn His Val Ser Pro Thr His Tyr Val Pro Glu<br>900 905 910 | 2736 |
| agc gac gcc gca gcg cgt gtt act cag atc ctc tcc agc ctt acc atc<br>Ser Asp Ala Ala Ala Arg Val Thr Gln Ile Leu Ser Ser Leu Thr Ile<br>915 920 925 | 2784 |
| act cag ctg ctg aaa agg ctc cac cag tgg att aat gaa gac tgc tcc<br>Thr Gln Leu Leu Lys Arg Leu His Gln Trp Ile Asn Glu Asp Cys Ser<br>930 935 940 | 2832 |
| aca ccg tgt tcc ggc tcg tgg cta agg gat gtt tgg gac tgg ata tgc<br>Thr Pro Cys Ser Gly Ser Trp Leu Arg Asp Val Trp Asp Trp Ile Cys<br>945 950 955 960 | 2880 |
| acg gtg ttg act gac ttc aag acc tgg ctc cag tcc aag ctc ctg ccg<br>Thr Val Leu Thr Asp Phe Lys Thr Trp Leu Gln Ser Lys Leu Leu Pro<br>965 970 975 | 2928 |
| cag cta ccg gga gtc cct ttt ttc tcg tgc caa cgc ggg tac aag gga<br>Gln Leu Pro Gly Val Pro Phe Phe Ser Cys Gln Arg Gly Tyr Lys Gly<br>980 985 990 | 2976 |
| gtc tgg cgg gga gac ggc atc atg caa acc acc tgc cca tgt gga gca<br>Val Trp Arg Gly Asp Gly Ile Met Gln Thr Thr Cys Pro Cys Gly Ala<br>995 1000 1005 | 3024 |
| cag atc acc gga cat gtc aaa aac ggt tcc atg agg atc gtc ggg cct<br>Gln Ile Thr Gly His Val Lys Asn Gly Ser Met Arg Ile Val Gly Pro<br>1010 1015 1020 | 3072 |
| aag acc tgc agc aac acg tgg cat gga aca ttc ccc atc aac gca tac<br>Lys Thr Cys Ser Asn Thr Trp His Gly Thr Phe Pro Ile Asn Ala Tyr<br>1025 1030 1035 1040 | 3120 |
| acc acg ggc ccc tgc aca ccc tct cca gcg cca aac tat tct agg gcg<br>Thr Thr Gly Pro Cys Thr Pro Ser Pro Ala Pro Asn Tyr Ser Arg Ala<br>1045 1050 1055 | 3168 |
| ctg tgg cgg gtg gcc gct gag gag tac gtg gag gtc acg cgg gtg ggg<br>Leu Trp Arg Val Ala Ala Glu Glu Tyr Val Glu Val Thr Arg Val Gly<br>1060 1065 1070 | 3216 |
| gat ttc cac tac gtg acg ggc atg acc act gac aac gta aag tgc cca<br>Asp Phe His Tyr Val Thr Gly Met Thr Thr Asp Asn Val Lys Cys Pro<br>1075 1080 1085 | 3264 |
| tgc cag gtt ccg gct cct gaa ttc ttc acg gag gtg gac gga gtg cgg<br>Cys Gln Val Pro Ala Pro Glu Phe Phe Thr Glu Val Asp Gly Val Arg<br>1090 1095 1100 | 3312 |
| ttg cac agg tac gct ccg gcg tgc agg cct ctc cta cgg gag gag gtt<br>Leu His Arg Tyr Ala Pro Ala Cys Arg Pro Leu Leu Arg Glu Glu Val<br>1105 1110 1115 1120 | 3360 |
| aca ttc cag gtc ggg ctc aac caa tac ctg gtt ggg tca cag cta cca<br>Thr Phe Gln Val Gly Leu Asn Gln Tyr Leu Val Gly Ser Gln Leu Pro<br>1125 1130 1135 | 3408 |
| tgc gag ccc gaa ccg gat gta gca gtg ctc act tcc atg ctc acc gac<br>Cys Glu Pro Glu Pro Asp Val Ala Val Leu Thr Ser Met Leu Thr Asp<br>1140 1145 1150 | 3456 |
| ccc tcc cac atc aca gca gaa acg gct aag cgt agg ttg gcc agg ggg<br>Pro Ser His Ile Thr Ala Glu Thr Ala Lys Arg Arg Leu Ala Arg Gly<br>1155 1160 1165 | 3504 |
| tct ccc ccc tcc ttg gcc agc tct tca gct agc cag ttg tct gcg cct<br>Ser Pro Pro Ser Leu Ala Ser Ser Ser Ala Ser Gln Leu Ser Ala Pro<br>1170 1175 1180 | 3552 |
| tcc ttg aag gcg aca tgc act acc cac cat gtc tct ccg gac gct gac<br>Ser Leu Lys Ala Thr Cys Thr Thr His His Val Ser Pro Asp Ala Asp<br>1185 1190 1195 1200 | 3600 |

-continued

| | |
|---|---|
| ctc atc gag gcc aac ctc ctg tgg cgg cag gag atg ggc ggg aac atc<br>Leu Ile Glu Ala Asn Leu Leu Trp Arg Gln Glu Met Gly Gly Asn Ile<br>                1205                    1210                  1215 | 3648 |
| acc cgc gtg gag tcg gag aac aag gtg gta gtc ctg gac tct ttc gac<br>Thr Arg Val Glu Ser Glu Asn Lys Val Val Val Leu Asp Ser Phe Asp<br>         1220                  1225                  1230 | 3696 |
| ccg ctt cga gcg gag gag gat gag agg gaa gta tcc gtt ccg gcg gag<br>Pro Leu Arg Ala Glu Glu Asp Glu Arg Glu Val Ser Val Pro Ala Glu<br>            1235                  1240                  1245 | 3744 |
| atc ctg cgg aaa tcc aag aag ttc ccc gca gcg atg ccc atc tgg gcg<br>Ile Leu Arg Lys Ser Lys Lys Phe Pro Ala Ala Met Pro Ile Trp Ala<br>        1250                  1255                  1260 | 3792 |
| cgc ccg gat tac aac cct cca ctg tta gag tcc tgg aag gac ccg gac<br>Arg Pro Asp Tyr Asn Pro Pro Leu Leu Glu Ser Trp Lys Asp Pro Asp<br>1265                  1270                  1275                  1280 | 3840 |
| tac gtc cct ccg gtg gtg cac ggg tgc ccg ttg cca cct atc aag gcc<br>Tyr Val Pro Pro Val Val His Gly Cys Pro Leu Pro Pro Ile Lys Ala<br>                      1285                  1290                  1295 | 3888 |
| cct cca ata cca cct cca cgg aga aag agg acg gtt gtc cta aca gag<br>Pro Pro Ile Pro Pro Pro Arg Arg Lys Arg Thr Val Val Leu Thr Glu<br>            1300                  1305                  1310 | 3936 |
| tcc tcc gtg tct tct gcc tta gcg gag ctc gct act aag acc ttc ggc<br>Ser Ser Val Ser Ser Ala Leu Ala Glu Leu Ala Thr Lys Thr Phe Gly<br>        1315                  1320                  1325 | 3984 |
| agc tcc gaa tca tcg gcc gtc gac agc ggc acg gcg acc gcc ctt cct<br>Ser Ser Glu Ser Ser Ala Val Asp Ser Gly Thr Ala Thr Ala Leu Pro<br>            1330                  1335                  1340 | 4032 |
| gac cag gcc tcc gac gac ggt gac aaa gga tcc gac gtt gag tcg tac<br>Asp Gln Ala Ser Asp Asp Gly Asp Lys Gly Ser Asp Val Glu Ser Tyr<br>1345                  1350                  1355                  1360 | 4080 |
| tcc tcc atg ccc ccc ctt gag ggg gaa ccg ggg gac ccc gat ctc agt<br>Ser Ser Met Pro Pro Leu Glu Gly Glu Pro Gly Asp Pro Asp Leu Ser<br>                      1365                  1370                  1375 | 4128 |
| gac ggg tct tgg tct acc gtg agc gag gaa gct agt gag gat gtc gtc<br>Asp Gly Ser Trp Ser Thr Val Ser Glu Glu Ala Ser Glu Asp Val Val<br>            1380                  1385                  1390 | 4176 |
| tgc tgc tca atg tcc tac aca tgg aca ggc gcc ttg atc acg cca tgc<br>Cys Cys Ser Met Ser Tyr Thr Trp Thr Gly Ala Leu Ile Thr Pro Cys<br>        1395                  1400                  1405 | 4224 |
| gct gcg gag gaa agc aag ctg ccc atc aac gcg ttg agc aac tct ttg<br>Ala Ala Glu Glu Ser Lys Leu Pro Ile Asn Ala Leu Ser Asn Ser Leu<br>            1410                  1415                  1420 | 4272 |
| ctg cgc cac cat aac atg gtt tat gcc aca aca tct cgc agc gca ggc<br>Leu Arg His His Asn Met Val Tyr Ala Thr Thr Ser Arg Ser Ala Gly<br>1425                  1430                  1435                  1440 | 4320 |
| ctg cgg cag aag aag gtc acc ttt gac aga ctg caa gtc ctg gac gac<br>Leu Arg Gln Lys Lys Val Thr Phe Asp Arg Leu Gln Val Leu Asp Asp<br>                    1445                  1450                  1455 | 4368 |
| cac tac cgg gac gtg ctc aag gag atg aag gcg aag gcg tcc aca gtt<br>His Tyr Arg Asp Val Leu Lys Glu Met Lys Ala Lys Ala Ser Thr Val<br>            1460                  1465                  1470 | 4416 |
| aag gct aaa ctc cta tcc gta gag gaa gcc tgc aag ctg acg ccc cca<br>Lys Ala Lys Leu Leu Ser Val Glu Glu Ala Cys Lys Leu Thr Pro Pro<br>        1475                  1480                  1485 | 4464 |
| cat tcg gcc aaa tcc aag ttt ggc tat ggg gca aag gac gtc cgg aac<br>His Ser Ala Lys Ser Lys Phe Gly Tyr Gly Ala Lys Asp Val Arg Asn<br>            1490                  1495                  1500 | 4512 |
| cta tcc agc aag gcc gtt aac cac atc cac tcc gtg tgg aag gac ttg<br>Leu Ser Ser Lys Ala Val Asn His Ile His Ser Val Trp Lys Asp Leu | 4560 |

```
              1505                1510                1515                1520
ctg gaa gac act gtg aca cca att gac acc acc atc atg gca aaa aat        4608
Leu Glu Asp Thr Val Thr Pro Ile Asp Thr Thr Ile Met Ala Lys Asn
                    1525                1530                1535 gag gtt ttc tgt gtc caa cca gag aaa gga ggc cgt aag cca gcc cgc        4656
Glu Val Phe Cys Val Gln Pro Glu Lys Gly Gly Arg Lys Pro Ala Arg
            1540                1545                1550 ctt atc gta ttc cca gat ctg gga gtc cgt gta tgc gag aag atg gcc        4704
Leu Ile Val Phe Pro Asp Leu Gly Val Arg Val Cys Glu Lys Met Ala
        1555                1560                1565 ctc tat gat gtg gtc tcc acc ctt cct cag gtc gtg atg ggc tcc tca        4752
Leu Tyr Asp Val Val Ser Thr Leu Pro Gln Val Val Met Gly Ser Ser
    1570                1575                1580 tac gga ttc cag tac tct cct ggg cag cga gtc gag ttc ctg gtg aat        4800
Tyr Gly Phe Gln Tyr Ser Pro Gly Gln Arg Val Glu Phe Leu Val Asn
1585                1590                1595                1600 acc tgg aaa tca aag aaa aac ccc atg ggc ttt tca tat gac act cgc        4848
Thr Trp Lys Ser Lys Lys Asn Pro Met Gly Phe Ser Tyr Asp Thr Arg
                1605                1610                1615 tgt ttc gac tca acg gtc acc gag aac gac atc cgt gtt gag gag tca        4896
Cys Phe Asp Ser Thr Val Thr Glu Asn Asp Ile Arg Val Glu Glu Ser
            1620                1625                1630 att tac caa tgt tgt gac ttg gcc ccc gaa gcc aga cag gcc ata aaa        4944
Ile Tyr Gln Cys Cys Asp Leu Ala Pro Glu Ala Arg Gln Ala Ile Lys
        1635                1640                1645 tcg ctc aca gag cgg ctt tat atc ggg ggt cct ctg act aat tca aaa        4992
Ser Leu Thr Glu Arg Leu Tyr Ile Gly Gly Pro Leu Thr Asn Ser Lys
    1650                1655                1660 ggg cag aac tgc ggt tat cgc cgg tgc cgc gcg agc ggc gtg ctg acg        5040
Gly Gln Asn Cys Gly Tyr Arg Arg Cys Arg Ala Ser Gly Val Leu Thr
1665                1670                1675                1680 act agc tgc ggt aac acc ctc aca tgt tac ttg aag gcc tct gca gcc        5088
Thr Ser Cys Gly Asn Thr Leu Thr Cys Tyr Leu Lys Ala Ser Ala Ala
                1685                1690                1695 tgt cga gct gcg aag ctc cag gac tgc acg atg ctc gtg aac gga gac        5136
Cys Arg Ala Ala Lys Leu Gln Asp Cys Thr Met Leu Val Asn Gly Asp
            1700                1705                1710 gac ctt gtc gtt atc tgt gaa agc gcg gga acc caa gag gac gcg gcg        5184
Asp Leu Val Val Ile Cys Glu Ser Ala Gly Thr Gln Glu Asp Ala Ala
        1715                1720                1725 agc cta cga gtc ttc acg gag gct atg act agg tac tct gcc ccc ccc        5232
Ser Leu Arg Val Phe Thr Glu Ala Met Thr Arg Tyr Ser Ala Pro Pro
    1730                1735                1740 ggg gac ccg ccc caa cca gaa tac gac ttg gag ctg ata aca tca tgt        5280
Gly Asp Pro Pro Gln Pro Glu Tyr Asp Leu Glu Leu Ile Thr Ser Cys
1745                1750                1755                1760 tcc tcc aat gtg tcg gtc gcc cac gat gca tca ggc aaa agg gtg tac        5328
Ser Ser Asn Val Ser Val Ala His Asp Ala Ser Gly Lys Arg Val Tyr
                1765                1770                1775 tac ctc acc cgt gat ccc acc acc ccc ctc gca cgg gct gcg tgg gaa        5376
Tyr Leu Thr Arg Asp Pro Thr Thr Pro Leu Ala Arg Ala Ala Trp Glu
            1780                1785                1790 aca gct aga cac act cca gtt aac tcc tgg cta ggc aac att atc atg        5424
Thr Ala Arg His Thr Pro Val Asn Ser Trp Leu Gly Asn Ile Ile Met
        1795                1800                1805 tat gcg ccc act ttg tgg gca agg atg att ctg atg act cac ttc ttc        5472
Tyr Ala Pro Thr Leu Trp Ala Arg Met Ile Leu Met Thr His Phe Phe
    1810                1815                1820 tcc atc ctt cta gca cag gag caa ctt gaa aaa gcc ctg gac tgc cag        5520
```

```
Ser Ile Leu Leu Ala Gln Glu Gln Leu Glu Lys Ala Leu Asp Cys Gln
1825                1830                1835                1840 atc tac ggg gcc tgt tac tcc att gag cca ctt gac cta cct cag atc    5568
Ile Tyr Gly Ala Cys Tyr Ser Ile Glu Pro Leu Asp Leu Pro Gln Ile
                1845                1850                1855 att gaa cga ctc cat ggc ctt agc gca ttt tca ctc cat agt tac tct    5616
Ile Glu Arg Leu His Gly Leu Ser Ala Phe Ser Leu His Ser Tyr Ser
        1860                1865                1870 cca ggt gag atc aat agg gtg gct tca tgc ctc agg aaa ctt ggg gta    5664
Pro Gly Glu Ile Asn Arg Val Ala Ser Cys Leu Arg Lys Leu Gly Val
    1875                1880                1885 cca ccc ttg cga gtc tgg aga cat cgg gcc agg agc gtc cgc gct agg    5712
Pro Pro Leu Arg Val Trp Arg His Arg Ala Arg Ser Val Arg Ala Arg
1890                1895                1900 cta ctg tcc cag ggg ggg agg gcc gcc act tgt ggc aag tac ctc ttc    5760
Leu Leu Ser Gln Gly Gly Arg Ala Ala Thr Cys Gly Lys Tyr Leu Phe
1905                1910                1915                1920 aac tgg gca gtg aag acc aaa ctc aaa ctc act cca atc ccg gct gcg    5808
Asn Trp Ala Val Lys Thr Lys Leu Lys Leu Thr Pro Ile Pro Ala Ala
                1925                1930                1935 tcc cag ctg gac ttg tcc ggc tgg ttc gtt gct ggt tac agc ggg gga    5856
Ser Gln Leu Asp Leu Ser Gly Trp Phe Val Ala Gly Tyr Ser Gly Gly
                1940                1945                1950 gac ata tat cac agc ctg tct cgt gcc cga ccc cgc tgg ttc atg ctg    5904
Asp Ile Tyr His Ser Leu Ser Arg Ala Arg Pro Arg Trp Phe Met Leu
        1955                1960                1965 tgc cta ctc cta ctt tct gta ggg gta ggc atc tac ctg ctc ccc aac    5952
Cys Leu Leu Leu Leu Ser Val Gly Val Gly Ile Tyr Leu Leu Pro Asn
    1970                1975                1980 cga                                                                 5955
Arg
1985

<210> SEQ ID NO 6
<211> LENGTH: 1985
<212> TYPE: PRT
<213> ORGANISM: Artificial Sequence
<220> FEATURE:
<223> OTHER INFORMATION: NS sequence

<400> SEQUENCE: 6

Met Ala Pro Ile Thr Ala Tyr Ser Gln Gln Thr Arg Gly Leu Leu Gly
1               5                   10                  15

Cys Ile Ile Thr Ser Leu Thr Gly Arg Asp Lys Asn Gln Val Glu Gly
                20                  25                  30

Glu Val Gln Val Val Ser Thr Ala Thr Gln Ser Phe Leu Ala Thr Cys
            35                  40                  45

Val Asn Gly Val Cys Trp Thr Val Tyr His Gly Ala Gly Ser Lys Thr
        50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140
```

-continued

```
Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Val Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ser Thr Thr Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Asn Thr Gly Glu Ile Pro Phe Tyr Gly
            340                 345                 350

Lys Ala Ile Pro Ile Glu Ala Ile Arg Gly Gly Arg His Leu Ile Phe
        355                 360                 365

Cys His Ser Lys Lys Cys Asp Glu Leu Ala Ala Lys Leu Ser Gly Leu
    370                 375                 380

Leu Gly Ile Asn Ala Val Ala Tyr Tyr Arg Gly Leu Asp Val Ser Val
385                 390                 395                 400

Ile Pro Thr Ile Gly Asp Val Val Val Ala Thr Asp Ala Leu Met
                405                 410                 415

Thr Gly Tyr Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Thr Thr Val Pro Gln Asp Ala Val Ser Arg Ser Gln Arg Arg Gly
    450                 455                 460

Arg Thr Gly Arg Gly Arg Gly Ile Tyr Arg Phe Val Thr Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
        515                 520                 525

His Leu Glu Phe Trp Glu Ser Val Phe Thr Gly Leu Thr His Ile Asp
    530                 535                 540

Ala His Phe Leu Ser Gln Thr Lys Gln Ala Gly Asp Asn Phe Pro Tyr
545                 550                 555                 560
```

-continued

```
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
            580                 585                 590
Leu His Gly Pro Thr Pro Leu Leu Tyr Arg Leu Gly Ala Val Gln Asn
        595                 600                 605
Glu Val Thr Leu Thr His Pro Ile Thr Lys Tyr Ile Met Ala Cys Met
    610                 615                 620
Ser Ala Asp Leu Glu Val Val Thr Ser Thr Trp Val Leu Val Gly Gly
625                 630                 635                 640
Val Leu Ala Ala Leu Ala Ala Tyr Cys Leu Thr Thr Gly Ser Val Val
                645                 650                 655
Ile Val Gly Arg Ile Ile Leu Ser Gly Arg Pro Ala Ile Val Pro Asp
                660                 665                 670
Arg Glu Phe Leu Tyr Gln Glu Phe Asp Glu Met Glu Glu Cys Ala Ser
                675                 680                 685
His Leu Pro Tyr Ile Glu Gln Gly Met Gln Leu Ala Glu Gln Phe Lys
            690                 695                 700
Gln Lys Ala Leu Gly Leu Leu Gln Thr Ala Thr Lys Gln Ala Glu Ala
705                 710                 715                 720
Ala Ala Pro Val Val Glu Ser Lys Trp Arg Ala Leu Glu Thr Phe Trp
                725                 730                 735
Ala Lys His Met Trp Asn Phe Ile Ser Gly Ile Gln Tyr Leu Ala Gly
            740                 745                 750
Leu Ser Thr Leu Pro Gly Asn Pro Ala Ile Ala Ser Leu Met Ala Phe
        755                 760                 765
Thr Ala Ser Ile Thr Ser Pro Leu Thr Thr Gln Ser Thr Leu Leu Phe
    770                 775                 780
Asn Ile Leu Gly Gly Trp Val Ala Ala Gln Leu Ala Pro Pro Ser Ala
785                 790                 795                 800
Ala Ser Ala Phe Val Gly Ala Gly Ile Ala Gly Ala Ala Val Gly Ser
                805                 810                 815
Ile Gly Leu Gly Lys Val Leu Val Asp Ile Leu Ala Gly Tyr Gly Ala
                820                 825                 830
Gly Val Ala Gly Ala Leu Val Ala Phe Lys Val Met Ser Gly Glu Met
            835                 840                 845
Pro Ser Thr Glu Asp Leu Val Asn Leu Leu Pro Ala Ile Leu Ser Pro
        850                 855                 860
Gly Ala Leu Val Val Gly Val Val Cys Ala Ala Ile Leu Arg Arg His
865                 870                 875                 880
Val Gly Pro Gly Glu Gly Ala Val Gln Trp Met Asn Arg Leu Ile Ala
                885                 890                 895
Phe Ala Ser Arg Gly Asn His Val Ser Pro Thr His Tyr Val Pro Glu
            900                 905                 910
Ser Asp Ala Ala Ala Arg Val Thr Gln Ile Leu Ser Ser Leu Thr Ile
        915                 920                 925
Thr Gln Leu Leu Lys Arg Leu His Gln Trp Ile Asn Glu Asp Cys Ser
    930                 935                 940
Thr Pro Cys Ser Gly Ser Trp Leu Arg Asp Val Trp Asp Trp Ile Cys
945                 950                 955                 960
Thr Val Leu Thr Asp Phe Lys Thr Trp Leu Gln Ser Lys Leu Leu Pro
                965                 970                 975
Gln Leu Pro Gly Val Pro Phe Phe Ser Cys Gln Arg Gly Tyr Lys Gly
```

-continued

```
                980             985             990
Val Trp Arg Gly Asp Gly Ile Met Gln Thr Thr Cys Pro Cys Gly Ala
        995                 1000                1005
Gln Ile Thr Gly His Val Lys Asn Gly Ser Met Arg Ile Val Gly Pro
        1010                1015                1020
Lys Thr Cys Ser Asn Thr Trp His Gly Thr Phe Pro Ile Asn Ala Tyr
1025                1030                1035                1040
Thr Thr Gly Pro Cys Thr Pro Ser Pro Ala Pro Asn Tyr Ser Arg Ala
                1045                1050                1055
Leu Trp Arg Val Ala Ala Glu Glu Tyr Val Glu Val Thr Arg Val Gly
                1060                1065                1070
Asp Phe His Tyr Val Thr Gly Met Thr Thr Asp Asn Val Lys Cys Pro
                1075                1080                1085
Cys Gln Val Pro Ala Pro Glu Phe Phe Thr Glu Val Asp Gly Val Arg
                1090                1095                1100
Leu His Arg Tyr Ala Pro Ala Cys Arg Pro Leu Leu Arg Glu Glu Val
1105                1110                1115                1120
Thr Phe Gln Val Gly Leu Asn Gln Tyr Leu Val Gly Ser Gln Leu Pro
                1125                1130                1135
Cys Glu Pro Glu Pro Asp Val Ala Val Leu Thr Ser Met Leu Thr Asp
                1140                1145                1150
Pro Ser His Ile Thr Ala Glu Thr Ala Lys Arg Arg Leu Ala Arg Gly
                1155                1160                1165
Ser Pro Pro Ser Leu Ala Ser Ser Ser Ala Ser Gln Leu Ser Ala Pro
                1170                1175                1180
Ser Leu Lys Ala Thr Cys Thr Thr His His Val Ser Pro Asp Ala Asp
1185                1190                1195                1200
Leu Ile Glu Ala Asn Leu Leu Trp Arg Gln Glu Met Gly Gly Asn Ile
                1205                1210                1215
Thr Arg Val Glu Ser Glu Asn Lys Val Val Leu Asp Ser Phe Asp
                1220                1225                1230
Pro Leu Arg Ala Glu Glu Asp Glu Arg Glu Val Ser Val Pro Ala Glu
                1235                1240                1245
Ile Leu Arg Lys Ser Lys Lys Phe Pro Ala Ala Met Pro Ile Trp Ala
1250                1255                1260
Arg Pro Asp Tyr Asn Pro Pro Leu Leu Glu Ser Trp Lys Asp Pro Asp
1265                1270                1275                1280
Tyr Val Pro Pro Val Val His Gly Cys Pro Leu Pro Pro Ile Lys Ala
                1285                1290                1295
Pro Pro Ile Pro Pro Pro Arg Arg Lys Arg Thr Val Val Leu Thr Glu
                1300                1305                1310
Ser Ser Val Ser Ser Ala Leu Ala Glu Leu Ala Thr Lys Thr Phe Gly
                1315                1320                1325
Ser Ser Glu Ser Ser Ala Val Asp Ser Gly Thr Ala Thr Ala Leu Pro
                1330                1335                1340
Asp Gln Ala Ser Asp Asp Gly Asp Lys Gly Ser Asp Val Glu Ser Tyr
1345                1350                1355                1360
Ser Ser Met Pro Pro Leu Glu Gly Glu Pro Gly Asp Pro Asp Leu Ser
                1365                1370                1375
Asp Gly Ser Trp Ser Thr Val Ser Glu Glu Ala Ser Glu Asp Val Val
                1380                1385                1390
Cys Cys Ser Met Ser Tyr Thr Trp Thr Gly Ala Leu Ile Thr Pro Cys
                1395                1400                1405
```

-continued

```
Ala Ala Glu Glu Ser Lys Leu Pro Ile Asn Ala Leu Ser Asn Ser Leu
    1410                1415                1420

Leu Arg His His Asn Met Val Tyr Ala Thr Thr Ser Arg Ser Ala Gly
1425            1430                1435                1440

Leu Arg Gln Lys Lys Val Thr Phe Asp Arg Leu Gln Val Leu Asp Asp
            1445                1450                1455

His Tyr Arg Asp Val Leu Lys Glu Met Lys Ala Lys Ala Ser Thr Val
        1460                1465                1470

Lys Ala Lys Leu Leu Ser Val Glu Glu Ala Cys Lys Leu Thr Pro Pro
    1475                1480                1485

His Ser Ala Lys Ser Lys Phe Gly Tyr Gly Ala Lys Asp Val Arg Asn
1490                1495                1500

Leu Ser Ser Lys Ala Val Asn His Ile His Ser Val Trp Lys Asp Leu
1505                1510                1515                1520

Leu Glu Asp Thr Val Thr Pro Ile Asp Thr Thr Ile Met Ala Lys Asn
            1525                1530                1535

Glu Val Phe Cys Val Gln Pro Glu Lys Gly Gly Arg Lys Pro Ala Arg
        1540                1545                1550

Leu Ile Val Phe Pro Asp Leu Gly Val Arg Val Cys Glu Lys Met Ala
    1555                1560                1565

Leu Tyr Asp Val Val Ser Thr Leu Pro Gln Val Val Met Gly Ser Ser
    1570                1575                1580

Tyr Gly Phe Gln Tyr Ser Pro Gly Gln Arg Val Glu Phe Leu Val Asn
1585                1590                1595                1600

Thr Trp Lys Ser Lys Lys Asn Pro Met Gly Phe Ser Tyr Asp Thr Arg
            1605                1610                1615

Cys Phe Asp Ser Thr Val Thr Glu Asn Asp Ile Arg Val Glu Glu Ser
        1620                1625                1630

Ile Tyr Gln Cys Cys Asp Leu Ala Pro Glu Ala Arg Gln Ala Ile Lys
    1635                1640                1645

Ser Leu Thr Glu Arg Leu Tyr Ile Gly Gly Pro Leu Thr Asn Ser Lys
    1650                1655                1660

Gly Gln Asn Cys Gly Tyr Arg Arg Cys Arg Ala Ser Gly Val Leu Thr
1665                1670                1675                1680

Thr Ser Cys Gly Asn Thr Leu Thr Cys Tyr Leu Lys Ala Ser Ala Ala
            1685                1690                1695

Cys Arg Ala Ala Lys Leu Gln Asp Cys Thr Met Leu Val Asn Gly Asp
        1700                1705                1710

Asp Leu Val Val Ile Cys Glu Ser Ala Gly Thr Gln Glu Asp Ala Ala
    1715                1720                1725

Ser Leu Arg Val Phe Thr Glu Ala Met Thr Arg Tyr Ser Ala Pro Pro
    1730                1735                1740

Gly Asp Pro Pro Gln Pro Glu Tyr Asp Leu Glu Leu Ile Thr Ser Cys
1745                1750                1755                1760

Ser Ser Asn Val Ser Val Ala His Asp Ala Ser Gly Lys Arg Val Tyr
            1765                1770                1775

Tyr Leu Thr Arg Asp Pro Thr Thr Pro Leu Ala Arg Ala Ala Trp Glu
        1780                1785                1790

Thr Ala Arg His Thr Pro Val Asn Ser Trp Leu Gly Asn Ile Ile Met
    1795                1800                1805

Tyr Ala Pro Thr Leu Trp Ala Arg Met Ile Leu Met Thr His Phe Phe
    1810                1815                1820
```

-continued

Ser Ile Leu Leu Ala Gln Glu Gln Leu Glu Lys Ala Leu Asp Cys Gln
1825                1830                1835                1840

Ile Tyr Gly Ala Cys Tyr Ser Ile Glu Pro Leu Asp Leu Pro Gln Ile
            1845                1850                1855

Ile Glu Arg Leu His Gly Leu Ser Ala Phe Ser Leu His Ser Tyr Ser
        1860                1865                1870

Pro Gly Glu Ile Asn Arg Val Ala Ser Cys Leu Arg Lys Leu Gly Val
    1875                1880                1885

Pro Pro Leu Arg Val Trp Arg His Arg Ala Arg Ser Val Arg Ala Arg
        1890                1895                1900

Leu Leu Ser Gln Gly Gly Arg Ala Ala Thr Cys Gly Lys Tyr Leu Phe
1905                1910                1915                1920

Asn Trp Ala Val Lys Thr Lys Leu Lys Leu Thr Pro Ile Pro Ala Ala
            1925                1930                1935

Ser Gln Leu Asp Leu Ser Gly Trp Phe Val Ala Gly Tyr Ser Gly Gly
        1940                1945                1950

Asp Ile Tyr His Ser Leu Ser Arg Ala Arg Pro Arg Trp Phe Met Leu
    1955                1960                1965

Cys Leu Leu Leu Leu Ser Val Gly Val Gly Ile Tyr Leu Leu Pro Asn
        1970                1975                1980

Arg
1985

<210> SEQ ID NO 7
<211> LENGTH: 4909
<212> TYPE: DNA
<213> ORGANISM: Artificial Sequence
<220> FEATURE:
<223> OTHER INFORMATION: pV1J nucleic acid

<400> SEQUENCE: 7

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccctttggc     1080
```

```
tcttatgcat gctatactgt ttttggcttg gggcctatac accccgcttc cctatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tattttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtccttagat ctaggtacca gatatcagaa ttcagtcgac agcggccgcg   1920
atctgctgtg ccttctagtt gccagccatc tgttgtttgc ccctccccg tgccttcctt   1980
gaccctggaa ggtgccactc ccactgtcct ttcctaataa aatgaggaaa ttgcatcgca   2040
ttgtctgagt aggtgtcatt ctattctggg gggtggggtg gggcaggaca gcaaggggga   2100
ggattgggaa gacaatagca ggcatgctgg ggatgcggtg ggctctatgg ccgctgcggc   2160
caggtgctga agaattgacc cggttcctcc tgggccagaa agaagcaggc acatcccctt   2220
ctctgtgaca caccctgtcc acgccctggg ttcttagttc cagccccact cataggacac   2280
tcatagctca ggagggctcc gccttcaatc ccaccgcta aagtacttgg agcggtctct   2340
ccctccctca tcagcccacc aaaccaaacc tagcctccaa gagtgggaag aaattaaagc   2400
aagataggct attaagtgca gagggagaga aaatgcctcc aacatgtgag gaagtaatga   2460
gagaaatcat agaatttctt ccgcttcctc gctcactgac tcgctgcgct cggtcgttcg   2520
gctgcggcga gcggtatcag ctcactcaaa ggcggtaata cggttatcca cagaatcagg   2580
ggataacgca ggaaagaaca tgtgagcaaa aggccagcaa aaggccagga accgtaaaaa   2640
ggccgcgttg ctggcgtttt tccataggct ccgcccccct gacgagcatc acaaaaatcg   2700
acgctcaagt cagaggtggc gaaacccgac aggactataa agataccagg cgtttccccc   2760
tggaagctcc ctcgtgcgct ctcctgttcc gaccctgccg cttaccggat acctgtccgc   2820
ctttctccct tcgggaagcg tggcgctttc tcatagctca cgctgtaggt atctcagttc   2880
ggtgtaggtc gttcgctcca agctgggctg tgtgcacgaa ccccccgttc agcccgaccg   2940
ctgcgcctta tccggtaact atcgtcttga gtccaacccg gtaagacacg acttatcgcc   3000
actggcagca gccactggta acaggattag cagagcgagg tatgtaggcg gtgctacaga   3060
gttcttgaag tggtggccta actacggcta cactagaaga acagtatttg gtatctgcgc   3120
tctgctgaag ccagttacct tcggaaaaag agttggtagc tcttgatccg gcaaacaaac   3180
caccgctggt agcggtggtt ttttgtttg caagcagcag attacgcgca gaaaaaagg   3240
atctcaagaa gatcctttga tcttttctac ggggtctgac gctcagtgga acgaaaactc   3300
acgttaaggg attttggtca tgagattatc aaaaaggatc ttcacctaga tccttttaaa   3360
ttaaaaatga agttttaaat caatctaaag tatatatgag taaacttggt ctgacagtta   3420
ccaatgctta atcagtgagg cacctatctc agcgatctgt ctatttcgtt catccatagt   3480
```

| | |
|---|---|
| tgcctgactc gggggggggg ggcgctgagg tctgcctcgt gaagaaggtg ttgctgactc | 3540 |
| ataccaggcc tgaatcgccc catcatccag ccagaaagtg agggagccac ggttgatgag | 3600 |
| agctttgttg taggtggacc agttggtgat tttgaacttt tgctttgcca cggaacggtc | 3660 |
| tgcgttgtcg ggaagatgcg tgatctgatc cttcaactca gcaaaagttc gatttattca | 3720 |
| acaaagccgc cgtcccgtca agtcagcgta atgctctgcc agtgttacaa ccaattaacc | 3780 |
| aattctgatt agaaaaactc atcgagcatc aaatgaaact gcaatttatt catatcagga | 3840 |
| ttatcaatac catattttg aaaaagccgt ttctgtaatg aaggagaaaa ctcaccgagg | 3900 |
| cagttccata ggatggcaag atcctggtat cggtctgcga ttccgactcg tccaacatca | 3960 |
| atacaaccta ttaatttccc ctcgtcaaaa ataaggttat caagtgagaa atcaccatga | 4020 |
| gtgacgactg aatccggtga gaatggcaaa agcttatgca tttctttcca gacttgttca | 4080 |
| acaggccagc cattacgctc gtcatcaaaa tcactcgcat caaccaaacc gttattcatt | 4140 |
| cgtgattgcg cctgagcgag acgaaatacg cgatcgctgt taaaaggaca attacaaaca | 4200 |
| ggaatcgaat gcaaccggcg caggaacact gccagcgcat caacaatatt ttcacctgaa | 4260 |
| tcaggatatt cttctaatac ctggaatgct gttttcccgg ggatcgcagt ggtgagtaac | 4320 |
| catgcatcat caggagtacg gataaaatgc ttgatggtcg gaagaggcat aaattccgtc | 4380 |
| agccagttta gtctgaccat ctcatctgta acatcattgg caacgctacc tttgccatgt | 4440 |
| ttcagaaaca actctggcgc atcgggcttc ccatacaatc gatagattgt cgcacctgat | 4500 |
| tgcccgacat tatcgcgagc ccatttatac ccatataaat cagcatccat gttggaattt | 4560 |
| aatcgcggcc tcgagcaaga cgtttcccgt tgaatatggc tcataacacc ccttgtatta | 4620 |
| ctgtttatgt aagcagacag ttttattgtt catgatgata tatttttatc ttgtgcaatg | 4680 |
| taacatcaga gattttgaga cacaacgtgg ctttcccccc ccccccatta ttgaagcatt | 4740 |
| tatcagggtt attgtctcat gagcggatac atatttgaat gtatttagaa aaataaacaa | 4800 |
| atagggttc cgcgcacatt tccccgaaaa gtgccacctg acgtctaaga aaccattatt | 4860 |
| atcatgacat taacctataa aaataggcgt atcacgaggc cctttcgtc | 4909 |

<210> SEQ ID NO 8
<211> LENGTH: 35935
<212> TYPE: DNA
<213> ORGANISM: Adenovirus serotype 6

<400> SEQUENCE: 8

| | |
|---|---|
| catcatcaat aatataccett attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgtttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggccgcggg | 360 |
| gactttgacc gtttacgtgg agactcgccc aggtgttttt ctcaggtgtt ttccgcgttc | 420 |
| cgggtcaaag ttggcgtttt attattatag tcagctgacg tgtagtgtat ttatacccgg | 480 |
| tgagttcctc aagaggccac tcttgagtgc cagcgagtag agtttctcc tccgagccgc | 540 |
| tccgacaccg ggactgaaaa tgagacatat tatctgccac ggaggtgtta ttaccgaaga | 600 |
| aatggccgcc agtcttttgg accagctgat cgaagaggta ctggctgata atcttccacc | 660 |

```
tcctagccat tttgaaccac ctacccttca cgaactgtat gatttagacg tgacggcccc      720
cgaagatccc aacgaggagg cggtttcgca gattttccc gactctgtaa tgttggcggt       780
gcaggaaggg attgacttac tcacttttcc gccggcgccc ggttctccgg agccgcctca      840
cctttcccgg cagcccgagc agccggagca gagagccttg ggtccggttt ctatgccaaa     900
ccttgtaccg gaggtgatcg atcttacctg ccacgaggct ggcttccac ccagtgacga       960 cgaggatgaa gagggtgagg agtttgtgtt agattatgtg gagcaccccg ggcacggttg     1020
caggtcttgt cattatcacc ggaggaatac gggggaccca gatattatgt gttcgctttg     1080
ctatatgagg acctgtggca tgtttgtcta cagtaagtga aaattatggg cagtgggtga     1140
tagagtggtg ggtttggtgt ggtaattttt tttttaattt ttacagtttt gtggtttaaa     1200
gaattttgta ttgtgatttt tttaaaaggt cctgtgtctg aacctgagcc tgagcccgag     1260
ccagaaccgg agcctgcaag acctacccgc cgtcctaaaa tggcgcctgc tatcctgaga     1320
cgcccgacat cacctgtgtc tagagaatgc aatagtagta cggatagctg tgactccggt     1380
ccttctaaca cacctcctga gatacacccg gtggtcccgc tgtgccccat taaaccagtt     1440
gccgtgagag ttggtgggcg tcgccaggct gtggaatgta tcgaggactt gcttaacgag     1500
cctgggcaac ctttggactt gagctgtaaa cgccccaggc cataaggtgt aaacctgtga     1560
ttgcgtgtgt ggttaacgcc tttgtttgct gaatgagttg atgtaagttt aataaagggt     1620
gagataatgt ttaacttgca tggcgtgtta aatggggcgg ggcttaaagg gtatataatg     1680
cgccgtgggc taatcttggt tacatctgac ctcatggagg cttgggagtg tttggaagat     1740
ttttctgctg tgcgtaactt gctggaacag agctctaaca gtacctcttg gttttggagg     1800
tttctgtggg gctcatccca ggcaaagtta gtctgcagaa ttaaggagga ttacaagtgg     1860
gaatttgaag agcttttgaa atcctgtggt gagctgtttg attctttgaa tctgggtcac     1920
caggcgcttt tccaagagaa ggtcatcaag actttggatt tttccacacc ggggcgcgct     1980
gcggctgctg ttgcttttttt gagttttata aaggataaat ggagcgaaga aacccatctg     2040 agcgggggt acctgctgga ttttctggcc atgcatctgt ggagagcggt tgtgagacac      2100
aagaatcgcc tgctactgtt gtcttccgtc cgcccggcga taataccgac ggaggagcag     2160
cagcagcagc aggaggaagc caggcggcgg cggcaggagc agagcccatg gaacccgaga     2220
gccggcctgg accctcggga atgaatgttg tacaggtggc tgaactgtat ccagaactga     2280
gacgcatttt gacaattaca gaggatgggc aggggctaaa gggggtaaag agggagcggg     2340
gggcttgtga ggctacagag gaggctagga atctagcttt tagcttaatg accagacacc     2400
gtcctgagtg tattactttt caacagatca aggataattg cgctaatgag cttgatctgc     2460
tggcgcagaa gtattccata gagcagctga ccacttactg gctgcagcca ggggatgatt     2520
ttgaggaggc tattagggta tatgcaaagg tggcacttag gccagattgc aagtacaaga     2580
tcagcaaact tgtaaatatc aggaattgtt gctacatttc tgggaacggg gccgaggtgg     2640
agatagatac ggaggatagg gtggccttta gatgtagcat gataaatatg tggccggggg     2700
tgcttggcat ggacgggtg gttattatga atgtaaggtt tactggcccc aattttagcg      2760
gtacggtttt cctggccaat accaacctta tcctacacgg tgtaagcttc tatgggttta     2820
acaatacctg tgtggaagcc tggaccgatg taagggttcg gggctgtgcc ttttactgct     2880
gctggaaggg ggtggtgtgt cgccccaaaa gcagggcttc aattaagaaa tgcctctttg     2940
aaaggtgtac cttgggtatc ctgtctgagg gtaactccag ggtgcgccac aatgtggcct     3000
ccgactgtgg ttgcttcatg ctagtgaaaa gcgtggctgt gattaagcat aacatggtat     3060
```

```
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag gggggtgttc ctaccttacc   3240
aatgcaattt gagtcacact aagatattgc ttgagcccga gagcatgtcc aaggtgaacc   3300 tgaacgggt gtttgacatg accatgaaga tctggaaggt gctgaggtac gatgagaccc    3360
gcaccaggtg cagaccctgc gagtgtggcg gtaaacatat taggaaccag cctgtgatgc   3420
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctctttg gcacaattgg attctttgac ccgggaactt aatgtcgttt    3960
ctcagcagct gttggatctg cgccagcagg tttctgccct gaaggcttcc tcccctccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320 cttttcagtag caagctgatt gccaggggca ggcccttggt gtaagtgttt acaaagcggt   4380
taagctggga tgggtgcata cgtggggata tgagatgcat cttggactgt attttaggt    4440 tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
ccaggatgag atcgtcatag gccatttta caaagcgcgg gcggagggtg ccagactgcg    4740
gtataatggt tccatccggc ccaggggcgt agttaccctc acagatttgc atttcccacg   4800
ctttgagttc agatgggggg atcatgtcta cctgcgggc gatgaagaaa acggtttccg    4860
gggtagggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct gcaaggaag    5100 caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacggggcg cagggtcctc gtcagcgtag tctgggtcac   5340
ggtgaagggg tgcgctccgg gctgcgcgct ggccagggtg cgcttgaggc tggtcctgct   5400
```

```
ggtgctgaag cgctgccggt cttcgccctg cgcgtcggcc aggtagcatt tgaccatggt    5460
gtcatagtcc agcccctccg cggcgtggcc cttggcgcgc agcttgccct tggaggaggc    5520
gccgcacgag gggcagtgca gacttttgag ggcgtagagc ttgggcgcga gaaataccga    5580
ttccggggag taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa gggggctat aaaagggggt gggggcgcgt tcgtcctcac tctcttccgc     6060
atcgctgtct gcgagggcca gctgttgggg tgagtactcc ctctgaaaag cgggcatgac    6120
ttctgcgcta agattgtcag tttccaaaaa cgaggaggat ttgatattca cctggcccgc    6180
ggtgatgcct ttgaggggtgg ccgcatccat ctggtcagaa aagacaatct tttttgttgtc  6240 aagcttggtg gcaaacgacc cgtagagggc gttggacagc aacttggcga tggagcgcag    6300
ggtttggttt ttgtcgcgat cggcgcgctc cttggccgcg atgtttagct gcacgtattc    6360
gcgcgcaacg caccgccatt cgggaaagac ggtggtgcgc tcgtcgggca ccaggtgcac    6420
gcgccaaccg cggttgtgca gggtgacaag gtcaacgctg gtggctacct ctccgcgtag    6480
gcgctcgttg gtccagcaga ggcggccgcc cttgcgcgag cagaatggcg gtaggggggtc   6540 tagctgcgtc tcgtccgggg ggtctgcgtc cacggtaaag accccgggca gcaggcgcgc    6600
gtcgaagtag tctatcttgc atccttgcaa gtctagcgcc tgctgccatg cgcgggcggc    6660
aagcgcgcgc tcgtatgggt tgagtggggg accccatggc atgggtggg tgagcgcgga     6720 ggcgtacatg ccgcaaatgt cgtaaacgta gaggggctct ctgagtattc caagatatgt    6780
agggtagcat cttccaccgc ggatgctggc gcgcacgtaa tcgtatagtt cgtgcgaggg    6840
agcgaggagg tcgggaccga ggttgctacg ggcgggctgc tctgctcgga agactatctg    6900
cctgaagatg gcatgtgagt tggatgatat ggttggacgc tggaagacgt tgaagctggc    6960
gtctgtgaga cctaccgcgt cacgcacgaa ggaggcgtag gagtcgcgca gcttgttgac    7020
cagctcggcg gtgacctgca cgtctagggc gcagtagtcc agggtttcct tgatgatgtc    7080
atacttatcc tgtccctttt ttttccacag ctcgcggttg aggacaaact cttcgcggtc    7140
tttccagtac tcttggatcg gaaacccgtc ggcctccgaa cggtaagagc ctagcatgta    7200
gaactggttg acggcctggt aggcgcagca tcccttttct acgggtagcg cgtatgcctg    7260
cgcggccttc cggagcgagg tgtgggtgag cgcaaaggtg tccctgacca tgactttgag    7320
gtactggtat ttgaagtcag tgtcgtcgca tccgccctgc tccagagcaa aaagtccgt    7380 gcgcttttg gaacgcggat ttggcagggc gaaggtgaca tcgttgaaga gtatctttcc     7440
cgcgcgaggc ataaagttgc gtgtgatgcg gaagggtccc ggcacctcgg aacggttgtt    7500
aattacctgg gcggcgagca cgatctcgtc aaagccgttg atgttgtggc ccacaatgta    7560
aagttccaag aagcgcggga tgcccttgat ggaaggcaat tttttaagtt cctcgtaggt    7620
gagctcttca ggggagctga gcccgtgctc tgaaagggcc cagtctgcaa gatgagggtt    7680
ggaagcgacg aatgagctcc acaggtcacg ggccattagc atttgcaggt ggtcgcgaaa    7740
ggtcctaaac tggcgaccta tggccatttt ttctggggtg atgcagtaga aggtaagcgg    7800
```

```
gtcttgttcc cagcggtccc atccaaggtt cgcggctagg tctcgcgcgg cagtcactag    7860
aggctcatct ccgccgaact tcatgaccag catgaagggc acgagctgct tcccaaaggc    7920
ccccatccaa gtataggtct ctacatcgta ggtgacaaag agacgctcgg tgcgaggatg    7980
cgagccgatc gggaagaact ggatctcccg ccaccaattg gaggagtggc tattgatgtg    8040
gtgaaagtag aagtccctgc gacgggccga acactcgtgc tggcttttgt aaaaacgtgc    8100
gcagtactgg cagcggtgca cgggctgtac atcctgcacg aggttgacct gacgaccgcg    8160
cacaaggaag cagagtggga atttgagccc ctcgcctggc gggtttggct ggtggtcttc    8220
tacttcggct gcttgtcctt gaccgtctgg ctgctcgagg ggagttacgg tggatcggac    8280
caccacgccg cgcgagccca aagtccagat gtccgcgcgc ggcggtcgga gcttgatgac    8340
aacatcgcgc agatgggagc tgtccatggt ctggagctcc cgcggcgtca ggtcaggcgg    8400
gagctcctgc aggtttacct cgcatagacg ggtcagggcg cgggctagat ccaggtgata    8460
cctaatttcc aggggctggt tggtggcggc gtcgatggct tgcaagaggc cgcatccccg    8520
cggcgcgact acggtaccgc gcggcggcg gtgggccgcg ggggtgtcct tggatgatgc    8580
atctaaaagc ggtgacgcgg gcgagccccc ggaggtaggg ggggctccgg accgccgggg    8640
agaggggca ggggcacgtc ggccgccgcg cgggcagga gctggtgctg cgcgcgtagg    8700
ttgctggcga acgcgacgac gcggcggttg atctcctgaa tctggcgcct ctgcgtgaag    8760
acgacgggcc cggtgagctt gagcctgaaa gagagttcga cagaatcaat ttcggtgtcg    8820
ttgacggcgg cctggcgcaa aatctcctgc acgtctcctg agttgtcttg ataggcgatc    8880
tcggccatga actgctcgat ctcttcctcc tggagatctc cgcgtccggc tcgctccacg    8940
gtggcggcga ggtcgttgga aatgcgggcc atgagctgcg agaaggcgtt gaggcctccc    9000
tcgttccaga cgcggctgta gaccacgccc ccttcggcat cgcgggcgcg catgaccacc    9060
tgcgcgagat tgagctccac gtgccgggcg aagacgcgcg agtttcgcag gcgctgaaag    9120
aggtagttga gggtggtggc ggtgtgttct gccacgaaga agtacataac ccagcgtcgc    9180
aacgtggatt cgttgatatc ccccaaggcc tcaaggcgct ccatggcctc gtagaagtcc    9240
acggcgaagt tgaaaaactg ggagttgcgc gccgacacgg ttaactcctc ctccagaaga    9300
cggatgagct cggcgacagt gtcgcgcacc tcgcgctcaa aggctacagg ggcctcttct    9360
tcttcttcaa tctcctcttc cataagggcc tcccctttctt cttcttctgg cggcggtggg    9420
ggagggggga cacggcggcg acgacggcgc accgggaggc ggtcgacaaa gcgctcgatc    9480
atctccccgc ggcgacggcg catggtctcg gtgacggcgc ggccgttctc gcggggcgc    9540
agttggaaga cgccgcccgt catgtcccgg ttatgggttg gcgggggct gccatgcggc    9600
agggatacgg cgctaacgat gcatctcaac aattgttgtg taggtactcc gccgccgagg    9660
gacctgagcg agtccgcatc gaccggatcg gaaaacctct cgagaaaggc gtctaaccag    9720
tcacagtcgc aaggtaggct gagcaccgtg gcgggcggca gcgggcggcg gtcggggttg    9780
tttctggcgg aggtgctgct gatgatgtaa ttaaagtagg cggtcttgag acggcggatg    9840
gtcgacagaa gcaccatgtc cttgggtccg gcctgctgaa tgcgcaggcg gtcggccatg    9900
ccccaggctt cgttttgaca tcggcgcagg tcttttgtagt agtcttgcat gagcctttct    9960
accggcactt cttcttctcc ttcctcttgt cctgcatctc ttgcatctat cgctgcgcg   10020
gcggcggagt ttggccgtag gtggcgccct cttcctccca tgcgtgtgac cccgaagccc   10080
ctcatcggct gaagcagggc taggtcggcg acaacgcgct cggctaatat ggcctgctgc   10140
```

```
acctgcgtga gggtagactg gaagtcatcc atgtccacaa agcggtggta tgcgcccgtg   10200
ttgatggtgt aagtgcagtt ggccataacg gaccagttaa cggtctggtg acccggctgc   10260
gagagctcgg tgtacctgag acgcgagtaa gccctcgagt caaatacgta gtcgttgcaa   10320
gtccgcacca ggtactggta tcccaccaaa aagtgcggcg gcggctggcg gtagaggggc   10380
cagcgtaggg tggccggggc tccggggcg agatcttcca acataaggcg atgatatccg   10440
tagatgtacc tggacatcca ggtgatgccg gcggcgtgg tggaggcgcg cggaaagtcg   10500
cggacgcggt tccagatgtt gcgcagcggc aaaaagtgct ccatggtcgg gacgctctgg   10560
ccggtcaggc gcgcgcaatc gttgacgctc tagaccgtgc aaaaggagag cctgtaagcg   10620
ggcactcttc cgtggtctgg tggataaatt cgcaagggta tcatggcgga cgaccggggt   10680
tcgagccccg tatccggccg tccgccgtga tccatgcgt taccgcccgc gtgtcgaacc   10740
caggtgtgcg acgtcagaca acgggggagt gctccttttg gcttccttcc aggcgcggcg   10800
gctgctgcgc tagctttttt ggccactggc cgcgcgcagc gtaagcggtt aggctggaaa   10860
gcgaaagcat taagtggctc gctccctgta gccggagggt tattttccaa gggttgagtc   10920
gcgggacccc cggttcgagt ctcggaccgg ccggactgcg gcgaacgggg gtttgcctcc   10980
ccgtcatgca agacccgct tgcaaattcc tccggaaaca gggacgagcc cctttttttgc   11040 tttttcccaga tgcatccggt gctgcggcag atgcgccccc ctcctcagca gcggcaagag   11100
caagagcagc ggcagacatg cagggcaccc tccctcctc ctaccgcgtc aggaggggcg   11160
acatccgcgg ttgacgcggc agcagatggt gattacgaac ccccgcggcg ccgggcccgg   11220
cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccatacccct tacgttccca tagacaagga ggtaaagatc   11940 gagggggttct acatgcgcat ggcgctgaag gtgcttacct tgagcgacga cctgggcgtt   12000
tatcgcaacg agcgcatcca caaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg ccccaagccg acgcgccctg   12180
gaggcagctg gggccggacc tgggctgcg gtggcacccg cgcgcgctgg caacgtcggc   12240
ggcgtggagg aatatgacga ggacgatgag tacgagccag aggacggcga gtactaagcg   12300
gtgatgtttc tgatcagatg atgcaagacg caacggaccc ggcggtgcgg gcggcgctgc   12360
agagccagcc gtccggcctt aactccacgg acgactggcg ccaggtcatg gaccgcatca   12420
tgtcgctgac tgcgcgcaat cctgacgcgt tccggcagca gccgcaggcc aaccggctct   12480
ccgcaattct ggaagcggtg gtcccggcgc gcgcaaaccc cacgcacgag aaggtgctgg   12540
```

```
cgatcgtaaa cgcgctggcc gaaaacaggg ccatccggcc cgacgaggcc ggcctggtct    12600
acgacgcgct gcttcagcgc gtggctcgtt acaacagcgg caacgtgcag accaacctgg    12660
accggctggt gggggatgtg cgcgaggccg tggcgcagcg tgagcgcgcg cagcagcagg    12720
gcaacctggg ctccatggtt gcactaaacg ccttcctgag tacacagccc gccaacgtgc    12780
cgcggggaca ggaggactac accaactttg tgagcgcact gcggctaatg gtgactgaga    12840
caccgcaaag tgaggtgtac cagtctgggc cagactattt tttccagacc agtagacaag    12900
gcctgcagac cgtaaacctg agccaggctt caaaaacttt gcaggggctg tggggggtgc    12960
gggctcccac aggcgaccgc gcgaccgtgt ctagcttgct gacgcccaac tcgcgcctgt    13020
tgctgctgct aatagcgccc ttcacggaca gtggcagcgt gtcccgggac acatacctag    13080
gtcacttgct gacactgtac cgcgaggcca taggtcaggc gcatgtggac gagcatactt    13140
tccaggagat tacaagtgtc agccgcgcgc tggggcagga ggacacgggc agcctggagg    13200
caaccctaaa ctacctgctg accaaccggc ggcagaagat cccctcgttg cacagtttaa    13260
acagcgagga ggagcgcatt ttgcgctacg tgcagcagag cgtgagcctt aacctgatgc    13320
gcgacggggt aacgcccagc gtggcgctgg acatgaccgc gcgcaacatg gaaccgggca    13380
tgtatgcctc aaaccggccg tttatcaacc gcctaatgga ctacttgcat cgcgcggccg    13440
ccgtgaaccc cgagtatttc accaatgcca tcttgaaccc gcactggcta ccgccccctg    13500
gtttctacac cggggggattc gaggtgcccg agggtaacga tggattcctc tgggacgaca    13560
tagacgacag cgtgttttcc ccgcaaccgc agaccctgct agagttgcaa cagcgcgagc    13620
aggcagaggc ggcgctgcga aaggaaagct ccgcaggcc aagcagcttg tccgatctag    13680
gcgctgcggc cccgcggtca gatgctagta gcccatttcc aagcttgata gggtctctta    13740
ccagcactcg caccacccgc ccgcgcctgc tgggcgagga ggagtaccta aacaactcgc    13800
tgctgcagcc gcagcgcgaa aaaaacctgc ctccggcatt tcccaacaac gggatagaga    13860
gcctagtgga caagatgagt agatggaaga cgtacgcgca ggagcacagg gacgtgccag    13920 gccccgcgccc gcccacccgt cgtcaaaggc acgaccgtca gcggggtctg gtgtgggagg    13980
acgatgactc ggcagacgac agcagcgtcc tggatttggg agggagtggc aacccgtttg    14040
cgcaccttcg ccccaggctg gggagaatgt tttaaaaaaa aaaaagcatg atgcaaaata    14100
aaaaactcac caaggccatg gcaccgagcg ttggttttct tgtattcccc ttagtatgcg    14160
gcgcgcggcg atgtatgagg aaggtcctcc tccctcctac gagagtgtgg tgagcgcggc    14220
gccagtggcg gcggcgctgg gttctccctt cgatgctccc ctggaccgc cgtttgtgcc    14280 tccgcggtac ctgcggccta ccgggggagg aaaacagcatc cgttactctg agttggcacc    14340
cctattcgac accacccgtg tgtacctggt ggacaacaag tcaacggatg tggcatccct    14400
gaactaccag aacgaccaca gcaactttct gaccacggtc attcaaaaca atgactacag    14460
cccgggggag gcaagcacac agaccatcaa tcttgacgac cggtcgcact ggggcggcga    14520
cctgaaaacc atcctgcata ccaacatgcc aaatgtgaac gagttcatgt ttaccaataa    14580
gtttaaggcg cgggtgatgg tgtcgcgctt gcctactaag gacaatcagg tggagctgaa    14640
atacgagtgg gtggagttca cgctgcccga gggcaactac tccgagacca tgaccataga    14700
ccttatgaac aacgcgatcg tggagcacta cttgaaagtg gcagacaga acggggttct    14760 ggaaagcgac atcggggtaa agtttgacac ccgcaacttc agactggggt ttgaccccgt    14820
cactggtctt gtcatgcctg gggtatatac aaacgaagcc ttccatccag acatcatttt    14880
```

```
gctgccagga tgcggggtgg acttcaccca cagccgcctg agcaacttgt tgggcatccg    14940
caagcggcaa cccttccagg agggctttag gatcacctac gatgatctgg agggtggtaa    15000
cattcccgca ctgttggatg tggacgccta ccaggcgagc ttgaaagatg acaccgaaca    15060
gggcggggt ggcgcaggcg gcagcaacag cagtggcagc ggcgcggaag agaactccaa     15120
cgcggcagcc gcggcaatgc agccggtgga ggacatgaac gatcatgcca ttcgcggcga    15180
caccttttgcc acacgggctg aggagaagcg cgctgaggcc gaagcagcgg ccgaagctgc   15240
cgcccccgct cgcaaccccg aggtcgagaa gcctcagaag aaaccggtga tcaaacccct   15300
gacagaggac agcaagaaac gcagttacaa cctaataagc aatgacagca ccttcaccca    15360
gtaccgcagc tggtaccttg catacaacta cggcgaccct cagaccggaa tccgctcatg    15420
gaccctgctt tgcactcctg acgtaacctg cggctcggag caggtctact ggtcgttgcc    15480
agacatgatg caagaccccg tgaccttccg ctccacgcgc cagatcagca ctttccggt     15540
ggtgggcgcc gagctgttgc ccgtgcactc caagagcttc tacaacgacc aggccgtcta    15600
ctcccaactc atccgccagt ttacctctct gacccacgtg ttcaatcgct ttcccgagaa    15660
ccagattttg gcgcgcccgc cagccccac catcaccacc gtcagtgaaa cgttcctgc      15720
tctcacagat cacgggacgc taccgctgcg caacagcatc ggaggagtcc agcgagtgac    15780
cattactgac gccagacgcc gcacctgccc ctacgtttac aaggccctgg gcatagtctc    15840
gccgcgcgtc ctatcgagcc gcacttttttg agcaagcatg tccatcctta tatcgcccag   15900
caataacaca ggctgggcc tgcgcttccc aagcaagatg tttggcgggg ccaagaagcg     15960
ctccgaccaa cacccagtgc gcgtgcgcgg gcactaccgc gcgccctggg gcgcgcacaa    16020
acgcggccgc actgggcgca ccaccgtcga tgacgccatc gacgcggtgg tggaggaggc    16080
gcgcaactac acgcccacgc cgccaccagt gtccacagtg gacgcggcca ttcagaccgt    16140
ggtgcgcgga gcccggcgct atgctaaaat gaagagacgg cggaggcgcg tagcacgtcg    16200
ccaccgccgc cgacccggca ctgccgccca acgcgcggcg gcggccctgc ttaaccgcgc    16260
acgtcgcacc ggccgacggg cggccatgcg ggccgctcga aggctggccg cgggtattgt    16320
cactgtgccc cccaggtcca ggcgacgagc ggccgccgca cagccgcgg ccattagtgc     16380
tatgactcag ggtcgcaggg gcaacgtgta ttgggtgcgc gactcggtta gcggcctgcg    16440
cgtgcccgtg cgcacccgcc ccccgcgcaa ctagattgca agaaaaaact acttagactc    16500
gtactgttgt atgtatccag cggcggcggc gcgcaacgaa gctatgtcca agcgcaaaat    16560
caaagaagag atgctccagg tcatcgcgcc ggagatctat ggccccccga agaaggaaga    16620
gcaggattac aagcccccgaa agctaaagcg ggtcaaaaag aaaaagaaag atgatgatga   16680
tgaacttgac gacgaggtgg aactgctgca cgctaccgcg cccaggcgac gggtacagtg    16740
gaaaggtcga cgcgtaaaac gtgttttgcg accggcacc accgtagtct ttacgcccgg    16800
tgagcgctcc acccgcacct acaagcgcgt gtatgatgag gtgtacgcg acgaggacct     16860
gcttgagcag gccaacgagc gcctcgggga gttgcctac ggaaagcggc ataaggacat     16920
gctggcgttg ccgctggacg agggcaaccc aacaccagc ctaaagcccg taacactgca     16980
gcaggtgctg cccgcgcttg caccgtccga agaaaagcgc ggcctaaagc gcgagtctgg    17040
tgacttggca cccaccgtgc agctgatggt acccaagcgc cagcgactgg aagatgtctt    17100
ggaaaaaatg accgtggaac ctgggctgga gcccgaggtc cgcgtgcggc caatcaagca    17160
ggtggcgccg ggactgggcg tgcagaccgt ggacgttcag ataccactac ccagtagcac    17220
cagtattgcc accgccacag agggcatgga gacacaaacg tccccggttg cctcagcggt    17280
```

-continued

```
ggcggatgcc gcggtgcagg cggtcgctgc ggccgcgtcc aagacctcta cggaggtgca   17340
aacggacccg tggatgtttc gcgtttcagc cccccggcgc ccgcgcggtt cgaggaagta   17400 cggcgccgc agcgcgctac tgcccgaata tgcctacat ccttccattg cgcctacccc    17460
cggctatcgt ggctacacct accgcccag aagacgagca actacccgac gccgaaccac    17520
cactggaacc cgccgccgcc gtcgccgtcg ccagcccgtg ctggcccga tttccgtgcg    17580 cagggtggct cgcgaaggag gcaggaccct ggtgctgcca acagcgcgct accaccccag   17640
catcgtttaa aagccggtct ttgtggttct tgcagatatg gccctcacct gccgcctccg   17700
tttcccggtg ccgggattcc gaggaagaat gcaccgtagg aggggcatgg ccggccacgg   17760
cctgacgggc ggcatgcgtc gtgcgcacca ccggcggcgg cgcgcgtcgc accgtcgcat   17820
gcgcggcggt atcctgcccc tccttattcc actgatcgcc gcggcgattg gcgccgtgcc   17880
cggaattgca tccgtggcct tgcaggcgca gagacactga ttaaaaacaa gttgcatgtg   17940
gaaaaatcaa aataaaaagt ctggactctc acgctcgctt ggtcctgtaa ctattttgta   18000
gaatggaaga catcaacttt gcgtctctgg ccccgcgaca cggctcgcgc ccgttcatgg   18060
gaaactggca agatatcggc accagcaata tgagcggtgg cgccttcagc tggggctcgc   18120
tgtggagcgg cattaaaaat ttcggttcca ccgttaagaa ctatggcagc aaggcctgga   18180
acagcagcac aggccagatg ctgagggata agttgaaaga gcaaaatttc caacaaaagg   18240
tggtagatgg cctggcctct ggcattagcg gggtggtgga cctggccaac caggcagtgc   18300
aaaataagat taacagtaag cttgatcccc gccctcccgt agaggagcct ccaccggccg   18360
tggagacagt gtctccagag gggcgtggcg aaaagcgtcc gcgccccgac agggaagaaa   18420
ctctggtgac gcaaatagac gagcctccct cgtacgagga ggcactaaag caaggcctgc   18480
ccaccacccg tcccatcgcg cccatggcta ccggagtgct gggccagcac acacccgtaa   18540
cgctggacct gcctcccccc gccgacaccc agcagaaacc tgtgctgcca ggcccgaccg   18600
ccgttgttgt aacccgtcct agccgcgcgt ccctgcgccg cgccgccagc ggtccgcgat   18660
cgttgcggcc cgtagccagt ggcaactggc aaagcacact gaacagcatc gtgggtctgg   18720
gggtgcaatc cctgaagcgc cgacgatgct tctgaatagc taacgtgtcg tatgtgtgtc   18780
atgtatgcgt ccatgtcgcc gccagaggag ctgctgagcc gccgcgcgcc cgcttcccaa   18840
gatggctacc ccttcgatga tgccgcagtg gtcttacatg cacatctcgg gccaggacgc   18900
ctcggagtac ctgagccccg ggctggtgca gtttgcccgc gccaccgaga cgtacttcag   18960
cctgaataac aagtttagaa accccacggt ggcgcctacg cacgacgtga ccacagaccg   19020
gtcccagcgt ttgacgctgc ggttcatccc tgtggaccgt gaggatactg cgtactcgta   19080
caaggcgcgg ttcaccctag ctgtgggtga taaccgtgtg ctggacatgg cttccacgta   19140
ctttgacatc cgcggcgtgc tggacagggg ccctactttt aagccctact ctggcactgc   19200
ctacaacgcc ctggctccca gggtgccccc aaatccttgc gaatgggatg aagctgctac   19260
tgctcttgaa ataaacctag aagaagagga cgatgacaac gaagacgaag tagacgagca   19320
agctgagcag caaaaaactc acgtatttgg gcaggcgcct tattctggta taaatattac   19380
aaaggagggt attcaaatag gtgtcgaagg tcaaacacct aaatatgccg ataaaacatt   19440
tcaacctgaa cctcaaatag gagaatctca gtggtacgaa actgaaatta atcatgcagc   19500
tgggagagtc cttaaaaaga ctaccccaat gaaaccatgt tacggttcat atgcaaaacc   19560
cacaaatgaa aatggagggc aaggcattct tgtaaagcaa caaaatggaa agctagaaag   19620
```

```
tcaagtggaa atgcaatttt tctcaactac tgaggcgacc gcaggcaatg gtgataactt   19680
gactcctaaa gtggtattgt acagtgaaga tgtagatata gaaaccccag acactcatat   19740
ttcttacatg cccactatta aggaaggtaa ctcacgagaa ctaatgggcc aacaatctat   19800
gcccaacagg cctaattaca ttgcttttag ggacaatttt attggtctaa tgtattacaa   19860
cagcacgggt aatatgggtg ttctggcggg ccaagcatcg cagttgaatg ctgttgtaga   19920
tttgcaagac agaaacacag agctttcata ccagcttttg cttgattcca ttggtgatag   19980
aaccaggtac ttttctatgt ggaatcaggc tgttgacagc tatgatccag atgttagaat   20040
tattgaaaat catggaactg aagatgaact tccaaattac tgctttccac tgggaggtgt   20100
gattaataca gagactctta ccaaggtaaa acctaaaaca ggtcaggaaa atggatggga   20160
aaaagatgct acagaatttt cagataaaaa tgaaataaga gttggaaata attttgccat   20220
ggaaatcaat ctaaatgcca acctgtggag aaatttcctg tactccaaca tagcgctgta   20280
tttgcccgac aagctaaagt acagtccttc caacgtaaaa atttctgata cccaaacac    20340 ctacgactac atgaacaagc gagtggtggc tcccgggtta gtggactgct acattaacct   20400
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct tgccattaa aaacctcctt ctcctgccgg gctcatacac    20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
ccccatggcc cacaacaccg cctccacgct tgaggccatg cttagaaacg acaccaacga   20760
ccagtccttt aacgactatc tctccgccgc caacatgctc taccctatac cgccaacgc    20820 taccaacgtg cccatatcca tcccctcccg caactgggcg gctttccgcg gctgggcctt   20880
cacgcgcctt aagactaagg aaaccccatc actgggctcg ggctacgacc cttattacac   20940
ctactctggc tctataccct acctagatgg aacctttac ctcaaccaca cctttaagaa    21000
ggtggccatt accttttgact cttctgtcag ctggcctggc aatgaccgcc tgcttacccc   21060
caacgagttt gaaattaagc gctcagttga cggggagggt acaacgttg cccagtgtaa    21120 catgaccaaa gactggttcc tggtacaaat gctagctaac tacaacattg gctaccaggg   21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
ggcctaccct gctaacttcc cctatccgct tataggcaag accgcagttg acagcattac   21420
ccagaaaaag tttctttgcg atcgcaccct ttggcgcatc ccattctcca gtaacttat    21480 gtccatgggc gcactcacag acctgggcca aaaccttctc tacgccaact ccgcccacgc   21540
gctagacatg acttttgagg tggatccat ggacgagccc accttctttt atgttttgtt    21600
tgaagtcttt gacgtggtcc gtgtgcaccg gccgcaccgc ggcgtcatcg aaaccgtgta   21660
cctgcgcacg cccttctcgg ccggcaacgc cacaacataa agaagcaagc aacatcaaca   21720
acagctgccg ccatgggctc cagtgagcag gaactgaaag ccattgtcaa agatcttggt   21780
tgtgggccat atttttggg cacctatgac aagcgctttc caggctttgt ttctccacac    21840
aagctcgcct gcgccatagt caatacggcc ggtcgcgaga ctggggcgt acactggatg    21900 gcctttgcct ggaacccgca ctcaaaaaca tgctacctct tgagcccctt ggcttttct    21960 gaccagcgac tcaagcaggt ttaccagttt gagtacgagt cactcctgcg ccgtagcgcc   22020
```

```
attgcttctt cccccgaccg ctgtataacg ctggaaaagt ccacccaaag cgtacagggg   22080
cccaactcgg ccgcctgtgg actattctgc tgcatgtttc tccacgcctt tgccaactgg   22140
ccccaaactc ccatggatca aaccccacc atgaaccta ttaccggggt acccaactcc   22200
```

```
catctgcagc gccagtgcgc cattatctgc gacgcgttgc aagagcgcag cgatgtgccc   24420
ctcgccatag cggatgtcag ccttgcctac gaacgccacc tattctcacc gcgcgtaccc   24480
cccaaacgcc aagaaaacgg cacatgcgag cccaacccgc gcctcaactt ctacccccgta  24540 tttgccgtgc cagaggtgct tgccacctat cacatctttt tccaaaactg caagataccc   24600
ctatcctgcc gtgccaaccg cagccgagcg gacaagcagc tggccttgcg gcagggcgct   24660
gtcatacctg atatcgcctc gctcaacgaa gtgccaaaaa tctttgaggg tcttggacgc   24720
gacgagaagc gcgcggcaaa cgctctgcaa caggaaaaca gcgaaaatga aagtcactct   24780
ggagtgttgg tggaactcga gggtgacaac gcgcgcctag ccgtactaaa acgcagcatc   24840
gaggtcaccc actttgccta cccggcactt aacctacccc ccaaggtcat gagcacagtc   24900
atgagtgagc tgatcgtgcg ccgtgcgcag cccctggaga gggatgcaaa tttgcaagaa   24960
caaacagagg agggcctacc cgcagttggc gacgagcagc tagcgcgctg gcttcaaacg   25020
cgcgagcctg ccgacttgga ggagcgacgc aaactaatga tggccgcagt gctcgttacc   25080
gtggagcttg agtgcatgca gcggttcttt gctgacccgg agatgcagcg caagctagag   25140
gaaacattgc actacacctt tcgacagggc tacgtacgcc aggcctgcaa gatctccaac   25200
gtggagctct gcaacctggt ctcctacctt ggaattttgc acgaaaaccg ccttgggcaa   25260
aacgtgcttc attccacgct caagggcgag gcgcgccgcg actacgtccg cgactgcgtt   25320
tacttatttc tatgctacac ctggcagacg gccatgggcg tttggcagca gtgcttggag   25380
gagtgcaacc tcaaggagct gcagaaactg ctaaagcaaa acttgaagga cctatggacg   25440
gccttcaacg agcgctccgt ggccgcgcac ctggcggaca tcattttccc cgaacgcctg   25500
cttaaaaccc tgcaacaggg tctgccagac ttcaccagtc aaagcatgtt gcagaacttt   25560
aggaacttta tcctagagcg ctcaggaatc ttgcccgcca cctgctgtgc acttcctagc   25620
gactttgtgc ccattaagta ccgcgaatgc cctccgccgc tttggggcca ctgctacctt   25680
ctgcagctag ccaactacct tgcctaccac tctgacataa tggaagacgt gagcggtgac   25740
ggtctactgg agtgtcactg tcgctgcaac ctatgcaccc cgcaccgctc cctggttttgc   25800 aattcgcagc tgcttaacga aagtcaaatt atcggtacct ttgagctgca gggtccctcg   25860
cctgacgaaa agtccgcggc tccggggttg aaactcactc cggggctgtg gacgtcggct   25920
taccttcgca aatttgtacc tgaggactac cacgcccacg agattaggtt ctacgaagac   25980
caatcccgcc cgccaaatgc ggagcttacc gcctgcgtca ttacccaggg ccacattctt   26040
ggccaattgc aagccatcaa caaagcccgc aagagtttc tgctacgaaa gggacggggg   26100
gtttacttgg accccagtc cggcgaggag ctcaacccaa tcccccgcc gccgcagccc   26160 tatcagcagc agccgcgggc ccttgcttcc caggatggca cccaaaaaga agctgcagct   26220
gccgccgcca cccacggacg aggaggaata ctgggacagt caggcagagg aggttttgga   26280
cgaggaggag gaggacatga tggaagactg ggagagccta gacgaggaag cttccgaggt   26340
cgaagaggtg tcagacgaaa caccgtcacc ctcggtcgca ttcccctcgc cggcgcccca   26400
gaaatcggca accggttcca gcatggctac aacctccgct cctcaggcgc gccggcact   26460 gcccgttcgc cgacccaacc gtagatggga caccactgga accagggccg gtaagtccaa   26520
gcagccgccg ccgttagccc aagagcaaca acagcgccaa ggctaccgct catgcgcgg   26580 gcacaagaac gccatagttg cttgcttgca agactgtggg gcaacatct ccttcgcccg   26640 ccgctttctt ctctaccatc acggcgtggc cttccccgt aacatcctgc attactaccg   26700
tcatctctac agcccatact gcaccggcgg cagcggcagc ggcagcaaca gcagcggcca   26760
```

```
cacagaagca aaggcgaccg gatagcaaga ctctgacaaa gcccaagaaa tccacagcgg   26820
cggcagcagc aggaggagga gcgctgcgtc tggcgcccaa cgaacccgta tcgacccgcg   26880
agcttagaaa caggattttt cccactctgt atgctatatt tcaacagagc aggggccaag   26940
aacaagagct gaaaataaaa aacaggtctc tgcgatccct cacccgcagc tgcctgtatc   27000
acaaaagcga agatcagctt cggcgcacgc tggaagacgc ggaggctctc ttcagtaaat   27060
actgcgcgct gactcttaag gactagtttc gcgcccttc  tcaaatttaa gcgcgaaaac   27120
tacgtcatct ccagcggcca cacccggcgc cagcacctgt cgtcagcgcc attatgagca   27180
aggaaattcc cacgccctac atgtggagtt accagccaca aatgggactt gcggctggag   27240
ctgcccaaga ctactcaacc cgaataaact acatgagcgc gggaccccac atgatatccc   27300
gggtcaacgg aatccgcgcc caccgaaacc gaattctctt ggaacaggcg gctattacca   27360
ccacacctcg taataacctt aatccccgta gttggcccgc tgccctggtg taccaggaaa   27420
gtcccgctcc caccactgtg gtacttccca gagacgccca ggccgaagtt cagatgacta   27480
actcaggggc gcagcttgcg gcggctttc  gtcacagggt gcggtcgccc gggcagggta   27540
taactcacct gacaatcaga gggcgaggta ttcagctcaa cgacgagtcg gtgagctcct   27600
cgcttggtct ccgtccggac gggacatttc agatcggcgg cgccggccgt ccttcattca   27660
cgcctcgtca ggcaatccta actctgcaga cctcgtcctc tgagccgcgc tctggaggca   27720
ttggaactct gcaatttatt gaggagtttg tgccatcggt ctactttaac cccttctcgg   27780
gacctcccgg ccactatccg gatcaattta ttcctaactt tgacgcggta aaggactcgg   27840
cggacggcta cgactgaatg ttaagtggag aggcagagca actgcgcctg aaacacctgg   27900
tccactgtcg ccgccacaag tgctttgccc gcgactccgg tgagttttgc tactttgaat   27960
tgcccgagga tcatatcgag ggccggcgc  acggcgtccg gcttaccgcc cagggagagc   28020
ttgcccgtag cctgattcgg gagtttaccc agcgcccct  gctagttgag cgggacaggg   28080
gaccctgtgt tctcactgtg atttgcaact gtcctaacct tggattacat caagatcttt   28140
gttgccatct ctgtgctgag tataataaat acagaaatta aaatatactg gggctcctat   28200
cgccatcctg taaacgccac cgtcttcacc cgcccaagca aaccaaggcg aaccttacct   28260 ggtacttta  acatctctcc ctctgtgatt tacaacagtt tcaacccaga cggagtgagt   28320
ctacgagaga acctctccga gctcagctac tccatcagaa aaaacaccac cctccttacc   28380
tgccgggaac gtacgagtgc gtcaccggcc gctgcaccac acctaccgcc tgaccgtaaa   28440
ccagactttt tccggacaga cctcaataac tctgtttacc agaacaggag gtgagcttag   28500 aaaacccta  gggtattagg ccaaaggcgc agctactgtg gggtttatga acaattcaag   28560
caactctacg ggctattcta attcaggttt ctctagaatc ggggttgggg ttattctctg   28620
tcttgtgatt ctctttattc ttatactaac gcttctctgc ctaaggctcg ccgcctgctg   28680
tgtgcacatt tgcatttatt gtcagctttt taaacgctgg ggtcgccacc caagatgatt   28740
aggtacataa tcctaggttt actcacccett gcgtcagccc acggtaccac ccaaaaggtg   28800
gattttaagg agccagcctg taatgttaca ttcgcagctg aagctaatga gtgcaccact   28860
cttataaaat gcaccacaga acatgaaaag ctgcttattc gccacaaaaa caaaattggc   28920
aagtatgctg tttatgctat ttggcagcca ggtgacacta cagagtataa tgttacagtt   28980
ttccagggta aaagtcataa aactttatg  tatactttc  catttatga aatgtgcgac   29040 attaccatgt acatgagcaa acagtataag ttgtggcccc cacaaaattg tgtggaaaac   29100
```

```
actggcactt tctgctgcac tgctatgcta attacagtgc tcgctttggt ctgtaccccta   29160 ctctatatta aatacaaaag cagacgcagc tttattgagg aaaagaaaat gccttaattt   29220
actaagttac aaagctaatg tcaccactaa ctgctttact cgctgcttgc aaaacaaatt   29280
caaaaagtta gcattataat tagaatagga tttaaacccc ccggtcattt cctgctcaat   29340
accattcccc tgaacaattg actctatgtg ggatatgctc cagcgctaca accttgaagt   29400
caggcttcct ggatgtcagc atctgacttt ggccagcacc tgtcccgcgg atttgttcca   29460
gtccaactac agcgacccac cctaacagag atgaccaaca caaccaacgc ggccgccgct   29520
accggactta catctaccac aaatacaccc caagtttctg cctttgtcaa taactgggat   29580
aacttgggca tgtggtggtt ctccatagcg cttatgtttg tatgccttat tattatgtgg   29640
ctcatctgct gcctaaagcg caaacgcgcc cgaccaccca tctatagtcc catcattgtg   29700
ctacacccaa acaatgatgg aatccataga ttggacggac tgaaacacat gttcttttct   29760
cttacagtat gattaaatga gacatgattc ctcgagtttt tatattactg acccttgttg   29820
cgcttttttg tgcgtgctcc acattggctg cggtttctca catcgaagta gactgcattc   29880
cagccttcac agtctatttg ctttacggat tgtcaccct cacgctcatc tgcagcctca    29940
tcactgtggt catcgccttt atccagtgca ttgactgggt ctgtgtgcgc tttgcatatc   30000
tcagacacca tccccagtac agggacagga ctatagctga gcttcttaga attctttaat   30060
tatgaaattt actgtgactt ttctgctgat tatttgcacc ctatctgcgt tttgttcccc   30120
gacctccaag cctcaaagac atatatcatg cagattcact cgtatatgga atattccaag   30180
ttgctacaat gaaaaaagcg atctttccga agcctggtta tatgcaatca tctctgttat   30240
ggtgttctgc agtaccatct tagccctagc tatatatccc taccttgaca ttggctggaa   30300
acgaatagat gccatgaacc acccaacttt ccccgcgccc gctatgcttc cactgcaaca   30360
agttgttgcc ggcggctttg tcccagccaa tcagcctcgc cccacttctc ccaccccac    30420 tgaaatcagc tactttaatc taacaggagg agatgactga caccctagat ctagaaatgg   30480
acggaattat tacagagcag cgcctgctag aaagacgcag ggcagcggcc gagcaacagc   30540
gcatgaatca agagctccaa gacatggtta acttgcacca gtgcaaaagg ggtatctttt   30600
gtctggtaaa gcaggccaaa gtcacctacg acagtaatac caccggacac cgccttagct   30660
acaagttgcc aaccaagcgt cagaaattgg tggtcatggt gggagaaaag cccattacca   30720
taactcagca ctcggtagaa accgaaggct gcattcactc accttgtcaa ggacctgagg   30780
atctctgcac cctattaag accctgtgcg gtctcaaaga tcttattccc tttaactaat    30840
aaaaaaaaat aataaagcat cacttactta aaatcagtta gcaaatttct gtccagttta   30900
ttcagcagca cctccttgcc ctcctcccag ctctggtatt gcagcttcct cctggctgca   30960
aactttctcc acaatctaaa tggaatgtca gtttcctcct gttcctgtcc atccgcaccc   31020
actatcttca tgttgttgca gatgaagcgc gcaagaccgt ctgaagatac cttcaacccc   31080
gtgtatccat atgacacgga aaccggtcct ccaactgtgc cttttcttac tcctccctt    31140 gtatccccca atgggtttca agagagtccc cctggggtac tctctttgcg cctatccgaa   31200
cctctagtta cctccaatgg catgcttgcg ctcaaaatgg caacggcct ctctctggac     31260 gaggccggca accttacctc ccaaaatgta accactgtga gcccacctct caaaaaaacc   31320
aagtcaaaca taaacctgga aatatctgca cccctcacag ttacctcaga gccctaact    31380 gtggctgccg ccgcacctct aatggtcgcg ggcaacacac tcaccatgca atcacaggcc   31440
ccgctaaccg tgcacgactc caaacttagc attgccaccc aaggacccct cacagtgtca   31500
```

```
gaaggaaagc tagccctgca aacatcaggc cccctcacca ccaccgatag cagtaccctt    31560
actatcactg cctcaccccc tctaactact gccactggta gcttgggcat tgacttgaaa    31620
gagcccattt atacacaaaa tggaaaacta ggactaaagt acggggctcc tttgcatgta    31680
acagacgacc taaacacttt gaccgtagca actggtccag gtgtgactat taataatact    31740
tccttgcaaa ctaaagttac tggagccttg ggttttgatt cacaaggcaa tatgcaactt    31800
aatgtagcag gaggactaag gattgattct caaaacagac gccttatact tgatgttagt    31860
tatccgtttg atgctcaaaa ccaactaaat ctaagactag acagggccc tctttttata    31920 aactcagccc acaacttgga tattaactac aacaaaggcc tttacttgtt tacagcttca    31980
aacaattcca aaaagcttga ggttaaccta agcactgcca aggggttgat gtttgacgct    32040
acagccatag ccattaatgc aggagatggg cttgaatttg gttcacctaa tgcaccaaac    32100
acaaatcccc tcaaaacaaa aattggccat ggcctagaat ttgattcaaa caaggctatg    32160
gttcctaaac taggaactgg ccttagtttt gacagcacag gtgccattac agtaggaaac    32220
aaaaataatg ataagctaac tttgtggacc acaccagctc catctcctaa ctgtagacta    32280
aatgcagaga aagatgctaa actcactttg gtcttaacaa aatgtggcag tcaaatactt    32340
gctacagttt cagttttggc tgttaaaggc agtttggctc caatatctgg aacagttcaa    32400
agtgctcatc ttattataag atttgacgaa aatggagtgc tactaaacaa ttccttcctg    32460
gacccagaat attggaactt tagaaatgga gatcttactg aaggcacagc ctatacaaac    32520
gctgttggat ttatgcctaa cctatcagct tatccaaaat ctcacggtaa aactgccaaa    32580
agtaacattg tcagtcaagt ttacttaaac ggagacaaaa ctaaacctgt aacactaacc    32640
attacactaa acggtacaca ggaaacagga gacacaactc caagtgcata ctctatgtca    32700 tttttcatggg actggtctgg ccacaactac attaatgaaa tatttgccac atcctcttac    32760 acttttcat acattgccca agaataaaga atcgtttgtg ttatgtttca acgtgtttat    32820
ttttcaattg cagaaaattt caagtcattt ttcattcagt agtatagccc caccaccaca    32880
tagcttatac agatcaccgt accttaatca aactcacaga accctagtat tcaacctgcc    32940
acctccctcc caacacacag agtacacagt cctttctccc cggctggcct taaaaagcat    33000
catatcatgg gtaacagaca tattcttagg tgttatattc cacacggttt cctgtcgagc    33060
caaacgctca tcagtgatat taataaactc cccgggcagc tcacttaagt tcatgtcgct    33120
gtccagctgc tgagccacag gctgctgtcc aacttgcggt tgcttaacgg gcggcgaagg    33180
agaagtccac gcctacatgg gggtagagtc ataatcgtgc atcaggatag ggcggtggtg    33240
ctgcagcagc gcgcgaataa actgctgccg ccgccgctcc gtcctgcagg aatacaacat    33300
ggcagtggtc tcctcagcga tgattcgcac cgcccgcagc ataaggcgcc ttgtcctccg    33360
ggcacagcag cgcaccctga tctcacttaa atcagcacag taactgcagc acagcaccac    33420
aatattgttc aaaatcccac agtgcaaggc gctgtatcca aagctcatgg cggggaccac    33480
agaacccacg tggccatcat accacaagcg caggtagatt aagtggcgac ccctcataaa    33540
cacgctggac ataaacatta cctctttttgg catgttgtaa ttcaccacct cccggtacca    33600
tataaacctc tgattaaaca tggcgccatc caccaccatc ctaaaccagc tggccaaaac    33660
ctgcccgccg gctatacact gcagggaacc gggactggaa caatgacagt ggagagccca    33720
ggactcgtaa ccatggatca tcatgctcgt catgatatca atgttggcac aacacaggca    33780
cacgtgcata cacttcctca ggattacaag ctcctcccgc gttagaacca tatcccaggg    33840
```

```
aacaacccat tcctgaatca gcgtaaatcc cacactgcag ggaagacctc gcacgtaact    33900
cacgttgtgc attgtcaaag tgttacattc gggcagcagc ggatgatcct ccagtatggt    33960
agcgcgggtt tctgtctcaa aaggaggtag acgatcccta ctgtacgag tgcgccgaga     34020 caaccgagat cgtgttggtc gtagtgtcat gccaaatgga acgccggacg tagtcatatt    34080
tcctgaagca aaaccaggtg cgggcgtgac aaacagatct gcgtctccgg tctcgccgct    34140
tagatcgctc tgtgtagtag ttgtagtata tccactctct caaagcatcc aggcgccccc    34200
tggcttcggg ttctatgtaa actccttcat gcgccgctgc cctgataaca tccaccaccg    34260
cagaataagc cacacccagc caacctacac attcgttctg cgagtcacac acgggaggag    34320
cgggaagagc tggaagaacc atgttttttt ttttattcca aaagattatc caaaacctca    34380
aaatgaagat ctattaagtg aacgcgctcc cctccggtgg cgtggtcaaa ctctacagcc    34440
aaagaacaga taatggcatt tgtaagatgt tgcacaatgg cttccaaaag gcaaacggcc    34500
ctcacgtcca agtggacgta aaggctaaac ccttcagggt gaatctcctc tataaacatt    34560
ccagcacctt caaccatgcc caaataattc tcatctcgcc accttctcaa tatatctcta    34620
agcaaatccc gaatattaag tccggccatt gtaaaaatct gctccagagc gccctccacc    34680
ttcagcctca agcagcgaat catgattgca aaaattcagg ttcctcacag acctgtataa    34740
gattcaaaag cggaacatta acaaaaatac cgcgatcccg taggtccctt cgcagggcca    34800
gctgaacata atcgtgcagg tctgcacgga ccagcgcggc cacttccccg ccaggaacct    34860
tgacaaaaga acccacactg attatgcac gcatactcgg agctatgcta accagcgtag     34920
ccccgatgta agctttgttg catgggcggc gatataaaat gcaaggtgct gctcaaaaaa    34980
tcaggcaaag cctcgcgcaa aaagaaagc acatcgtagt catgctcatg cagataaagg     35040
caggtaagct ccggaaccac cacagaaaaa gacaccattt ttctctcaaa catgtctgcg    35100
ggtttctgca taaacacaaa ataaaataac aaaaaaacat ttaaacatta gaagcctgtc    35160
ttacaacagg aaaaacaacc cttataagca taagacggac tacggccatg ccggcgtgac    35220
cgtaaaaaaa ctggtcaccg tgattaaaaa gcaccaccga cagctcctcg gtcatgtccg    35280
gagtcataat gtaagactcg gtaaacacat caggttgatt catcggtcag tgctaaaaag    35340
cgaccgaaat agcccggggg aatacatacc cgcaggcgta gagacaacat tacagccccc    35400
ataggaggta taacaaaatt aataggagag aaaaacacat aaacacctga aaaccctcc     35460 tgcctaggca aaatagcacc ctcccgctcc agaacaacat acagcgcttc acagcggcag    35520
cctaacagtc agccttacca gtaaaaaaga aaacctatta aaaaaacacc actcgacacg    35580
gcaccagctc aatcagtcac agtgtaaaaa agggccaagt gcagagcgag tatatatagg    35640
actaaaaaat gacgtaacgg ttaaagtcca caaaaaacac ccagaaaacc gcacgcgaac    35700
ctacgcccag aaacgaaagc caaaaaaccc acaacttcct caaatcgtca cttccgtttt    35760
cccacgttac gtaacttccc attttaagaa aactacaatt cccaacacat acaagttact    35820
ccgccctaaa acctacgtca cccgccccgt tccacgccc cgcgccacgt cacaaactcc     35880
accccctcat tatcatattg gcttcaatcc aaaataaggt atattattga tgatg          35935

<210> SEQ ID NO 9
<211> LENGTH: 35935
<212> TYPE: DNA
<213> ORGANISM: Adenovirus serotype 5

<400> SEQUENCE: 9
catcatcaat aatatacctt attttggatt gaagccaata tgataatgag ggggtggagt        60
```

```
ttgtgacgtg gcgcggggcg tgggaacggg gcgggtgacg tagtagtgtg gcggaagtgt      120
gatgttgcaa gtgtggcgga acacatgtaa gcgacggatg tggcaaaagt gacgttttg       180
gtgtgcgccg gtgtacacag gaagtgacaa ttttcgcgcg gttttaggcg gatgttgtag      240
taaatttggg cgtaaccgag taagatttgg ccattttcgc gggaaaactg aataagagga      300
agtgaaatct gaataatttt gtgttactca tagcgcgtaa tatttgtcta gggccgcggg      360
gactttgacc gtttacgtgg agactcgccc aggtgttttt ctcaggtgtt ttccgcgttc      420
cgggtcaaag ttggcgtttt attattatag tcagctgacg tgtagtgtat ttatacccgg      480
tgagttcctc aagaggccac tcttgagtgc cagcgagtag agttttctcc tccgagccgc      540
tccgacaccg ggactgaaaa tgagacatat tatctgccac ggaggtgtta ttaccgaaga      600
aatggccgcc agtcttttgg accagctgat cgaagaggta ctggctgata atcttccacc      660
tcctagccat tttgaaccac ctacccttca cgaactgtat gatttagacg tgacggcccc      720
cgaagatccc aacgaggagg cggtttcgca gattttttcc gactctgtaa tgttggcggt      780
gcaggaaggg attgacttac tcacttttcc gccggcgccc ggttctccgg agccgcctca      840
cctttcccgg cagcccgagc agccggagca gagagccttg ggtccggttt ctatgccaaa      900
ccttgtaccg gaggtgatcg atcttacctg ccacgaggct ggcttccac ccagtgacga      960
cgaggatgaa gagggtgagg agtttgtgtt agattatgtg gagcaccccg ggcacggttg     1020
caggtcttgt cattatcacc ggaggaatac gggggaccca gatattatgt gttcgctttg     1080
ctatatgagg acctgtggca tgtttgtcta cagtaagtga aaattatggg cagtgggtga     1140
tagagtggtg ggtttggtgt ggtaattttt ttttttaattt ttacagtttt gtggtttaaa    1200
gaattttgta ttgtgatttt tttaaaaggt cctgtgtctg aacctgagcc tgagcccgag     1260
ccagaaccgg agcctgcaag acctacccgc cgtcctaaaa tggcgcctgc tatcctgaga     1320
cgcccgacat cacctgtgtc tagagaatgc aatagtagta cggatagctg tgactccggt     1380
ccttctaaca cacctcctga gatacacccg gtggtcccgc tgtgccccat taaaccagtt     1440
gccgtgagag ttggtgggcg tcgccaggct gtggaatgta tcgaggactt gcttaacgag     1500
cctgggcaac ctttggactt gagctgtaaa cgccccaggc cataaggtgt aaacctgtga     1560
ttgcgtgtgt ggtaacgcc tttgtttgct gaatgagttg atgtaagttt aataaagggt      1620
gagataatgt ttaacttgca tggcgtgtta aatggggcgg ggcttaaagg gtatataatg     1680
cgccgtgggc taatcttggt tacatctgac ctcatggagg cttgggagtg tttggaagat     1740
ttttctgctg tgcgtaactt gctggaacag agctctaaca gtacctcttg gttttggagg     1800
tttctgtggg gctcatccca ggcaaagtta gtctgcagaa ttaaggagga ttacaagtgg     1860
gaatttgaag agcttttgaa atcctgtggt gagctgtttg attctttgaa tctgggtcac     1920
caggcgcttt tccaagagaa ggtcatcaag actttggatt tttccacacc ggggcgcgct     1980
gcggctgctg ttgctttttt gagttttata aaggataaat ggagcgaaga aacccatctg     2040
agcgggggt acctgctgga ttttctggcc atgcatctgt ggagagcggt tgtgagacac      2100
aagaatcgcc tgctactgtt gtcttccgtc cgcccggcga taataccgac ggaggagcag     2160
cagcagcagc aggaggaagc caggcggcgg cggcaggagc agagcccatg gaacccgaga     2220
gccggcctgg accctcggga atgaatgttg tacaggtggc tgaactgtat ccagaactga     2280
gacgcatttt gacaattaca gaggatgggc aggggctaaa gggggtaaag agggagcggg     2340
gggcttgtga ggctacagag gaggctagga atctagcttt tagcttaatg accagacacc     2400
```

```
gtcctgagtg tattactttt caacagatca aggataattg cgctaatgag cttgatctgc    2460
tggcgcagaa gtattccata gagcagctga ccacttactg gctgcagcca ggggatgatt    2520
ttgaggaggc tattagggta tatgcaaagg tggcacttag gccagattgc aagtacaaga    2580
tcagcaaact tgtaaatatc aggaattgtt gctacatttc tgggaacggg gccgaggtgg    2640
agatagatac ggaggatagg gtggccttta gatgtagcat gataaatatg tggccggggg    2700
tgcttggcat ggacgggtg gttattatga atgtaaggtt tactgccccc aattttagcg     2760
gtacggtttt cctggccaat accaacctta tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgg ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggccagtg tttgagcata    3180
acatactgac ccgctgttcc ttgcatttgg gtaacaggag gggggtgttc ctaccttacc    3240
aatgcaattt gagtcacact aagatattgc ttgagcccga gagcatgtcc aaggtgaacc    3300
tgaacggggt gtttgacatg accatgaaga tctggaaggt gctgaggtac gatgagaccc    3360
gcaccaggtg cagaccctgc gagtgtggcg gtaaacatat taggaaccag cctgtgatgc    3420
tggatgtgac cgaggagctg aggcccgatc acttggtgct ggcctgcacc cgcgctgagt    3480
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
agactgcagc ctccgccgcc gcttcagccg ctgcagccac cgcccgcggg attgtgactg    3840 actttgctt cctgagcccg cttgcaagca gtgcagcttc ccgttcatcc gcccgcgatg     3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aaacataaat aaaaaaccag actctgtttg gatttggatc aagcaagtgt    4080
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320 cttttcagtag caagctgatt gccagggca ggcccttggt gtaagtgttt acaaagcggt    4380
taagctggga tgggtgcata cgtggggata tgagatgcat cttggactgt attttaggt    4440 tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccattttta caaagcgcgg gcgagggtg ccagactgcg     4740 gtataatggt tccatccggc ccaggggcgt agttaccctc acagatttgc atttcccacg    4800
```

```
ctttgagttc agatggggggg atcatgtcta cctgcggggc gatgaagaaa acggtttccg   4860
gggtagggga gatcagctgg aagaaagca ggttcctgag cagctgcgac ttaccgcagc    4920
cggtgggccc gtaaatcaca cctattaccg ggtgcaactg gtagttaaga gagctgcagc   4980
tgccgtcatc cctgagcagg gggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacggggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag gggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa gggggggctat aaaagggggt ggggcgcgt tcgtcctcac tctcttccgc    6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttcgcgcag cagaatggcg gtaggggtc   6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atgggtggg tgagcgcgga   6720
ggcgtacatg ccgcaaatgt cgtaaacgta gaggggctct ctgagtattc aagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtcccttttt ttttccacag ctcgcggttg aggacaaaact cttcgcggtc   7140
```

```
tttccagtac tcttggatcg gaaacccgtc ggcctccgaa cggtaagagc ctagcatgta    7200
gaactggttg acggcctggt aggcgcagca tcccttttct acgggtagcg cgtatgcctg    7260
cgcggccttc cggagcgagg tgtgggtgag cgcaaaggtg tccctgacca tgactttgag    7320
gtactggtat ttgaagtcag tgtcgtcgca tccgccctgc tcccagagca aaaagtccgt    7380 gcgcttttg gaacgcggat ttggcagggc gaaggtgaca tcgttgaaga gtatctttcc     7440
cgcgcgaggc ataaagttgc gtgtgatgcg gaagggtccc ggcacctcgg aacgttgtt    7500 aattacctgg gcggcgagca cgatctcgtc aaagccgttg atgttgtggc ccacaatgta    7560
aagttccaag aagcgcggga tgcccttgat ggaaggcaat tttttaagtt cctcgtaggt    7620
gagctcttca ggggagctga gcccgtgctc tgaagggcc cagtctgcaa gatgagggtt     7680
ggaagcgacg aatgagctcc acaggtcacg ggccattagc atttgcaggt ggtcgcgaaa    7740
ggtcctaaac tggcgaccta tggccatttt ttctggggtg atgcagtaga aggtaagcgg    7800
gtcttgttcc cagcggtccc atccaaggtt cgcggctagg tctcgcgcgg cagtcactag    7860
aggctcatct ccgccgaact tcatgaccag catgaagggc acgagctgct cccaaaggc     7920 ccccatccaa gtataggtct ctacatcgta ggtgacaaag agacgctcgg tgcgaggatg    7980
cgagccgatc gggaagaact ggatctcccg ccaccaattg gaggagtggc tattgatgtg    8040
gtgaaagtag aagtccctgc gacgggccga acactcgtgc tggcttttgt aaaaacgtgc    8100
gcagtactgg cagcggtgca cgggctgtac atcctgcacg aggttgacct gacgaccgcg    8160
cacaaggaag cagagtggga atttgagccc ctcgcctggc gggtttggct ggtggtcttc    8220
tacttcggct gcttgtcctt gaccgtctgg ctgctcgagg ggagttacgg tggatcggac    8280
caccacgccg cgcgagccca aagtccagat gtccgcgcgc ggcggtcgga gcttgatgac    8340
aacatcgcgc agatgggagc tgtccatggt ctggagctcc cgcggcgtca ggtcaggcgg    8400
gagctcctgc aggtttacct cgcatagacg ggtcagggcg cgggctagat ccaggtgata    8460
cctaatttcc aggggctggt tggtggcggc gtcgatggct tgcaagaggc cgcatccccg    8520
cggcgcgact acggtaccgc gcggcgggcg gtgggccgcg ggggtgtcct tggatgatgc    8580
atctaaaagc ggtgacgcgg gcgagccccc ggaggtaggg ggggctccgg acccgccggg    8640 agaggggca ggggcacgtc ggcgccgcgc gcgggcagga gctggtgctg cgcgcgtagg      8700
ttgctggcga acgcgacgac gcggcggttg atctcctgaa tctggcgcct ctgcgtgaag    8760
acgacgggcc cggtgagctt gagcctgaaa gagagttcga cagaatcaat ttcggtgtcg    8820
ttgacggcgg cctggcgcaa aatctcctgc acgtctcctg agttgtcttg ataggcgatc    8880
tcggccatga actgctcgat ctcttcctcc tggagatctc cgcgtccggc tcgctccacg    8940
gtggcggcga ggtcgttgga aatgcgggcc atgagctgcg agaaggcgtt gaggcctccc    9000
tcgttccaga cgcggctgta gaccacgccc ccttcggcat cgcgggcgcg catgaccacc    9060
tgcgcgagat tgagctccac gtgccgggcg aagacgcgcg agtttcgcag gcgctgaaag    9120
aggtagttga gggtggtggc ggtgtgttct gccacgaaga agtacataac ccagcgtcgc    9180
aacgtggatt cgttgatatc ccccaaggcc tcaaggcgct ccatggcctc gtagaagtcc    9240
acggcgaagt tgaaaaactg ggagttgcgc gccgacacgg ttaactcctc ctccagaaga    9300
cggatgagct cggcgacagt gtcgcgcacc tcgcgctcaa aggctacagg ggcctcttct    9360
tcttcttcaa tctcctcttc cataagggcc tcccttctt cttcttctgg cggcggtggg      9420
ggagggggga cacggcggcg acgacggcgc accgggaggc ggtcgacaaa gcgctcgatc    9480
atctccccgc ggcgacggcg catggtctcg gtgacggcgc ggccgttctc gcggggcgc     9540
```

```
agttggaaga cgccgcccgt catgtcccgg ttatgggttg gcggggggct gccatgcggc    9600
agggatacgg cgctaacgat gcatctcaac aattgttgtg taggtactcc gccgccgagg    9660
gacctgagcg agtccgcatc gaccggatcg gaaaacctct cgagaaaggc gtctaaccag    9720
tcacagtcgc aaggtaggct gagcaccgtg gcgggcggca gcgggcggcg gtcggggttg    9780
tttctggcgg aggtgctgct gatgatgtaa ttaaagtagg cggtcttgag acggcggatg    9840
gtcgacagaa gcaccatgtc cttgggtccg gcctgctgaa tgcgcaggcg gtcggccatg    9900
ccccaggctt cgttttgaca tcggcgcagg tctttgtagt agtcttgcat gagcctttct    9960
accggcactt cttcttctcc ttcctcttgt cctgcatctc ttgcatctat cgctgcggcg   10020
gcggcggagt ttggccgtag gtggcgccct cttcctccca tgcgtgtgac cccgaagccc   10080
ctcatcggct gaagcagggc taggtcggcg acaacgcgct cggctaatat ggcctgctgc   10140
acctgcgtga gggtagactg gaagtcatcc atgtccacaa agcggtggta tgcgcccgtg   10200
ttgatggtgt aagtgcagtt ggccataacg gaccagttaa cggtctggtg accggctgc    10260
gagagctcgg tgtacctgag acgcgagtaa gccctcgagt caaatacgta gtcgttgcaa   10320
gtccgcacca ggtactggta tcccaccaaa aagtgcggcg gcggctggcg gtagaggggc   10380
cagcgtaggg tggccggggc tccggggcg agatcttcca acataaggcg atgatatccg    10440
tagatgtacc tggacatcca ggtgatgccg gcggcggtgg tggaggcgcg cggaaagtcg   10500
cggacgcggt tccagatgtt gcgcagcggc aaaaagtgct ccatggtcgg gacgctctgg   10560
ccggtcaggc gcgcgcaatc gttgacgctc tagaccgtgc aaaaggagag cctgtaagcg   10620
ggcactcttc cgtggtctgg tggataaatt cgcaagggta tcatggcgga cgaccggggt   10680
tcgagccccg tatccggccg tccgccgtga tccatgcggt taccgcccgc gtgtcgaacc   10740
caggtgtgcg acgtcagaca acgggggagt gctccttttg gcttccttcc aggcgcggcg   10800
gctgctgcgc tagcttttt ggccactggc cgcgcgcagc gtaagcggtt aggctggaaa    10860
gcgaaagcat taagtggctc gctccctgta gccggagggt tattttccaa gggttgagtc   10920
gcgggacccc cggttcgagt ctcggaccgg ccggactgcg gcgaacgggg gtttgcctcc   10980
ccgtcatgca agaccccgct tgcaaattcc tccggaaaca gggacgagcc cctttttgc    11040
ttttcccaga tgcatccggt gctgcggcag atgcgccccc ctcctcagca gcggcaagag   11100
caagagcagc ggcagacatg cagggcaccc tcccctcctc ctaccgcgtc aggaggggcg   11160
acatccgcgg ttgacgcggc agcagatggt gattacgaac cccgcgcgcg ccgggcccgg   11220
cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
```

```
ttttacgccc gcaagatata ccatacccct tacgttccca tagacaagga ggtaaagatc    11940
gaggggttct acatgcgcat ggcgctgaag gtgcttacct tgagcgacga cctgggcgtt    12000
tatcgcaacg agcgcatcca caaggccgtg agcgtgagcc ggcggcgcga gctcagcgac    12060
cgcgagctga tgcacagcct gcaaagggcc ctggctggca cgggcagcgg cgatagagag    12120
gccgagtcct actttgacgc gggcgctgac ctgcgctggg ccccaagccg acgcgccctg    12180
gaggcagctg gggccggacc tgggctggcg gtggcacccg cgcgcgctgg caacgtcggc    12240
ggcgtggagg aatatgacga ggacgatgag tacgagccag aggacggcga gtactaagcg    12300
gtgatgtttc tgatcagatg atgcaagacg caacggaccc ggcggtgcgg gcggcgctgc    12360
agagccagcc gtccggcctt aactccacgg acgactggcg ccaggtcatg gaccgcatca    12420
tgtcgctgac tgcgcgcaat cctgacgcgt tccggcagca gccgcaggcc aaccggctct    12480
ccgcaattct ggaagcggtg gtcccggcgc gcgcaaaccc cacgcacgag aaggtgctgg    12540
cgatcgtaaa cgcgctggcc gaaaacaggg ccatccggcc cgacgaggcc ggcctggtct    12600
acgacgcgct gcttcagcgc gtggctcgtt acaacagcgg caacgtgcag accaacctgg    12660
accggctggt gggggatgtg cgcgaggcc tggcgcagcg tgagcgcgcg cagcagcagg    12720
gcaacctggg ctccatggtt gcactaaacg ccttcctgag tacacagccc gccaacgtgc    12780
cgcggggaca ggaggactac accaactttg tgagcgcact gcggctaatg gtgactgaga    12840
caccgcaaag tgaggtgtac cagtctgggc cagactattt tttccagacc agtagacaag    12900
gcctgcagac cgtaaacctg agccaggctt caaaaactt gcaggggctg tgggggtgc    12960
gggctcccac aggcgaccgc gcgaccgtgt ctagcttgct gacgcccaac tcgcgcctgt    13020
tgctgctgct aatagcgccc ttcacggaca gtggcagcgt gtcccgggac acatacctag    13080
gtcacttgct gacactgtac cgcgaggcca taggtcaggc gcatgtggac gagcatactt    13140
tccaggagat tacaagtgtc agccgcgcgc tggggcagga ggacacgggc agcctggagg    13200
caaccctaaa ctacctgctg accaaccggc ggcagaagat cccctcgttg cacagtttaa    13260
acagcgagga ggagcgcatt ttgcgctacg tgcagcagag cgtgagccctt aacctgatgc    13320
gcgacggggt aacgcccagc gtggcgctgg acatgaccgc gcgcaacatg gaaccgggca    13380
tgtatgcctc aaaccggccg tttatcaacc gcctaatgga ctacttgcat cgcgcggccg    13440
ccgtgaaccc cgagtatttc accaatgcca tcttgaaccc gcactggcta ccgccccctg    13500
gtttctacac cggggattc gaggtgcccg agggtaacga tggattcctc tgggacgaca    13560
tagacgacag cgtgttttcc ccgcaaccgc agaccctgct agagttgcaa cagcgcgagc    13620
aggcagaggc ggcgctgcga aaggaaagct tccgcaggcc aagcagcttg tccgatctag    13680
gcgctgcggc cccgcggtca gatgctagta gcccatttcc aagcttgata gggtctctta    13740
ccagcactcg caccacccgc ccgcgcctgc tgggcgagga ggagtaccta aacaactcgc    13800
tgctgcagcc gcagcgcgaa aaaaacctgc ctccggcatt tcccaacaac gggatagaga    13860
gcctagtgga caagatgagt agatggaaga cgtacgcgca ggagcacagg gacgtgccag    13920
gcccgcgccc gcccacccgt cgtcaaaggc acgaccgtca gcggggtctg tgtgggagg    13980
acgatgactc ggcagacgac agcagcgtcc tggatttggg agggagtggc aacccgtttg    14040
cgcaccttcg ccccaggctg gggagaatgt tttaaaaaaa aaaagcatg atgcaaaata    14100
aaaaactcac caaggccatg gcaccgagcg ttggttttct tgtattcccc ttagtatgcg    14160
gcgcgcggcg atgtatgagg aaggtcctcc tccctcctac gagagtgtgg tgagcgcggc    14220
gccagtggcg gcggcgctgg gttctccctt cgatgctccc ctggaccgc cgtttgtgcc    14280
```

```
tccgcggtac ctgcggccta ccggggggag aaacagcatc cgttactctg agttggcacc   14340
cctattcgac accacccgtg tgtacctggt ggacaacaag tcaacggatg tggcatccct   14400
gaactaccag aacgaccaca gcaactttct gaccacggtc attcaaaaca atgactacag   14460
ccccgggggag gcaagcacac agaccatcaa tcttgacgac cggtcgcact ggggcggcga   14520
cctgaaaacc atcctgcata ccaacatgcc aaatgtgaac gagttcatgt ttaccaataa   14580
gtttaaggcg cgggtgatgg tgtcgcgctt gcctactaag gacaatcagg tggagctgaa   14640
atacgagtgg gtggagttca cgctgcccga gggcaactac tccgagacca tgaccataga   14700
ccttatgaac aacgcgatcg tggagcacta cttgaaagtg ggcagacaga acggggttct   14760
ggaaagcgac atcggggtaa agtttgacac ccgcaacttc agactggggt ttgaccccgt   14820
cactggtctt gtcatgcctg ggtatatac aaacgaagcc ttccatccag acatcatttt   14880
gctgccagga tgcggggtgg acttcaccca cagccgcctg agcaacttgt tgggcatccg   14940
caagcggcaa cccttccagg agggctttag gatcacctac gatgatctgg agggtggtaa   15000
cattcccgca ctgttggatg tggacgccta ccaggcgagc ttgaaagatg acaccgaaca   15060
gggcggggt ggcgcaggcg gcagcaacag cagtggcagc ggcgcggaag agaactccaa   15120
cgcggcagcc gcggcaatgc agccggtgga ggacatgaac gatcatgcca ttcgcggcga   15180
cacctttgcc acacgggctg aggagaagcg cgctgaggcc gaagcagcgg ccgaagctgc   15240
cgcccccgct gcgcaacccg aggtcgagaa gcctcagaag aaaccggtga tcaaaccccct   15300
gacagaggac agcaagaaac gcagttacaa cctaataagc aatgacagca ccttcaccca   15360
gtaccgcagc tggtaccttg catacaacta cggcgaccct cagaccggaa tccgctcatg   15420
gaccctgctt tgcactcctg acgtaacctg cggctcggag caggtctact ggtcgttgcc   15480
agacatgatg caagaccccg tgaccttccg ctccacgcgc cagatcagca actttccggt   15540
ggtgggcgcc gagctgttgc ccgtgcactc caagagcttc tacaacgacc aggccgtcta   15600
ctcccaactc atccgccagt ttacctctct gacccacgtg ttcaatcgct ttcccgagaa   15660
ccagattttg gcgcgcccgc cagccccac catcaccacc gtcagtgaaa cgttcctgc   15720
tctcacagat cacgggacgc taccgctgcg caacagcatc ggaggagtcc agcgagtgac   15780
cattactgac gccagacgcc gcacctgccc ctacgtttac aaggccctgg gcatagtctc   15840
gccgcgcgtc ctatcgagcc gcactttttg agcaagcatg tccatcctta tatcgcccag   15900
caataacaca ggctggggcc tgcgcttccc aagcaagatg tttggcgggg ccaagaagcg   15960
ctccgaccaa cacccagtgc gcgtgcgcgg gcactaccgc gcgccctggg gcgcgcacaa   16020
acgcggccgc actgggcgca ccaccgtcga tgacgccatc gacgcggtgg tggaggaggc   16080
gcgcaactac acgcccacgc cgccaccagt gtccacagtg gacgcggcca ttcagaccgt   16140
ggtgcgcgga gcccggcgct atgctaaaat gaagagacgg cggaggcgcg tagcacgtcg   16200
ccaccgccgc cgacccggca ctgccgccca acgcgcggcg gcggccctgc ttaaccgcgc   16260
acgtcgcacc ggccgacggg cggccatgcg ggccgctcga aggctggccg cgggtattgt   16320
cactgtgccc cccaggtcca ggcgacgagc ggccgccgca gcagccgcgg ccattagtgc   16380
tatgactcag ggtcgcaggg gcaacgtgta ttgggtgcgc gactcggtta gcggcctgcg   16440
cgtgcccgtg cgcacccgcc cccgcgcaa ctagattgca agaaaaaact acttagactc   16500
gtactgttgt atgtatccag cggcggcggc gcgcaacgaa gctatgtcca agcgcaaaat   16560
caaagaagag atgctccagg tcatcgcgcc ggagatctat ggccccccga agaaggaaga   16620
```

```
gcaggattac aagccccgaa agctaaagcg ggtcaaaaag aaaaagaaag atgatgatga   16680
tgaacttgac gacgaggtgg aactgctgca cgctaccgcg cccaggcgac gggtacagtg   16740
gaaaggtcga cgcgtaaaac gtgttttgcg acccggcacc accgtagtct ttacgcccgg   16800
tgagcgctcc acccgcacct acaagcgcgt gtatgatgag gtgtacggcg acgaggacct   16860
gcttgagcag gccaacgagc gcctcgggga gtttgcctac ggaaagcggc ataaggacat   16920
gctggcgttg ccgctggacg agggcaaccc aacacctagc ctaaagcccg taacactgca   16980
gcaggtgctg cccgcgcttg caccgtccga agaaaagcgc ggcctaaagc gcgagtctgg   17040
tgacttggca cccaccgtgc agctgatggt acccaagcgc cagcgactgg aagatgtctt   17100
ggaaaaaatg accgtggaac ctgggctgga gcccgaggtc cgcgtgcggc aatcaagca    17160 ggtggcgccg gactgggcg tgcagaccgt ggacgttcag atacccacta ccagtagcac    17220
cagtattgcc accgccacag agggcatgga gacacaaacg tcccccggttg cctcagcggt   17280 ggcggatgcc gcggtgcagg cggtcgctgc ggccgcgtcc aagacctcta cggaggtgca   17340
aacggacccg tggatgtttc gcgtttcagc cccccggcgc ccgcgcggtt cgaggaagta   17400
cggcgccgcc agcgcgctac tgcccgaata tgccctacat ccttccattg cgcctacccc   17460
cggctatcgt ggctacacct accgcccag aagacgagca actacccgac gccgaaccac    17520
cactggaacc cgccgccgcc gtcgccgtcg ccagcccgtg ctggccccga tttccgtgcg   17580
cagggtggct cgcgaaggag gcaggaccct ggtgctgcca acagcgcgct accaccccag   17640
catcgtttaa aagccggtct ttgtggttct tgcagatatg gccctcacct gccgcctccg   17700
tttcccggtg ccgggattcc gaggaagaat gcaccgtagg aggggcatgg ccggccacgg   17760
cctgacgggc ggcatgcgtc gtgcgcacca ccggcggcgg cgcgcgtcgc accgtcgcat   17820
gcgcggcggt atcctgcccc tccttattcc actgatcgcc gcggcgattg gcgccgtgcc   17880
cggaattgca tccgtggcct tgcaggcgca gagacactga ttaaaaacaa gttgcatgtg   17940
gaaaaatcaa aataaaaagt ctggactctc acgctcgctt ggtcctgtaa ctattttgta   18000
gaatggaaga catcaacttt gcgtctctgg ccccgcgaca cggctcgcgc ccgttcatgg   18060
gaaactggca agatatcggc accagcaata tgagcggtgg cgccttcagc tggggctcgc   18120
tgtggagcgg cattaaaaat ttcggttcca ccgttaagaa ctatggcagc aaggcctgga   18180
acagcagcac aggccagatg ctgagggata agttgaaaga gcaaaatttc caacaaaagg   18240
tggtagatgg cctggcctct ggcattagcg gggtggtgga cctggccaac caggcagtgc   18300
aaaataagat taacagtaag cttgatcccc gccctcccgt agaggagcct ccaccggccg   18360
tggagacagt gtctccagag gggcgtggcg aaaagcgtcc gcgccccgac agggaagaaa   18420
ctctggtgac gcaaatagac gagcctccct cgtacgagga ggcactaaag caaggcctgc   18480
ccaccacccg tcccatcgcg cccatggcta ccggagtgct gggccagcac acacccgtaa   18540
cgctggacct gcctccccc gccgacaccc agcagaaacc tgtgctgcca ggcccgaccg    18600
ccgttgttgt aaccegtcct agccgcgcgt ccctgcgccg cgccgccagc ggtccgcgat   18660
cgttgcggcc cgtagccagt ggcaactggc aaagcacact gaacagcatc gtgggtctgg   18720
gggtgcaatc cctgaagcgc cgacgatgct tctgaatagc taacgtgtcg tatgtgtgtc   18780
atgtatgcgt ccatgtcgcc gccagaggag ctgctgagcc gccgcgcgcc cgcttttcaa   18840
gatggctacc ccttcgatga tgccgcagtg gtcttacatg cacatctcgg gccaggacgc   18900
ctcggagtac ctgagccccg ggctggtgca gtttgcccgc gccaccgaga cgtacttcag   18960
cctgaataac aagtttagaa accccacggt ggcgcctacg cacgacgtga ccacagaccg   19020
```

```
gtcccagcgt tgacgctgc ggttcatccc tgtggaccgt gaggatactg cgtactcgta   19080
caaggcgcgg ttcaccctag ctgtgggtga taaccgtgtg ctggacatgg cttccacgta   19140
ctttgacatc cgcggcgtgc tggacagggg ccctactttt aagccctact ctggcactgc   19200
ctacaacgcc ctggctccca agggtgcccc aaatccttgc gaatgggatg aagctgctac   19260
tgctcttgaa ataaacctag aagaagagga cgatgacaac gaagacgaag tagacgagca   19320
agctgagcag caaaaaactc acgtatttgg gcaggcgcct tattctggta taaatattac   19380
aaaggagggt attcaaatag gtgtcgaagg tcaaacacct aaatatgccg ataaaacatt   19440
tcaacctgaa cctcaaatag gagaatctca gtggtacgaa actgaaatta atcatgcagc   19500
tgggagagtc cttaaaaaga ctaccccaat gaaaccatgt tacggttcat atgcaaaacc   19560
cacaaatgaa aatggagggc aaggcattct tgtaaagcaa caaatggaa agctagaaag   19620 tcaagtggaa atgcaatttt tctcaactac tgaggcgacc gcaggcaatg gtgataactt   19680
gactcctaaa gtggtattgt acagtgaaga tgtagatata gaaaccccag acactcatat   19740
ttcttacatg cccactatta aggaaggtaa ctcacgagaa ctaatgggcc aacaatctat   19800
gcccaacagg cctaattaca ttgcttttag ggacaatttt attggtctaa tgtattacaa   19860
cagcacgggt aatatgggtg ttctggcggg ccaagcatcg cagttgaatg ctgttgtaga   19920
tttgcaagac agaaacacag agctttcata ccagcttttg cttgattcca ttggtgatag   19980
aaccaggtac ttttctatgt ggaatcaggc tgttgacagc tatgatccag atgttagaat   20040
tattgaaaat catggaactg aagatgaact tccaaattac tgctttccac tgggaggtgt   20100
gattaataca gagactctta ccaaggtaaa acctaaaaca ggtcaggaaa atggatggga   20160
aaaagatgct acagaatttt cagataaaaa tgaaataaga gttggaaata attttgccat   20220
ggaaatcaat ctaaatgcca acctgtggag aaatttcctg tactccaaca tagcgctgta   20280
tttgcccgac aagctaaagt acagtccttc caacgtaaaa atttctgata cccaaaacac   20340
ctacgactac atgaacaagc gagtggtggc tcccgggtta gtggactgct acattaacct   20400
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct tgccattaa aaacctcctt ctcctgccgg gctcatacac   20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
ccccatggcc cacaacaccg cctccacgct tgaggccatg cttagaaacg acaccaacga   20760
ccagtccttt aacgactatc tctccgccgc caacatgctc taccctatac ccgccaacgc   20820
taccaacgtg cccatatcca tccctcccg caactgggcg ctttccgcg ctgggcctt   20880 cacgcgcctt aagactaagg aaaccccatc actgggctcg gctacgacc cttattacac   20940 ctactctggc tctatacccc acctagatgg aaccttttac ctcaaccaca cctttaagaa   21000
ggtggccatt acctttgact cttctgtcag ctggcctggc aatgaccgcc tgcttacccc   21060
caacgagttt gaaattaagc gctcagttga cggggagggt tacaacgttg cccagtgtaa   21120
catgaccaaa gactggttcc tggtacaaat gctagctaac tacaacattg gctaccaggg   21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
```

```
ggcctaccct gctaacttcc cctatccgct tataggcaag accgcagttg acagcattac   21420
ccagaaaaag tttctttgcg atcgcaccct ttggcgcatc ccattctcca gtaactttat   21480
gtccatgggc gcactcacag acctgggcca aaaccttctc tacgccaact ccgcccacgc   21540
gctagacatg acttttgagg tggatcccat ggacgagccc acccttcttt atgttttgtt   21600
tgaagtcttt gacgtggtcc gtgtgcaccg gccgcaccgc ggcgtcatcg aaaccgtgta   21660
cctgcgcacg cccttctcgg ccggcaacgc cacaacataa agaagcaagc aacatcaaca   21720
acagctgccg ccatgggctc cagtgagcag gaactgaaag ccattgtcaa agatcttggt   21780
tgtgggccat attttttggg cacctatgac aagcgctttc caggctttgt ttctccacac   21840
aagctcgcct gcgccatagt caatacggcc ggtcgcgaga ctggggcgt acactggatg    21900
gcctttgcct ggaacccgca ctcaaaaaca tgctacctct ttgagccctt tggcttttct   21960
gaccagcgac tcaagcaggt ttaccagttt gagtacgagt cactcctgcg ccgtagcgcc   22020
attgcttctt cccccgaccg ctgtataacg ctggaaaagt ccacccaaag cgtacagggg   22080
cccaactcgg ccgcctgtgg actattctgc tgcatgtttc tccacgcctt gccaactgg    22140
ccccaaactc ccatggatca aaccccacc atgaaccttta ttaccggggt acccaactcc    22200
atgctcaaca gtccccaggt acagcccacc ctgcgtcgca accaggaaca gctctacagc   22260
ttcctggagc gccactcgcc ctacttccgc agccacagtg cgcagattag gagcgccact   22320
tcttttttgtc acttgaaaaa catgtaaaaa taatgtacta gagacactttt caataaaggc   22380
aaatgcttttt atttgtacac tctcgggtga ttatttaccc ccaccccttgc cgtctgcgcc   22440
gtttaaaaat caaaggggttt ctgccgcgca tcgctatgcg ccactggcag ggacacgttg   22500
cgatactggt gtttagtgct ccacttaaac tcaggcacaa ccatccgcgg cagctcggtg   22560
aagttttcac tccacaggct gcgcaccatc accaacgcgt ttagcaggtc gggcgccgat   22620
atcttgaagt cgcagttggg gcctccgccc tgcgcgcgcg agttgcgata cacagggttg   22680
cagcactgga acactatcag cgccgggtgg tgcacgctgg ccagcacgct cttgtcggag   22740
atcagatccg cgtccaggtc ctccgcgttg ctcaggcga acggagtcaa ctttggtagc    22800
tgccttccca aaagggcgc gtgcccaggc tttgagttgc actcgcaccg tagtggcatc   22860
aaaaggtgac cgtgcccggt ctgggcgtta ggatacagcg cctgcataaa agccttgatc   22920
tgcttaaaag ccacctgagc cttttgcgcct tcagagaaga acatgccgca agacttgccg   22980
gaaaactgat tggccggaca ggccgcgtcg tgcacgcagc accttgcgtc ggtgttggag   23040
atctgcacca catttcggcc ccaccggttc ttcacgatct tggccttgct agactgctcc   23100
ttcagcgcgc gctgcccgtt ttcgctcgtc acatccattt caatcacgtg ctccttattt   23160
atcataatgc ttccgtgtag acacttaagc tcgccttcga tctcagcgca gcggtgcagc   23220
cacaacgcgc agcccgtggg ctcgtgatgc ttgtaggtca cctctgcaaa cgactgcagg   23280
tacgcctgca ggaatcgccc catcatcgtc acaaaggtct tgttgctggt gaaggtcagc   23340
tgcaacccgc ggtgctcctc gttcagccag gtcttgcata cggccgccag agcttccact   23400
tggtcaggca gtagtttgaa gttcgccttt agatcgttat ccacgtggta cttgtccatc   23460
agcgcgcgcg cagcctccat gcccttctcc cacgcagaca cgatcggcac actcagcggg   23520
ttcatcaccg taatttcact ttccgcttcg ctgggctctt cctcttcctc ttgcgtccgc   23580
ataccacgcg ccactgggtc gtcttcattc agccgccgca ctgtgcgctt acctcctttg   23640
ccatgcttga ttagcaccgg tgggttgctg aaacccacca tttgtagcgc cacatcttct   23700
cttttcttcct cgctgtccac gattacctct ggtgatggcg ggcgctcggg cttgggagaa   23760
```

```
gggcgcttct ttttcttctt gggcgcaatg gccaaatccg ccgccgaggt cgatggccgc    23820
gggctgggtg tgcgcggcac cagcgcgtct tgtgatgagt cttcctcgtc ctcggactcg    23880
atacgccgcc tcatccgctt ttttgggggc gcccggggag gcggcggcga cggggacggg    23940
gacgacacgt cctccatggt tgggggacgt cgcgccgcac cgcgtccgcg ctcggggggtg   24000 gtttcgcgct gctcctcttc ccgactggcc atttccttct cctataggca gaaaaagatc    24060
atggagtcag tcgagaagaa ggacagccta accgccccct ctgagttcgc caccaccgcc    24120
tccaccgatg ccgccaacgc gcctaccacc ttccccgtcg aggcaccccc gcttgaggag    24180
gaggaagtga ttatcgagca ggacccaggt tttgtaagcg aagacgacga ggaccgctca    24240
gtaccaacag aggataaaaa gcaagaccag gacaacgcag aggcaaacga gaacaagtc     24300 gggcggggggg acgaaaggca tggcgactac ctagatgtgg gagacgacgt gctgttgaag    24360
catctgcagc gccagtgcgc cattatctgc gacgcgttgc aagagcgcag cgatgtgccc    24420
ctcgccatag cggatgtcag ccttgcctac gaacgccacc tattctcacc gcgcgtaccc    24480
cccaaacgcc aagaaaacgg cacatgcgag cccaacccgc gcctcaactt ctaccccgta    24540
tttgccgtgc cagaggtgct tgccacctat cacatctttt tccaaaactg caagataccc    24600
ctatcctgcc gtgccaaccg cagccgagcg gacaagcagc tggccttgcg gcagggcgct    24660
gtcatacctg atatcgcctc gctcaacgaa gtgccaaaaa tctttgaggg tcttggacgc    24720
gacgagaagc gcgcggcaaa cgctctgcaa caggaaaaca gcgaaaatga aagtcactct    24780
ggagtgttgg tggaactcga gggtgacaac gcgcgcctag ccgtactaaa acgcagcatc    24840
gaggtcaccc actttgccta cccggcactt aacctacccc ccaaggtcat gagcacagtc    24900
atgagtgagc tgatcgtgcg ccgtgcgcag ccctggaga gggatgcaaa tttgcaagaa    24960
caaacagagg agggcctacc cgcagttggc gacgagcagc tagcgcgctg gcttcaaacg    25020
cgcgagcctg ccgacttgga ggagcgacgc aaactaatga tggccgcagt gctcgttacc    25080
gtggagcttg agtgcatgca gcggttcttt gctgacccgg agatgcagcg caagctagag    25140
gaaacattgc actacacctt tcgacagggc tacgtacgcc aggcctgcaa gatctccaac    25200
gtggagctct gcaacctggt ctcctacctt ggaattttgc acgaaaaccg ccttgggcaa    25260
aacgtgcttc attccacgct caagggcgag gcgcgccgcg actacgtccg cgactgcgtt    25320
tacttatttc tatgctacac ctggcagacg gccatgggcg tttggcagca gtgcttggag    25380
gagtgcaacc tcaaggagct gcagaaactg ctaaagcaaa acttgaagga cctatggacg    25440
gccttcaacg agcgctccgt ggccgcgcac ctggcggaca tcattttccc cgaacgcctg    25500
cttaaaaccc tgcaacaggg tctgccgaca ttcaccagtc aaagcatgtt gcagaacttt    25560
aggaactttt cctagagcg ctcaggaatc ttgcccgcca cctgctgtgc acttcctagc    25620
gactttgtgc ccattaagta ccgcgaatgc cctccgccgc tttggggcca ctgctacctt    25680
ctgcagctag ccaactacct tgcctaccac tctgacataa tggaagacgt gagcggtgac    25740
ggtctactgg agtgtcactg tcgctgcaac ctatgcaccc cgcaccgctc cctggttttgc    25800 aattcgcagc tgcttaacga aagtcaaatt atcggtacct ttgagctgca gggtccctcg    25860
cctgacgaaa agtccgcggc tccggggttg aaactcactc cggggctgtg gacgtcggct    25920
taccttcgca aatttgtacc tgaggactac cacgcccacg agattaggtt ctacgaagac    25980
caatcccgcc cgccaaatgc ggagcttacc gcctgcgtca ttacccaggg ccacattctt    26040
ggccaattgc aagccatcaa caaagcccgc caagagtttc tgctacgaaa gggacggggg    26100
```

```
gtttacttgg accccagtc cggcgaggag ctcaacccaa tcccccgcc gccgcagccc   26160
tatcagcagc agccgcggc ccttgcttcc caggatggca cccaaaaaga agctgcagct   26220
gccgccgcca cccacggacg aggaggaata ctgggacagt caggcagagg aggttttgga   26280
cgaggaggag gaggacatga tggaagactg ggagagccta gacgaggaag cttccgaggt   26340
cgaagaggtg tcagacgaaa caccgtcacc ctcggtcgca ttcccctcgc cggcgcccca   26400
gaaatcggca accggttcca gcatggctac aacctccgct cctcaggcgc cgccggcact   26460
gcccgttcgc cgacccaacc gtagatggga caccactgga accagggccg gtaagtccaa   26520
gcagccgccg ccgttagccc aagagcaaca acagcgccaa ggctaccgct catggcgcgg   26580
gcacaagaac gccatagttg cttgcttgca agactgtggg ggcaacatct ccttcgcccg   26640
ccgctttctt ctctaccatc acggcgtggc cttccccgt aacatcctgc attactaccg   26700
tcatctctac agcccatact gcaccggcgg cagcggcagc ggcagcaaca gcagcggcca   26760
cacagaagca aaggcgaccg gatagcaaga ctctgacaaa gcccaagaaa tccacagcgg   26820
cggcagcagc aggaggagga gcgctgcgtc tggcgcccaa cgaacccgta tcgacccgcg   26880
agcttagaaa caggattttt cccactctgt atgctatatt tcaacagagc aggggccaag   26940
aacaagagct gaaaataaaa aacaggtctc tgcgatccct cacccgcagc tgcctgtatc   27000
acaaaagcga agatcagctt cggcgcacgc tggaagacgc ggaggctctc ttcagtaaat   27060
actgcgcgct gactcttaag gactagtttc gcgcccttc tcaaatttaa gcgcgaaaac   27120
tacgtcatct ccagcggcca cacccggcgc cagcacctgt cgtcagcgcc attatgagca   27180
aggaaattcc cacgccctac atgtggagtt accagccaca aatgggactt gcggctggag   27240
ctgcccaaga ctactcaacc cgaataaact acatgagcgc gggacccac atgatatccc   27300
gggtcaacgg aatccgcgcc caccgaaacc gaattctctt ggaacaggcg gctattacca   27360
ccacacctcg taataacctt aatccccgta gttggcccgc tgccctggtg taccaggaaa   27420
gtcccgctcc caccactgtg gtacttccca gagacgccca ggccgaagtt cagatgacta   27480
actcaggggc gcagcttgcg ggcggcttc gtcacagggt gcggtcgccc gggcagggta   27540
taactcacct gacaatcaga gggcgaggta ttcagctcaa cgacgagtcg gtgagctcct   27600
cgcttggtct ccgtccggac gggacatttc agatcggcgg cgccggccgt ccttcattca   27660
cgcctcgtca ggcaatccta actctgcaga cctcgtcctc tgagccgcgc tctggaggca   27720
ttggaactct gcaatttatt gaggagtttg tgccatcggt ctactttaac cccttctcgg   27780
gacctcccgg ccactatccg gatcaattta ttcctaactt tgacgcggta aaggactcgg   27840
cggacggcta cgactgaatg ttaagtggag aggcagagca actgcgcctg aaacacctgg   27900
tccactgtcg ccgccacaag tgctttgccc gcgactccgg tgagttttgc tactttgaat   27960
tgcccgagga tcatatcgag ggcccggcgc acggcgtccg gcttaccgcc cagggagagc   28020
ttgcccgtag cctgattcgg gagtttaccc agcgccccct gctagttgag cgggacaggg   28080
gaccctgtgt tctcactgtg atttgcaact gtcctaacct tggattacat caagatcttt   28140
gttgccatct ctgtgctgag tataataaat acagaaatta aaatatactg gggctcctat   28200
cgccatcctg taaacgccac cgtcttcacc cgcccaagca aaccaaggcg aaccttacct   28260
ggtacttta acatctctcc ctctgtgatt tacaacagtt tcaaccccaga cggagtgagt   28320
ctacgagaga acctctccga gctcagctac tccatcagaa aaaacaccac cctccttacc   28380
tgccgggaac gtacgagtgc gtcaccgcc gctgcaccac acctaccgcc tgaccgtaaa   28440
ccagactttt tccggacaga cctcaataac tctgtttacc agaacaggag gtgagcttag   28500
```

```
aaaacccta gggtattagg ccaaaggcgc agctactgtg gggtttatga acaattcaag    28560
caactctacg ggctattcta attcaggttt ctctagaatc ggggttgggg ttattctctg    28620
tcttgtgatt ctctttattc ttatactaac gcttctctgc ctaaggctcg ccgcctgctg    28680
tgtgcacatt tgcatttatt gtcagctttt taaacgctgg ggtcgccacc caagatgatt    28740
aggtacataa tcctaggttt actcacccct gcgtcagccc acggtaccac ccaaaaggtg    28800
gattttaagg agccagcctg taatgttaca ttcgcagctg aagctaatga gtgcaccact    28860
cttataaaat gcaccacaga acatgaaaag ctgcttattc gccacaaaaa caaaattggc    28920
aagtatgctg tttatgctat ttggcagcca ggtgacacta cagagtataa tgttacagtt    28980
ttccagggta aaagtcataa aacttttatg tatacttttc cattttatga aatgtgcgac    29040
attaccatgt acatgagcaa acagtataag ttgtggcccc cacaaaattg tgtggaaaac    29100
actggcactt tctgctgcac tgctatgcta attacagtgc tcgctttggt ctgtaccccta   29160 ctctatatta aatacaaaag cagacgcagc tttattgagg aaaagaaaat gccttaattt    29220
actaagttac aaagctaatg tcaccactaa ctgctttact cgctgcttgc aaaacaaatt    29280
caaaaagtta gcattataat tagaatagga tttaaacccc ccggtcattt cctgctcaat    29340
accattcccc tgaacaattg actctatgtg ggatatgctc cagcgctaca accttgaagt    29400
caggcttcct ggatgtcagc atctgacttt ggccagcacc tgtcccgcgg atttgttcca    29460
gtccaactac agcgacccac cctaacagag atgaccaaca caaccaacgc ggccgccgct    29520
accggactta catctaccac aaatacaccc caagtttctg cctttgtcaa taactgggat    29580
aacttgggca tgtggtggtt ctccatagcg cttatgtttg tatgccttat tattatgtgg    29640
ctcatctgct gcctaaagcg caaacgcgcc cgaccaccca tctatagtcc catcattgtg    29700
ctacacccaa acaatgatgg aatccataga ttggacggac tgaaacacat gttcttttct    29760
cttacagtat gattaaatga gacatgattc ctcgagtttt tatattactg acccttgttg    29820 cgctttttg tgcgtgctcc acattggctg cggtttctca catcgaagta gactgcattc    29880
cagccttcac agtctatttg ctttacggat ttgtcaccct cacgctcatc tgcagcctca    29940
tcactgtggt catcgccttt atccagtgca ttgactgggt ctgtgtgcgc tttgcatatc    30000
tcagacacca tccccagtac agggacagga ctatagctga gcttcttaga attctttaat    30060
tatgaaattt actgtgactt ttctgctgat tatttgcacc ctatctgcgt tttgttcccc    30120
gacctccaag cctcaaagac atatatcatg cagattcact cgtatatgga atattccaag    30180
ttgctacaat gaaaaaagcg atctttccga agcctggtta tatgcaatca tctctgttat    30240
ggtgttctgc agtaccatct tagccctagc tatatatccc taccttgaca ttggctggaa    30300
acgaatagat gccatgaacc acccaacttt cccgcgcc gctatgcttc cactgcaaca    30360
agttgttgcc ggcggctttg tcccagccaa tcagcctcgc cccacttctc ccaccccac     30420 tgaaatcagc tactttaatc taacaggagg agatgactga caccctagat ctagaaatgg    30480
acggaattat tacagagcag cgcctgctag aaagacgcag ggcagcggcc gagcaacagc    30540
gcatgaatca agagctccaa gacatggtta acttgcacca gtgcaaaagg ggtatctttt    30600
gtctggtaaa gcaggccaaa gtcacctacg acagtaatac caccgacac cgccttagct    30660 acaagttgcc aaccaagcgt cagaaattgg tggtcatggt gggagaaaag cccattacca    30720
taactcagca ctcggtagaa accgaaggct gcattcactc accttgtcaa ggacctgagg    30780
atctctgcac ccttattaag accctgtgcg gtctcaaaga tcttattccc tttaactaat    30840
```

```
aaaaaaaaat aataaagcat cacttactta aaatcagtta gcaaatttct gtccagttta   30900
ttcagcagca cctccttgcc ctcctcccag ctctggtatt gcagcttcct cctggctgca   30960
aactttctcc acaatctaaa tggaatgtca gtttcctcct gttcctgtcc atccgcaccc   31020
actatcttca tgttgttgca gatgaagcgc gcaagaccgt ctgaagatac cttcaacccc   31080
gtgtatccat atgacacgga aaccggtcct ccaactgtgc cttttcttac tcctcccttt   31140
gtatccccca atgggtttca agagagtccc cctggggtac tctctttgcg cctatccgaa   31200
cctctagtta cctccaatgg catgcttgcg ctcaaaatgg caacggcct ctctctggac    31260
gaggccggca accttacctc ccaaaatgta accactgtga gcccacctct caaaaaaacc   31320
aagtcaaaca taaacctgga aatatctgca ccctcacag ttacctcaga agccctaact    31380
gtggctgccg ccgcacctct aatggtcgcg ggcaacacac tcaccatgca atcacaggcc   31440
ccgctaaccg tgcacgactc caaacttagc attgccaccc aaggacccct cacagtgtca   31500
gaaggaaagc tagccctgca aacatcaggc cccctcacca ccaccgatag cagtacccct   31560
actatcactg cctcacccc tctaactact gccactggta gcttgggcat tgacttgaaa    31620
gagcccattt atacacaaaa tggaaaacta ggactaaagt acggggctcc tttgcatgta   31680
acagacgacc taaacacttt gaccgtagca actggtccag gtgtgactat taataatact   31740
tccttgcaaa ctaaagttac tggagccttg ggttttgatt cacaaggcaa tatgcaactt   31800
aatgtagcag gaggactaag gattgattct caaaacagac gccttatact tgatgttagt   31860
tatccgtttg atgctcaaaa ccaactaaat ctaagactag gacagggccc tcttttttata   31920
aactcagccc acaacttgga tattaactac aacaaaggcc tttacttgtt tacagcttca   31980
aacaattcca aaaagcttga ggttaaccta agcactgcca aggggttgat gtttgacgct   32040
acagccatag ccattaatgc aggagatggg cttgaatttg gttcacctaa tgcaccaaac   32100
acaaatcccc tcaaaacaaa aattggccat ggcctagaat ttgattcaaa caaggctatg   32160
gttcctaaac taggaactgg ccttagtttt gacagcacag gtgccattac agtaggaaac   32220
aaaaataatg ataagctaac tttgtggacc acaccagctc catctcctaa ctgtagacta   32280
aatgcagaga aagatgctaa actcactttg gtcttaacaa aatgtggcag tcaaatactt   32340
gctacagttt cagttttggc tgttaaaggc agtttggctc caatatctgg aacagttcaa   32400
agtgctcatc ttattataag atttgacgaa aatggagtgc tactaaacaa ttccttcctg   32460
gacccagaat attggaactt tagaaatgga gatcttactg aaggcacagc ctatacaaac   32520
gctgttggat ttatgcctaa cctatcagct tatccaaaat ctcacggtaa aactgccaaa   32580
agtaacattg tcagtcaagt ttacttaaac ggagacaaaa ctaaacctgt aacactaacc   32640
attacactaa acggtacaca ggaaacagga gacacaactc caagtgcata ctctatgtca   32700
ttttcatggg actggtctgg ccacaactac attaatgaaa tatttgccac atcctcttac   32760
actttttcat acattgccca agaataaaga atcgttgtg ttatgtttca acgtgtttat    32820
ttttcaattg cagaaaattt caagtcattt ttcattcagt agtatagccc caccaccaca   32880
tagcttatac agatcaccgt accttaatca aactcacaga accctagtat tcaacctgcc   32940
acctccctcc caacacacag agtacacagt cctttctccc cggctggcct taaaaagcat   33000
catatcatgg gtaacagaca tattcttagg tgttatattc cacacggttt cctgtcgagc   33060
caaacgctca tcagtgatat taataaactc cccgggcagc tcacttaagt tcatgtcgct   33120
gtccagctgc tgagccacag gctgctgtcc aacttgcggt tgcttaacgg gcggcgaagg   33180
agaagtccac gcctacatgg gggtagagtc ataatcgtgc atcaggatag ggcggtggtg   33240
```

```
ctgcagcagc gcgcgaataa actgctgccg ccgccgctcc gtcctgcagg aatacaacat    33300
ggcagtggtc tcctcagcga tgattcgcac cgcccgcagc ataaggcgcc ttgtcctccg    33360
ggcacagcag cgcaccctga tctcacttaa atcagcacag taactgcagc acagcaccac    33420
aatattgttc aaaatcccac agtgcaaggc gctgtatcca aagctcatgg cggggaccac    33480
agaacccacg tggccatcat accacaagcg caggtagatt aagtggcgac ccctcataaa    33540
cacgctggac ataaacatta cctcttttgg catgttgtaa ttcaccacct cccggtacca    33600
tataaacctc tgattaaaca tggcgccatc caccaccatc ctaaaccagc tggccaaaac    33660
ctgcccgccg gctatacact gcagggaacc gggactggaa caatgacagt ggagagccca    33720
ggactcgtaa ccatggatca tcatgctcgt catgatatca atgttggcac aacacaggca    33780
cacgtgcata cacttcctca ggattacaag ctcctcccgc gttagaacca tatcccaggg    33840
aacaacccat tcctgaatca gcgtaaatcc cacactgcag ggaagacctc gcacgtaact    33900
cacgttgtgc attgtcaaag tgttacattc gggcagcagc ggatgatcct ccagtatggt    33960
agcgcgggtt tctgtctcaa aaggaggtag acgatcccta ctgtacggag tgcgccgaga    34020
caaccgagat cgtgttggtc gtagtgtcat gccaaatgga acgccggacg tagtcatatt    34080
tcctgaagca aaaccaggtg cgggcgtgac aaacagatct gcgtctccgg tctcgccgct    34140
tagatcgctc tgtgtagtag ttgtagtata tccactctct caaagcatcc aggcgccccc    34200
tggcttcggg ttctatgtaa actccttcat gcgccgctgc cctgataaca tccaccaccg    34260
cagaataagc cacacccagc caacctacac attcgttctg cgagtcacac acgggaggag    34320
cgggaagagc tggaagaacc atgttttttt ttttattcca aaagattatc caaaacctca    34380
aaatgaagat ctattaagtg aacgcgctcc cctccggtgg cgtggtcaaa ctctacagcc    34440
aaagaacaga taatggcatt tgtaagatgt tgcacaatgg cttccaaaag gcaaacggcc    34500
ctcacgtcca agtggacgta aaggctaaac ccttcagggt gaatctcctc tataaacatt    34560
ccagcacctt caaccatgcc caaataattc tcatctcgcc accttctcaa tatatctcta    34620
agcaaatccc gaatattaag tccggccatt gtaaaaatct gctccagagc gccctccacc    34680
ttcagcctca agcagcgaat catgattgca aaaattcagg ttcctcacag acctgtataa    34740
gattcaaaag cggaacatta acaaaaatac cgcgatcccg taggtccctt cgcagggcca    34800
gctgaacata atcgtgcagg tctgcacgga ccagcgcggc cacttccccg ccaggaacct    34860
tgacaaaaga acccacactg attatgcaca gcatactcgg agctatgcta accagcgtag    34920
ccccgatgta agctttgttg catgggcggc gatataaaat gcaaggtgct gctcaaaaaa    34980
tcaggcaaag cctcgcgcaa aaaagaaagc acatcgtagt catgctcatg cagataaagg    35040
caggtaagct ccggaaccac cacagaaaaa gacaccattt ttctctcaaa catgtctgcg    35100
ggtttctgca taaacacaaa ataaaataac aaaaaaacat ttaaacatta gaagcctgtc    35160
ttacaacagg aaaaacaacc cttataagca taagacggac tacggccatg ccggcgtgac    35220
cgtaaaaaaa ctggtcaccg tgattaaaaa gcaccaccga cagctcctcg gtcatgtccg    35280
gagtcataat gtaagactcg gtaaacacat caggttgatt catcggtcag tgctaaaaag    35340
cgaccgaaat agcccggggg aatacatacc cgcaggcgta gagacaacat tacagccccc    35400
ataggaggta taacaaaatt aataggagag aaaaacacat aaacacctga aaaccctcc    35460
tgcctaggca aaatagcacc ctcccgctcc agaacaacat acagcgcttc acagcggcag    35520
cctaacagtc agccttacca gtaaaaaaga aaacctatta aaaaaacacc actcgacacg    35580
```

-continued

```
gcaccagctc aatcagtcac agtgtaaaaa agggccaagt gcagagcgag tatatatagg    35640
actaaaaaat gacgtaacgg ttaaagtcca caaaaaacac ccagaaaacc gcacgcgaac    35700
ctacgcccag aaacgaaagc caaaaaaccc acaacttcct caaatcgtca cttccgtttt    35760
cccacgttac gtaacttccc attttaagaa aactacaatt cccaacacat acaagttact    35820
ccgccctaaa acctacgtca cccgccccgt tcccacgccc cgcgccacgt cacaaactcc    35880
accccctcat tatcatattg gcttcaatcc aaaataaggt atattattga tgatg         35935
```

<210> SEQ ID NO 10
<211> LENGTH: 5965
<212> TYPE: DNA
<213> ORGANISM: Artificial Sequence
<220> FEATURE:
<223> OTHER INFORMATION: NSsuboptmut

<400> SEQUENCE: 10

```
gccaccatgg cccccatcac cgcctacagc cagcagacca ggggcctgct gggctgcatc      60
atcaccagcc tgaccggacg cgacaagaac caggtggagg agaggtgca ggtggtgagc     120 accgctaccc agagcttcct ggccaccgtg gtgaacggcg tgtgctggac cgtgtaccac    180
ggagccggaa gcaagaccct ggccggaccc aagggcccta tcacccagat gtacaccaat    240
gtggatcagg atctggtggg ctggcaggcc cctcccggag ccaggagcct gacaccctgt    300
acctgtggaa gcagcgacct gtacctggtg acacgccacg ccgatgtgat ccccgtgagg    360
cgcaggggcg attctcgcgg aagcctgctg agccctaggc ccgtgagcta cctgaagggc    420
agcagcggag gaccccctgct gtgtccttct ggccatgccg tgggcatttt tcgcgctgcc    480
gtgtgtacca ggggcgtggc caaagccgtg gattttgtgc ccgtggaaag catggagacc    540
accatgcgca gccctgtgtt caccgacaac agctctcccc ctgccgtgcc ccaatcattc    600
caggtggctc acctgcacgc ccctaccgga tctggcaaga gcaccaaggt gcccgctgcc    660
tacgccgctc agggctacaa ggtgctggtg ctgaacccca gcgtggccgc taccctgggc    720
ttcggcgctt acatgagcaa ggcccatggc atcgacccca catccgcac aggcgtgcgc    780 accatcacca ccggagctcc cgtgacctac agcacctacg gcaagttcct ggccgatgga    840
ggctgcagcg gaggagccta cgacatcatc atctgcgacg agtgccacag caccgacagc    900
accaccatcc tgggcattgg caccgtgctg gatcaggccg aaacagctgg agccaggctg    960
gtggtgctgg ccacagctac ccctcctggc agcgtgaccg tgccccatcc caatatcgag   1020
gaggtggccc tgagcaacac aggcgagatc cccttctacg gcaaggccat ccccatcgag   1080
gccatccgcg gaggcaggca cctgatcttc tgccacagca gaagaagtg cgacgagctg   1140 gctgccaagc tgagcggact gggcatcaac gccgtggcct actacagggg cctggacgtg   1200
tcagtgatcc ccaccatcgg cgatgtggtg gtggtggcca ccgacgccct gatgacaggc   1260
tacaccggag acttcgacag cgtgatcgac tgcaacacct gcgtgaccca gaccgtggac   1320
ttcagcctgg acccccacctt caccatcgaa accaccaccg tgcctcagga tgctgtgagc   1380
aggagccaga ggcgcggacg caccggaagg ggcaggcgcg gaatttatcg ctttgtgacc   1440
cctggcgaaa ggccctctgg catgttcgac agcagcgtgc tgtgcgagtg ctacgacgct   1500
ggctgcgctt ggtacgagct gacacccgct gaaaccagcg tgcgcctgcg cgcttatctg   1560 aataccctg gcctgccgt gtgtcaggac cacctggagt tctgggagag cgtgttcaca   1620
ggactgaccc acatcgacgc ccatttcctg agccagacca gcaggctgg cgacaacttc   1680 ccctatctgg tggcctatca ggccaccgtg tgtgctaggg cccaagctcc acctccttca   1740
```

```
tgggaccaga tgtggaagtg cctgatccgc ctgaagccca ccctgcacgg ccctaccccct  1800
ctgctgtacc gcctgggagc cgtgcagaac gaggtgaccc tgacccaccc catcaccaag  1860
tacatcatgg cctgcatgag cgctgatctg aagtggtga ccagcacctg ggtgctggtg   1920
ggaggcgtgc tggccgctct ggctgcctac tgcctgacca ccggaagcgt ggtgatcgtg  1980
ggacgcatca tcctgagcgg aaggcccgct atcgtgcccg atcgcgagtt cctgtaccag  2040
gagttcgacg agatggagga gtgtgccagc cacctgccct acatcgagca gggcatgcag  2100
ctggccgaac agttcaagca gaaggccctg ggcctgctgc agacagccac caaacaggcc  2160
gaagctgccg ctcccgtggt ggaaagcaag tggagggccc tggagacctt ctgggctaag  2220
cacatgtgga acttcatctc tggcatccag tacctggccg gactgagcac cctgcctggc  2280
aaccccgcta tcgccagcct gatggccttc accgctagca tcacctctcc cctgaccacc  2340
cagagcaccc tgctgttcaa cattctgggc ggatgggtgg ccgctcagct ggcccctcct  2400
tcagctgctt ctgccttgt gggcgctggc attgccggag ccgctgtggg cagcattggc   2460
ctgggcaaag tgctggtgga tattctggct ggctatggcg ctggcgtggc cggagccctg  2520
gtggccttca aggtgatgag cggagagatg cccagcaccg aggacctggt gaacctgctg  2580
cctgccattc tgagccctgg agccctggtg gtgggcgtgg tgtgtgctgc cattctgagg  2640
cgccatgtgg gacccggaga gggcgctgtg cagtggatga accgcctgat cgccttcgcc  2700
tctcgcggaa accacgtgag ccctacccac tacgtgcctg agagcgacgc cgctgccagg  2760
gtgacccaga tcctgagcag cctgaccatc acccagctgc tgaagcgcct gcaccagtgg  2820
atcaacgagg actgcagcac accctgcagc ggaagctggc tgagggacgt gtgggactgg  2880
atctgcaccg tgctgaccga cttcaagacc tggctgcaga gcaagctgct gccccaactg  2940
cctggcgtgc ccttcttctc atgccagcgc ggatacaagg gcgtgtggag gggcgatggc  3000
atcatgcaga ccacctgtcc ctgcggagcc cagatcacag gccacgtgaa gaacggcagc  3060
atgcgcatcg tgggccctaa gacctgcagc aacacctggc acggcacctt ccccatcaac  3120
gcctacacca ccgaccctg cacacccagc cctgctccca actacagcag ggccctgtgg   3180
agggtggctg ccgaggagta cgtggaggtg accagggtgg agacttcca ctacgtgacc   3240
ggaatgacca ccgacaacgt gaagtgtccc tgtcaggtgc ccgctcccga atttttacc   3300
gaagtggatg gcgtgcgcct gcatcgctat gcccctgcct gtaggcccct gctgcgcgaa  3360
gaagtgacct tccaggtggg cctgaaccag tacctggtgg cagccagct gccctgcgag   3420
cctgagcccg atgtggccgt gctgaccagc atgctgaccg accccagcca catcacagcc  3480
gaaaccgcta aaaggcgcct ggccaggggc tctcctccaa gcctggcctc aagcagcgct  3540
agccagctgt ctgctcccag cctgaaggcc acctgcacca cccaccacgt gagccccgac  3600
gccgacctga tcgaggccaa cctgctgtgg cgccaggaga tgggcggcaa catcacccgc  3660
gtggagagcg agaacaaggt ggtggtgctg gacagcttcg accccctgcg cgccgaggag  3720
gacgagcgcg aggtgagcgt gcccgccgag atcctgcgca gagcaagaa gttccccgct  3780
gccatgccca tctgggctag acctgattac aaccctccc tgctggagag ctggaaggac   3840
cctgattacg tgcctccagt ggtgcatggc tgtcctctgc ctcccattaa agcccctcct  3900
attccacctc ctaggcgcaa aaggaccgtg gtgctgacag aaagcagcgt gagctctgct  3960
ctggccgaac tggccaccaa gaccttggc agcagcgaga gctctgccgt ggacagcgga   4020
acagccaccg ctctgcctga ccaggccagc gacgacggcg ataagggcag cgatgtggag  4080
```

```
agctatagca gcatgcctcc cctggaaggc gaacctggcg atcccgatct gagcgatggc    4140
agctggagca ccgtgagcga agaggccagc gaggacgtgg tgtgttgcag catgagctac    4200
acctggacag cgctctgat cacaccctgc gctgccgagg agagcaagct gcccatcaac     4260
gccctgagca acagcctgct gaggcaccac aacatggtgt acgccaccac cagcaggtct    4320
gccggactga ggcagaagaa ggtgaccttc gaccgcctgc aggtgctgga cgaccactac    4380
cgcgatgtgc tgaaggagat gaaggccaag gccagcaccg tgaaggccaa gctgctgagc    4440
gtggaggagg cctgcaagct gaccccccc cacagcgcca agagcaagtt cggctacggc     4500
gccaaggacg tgcgcaacct gagcagcaag gccgtgaacc acatccacag cgtgtggaag    4560
gacctgctgg aggacaccgt gaccccccatc gacaccacca tcatggccaa gaacgaggtg   4620
ttctgcgtgc agcccgagaa gggcggccgc aagcccgctc gcctgatcgt gttccccgat    4680
ctgggcgtgc gcgtgtgcga gaagatggcc ctgtacgacg tggtgagcac cctgcctcag    4740
gtggtgatgg gctcaagcta cggcttccag tacagccctg gccagcgcgt ggagttcctg    4800
gtgaacacct ggaagagcaa gaagaaccccc atgggcttca gctacgacac acgctgcttc    4860
gacagcaccg tgaccgagaa cgacatccgc gtggaggaga gcatctacca gtgctgcgac    4920
ctggcccctg aggccaggca ggccatcaag agcctgaccg agcgcctgta catcggaggc    4980
cctctgacca cagcaaggg acagaactgc ggatacaggc gctgtagggc ctctggcgtg    5040
ctgaccacca gctgtggcaa caccctgacc tgctacctga aggccagcgc tgcctgtcgc    5100
gctgccaagc tgcaggactg caccatgctg gtgaacgccg ctggcctggt ggtgatttgt    5160
gaaagcgctg gcacccagga agatgctgcc agcctgcgcg tgttcaccga ggccatgacc    5220
aggtactctg ccccctcccgg agacccccct cagcccgaat acgacctgga gctgatcacc    5280
agctgctcaa gcaacgtgag cgtggctcac gacgccagcg gaaagcgcgt gtactacctg    5340
acacgcgatc ccaccacccc tctggctcgc gctgcctggg aaaccgctcg ccatacaccc    5400
gtgaacagct ggctgggcaa catcatcatg tacgccccta ccctgtgggc tcgcatgatc    5460
ctgatgaccc acttcttcag catcctgctg gctcaggagc agctggagaa ggccctggac    5520
tgccagattt acggcgcttg ctacagcatc gagcccctgg acctgcccca aatcatcgag    5580
cgcctgcacg gcctgtctgc cttcagcctg cacagctaca gccctggcga aattaatcgc    5640
gtggccagct gtctgcgcaa actgggcgtg cctcctctgc gcgtgtggag catagggct    5700
aggagcgtga gggctaggct gctgagccag ggaggcaggg ccgctacctg tggaaagtac    5760
ctgttcaact gggccgtgaa gaccaagctg aagctgaccc ctatccctgc cgctagccag    5820
ctggacctga gcggatggtt cgtggctggc tacagcggag cgacatcta ccacagcctg    5880
tctcgcgctc gccctcgctg gttcatgctg tgcctgctgc tgctgagcgt gggcgtgggc    5940
atctacctgc tgcccaaccg ctaaa                                          5965
```

<210> SEQ ID NO 11
<211> LENGTH: 5965
<212> TYPE: DNA
<213> ORGANISM: Artificial Sequence
<220> FEATURE:
<223> OTHER INFORMATION: Chimeric NSsuboptmut

<400> SEQUENCE: 11

```
gccaccatgg cccccatcac cgcctacagc cagcagaccc gcggcctgct gggctgcatc      60
atcaccagcc tgaccggccg cgacaagaac caggtggagg cgaggtgca ggtggtgagc     120
accgccaccc agagcttcct ggccacctgc gtgaacggcg tgtgctggac cgtgtaccac    180
```

```
ggcgccggca gcaagaccct ggccggcccc aagggcccca tcacccagat gtacaccaac    240
gtggaccagg acctggtggg ctggcaggcc ccccccggcg cccgcagcct gacccccctgc   300 acctgcggca gcagcgacct gtacctggtg acccgccacg ccgacgtgat ccccgtgcgc    360
cgccgcggcg acagccgcgg cagcctgctg agcccccgcc ccgtgagcta cctgaagggc    420
agcagcggcg cccccctgct gtgccccagc ggccacgccg tgggcatctt ccgcgccgcc    480
gtgtgcaccc gcggcgtggc caaggccgtg gacttcgtgc ccgtggagag catggagacc    540
accatgcgca gccccgtgtt caccgacaac agcagccccc ccgccgtgcc ccagagcttc    600
caggtggccc acctgcacgc ccccaccggc agcggcaaga gcaccaaggt gcccgccgcc    660
tacgccgccc agggctacaa ggtgctggtg ctgaacccca gcgtggccgc caccctgggc    720
ttcggcgcct acatgagcaa ggcccacggc atcgacccca catccgcac cggcgtgcgc     780 accatcacca ccggcgcccc cgtgacctac agcacctacg caagttcct ggccgacggc     840 ggctgcagcg gcggcgccta cgacatcatc atctgcgacg agtgccacag caccgacagc    900
accaccatcc tgggcatcgg caccgtgctg gaccaggccg agaccgccgg cgcccgcctg    960
gtggtgctgg ccaccgccac ccccccggc agcgtgaccg tgccccaccc caacatcgag    1020
gaggtggccc tgagcaacac cggcgagatc cccttctacg gcaaggccat ccccatcgag    1080
gccatccgcg gcggccgcca cctgatcttc tgccacagca agaagaagtg cgacgagctg    1140
gccgccaagc tgagcggcct gggcatcaac gccgtggcct actaccgcgg cctggacgtg    1200
agcgtgatcc ccaccatcgg cgacgtggtg gtggtggcca ccgacgccct gatgaccggc    1260
tacaccggcg acttcgacag cgtgatcgac tgcaacacct gcgtgaccca gaccgtggac    1320
ttcagcctgg accccacctt caccatcgag accaccaccg tgcccaggga cgccgtgagc    1380
cgcagccagc gccgcggccg caccggccgc ggccgccgcg gcatctaccg cttcgtgacc    1440 cccgcgagc gccccagcgg catgttcgac agcagcgtgc tgtgcgagtg ctacgacgcc    1500
ggctgcgcct ggtacgagct gacccccgcc gagaccagcg tgcgcctgcg cgcctacctg    1560
aacacccccg gcctgcccgt gtgccaggac cacctggagt tctgggagag cgtgttcacc    1620
ggcctgaccc acatcgacgc ccacttcctg agccagacca agcaggccgg cgacaacttc    1680
ccctacctgg tggcctacca ggccaccgtg tgcgcccgcg cccaggcccc ccccccagc    1740 tgggaccaga tgtggaagtg cctgatccgc ctgaagccca ccctgcacgg ccccaccccc   1800
ctgctgtacc gcctgggcgc cgtgcagaac gaggtgaccc tgacccaccc catcaccaag   1860
tacatcatgg cctgcatgag cgccgacctg gaggtggtga ccagcacctg ggtgctggtg   1920
ggcggcgtgc tggccgccct ggccgcctac tgcctgacca ccggcagcgt ggtgatcgtg   1980
ggccgcatca tcctgagcgg ccgccccgcc atcgtgcccg accgcgagtt cctgtaccag   2040
gagttcgacg agatggagga gtgcgccagc cacctgccct acatcgagca gggcatgcag   2100
ctggccgagc agttcaagca gaaggccctg ggcctgctgc agaccgccac caagcaggcc   2160
gaggccgccg ccccgtggt ggagagcaag tggcgcgccc tggagacctt ctgggccaag   2220
cacatgtgga acttcatcag cggcatccag tacctggccg cctgagcac cctgcccggc    2280 aaccccgcca tcgccagcct gatggccttc accgccagca tcaccagccc cctgaccacc    2340
cagagcaccc tgctgttcaa catcctgggc ggctgggtgg ccgcccagct ggccccccc    2400 agcgccgcca gcgccttcgt gggcgccggc atcgccggcg ccgccgtggg cagcatcggc    2460
ctgggcaagg tgctggtgga catcctggcc ggctacggcg ccggcgtggc cggcgccctg    2520
```

```
gtggccttca aggtgatgag cggcgagatg cccagcaccg aggacctggt gaacctgctg    2580
cccgccatcc tgagccccgg cgccctggtg gtgggcgtgg tgtgcgccgc catcctgcgc    2640
cgccacgtgg gccccggcga gggcgccgtg cagtggatga accgcctgat cgccttcgcc    2700
agccgcggca accacgtgag ccccacccac tacgtgcccg agagcgacgc cgccgcccgc    2760
gtgacccaga tcctgagcag cctgaccatc acccagctgc tgaagcgcct gcaccagtgg    2820
atcaacgagg actgcagcac cccctgcagc ggcagctggc tgcgcgacgt gtgggactgg    2880
atctgcaccg tgctgaccga cttcaagacc tggctgcaga gcaagctgct gccccagctg    2940
cccggcgtgc ccttcttcag ctgccagcgc ggctacaagg gcgtgtggcg cggcgacggc    3000
atcatgcaga ccacctgccc ctgcggcgcc cagatcaccg ccacgtgaa gaacggcagc      3060
atgcgcatcg tgggccccaa gacctgcagc aacacctggc acggcacctt ccccatcaac    3120
gcctacacca ccggcccctg cacccccagc cccgccccca actacagccg cgccctgtgg    3180
cgcgtggccg ccgaggagta cgtggaggtg acccgcgtgg gcgacttcca ctacgtgacc    3240
ggcatgacca ccgacaacgt gaagtgcccc tgccaggtgc ccgcccccga gttcttcacc    3300
gaggtggacg gcgtgcgcct gcaccgctac gcccccgcct gccgcccct gctgcgcgag     3360
gaggtgacct tccaggtggg cctgaaccag tacctggtgg cagccagct gccctgcgag     3420
cccgagcccg acgtggccgt gctgaccagc atgctgaccg accccagcca catcaccgcc    3480
gagaccgcca agcgccgcct ggcccgcggc agccccccca gcctggccag cagcagcgcc    3540
agccagctga gcgcccccag cctgaaggcc acctgcacca cccaccacgt gagccccgac    3600
gccgacctga tcgaggccaa cctgctgtgg cgccaggaga tgggcggcaa catcacccgc    3660
gtggagagcg agaacaaggt ggtggtgctg gacagcttcg acccctgcg cgccgaggag     3720
gacgagcgcg aggtgagcgt gcccgccgag atcctgcgca gagcaagaa gttccccgct     3780
gccatgccca tctgggctag acctgattac aaccctcccc tgctggagag ctggaaggac    3840
cctgattacg tgcctccagt ggtgcatggc tgtcctctgc ctcccattaa agcccctcct    3900
attccacctc ctaggcgcaa aaggaccgtg gtgctgacag aaagcagcgt gagctctgct    3960
ctggccgaac tggccaccaa gacctttggc agcagcgaga gctctgccgt ggacagcgga    4020
acagccaccg ctctgcctga ccaggccagc gacgacggcg ataagggcag cgatgtggag    4080
agctatagca gcatgcctcc cctggaaggc gaacctggcg atcccgatct gagcgatggc    4140
agctggagca ccgtgagcga agaggccagc gaggacgtgg tgtgttgcag catgagctac    4200
acctggacag gcgctctgat cacaccctgc gctgccgagg agagcaagct gcccatcaac    4260
gccctgagca acagcctgct gaggcaccac aacatggtgt acgccaccac cagcaggtct    4320
gccggactga ggcagaagaa ggtgaccttc gaccgcctgc aggtgctgga cgaccactac    4380
cgcgatgtgc tgaaggagat gaaggccaag gccagcaccg tgaaggccaa gctgctgagc    4440
gtggaggagg cctgcaagct gacccccccc cacagcgcca agagcaagtt cggctacggc    4500
gccaaggacg tgcgcaacct gagcagcaag gccgtgaacc acatccacag cgtgtggaag    4560
gacctgctgg aggacaccgt gacccccatc gacaccacca tcatggccaa gaacgaggtg    4620
ttctgcgtgc agcccgagaa gggcggccgc aagcccgccc gcctgatcgt gttccccgac    4680
ctgggcgtgc gcgtgtgcga aagatggcc ctgtacgacg tggtgagcac cctgcccag      4740
gtggtgatgg gcagcagcta cggcttccag tacagccccg ccagcgcgt ggagttcctg     4800
gtgaacacct ggaagagcaa gaagaacccc atgggcttca gctacgacac ccgctgcttc    4860
gacagcaccg tgaccgagaa cgacatccgc gtggaggaga gcatctacca gtgctgcgac    4920
```

```
ctggccccg aggcccgcca ggccatcaag agcctgaccg agcgcctgta catcggcggc    4980
cccctgacca acagcaaggg ccagaactgc ggctaccgcc gctgccgcgc cagcggcgtg    5040
ctgaccacca gctgcggcaa cacccctgacc tgctacctga aggccagcgc cgcctgccgc    5100
gccgccaagc tgcaggactg caccatgctg gtgaacgccg ccggcctggt ggtgatctgc    5160
gagagcgccg gcacccagga ggacgccgcc agcctgcgcg tgttcaccga ggccatgacc    5220
cgctacagcg cccccccgg cgacccccc cagcccgagt acgacctgga gctgatcacc    5280
agctgcagca gcaacgtgag cgtggccac gacgccagcg gcaagcgcgt gtactacctg    5340
acccgcgacc ccaccacccc cctggcccgc gccgcctggg agaccgcccg ccacaccccc    5400
gtgaacagct ggctgggcaa catcatcatg tacgccccca ccctgtgggc ccgcatgatc    5460
ctgatgaccc acttcttcag catcctgctg gcccaggagc agctggagaa ggccctggac    5520
tgccagatct acggcgcctg ctacagcatc gagcccctgg acctgcccca gatcatcgag    5580
cgcctgcacg gcctgagcgc cttcagcctg cacagctaca gccccggcga gatcaaccgc    5640
gtggccagct gcctgcgcaa gctgggcgtg cccccctgc gcgtgtggcg ccaccgcgcc    5700
cgcagcgtgc gcgcccgcct gctgagccag ggcggccgcg ccgccacctg cggcaagtac    5760
ctgttcaact gggccgtgaa gaccaagctg aagctgaccc ccatccccgc cgccagccag    5820
ctggacctga gcggctggtt cgtggccggc tacagcggcg gcgacatcta ccacagcctg    5880
agccgcgccc gccccgctg gttcatgctg tgcctgctgc tgctgagcgt gggcgtgggc    5940
atctacctgc tgcccaaccg ctaaa                                          5965

<210> SEQ ID NO 12
<211> LENGTH: 10
<212> TYPE: RNA
<213> ORGANISM: Artificial Sequence
<220> FEATURE:
<223> OTHER INFORMATION: Ribosome binding site

<400> SEQUENCE: 12
gccaccaugg                                                            10

<210> SEQ ID NO 13
<211> LENGTH: 49
<212> TYPE: RNA
<213> ORGANISM: Artificial Sequence
<220> FEATURE:
<223> OTHER INFORMATION: Synthetic polyadenylation signal

<400> SEQUENCE: 13
aauaaaagau cuuuauuuuc auuagaucug uguguuggu uuuugugug                  49

<210> SEQ ID NO 14
<211> LENGTH: 28
<212> TYPE: DNA
<213> ORGANISM: Artificial Sequence
<220> FEATURE:
<223> OTHER INFORMATION: Additional nucleotides present in pVIJns-NS

<400> SEQUENCE: 14
tctagagcgt ttaacccctt aattaagg                                        28

<210> SEQ ID NO 15
<211> LENGTH: 15
<212> TYPE: DNA
<213> ORGANISM: Artificial Sequence
<220> FEATURE:
```

-continued

```
<223> OTHER INFORMATION: Additional nucleotides present in
      pV1Jns-NSOPTmut

<400> SEQUENCE: 15
tttaaatgtt taaac                                                        15

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 16
tcgaatcgat acgcgaacct acgc                                              24

<210> SEQ ID NO 17
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 17
tcgacgtgtc gacttcgaag cgcacaccaa aaacgtc                                37
```